(12) United States Patent
Durack et al.

(10) Patent No.: US 8,709,825 B2
(45) Date of Patent: *Apr. 29, 2014

(54) FLOW CYTOMETER METHOD AND APPARATUS

(71) Applicant: Inguran, LLC, Navasota, TX (US)

(72) Inventors: Gary Durack, Urbana, IL (US); Jeffrey D. Wallace, Rantoul, IL (US); Gary P. Vandre, Mahomet, IL (US); Lon A. Westfall, Mahomet, IL (US); Jeremy T. Hatcher, Urbana, IL (US); Niraj V. Nayak, Redondo Beach, CA (US)

(73) Assignee: Inguran, LLC, Navasota, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/782,459

(22) Filed: Mar. 1, 2013

(65) Prior Publication Data

US 2013/0224787 A1 Aug. 29, 2013

Related U.S. Application Data

(60) Continuation of application No. 13/422,705, filed on Mar. 16, 2012, which is a continuation of application No. 13/106,671, filed on May 12, 2011, now Pat. No. 8,206,987, and a division of application No. 12/794,921, filed on Jun. 7, 2010, now Pat. No. 7,943,384, which is a continuation of application No. 10/812,351, filed on Mar. 29, 2004, now Pat. No. 7,758,811.

(60) Provisional application No. 60/458,607, filed on Mar. 28, 2003, provisional application No. 60/458,731, filed on Mar. 28, 2003.

(51) Int. Cl.
*G01N 1/10* (2006.01)
*G01N 1/14* (2006.01)
*G01N 33/48* (2006.01)

(52) U.S. Cl.
USPC ............... 436/180; 436/63; 422/73; 422/501; 422/509; 422/515; 435/29; 435/286.4

(58) Field of Classification Search
USPC ......... 422/67, 68.1, 73, 82.05, 501, 509, 515; 436/63, 164, 165, 43, 50, 55, 180; 435/2, 287.1, 286.4, 288.7, 366, 29
See application file for complete search history.

(56) References Cited

U.S. PATENT DOCUMENTS 2,217,342 A 10/1940 Ladrach
3,005,756 A 10/1961 VanDemark et al.
(Continued)

FOREIGN PATENT DOCUMENTS

BR 9704313 6/1999
CA 1029833 4/1978
(Continued)

OTHER PUBLICATIONS

Rens et al. Cytometry, vol. 33, 1998, pp. 476-481.*

(Continued)

*Primary Examiner* — Maureen Wallenhorst
(74) *Attorney, Agent, or Firm* — Cindee R. Ewell; Ryan Christensen

(57) ABSTRACT

A nozzle for use in a flow cytometer and a method of orienting particles with a baffle disposed within a nozzle. The baffle may be a baffle plate positioned in a fluid flow path to deflect a fluid stream and to orient particles in a desired orientation as they exit the nozzle.

25 Claims, 134 Drawing Sheets

(56) References Cited

U.S. PATENT DOCUMENTS

| | | |
|---|---|---|
| 3,299,354 A | 1/1967 | Hogg |
| 3,499,435 A | 3/1970 | Rockwell et al. |
| 3,547,526 A | 12/1970 | Devereux |
| 3,644,128 A | 2/1972 | Lipner |
| 3,661,460 A | 5/1972 | Elking et al. |
| 3,687,806 A | 8/1972 | Van den Bovenkamp |
| 3,710,933 A | 1/1973 | Fulwyler et al. |
| 3,738,759 A | 6/1973 | Dittrich et al. |
| 3,756,459 A | 9/1973 | Bannister |
| 3,761,187 A | 9/1973 | Dittrich et al. |
| 3,761,941 A | 9/1973 | Robertson |
| 3,788,744 A | 1/1974 | Friedman et al. |
| 3,791,384 A | 2/1974 | Richter et al. |
| 3,791,517 A | 2/1974 | Friedman |
| 3,810,010 A | 5/1974 | Thom |
| 3,816,249 A | 6/1974 | Bhattacharya |
| 3,826,364 A | 7/1974 | Bonner et al. |
| 3,829,216 A | 8/1974 | Persidsky |
| 3,833,796 A | 9/1974 | Fetner et al. |
| 3,877,430 A | 4/1975 | Wieder |
| 3,893,766 A | 7/1975 | Hogg |
| 3,894,529 A | 7/1975 | Shrimpton |
| 3,906,929 A | 9/1975 | Augspurger |
| 3,909,744 A | 9/1975 | Wisner et al. |
| 3,940,943 A | 3/1976 | Sikes et al. |
| 3,944,917 A | 3/1976 | Hogg et al. |
| 3,947,093 A | 3/1976 | Goshima et al. |
| 3,960,449 A | 6/1976 | Carleton et al. |
| 3,963,606 A | 6/1976 | Hogg |
| 3,973,003 A | 8/1976 | Colas |
| 3,973,196 A | 8/1976 | Hogg |
| 4,006,360 A | 2/1977 | Mueller |
| 4,007,087 A | 2/1977 | Ericsson |
| 4,009,260 A | 2/1977 | Ericsson |
| 4,014,611 A | 3/1977 | Simpson et al. |
| 4,021,117 A | 5/1977 | Gohde et al. |
| 4,056,324 A | 11/1977 | Gohde |
| 4,058,732 A | 11/1977 | Wieder |
| 4,067,965 A | 1/1978 | Bhattacharya |
| 4,070,617 A | 1/1978 | Kachel et al. |
| 4,083,957 A | 4/1978 | Lang |
| 4,085,205 A | 4/1978 | Hancock |
| 4,092,229 A | 5/1978 | Bhattacharya |
| 4,110,604 A | 8/1978 | Haynes et al. |
| 4,148,718 A | 4/1979 | Fulwyler |
| 4,155,831 A | 5/1979 | Bhattacharya |
| 4,162,282 A | 7/1979 | Fulwyler et al. |
| 4,175,662 A | 11/1979 | Zold |
| 4,178,936 A | 12/1979 | Newcomb |
| 4,179,218 A | 12/1979 | Erdmann et al. |
| 4,189,236 A | 2/1980 | Hogg et al. |
| 4,191,749 A | 3/1980 | Bryant |
| 4,200,802 A | 4/1980 | Salzman et al. |
| 4,225,229 A | 9/1980 | Gohde |
| 4,225,405 A | 9/1980 | Lawson |
| 4,230,558 A | 10/1980 | Fulwyler |
| 4,255,021 A | 3/1981 | Brunsden |
| 4,263,508 A | 4/1981 | Leary et al. |
| 4,267,268 A | 5/1981 | Nelson, Jr. |
| 4,274,408 A | 6/1981 | Nimrod |
| 4,274,740 A | 6/1981 | Eidenschink et al. |
| 4,276,139 A | 6/1981 | Lawson |
| 4,293,221 A | 10/1981 | Kay et al. |
| 4,302,166 A | 11/1981 | Fulwyler et al. |
| 4,317,520 A | 3/1982 | Lombardo et al. |
| 4,318,480 A | 3/1982 | Lombardo et al. |
| 4,318,481 A | 3/1982 | Lombardo et al. |
| 4,318,482 A | 3/1982 | Barry et al. |
| 4,318,483 A | 3/1982 | Lombardo et al. |
| 4,325,483 A | 4/1982 | Lombardo et al. |
| 4,327,177 A | 4/1982 | Shrimpton |
| 4,339,434 A | 7/1982 | Ericsson |
| 4,341,471 A | 7/1982 | Hogg et al. |
| 4,348,107 A | 9/1982 | Leif |
| 4,350,410 A | 9/1982 | Minott |
| 4,352,558 A | 10/1982 | Eisert |
| 4,361,400 A | 11/1982 | Gray et al. |
| 4,362,246 A | 12/1982 | Adair |
| 4,367,043 A | 1/1983 | Sweet et al. |
| 4,395,397 A | 7/1983 | Shapiro |
| 4,395,676 A | 7/1983 | Hollinger et al. |
| 4,400,764 A | 8/1983 | Kenyon |
| 4,408,877 A | 10/1983 | Lindmo et al. |
| 4,422,761 A | 12/1983 | Frommer |
| 4,448,767 A | 5/1984 | Bryant |
| 4,474,875 A | 10/1984 | Shrimpton |
| 4,487,320 A | 12/1984 | Auer |
| 4,492,436 A | 1/1985 | Bergmann |
| 4,498,766 A | 2/1985 | Unterleitner |
| 4,501,366 A | 2/1985 | Thompson |
| 4,511,661 A | 4/1985 | Goldberg |
| 4,515,274 A | 5/1985 | Hollinger et al. |
| 4,523,809 A | 6/1985 | Taboada et al. |
| 4,538,733 A | 9/1985 | Hoffman |
| 4,545,677 A | 10/1985 | Chupp |
| 4,559,309 A | 12/1985 | Evenson |
| 4,573,796 A | 3/1986 | Martin |
| 4,585,736 A | 4/1986 | Dolbeare et al. |
| 4,598,408 A | 7/1986 | O'Keefe |
| 4,600,302 A | 7/1986 | Sage, Jr. |
| 4,605,558 A | 8/1986 | Shrimpton |
| 4,609,286 A | 9/1986 | Sage, Jr. |
| 4,629,687 A | 12/1986 | Schindler et al. |
| 4,631,483 A | 12/1986 | Proni et al. |
| 4,637,691 A | 1/1987 | Uehara et al. |
| 4,654,025 A | 3/1987 | Cassou et al. |
| 4,659,185 A | 4/1987 | Aughton |
| 4,660,971 A | 4/1987 | Sage et al. |
| 4,661,913 A | 4/1987 | Wu et al. |
| 4,662,742 A | 5/1987 | Chupp |
| 4,673,288 A | 6/1987 | Thomas et al. |
| 4,673,289 A | 6/1987 | Gaucher |
| 4,680,258 A | 7/1987 | Hammerling et al. |
| 4,683,195 A | 7/1987 | Mullis et al. |
| 4,683,202 A | 7/1987 | Mullis |
| 4,691,829 A | 9/1987 | Auer |
| 4,698,142 A | 10/1987 | Muroi et al. |
| 4,702,598 A | 10/1987 | Böhmer |
| 4,704,891 A | 11/1987 | Recktenwald et al. |
| 4,710,635 A | 12/1987 | Chupp |
| 4,714,680 A | 12/1987 | Civin |
| 4,737,025 A | 4/1988 | Steen |
| 4,744,090 A | 5/1988 | Freiberg |
| 4,749,458 A | 6/1988 | Muroi et al. |
| 4,752,131 A | 6/1988 | Eisenlauer et al. |
| 4,756,427 A | 7/1988 | Gohde et al. |
| 4,758,729 A | 7/1988 | Monnin |
| 4,764,013 A | 8/1988 | Johnston |
| 4,765,737 A | 8/1988 | Harris et al. |
| 4,770,992 A | 9/1988 | Van den Engh et al. |
| 4,778,593 A | 10/1988 | Yamashita et al. |
| 4,780,406 A | 10/1988 | Dolbeare et al. |
| 4,780,451 A | 10/1988 | Donaldson |
| 4,786,165 A | 11/1988 | Yamamoto et al. |
| 4,790,653 A | 12/1988 | North, Jr. |
| 4,794,086 A | 12/1988 | Kasper et al. |
| 4,796,788 A | 1/1989 | Bond |
| 4,818,103 A | 4/1989 | Thomas et al. |
| 4,831,385 A | 5/1989 | Archer et al. |
| 4,836,038 A | 6/1989 | Baldwyn |
| 4,845,025 A | 7/1989 | Lary et al. |
| 4,846,785 A | 7/1989 | Cassou |
| 4,867,908 A | 9/1989 | Recktenwald et al. |
| 4,871,249 A | 10/1989 | Watson |
| 4,876,458 A | 10/1989 | Takeda et al. |
| 4,877,965 A | 10/1989 | Dandliker et al. |
| 4,887,721 A | 12/1989 | Martin et al. |
| 4,915,501 A | 4/1990 | Steen |
| 4,936,465 A | 6/1990 | Zold |
| 4,942,305 A | 7/1990 | Sommer |
| 4,954,715 A | 9/1990 | Zold |
| 4,957,363 A | 9/1990 | Takeda et al. |
| 4,959,354 A | 9/1990 | Barbetti |
| 4,965,204 A | 10/1990 | Civin |

(56) References Cited

U.S. PATENT DOCUMENTS

| | | |
|---|---|---|
| 4,979,093 A | 12/1990 | Laine et al. |
| 4,980,277 A | 12/1990 | Junnila |
| 4,981,580 A | 1/1991 | Auer |
| 4,983,038 A | 1/1991 | Ohki et al. |
| 4,987,539 A | 1/1991 | Moore et al. |
| 4,988,619 A * | 1/1991 | Pinkel .............................. 435/30 |
| 4,989,977 A | 2/1991 | North, Jr. |
| 4,999,283 A | 3/1991 | Zavos et al. |
| 4,999,513 A | 3/1991 | Ito et al. |
| 5,005,981 A | 4/1991 | Schulte et al. |
| 5,007,732 A | 4/1991 | Ohki et al. |
| 5,017,497 A | 5/1991 | Gerard de Grooth et al. |
| 5,021,244 A | 6/1991 | Spaulding |
| 5,030,002 A | 7/1991 | North, Jr. |
| 5,034,613 A | 7/1991 | Denk et al. |
| 5,040,890 A | 8/1991 | North, Jr. |
| 5,043,591 A | 8/1991 | Ludlow et al. |
| 5,055,393 A | 10/1991 | Kwoh et al. |
| 5,057,413 A | 10/1991 | Terstappen et al. |
| 5,072,382 A | 12/1991 | Kamentsky |
| 5,076,472 A | 12/1991 | Gross et al. |
| 5,079,959 A | 1/1992 | Miyake et al. |
| 5,084,004 A | 1/1992 | Ranoux |
| 5,087,295 A | 2/1992 | Gross et al. |
| 5,088,816 A | 2/1992 | Tomioka et al. |
| 5,089,714 A | 2/1992 | Ludlow et al. |
| 5,098,657 A | 3/1992 | Blackford et al. |
| 5,101,978 A | 4/1992 | Marcus |
| 5,116,125 A | 5/1992 | Rigler |
| 5,127,729 A | 7/1992 | Oetliker et al. |
| 5,132,548 A | 7/1992 | Borden et al. |
| 5,135,759 A | 8/1992 | Johnson |
| 5,138,181 A | 8/1992 | Lefevre et al. |
| 5,142,140 A | 8/1992 | Yamazaki et al. |
| 5,142,462 A | 8/1992 | Kashima |
| 5,144,224 A | 9/1992 | Larsen |
| 5,150,313 A | 9/1992 | Van den Engh et al. |
| 5,158,889 A | 10/1992 | Hirako et al. |
| 5,159,397 A | 10/1992 | Kosaka et al. |
| 5,159,403 A * | 10/1992 | Kosaka ..................... 356/243.2 |
| 5,162,306 A | 11/1992 | Donaldson |
| 5,167,926 A | 12/1992 | Kimura et al. |
| 5,180,065 A | 1/1993 | Touge et al. |
| 5,182,617 A | 1/1993 | Yoneyama et al. |
| 5,195,979 A | 3/1993 | Schinkel et al. |
| 5,199,576 A | 4/1993 | Corio et al. |
| 5,204,884 A | 4/1993 | Leary et al. |
| 5,215,376 A | 6/1993 | Schulte et al. |
| 5,219,729 A | 6/1993 | Hodgen |
| 5,247,339 A | 9/1993 | Ogino |
| 5,259,593 A | 11/1993 | Orme et al. |
| 5,260,764 A | 11/1993 | Fukuda et al. |
| 5,274,240 A | 12/1993 | Mathies et al. |
| 5,275,787 A | 1/1994 | Yuguchi et al. |
| 5,298,967 A | 3/1994 | Wells |
| 5,315,122 A | 5/1994 | Pinsky et al. |
| 5,316,540 A | 5/1994 | McMannis et al. |
| 5,317,162 A | 5/1994 | Pinsky et al. |
| 5,346,990 A | 9/1994 | Spaulding |
| RE34,782 E | 11/1994 | Dandliker et al. |
| 5,359,907 A | 11/1994 | Baker et al. |
| 5,366,888 A | 11/1994 | Fry et al. |
| 5,367,474 A | 11/1994 | Auer et al. |
| 5,370,842 A | 12/1994 | Miyazaki et al. |
| 5,371,585 A | 12/1994 | Morgan et al. |
| 5,395,588 A | 3/1995 | North, Jr. et al. |
| 5,400,179 A | 3/1995 | Ito |
| 5,412,466 A * | 5/1995 | Ogino ........................... 356/246 |
| 5,437,987 A | 8/1995 | Teng et al. |
| 5,439,362 A | 8/1995 | Spaulding |
| 5,444,527 A | 8/1995 | Kosaka |
| 5,447,841 A | 9/1995 | Grey et al. |
| 5,447,842 A | 9/1995 | Simons |
| 5,452,054 A | 9/1995 | Dewa et al. |
| 5,457,526 A | 10/1995 | Kosaka |
| 5,461,145 A | 10/1995 | Kudo et al. |
| 5,464,581 A | 11/1995 | Van den Engh |
| 5,466,572 A | 11/1995 | Sasaki et al. |
| 5,467,189 A | 11/1995 | Kreikebaum et al. |
| 5,469,375 A | 11/1995 | Kosaka |
| 5,471,294 A | 11/1995 | Ogino |
| 5,471,299 A | 11/1995 | Kaye et al. |
| 5,475,487 A | 12/1995 | Mariella, Jr. et al. |
| 5,480,774 A | 1/1996 | Hew et al. |
| 5,480,775 A | 1/1996 | Ito et al. |
| 5,483,469 A | 1/1996 | Van den Engh et al. |
| 5,488,469 A | 1/1996 | Yamamoto et al. |
| 5,492,534 A | 2/1996 | Athayde |
| 5,494,795 A | 2/1996 | Guerry et al. |
| 5,495,719 A | 3/1996 | Gray, Jr. |
| 5,496,272 A | 3/1996 | Chung et al. |
| 5,503,994 A | 4/1996 | Shear et al. |
| 5,514,537 A | 5/1996 | Chandler |
| 5,523,573 A | 6/1996 | Hanninen et al. |
| 5,532,155 A | 7/1996 | Ranoux |
| 5,547,849 A | 8/1996 | Baer et al. |
| 5,548,395 A | 8/1996 | Kosaka |
| 5,548,661 A | 8/1996 | Price et al. |
| 5,550,058 A | 8/1996 | Corio et al. |
| 5,556,764 A | 9/1996 | Sizto et al. |
| 5,558,998 A | 9/1996 | Hammond et al. |
| 5,559,032 A | 9/1996 | Pomeroy et al. |
| 5,575,914 A | 11/1996 | Jeyendran |
| 5,578,449 A | 11/1996 | Fr asch et al. |
| 5,579,159 A | 11/1996 | Ito |
| 5,584,982 A | 12/1996 | Dovichi et al. |
| 5,589,457 A | 12/1996 | Wiltbank |
| 5,594,544 A | 1/1997 | Horiuchi |
| 5,596,401 A | 1/1997 | Kusuzawa |
| 5,601,234 A | 2/1997 | Larue |
| 5,601,235 A | 2/1997 | Booker et al. |
| 5,601,533 A | 2/1997 | Hancke et al. |
| 5,602,039 A | 2/1997 | Van den Engh |
| 5,602,349 A | 2/1997 | Van den Engh |
| 5,608,519 A | 3/1997 | Grouley et al. |
| 5,620,842 A | 4/1997 | Davis et al. |
| 5,622,820 A | 4/1997 | Rossi |
| 5,627,037 A | 5/1997 | Ward et al. |
| 5,633,503 A | 5/1997 | Kosaka |
| 5,641,457 A | 6/1997 | Vardanega |
| 5,643,796 A | 7/1997 | Van Den Engh et al. |
| 5,644,388 A | 7/1997 | Maekawa et al. |
| 5,650,847 A | 7/1997 | Maltsev et al. |
| 5,658,751 A | 8/1997 | Yue et al. |
| 5,660,997 A | 8/1997 | Spaulding |
| 5,663,048 A | 9/1997 | Winkfein et al. |
| 5,665,315 A | 9/1997 | Robert et al. |
| 5,672,880 A | 9/1997 | Kain |
| 5,674,743 A | 10/1997 | Ulmer |
| 5,675,401 A | 10/1997 | Wangler et al. |
| 5,682,038 A | 10/1997 | Hoffman |
| 5,684,575 A | 11/1997 | Steen |
| 5,687,727 A | 11/1997 | Kraus et al. |
| 5,690,815 A | 11/1997 | Krasnoff et al. |
| 5,690,895 A | 11/1997 | Matsumoto et al. |
| 5,691,133 A | 11/1997 | Critser et al. |
| 5,693,534 A | 12/1997 | Alak et al. |
| 5,696,157 A | 12/1997 | Wang et al. |
| 5,700,692 A | 12/1997 | Sweet |
| 5,701,012 A | 12/1997 | Ho |
| 5,707,808 A | 1/1998 | Roslaniec et al. |
| 5,708,868 A | 1/1998 | Ishikawa |
| 5,712,807 A | 1/1998 | Bangham |
| 5,719,666 A | 2/1998 | Fukuda et al. |
| 5,719,667 A | 2/1998 | Miers |
| 5,726,009 A | 3/1998 | Connors et al. |
| 5,726,364 A | 3/1998 | Van den Engh |
| 5,726,751 A | 3/1998 | Altendorf et al. |
| 5,730,941 A | 3/1998 | Lefevre et al. |
| 5,736,330 A | 4/1998 | Fulton |
| 5,739,902 A | 4/1998 | Gjelsnes et al. |
| 5,745,308 A | 4/1998 | Spangenberg |
| 5,747,349 A | 5/1998 | van den Engh et al. |
| 5,759,767 A | 6/1998 | Lakowicz et al. |

(56) References Cited

U.S. PATENT DOCUMENTS

| | | |
|---|---|---|
| 5,777,732 A | 7/1998 | Hanninen et al. |
| 5,780,230 A | 7/1998 | Li et al. |
| 5,786,560 A | 7/1998 | Tatah et al. |
| 5,790,692 A | 8/1998 | Price et al. |
| 5,793,485 A | 8/1998 | Gourley |
| 5,796,112 A | 8/1998 | Ichie |
| 5,798,276 A | 8/1998 | Haugland et al. |
| 5,799,830 A | 9/1998 | Carroll et al. |
| 5,804,436 A | 9/1998 | Okun et al. |
| 5,815,262 A | 9/1998 | Schrof et al. |
| 5,819,948 A | 10/1998 | Van den Engh |
| 5,824,269 A | 10/1998 | Kosaka et al. |
| 5,831,723 A | 11/1998 | Kubota et al. |
| 5,835,262 A | 11/1998 | Iketaki et al. |
| 5,840,504 A | 11/1998 | Blecher |
| 5,844,685 A | 12/1998 | Gontin |
| 5,846,737 A | 12/1998 | Kang |
| 5,866,344 A | 2/1999 | Georgiou |
| 5,868,767 A | 2/1999 | Farley et al. |
| 5,872,627 A | 2/1999 | Miers |
| 5,873,254 A | 2/1999 | Arav |
| 5,874,266 A | 2/1999 | Palsson |
| 5,876,942 A | 3/1999 | Cheng et al. |
| 5,880,457 A | 3/1999 | Tomiyama et al. |
| 5,880,474 A | 3/1999 | Norton et al. |
| 5,883,378 A | 3/1999 | Irish et al. |
| 5,888,730 A | 3/1999 | Gray et al. |
| 5,891,734 A | 4/1999 | Gill et al. |
| 5,893,843 A | 4/1999 | Rodrigues Claro |
| 5,895,764 A | 4/1999 | Sklar et al. |
| 5,895,922 A | 4/1999 | Ho |
| 5,899,848 A | 5/1999 | Haubrich |
| 5,909,278 A | 6/1999 | Deka et al. |
| 5,912,257 A | 6/1999 | Prasad et al. |
| 5,916,144 A | 6/1999 | Prather et al. |
| 5,916,449 A | 6/1999 | Ellwart et al. |
| 5,917,733 A | 6/1999 | Bangham |
| 5,919,360 A | 7/1999 | Contaxis, III et al. |
| 5,919,621 A | 7/1999 | Brown |
| 5,934,885 A | 8/1999 | Farrell et al. |
| 5,962,238 A | 10/1999 | Sizto et al. |
| 5,972,710 A | 10/1999 | Weigl et al. |
| 5,973,842 A | 10/1999 | Spangenberg |
| 5,976,389 A | 11/1999 | Zavos |
| 5,985,216 A * | 11/1999 | Rens et al. ............... 422/73 |
| 5,985,538 A | 11/1999 | Stachecju |
| 5,990,479 A | 11/1999 | Weiss et al. |
| 5,991,028 A | 11/1999 | Cabib et al. |
| 5,998,140 A | 12/1999 | Dervan et al. |
| 5,998,212 A | 12/1999 | Corio et al. |
| 6,002,471 A | 12/1999 | Quake |
| 6,003,678 A | 12/1999 | Van den Engh |
| 6,042,025 A * | 3/2000 | Crampton et al. ............. 239/337 |
| 6,042,249 A | 3/2000 | Spangenberg |
| 6,050,935 A | 4/2000 | Ranoux et al. |
| 6,071,689 A | 6/2000 | Seidel et al. |
| 6,079,836 A | 6/2000 | Burr et al. |
| 6,086,574 A | 7/2000 | Carroll et al. |
| 6,087,352 A | 7/2000 | Trout |
| 6,090,947 A | 7/2000 | Dervan et al. |
| 6,097,485 A | 8/2000 | Lievan |
| 6,111,398 A | 8/2000 | Graham |
| 6,117,068 A | 9/2000 | Gourley et al. |
| 6,119,465 A | 9/2000 | Mullens et al. |
| 6,120,735 A | 9/2000 | Zborowski et al. |
| 6,128,133 A | 10/2000 | Bergmann |
| 6,130,034 A | 10/2000 | Aitken |
| 6,132,961 A | 10/2000 | Gray et al. |
| 6,133,044 A | 10/2000 | Van den Engh |
| 6,133,995 A | 10/2000 | Kubota |
| 6,139,800 A | 10/2000 | Chandler |
| 6,140,121 A | 10/2000 | Ellington et al. |
| 6,143,535 A | 11/2000 | Palsson |
| 6,143,901 A | 11/2000 | Dervan |
| 6,146,837 A | 11/2000 | van de Winkel |
| 6,149,867 A | 11/2000 | Seidel et al. |
| 6,153,373 A | 11/2000 | Benjamin et al. |
| 6,154,276 A | 11/2000 | Mariella, Jr. |
| 6,175,409 B1 | 1/2001 | Nielsen et al. |
| 6,177,277 B1 | 1/2001 | Soini |
| 6,193,647 B1 | 2/2001 | Beebe et al. |
| 6,201,628 B1 | 3/2001 | Basiji et al. |
| 6,207,392 B1 | 3/2001 | Weiss et al. |
| 6,208,411 B1 | 3/2001 | Vaez-Iravani |
| 6,211,477 B1 | 4/2001 | Cardott et al. |
| 6,214,560 B1 | 4/2001 | Yguerabide et al. |
| 6,221,654 B1 | 4/2001 | Quake et al. |
| 6,221,671 B1 | 4/2001 | Groner et al. |
| 6,238,920 B1 | 5/2001 | Nagai et al. |
| 6,247,323 B1 | 6/2001 | Maeda |
| 6,248,590 B1 | 6/2001 | Malachowski |
| 6,256,096 B1 | 7/2001 | Johnson |
| 6,263,745 B1 * | 7/2001 | Buchanan et al. ........... 73/865.5 |
| 6,283,920 B1 | 9/2001 | Eberle et al. |
| 6,296,810 B1 | 10/2001 | Ulmer |
| 6,309,815 B1 | 10/2001 | Tash et al. |
| 6,316,234 B1 | 11/2001 | Bova |
| 6,317,511 B1 | 11/2001 | Horiuchi |
| 6,322,901 B1 | 11/2001 | Bawendi et al. |
| 6,323,632 B1 | 11/2001 | Husher et al. |
| 6,326,144 B1 | 12/2001 | Bawendi et al. |
| 6,328,071 B1 | 12/2001 | Austin |
| 6,329,158 B1 | 12/2001 | Hoffman et al. |
| 6,332,540 B1 | 12/2001 | Paul et al. |
| 6,357,307 B2 | 3/2002 | Buchanan et al. |
| 6,368,786 B1 | 4/2002 | Saint-Ramon et al. |
| 6,372,422 B1 | 4/2002 | Seidel et al. |
| 6,372,506 B1 | 4/2002 | Norton |
| 6,384,951 B1 | 5/2002 | Basiji et al. |
| 6,391,654 B1 | 5/2002 | Bateman |
| 6,395,305 B1 | 5/2002 | Buhr et al. |
| 6,398,719 B1 | 6/2002 | Kaneko et al. |
| 6,400,453 B1 | 6/2002 | Hansen |
| 6,411,835 B1 | 6/2002 | Modell et al. |
| 6,411,904 B1 | 6/2002 | Chandler |
| 6,416,190 B1 | 7/2002 | Grier et al. |
| 6,423,505 B1 | 7/2002 | Davis |
| 6,423,551 B1 | 7/2002 | Weiss et al. |
| 6,432,630 B1 | 8/2002 | Blankenstein |
| 6,432,638 B2 | 8/2002 | Dervan et al. |
| 6,452,372 B1 | 9/2002 | Husher et al. |
| 6,454,945 B1 | 9/2002 | Weigl et al. |
| 6,456,055 B2 | 9/2002 | Shinabe et al. |
| 6,463,314 B1 | 10/2002 | Haruna |
| 6,465,169 B2 | 10/2002 | Walderich et al. |
| 6,473,176 B2 | 10/2002 | Basiji et al. |
| 6,482,652 B2 | 11/2002 | Furlong et al. |
| 6,489,092 B1 | 12/2002 | Benjamin et al. |
| 6,495,333 B1 | 12/2002 | Willmann et al. |
| 6,495,366 B1 | 12/2002 | Briggs |
| 6,503,698 B1 | 1/2003 | Dobrinsky et al. |
| 6,511,853 B1 | 1/2003 | Kopf-Sill et al. |
| 6,514,722 B2 | 2/2003 | Paisson et al. |
| 6,524,860 B1 | 2/2003 | Seidel et al. |
| 6,528,802 B1 | 3/2003 | Koenig et al. |
| 6,534,308 B1 | 3/2003 | Palsson et al. |
| 6,537,829 B1 | 3/2003 | Zarling et al. |
| 6,540,895 B1 | 4/2003 | Spence et al. |
| 6,558,911 B1 | 5/2003 | Sutovsky |
| 6,563,583 B2 | 5/2003 | Ortyn et al. |
| 6,576,291 B2 | 6/2003 | Bawendi et al. |
| 6,577,387 B2 | 6/2003 | Ross, III et al. |
| 6,580,504 B1 | 6/2003 | Ortyn et al. |
| 6,587,203 B2 | 7/2003 | Colon |
| 6,589,792 B1 | 7/2003 | Malachowski |
| 6,590,911 B1 | 7/2003 | Spinelli et al. |
| 6,596,143 B1 | 7/2003 | Wang et al. |
| 6,596,499 B2 | 7/2003 | Jalink |
| 6,604,435 B2 | 8/2003 | Buchanan et al. |
| 6,613,525 B2 | 9/2003 | Nelson et al. |
| 6,617,107 B1 | 9/2003 | Dean |
| 6,618,143 B2 | 9/2003 | Roche et al. |
| 6,618,679 B2 | 9/2003 | Loehrlein et al. |
| 6,641,708 B1 | 11/2003 | Becker et al. |

(56) References Cited

U.S. PATENT DOCUMENTS

| | | | |
|---|---|---|---|
| 6,642,018 B1 | 11/2003 | Koller et al. | |
| 6,657,713 B2 | 12/2003 | Hansen | |
| 6,658,357 B2 | 12/2003 | Chandler | |
| 6,664,550 B2 | 12/2003 | Rader et al. | |
| 6,667,459 B1 * | 12/2003 | Woods et al. | 219/121.84 |
| 6,667,830 B1 | 12/2003 | Iketaki et al. | |
| 6,671,044 B2 | 12/2003 | Ortyn et al. | |
| 6,673,095 B2 | 1/2004 | Nordquist | |
| 6,674,525 B2 | 1/2004 | Bardell et al. | |
| 6,698,627 B2 | 3/2004 | Garcia et al. | |
| 6,700,130 B2 | 3/2004 | Fritz | |
| 6,703,621 B2 | 3/2004 | Wolleschensky | |
| 6,704,313 B1 | 3/2004 | Duret et al. | |
| 6,706,163 B2 | 3/2004 | Seul et al. | |
| 6,707,555 B1 | 3/2004 | Kusuzawa et al. | |
| 6,713,019 B2 | 3/2004 | Ozasa et al. | |
| 6,729,369 B2 | 5/2004 | Neas et al. | |
| 6,746,873 B1 | 6/2004 | Buchanan et al. | |
| 6,752,298 B2 | 6/2004 | Garcia et al. | |
| 6,753,161 B2 | 6/2004 | Koller et al. | |
| 6,761,286 B2 | 7/2004 | Py et al. | |
| 6,761,288 B2 | 7/2004 | Garcia | |
| 6,767,706 B2 | 7/2004 | Quake | |
| 6,780,377 B2 | 8/2004 | Hall et al. | |
| 6,782,768 B2 | 8/2004 | Buchanan et al. | |
| 6,789,706 B2 | 9/2004 | Abergel et al. | |
| 6,789,750 B1 | 9/2004 | Heldt | |
| 6,793,387 B1 | 9/2004 | Neas et al. | |
| 6,797,139 B2 | 9/2004 | Bahatt et al. | |
| 6,813,017 B1 | 11/2004 | Hoffman et al. | |
| 6,819,411 B1 | 11/2004 | Sharpe et al. | |
| 6,849,394 B2 | 2/2005 | Rozenboom et al. | |
| 6,849,423 B2 | 2/2005 | Mutz et al. | |
| 6,861,265 B1 | 3/2005 | Van den Engh | |
| 6,941,005 B2 | 9/2005 | Lary et al. | |
| 7,015,310 B2 | 3/2006 | Remington et al. | |
| 7,024,316 B1 | 4/2006 | Ellison et al. | |
| 7,094,527 B2 | 8/2006 | Seidel et al. | |
| 7,105,355 B2 | 9/2006 | Kurabayashi et al. | |
| 7,195,920 B2 | 3/2007 | Seidel et al. | |
| 7,208,265 B1 | 4/2007 | Schenk | |
| 7,221,453 B2 | 5/2007 | Sharpe et al. | |
| 7,723,116 B2 | 5/2010 | Evans et al. | |
| 7,758,811 B2 | 7/2010 | Durack et al. | |
| 7,943,384 B2 | 5/2011 | Durack et al. | |
| 8,004,661 B2 | 8/2011 | Luscher | |
| 8,198,092 B2 | 6/2012 | Durack et al. | |
| 8,198,093 B2 | 6/2012 | Durack et al. | |
| 8,206,987 B2 | 6/2012 | Durack et al. | |
| 8,206,988 B2 * | 6/2012 | Durack et al. | 436/63 |
| 8,241,914 B2 | 8/2012 | Durack et al. | |
| 2001/0006416 A1 | 7/2001 | Johnson | |
| 2002/0018211 A1 | 2/2002 | Megerle | |
| 2002/0033939 A1 | 3/2002 | Hansen | |
| 2002/0047697 A1 | 4/2002 | Husher et al. | |
| 2002/0058332 A1 | 5/2002 | Quake et al. | |
| 2002/0064809 A1 | 5/2002 | Mutz et al. | |
| 2002/0096123 A1 | 7/2002 | Whittier et al. | |
| 2002/0115055 A1 | 8/2002 | Matta | |
| 2002/0119558 A1 | 8/2002 | Seidel et al. | |
| 2002/0125230 A1 | 9/2002 | Haight et al. | |
| 2002/0131957 A1 | 9/2002 | Gavin et al. | |
| 2002/0171827 A1 | 11/2002 | Van den Engh | |
| 2002/0182590 A1 | 12/2002 | Strange et al. | |
| 2002/0186375 A1 | 12/2002 | Asbury et al. | |
| 2002/0186874 A1 | 12/2002 | Price et al. | |
| 2002/0198928 A1 | 12/2002 | Bukshpan et al. | |
| 2003/0048433 A1 | 3/2003 | Desjonqueres | |
| 2003/0059764 A1 | 3/2003 | Ravkin et al. | |
| 2003/0059945 A1 | 3/2003 | Dzekunov et al. | |
| 2003/0078703 A1 | 4/2003 | Potts et al. | |
| 2003/0096405 A1 | 5/2003 | Takayama et al. | |
| 2003/0098421 A1 | 5/2003 | Ho | |
| 2003/0113765 A1 | 6/2003 | Dempcy et al. | |
| 2003/0119050 A1 | 6/2003 | Shai | |
| 2003/0119206 A1 | 6/2003 | Shai | |
| 2003/0129091 A1 | 7/2003 | Seidel et al. | |
| 2003/0137661 A1 | 7/2003 | Ortyn et al. | |
| 2003/0157475 A1 | 8/2003 | Schenk | |
| 2003/0165812 A1 | 9/2003 | Takayama et al. | |
| 2003/0175917 A1 | 9/2003 | Cumming | |
| 2003/0175980 A1 | 9/2003 | Hayenga et al. | |
| 2003/0190681 A1 | 10/2003 | Shai | |
| 2003/0207461 A1 | 11/2003 | Bell et al. | |
| 2003/0209059 A1 | 11/2003 | Kawano | |
| 2004/0005582 A1 | 1/2004 | Shipwast | |
| 2004/0031071 A1 | 2/2004 | Morris et al. | |
| 2004/0034879 A1 | 2/2004 | Rothstein et al. | |
| 2004/0049801 A1 | 3/2004 | Seidel | |
| 2004/0053243 A1 | 3/2004 | Evans | |
| 2004/0055030 A1 | 3/2004 | Maxwell et al. | |
| 2004/0061070 A1 | 4/2004 | Hansen | |
| 2004/0061853 A1 | 4/2004 | Blasenheim | |
| 2004/0062685 A1 | 4/2004 | Norton et al. | |
| 2004/0107150 A1 | 6/2004 | Neas et al. | |
| 2004/0132001 A1 | 7/2004 | Seidel et al. | |
| 2005/0003472 A1 | 1/2005 | Anzar et al. | |
| 2005/0011582 A1 | 1/2005 | Haug | |
| 2005/0064383 A1 | 3/2005 | Bashkin et al. | |
| 2005/0112541 A1 | 5/2005 | Durack | |
| 2005/0214733 A1 | 9/2005 | Graham | |
| 2005/0244805 A1 | 11/2005 | Ludwig et al. | |
| 2005/0282245 A1 | 12/2005 | Ludwig et al. | |
| 2006/0118167 A1 | 6/2006 | Neas et al. | |
| 2006/0147894 A1 | 7/2006 | Sowter | |
| 2006/0263829 A1 | 11/2006 | Evans et al. | |
| 2006/0281176 A1 | 12/2006 | Seidel et al. | |
| 2007/0017086 A1 | 1/2007 | McFadyen | |
| 2007/0026378 A1 | 2/2007 | Schenk | |
| 2007/0026379 A1 | 2/2007 | Seidel et al. | |
| 2007/0042342 A1 | 2/2007 | Seidel et al. | |
| 2007/0092860 A1 | 4/2007 | Schenk | |
| 2007/0099171 A1 | 5/2007 | Schenk | |
| 2007/0099260 A1 | 5/2007 | Seidel et al. | |
| 2012/0081709 A1 | 4/2012 | Durack | |
| 2013/0224843 A1 | 8/2013 | Evans et al. | |

FOREIGN PATENT DOCUMENTS

| | | |
|---|---|---|
| CA | 1 250 808 | 3/1989 |
| CA | 2113957 A1 | 1/1994 |
| CA | 2752244 | 10/2004 |
| CN | 1130104 A | 4/1996 |
| CN | 1685226 A | 10/2005 |
| EP | 0025296 A2 | 3/1981 |
| EP | 0 046 345 A2 | 2/1982 |
| EP | 0 068 404 B1 | 1/1983 |
| EP | 0 026 770 B1 | 3/1983 |
| EP | 0 029 662 B1 | 2/1984 |
| EP | 0 121 261 A2 | 10/1984 |
| EP | 0 025 296 B1 | 5/1985 |
| EP | 0140616 | 5/1985 |
| EP | 0 158 147 A2 | 10/1985 |
| EP | 0 160 201 A2 | 11/1985 |
| EP | 0 229 814 B1 | 7/1987 |
| EP | 0 246 604 A2 | 11/1987 |
| EP | 0288029 B1 | 4/1988 |
| EP | 0276166 A2 | 7/1988 |
| EP | 0 289 677 A2 | 11/1988 |
| EP | 0 316 173 A1 | 5/1989 |
| EP | 0 317 809 A2 | 5/1989 |
| EP | A-0 366794 | 5/1990 |
| EP | 0 409 293 A2 | 1/1991 |
| EP | 0 461 618 | 12/1991 |
| EP | 0 463 562 A1 | 1/1992 |
| EP | 0468100 A1 | 1/1992 |
| EP | 0474 187 A2 | 3/1992 |
| EP | 0 316 172 B1 | 7/1992 |
| EP | 0 316 171 B1 | 9/1992 |
| EP | 0570102 A1 | 3/1993 |
| EP | 0538786 A | 4/1993 |
| EP | 0 279 000 B1 | 7/1993 |
| EP | 0 553 951 A1 | 8/1993 |
| EP | 0 288 029 B1 | 1/1994 |

(56) References Cited

FOREIGN PATENT DOCUMENTS

| | | |
|---|---|---|
| EP | 0 381 694 B1 | 6/1994 |
| EP | 0 361 504 81 | 7/1994 |
| EP | 606847 A2 | 7/1994 |
| EP | 0 289 200 B2 | 8/1994 |
| EP | 0 555 212 B1 | 10/1994 |
| EP | 0 361 503 B1 | 11/1994 |
| EP | 0 696 731 A2 | 2/1996 |
| EP | 0 705 978 A2 | 4/1996 |
| EP | 0 711 991 A1 | 5/1996 |
| EP | 0 471 758 B1 | 9/1996 |
| EP | 0 736 765 A1 | 10/1996 |
| EP | 0 545 284 B1 | 2/1997 |
| EP | 0 360 487 B1 | 7/1997 |
| EP | 0 412 431 B1 | 10/1997 |
| EP | 0 526 131 B1 | 1/1998 |
| EP | A-0 478155 | 1/1998 |
| EP | 0 822 404 A3 | 2/1998 |
| EP | 0 822 401 A2 | 4/1998 |
| EP | 0 556 748 B1 | 10/1998 |
| EP | 0 430 402 B1 | 1/1999 |
| EP | 0 529 666 B1 | 4/2000 |
| EP | 0 994 342 A3 | 4/2000 |
| EP | 0 752 133 B1 | 6/2000 |
| EP | 1 018 644 A2 | 7/2000 |
| EP | 1 118 268 A1 | 7/2001 |
| EP | 1 147 774 A1 | 10/2001 |
| EP | 0 534 033 B1 | 11/2001 |
| EP | 0 925 494 B1 | 12/2001 |
| EP | 0 748 316 B1 | 5/2002 |
| EP | 0 662 124 B1 | 6/2002 |
| EP | 1 245 944 A3 | 10/2002 |
| EP | 1 249 502 A2 | 10/2002 |
| EP | 1250897 A1 | 10/2002 |
| EP | 1 380 304 A2 | 1/2004 |
| EP | 1 403 633 A3 | 4/2004 |
| EP | 1 100 400 B1 | 5/2004 |
| EP | 1 257 168 B1 | 2/2005 |
| FR | 2813182 A1 | 3/2002 |
| GB | 1471019 | 4/1977 |
| GB | 2 121 976 A | 1/1984 |
| GB | 2 122 369 A | 1/1984 |
| GB | 2 125 181 A | 2/1984 |
| GB | 2 136 561 A | 9/1984 |
| GB | 2 137 352 A | 10/1984 |
| GB | 2145112 | 2/1985 |
| GB | 2 144 542 A | 3/1985 |
| GB | 2 153 521 A | 8/1985 |
| GB | 2 243 681 A | 11/1991 |
| GB | 2 360 360 A | 9/2001 |
| GB | 03109426 | 12/2005 |
| JP | 61139747 A | 6/1986 |
| JP | 61159135 A | 7/1986 |
| JP | 2024535 | 1/1990 |
| JP | 4126064 A | 4/1992 |
| JP | 4126065 A | 4/1992 |
| JP | 4126066 A | 4/1992 |
| JP | 4126079 A | 4/1992 |
| JP | 4126080 A | 4/1992 |
| JP | 4126081 A | 4/1992 |
| JP | 2010216992 | 9/2010 |
| SU | 1267231 | 10/1986 |
| WO | WO 84/01265 A1 | 4/1984 |
| WO | WO 85/04014 A1 | 9/1985 |
| WO | WO 88/07198 | 9/1988 |
| WO | WO 89/04470 A1 | 5/1989 |
| WO | WO 89/04471 A1 | 5/1989 |
| WO | WO 90/13315 A1 | 11/1990 |
| WO | WO 9105236 | 4/1991 |
| WO | 9208120 | 5/1992 |
| WO | WO 92/08120 A1 | 5/1992 |
| WO | WO 92/17288 A1 | 10/1992 |
| WO | WO 93/10803 | 6/1993 |
| WO | WO 9317322 A1 | 9/1993 |
| WO | WO 94/22001 A1 | 9/1994 |
| WO | WO 96/04542 A1 | 2/1996 |
| WO | WO 96/12171 A2 | 4/1996 |
| WO | WO 96/12172 | 4/1996 |
| WO | WO 96/12173 A1 | 4/1996 |
| WO | WO 96/31764 | 10/1996 |
| WO | WO 96/33806 A1 | 10/1996 |
| WO | WO 97/29354 A1 | 8/1997 |
| WO | WO 97/30338 A1 | 8/1997 |
| WO | WO 97/35189 A1 | 9/1997 |
| WO | WO 97/43620 A1 | 11/1997 |
| WO | WO 89/04472 A1 | 5/1998 |
| WO | WO 98/34094 A1 | 8/1998 |
| WO | WO 98/57152 A1 | 12/1998 |
| WO | WO 99/05504 A2 | 2/1999 |
| WO | WO 99/33956 A1 | 7/1999 |
| WO | WO 99/38883 A1 | 8/1999 |
| WO | WO 99/42810 A1 | 8/1999 |
| WO | WO 99/44035 | 9/1999 |
| WO | WO 99/44037 A1 | 9/1999 |
| WO | WO 99/47906 A1 | 9/1999 |
| WO | 9958955 | 11/1999 |
| WO | WO 99/60397 A1 | 11/1999 |
| WO | WO 99/61888 A2 | 12/1999 |
| WO | WO 00/06193 A1 | 2/2000 |
| WO | WO 00/12204 | 3/2000 |
| WO | WO 00/36396 | 6/2000 |
| WO | WO 00/49387 | 8/2000 |
| WO | WO 00/54026 | 9/2000 |
| WO | WO 00/56444 | 9/2000 |
| WO | WO 00/70080 | 11/2000 |
| WO | WO 01/02836 A1 | 1/2001 |
| WO | 0129538 A1 | 4/2001 |
| WO | WO 01/28700 A1 | 4/2001 |
| WO | WO 01029538 | 4/2001 |
| WO | WO 01/37655 A1 | 5/2001 |
| WO | WO 01/40765 A2 | 6/2001 |
| WO | WO 01/40765 A3 | 6/2001 |
| WO | WO 01/42757 A2 | 6/2001 |
| WO | WO 01/51612 A1 | 7/2001 |
| WO | WO 01/61313 A2 | 8/2001 |
| WO | WO 01/68110 | 9/2001 |
| WO | WO 01/68226 A2 | 9/2001 |
| WO | WO 01/71348 A1 | 9/2001 |
| WO | 0175176 | 10/2001 |
| WO | WO 01/85913 A2 | 11/2001 |
| WO | WO 01/85913 A3 | 11/2001 |
| WO | WO 01/90295 A1 | 11/2001 |
| WO | WO 01/95815 A1 | 12/2001 |
| WO | WO 02/01189 A1 | 1/2002 |
| WO | WO 02/04666 A2 | 1/2002 |
| WO | WO 02/19594 | 3/2002 |
| WO | WO 02/19943 A1 | 3/2002 |
| WO | WO 02/20850 A2 | 3/2002 |
| WO | WO 02/21102 A2 | 3/2002 |
| WO | WO 02/23163 A1 | 3/2002 |
| WO | WO 02/25269 A2 | 3/2002 |
| WO | WO 02/26114 A2 | 4/2002 |
| WO | WO 02/28311 A1 | 4/2002 |
| WO | WO 02/29106 A2 | 4/2002 |
| WO | WO 02/41906 A2 | 5/2002 |
| WO | WO 0241906 A2 | 5/2002 |
| WO | WO 02/43486 A1 | 6/2002 |
| WO | WO 02/43574 A3 | 6/2002 |
| WO | WO 02/44319 A2 | 6/2002 |
| WO | WO 02/052244 A2 | 7/2002 |
| WO | WO 02/054044 A2 | 7/2002 |
| WO | WO 02/057775 A1 | 7/2002 |
| WO | WO 02/060880 A2 | 8/2002 |
| WO | WO 02/077637 A1 | 10/2002 |
| WO | WO 02/092161 A1 | 11/2002 |
| WO | WO 02/092247 A1 | 11/2002 |
| WO | WO 03/008102 A1 | 1/2003 |
| WO | WO 03/008937 A1 | 1/2003 |
| WO | WO 03/012403 A1 | 2/2003 |
| WO | WO 03/016875 A2 | 2/2003 |
| WO | WO 03020877 A2 | 3/2003 |
| WO | WO 03/056330 A2 | 7/2003 |
| WO | WO 03/056335 A2 | 7/2003 |
| WO | WO 03/072765 A1 | 9/2003 |
| WO | WO 03/078065 A1 | 9/2003 |

(56) References Cited

FOREIGN PATENT DOCUMENTS

| | | |
|---|---|---|
| WO | WO 03/078972 A1 | 9/2003 |
| WO | 2004001401 | 12/2003 |
| WO | WO 2004/006916 A1 | 1/2004 |
| WO | WO 2004/009237 A2 | 1/2004 |
| WO | WO 2004/009237 A3 | 1/2004 |
| WO | WO 2004/012837 A2 | 2/2004 |
| WO | WO 2004/012837 A3 | 2/2004 |
| WO | WO 2004/017041 A2 | 2/2004 |
| WO | WO 2004/017041 A3 | 2/2004 |
| WO | WO 2004/024227 A2 | 3/2004 |
| WO | WO 2004/024227 A3 | 3/2004 |
| WO | WO 2004/046712 A2 | 6/2004 |
| WO | WO 2004/059282 A2 | 7/2004 |
| WO | WO 2004/003697 A2 | 10/2004 |
| WO | WO 2004/087177 A1 | 10/2004 |
| WO | WO 2004/088283 A2 | 10/2004 |
| WO | WO 2004/104178 A2 | 12/2004 |
| WO | WO 2004/104178 A3 | 12/2004 |
| WO | WO 2005/094852 A2 | 10/2005 |
| WO | WO 2005/095590 A2 | 10/2005 |
| WO | WO 2005/095960 A1 | 10/2005 |
| WO | WO 2006/015056 A2 | 2/2006 |
| WO | WO 2006012597 A2 | 2/2006 |
| WO | WO 2006060770 A2 | 8/2006 |
| WO | WO 2007016090 A2 | 2/2007 |
| WO | WO 01/75161 A2 | 10/2011 |

OTHER PUBLICATIONS

Chapman, Graeme V., "Instrumentation for Flow Cytometry"; Article, 2000, pp. 3-12, vol. 243, Journal of Immunological Methods (10 pages).
Fisher, Derek, et al.; "Cell Separation: A Practical Approach"; Article, 1998, pp. 1-5; Oxford University Press (5 pages).
Grant, Kenneth J., et al.; "Pulsed Lasers in Particle Detection and Sizing"; Article, Feb. 1, 1993, pp. 416-417; vol. 32, No. 4; Applied Optics (2 pages).
Seidel, George E., et al.; "Current Status of Sexing Mammalian Spermatozoa"; Article, 2002, pp. 733-743, vol. 124; Society for Reproduction and Fertility (11 pages).
Daugherty, Patrick S., et al.; "Flow Cytometric Screening of Cell-Based Libraries"; Article, 2000, pp. 211-227, vol. 243; Journal of Immunological Methods (17 pages).
Keij, Jan F., et al.; "Coincidence in High-Speed Flow Cytometry: Models and Measurements"; Article, 1991, pp. 398-404; vol. 12; Cytometry (7 pages).
Keij, Jan F., et al.; "High-Speed Photodamage Cell Sorting: An Evaluation of the Zapper Prototype"; Book, Chapter 22, 1994, pp. 371-386; vol. 42, Methods in Cell Biology (16 pages).
Kubota, Fumio, et al.; "Flow Cytometer and Imaging Device Used in Combination"; Article, 1995, pp. 129-132, vol. 21, Cytometry (4 pages).
Leary, James F., et al.; "New Methods for Detection, Analysis and Isolation of Rare Cell Populations"; Article, pp. 240-253, vol. 2678; SPIE Digital Library (14 pages).
Maltsev, Valeri P.; "Scanning Flow Cytometry for Individual Particle Analysis"; Article, Jan. 2000, pp. 243-255, vol. 71, No. 1, Review of Scientific Instruments, American Institute of Physics (13 pages).
U.S. Appl. No. 13/782,417 (no attachment provided).
Shapiro, Howard M., et al.; "Multistation Multiparameter Flow Cytometry: Some Influences of Instrumental Factors on System Performance 1"; Article, 1983, pp. 11-19, vol. 4; Cytometry (9 pages).
Verwer, Ben; "BD FACSDiva Option"; White Paper; 2002, pp. 1-22; BD Biosciences, Pharmingen; Becton, Dickson and Company (22 pages).
US Office Action dated Jul. 9, 2013 issued in corresponding U.S. Appl. No. 13/782,417 (11 pages).
Argentine Examination Report dated Mar. 6, 2013 issued in corresponding AR Application No. P 10 01 00108 (1 page).
Australian Patent Examination Report No. 1 dated Jan. 22, 2013 issued in corresponding AU Application No. 2012227165 (3 pages).
Canadian Examination Report dated Oct. 18, 2012 issued in corresponding CA Application No. 2,518,882 (5 pages).
Canadian Examination Report dated Mar. 28, 2013 issued in corresponding CA Application No. 2,752,312 (4 pages).
Canadian Examination Report dated Apr. 16, 2013 issued in corresponding CA Application No. 2,752,244 (5 pages).
Canadian Examination Report dated May 17, 2013 issued in corresponding CA Application No. 2,752,218 (4 pages).
Canadian Examination Report dated May 23, 2013 issued in corresponding CA Application No. 2,752,247 (5 pages).
Chinese Second Office Action dated Dec. 17, 2012 issued in corresponding CN Application No. 200910146867.7 (9 pages).
European Search Report dated Feb. 25, 2013 issued in corresponding EP Application No. 10184282.1 (4 pages).
European Search Report dated Feb. 25, 2013 issued in corresponding EP Application No. 10183913.2 (8 pages).
European Search Report dated Feb. 25, 2013 issued in corresponding EP Application No. 10184097.3 (7 pages).
European Search Report dated Feb. 25, 2013 issued in corresponding EP Application No. 10184180.7 (6 pages).
European Search Report dated Feb. 25, 2013 issued in corresponding EP Application No. 10184240.9 (5 pages).
European Search Report dated Feb. 25, 2013 issued in corresponding EP Application No. 10184826.5 (6 pages).
European Search Report dated Feb. 25, 2013 issued in corresponding EP Application No. 10184852.1 (5 pages).
European Search Report dated Feb. 25, 2013 issued in corresponding EP Application No. 10184098.1 (6 pages).
European Search Report dated Feb. 25, 2013 issued in corresponding EP Application No. 10184321.7 (5 pages).
European Search Report dated Feb. 4, 2013 issued in corresponding EP Application No. 10184018.9 (5 pages).
European Search Report dated Feb. 4, 2013 issued in corresponding EP Application No. 10183943.9 (5 pages).
European Search Report dated Feb. 25, 2013 issued in corresponding EP Application No. 10185957.7 (7 pages).
European Search Report dated Feb. 25, 2013 issued in corresponding EP Application No. 10184303.5 (5 pages).
European Search Report dated Feb. 25, 2013 issued in corresponding EP Application No. 10184840.6 (5 pages).
European Search Report dated Feb. 25, 2013 issued in corresponding EP Application No. 10184283.9 (6 pages).
European Search Report dated Feb. 25, 2013 issued in corresponding EP Application No. 10184868.7 (7 pages).
European Search Report dated Feb. 25, 2013 issued in corresponding EP Application No. 10184426.4 (5 pages).
US Office Action dated Jul. 1, 2013 issued in corresponding U.S. Appl. No. 13/761,989 (14 pages).
Japanese Office Action dated Oct. 23, 2012 issued in corresponding JP Application No. 2012-008334 (9 pages).
US Office Action dated Jun. 27, 2013 issued in corresponding U.S. Appl. No. 13/762,003 (13 pages).
US Office Action dated May 28, 2013 issued in corresponding U.S. Appl. No. 13/776,294 (10 pages).
US Office Action dated Apr. 17, 2013 issued in corresponding U.S. Appl. No. 13/762,110 (12 pages).
US Office Action dated May 14, 2013 issued in corresponding U.S. Appl. No. 13/776,252 (8 pages).
US Notice of Allowance dated Jun. 11, 2013 issued in corresponding U.S. Appl. No. 13/422,705 (9 pages).
U.S. Appl. No. 13/776,294 (no attachment provided).
U.S. Appl. No. 13/776,252 (no attachment provided).
U.S. Appl. No. 13/782,469 (no attachment provided).
U.S. Appl. No. 13/762,110 (no attachment provided).
U.S. Appl. No. 13/422,705 (no attachment provided.
U.S. Appl. No. 13/762,014 (no attachment provided).
AU Notice of Acceptance dated Sep. 6, 2012 issued in corresponding AU Application No. 2012200712 (4 pages).
AU Notice of Acceptance dated Sep. 6, 2012 issued in corresponding AU Application No. 2012200707 (4 pages).
AU Notice of Acceptance dated Sep. 6, 2012 issued in corresponding AU Application No. 2012200709 (4 pages).

(56) References Cited

OTHER PUBLICATIONS

AU Notice of Acceptance dated Sep. 6, 2012 issued in corresponding AU Application No. 2012200706 (4 pages).
AU Notice of Acceptance dated Sep. 6, 2012 issued in corresponding AU Application No. 2012200711 (4 pages).
AU Notice of Acceptance dated Sep. 6, 2012 issued in corresponding AU Application No. 2012200713 (4 pages).
List of art cited in related U.S. Appl. No. 13/106,671 (31 pages).
US Notice of Allowance dated Jul. 25, 2013 issued in corresponding U.S. Appl. No. 13/762,110 (6 pages).
US Office Action dated Jul. 19, 2013 issued in corresponding U.S. Appl. No. 13/762,014.
U.S. Appl. No. 13/776,379 (no attachment provided).
U.S. Appl. No. 13/762,003 (no attachment provided).
Durack, Gary, et al.; "Emerging Tools for Single-Cell Analysis-Advances in Optical Measurement Technologies"; Book, 2000, Wiley-Liss Publications (364 pages).
Japanese Decision on Final Rejection dated Oct. 2, 2012 issued in corresponding JP Application No. 2010-108540 (11 pages).
Johnson, L.A., et al.; "Sex Preselection: High-Speed Flow Cytometric Sorting of X and Y Sperm for Maximum Efficiency"; Article, 1999, pp. 1323-1341, vol. 52, Theriogenology (19 pages).
Australian Notice of Acceptance dated Aug. 12, 2013 issued in corresponding AU Application No. 2012227165 (3 pages).
Canadian Office Action dated Jul. 30, 2013 issued in corresponding CA Application No. 2,518,882 (6 pages).
Chinese Third Office Action dated Aug. 20, 2013 issued in corresponding Chinese Application No. 200910146867.7 (with English Translation 13 pages).
European Examination Report dated Sep. 30, 2013 issued in corresponding EP Application No. 10184097.3 (4 pages).
European Examination Report dated Sep. 30, 2013 issued in corresponding EP Application No. 10184180.7 (4 pages).
European Examination Report dated Sep. 30, 2013 issued in corresponding EP Application No. 10184240.9 (4 pages).
European Examination Report dated Oct. 1, 2013 issued in corresponding EP Application No. 10184826.5 (6 pages).
European Examination Report dated Sep. 30, 2013 issued in corresponding EP Application No. 10184098.1 (4 pages).
European Examination Report dated Oct. 2, 2013 issued in corresponding EP Application No. 10184321.7 (4 pages).
European Examination Report dated Oct. 1, 2013 issued in corresponding EP Application No. 10185957.7 (4 pages).
European Examination Report dated Oct. 1, 2013 issued in corresponding EP Application No. 10184840.6 (4 pages).
European Examination Report dated Sep. 30, 2013 issued in corresponding EP Application No. 10184283.9 (3 pages).
European Examination Report dated Oct. 1, 2013 issued in corresponding EP Application No. 10184426.4 (5 pages).
European Examination Report dated Oct. 1, 2013 issued in corresponding EP Application No. 10184282.1 (3 pages).
European Examination Report dated Oct. 7, 2013 issued in corresponding EP Application No. 09014407.2 (5 pages).
European Examination Report dated Sep. 6, 2013 issued in corresponding EP Application No. 10184852.1 (5 pages).
European Examination Report dated Sep. 6, 2013 issued in corresponding EP Application No. 10183913.2 (4 pages).
European Examination Report dated Sep. 5, 2013 issued in corresponding EP Application No. 10183943.9 (4 pages).
European Examination Report dated Sep. 6, 2013 issued in corresponding EP Application No. 10184018.9 (3 pages).
US Notice of Allowance dated Sep. 3, 2013 issued in corresponding U.S. Appl. No. 13/761,989 (10 pages).
US Notice of Allowance dated Aug. 29, 2013 issued in corresponding U.S. Appl. No. 13/762,110 (6 pages).
US Notice of Allowance dated Sep. 20, 2013 issued in corresponding U.S. Appl. No. 13/776,294 (9 pages).
US Office Action dated Sep. 9, 2013 issued in corresponding U.S. Appl. No. 13/782,469 (13 pages).
US Office Action dated Aug. 19, 2013 issued in corresponding U.S. Appl. No. 13/776,379 (14 pages).
US Office Action dated Aug. 23, 2013 issued in corresponding U.S. Appl. No. 13/776,252 (8 pages).
US Office Action dated Sep. 17, 2013 issued in corresponding U.S. Appl. No. 13/782,417 (8 pages).
US Office Action dated Nov. 8, 2013 issued in corresponding U.S. Appl. No. 13/762,014 (14 pages).
EP Office Action dated Nov. 5, 2013 issued in corresponding EP Application No. 10184303.5 (5 pages).
Benaron et al. Cytometry, vol. 2, No. 5, 1982, pp. 344-349.
Rens, et al., Cytometry, vol. 25, 1996, pp. 191-199.
US Office Action dated Oct. 18, 2013 issued in corresponding U.S. Appl. No. 13/762,003 (14 pages).
EP second Examination Report dated Nov. 5, 2013, issued in related EP Patent Application No. 10184303.5 (5 pages).
Parallel European Regional Application No. 04 749 513.0; Office action dated Jun. 4, 2008.
Parallel European Regional Application No. 04 749 513.0; Office action dated Aug. 7, 2007.
Parallel European Regional Application No. 04 749 513.0; Office action dated Sep. 29, 2006.
Parallel U.S. Appl. No. 11/442,735, Office action dated Apr. 24, 2008.
Parallel U.S. Appl. No. 11/442,735, Office action dated Aug. 16, 2007.
Parallel U.S. Appl. No. 10/556,981, Office action dated Sep. 19, 2008.
International Application No. PCT/US/2004/009646; International Search Report dated Jun. 10, 2005.
International Application No. PCT/US/2004/009646; International Written Opinion dated Jun. 10, 2005.
International Application No. PCT/US/2004/009646; International Preliminary Report on Patentability dated Oct. 1, 2005.
Studt, T., MEMS-based Cell Sorter Speeds Clinical Studies, R&D Magazine, Dec. 2003: pp. 36-37 as currently presented on and printed from http://www.rdmag.com, 2 pgs.
Shapiro, Howard M., Practical Flow Cytometry—3rd Edition, Wiley-Liss, Inc., 1995, Cover page, Publisher page, pp. 65-66.
Lee, Gwo-Bin et al., Multi-Cell-Line Micro Flow Cytometers with Buried SU-8/SOG Optical Waveguides, IEEE, 2002, pp. 503-506.
Shapiro, Howard M. et al., Multistation Multiparameter Flow Cytometry: Some Influences of Instrumental Factors on System Performance, 1983, pp. 11-19, 4, Allan R. Liss, Inc.
Abdel-Ghaffar, A. E., et al., "Rabbit Semen Metabolism in Rabbit Production in Hot Climates" Baselga and Marai (eds); International Conference of Rabbit Production in Hot Climates 1994, p. 305-312.
Akhtar, S., et al., "Prevalence of Five Stereotypes of Bluetongue Virus in a Rambouillet Sheep Flock in Pakistan", Veterinary Record 136, p. 495. (1995).
Aldrich, S. L., et al., "Parturition and Periparturient Reproductive and Metabolic Hormone Concentration in Prenatally Androgenized Beef Heifers", J. Anim. Sci. 73:3712. (1995).
Amann, R. P. et al, "Issues Affecting Commercialization of Sexed Sperm" Therio. 52:1441. (1999).
Amann, R. P., et al. "Prospects for Sexing Mammalian Sperm," Animal Reproduction Laboratory College of Veterinary Medicine and Biomedical Sciences, Colorado State University. (1982).
Amann, R.P. "Fertilizing Potential Vitro of Semen from Young Beef Bulls Containing a High or Low Percentage of Sperm with a Proximal Droplet" Theriogenology 54: 1499-1515, 2000.
Amann, Rupert P. "Cryopreservation of Sperm" 1999, Encyclopedia of Reproduction 1:733-783.
American Meat and Science Association in Cooperation with National Livestock and Meat Board, "Research Guidelines for Cookery and Sensory Evaluation and Instrumental Tenderness Measurements for Fresh Meat". (1995).
Amoah, E. A. and Gelaye, S., "Biotechnological Advances in Goat Reproduction", J. Anim. Sci. 75(2): 578-585. (1996).
Anderson, V. K., et al., Intrauterine und tiefzervikale Insemination mit Gefriersperma bein Schat (Intrauterine and Deep Cervical Insemination With Frozen Semen in Sheep). Zuchthygiene 8:113-118. (1973).

(56) References Cited

OTHER PUBLICATIONS

Arriola, J. and Foote, R.H.: "Glycerolation and Thawing Effects on Bull Spermatozoa frozen in Detergent-Treated Egg Yok and Whole Egg Extenders," J Dairy Sci, 70:1664-1670 (1987).
Asbury, Charles A. "Fluorescence Spectra of DNA Dyes Measured in a Flow Cytometer," University of Washington Feb. 19, 1996.
Bagley, C. P. "Nutritional Management of Replacement Beef Heifers: a Review" J. Anim. Science 71:3155-3163. (1993).
Bailey, C. M. et al., "Nulliparous Versus Primiparous Crossbred Females for Beer", J. Anim. Sci. 69:1403. (1991).
Baker, R.D., et al., "Effect of Volume of Semen, Number of Sperm and Drugs on Transport of Sperm in Artificially Inseminated Gilts", J. Anim. Sci. 27:88-93. (1968).
Bakker Schut, Tom C. "A New Principle of Cell Sorting by Using Selective Electroportation in a Modified Flow Cytometry," University of Twente, Mar. 10, 1990.
Barnes, F. L. and Eyestone, W. H., "Early Cleavage and the Maternal Zygotic Transition in Bovine Embryos", Therio. vol. 33, No. 1, pp. 141-149. (1990).
Batellier, F. et al., "Advances in Cooled Semen Technology" Animal Reproduction Science 68 p. 181-190 (2001).
Becker, S.E. and Johnson, A. L. "Effects of Gonadotropin-Releasing Hormone Infused in a Pulsatile or Continuous Fashion on Serum Gonadotropin Concentrations and Ovulation in the Mare", J. Anim. Sci. 70:1208-1215. (1992).
Bedford, S .J. and Hinrichs, K., "The Effect of Insemination Volume on Pregnancy Rates of Pony Mares", Therio. 42:571-578. (1994).
Behrman, S. J., et al., "Freeze Preservation of Human Sperm" American Journal of Obstetrics and Gynecology vol. 103 (5) p. 654-664 Mar. 1, 1969.
Bellows, R. A., et al., "Cause and Effect Relationships Associated With Calving Difficulty and Calf Birth Weight", J. Anim. Sci. 33:407. (1971).
Berardinelli, J. G., et al., "Source of Progesterolle Prior to Puberty in Beef Heifers". J. Anim. Sci. 49:1276. (1979).
Berger, G. S. "Intratubal Insemination", Fertil. Steril. 48:328-330, (1987).
Bergfeld, E. G., et al., "Ovarian Follicular Development in Prepubertal Heifers is Influenced by Level of Dietary Energy Intake", Bio. of Repro. 51:1051. (1994).
Berry, B. W., et al., "Beef Carcass Maturity Indicators and Palatability Attributes", J. Anim. Sci. 38:507 (1974).
Beyhan, Z., et al., "Sexual Dimorphism in IVF Bovine Embryos Produced by Sperm Sorted by High Speed Flow Cytometry", abstr. Therio. 49(1): 359 (1998).
Beyhan, Z., et al., 1999 Sexual Dimorphism in IVM-IVF Bovine Embryos Produced from X and Y Chromosome-Bearing Spermatozoa Sorted by High Speed Flow Cytometry. Theriogenology. 52: 35-48.
Bigos, Martin "Nine Color Eleven Parameter Immunophenotyping Using Three Laser Flow Cytometry," Stanford University Dec. 22, 1998.
Bioxcell, Bovine Sperm Preservation, Advertisement Jun. 28, 2005.
Bond, J., et al., "Growth and Carcass Traits of Open Beef Heifers Versus Beef Heifers That Have Calved", Nutrition Reports International 34:621. 1986.
Boucque, C. V., et al., "Beef-Production With Maiden and Once-Calved Heifers", Livestock Prod. Sci. 7:121. 1980.
Bourdon, R. M. and J. S. Brinks. "Simulated Efficiency of Range Beef—Production III. Culling Strategies and Nontraditional Management-Systems", J. Anim. Sci. 65:963. 1987.
Bracher, V. and Allen, W.R., "Videoendoscopic Examination of the Mare's Uterus: I. Findings in Normal Fertile Mares", Equine Veterinary Journal, vol. 24, p. 274-278. 1992.
Braselton, W. E. and McShan, W. H., "Purification and Properties of Follicle Stimulating and Luteinizing Hormones From Horse Pituitary Glands" Arch. Biochem. Biophys. 139:45-48. 1970.
Braun, J. et al, "Effect of Different Protein Supplements on Motility and Plasma Membrane Integrity of Frozen-Thawed Stallion Spermatozoa", Cryobiology (1995) 32:487-492.

Brethour, J. R. and Jaeger, J. R., "The Single Calf Heifer System", Kansas Agric. Sta. Rep of Progress 570. 1989.
Brinsko, S.P. et al., "Artificial Insemination and Preservation of Semen." Veterinary Clinics of North America:Equine Practice Vol. 8 No. 1 Apr. 1992 pp. 205-218.
Bristol, F. "Breeding Behavior of a Stallion at Pasture With 20 Mares in Synchronized Oestrus" J. Reprod. Fertil. Suppl. 32:71. 1982.
Brookes, A. J. and O'Byrne, M., "Use of Cow-Heifers in Beef Production" J. of the Royal Agricultural Society of England 126:30. 1965.
Buchanan, B. R., et al, "Insemination of Mares with Low Numbers of Either Unsexed or Sexed Spermatozoa", Therio. vol. 53, p. 1333-1344. 2000.
Buchanan, B.R. " Pregnancy Rates in Mares Following a Single Insemination with a Low Number of Spermatozoa into the Tip of the Uterine Horn" Theriogenology p. 395 1999.
Bums, P. D. and Spitzer, J.C., "Influence of Biostimulation on Reproduction in Postpartum Beef-Cows", J. Anim. Sci. 70:358. 1992.
Burwash, L. D., et al., "Relationship of Duration of Estrus to Pregnancy Rate in Normally Cycling, Non Lactating Mares" J.A.V.M.A. 165:714-716. 1974.
Byerley, D. J., et al., "Pregnancy Rates of Beef Heifers Bred Either on Puberal or Third Estrus". J Anim. Sci. 65:645. 1987.
Caslick, E. A., "The Vulva and the Vulvo-Vaginal Orifice and its Relation to Genital Health of the Thoroughbred Mare", Cornell Veterinarian, vol. 27, p. 178-187. 1937.
Catt, et al., "Assessment of Ram and Boar Spermatozoa During Cell-Sorting by Flow Cytometry", Reproduction Dom Animal, vol. 32, pp. 251-258. 1997.
Catt, S. L., et al., "Birth of a Male Lamb Derived from an In Vitro Matured Oocyte Fertilized by Intracytoplasmic Injection of a Single Presumptive Male Sperm", Veterinary Record 139, p. 494-495. 1996.
Cave-Penney, Tony, "Sexed Semen Offers Faster Genetic Gain", Farming News, Livestock Supplement, Feb. 1997, p. 28.
Celestron: Telescope Basics: www.celestron.com/tb-2ref/htm; 4 pages, Oct. 20, 2003.
Chandler, J. E., "Videomicroscopic Comparison of Bull Sperm and Leukocyte Chromosome Areas as Related to Gender", J Dairy Sci 73, p. 2129-2135. 1990.
Chandler, J. E., et al, "Bovine Spermatozoal Head Size Variation and Evaluation of a Separation Technique Based on this Size", Therio. 52, p. 1021-1034. 1999.
Chen, S.H. "Effects of Oocyte Activation and Treatment of Spermatozoa on Embryonic Development Following Intracytoplasmic Sperm Injection in Cattle" Theriogenology 48: 1265-1273, 1997.
Chen, Y. et al., Survival of Bull Spermatozoa Seeded and Frozen at Different Rates in Egg Yolk-Tris and Whole Milk Extenders, 1993 J Dairy Sci 76:1028-1034.
Chin, W. W. and Boime, I. 1990. In Glycoprotein Hormones. Serona Symp. Norwell, MA. pp. 19-20.
Choi, Y.H. "Developmental Cappacity of Equine Oocytes Matured and Cultured in Equine Trophoblast-Conditioned Media" Theriogenoogy 56: 320-339, 2001.
Chung, Y. G., et al. "Artificial insemination of Superovulated Heifers With 600,000 Sexed Sperm". J Anim. Sci. Suppl. 1. 836:215. 1998 abstr.
Clement, F., et al., "Which Insemination Fertilizes When Several Successive Inseminations are Performed Before Ovulation" 7th Int. Symp. Eq. Repro. 151. 1998 abstr.
Cran, D. G., et al, "Production of Lambs by Low Dose Intrauterine Insemination With Flow Cytometrically Sorted and Unsorted Semen", Therio. p. 267. 1997.
Cran, D. G., et al., "Sex Preselected in Cattle: A Field Trial", Veterinary Record 136, 1995, p. 495-496.
Cran, D. G., et al., "Production of Bovine Calves Following Separation of X- and Y-Chromosome Bearing Sperm and In Vitro Fertilization". Vet. Rec. 132:40-41. 1993.
Cran, D. G., et al., "The Predetermination of Embryonic Sex Using Flow Cytometrically Separated X and Y Spermatozoa" Human Reproduction Update 1996, vol. 2 (4) p. 355-63.
Crowley, J. P. "The facts of Once-Bred Heifer Production" School of Agric., Univ. of Aberdeen, Scotland. 1973.

(56) References Cited

OTHER PUBLICATIONS

Cui, K. et al, "X Larger than Y", Nature 366, p. 177-118, 1993.
Cui, K., "Size Differences Between Human X and Y Spermatozoa and Prefertilization Diagnosis", Molecular Human Reproduction, vol. 3, No. 1, pp. 61-67. 1997.
Curran, S. "Fetal Gender Determination" in *Equine Diagnostic Ultrasonography* 1st ed. Rantanen, N.W. and McKinnon A.O. (eds.) Williams and Williams, 1998, p. 165-69.
Da Silva, Coutinho M.A.."Effect of time of oocyte collection and site of insemination on oocyte transfer in mares." Animal Reproduction and Biotechnology Laboratiory, Colorado State Uniuversity, Fort Collins Journal of Animal Science 2002. 80:1275-1279.
DakoCytomation, "MoFlo® Sorters"http://www.dakocytomation.us/prod_productrelatedinformation?url=gprod_moflo_index.htm one page, printed Jun. 26, 2003.
Database up 1 BR9704313 (Alves, De Resende et al) Jun. 4, 1999.
Day, B. N., et al. Birth of Piglets Preselected for Gender Following In Vitro Fertilization of In Vitro Matured Pig Oocytes by X and Y Bearing Spermatozoa Sorted by High Speed Flow Cytometry. Therio. 49(1): 360. 1998 abstr.
De Leeuw, F.E. et al:"Effects of carious cryoprotective agents and membrane-stabilizing compounds on bull sperm emebrane integrity after cooling and freezing" Cryobiology US, Academic Press Inc 1993 pp. 32-44.
Dean, P.N., et al. "Hydrodynamic Orientation of Spermatozoa Heads for Flow Cytometry". Biophys. J. 23:7-13. 1978.
Demick, D.S., et al. "Effect of Cooling, Storage, Glycerization and Spermatozoal Numbers on Equine Fertility" J. Anim. Sci. 43:633-637. 1976.
DenDaas, J. H. G., et al. "The relationship between the number of spermatozoa inseminated and the reproductive efficiency of dairy bulls" J Dairy Sci. 81: 1714-1723. 1998.
Denham, A. "In-vitro studies on Sandhill Range Forage as Related to Cattle Preference", M.S. Thesis. Colorado State University. 1965.
Denk, Winfried. "Two-Photon Molecular Excitation in Laser-Scanning Microscopy," Handbook of Biological Confocal Microscopy. 1995.
Deutscher, G. H. "Extending Interval From Seventeen to Nineteen Days in the Melengestrol Acetate-Prostaglandin Estrous Synchronization Program for Heifers". The Professional Animal Scientist 16:164. 2000.
Diagnostic Products Corporation, "Coat-A-Count" http://www.Progesterone.com. 1998.
Dikeman, M. E. "Cattle Production Systems to Meet Future Consumer Demands" J. Anim. Sci. 59:1631, 1984.
Dinnyes, A., et al., "Timing of the First Cleavage Post-Insemination Affects Cryosurvival of In Vitro-produced Bovine Blastocysts", Molec. Reprod. Develop. 53, p. 318-324. 1999.
Dippert, K.D. "Fertilization Rates in Superovulated and Spontaneously Ovulating Mares" Theriogenology 41: 1411-1423, 1994.
Donaldson, L. E., "Effect of Insemination Regimen on Embryo Production in Superovulated Cows", The Veterinary Record, Jul. 13, p. 35-37, 1985.
Donoghue, A.M., et al. "Timing of Ovulation after Gonadotropin Induction and its Importance to Successful Intrauterine Insemination in the Tiger (*Panthera tigris*)" J. Reprod. Fertil. 107:53-58. 1996.
Douglas, R. H., "Review of Induction of Superovulation and Embryo Transfer in the Equine" Therio. 11:33-46. 1979.
Douglas, R. H., et al. "Induction of Ovulation and Multiple Ovulation on Seasonally-Anovulatory Mares with Equine Pituitary Fractions." Therio. 2(6): 133-142. 1974.
Doyle, S. P., et al. "Artificial Insemination of Lactating Angus Cows with Sexed Semen". Proc. Western Sect. Am. Soc. Anim. Sci. 50:203. 1999.
Dresser D.W. et al. Analyses of DNA content ofLiving Spermatozoa Using Flow Cytometry Technique Journal of Reproduction and Fertility, 1993, vol. 98, pp. 357-365.
Duchamp, G., et al. "Alternative Solutions to hCG Induction of Ovulation in the Mare" J. Reprod. Fertil. Suppl. 35:221-228. 1987.

Evans, M. J. and Irvine, C. H. G. "Induction of Follicular Development, Maturation and Ovulation by Gonadotropin Releasing Hormone Administration to Acyclic Mares" Bio. Reprod. 16:452-462. 1977.
Ferrell, C. L. Effects of Post-Weaning Rate of Gain on Onset of Puberty and Productive Performance of Heifers of Different Breeds. J. Anim. Sci. 55:1272. 1982.
Ferrell, C. L. and T. G. Jenkins. "Energy-Utilization by Mature, Nonpregnant, Nonlactating Cows of Different Types" J. Anim. Sci. 58:234. 1984.
Field, R. A., et al., "Bone-Ossification and Carcass Characteristics of Wethers Given Silastic Implants Containing Estradiol", J. Anim. Sci. 68:3663-3668. 1990.
Field, R. et al., "Growth, Carcass, and Tenderness Characteristics of Virgin, Spayed, and Single-Calf Heifers", J. Anim. Sci. 74:2178. 1996.
Fitzgerald, B. P., et al. "Effect of Constant Administration of a Gonadotropin-Releasing Hormone Agonist on Reproductive Activity in Mares: Preliminary Evidence on Suppression of Ovulation During the Breeding Season." Am. J. Vet. Res. 54:1746-1751. 1993.
Fluharty, F. L., et al., "Effects of Age at Weaning and Diet on Growth of Calves",Ohio State University Dept. of Animal Scieneces. 1966 Ohio Agri. Res. and Den. Circular, 156:29 1966.
Foote, et al. Motility and Fertility of Bull Sperm Frozen-Thawed Differently in Egg Yolk and Milk Extenders Containing Detergent, 1987 J Dairy Sci 70:2642-2647.
Foote, R.H., "Buffers and Extenders: What Do They Do? Why Are They Important?" Proc of the NAAB Tech. Conf. On Artificial Insemination and Reproduction, 62-70 (1984).
Foulkes, J. A., et al. "Artificial Insemination of Cattle Using Varying Numbers of Spermatozoa." Vet. Rec. 101:205. 1977.
Francon, M. and Yamamoto, T., "Un Noveau et tres simple dispositif interferentiel applicable as microscope" Optica Acta 9, p. 395-408. 1962.
Fugger, E. F. "Clinical Experience with Flow Cytometric Separation of Human X- and Y-Chromosome Bearing Sperm", Therio. vol. 52, pp. 1435-1440.1999.
Fuller, Robert R. "Characterizing Submicron Vesicles With Wavelength-Resolved Fluorescence in Flow Cytometry," University of Illinois, May 13, 1996.
Fulwyler, M. J. "Electronic Separation of Biological Cells by Volume." Science. 150:910. 1965.
Fulwyler, M. J. "Hydrodynamic Orientation of Cells." J of Histochem. and Cytochem. 25:781-783. 1977.
Garner, D. L., et al. "Quantification of the X and Y Chromosome-Bearing Spermatozoa of Domestic Animals by Flow Cytometry." Biol. Reprod. 28:312-321. 1983.
Ginther, O. J., "Sexual Behavior Following Introduction of a Stallion into a Group of Mares" Therio. vol. 19 (6) Jun. 1983.
Ginther, O. J., "Some Factors Which Alter Estrus Cycle in Mares." J. Anim. Sci. 33:1158. 1971 abstr.
Ginther, O. J., Reproductive Biology of the Mare. (2nd Ed.) Equiservices, Cross Plains, WI. 1992.
Gledhill, B. L. "Gender Preselection: Historical, Technical and Ethical Perspective." Semen Reprod. Endocrinol. 6:385-395. 1988.
Gombe, S. and Hansel, W. "Plasma Luteinizing Hormone (LH) and Progesterone Levels in Heifers on Restricted Energy Intakes." J. Anim. Sci. 37:728. 1973.
Gottlinger et al., "Operation of a Flow Cytometer", Flow Cytometry and Cell Sorting, A. Radbruch (Ed.), 1992, pp. 7-23.
Gourley, D. D. and Riese, R. L. "Laparoscopic Artificial Insemination in Sheep." Vet. Clin. N. Amer: Food Anim. Prac. 6(3): 615-633 (1990).
Graham, J. Analysis of Stallion semen and its Relation to Fertility. Abstract Complete article from Reproductive Technology vol. 12 # Apr. 1, 1996 now included in XYIDS000213.
Graham, J.K. and Hammerstedt, R.H.: "Differential Effects of Butylated Hydroxytoluene Analogs on Bull Sperm Subjected to Cold-Induced Membrane Stress," Cryobiology, 29:106-117 (1992).
Graham, James K., "Effect of Cholesterol-Loaded Cyclodextrins in Semen Extenders", Proceedings of the 19th Technical Conference on Artificial Insemination & Reproduction, 2003, pp. 91-95.

(56) References Cited

OTHER PUBLICATIONS

Gravert, H. O., "Genetic Aspects of Early Calving." In: J.C. Taylor (Ed.) *The Early Calving of Heifers and Its Impact on Beef Production.* 59 (1975).
Gregory, K. E., et al., "Characterization of Biological Types of Cattle—Cycle III: II Growth Rate and Puberty in Females" J. Anim. Sci. 49:461 (1979).
Grimes, I. F, and T. B. Turner. "Early Weaning of Fall Born Calves II. Post Weaning Performance of Early and Normal Weaned Calves". I. Prod. Agric. 4:168 (1991).
Grondahl, C., et al, "In Vitro Production of Equine Embryos", Biology of Reproduction, Monograph Series I, p. 299-307 (1995).
Guillou, F. and Combarnous, Y. "Purification of Equine Gonadotropins and Comparative Study of Their Acid-Dissociation and Receptor-Binding Specificity." Biochemica Et Biophysica Acta 755:229-236 (1983).
Gurnsey, M. P., and Johnson, L.A., "Recent Improvements in Efficiency of Flow Cytometric Sorting of X and Y-Chromosome Bering Sperm of Domestic Animals: a Review" New Zealand Society of Animal Protection, three pages (1998).
Hall, J. B., et al., "Effect of Age and Pattern of Gain on Induction of Puberty with a Progestin in Beef Heifers." J. Anim. Sci. 75:1606 (1997).
Hamamatsu, "Technical Information, Optical Detector Selection: A Delicate Balancing Act", web page, http://www.optics.org/hamamatsu/photodiode.html. printed on Apr. 15, 2000, 6 pages total.
Hamano, K., et al., "Gender Preselection in Cattle with Intracytoplasmically Injected, Flow Cytometrically Sorted Sperm Heads", Biology of Reproduction 60, p. 1194-1197 (1999).
Hammerstedt, et al., "Cryopreservation of Mammalian Sperm: What We Ask Them to Survive," Journal of Andrology, 11:1:73-88 (1990).
Harrison, L.A., et al., "Comparison of HCG, Buserelin and Luprostiol for Induction of Ovulation in Cycling Mares." Eq. Vet. Sci. 3:163-166 (1991).
Harte, F. J. "System of Production of Beef From Once Calved Heifers." In: J.C. Taylor (Ed.) *The Early Calving of Heifers and its Impact on Beef Production.* 123 (1975).
Hawk, H. W., et al., "Fertilization Rates in Superovulating Cows After Deposition of Semen on the Infundibulum Near the Uterotubal Junction or After Insemination with High Numbers of Sperm", XP-002103478, Therio. vol. 29, No. 5, p. 1131-1142 (1988).
Hermesmeyer, G. N., et al. "Effects of Prenatal Androgenization and Implantation on the Performance and Carcass Composition of Lactating Heifers in the Single-Calf Heifer System." The Professional Animal Scientist 15:173. 1999.
Herweijer, Hans. "High-Speed Photodamage Cell Selection Uing Bromodeoxyuridine/Hoechst 33342 Photosensitized Cell Killing," Sep. 23, 1987.
Herzenberg, Leonard A. "Flourescence-activated Cell Sorting," Sci. Am. 1976; 234, pp. 108-117.
Hilton, G. G., et al., "An Evaluation of Current and Alternative Systems for Quality Grading Carcasses of Mature Slaughter Cows." J. Anim. Sci. 76:2094. 1998.
Ho, L., et al., "Influence of Gender, Breed and Age on Maturity Characteristics of Sheep." J. Anim. Sci. 67:2460-2470. 1989.
Hofferer, S., et al. "Induction of Ovulation and Superovulation in Mares Using Equine LH and FSH Separated by Hydrophobic Interaction Chromatography." J. Reprod. Fertil. 98:597-602. 1993.
Hohenboken, W. D. "Applications of sexed semen in cattle production." Therio. 52:1421. 1999.
Holtan, D. W., et al., "Estrus, Ovulation and Conception Following Synchronization With Progesterone, Prostaglandin F2a and Human Chorionic Gonadotropin in Pony Mares." J. Anim. Sci. 44:431-437. 1977.
Horan, Paul K. "Quantitative Single Cell Ana,lysis and Sorting, Rapid Analysis and sorting of cells is emerging as an important new technology in research and medicine." Science, Oct. 1977.
Householder, D. D., et al. "Effect of Extender, Number of Spermatozoa and hCG on Equine Fertility." J. Equine Vet. Sci. 1:9-13. 1981.

Howard, J. G., et al., "Comparative Semen Cryopreservation in Ferrets (Mustela putorious furo) and Pregnancies After Laparoscopic Intrauterine Insemination With Frozen-Thawed Spermatozoa." J. Reprod. Fertil. 92:109-118. 1991.
Howard, J. G., et al., "Sensitivity to Exogenous Gonadotropins for Ovulation and Laparoscopic Artificial Insemination in the Cheetah and Clouded Leopard." Biol. Reprod. 56:1059-1068. 1997.
Hunter, R. H. F. "Transport and Storage of Spermatozoa in the Female Tract." Proc 4th Int. Congress Anim. Repro. and A. I. 9:227-233. 1980.
Hyland, J. H., et al., "Gonadotropin Releasing Hormone (GnRH) Delivered by Continuous Infusion Induces Fertile Estrus in Mares During Seasonal Acyclity" Proceedings of the Annual Convention of the American Association of Equine Practitioners (34th) 1989, p. 181-190.
IMV Technologies, Protocol of Bioxcell with Fresh Semen, 1 page, 2000.
IMV Technologies, Protocol of Bioxcell with Frozen Semen, 2 pages, 2000.
Irvine, C H. G. and Alexander, S. L. "GnRH" Chapter 4 in Equine Reproduction, McKinnon and Voss eds. Lea and Febiger. Philadelphia, London. p. 37. (1993).
Iwazumi, Y., et al., "Superovulation Using CIDR in Holstein Cows" J. of Reprod. Dev. vol. 40 (3) 1994, pp. 259-66.
Jafar, et al., "Sex Selection in Mammals: A Review", Therio. vol. 46, p. 191-200. (1996).
Jakubiczka, S. et al. "A Bovine Homologue of the Human TSPY Gene." Genomics. 1993, vol. 17, No. 3, pp. 732-735.
Jarriage, R. "Age of Cows at First Calving in France." In: J.C. Taylor (Ed.) *The Early Calving of Heifers and its Impact on Beef Production.* 10. (1975).
Jasko, D. J., et al., "Effect of Insemination Volume and Concentration of Spermatozoa on Embryo Recovery in Mares", Therio. 37:1233-1239, (1992).
Jasko, D. J., et al., "Pregnancy Rates Utilizing Fresh, Cooled and Frozen-Thawed Stallion Semen", American Association of Equine Practitioners 38th Annual Convention Proceedings, 1992, p. 649-660.
Johnson, A. L. "Pulsatile Administration of Gonadotropin Releasing Hormone Advances Ovulation in Cycling Mares", Biol. Reprod. 35:1123-1130, (1986).
Johnson, A. L., et al. "Use of Gonadotropin-Releasing Hormone (GnRH) Treatment to Induce Multiple Ovulations in the Anestrous Mare" Eq. Vet. Sci. 8:130-134, (1988).
Johnson, L.A., "Flow Cytometric Determination of Spermatozoa Sex Ratio in Semen Purportedly Enriched for X or Y Bearing Spermatozoa", Therio. 1988 29:265 abstr.
Johnson, L.A., "Gender Preselection in Domestic Animals Using Flow Cytometrically Sorted Sperm" J. Anim. Sci. (Suppl I) 70:8-18. (1992).
Johnson, L.A., "The Safety of Sperm Selection by Flow Cytometry" Ham. Reprod. 9(5): 758. (1994).
Johnson, L.A., "Advances in Gender Preselection in Swine" Journal of Reproduction and Fertility Supplement, vol. 52, p. 255-266 (1997).
Johnson, L.A., "Gender Preselection in Humans? Flow Cytometric Separation of X and Y Spermatozoa for the Prevention of X-Linked Diseases" Human Reproduction vol. 8 No. 10, p. 1733-1739 (1993).
Johnson, L.A., "Gender Preselection in Mammals: An Overview", Deutsch. Tierarztl. Wschr, vol. 103, p. 288-291 (1996).
Johnson, L.A., "Isolation of X- and Y-Bearing Spermatozoa for Sex Preselection." Oxford Reviews of Reproductive Biology. Ed. H. H. Charlton. Oxford University Press. 303-326. (1994).
Johnson, L.A., "Sex Preselection by Flow Cytometric Separation of X and Y Chromosome Bearing Spermatozoa Based on DNA Difference: a Review." Reprod. Fertil. Dev. 7:893-903. (1995).
Johnson, L.A., "Sex Preselection in Rabbits: Live Births from X and Y Sperm Separated by DNA and Cell Sorting", Biology of Reproduction 41, pp. 199-203 (1989).
Johnson, L.A., "Sex Preselection in Swine: Altered Sex Rations in Offspring Following Surgical Insemination of Flow Sorted X- and Y-Bearing Sperm", Reproduction in Domestic Animals, vol. 26, pp. 309-314 (1991).

(56) References Cited

OTHER PUBLICATIONS

Johnson, L.A., "Sex Preselection in Swine: Flow Cytometric Sorting of X- and Y- Chromosome Bearing Sperm to Produce Offspring", Boar Semen Preservation IV, p. 107-114. (2000).
Johnson, L.A., "Successful Gender Preselection in Farm Animals", Agricultural Biotechnology, p. 439-452. (1998).
Johnson, L.A., et al., "Enhanced Flow Cytometric Sorting of Mammalian X and Y Sperm: High Speed sorting and Orienting Nozzle for Artificial Insemination", Therio. 49(1): 361 (1988) abstr.
Johnson, L.A., et al., "Flow Sorting of X and Y Chromosome-Bearing Spermatozoa into Two Populations", Gamete Res. 16:203-212. (1987).
Johnson, L.A., et al., "Improved Flow Sorting Resolution of X- and Y-Chromosome Bearing Viable Sperm Separation Using Dual Staining and Dead Cell Gating" Cytometry 17 (suppl 7): 83, (1994).
Johnson, L.A., et al., "Flow Cytometry of X- and Y-Chromosome Bearing Sperm for DNA Using an Improved Preparation Method and Staining with Hoechst 33342." Gamete Research 17: 203-212. (1987).
Johnson, L.A., et al., "Modification of a Laser-Based Flow Cytometer for High-Resolution DNA Analysis of Mammalian Spermatozoa" Cytometry 7, pp. 268-273 (1986).
Joseph, R. L. "Carcass composition and meat quality in once calved heifers." In: J.C. Taylor (Ed.) *The Early Calving of Heifers and its Impact on Beef Production*. 143. (1975).
Joseph, R. L. and J. P. Crowley. "Meat Quality of Once-Calved Heifers." Irish J. of Agric. Research 10:281. (1971).
Kachel, V., et al., "Uniform Lateral Orientation, Caused by Flow Forces, of Flat Particles in Flow-Through Systems", The Journal of Histochemistry and Cytochemistry, vol. 25, No. 7, pp. 774-780. (1997).
Kanayama, K., et al., "Pregnancy by Means of Tubal Insemination and Subsequent Spontaneous Pregnancy in Rabbits." J. Int. Med. Res. 20:401-405. (1992).
Karabinus, et al., "Effects of Egg Yolk-Citrate and Milk Extenders on Chromatin Structured Viability of Cryopreserved Bull Sperm", Journal of Dairy Science, vol. 74, No. 11, p. 3836-3848. (1999).
Keeling, P. "A Modeling Study of Once-Bred Heifer Beef Production." Proceedings of the New Zealand Society of Animal Production. 51. (1991).
Kilicarslan, M. R., et al., "Effect of GnRH and hCG on Ovulation and Pregnancy in Mares." Vet. Rec. 139:119-120. (1996).
Kinder, J. E., et al. "Endocrine Basis for Puberty in Heifers and Ewes." J. Repro. and Fertility, p. 393. (1995).
Kinder, J. E., et al., "Endocrine Regulation of Puberty in Cows and Ewes." J. Repro. and Fertility, Suppl. 34:167. (1987).
Kinoshita, Shuichi. "Spectroscopic Properties of Fluorescein in Living Lymphocytes," Osaka Uinversity Aug. 7, 1986.
Klindt, J. and J. D. Crouse. "Effect of Ovariectomy and Ovariectomy with Ovarian Autotransplantation on Feedlot Performance and Carcass Characteristics of Heifers." J. Anim. Sci. 68:3481. (1990).
Klosterman, E. W. and C. F. Parker. "Effect of Size, Breed and Sex Upon Feed Efficiency in Beef Cattle." North Central Regional Research Publication 235, Ohio Agric. Research and Development Center 1090:3. (1976).
Kniffen, D. M., et al., "Effects of Long-Term Estrogen Implants in Beef Heifers." J. Anim. Sci. 77:2886. (1999).
Kobata, Akira, "Structures and Functions of the Sugar Chains of Human Chorionic Gonadotropin", in *Glycoprotein Hormones* Chin, W.W. and Boime, I., eds. Serono Symposia, Norwell, MA. p. 19-20. 1990.
Koch, R. M., et al., "Characterization of Biological Types of Cattle-Cycle-II .3." Carcass Composition, Quality and Palatability. J. Anim. Sci. 49:448. (1919).
Kommisrud E., et al. "Comparison of Two Processing Systems for Bull Semen with Regard to Post-Thaw Motility and Nonreturn Rates." Theriogenology, vol. 45, 1996, pp. 1515-1521.
Lapin, D. R. and Ginter, O. J. "Induction of Ovulation and Multiple Ovulations in Seasonally Anovulatory and Ovulatory Mares with an Equine Pituitary Extract." J. Anim. Sci. 44:834-842. (1977).
Laster, D. B., "Factors Affecting Dystocia and Effects of Dystocia on Subsequent Reproduction in Beef-Cattle." J. Anim. Sci. 36:695. (1973).
Lawrenz, R. "Preliminary Results of Non-Surgical Intrauterine Insemination of Sheep With Thawed Frozen Semen." J S Afr. Vet. Assoc. 56(2): 61-63. (1985).
Levinson, G., et al., "DNA-based X-Enriched Sperm Separation as an Adjunct to Preimplantation Genetic Testing for the Preparation of X-linked Disease." Mol. Human Reprod. 10:979-982. (1995).
Lightwave Electronics, "Xcyte," www.LightwaveElecronics.com.
Lindsey, A. C., et al., "Low Dose Insemination of Mares Using Non-Sorted and Sex-Sorted Sperm" Animal Reproduction Science 68 p. 279-89 (2001).
Lindsey, A.C. Hysteroscope insemination of mares with nonfrozen low-dose unsexed or sex-sorted spermatozoa.
Liu, Z, et al. "Survival of Bull Sperm Frozen at Different rates in Media Varying in Osmolarity." Cryobiology, vol. 27, 1998, pp. 219-230.
Lonergan, P., et al., "Effect of Time Interval from Insemination to First Cleavage on the Development of Bovine Embryos In Vitro and In Vivo", Therio. p. 326 (1999).
Long, C.R., et al., "In Vitro Production of Porcine Embryos From Semen Sorted for Sex With a High Speed Cell Sorter: Comparison of Two Fertilization Media." Therio. 49(1): 363 (1998) abstr.
Loy, R. G. and Hughes, J.P. "The Effects of Human Chorionic Gonadotropin on Ovulation, Length of Estrus, and Fertility in the Mare." Cornell Vet. 56:41-50 (1965).
Lu, K. H. et al., "In Vitro Fertilization of Bovine Oocytes with Flow-Cytometrically Sorted and Unsorted Sperm from Different Bulls" Therio. 2001 abstr.
Lu, K. H., et al., "In Vitro Fertilization with Flow-Cytometrically-Sorted Bovine Sperm", Therio 52, p. 1393-1405. (1999).
Lynch, I. M., et al., "Influence of timing of gain on growth and reproductive performance of beef replacement heifers." J. Anim. Sci. 75:1715. (1997).
Macmillan, K. L. and Day, A.M., "Prostaglandin F2a: A Fertility Drug in Dairy Cattle?", Animal Research Station, Private Bag, Hamilton, New Zealand, Therio. vol. 18, No. 3, p. 245-253 (1982).
Manni, Jeff. "To-Photon Excitation Expands the Capabilities of Laser-Scanning Microscopy," 1996 Biophotonics International.
Manning, S.T., et al., "Development of Hysteroscopic Insemination of the Uterine Tube in the Mare", Proceedings of the Annual Meeting of the Society for Theriogenology, 1998, p. 84-85.
Martin, A. H., et al., "Characteristics of Youthful Beef Carcasses in Relation to Weight, Age and Sex. III. Meat Quality Attributes." Canadian J. Anim. Sci. 51:305. (1971).
Martin, L. C., et al., "Genetic-effects on Beef Heifer Puberty and Subsequent Reproduction." J. Anim. Sci. 70:4006. (1992).
Martinez, E. A., et al., "Successful Low-Dose Insemination by a Fiberoptic Endoscope Technique in the Sow ", Proceedings Annual Conference of the International Embryo Transfer Society, Netherlands, Therio. vol. 53 p. 201, Jan. 2000.
Matsuda, Y. and Tobari, I. "Chromosomal Analysis in Mouse Eggs Fertilized In Vitro With Sperm Exposed to Ultraviolet Light (UV) and Methyl and Ethyl Methanesulfonate (MMS and EMS)." Mutat. Res. 198:131-144. (1988).
Matulis, R. J., "Growth and carcass characteristics of cull cows after different times-on-feed." J. Anim. Sci. 65:669. (1987).
Mauleon, P. "Recent research related to the physiology of puberty." In: J.C. Taylor (ed.) *The Early Calving of Heifers and its Impact on Beef Production*. (1975).
Maxwell, W. and Johnson, L., "Chlortetracycline Analysis of Boar Spermatozoa After Incubation, Flow Cytometric Sorting, Cooling, or Cryopreservation", Molecular Reproduction and Development 46, p. 408-418. (1997).
Maxwell, W. M. C., et al., "Fertility of Superovulated Ewes After Intrauterine or Oviductal Insemination with Low Numbers of Fresh or Frozen-Thawed Spermatozoa." Reprod. Fertil. Dev. 5:57-63. (1993).
Maxwell, W. M. C., et al., "The Relationship Between Membrane Status and Fertility of Boar Spermatozoa After Flow Cytometric Sorting in the Presence or Absence of Seminal Plasma" Reprod. Fertil. Dev. vol. 10 p. 433-440 (1998).

(56) References Cited

OTHER PUBLICATIONS

Maxwell, W. M. C., et al., "Viability and Membrane Integrity of Spermazota after Dilution and Flow Cytometric Sorting in the Presence or Absence of Seminal Plasma." Reprod. Fertil. Dev. 8:1165-78. (1997).

McCormick, R. J. "The Flexibility of the Collagen Compartment of Muscle." Meat Sci. 36:79. (1994).

McCue, P.M. "Superovulation" Vet. Clin. N. Amer. Eq. Prac. 12:1-11. (1996).

McCue, P.M., et al., "Oviductal insemination in the mare." 7th Internat. Symp. Eq. Reprod. 133 (1997) abstr.

McDonald, L. E. "Hormones of the Pituitary Gland." Veterinary Pharmacology and Therapeutics. 6th ed. Edited by N. H. Booth and L. E. McDonald. Ames, Iowa State Univ. Press. p. 590 (1988).

McKenna, T. et al., "Nonretum Rates of Dairy Cattle Following Uterine Body or Cornual Insemination." J. Dairy Sci. 73:1179-1783 (1990).

McKinnon, A.O. and Voss, J. L. *Equine Reproduction*. Lea and Febiger. Philadelphia, London (1993).

McKinnon, A.O., et al., "Predictable Ovulation in Mares Treated With an Implant of the GnRH Analogue Deslorelin." Eq. Vet. J. 25:321-323. (1993).

McKinnon, A.O., et al., "Repeated Use of a GnRH Analogue Deslorelin (Ovuplant) for Hastening Ovulation in the Transitional Mare." Eq. Vet. J. 29:153-155. (1996).

McLeod, John H., "The Axicon: A New type of Optical Element", Journal of the Optical Society of America, vol. 44 No. 8, Aug. 1954, Eastman Kodak Company, Hawk-Eye Works, Rochester, New York.

McNutt, T. L. et al., "Flow Cytometric Sorting of Sperm: Influence on Fertilization and Embryo/Fetal Development in the Rabbit", Molecular Reproduction and Development, vol. 43, p. 261-267 (1996).

Meilgaard, M., et al., "Sensor Evaluation Techniques." CRC Press Inc., Boca Raton, FL. (1991).

Meinert, C., et al., "Advancing the Time of Ovulation in the Mare With a Short-Term Implant Releasing the GnRH Analogue Deslorelin", Equine Veterinary Journal, 25, p. 65-68 (1993).

Melamed et al, "An Historical Review of the Development of Flow Cytometers and Sorters", 1979, pp. 3-9.

Mendes Jr., J.O.B. "Effect of heparin on cleavage rates and embryo production with four bovine sperm prepration protocols" Theriogenology 60 (2003) 331-340.

Menke, E. A Volume Activated Cell Sorter Journal of Histo chemistry and Cyto Chemistry, 1977, vol. 25,No. 7, pp. 796-803.

Merton, J., et al., "Effect of Flow Cytometrically Sorted Frozen/Thawed Semen on Success Rate of In Vitro Bovine Embryo Production", Therio. 47, p. 295. (1997).

Metezeau P. et al. Improvement of Flow Cytometry Analysis and Sorting of Bull Spermatozoa by Optical Monitoring of Cell Orientation as Evaluated by DNA Specific Probing Molecular Reproduction and Development, 1991,vol. 30 pp. 250-257.

Meyers, P. J., et al., "Use of the GnRH Analogue, Deslorelin Acetate, in a Slow Release Implant to Accelerate Ovulation in Oestrous Mares." Vet. Rec. 140:249-252. (1997).

Michaels, C., "Beef A. I. Facilities That Work", Proc. Fifth N.A.A.B Tech. Conf. A. I. Reprod. Columbia, MO. pp. 20-22.

Michel, T. H., et al., "Efficacy of Human Chorionic Gonadotropin and Gonadotropin Releasing Hormone for Hastening Ovulation in Thoroughbred Mares." Eq. Vet. J. 6:438-442. (1986).

Miller, S. J. "Artificial Breeding Techniques in Sheep." Morrow, D.A. (ed): Current Therapy in Therio 2. Philadelphia, WB Saunders. (1986).

Mirskaja, L. M. and Petropavloskii, V.V. "The Reduction of Normal Duration of Heat in the Mare by the Administration of Prolan." Probl. Zivotn. Anim. Breed. Abstr. 5:387. (1937).

Moe, P. W., "Energetics of Body Tissue Mobilization." J. of Dairy Sci. 1971 54:548.

Molinia, F. C., et al., "Successful Fertilization After Superovulation and Laparoscopic Intrauterine Insemination of the Brushtail Possum Trichosurus vulpecula, and Tammar Wallaby, *Macropus eugenii*." J. Reprod. Fertil. 112:9-17. (1998).

Moran, C., et al., "Puberty in Heifers—a Review." Animal Reproduction Sci. 18:167. (1989).

Moran, D. M. et al., "Determination of Temperature and Cooling Rate Which Induce Cold Shock in Stallion Spermatozoa", Therio. vol. 38 p. 999-1012 (1992).

Morcom, C. B. and Dukelow, W.R. "A Research Technique for the Oviductal Insemination of Pigs Using Laparoscopy." Lab. Anim. Sci. p. 1030-1031. (1980).

Morgan, J. B., et al., "National Beef Tenderness Survey." J. Anim. Sci. 69: 3274. (1991).

Morris, L. H., et al., "Hysteroscopic Insemination of Small Numbers of Spermatozoa at the Uterotubal Junction of Preovulatory Mares", Journal of Reproduction and Fertility, vol. 118, pp. 95-100 (2000).

Morris, S. T., et al., "Biological efficiency: How relevant is this concept to beef cows in a mixed livestock seasonal pasture supply context?" Proceedings of the New Zealand Society of Animal Production 54:333. (1994).

Moseley, W. M., et al., "Relationship of Growth and Puberty in Beef Heifers Fed Monensin" J. Anim. Sci. vol. 55 No. 2 p. 357-62 (1982).

Mount, D. E. "Fibrous and Non-fibrous Carbohydrate Supplementation to Ruminants Grazing Forage From Small Grain Crops." M.S. Thesis. Abstr. Colorado State University. (2000).

Muller, W. and Gautier, F. "Interactions of Heteroaromatic Compounds with Nucleic Acids." Euro. J Biochem. 54:358. (1975).

Mullis, K. B. and F. A. Faloona, "Specific Synthesis of DNA in Vitro Via a Polymerase-Catalyzed Chain Reaction" Methods in Enzymology vol. 155 p. 335-350 (1978).

Munne, S. "Flow Cytometry Separation of X and Y Spermatozoa Could be Detrimental to Human Embryos", Hum. Reprod. 9(5): 758 (1994).

Myers, S. E., "Performance and Carcass Traits of Early-Weaned Steers Receiving Either a Pasture Growing Period or a Finishing Diet at Weaning." J. Anim. Sci. 77:311. (1999).

Myers, S. E., et al., "Comparison of Three Weaning Ages on Cow-Calf Performance and Steer Carcass Traits." J. Anim. Sci. 77:323. (1999).

Myers, S. E., et al., "Production Systems Comparing Early Weaning to Normal Weaning With or Without Creep Feeding for Beef Steers." J. Anim. Sci. 77:300. (1999).

Nix, J. P., et al., "Serum Testosterone Concentration, Efficiency of Estrus Detection and Libido Expression in Androgenized Beef Cows." Therio. 49: 1195. (1998).

Nowshari, et al., "Superovulation of Goats with Purified pFSH Supplemented with Defined Amounts of pLH", Therio. vol. 43, p. 797-802 (1995).

NRC. "Nutrient Requirements for Beef Cattle." National Academy of Sci. National Research Council, Washington, DC. (1996).

O'Brien, Justine K. et al., "Preliminary Developments of Sperm Sorting Technology in Non-human Primates", Biology of Reproduction 2001 (Suppl. 1) 64:158.

Olive, M.D., "Detection of Enterotoxigenic *Escherichia coli* after Polymerase Chain Reaction Amplification with a Tehrmostable DNA Polymerase", J of Clinical Microbiology, Feb. 1989 p. 261265.

Olson, S.E. and Seidel, G. E. Jr., "Reduced Oxygen Tension and EDTA improve Bovine Zygote Development in a Chemically Defined Medium", J. of Anim. Sci. 78, pp. 152-157. (2000).

Owen, J. B. "The Maiden Female-A Means of Increasing Meat Production." Proc. Symp. on the Use of Once Bred Heifers and Gilts. (1973).

Ozhin F.V. et al. Artificial insemination of farm animals. Moscow, Izdatelstvo Selskokhozyaastvennoi Literatury, 1961, pp. 350-361 and pp. 380-393.

Pace, M. M. and Sullivan, J. J. "Effect of Timing of Insemination, Numbers of Spermatozoa and Extender Components on Pregnancy Rates in Mares Inseminated with Frozen Stallion Semen." J. Reprod. Fertil. Suppl. 2001, 23:115-121.

Parrish, J. J., et al., "Capacitation of Bovine Sperm by Heparin", Department of Meat and Animal Science, Biology of Reproduction 38, p. 1171-1180 (1988).

Patterson, D. J., et al., "Estrus Synchronization with an Oral Progestogen Prior to Superovulation of Postpartum Beef Cows" Therio. 48, 1025-33 (1997).

(56) References Cited

OTHER PUBLICATIONS

Peippo, J., et al., "Sex Diagnosis of Equine Preimplantation Embryos Using the Polymerase Chain Reaction", Therio. vol. 44:619-627 (1995).
Penfold, L.M.et at., "Comparative Motility of X and Y Chromosome-Bearing Bovine Sperm Separated on the Basis of DNA Content", Mol. Reprod. and Develop. 1998, vol. 50,pp. 323-327.
Perry, E. J., "Historical Background" The Artificial Insemination of Farm Animals. 4th ed. E. J. Perry (ed.) New Brunswick, Rutgers University Press, pp. 3-12. (1968).
Petersen, G. A., et al, "Cow and Calf Performance and Economic-Considerations of Early Weaning of Fall-Born Beef Claves", J. Anim. Sci., 64:15, pp. 15-22. (1987).
Petit, M. "Early Calving in Suckling Herds." In: J.C. Taylor (ed.) *The Early Calving of Heifers and its Impact on Beef Production*. p. 157-176. (1975).
Pickett B.W., et al., Recent Developments in Artificial Inseminatin in Horses Livestock Production Science,1998.
Pickett, B. W, et al., "Factors Influencing the Fertility of Stallion Spermatozoa in an A. I. Program." Proc. 8th International Congress Anim. Reprod. A. I. Krakow, Poland. 4:1049-1052. (1976).
Pickett, B. W., et al., "Effect of Seminal Extenders on Equine Fertility." J. Anim. Sci. 40:1136-1143. (1975).
Pickett, B. W., et al., "Influence of Seminal Additives and Packaging Systems on Fertility of Bovine Spermatozoa." J. Anim. Sci. Suppl. II. 47:12. (1978).
Pickett, B. W., et al., "Management of the Mare for Maximum Reproductive Efficiency." CSU Anim. Repro. Lab. Bull. No. 6. Fort Collins CO. (1989).
Pickett, B. W., et al., "Procedures for Preparation, Collection, Evaluation and Insemination of Stallion Semen." CSU Exp. Sta. Artira. Reprod. Lab. Gen. Series Bull. 935. (1973).
Pickett, B. W., et al., "Recent Developments in Artificial Insemination in Horses", Livestock Production Science, 40, p. 31-36 (1994).
Pickett, B. W., et al., "The Effect of Extenders, Spermatozoal Numbers and Rectal Palpation on Equine Fertility." Proc. Fifth N.A.A.B Tech. Conf. A. I. Reprod. Columbia, MO. pp. 20-22. (1974).
Pinkel et al., "Flow Chambers and Sample Handling", Flow Cytometry: Instrumentation and Data Analysis, Van Dilla et al. (Eds. ), 1985, pp. 77-128.
Pinkel, D., et al, "Flow Cytometric Determination of the Proportions of X- and Y- Chromosome-Bearing Sperm in Samples of Purportedly Separated Bull Sperm", J. of Anim. Sci., vol. 60, p. 1303-1307 (1998).
Pinkel, D., et al., "High Resolution DNA Content Measurements of Mammalian Sperm", Cytometry 3:1-9. (1982).
Pinkel, D., et al., "Sex Preselection in Mammals? Separation of Sperm Bearing the Y and "O" Chromosomes in the Vole Microtus Oregoni", Science vol. 218 p. 904 (1982).
Piston, D.W. "Three-dimensionally resolved NAD(P)H cellular metabolic redox imaging of the in situ cornea with two-photon excitation laser scanning microscopy," Journal of Microscopy, vol. 178, Nov. 29, 1994.
Polge, E. J., "Historical Perspective of AI: Commercial Methods of Producing Sex Specific Semen, IVF Procedures", Proceedings of the 16th Technical Conference on Artificial Insemination & Reproduction, Cambridge, England, pp. 7-11. (1996).
Polge, et al, "Revival of Spermatozoa After Vitrification and Dehydration at Low Temperatures," Nature, 164:666 (1994).
Preza, C. et al, "Determination of Direction-Independent Optical Path-Length Distribution of Cells Using Rotational-Diversity Transmitted-Light Differential Interference Contrast (DIC) Images", Presented at the Multidimensional Microscopy: Image Acquisition and Processing V, p. 1-11 (1998).
Province, C.A., et al., Cooling Rates, Storage, Temperatures and Fertility of Extended Equine Spermatozoa Therio. vol. 23 (6) p. 925-934, Jun. 1985.
Pursel, et al, "Effect of Orvus ES Paste on Acrosome Morphology, Motility and Fertilizing Capacity of Frozen-Thawed Boar Sperm," Journal of Animal Science, 47:1:198-202 (1978).
Purvis, H. T. and J. C. Whittier. "Effects of Ionophore Feeding and Anthelmintic Administration on Age and Weight at Puberty in Spring-Born Beef Heifers." J. Anim. Sci. 74:736-744. (1996).
Randel, R. D. "Nutrition and Postpartum Rebreeding in Cattle." J. Anim. Sci. 68:853. (1990).
Rath, D., et al., "Low Dose Insemination Technique in the Pig", Boar Semen Preservation IV, p. 115-118. (2000).
Rath, D., et al., "Production of Piglets Preselected for Sex Following in Vitro Fertilization with X and Y Chromosome-Bearing Spermatozoa Sorted by Flow Cytometry", Therio. 47, p. 795-800 (1997).
Rathi, R. et al., "Evaluation of In Vitro Capacitation of Stallion Spermatoza", Biology of Reproduction 2001,vol. 65, pp. 462-470.
Recktenwald, Diether. "Cell Separation Methods and Applications," New York 1997.
Reiling, B.A., et al., "Effect of Prenatal Androgenization on Performance, Location, and Carcass and Sensory Traits on Heifers in Single Calf Heifer System", J. Anim. Sci., 1995, 73: 986, p. 986-992.
Reiling, B.A., et al., "Effects of Prenatal Androgenization and Lactation on Adipose Tissue Metabolism in Finishing Single-Calf Heifers" J. Anim. Sci. vol. 75 p. 1504-1512 (1997).
Reiling, B.A., et al., "Effects of prenatal Androgenization, Melengestrol Acetate, and Synovex-H on Feedlot Performance, Carcass, and Sensory Traits of Once-Calved Heifers" J. Anim. Sci. vol. 74 p. 2043-51 (1996).
Rens, W., et al., "A Novel Nozzle for More Efficient Sperm Orientation to Improve Sorting Efficiency of X and Y Chromosome-Bearing Sperm", Technical Notes, Cytometry 33, p. 476-481 (1998).
Rens, W., et al., "Improved Flow Cytometric Sorting of X- and Y- Chromosome Bearing Sperm: Substantial Increase in Yield of Sexed Semen", Molecular Reproduction and Development, p. 50-56(1999).
Rieger, D., et al, "The Relationship Between the Time of First Cleavage of Fertilized Cattle Oocytes and Their Development to the Blastocyst Stage", Therio. 1999, p. 190.
Rigby, S. L., et al., "Pregnancy Rates in Mares Following Hysterscopic or Rectally-Guided Utero-Tubal insemination with Low Sperm Numbers" Abstracts/Animal Reproduction Science vol. 68 p. 331-333 (2001).
Riggs, B.A. "Integration of Early Weaning and Use of Sexed Semen in a Single-Calf Heifer System to Increase Value of Non-Replacement Heifers" MS Thesis, Colorado State University, Spring 2000.
Ritar, A. and Ball, A., "Fertility of Young Cashmere Goats After Laparoscopic Insemination." J. Agr. Sci. 117: p. 271-273. (1991).
Roberts, J. R., Veterinary Obstetrics and Genital Diseases. Ithaca, New York. p. 740-749. (1971).
Romero-Arredondo, A. " Effects of Bovine Folicular Fluid on Maturation of Bovine Oocytes" Theriogenology 41: 383-394, 1994.
Romero-Arrendondo, A. "Effects of Follicular Fluid dring In Virto Maturation of Bovine Oocytes on In Vitro Fertilization and Early Embryonic Development" Biology of Reproduction 55, 1012-1016 1996.
Romita, A. "Some Considerations on the Beef Situation in Italy." In: J.C. Taylor (ed.) *The Early calving of Heifers and its Impact on Beef Production*. 23. (1975).
Roser, J. F., et al., "Reproductive Efficiency in Mares With Anti-hCG Antibodies." Proc 9th Int. Congr. Anim. Repro. and A. I. 4:627 (1980) abstr.
Roth, T. L., et al., "Effects of Equine Chorionic Gonadotropin, Human Chorionic Gonadotropin, and Laparoscopic Artificial Insemination on Embryo, Endocrine, and Luteal Characteristics in the Domestic Cat." Bio. Reprod. 57:165-171 (1997).
Roux, M., et al., "Early Calving Heifers Versus Maiden Heifers for Beef-Production from Dairy herds. I. The Effects of Genotype (Friesian and Carloads x Friesian) and Two Feeding Levels in the Rearing Period on Growth and Carcass Quality." Livestock Prod. Sci. 16:1 (1987).
Rowley, H. S., et al., "Effect of Insemination Volume on Embryo Recovery in Mares." J. Equine Vet. Sci. 10:298-300 (1990).
Roy, J. H., "Rearing Dairy-Herd Replacements." Journal of the Society of Dairy Technology 31:73-79 (1978).
Rutter, L. M., et al, "Effect of Abomasal Infusion of Propionate on the GnRH-Induced Luteinizing Hormone Release in Prepuberal Heifers." J. Anim. Sci. 56:1167 (1983).

(56) References Cited

OTHER PUBLICATIONS

Salamon, S., *Artificial Insemination of Sheep*, Chippendale, New South Whales. Publicity Press. p. 83-84 (1976).

Salisbury, G. W. and VanDemark, N. L. "Physiology of Reproduction and Artificial Insemination of Cattle." San Francisco: Freeman and Company. p. 442-551 (1978) (1961 & 1978 Combined) Chapters 16 and 17 are the complete article. Published by W.H.Freeman Co., San Francisco California.

Schenk, J. L. "Applying Sperm Sexing Technology to the AI Industry", Proceedings of the 18th Technical Conference on Artificial insemination & Reproduction, Sep. 29-30, 2000.

Schenk, J. L, et al., "Imminent Commercialization of Sexed Bovine Sperm", Proceedings, The Range Beef Cow Symposium XVI p. 89-96 (1999) Greeley Colorado.

Schenk, J. L., "Cryopreservation of Flow-Sorted Bovine Spermatozoa", Therio. vol. 52, 1375-1391 (1999).

Schiewe, M. C., et al., "Transferable Embryo Recovery Rates Following Different Insemination Schedules in Superovulated Beef Cattle" Therio. 28 (4) Oct. 1997, pp. 395-406.

Schillo, K. K., et al, "Effects of Nutrition and Season on the Onset of Puberty in the Beef Heifer." J. Anim. Sci. 70:3994 (1992).

Schmid, R. L., et al, "Fertilization with Sexed Equine Spermatozoa Using Intracytoplasmic Sperm Injection and Oviductal Insemination", 7th International Symposium on Equine Reproduction, pp. 139 (1998) abstr.

Schnell, T. D., et al, "Performance, Carcass, and Palatability Traits for Cull Cows Fed High-Energy Concentrate Diets for 0, 14, 28, 42, or 56 days." J. Anim. Sci. 75:1195. (1997).

Schoonmaker, J. P., et al., "Effects of Age at Weaning and Implant Strategy on Growth of Steer Calves." J. Anim. Sci. (Suppl. II) 76:71. (1998) abstr.

Seidel, G. E. Jr. "Cryopreservation of Equine Embryos" Veterinary Cliniics of North America: Equine Practice vol. 12, No. 1, Apr. 1996.

Seidel, G. E. Jr. "Sexing Bovine Sperm" The AABP Proceedings—vol. 34, Sep. 2001.

Seidel, G. E. Jr. Sexing mammalian spermatozoa and embryos-state of the art Journal of Reproduction and Fertility Supp 54, 477-487 1999.

Seidel, G. E. Jr. "Uterine Horn Insemination of Heifers With Very Low Numbers Of Nonfrozen and Sexed Spermatozoa", Atlantic Breeders Cooperative, Therio. 48: pp. 1255-1264, (1997).

Seidel, G. E. Jr et al., "Current Status of Sexing Mammalian Spermatozoa," Society for Reproduction and fertiity, pp. 733-743, 2002.

Seidel, G. E. Jr., "Commercilizing Repreductive Biotechnology—The Approach used by XY, Inc.," Theriogenology, p. 5, 1999.

Seidel, G. E. Jr. et al., "Insemination of Heifers with Sexed Sperm", Therio, vol. 52, pp. 1407-1421 (1999).

Seidel, G. E. Jr., "Use of Sexed Bovine Sperm for In Vitro Fertilization and Superovulation", Animal Reproduction and Biotech Lab, CSU, Proceedings of the 2000 CETA/ACTE Convention, Charlottetown, Prince Edward Island, Aug. 2000, pp. 22-24.

Seidel, G. E. Jr., "Artificial Insemination With X-and Y-Bearing Bovine Sperm", Animal Reproduction and Biotechnology Laboratory, Colorado State University, (1996).

Seidel, G. E. Jr., "Status of Sexing Semen for Beef Cattle", Texas A & M University 45th Annual Beef Cattle Short Course and Trade Show Proceedings, Aug. 9-11, p. 11124-11127, (1999).

Seidel, G. E. Jr., et al, "Insemination of Heifers With Very Low Numbers of Frozen Spermatozoa", CSU, Atlantic Breeders Cooperative, Lancaster, PA, DUO Dairy, Loveland, CO, Jul. 1996.

Seidel, G. E. Jr., et al, "Insemination of Holstein Heifers With Very Low Numbers of Unfrozen Spermatozoa", CSU, Atlantic Breeders Cooperative, (1995).

Seidel, G. E. Jr., et al, "Sexing Mammalian Sperm—Overview", Therio. 52: 1267-1272, (1999).

Seidel, G. E. Jr., et al., "Artificial Insemination of Heifers with Cooled, Unfrozen Sexed Semen", Therio, vol. 49 pp. 365 (1998) abstr.

Seidel, G. E. Jr., et al., "Insemination of Heifers with Sexed Frozen or Sexed Liquid Semen." Therio. 51. (in press) (1999) abstr.

Seidel, G. E. Jr., Economics of Selecting for Sex: The Most Important Genetic Trait, Theriogenology 59, (2003), pp. 585-598.

Sell, R. S., et al., "Single-calf Heifer Profitability Compared to Other North Dakota Beef Production Systems." Department of Ag. Eco., North Dakota State University, Ag. Econ. Rpt. 20.; Oct. 1988.

Senger, P. L., et al., "Influence of Comual Insemination on Conception in Dairy Cattle." J Anim. Sci. 66:3010-3016. (1988).

Shabpareh, V. " Methods for Collecting and Maturing Equine Oocytes in Vitro " Theriogenology 40: 1161-1175, 1993.

Shackelford, S. D., et al, "Effects of Slaughter Age on Meat Tenderness and USDA Carcass Maturity Scores of Beef Females." J. Anim. Sci. 73:3304. (1995).

Sharpe, J.C., et al., "A New Optical Configuration for Flow Cytometric Sorting of Aspherical Cells" Horticulture and Food Research Institute of New Zealand Ltd., Hamilton, New Zealand (PNS) 11-02 1997 Abstract.

Sharpe, Johnathan, Thesis; "An Introduction of Flow Cytometry", Ch. 2-2.2, 1997.

Sharpe, Johnathan, Thesis; "Gender Preselection-Principle Scientific Options," Ch. 3.4-3.4.8, 1997.

Sharpe, Johnathan, Thesis; "Sperm Sexing using Flow Cytometry," Ch. 3.5-3.5.8, 1997.

Sharpe, Johnathan, Thesis; "Sperm Sexing-Method of Johnson et al," Ch. 3.6-4.3.4, 1997.

Shelton, J. N. and Moore, N. W. "The Response of the Ewe to Pregnant Serum Mare Gonadotropin and to Horse Anterior Pituitary Extract." J. Reprod. Fertil. 14:175-177. (1967).

Shilova, A. V., et al., "The Use of Human Chorionic Gonadotropin for Ovulation Date Regulation in Mares." VIIIth Int. Congress on Anim. Repro. and A. I. 204-208. (1976).

Shorthose, W. R. and P. V. Harris. "Effect of Animal Age on the Tenderness of Selected Beef Muscles." J. Food Sci. 55:1-. (1990).

Silbermann, M., "Hormones and Cartilage. Cartilage: Development, Differentiation, and Growth." pp. 327-368. Academic Press, Inc. (1983).

Simon, M., "The Effect of Management Option on the Performance of Pregnant Feedlot Heifers." M.S. Thesis. Kansas State University. (1983).

Skogen-Hagenson, M. J. et al; "A High Efficiency Flow Cytometer," The Journal of Histochemistry and Cytochemistry, vol. 25, No. 7, pp. 784-789, 1977, USA.

Smith, G. C., et al, "USDA Maturity Indexes and Palatability of Beef Rib Steaks." J. of Food Quality 11:1. (1988).

Smith, G. C., et al., "Relationship of USDA Maturity Groups to Palatability of Cooked Beef." J. of Food Sci. 47:1100. (1982).

Smith, R. L., et al, Influence of Percent Egg Yolk during Cooling and Freezing on Survival of Bovine Spermatozoa, Dairy Science 1979 J 62:1297-1303.

Spectra Physics, The Solid State Laser Company, "Vangaurd 4 Watts of UV from a Quasi-CW, All Solid State Laser," http://www.splasers.com/products/isl_products/vangaurd.html three pages, printed Nov. 14, 2002.

Spectra-Physics Products, "Fcbar" http://www.splasers.com/products/oem_products/ov_fcbar.html two pages printed Nov. 14, 2002.

Spectra-Physics, The Solid State Laser Company, Vanguard 2000-HMD 532, www.specra-physics.com, Copyright 2002.

Spectra-Physics, The Solid State Laser Company, Vanguard 350-HMD 355, www.specra-physics.com Copyright 2002.

Squires, E. L, et al., "Effect of Dose of GnRH Analog on Ovulation in Mares." Therio. 41:757-769. (1994).

Squires, E. L, "Simultaneous Analysis of Multiple Sperm Attributes by Flow Cytometry", Diagnostic Techniques and Assisted Reproductive Technology, The Veterinary Clinics of North America, Equine Practice, vol. 12, No. 1, p. 127-130 (1996).

Squires, E. L., "Early Embryonic Loss" *Equine Diagnostic Ultrasonography*, first ed., Rantanen & McKinnon. Williams and Wilkins, Baltimore, Maryland, p. 157-163 (1998).

Squires, E. L., et al, "Cooled and Frozen Stallion Semen", Bulletin No. 9, Colorado State University, Ft. Collins, CO. (1999).

Squires, E.L., "Procedures for Handling Frozen Equine Semen for Maximum Reproductive Efficiency", (1998) pp. 1, 39-41, 81-89.

(56) References Cited

OTHER PUBLICATIONS

Staigmiller, R.B. " Superovulation of Cattle with Equine Pituitary Extract and Porcine FSH" Theriogenology 37: 1091-1099 1992.
Stap J. Et al Improving the Resolution of Cryopreserved X- and Y-Sperm During DNA Flow Cytometric Analysis with the Addition of Percoll to quench the Fluorescence of Dead Sperm: Academic Medical Center, University of Amsterdam (1998) Journal of Animal Science vol. 76 1998, pp. 1896-1902.
Steel, N. L., "Cost Effectiveness of Utilizing Sexed-Semen in a Commercial Beef Cow Operation", MS Thesis, Colorado State University, Summer 1998.
Steinkamp: "Flow Cytometry" vol. 55, No. 9, Sep. 1984 pp. 1375-1400, New York Review of Scientific Instruments Abstract Only.
Stellflug, J. N., "Plasma Estrogens in Periparturient Cow." Therio 10:269. (1978).
Stevenson, J. S., et al., "Detection of Estrus by Visual Observation and Radiotelemetry in Peripubertal, Estrus-Synchronized Beef Heifers." J. Anim. Sci. 74:729. (1996).
Story, C. E., et al., "Age of Calf at Weaning of Spring-Calving Beef Cows and the Effect on Cow and Calf Performance and Production Economics." J. Anim. Sci. 78:1403. (2000).
Stovel R.T. A Means for Orienting Flat Cells in flow systems Biophysical Journal, 1978,vol. 23,pp. 1-5.
Sullivan, J. J., et al., "Duration of Estrus and Ovulation Time in Nonlactating Mares Given Human Chorionic Gonadotropin During Three Successive Estrous Periods." J.A.V.M.A. 162:895-898. (1973).
Sumner, A. T. and Robinson, J. A., "A Difference in Dry Mass Between the Heads of X and Y-Bearing Human Spermatozoa", J Reprod Fertil. 48, p. 9-15 (1976).
Swanson, E. W. "Future Research on Problems of Increasing Meat Production by Early Calving." In: J.C. Taylor (ed.) *The Early Calving of Heifers and its Impact on Beef Production*. (1975).
Swenson, S. L., et al., "PRRS Virus Infection in Boars: Isolation From Semen and Effect on Semen Quality" from the 1995 Research Investment Report, Iowa State University, Veterinary Clinical Sciences, Iowa State University.
Taljaard, T. L., et al., "The Effect of the Laparoscopic Insemination Technique on the Oestrus Cycle of the Ewe." J. South Afr. Vet. Assoc. 62(2): 60-61. (1991).
Tatum, J. D., et al., "Carcass Characteristics, Time on Feed and Cooked Beef Palatability Attributes." J. Anim. Sci. 50:833. (1980).
Taylor, C. S., "Efficiency of Food Utilization in Traditional and Sex-Controlled Systems of Beef Production", AFRC Animal Breeding Research Organization, West Mains Road, Edinburg EH9 3JQ; Animal Prod. 1985 40:401-440.
Tervit, H.R., et al., "Successful Culture in Vitro of Sheep and Cattle Ova", Agricultural Research Council, Unit of Reprod. Physio. and Biochem., Univ of Cambridge, p. 493-497 (1972).
Thun, Rico, et al., Comparison of Biociphos-Plus® and TRIS-Egg Yolk Extender for Cryopreservation of Bull Semen; Theriogenology Symposium, Dec. 1999, vol. 52, #8.
*Time-Bandwidth Products* "GE-100-XHP", www.tbsp.com. 2 pages, Jan. 2002.
Unruh, J. A. "Effects of Endogenous and Exogenous Growth-Promoting Compounds on Carcass Composition, Meat Quality and Meat Nutritional-Value." J. Anim. Sci. 62:1441. (1986).
USDA "Official United States Standards for Grades of Carcass Beef." Agric, Marketing Serv., USDA, Washington, DC. (1997).
Van Dilla, Martin, "Overview of Flow Cytometry: Instrumentation and Data Analysis", Flow Cytometry: Instrumentation and Data Analysis, Van Dilla et al. (Eds.), 1985, pp. 1-8.
Van Munster, E. B., et al, "Difference in Sperm Head Volume as a Theoretical Basis for Sorting X & Y-Bearing Spermatozoa: Potentials and Limitations", Therio 52, pp. 1281-1293 (1999).
Van Munster, E. B., et al, "Difference in Volume of X- and Y-chromosome Bearing Bovine Sperm Heads Matches Difference in DNA Content" Cytometry vol. 35 p. 125-128 (1999).
Van Munster, E. B., et al, "Measurement-Based Evaluation of Optical Path Length Distributions Reconstructed From Simulated Differential Interference Contrast Images", J of Microscopy 191, Pt. 2, p. 170-176 (1998).
Van Munster, E. B., et al, "Reconstruction of Optical Pathlength Distributions From Images Obtained by a Wide Field Differential Interference Contrast Microscope", J of Microscopy 188, Pt. 2, p. 149-157 (1997).
Vazquez, J. J. et al., "Nonsurgical Uterotubal Insemination in the Mare", Proceedings of the 44th Annual Convention of the American Association of Equine Practitioners, vol. 44, pp. 68-69 (1998).
Vazquez, J. M., et al., "A. I. in Swine; New Strategy for Deep Insemination with Low No. of Spermatozoa Using a Non-surgical Methodology", 14th International Congress on Animal Reproduction, vol. 2, Stockholm, Jul. 2000, p. 289.
Vazquez, J., et al., "Development of a Non-surgical Deep Intra Uterine Insemination Technique", Boar Semen Preservation IV, IVth International Conference on Boar Semen Preservation, Maryland, Aug. 8, 1999, pp. 262-263.
Vazquez, J., et al., "Hyposmotic Swelling Test as Predictor of the Membrane Integrity in Boar Spermatozoa", Boar Semen Preservation IV, IVth International Conference on Boar Semen Preservation, Maryland, pp. 263., Jun. 2004.
Vazquez, J., et al., "Successful low dose insemination by a fiber optic Endoscope technique in the Sow", Proceedings Annual Conference of the International Embryo Transfer Society, Netherlands, Theriogenology, vol. 53 Jan. 2000.
Vidament, M., et al., "Equine Frozen Semen Freezability and Fertility Field Results." Therio. 48:907. (1997).
Vincent, B.C., et al, "Carcass Characteristics and Meat Quality of Once-Calved Heifers." Canadian J. Anim. Sci. 71:311. (1991).
Vogel, T., et al, "Organization and Expression of Bovine TSPY", Mammalian Genome, vol. 8, pp. 491-496 (1997).
Voss, J. L. and Pickett, B. W., "Reproductive Management of the Broodmare." CSU Exp. Sta. Anim. Reprod. Lab. Gen. Series. Bull. 961. (1976).
Voss, J. L., et al., "Effect of Number and Frequency of Inseminations on Fertility in Mares." J. Reprod. Fertil. Suppl. 32:53-57. (1982).
Voss, J. L., et al., Effect of Human Chorionic Gonadotropin on Duration of Estrous Cycle and Fertility of Normally Cycling, Nonlactating Mares. J.A.V.M.A. 165:704-706. (1974).
Waggoner, A. W., et al., "Performance, Carcass, Cartilage Calcium, Sensory and Collagen Traits of Longissimus Muscles of Open Versus 30-month-old Heifers That Produced One Calf." J. Anim. Sci. 68:2380. 1990.
Watson, "Recent Developments and Concepts in the Cryopreservation of Spermatozoa and the Assessment of Their Post-Thawing Function," Reprod. Fertil. Dev. 7:871-891 (1995) Abstract.
Welch G., et al., Fluidic and Optical Modifications to a FACS IV for Flow Sorting of X- and Y-Chromosome Bearing Sperm Based on DNA. Cytometry 17 (Suppl. 7): 74. (1994).
Welch, G., et al., "Flow Cytometric Sperm Sorting and PCR to Confirm Separation of X- and Y-Chromosome Bearing Bovine Sperm", Animal Biotechnology, 6, pp. 131-139 (1995).
Wheeler, T. L., et al., "Effect of Marbling Degree on Beef Palatability in Bos-taurus and Bos-indicus cattle." J. Anim. Sci. 72:3145. (1994).
Wickersham, E. W. and L. H. Schultz. "Influence of Age at First Breeding on Growth, Reproduction, and Production of Well-Fed Holstein Heifers." J. Dairy Sci. 46:544. (1963).
Wilhelm, K.M. et al, "Effects of Phosphatidylserine and Cholesterol Liposomes on the Viability, Motility, and Acrosomal Integrity of Stallion Spermatozoa Prior to and after Cryopreservation", Cryobiology 33:320, 1996.
Wilson, C. G., et al., "Effects of Repeated hCG Injections on Reproductive Efficiency in Mares." Eq. Vet. Sci. 4:301-308. (1990).
Wilson, D. E. et al., "Mammal Species of the World", Smithsonian Institution Press, 1993, 1206 pp.
Wilson, M.S. "Non-surgical Intrauterine Artificial Insemination in Bitches Using Frozen Semen." J. Reprod. Fertil. Suppl. 47:307-311. (1993).
Windsor, D. P., et al, "Sex Predetermination by Separation of X and Y Chromosome-bearing Sperm: A Review", Reproduction of Fertilization and Development 5, pp. 155-171, (1993).

(56) References Cited

OTHER PUBLICATIONS

Woods, G. L. and Ginther, O. J. "Recent Studies Related to the Collection of Multiple Embryos in Mares." Therio. 19:101-108. (1983).
Woods, J., et al., "Effects of Time of Insemination Relative to Ovulation on Pregnancy Rate and Embryonic-Loss Rate in Mares." Eq. Vet. J. 22(6): 410-415. (1990).
Zhou, Hongwei, et al. "Research on and Development of Flow Cell Sorting Apparatuses," Gazette of Biophysics, vol. 13, ed. 3, 1997.
Hamamatsu. "Photomultiplier Tubes." web page. http://www.optics.org/hamamatsu/pmt.html. Printed on Apr. 15, 2000 4.
Hermesmeyer, G.N. ,et al. Effects of Lactation and Prenatal Androgenization on the Performance, Carcass Composition, and Longissimus muscle sensory characteristics of heifers in the single-calf heifer system. The Professional Animal Scientist 15: 14-23, (1995).
Seidel, G. E. Jr., "Fertility of Bulls on the Edge of the Dose-Response Curve for Numbers of Sperm per Inseminate"; Proceedings of the 17th Technical comference on Artificial Insemination & Reproduction, 1998.
Hollinshead, F.K. et al. "In vitro and in vivo assessment of functional capacity of flow cytometrically sorted ram spermatozoa after freezing and thawing." Reprod. Fertil. and Develop. 2003. vol. 15, pp. 351-359.
Hollinshead F. K. et al. "Production of lambs of predetermined sex after the insemination of ewes with low numbers of frozen-thawed sorted X- or Y- Chromosome-bearing spermatozoa", Reprod. Fertil. and Develop. 2002, vol. 14, pp. 503-508.
Hollinshead F. K. et al. "Sex-Sorting and Re-cryopreservation of Frozen-Thawed Ram Sperm for In Vitro Embryo Production" Theriogenology , vol. 59. (2003) pp. 209.
Dhali et al. Vitrification of Buffalo (Bubalus Bubalis)Oocytes, Embryo Theriogenology vol. 53, pp. 1295-1303 (2000).
Borini et al. Cryopreservation of Mature Oocytes: The use of a trypsin inhibitor enhances fertilization and obtained embryos rates, Fertil. Steril. (1997), vol. 68 (Suppl.).
Hamamatsu Photonics K.K. Electronic Tube Center, Photomultiplier Tubes, Brochure Dec. 1997.
Johnson, L. A., et al. The Beltsville Sperm Sexing Technology: High-speed sperm sorting gives improved sperm output for In Vitro fertiliation and AI, Journal of Animal Science,vol. 77, Suppl 2/J, Dairy Sci. vol. 82, Suppl. Feb. 1999 pp. 213-220.
Peters D., The LLNL high-speed sorter: Design features,operational characteristics, and bioloical utility, Cyometry, 6:290-301 (1985).
Rens W., et al Slit-scan flow cytometry for consistent high resdolution DNA analysis of X-and Y- chromosome bearing sperm, Cytometry 25:191-199 (1996).
Van Munster, E. B. Interferometry in flow to sort unstained X- and Y-Chromosome-Bearing Bull Spermatozoa, Cytometry 47:192-199 (2002).
Scmid, R. L., et al. Effects of follicular fluid or progesterone on in vitro maturation of equine oocytes before intracytoplasmic sperm injection with non-sorted and sex-sorted spermatozoa, Journal of Reproduction and Fertility 56:519-525, 2000.
Brink, Z et al. A reliable procedure for superovulating cattle to obtain zygotes and early emryos for microinjection, Theriogenology vol. 41, p. 168, (1994).
Spectra-Physics, The Solid State Laser Company, Vanguard 350-HMD 355, User's Manual, Dec. 2002.
Photon, Inc. Light MeasuringSolutions, NanoScan for High-powered beam Applications, 2005.
Fluorescense Lifetime Systems, www.picoquant.com, Jan. 28, 2005 pp. 2.
NCI ETI Branch, Flow CytometryCore Laboratory, http://home.ncifcrf.gov/ccr/flowcore/ndyag.htm, pp. 5, May 11, 2004.
NCI ETI Branch, Flow CytometryCore Laboratory, http://home.ncifcrtgov/ccr/flowcore/isrll.htm, pp. 14, May 11, 2004.
Saacke,R.G., Can Spermatozoa with abnormal heads gain access to the ovum in artificially inseminated super- and single-ovulating cattle?, Theriogenology 50:117-128. 1998.

Hawk, H.W., Gamete Transport in the Superovulated Cow. Theriogenology: Jan. 1998 vol. 29 No. 1 pp. 125-142.
Blecher, S.R., et al. A new approach to immunological sexing of sperm, Theriogenology, 59, pp. 1309-1321, 1999 vol.
Wheeler, M. B., et al. Application of sexed semen technology to in vitro embryo production in cattle, Theriogenology, vol. 65 (2006) 219-227.
Garverick, H. A., et al. mRNA and protein expression of P450 aromatase (AROM) and estrigen recepters (ER) α and β during early development of bovine fetal ovaries; The society for the study of reproduction 38th annual meeting Jul. 24-27, 2005; Abstract only.
Bodmer, M., et al., Fertility in heifers and cows after low does insemination with sex-sorted and non-sorted sperm under field conditions; Theriogenology, vol. 64, (2005) 1647-1655.
Schenk J. L., et al. Embryo production from superovulated cattle following insemination of sexed sperm, Theriogenology, 65 (2006) 299-307.
Garner, D. L., Flow cytometric sexing of mammalian sperm, Theriogenology, 65 (2006) 943-957.
Habermann F. A., et al., Validation of sperm sexing in the cattle (Bos taurus) by dual colour flourescence in situ hybridization; J Anim Breed Genet. Apr. 2005; 122 Suppl 1:22-7 (Abstract only).
Johnson, L. A., Sexing mammalian sperm for production of offspring: the state-of-the-art; Animal Reproduction Science; 60-61 (2000) pp. 93-107.
Seidel, G.E. Jr., et al., Methods of Ovum Recovery and Factors Affecting Fertilization of Superovulated Bovine Ova, Control of Reproduction in the Cow, Sneenan ed., 1978, pp. 268-280.
Hawk, H. W. et al., Effect of Unilateral Cornual Insemination upon Fertilization Rate in Superovulating and Single-Ovulating Cattle, Journal of Animal Sciences, 1986 vol. 63, pp. 551-560.
Andersson, M. et al., Pregnancy Rates in Lactating Holstein-Greisian Cows after Artificial Insemination with Sexed Sperm. Reprod. Dom. Anim 41, 95-97, 2006.
Morton, K. M., et al., in vitro and in vivo survival of bisected sheep embryos derived from frozen-thawed unsorted, and frozen-thawed sex-sorted and refrozen-thawed ram spermatozoa; Theriogenology, 65 (2006) 1333-1345.
Wilson, R. D., et al., In vitro production of bovine embryos using sex-sorted sperm, Theriogenology, 65 (2006) 1007-1015.
Johnson, L.A., et al, 1996 Gender preselection in mammals. XX Beltsville Symposium in Agricultural Research Technolgy's Role in the Genetic Improvement of Farm Animals. pp. 151-164, Amer. Soc. Anim. Sci. IL, USA.
Smorag, Z., et al., Cattle Sex Regulation by Separation of X and Y Spermatozoa—Preliminary Results of Field Experiment in Poland, Reproduction, Fertility and Development 17(2) 306-306; Jan. 1, 2005.
Crichton, E., et al. (Abstract) Artificial Insemination of Lactating Holstein Cows with Sexed Sperm, Reproduction, Fertility and Development 18(2) 281-281, Dec. 14, 2005.
Lindsey, A.C., et al. Hysteroscopic insemination of low numbers of flow sorted fresh and frozen/thawed stallion spermatozoa, Equine Vet J. Mar. 2002;34(2):106-7.
Drobnis, E. Z, Cold shock damage is due to lipid phase transitions in cell membranes : a demonstration using sperm as a model, Journal of experimental zoology (J. exp. zool.) 1993, vol. 265, No. 4, pp. 432-437 (22 ref.).
Hagele, W.C., et al., Effect of Separating Bull Semen into X and Y Chromosome-bearing Fractions on the Sex Ratio of Resulting Embryos; Cran J. Comp. Med, 1984: 48:294-298.
U.S. Appl. No. 11/422,735, filed May 25, 2006 entitled Apparatus, Methods and Processes for Sorting Particles and for Providing Sex-Sorted Animal Sperm.
Suh, T.K, et al., Pressure during flow sorting of bull sperm affects post-thaw motility characteristics; Theriogenology vol. 59, No. 1, Jan. 2003 p. 516.
Rath, D, et al., In Vitro Production of Sexed Embryos for Gender Preselection: High-speed sorting of X-Chromosome-Bearing Sperm to Produce Pigs After Embryo Transfer, J. Anim. Sci. 1999, 77:3346-3352.

(56) References Cited

OTHER PUBLICATIONS

Auchtung, T.L., et al., Effects of Photoperiod During the Dry Period on Prolactin, Prolactin Receptor, and Milk Production of Dairy Cows; Journal of Dairy Sci. 88: 121-127; American Dairy Sci. Assoc., 2005.

Bailey, T. et al., Milk Production Evaluation in First Lactation Heifers; 1999 Virginia Cooperation Extension/Dairy Science Publication 404-285.

Belloin, J.C., Milk and Dairy products: prduction and processing costs Food and Agriculture Organization of United Nations Rome 1988 FAO; web page where found: www.fao.org/docrep/003/x691e/X6931E00.htm.

Kume, Shin-ichi; Dept of Animal Nutrition National Institute of Animal Industry Tsukuba 305, Japan The Dairy Industry $in Asia B. Japan; www.agnet.org/library/article/eb384b.html.

Crichton,E. et al., 347 Artificial Insemination of Lactating Holstein Cows with sexed sperm: Abstract CSORP Publishing—Reproduction, Fertility and Development www.publish.csiro.au/nid/44/paper/RDv18n2Ab347.htm.

Lopez, H. et al., Relationship Between Level of Milk Production and Multiple Ovulation in Lactating Dairy Cows Journal of Dairy Sci. 88:2783-2793; American Dairy Science Association, 2005.

Managing the Dairy Cow During the Dry Period; Dairy Cattle Production 341-450A; Macdonald Campus of McGill University/Faculty of Agricultural & Environmental Sciences/Department of Animal Science.

Milk Production and Biosynthesis University of Guelph/Dairy Science and Technology (1998) www.foodsci.uoguelph.ca/dairyedu/biosyntheses.html.

Milk Production, Released Jul. 18, 2006, by the National Agricultural Statistics Service (NASS), Agri. Stats. Board, US Dept of Agri.

De Vries, A. Economic Value of Pregnancy in Dairy Cattle Journal of Dairy Sci. 89:3876-3885/American Dairy Sci. Assoc. 2006.

Garner, D.L. et al., Viability Assessment of Mammalian Sperm Using SYBR-14 and Propidium Lodide, 1996, Biology of Reproduction, vol. 53, pp. 276-284.

Wong, P.Y.D., et al. Potassium Movement During sodium-Induced Motility Initiation in the Rat Caudal Epididymal Spermatozoa; Biology of Reproduction 28, 206-212 (1983).

Shirai, H., et al. Regulation of Sperm Motility in Starfish; Development, Growth, and Differentiation; 24, (5), 419-428 (1982).

Padilla, A.W. et al. Extender and Centrifugation Effects on the Motility Patterns of Slow-Cooled Stallion Spermatozoa; J. Anim. Sci 1991, 69:3308-3313.

Ohta H., et al., Acquisition and Loss of Potential for Motility Ofspermatozoa of the Japanese Eel Anguilla Japonica, National Research Institute of Aquaculture, UNJR Aquiculture; 28th Panel Proceedings (1999).

Morisawa, M. The Process of the Initiation of Sperm Motility; Laboratory of Physiology, Ocean Research Institute, University of Tokyo (1986).

McGrady, A.V., et al. Cholinergic Effects on Bull and Chimpanzee Sperm Motility; Biology of Reproduction 15, 248-253 (1976).

Klinc, P. Dissertation—Improved Fertility of Flowcytometrically Sex Selected Bull Spermatozoa , School of Veterinary Medicine Hanover Germany, 2005.

Jones, J.M. et al Acidification of Intracellular pH in Bovine Spermatozoa Suppresses Motility and Extends Viable Life, Journal of Andrology, vol. 21, No. 5, Sep./Oct. 616-624.

Jenkins, A. D., et al. Concentrations of Seven Elements in the Intraluminal Fluids of the Rat Seminiferous Tubules, ReteTestis, and Epididymis; Biology of Reproduction 23, 981-987 (1980).

Darszon, A., et al. Ion Channels in Sperm Physiology, Physiological Reviews, vol. 27, No. 2, Apr. 1999.

Christen, R., et al. Metabolism of Sea Urchin Sperm, the Journal of Biological Chemistry, vol. 25, No. 9, Issue of May 10, pp.

Babcock, D. F., et al. Potassium-dependent increases in cytosolic pH stimulate metabolism and motility of mammalian sperm, Proc. Natl. Acad. Sci. USA, vol. 80, pp. 1327-1331, Mar. 1983.

Zilli, L., et al. Adenosine Triphosphate Concentration and -D-Glucuron idase Activity as Indicators of Sea Bass Semen Quality; Biology of Reproduction 70,1679-1684 (2004).

Hanania, E. G, et al. A novel Automated Method of Scanning Cytometry and Laser-Induced Necrosis Applied to Tumor Cell Purging, Blood. Nov. 15, 1999, vol. 94, No. 10, suppl 1 part 1.

Purdy, P. H. et al., Effect of Adding Cholesterol to Bull Sperm Membranes on Sperm Capacitation, the Acrosome Reaction, and Fertility, Biology of Reproduction 71, 522-527 (2004).

Purdy, P. H. et al., Effect of cholesterol-loaded cyclodextrin on the cryosurvival of bull sperm, Cryobiology 48 (2004) 36-45.

Moce E., et al., Cholesterol-loaded cyclodextrins added to fresh bull ejaculates improve sperm cryosurvival, J. Anim. Sci, 2006, 84:826-833.

Ereth, B.A., et al. Integration of Early Weaning and Sexed Semen into a Single-Calf Heifer System to Increase Value of Non-Replacement Heifers; Proceedings, Western Section, American Society of Animal Science, vol. 51,441-443, Jun. 2000.

Ereth, B.A., et al. Integration of Early Weaning and Sexed Semen into a Single-Calf Heifer System to Increase Value of Non-Replacement Heifers; Abstract Only, Journal of Animal Science, vol. 78, Supplement 2, 2000.

Bavister, B.D. et al., The effects of Sperm Extracts and Energy Sources on the Motility and Acromosome Reaction of hamster Spermatozoa in vitero; Biology of Reproduction 16, 228 237 (1997).

Fattouh, El-S.M. et al., Effect of Caffine on the Post-Thaw Motility of Buffalo Spermatozoa; Theriogenology, Jul. 1991, vol. 36 No. 1.

Koh-ichi Hamano, et al., Gender Preselection in Cattle with Intracytoplasmically injected, flow cytometrically sorted sperm heads, Biology of Reproduction 60, 1194-1197 (1990).

Hollinshead, F.K. et al., Birth of lambs of pre-determined sex after in vitro production of embryos using frozen-thawed sex-sorted and re-frozen-thawed ram spermatozoa, Reproduction (Cambridge, England) May 2004, vol. 127, o. 5, pp. 557-568.

Nikkei Biotech, Supplement, Latest Information of Biological Instruments and Reagents, 1988, pp. 93-94.

Pursley, J.R. et al., Reproductive Management of Lactating Dairy Cows Using Synchronization of Ovulation; 1997 J. Dairy Sci 80:301-306.

Bagnato, A., Genetic and Breeding; Phenotypic Evaluation of Fertility Traits and Their Association with Milk Production of Italian Friesian Cattle; 1994 J. Dairy Sci 77:874-882.

Panskowski, J., A., et al. Use of Prostaglandin F2a as a Postpartum Reproductive Management Tool for Lactating Dairy Cows; 1995 J. Dairy Sci 78:1477-1488.

Scipioni, R. L., et al., Short Communication: An Electronic Probe Versus Milk Protesterone as Aids for Reproductive Management of Small Dairy Herds; 1999 J. Dairy Sci 82:1742-1745.

Fricke, P. M., Scanning the Fugure—Ultrasonography as a Reproductive Management Tool for Dairy Cattle; J. Dairy Sci 85:1918-1926.

Grant, V. J., et al., Sex-Sorted Sperm and Fertility: An Alternative View; Biology of Reproduction 76, 184-188 (2007).

Garner, D. L., Sex-Sorting Mamallian Sperm: Concept to Application in Aminals; Journal of Andrology, vol. 22, No. 4 Jul./Aug. 2001.

Tubman, L.M. et al., Characteristics of calves produced with sperm sexed by flow cytometry/cell sorting; 2004 Amer. Society of Animal Sciences; 82:1029-1036.

Weigel, K. A., Exploring the Role of Sexed Semen in Dairy Production Systems; J. Dairy Sci. 87: (E.Suppl.): E120-E130; 2004 American Dairy Science Assoc.

Ferre, L., In vitro-derived embryo production with sexed and unsexed semen from different bulls; Reproduction Fertility and Development, vol. 16, Part 1/2, p. 253, 2004.

Dalton, J.C., et al., Effect of Time of Insemination on Number of Accessory Sperm, Fetilizationate Rate, and Embryo Quality in Nonlactating Dairy Cattle. J Dairy Sci. 84:2413-2418.

Dransfield, M.B.G., et al., Timing of Inseminatio for Dairy Cows Identified in Estrus by a Radiotelemetric Etrus Detection System. 1998 J Dairy Sci. 81: 1874-1882.

Maatje, K. et al. Predicting Optimal Time of Insemination in Cows that Show Visual Signs of Estrus by Estimating onset of Estrus with Pedometers.

(56) References Cited

OTHER PUBLICATIONS

Nebel, R.L. et al. Timing of Artificial Insemination of Dairy Cows: Fixed Time Once Daily Versus Morning and Afternoon 1994 J Dairy Sci. 77:3185-3191.

Pursley, J. Richard, et al. Effect of Time of Artificial Insemination on Pregnancy Rates, Calving Rates, Pregnancy Loss, and Gender Ratio After Synchronization of Ovulation in Lactating Dairy Cows. 1998 J Dairy Sci. 81: 2139-2144.

Rozeboom, K. J. et al. Late Estrus or Metestrus Insemination After Estrual Inseminations Decreases Farrowing Rate and Litter Size in Swine J. Animal Sci. 1997. 75: 2323-2327.

Peeler, I. D. et al. Pregnancy Rates After Times AI of Heifers Following Removal of Intravaginal Progesterone Inserts, J. Dair Sci., 87:2868-2873; 2004.

Rath, D. Low Dose Insemination in the Sow—A Review, Reprod. Dom Anim. 37, 201-205 (2002) www.blackwell.de/synergy.

Lukaszewicz, M. et al. Attempts on freezing the Greylag (Anser anser L.) gander semen Animal Reproduction Science 80 (2004) 163-173.

Foote, R. H. et al. Sperm Numbers Inseminated in Dairy Cattle and Nonreturn Rates Revisited 1997 J Dairy Science 80:3072-3076.

Conley, H.H. et at. Intensification by Intrauterine Devices of Sperm Loss from the Sheep Uterus Biology of Reproduction 2, 401-407 (1970).

Chrenek, Peter et al. Fertilizing Capacity of Transgenic and Non-Transgenic Rabbit Spermatozoa after Heterospermic Insemination Bull Vet. Inst. Pulawy 49, 307-310, 2005.

Bakst, Murray R. Fate of Fluorescent Stained Sperm following Insemination: New Light on Ovicucal Sperm Transport and Storage in the Turkey.

Johnson L.A., et al. use of boar spermatozoa for artificial insemination, II. Fertilization Capacity of fresh and frozen spermatozoa in gilts inseminated either at a fixed time or according to walsmeta readings, Journal of Animal Science, vol. 54 No. 1, 1982 pp. 126-131.

Pursel, V. G., et al. Distribution and morphology of fresh and frozen-thawed sperm in the reproductive tract of gilts after artificial insemination; Biology of Reproduction 19, 69-76 (1978).

Rath, D., "On the Status of Sex-Specific Sperm Sorting" Review lecture ET Conference 2002, Department of Animal Production and Animal Behaviour, Mariensee, Germany.

Grossfeld, R., "Experiments to Improve the Quality of Sex-Sorted Fresh and Frozen Porcine Spermatozoa" PhD thesis of the Faculty of Agricultural Sciences, Georg-August University, Gottingen, May 2007.

de Graaf, S.P. et al., Birth of offspring of pre-determined sex after artificial insemination of frozen-thawed, sex-sorted and re-frozen-thawed ram spermatozoa, Theriogenology, 67 (2007) 391-398.

O'Brien, J.K. et al., Development fo sperm sexing and associated assisted reproductive technology for sex preselection of captive bottlenose dolphins, Reproduction Fertility and Development, 2006, 18, 319-329.

Zhang, M, et al., In vitro fertilization with flow-sorted buffalo sperm, Reproduction Fertility and Development, 2005, 18(2), 283-284.

Schenk, J.L. et al., Insemination of cow elk with sexed frozen semen, 2003 Theriogenology 59, 514.

BD Biosciences Brochure, BD FACSCalibur Flow Cytometer, the Automated, Multicolor Flow Cytometry System, 2006.

Johnson, L. A. et al., Cryopreservation of flow cytometrically sorted boar sperm: effects on in vivo embryo developmen; J. Anim Sci. vol. 78, Suppl 1/J. Dairy Sci., vol. 83, Suppl 1, 2000.

Lindsey, A., et al., "Hysteroscopic Insemination of Fresh and Frozen Unsexed and Sexed Equine Spermatozoa", pp. 152-153, Proc. 5th Int. Symp. Equine Embryo Transfer, p. 13, 2000.

Presicce, G.A., et al., First established pregnancies in mediterranean italian buffaloes (bubalus bubalis) following deposition of sexed spermatozoa near the utero tubal junction, Reproduction in Domestic Animals, vol. 40, No. 1, Feb. 2005 , pp. 73-75(3).

Dielemann, S.J., Superovulation in cattle: from understanding the biological mechanisms to genomics of the oocyte; 23rd Annual Meeting A.E.T.E.—Alghero; Sep. 2007.

Hasler, J. F., Factors influencing the success of embryo transfer in cattle; 23rd World Buiatrics Congress, Quebec, Canada Jul. 2004.

Mapletoft, R. J. et al., Superovulation in perspective, Bioniche Animal Health, Dec. 2002.

Bahr, G.F. et al., Considerations of volume, mass, DNA, and arrangement of mitochondria in the midpiece of bull spermatozoa, Experimental Cell Research 60 (1970) 338-340.

Baumber, J., et al., "The Effect of Reactive Oxygen Species on Equine Sperm Motility, Viability, Acrosomal Integrity, Mitochondrial Membrane Potential, and Membrane Lipid Peroxidation", 2000, Journal of Andrology, vol. 21 (6),pp. 895-902.

BD LSR II Flow Cytometer, BD Biosciences Clontech Discovery labware Immunocytometry systems Pharmingen Jan. 28, 2004.

Bermudez, D.et al., The immediate effect of IR, laser radiation on rat , germ, cells, was studied by cytophotometric quantification, Scisearch 2001.

Sequent Biotechnologies Inc., Welcome to the Sequent Biotechnologies Inc. website., http://www.sequentbiotech.com/ Dec. 6, 2003.

Brooks, D.E., Manipulation of Mammalian Gametes in Vitro, Biennial Report, Waite Agricultural Research Institute 1986-1989.

Bruemmer, J.E. et al., "Effect of Pyruvate on the Function of Stallion Spermatozoa Stored for up to 48 Hours", Journal of Animal Science 2002, vol. 80*1, pp. 12-18.

Catt, S.L. et al., Hoechst staining and exposure to UV laser during flow cytometric sorting does not affect the frequency of detected endogenous DNA nicks in abnormal and normal human spermatozoa, Molecular Human Reproduction vol. 3 No. 9 pp. 821-825,(1997).

Chaudhry, P., et al., Casein Kinase II activity and polyamine-stimulated protein phosphorylation of cytosolic and plasma membrane protiens in bovine sperm, Archives of Biochemistry and Biophyeics vol. 271, No. 1 pp. 98-106, May 15, 1989.

Chen, Y. et al., Effects of sucrose, trehalose, hypotaurine, tauririe, and blood serum on survival of frozen bull sperm, Cryobiology 30,423-431 (1993).

Chapter 16 Semen processing, storage, thawing, and handling, http://nongae.gsnu.ac.kr/~cspark/teaching/chap16.html Sep. 23, 2002.

Conover,J. et al., Pre-loading of mouse oocytes with DNA-specific fluorochrome (Hoechst 33342) permits rapid detection of sperm-oocyte fusion, Journals of Reproductive & Fertility Ltd. 82, 681-690 (1988).

Cressman, B.E. MD, et al., Effect of sperm dose on pregnancy rate from intrauterine insemination: a retrospective analysis, Texas Medicine, 92:74-79 (1996).

Crissman, H.A. et al., Use of DIO-C5-3 to improve hoechst 33342 uptake, resolution of DNA content, and survival of CHO cells, Experimental cell research 174: 338-396 (1988).

Graves, C.N., et al., "Metabolism of Pyruvate by Epididymal-Like Bovine Spermatozoa", 1964 Journal of Dairy Science vol. 47 (12), pp. 1407-1411.

Certified Semen Services, CSS Minimum requirements for disease control of semen produced for AI, http://www.naab-css.org/about_css/disease_control-2002.html Sep. 22, 2003.

Culling, "Handbook of nown Histopathological and Histochemical Techniques, "3rd Ed., Butterworths, pp. 192.

De Grooth, B. et al., Simple delay monitor for droplet sorters, Cytometry 12:469-472 (1991).

Lodge, J.R., et al., "Carbon Dioxide in Anaerobic Spermatozoan Metabolism" 1968, Journal of Dairy Science, vol. 51(1), pp. 96-103.

Delgado,N. et al., Correlation between sperm membrane destabilization by heparin and aniline blue staining as membrane integrity index, Archives of Andrology40:147-152 (1998).

Denniston, D.J. et al., "Effect of Antioxidants on the Motility and Viability of Cooled Stallion Spermatozoa", Journal Reproduction Supplement 56, 2001, pp. 121-126.

Donoghue, A. et al., Effects of water- and lipid-soluble antioxidants on turkey sperm viability, membrane integrity, and motility during liquid storage, Poultry Science 76:1440-1445 (1997).

Durack, Gary; "Cell-Sorting Technology", Emerging Tools for Single-cell Analysis, Chapter 1 pp. 1-359.

Zucker, R. et al., Utility of light scatter in the Morphological analysis of sperm, Cytometry 13:39-47 (1992).

(56) References Cited

OTHER PUBLICATIONS

Ericsson, S. et al., Interrelationships among fluorometric analyses of spermatozoal function, classical semen quality parameters and the fertility of frozen-thawed bovine spermatozoal, Theriogenology 39:1009-1024 (1993).

Ericsson, et al. "Flow Cytometric Evaluation of Cryopreserved Bovine Spermatozoa Processed Using a New Antiobiotic Combination", Theriogenology, 1990, vol. 33(6), pp. 1211-1220.

Cho, et al. A microfluidic device for separating motile sperm from nomotile sprem via inter-streamline crossings.

Ericsson, R. et al., Functional differences between sperm bearing the X- or Y-chromosome.

Esteves, S. et al., Improvement in motion characteristics and acrosome status in cryopreserved human spermatozoa by swim-up processing before freezing, Human Reproduction vol. 15 No. 10 pp. 2173-2179 (2000).

Evenson, D.et al., Physiology and Management, Rapid determination on sperm cell concentration in bovine semen by flow cytometry, J Dairy Sci. 76: 86-94 (1993).

Farrell et al., "Quantification of Bull Sperm Characteristics measured by Computer-Assisted Sperm Analysis (CASA) and the Relationship of Fertility", Theriogenology, 1998, vol. 49 (4), pp. 871-879.

Fitzgerald, D., Cell sorting: An enriching Experience, The Scientist Jul. 23, 2001.

Foote,R., The history of artificial insemination: Selected notes and notables, American Society of Animal Science (2002).

Foote, R., Functional differences between sperm bearing the X- or Y-chromosome.

Garner, D., Past, Present and future perspectives on sexing sperm, CSAS Symposium SCSA: 67-78.

Johnson, L. et al., Sex preselection in mammals by DNA: A method for flow separation of X and Y Spermatozoa in humans.

Johnson, L. et al., Recent advances in sex preselection of cattle: Flow cytometric sorting of X-&Y-chromosome bearing sperm based on DNA to produce progeny, Theriogenology 41:51-56 (1994).

Ashwood-Smith, M., Debate Human sperm sex selection, Human Reproduction vol. 9 No. 5 pp. 757-759 ( 1994).

Pinkel,D.et al.,Flow cytometry of mammalian sperm progress in DNA and morphology measurement, The Journal of Histochemical and Cytochemistryvol.27 No. 1 pp. 353-358 (1979).

Fugger, E. et al., Birth of normal daughters after MicroSort sperm separation and intrauterine insemination, in-vitro fertilization, or intracytoplasmic sperm injection, http://www.microsort.net/HumRepro.htm Mar. 19, 2003.

Johnson, L. et al., Flow sorting of X and Y Chromosome-bearing Mammalian sperm: Activation and pronuclear development of sorted bull, boar, and ram sperm microinjected into hamster oocytes, Gamete Research 21:335-343 (1988).

Salisbury, G.W., et al., Reversal by Metabolic Regulators of $CO_2$-induced Inhibition of Mammalian Spermatozoa, 1959, Proc Soc Exp Biology Med, vol. 101 (1) pp. 187-189.

Centola, G.et al., Cryopreservation of human semen. Comparison of cryopreservatives, sources of variability, and prediction of post-thaw survival. PMID: 1601749 May-Jun. 1992.

Bencic, D.C., et al., "Carbon Dioxide Reversibly Inhibits Sperm Motility and Fertilizing Ability in Steelhead (Oncorhynchus mykiss)" 2000, Fish Physiology and Biochemistry, vol. 23(4), pp. 275-281.

Boatman, D.E. et al., "Bicarbonate Carbon Dioxide Regulation of Sperm Capacitation Hyperactivated Motility and Acrosome Reactions", 1991, Biology of Reproduction vol. 44(5), pp. 806-813.

Garcia, M.A. et al., "Development of a Buffer System for Dialysis of Bovine Spermatozoa Before Freezing III.Effect of Different Inorganic and Organic Salts on Fresh and Frozen-Thawed Semen", 1989, Theriogenology, vol. 31(5),pp. 1039-1048.

Courtens, J. et al., Numerical simulation for freezing and thawing mammalian spermatozoa. Evaluation of cell injuries at different depths in bags or straws during all steps of the technique.

Eiman, M.et al., Trehalose-enhanced fluidity of the goat sperm membrane and its protection during freezing, Biology of Reproduction 69: 1245-1250 (2003).

Foote, R.et al., Physiology and Management, Fertility of bull spermatozoa frozen in whole milk extender with trehalose, taurine, or blood serum, J. Dairy Sci. 76:1908-1913 (1993).

Johnson, L. et al., Storage of bull semen, Animal Reproduction Science 62: 143-172 (2000).

Johnson, L. et al.,Erratum to "Storage of bull semen", Animal Reproduction Science 62: 143-172 (2000).

McNutt,T.et al., Electrophoretic gel analysis of Hoechst 33342 stained and flow cytometrically sorted bovine sperm membrane proteins, Reprod. Dom Anim.31: 703-709 (1996).

Van der Werf, Julius, An overview of animal breeding programs; Animal Breeding Use of New Technologies (This is a Post Graduate Foundation Publication).

Best, T. P. et al. "Nuclear Localization of Pyrrole-Imidazole Ployamide-Flourescein Conjugates in Cell Culture", PNAS, 2003, vol. 100(21), pp. 12063-12068.

Gygi, M.P., et al. "Use of Fluorescent Sequence-Specific Polyamides to Discriminate Human Chromosomes by Microscopy and Flow Cytometry", Nuci Acids Res. 2002, vol. 30(13),pp. 2790-2799.

Young, L.et al., Prolonged feeding of low levels of zearalenone to young boars.

BD Biosciences, BD AccuDrop Potion, www.bdbiosciences.com, Sep. 2002.

Agarwal, A.et al., Filtration of spermatozoa through L4 membrane:a new method, Fertility and Sterility, vol. 6, No. 6, Dec. 1991.

Anzar, M.et al., Optimizing and Quantifing fusion of liposomes to mammalian sperm using resonance energy transfer and flow cytometric methods, Cytometry49:22-27 (2002).

Anzar, M.et al., Sperm Apoptosis in fresh and cryopreserved bull semen detected by flow cytometry and it's relationship with fertility, Biology of Reproduction 66: 354-360 (2002).

Arav, A.et al., New trends in gamete's cryopreservation, Molecular and Cellular Endocrinology 187:77-81 (2002).

Arndt-Jovin et al., "Analysis and Sorting of Living Cells According to Deoxyribonucleic Acid Content", Journal Histochem. and Cytochem., 1977, vol. 25(7), pp. 585-589.

Arts,E.et al.,Evidence for the existence of lipid-diffusion barriers in the equatorial segment of human spermatozoa, Boichem J.384:211-218 (1994).

Garner,D. et al., Spermatozoa and Seminal Plasma, Reproduction in farm animals 7th edition.

Gadella B,et al., Dynamics in the membrain organization of the mammalian sperm cell and functionality in fertilization, Vet Quart. 21:142-146 (1999).

Garner, D.et al., Chromatin stability in sex-sorted sperm, VII International Congress of Andrology.

Garner,D. et al., Morphological and ultrastrutural Characterization of mammalian spermatozoa processed for flow cytometric DNA analyses, Gamete Research 10:339-351 (1984).

Garner, D., et al., Effect of hoechst 33342 staining and laser illumination on the viability of sex-sorted bovine sperm, Theriogenology, vol. 57 No. 1, 1-810 (2002).

Garner, D. et al., Assessment of spermatozoal function using dual fluorescent staining and flow cytometric analyses, Biology of Reproduction 34:, 127-138 (1986).

Gebhard D., Sorting Viability . . . one more time, http://www.cyto.purdue.edu/hmarchiv/1998/2263.htm Feb. 14, 2004.

Givan,A., Flow Cytometry First Principles, (1992).

Gledhill, B.et al., Identifying and separating X- and Y- Chromosome-bearing mammalian sperm by flow cytometry, Lawrence Livermore National Laboratory, Feb. 8, 1984.

Gledhill, B.et al., Identifing X- and Y- chromosome- bearing sperm by DNA content:Retrospective perspectives and prospective opinions'.

Gledhill, B.et al., Flow microflurometric analysis of sperm DNA contemt: Effect of cell shape on the fluorescence distribution, J. Cell Physiol.87: 367-378.

Gledhill, B.et al., Flow cytometry and sorting of sperm and male germ cells, Flow Cytometry and sorting, second edition, pp. 531-551 (1990).

(56) References Cited

OTHER PUBLICATIONS

Gordon et al., "Genetic Transformation of Mouse Embryos by Microinjection of Purified DNA", Proc. Natil Acad. Sci., 1980, vol. 77 (12), pp. 7380-7384.
Graham, J.et al.,Analysis of sperm cell viability, Acrosomal integrity, and Mitocondrial function using flow cytometry, Biology of Reproduction 43: 55-64 (1990).
Graham, J.et al., Effect of some Zwitter Ion buffers on freezing and storage of spermatozoa I, Bull, J. Dairy Sci 55: 372-378 ( 1992).
Grogan, W. et al., DNA Analysis and sorting of viable mouse testis cells, The Journal of Histochemistry and Cytochemistry, vol. 29 No. 6 pp. 738-746, (1981).
Guthrie, et al., "Flow Cytometric Sperm Sorting: Effects of Varying laser Power on Embryo Development in Swine", Mol. Reprod. and Develop., 2002,vol. 61 (1), pp. 87-92.
Hacker-Klom, U.B., et al., Effect of doxorubicin and 4'-epi-doxorubicin on mouse spermatogenesis. Mutation Research International Journal on Mutagenesis vol. 159, pp. 39-46. 1986.
Hargrove, T. et al., Special Techniques, Part B Cryopreservation, Chapter 11B.
Hasler, J., Symposium: Reproductive Technology and Genetic improvementJ. Dairy Sci. 75:2857-2879 (1992).
Held, A.et al., Quasi—CW Solid—state lasers Expand their reach, Photonics Spectra, Dec. 2002.
Hinkley, R.et al., Rapid visual detection of sperm-egg fusion using the DNA-Specific Fluorochrome Hoechst 33342, Developmental Biology 118: 148-154 (1986).
Januskauskas, A.et al.,Assessment of sperm quality through Fluorometry and sperm chromatin structure assay in relation to field fertility of frozen-thawed semen from Swedish Al bulls, Theriogenology 55: 947-961 (2001).
Jeyendran, R.S. et al., Effect of glycerol and cryopreservation on oocyte penetration by human spermatozoa, PMID: 4025843, Jul. 6, 2006.
Johnson, L., A flow cytometric/ sorting method for sexing mammalian sperm validated by DNA analysis and live births, Cytometry, p. 42 of supplement , Sep. 4, 1990.
Johnson, L., Flow sorting of intact X & Y chromosome-bearingmammalian spermatozoa, The Journal of the Society for Analytical Cytology Cytometry, (1988).
Zhang,M. et al., Development of bovine embryos after in vitro fertilzation of oocytes with a flow cytometrically sorted, stained and unsorted sperm from different bulls, Theriogenology 60: 1657-1663 (2003).
Jones,R.et al., Effect of Osmolality and Phosphate, "Tris", "Tes", "Mes", nd "Herpes" Hydrogen ion buffers on the motility of bull spermatozoa stored at 37 or 5∘C, Ausi J. Biol. Sci.25:1047-1055 (1972).
Jones,R., Plasma membrane structures and remodelling during sperm maturation in the epididymis, Journal of Reproduction and Fertility (1998).
Gerrits, Roger J. Application of Biotechnology to Animal Production US Dept. of Agriculture, Beltsville Maryland.
Johnson, L., Separation of X and Y ChiOmosome-bearing mammalian sperm by DNA content cytometric analysis and sorting, US Department of Agriculture.
Johnson, M.,The Macromolecular Organization of membranes and its bearing on events leading up to Fertilization, Journal of Reproduction and Fertility (1975).
Johnson, L., Verified Sex Pre-Selection in Farm Animals.
Johnson, L., Prograss towards achieving sex preselection in farm animals, USDA Agricultural Research Service, (1989).
Keeler, K.et al., Flow microfluorometric analysis of living spermatozoa stained with Hoechst 33342, J. Reprod.Fert. 68:205-212 (1983).
Keij, J.et al., High speed Photodamage cell sorting: An evaluation of the Zapper Prototype, Methods in cell Biology vol. 42, (1994).
Kirchhoff, C.et al., The Molecular biology of the sperm surface:Post-Testicular Membrane Remodelling, The Fate of the Male Germ Cell, (1997).

Krueger, C.et al.,Low dose Insemination in synchronized gilts, Theriogenology 52: 1363-1373 (1999).
Landetie,J.,Induction and survival of micronuclei in rat spermatids. Comparison of two meiotic micronucleus techniques using cyclophosphamide, Mutation Research, 203:47-53 (1988).
Laser Innovations—Applications, http://www.laserinnovations.com/488nm.htm Feb. 2, 2004.
Libbus, B.et al.,Incidence of chromosome aberrations in mammalian sperm stained with Hoechst 33342 and UV-laser irradiated during flow sorting, Mutation Research, 182: 265-274 (1987).
Loken, M., Separation of viable T and B lymphocytes using a cytochemical stain, Hoechst 33342, The Journal of Histochemistry and Cytochemistry,vol. 28, No. 1, pp. 36-39 (1980).
Lucas, J.et al., Orientation measurments of microsphere doublets and metaphase chromosomes in flow, Cytometry 7:575-581 (1986).
Luttmer, S.et al.,Examination of living and fixed gametes and early embryos stained with supravital fluorochromes (Hoechst 33342 and 3,3'-dihexyloxacarocyanine Iodide), Gamete Research 15:267-283 (1986).
Masaki, J.et al., Effect of bull seminal plasma on the membrane characteristics of boarepididymal spermatozoa.
Maxwell, W.et al.,Physiology of spermatozoa at high dilution rates:the influence of seminal plasma, Theriogenology 52: 1353-1362 (1999).
Mazur, P., The role of Intracellular freezing in the death of cells cooled at supraoptimal rates, Cryobiology 14:251-272 (1977).
McSweeney,K.et al., Abstract: Insemination of lactating holstein cows with sexed frozen/thawed sperm, http://www.cvmbs.colostate.edu/physio/abstract/ges12.html Mar. 16, 2004.
Medeiros,C. et al., Current status of sperm cryopreservation: Why isn't it better? Theriogenology 57: 327-344 (2002).
Meistrich, M., Potential and limitations of physical methods for separation of sperm bearing an X- or Y- chromosome.
Meistrich, M.et al., "Cytogenetic" studies of spermatids of mice carrying Cattanach's translocation by flow cytometry, Chromosoma 74:141-151 (1979).
Morrell, J. et al., Offspring from inseminations with mammalian sperm stained with Hoechst 33342, either with or without flow cytometry, Mutation Research 224:177-183 (1989).
Morrell et al.,"Sexing of Sperm by Flow Cytometry", The Veterinary Record, 1988, pp. 322-324.
Morrier, A.et al., Glycerol addition and conservation of fresh and crypreserved ram spermatozoa, Canadian Journal of AnimalScience, Sep. 2002http://pubs.nrc-cnrc.gc.ca/aic-journals/2002ab/cjas02/sep02/cjas01-045.html.
Moruzzi, J., Selecting a mammalian species for the separationof X- and Y- chromosome-bearing spermatozoa, J. Reprod. Fert. 57:319-323 (1979).
Murthi S. et al., Improved data acquisition system for digital flow cytometry, (2002).
Gwo-Bin, L.et al., Multi-cell-line micro flow cytometers with buried SU-8/SOG Optical waveguides, Feb. 2002.
OcanaQuero, J.et al., Biological effects of helium-neon irradiation on acrosome reaction in bull, Scisearch Journal of Photochemistry and Photobiology, vol. 40 No. 3, pp. 294-298 (1997).
Pangawkar, G. et al., Physical and biochemical characteristics of semen in relation to fertility of Holstein-Friesian bulls, Indian vet. Med.J. vol. 13: 21-26 (1989).
Papa, S. et al., Chromatin organization in Isolated nuclei: Flow cytometric characterization employing forward and perpendicular light scatter, Cell Biochemistry and Function vol. 6: 31-38 (1988).
Parks, J. et al., Lipids of plasma membrane and outer acrosomal membrane from bovine spermatozoa, Biology of Reproduction 37:1249 -1258 (1987).
Parks, J. Processing and handling bull semen for artificial insemination—Don't add insult to injury!, Department of Animal Science Cornell University.
Partec, Taking flow cytometry to the next generation, Catalogue 2001-2002.
Perez-Pe, R.et al., Semen plasma proteins prevent cold shock membrane damage to ram spermatozoa, Theriogenology 56 (3) : 425-434, Aug. 1, 2001, PMID: 11516122 http.//www.ncbi.nlm.nih.gov/entrez/query.fcgi?CMD=search&DB=pubmed.

(56) References Cited

OTHER PUBLICATIONS

Peter, A. et al., Fractionation of bovine spermatozoa for sex selection: A rapid immunomagnetic technique to remove spermatozoa that contain the H-Y antigen, Theriogenology 40:1177-1185 (1993).

Petersen, Timothy W., et al, Stability of the Breakoff Point in a High-Speed Cell Sorter The Journal of the international society for Analytical Cytology, vol. 56A No. 2, Dec. 2003.

Pinkel Dan, Flow Cytometry and Sorting Analytical Chemistry, Mar. 1982 vol. 54 No. 3.

Pinkel Dan, Cytometric Analysis of Mammalian Sperm for Induced Morphologic and DNA Content Errors; Biological Dosimetry (Cytometric Approaches to Mammalian Systems) 1984.

Pinkel, D. et al; Radiation-Induced DNA Content Variability in Mouse Sperm. Radiation Research an International Journal, vol. 95, No. 3, Sep. 1983.

Piumi, F. et al., Specific cytogenetic labeling of bovine spermatozoa bearing X or Y chromosomes using florescent in situ hybridization (FISH), Genet, Sel. vol. 33: 89-98 (2001).

Polge, C., Low-temperature storage of mammalian spermatozoa, Unit of Reproductive Physiology and Biochemistry, Cambridge.

Edited by Bell-Prince, C., NFCR Newsletter, http://www.ls.lanl.gov/NFCR/newsletter-Oc98/oct98.html Jan. 6, 2004, Rasul, Z.et al., Changes in motion characteristics, plasma membrane integrity, and acrosome morphology during cryopreservation of buffalo spermatozoa, Journal of Andrology, vol. 22 No. 2, Mar. 4, 2001.

Rees, William A., et al,Betaine Can Eliminate the Base Pair Composition Dependence of DNA Melting; Biochemistry 1993, 32, pp. 137-144.

Rens, W.et al.,An X-Y paint set and sperm FISH protocol that can be used for validation of cattle sperm separation procedures, Journals of Reproduction and Fertility, 121: 541-546 (2001).

Reyes-Mereno, C.et al., Characterization of Secretory Proteins from cultured Cauda Epididymal Cells that significantly sustain bovine sperm motility, Molecular Reproduction and Development 63: 500-509 (2002).

Rippel,N. et al., Transcervical insemination: Effects of variation in total sperm number/dose on fertility, 83rd Annual Fall Conference for Veterinarians, Oct. 2002.

Rizzo, W. et al.,Liposome-mediated transfer of simian virus 40 DNA and minichromosome into mammalian cells, J. Gen. Virol 64:911-919 (1983).

Ruch, F., Determination of DNA content by microfluorometry, Introduction to Quanitative Cytochemistry, pp. 281-294 (1966).

Saacke, R.et al., Semen Quality test and their relationship to fertility, 4th National Association of Animal Breeders, (1972).

Salisbury, G.W.,et al."Preservation of Bovine Spermatozoa in Yolk-Citrate Diluent and Field Results from its Use", Journal of Dairy Science, 1941, vol. 24(11),pp. 905-910.

Schroter, S.et al., The glycocalyx of the sperm surface, Human Reproduction Update: vol. 5, No. 4, pp. 302-313 (1999).

Schuster, T. et al., Isolation of motile spermatozoa from semen samples using microfluidics, Reproductive BioMedicine Online,vol. 7 No. 1 75-81,www.rbmonline.com/Article/847, Apr. 16, 2003.

Seidel, George E. Jr. "What about sexed semen?" Hoard's Dairyman, The National Dairy Farm Magazine, May 10, 2001.

Sexing Technologies, Welcome to sexing Technologies, http://www.sexingtechnologies.com/ Dec. 11, 2003.

Shapiro, Howard M. M.D.,Building Flow Cytometers Chapter 9. Practical Flow Cytometry, second edition, Property of Washington University Medical Library.

Sharpe, J. et al., Radially symmetric excitation and collection optics for flow cytometric sorting of aspherical cells, Cytometry, 29:363-370 (1997).

Shapiro, H., Re: cheap laser idea??, http://www.cyto.purdue.edu/hmarchiv/1998/1015.htm Feb. 2, 2004.

Smith, P.et al., Characteristics of a Novel Deep Red/ Infrared Fluorescent Cell-Permeant DNA Probe, DRAQ5, in Intact human Cells Analyzed by Flow Cytometry, Confocal and Multiphoton Microscopy, Cytometry 40:280-291 (2000).

Stanger, J.et al., The Relationship between motility and the FITC-BSA binding Properties of Mouse epididymal spermatozoa, The Journal of Experimental Zoology 227: 323-327 (1983).

Stanic,P. et al.,Comparison of protective media and freezing techniques for cryopreservation of human semen, http://www.ncbi.nlm.nih.gov/entrez/query.fcgi?CMD=search&DB=pubmed , Jul. 11, 2000.

Stewart,R., Georgia Beef Challenge, Livestock Newsletter 1-Feb. 2002.

Takacs, T.et al.,Flow Cytometric determination of the sperm cell number in diluted bull semen samples by DNA staining method, Acta Biochim.Biophys.Hung. vol. 22 No. 1, pp. 45-57 (1987).

Thurston,L. et al., Identification of Amplified restriction fragment length polymorphism markers linked to genes controlling boar sperm viability following cryopreservation, Biology of Reproduction 66: 545-554 (2002).

Tone,S.et al., A method of vital staining of mouse eggs using Hoechst dye, Department of Developmential Biology (1986).

Tubman,L.et al., Abstract:Normality of calves resulting from sexed sperm, http://www.cvmbs.colostate.edu/bms/abstract/ges12.html Mar. 16, 2004.

Tucker,K.et al., Sperm separation techniques:Comparison of gradient products, Proceedings 2ed International workshop for Embryologists: Troubleshooting activities in the ART lab. (2002).

Van Dilla, M.et al., Measurement of Mammalian Sperm Deoxyribonucleic acid by Flow Cytometry, The journal of Histochemistry and Cytochemistry vol. 25 No. 7 pp. 763-773 (1977).

Vazquez, J.et al., Nonsurgical Uterotubal Insemination in the Mare, Reproduction: Mare vol. 44 (1998).

Vishwanath,R.et al., Storage of bovine semen in liquid and frozen state, Animal Reproduction Science 62: 23-53 (2000).

Washburn, S., Sex-Sorted Semen; Still several steps short of sensational, http://www.cals.ncsu.edu/an sci/extention/animal/news/apri196/april1965.html Mar. 16, 2004.

Welch,G.et al., Sex preselection: Laboratory Validation of the sperm sex ratio of Flow sorted X- and Y- sperm by sort reanal ysis for DNA, Theriogenology 52:1343-1352 (1999).

Welch, G.et al., Fluidic and optical modification to a facs IV for flow sorting of X&Y Chromosomes bearing sperm based on DNA, International Society for Analytical Cytology (1994).

Wiltshire, M.et al., A Novel Deep Red/ Low infrared fluorescent flow cytometric probe DRAQ5NO, For the Discrimination of intact nucleated cells in apoptotic cell populations, Cytometry 39: 217-223 (2000).

Woelders, H. et al., Effects of Trehalose and Sucrose, Osmolality oh the freezing medium, and cooling Rate on Viability and intactness of bull sperm after freezing and thawing, Cryobiology 35: 93-105 (1997).

Wolf, D., Lipid domains in sperm plasma membranes, Molecular Membrane Biology 12: 101-104 (1995).

Wolf, D.et al., Changes in sperm plasma membrane lipid diffusibility after hyperactivation during In vitro capacitation in the mouse, The Journal of Cell Biology, vol. 102: 1372-1377(1986).

Wolf, D.et al., Diffusion and regionalization in membranes of maturing ram spermatozoa,The Journal of Cell Biology, vol. 98:1678-1684 (1984).

XY Files, Issue 1 Jun. 1999.

XY, Inc. , Sex selection Procedure, http://www.xyinc.com/sex select.html, Feb. 21, 2003.

XY Files, Issue 4 Aug. 2000.

XY Files, Issue 2 Oct. 1999.

XY Files, Issue 3 Mar. 2000.

XY Files, Issue 5 Mar. 2001.

XY Files, Issue 6 Mar. 2002.

Lindsey, A. C., et al., Hysteroscopic inseminatin of mares with low numbers of nonsorted or flow sorted spermatozoa; Equine vet. J. (2002) 34(2) 128-132.

Sharpe, Johnathan, Advances in flow cytometry for sperm sexing, Unpublished paper, 2008.

Johnson, S.K., Possibilities with today's reproductive technologies. Available online at www.sciencedirect.com; Therio 64(2005) pp. 639-656.

(56) References Cited

OTHER PUBLICATIONS

Brogliatti, G. et al., Pregnancy Rates and First Born Calves by Artificial Insemination using Sexed Semen in Argentina: Therio. Jan. 2, 2002, vol. 57, No. 1 . p. 369.
Palma, G. et al., Sperm Physiology: The Ability to Produce Embryos In Vitro using Semen from Bulls with a Low Non-Return Rate. Therio. p. 308.
Gottlinger, Christopher et al., Cell-Cooling in Flow Cytometry by Peltier Elements. Cytometry 7:295-297 (1986).
Request for Ex-Partes Re-Examination of U.S. Patent No. 8,004,661 filed Feb. 13, 2012 (137 pages).
Request for Inter Partes Reexamination of U.S. Patent No. 8,004,661 filed Aug. 30, 2011 (94 pages).
Gledhill, Barton L, et al.; "Chapter 26: Flow Cytometry and Sorting of Sperm and Male Germ Cells"; Article, 1990, pp. 531-551, Second Edition, Flow Cytometry and Sorting, Wiley-Liss, Inc. USA (23 pages).
Severin, E., et al.; "A New Flow Chamber and Processing Electronics for Combined Laser and Mercury Arc Illumination in an Impulscytophotometer Flow Cytometry"; Article, 1983, pp. 308-310; vol. 3, No. 4, Cytometry USA (3 pages).
Lindmo, Tore, et al.; "Chapter 8: Flow Sorters for Biological Cells"; Chapter, 1990, pp. 143-169, Second Edition, Flow Cytometry and Sorting, Wiley-Liss USA (27 pages).
Pinkel, D., et al.; "High Resolution DNA Content Measurements of mammalian Sperm"; Article, 1982, pp. 1-9, vol. 3, No. 1, Cytometry, Society for Analytical Cytology USA (9 pages).
Johnson, L.A., et al.; "Flow Sorting of X and Y Chromosome-Bearing Spermatozoa Into Two Populations"; Article, 1987, pp. 1-9, vol. 16, Alan R. Liss, Inc., Gamete Research USA (9 pages).
Beisker, W., et al.; "Double Beam Autocompensation for Fluorescence Polarization Measurements in Flow Cytometry"; Article, May 1985, pp. 607-612, vol. 47, Journal of Biophys. USA (6 pages).

\* cited by examiner

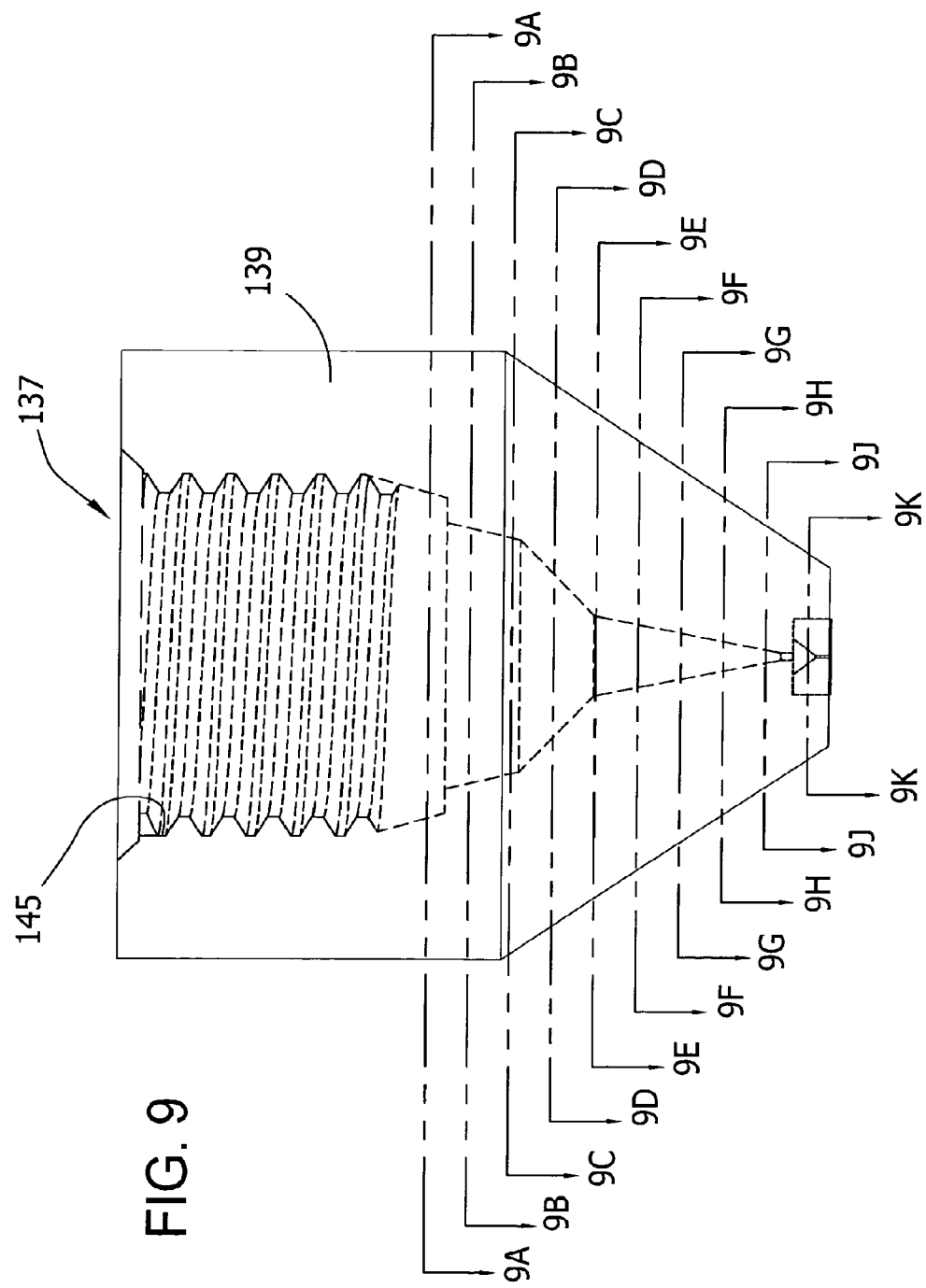

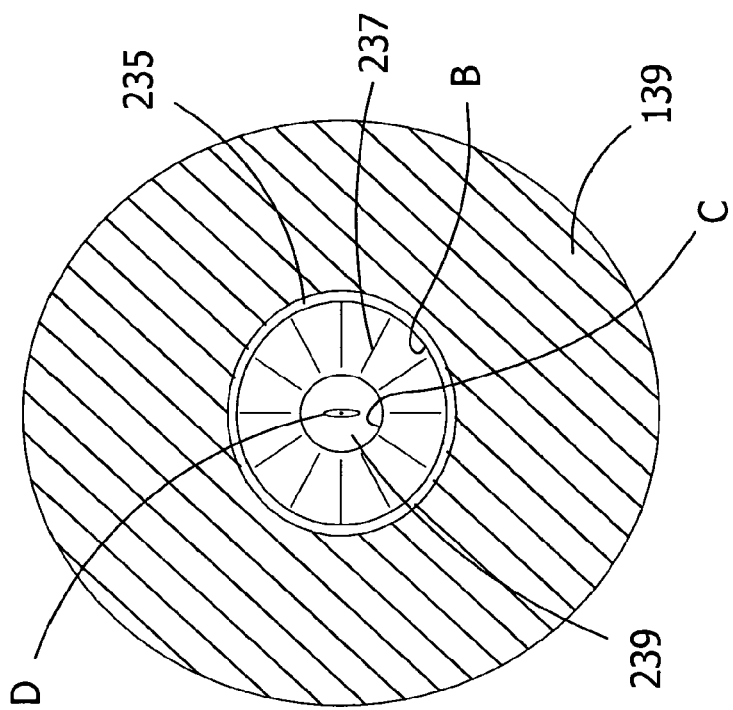
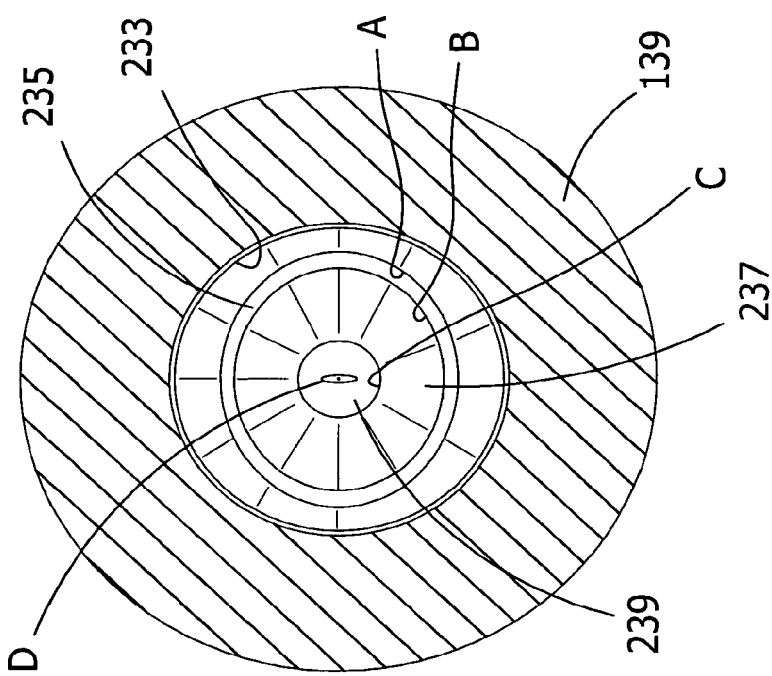
FIG. 9A
FIG. 9B

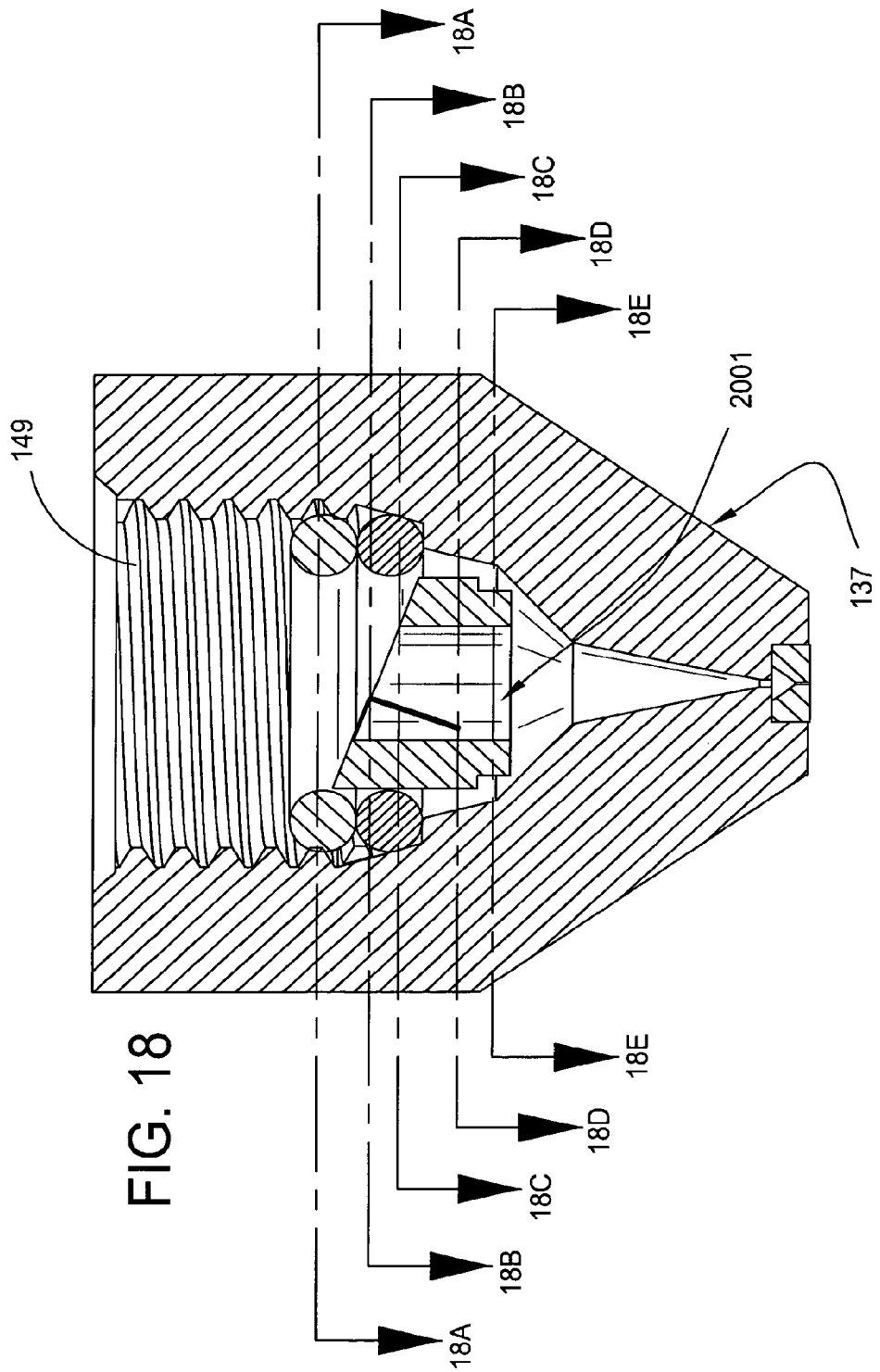

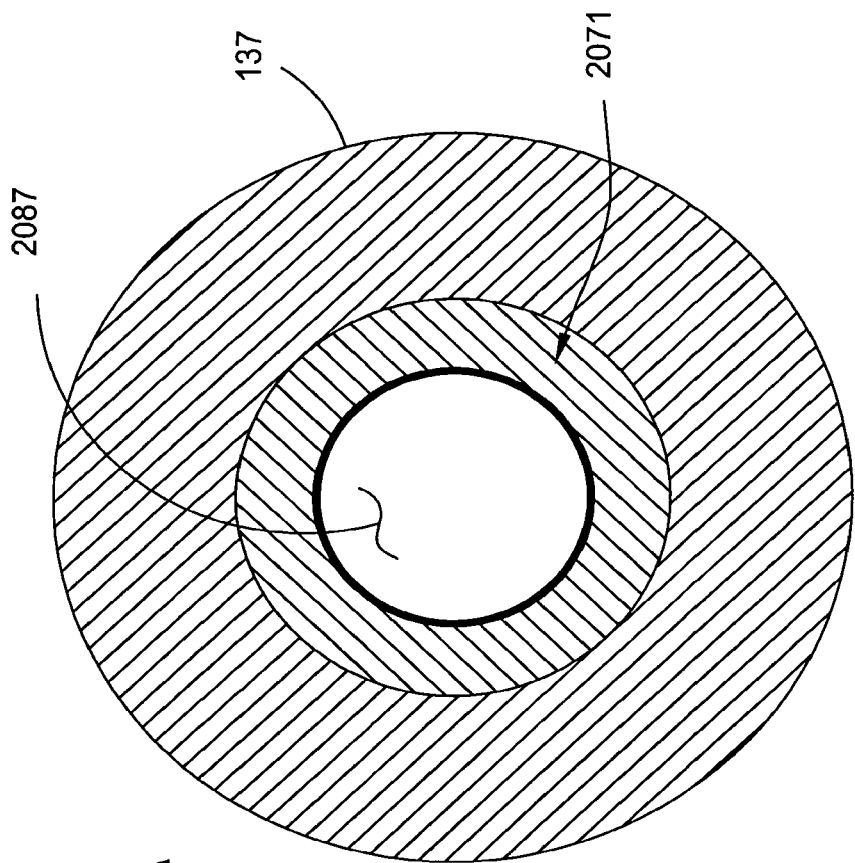

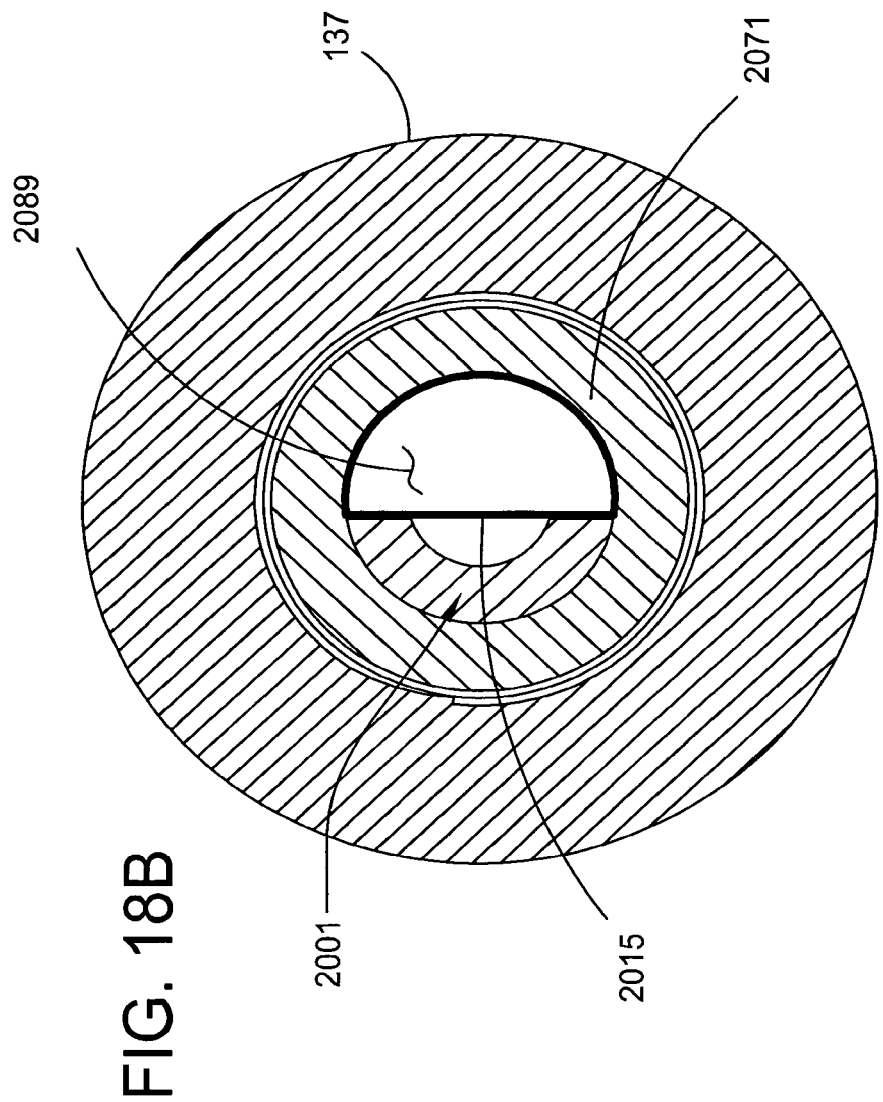

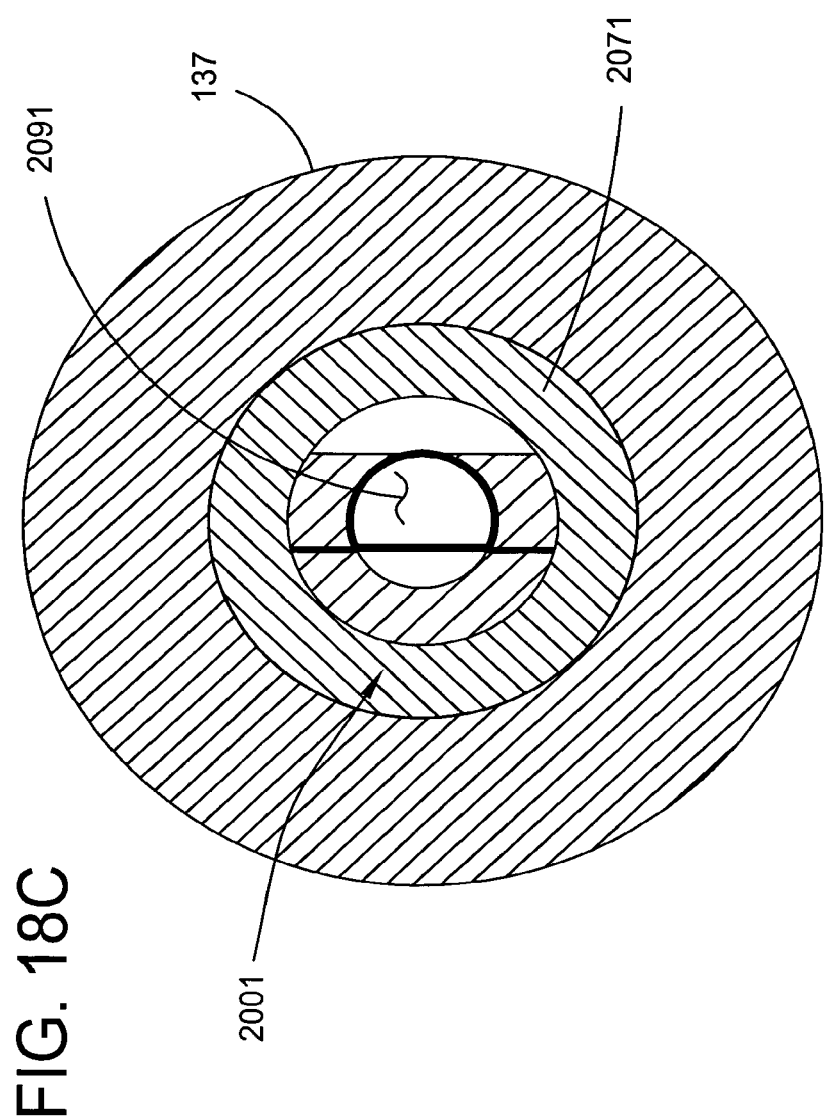

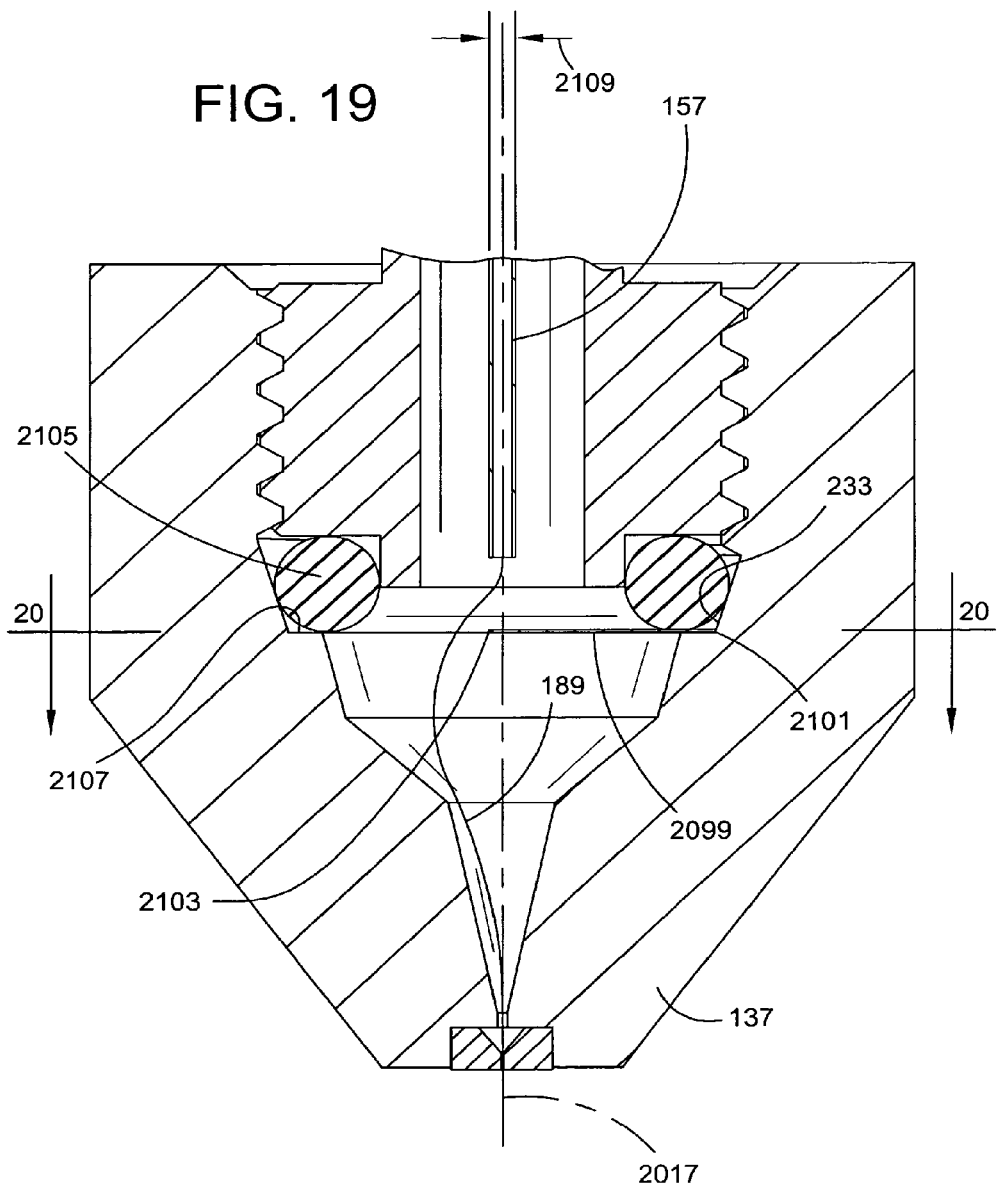

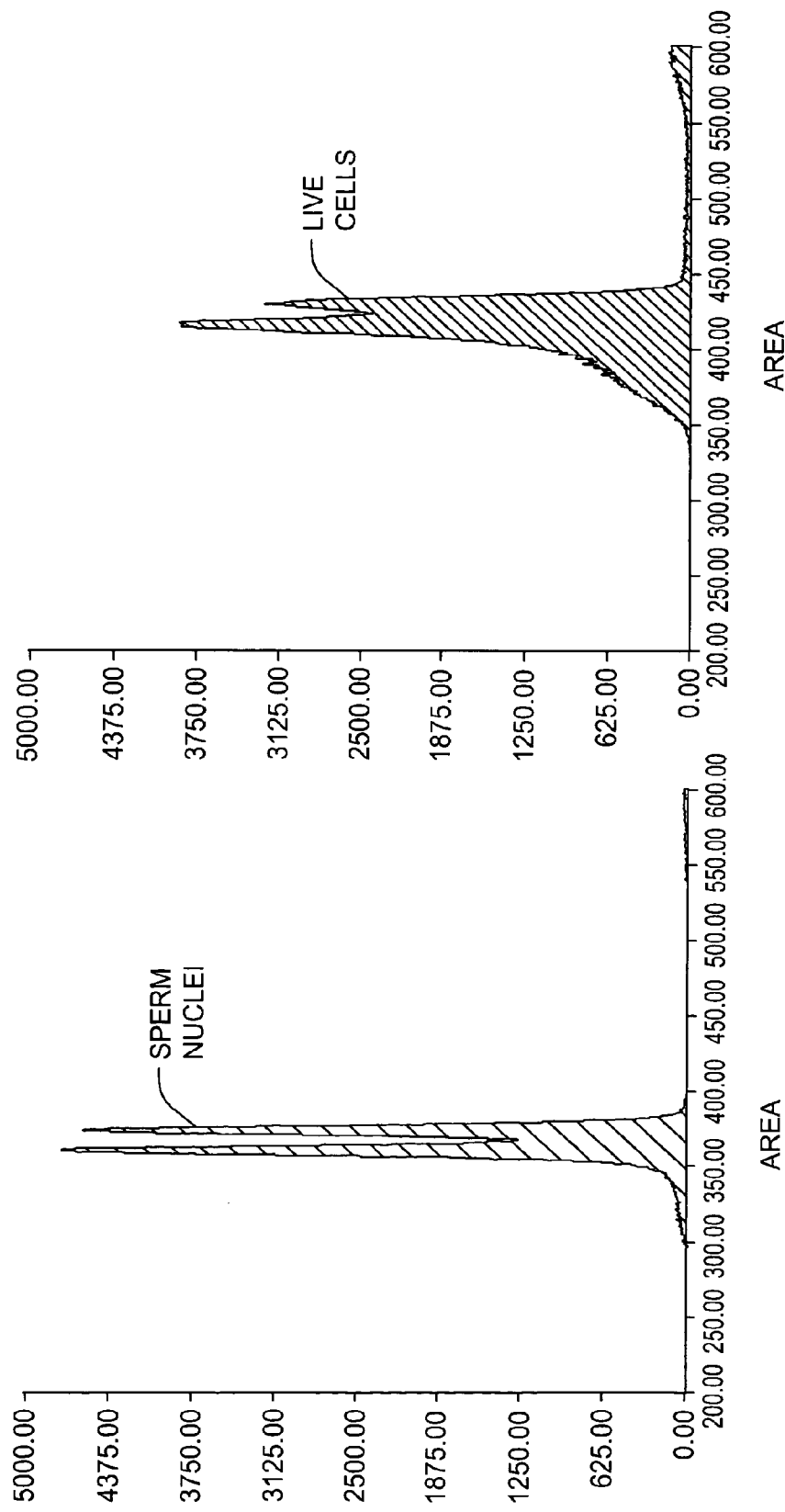

1 = FIRST PARTICLE SET
2 = SECOND PARTICLE SET
3 = THIRD PARTICLE SET

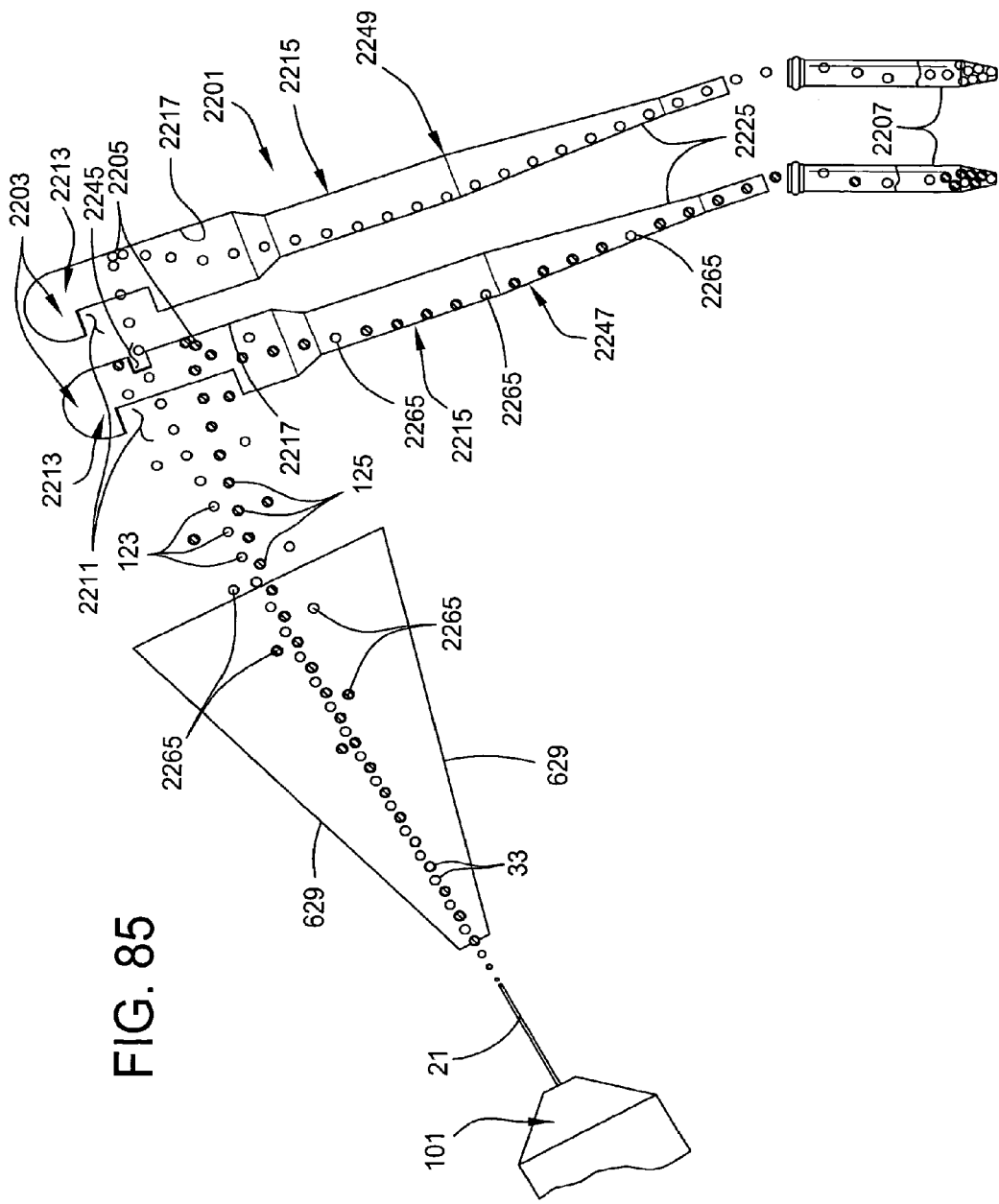

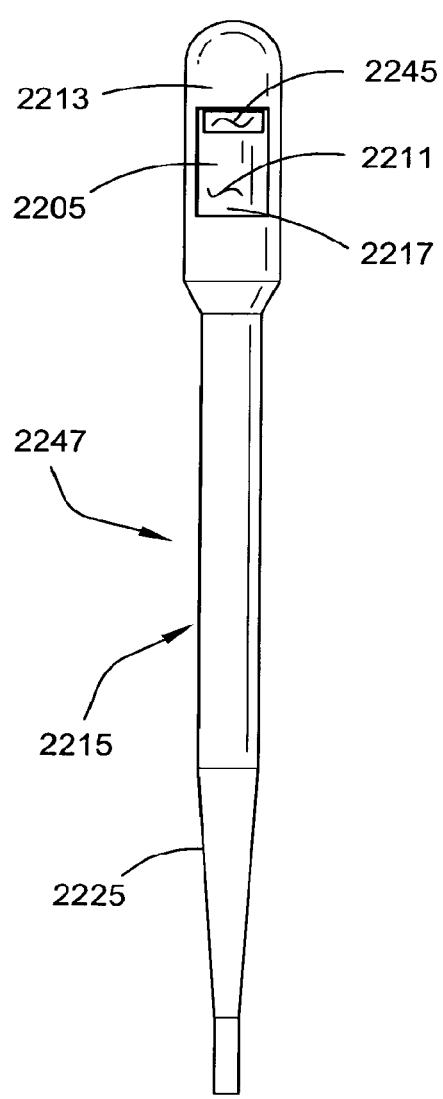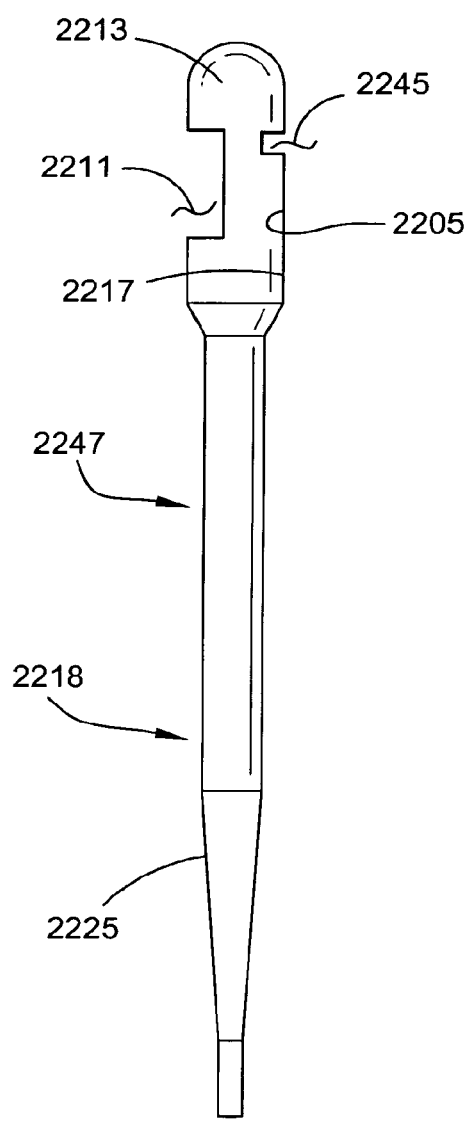

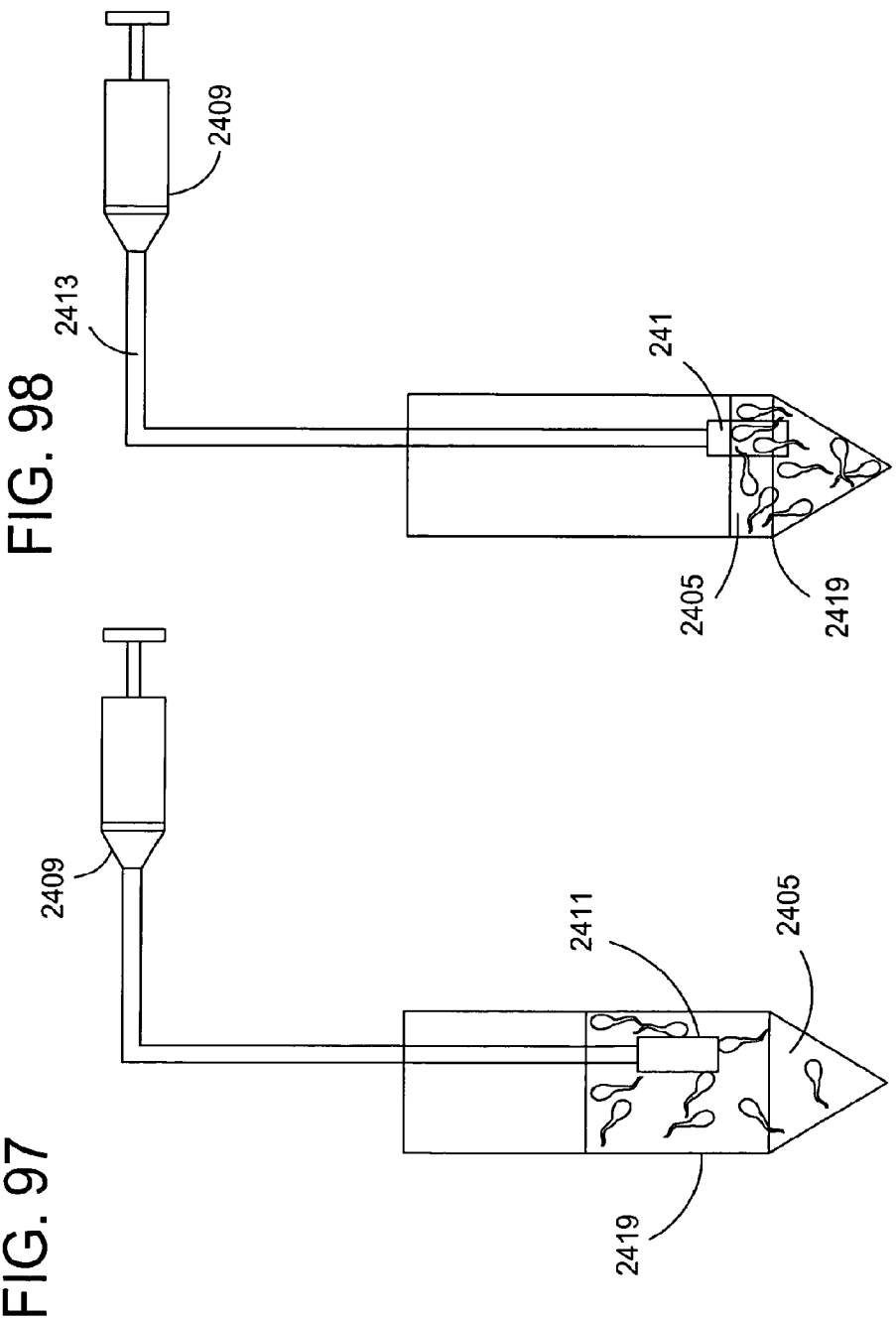

FLOW CYTOMETER METHOD AND APPARATUS

CROSS-REFERENCE TO RELATED APPLICATIONS

This Application is a continuation of U.S. patent application Ser. No. 13/422,705, filed Mar. 16, 2012 now U.S. Pat. No. 8,535,938, which is a continuation of U.S. patent application Ser. No. 13/106,671, filed on May 12, 2011, now U.S. Pat. No. 8,206,987, which is a continuation of U.S. patent application Ser. No. 12/794,921, filed on Jun. 7, 2010, now U.S. Pat. No. 7,943,384, which is a continuation of U.S. patent application Ser. No. 10/812,351 filed Mar. 29, 2004, now U.S. Pat. No. 7,758,811, which claims priority from U.S. Patent Application No. 60/458,607 and U.S. Patent Application No. 60/458,731, both filed Mar. 28, 2003. The entire disclosure of each application is incorporated herein by reference.

BACKGROUND OF THE INVENTION

This invention relates generally to apparatus and methods for animal semen collection, and more particularly to apparatus and methods using various techniques, including flow cytometry, to yield sperm populations that are enriched with sperm cells having one or more desired characteristics, such as viable populations of sperm cells sorted according to DNA characteristics for use by the animal production industry to preselect the sex of animal offspring.

The fertilization of animals by artificial insemination (AI) and embryo transplant following in vitro fertilization is an established practice. In the livestock production industry, the ability to influence the reproductive outcome toward offspring having one or more desired characteristics has obvious advantages. By way of example, there would be an economic benefit in the dairy industry to preselect offspring in favor of the female sex to ensure the production of dairy cows. Efforts have been made toward achieving this goal by using flow cytometry to sort X and Y sperm cells, as evidenced by the disclosures in U.S. Pat. No. 6,357,307 (Buchanan, et al.), U.S. Pat. No. 5,985,216 (Rens, et al.), and U.S. Pat. No. 5,135,759 (Johnson). However, none of these efforts has resulted in the introduction of a commercially successful high-throughput system capable of producing production volumes of relatively pure sexed sperm cells having a motility sufficient for effective fertilization.

Accordingly, there is a current need in the animal production industry for a viable high-speed system for efficiently isolating sperm cells based on a specified DNA characteristic (or other characteristics) to produce quantities of such cells, which can be used on a commercial scale. Also needed is a sperm handling system that preserves the viability of such isolated sperm as it is processed by the isolating system and that allows for preservation of such isolated sperm until such time that it is ready for use. The present invention addresses these needs.

This invention also has application to improvements in the field of flow cytometry on a more general basis. Flow cytometry may broadly be defined as measuring characteristics of individual particles as they pass generally single file in a fluid stream through a measuring device which, typically, provides information for classifying the particles according to selected characteristics. Optionally, the particles may then be separated into populations using any number of techniques, including droplet sorting, droplet interference sorting, and fluid switching. Another option is to selectively destroy unwanted particles, for example by photo ablation.

In an optically-based flow cytometry system, optics are used to direct and focus a beam of light (e.g., visible light or UV light) on the stream containing the particles, and to collect emissions from the particles, including scattered light and/or fluorescence emissions from the particles. In one common optic system, for example, a beam of light (e.g., a laser beam) is focused on the stream and emissions are collected by a pair of collection units, one positioned forward of the laser for collecting scattered light emissions and another positioned orthoganally to both stream and the laser for collecting fluorescence emissions. Each collection unit includes a separate photodetector, which increases the cost of the system. Further, in traditional optic systems the photodetectors translate the collected emissions into electrical signals, which are analyzed using analog systems to classify the particles according to selected characteristics of the particles. Analog systems are relatively inexpensive, but only limited information can be derived from the signals.

Others have tried to develop technology that can be used to process sperm cells to obtain populations of sperm cells that are enriched with sperm that have a desired sex chromosome. However, the existing technology falls short of the inventive technologies described herein.

For example, Johnson et al. (U.S. Pat. No. 5,135,759) describe the separation of intact X and Y chromosome-bearing sperm populations according to DNA content using a flow cytometer/cell sorter into X and Y chromosome-bearing sperm enriched populations. As described, the sperm is combined with a DNA selective dye at a temperature of 30 to 39° C. for a period of 1 hour (39° C.) to 1.5 hours (30° C.). A flow cytometer is then used to measure the amount of fluorescent light emitted as the sperm passes through a laser beam that excites the dye. Because the X chromosome-bearing sperm contains more DNA than the Y chromosome-bearing sperm, with most species of mammal having about 3 to 5% difference, the X chromosome-bearing sperm emits more fluorescent light than the Y chromosome-bearing sperm. In order to account for the fact that the fluorescence measurement may vary depending on the rotational orientation of the sperm cells, two photo detectors are used. The first determines whether the sperm cells are properly oriented, while the second takes a measurement that is used to classify the sperm as having an X or Y chromosome. An oscillator is used to cause the stream containing the sperm to break into droplets downstream of the place where the sperm pass through the laser beam. Droplets containing single sperm of a predetermined fluorescent intensity are given a charge and electrostatically deflected into collection vessels. The collected, gender enriched sperm population, is then used for microinjection, in vitro fertilization, or artificial insemination.

Seidel et al. (WO 02/43574) also describe separation of sperm into gender enriched populations of X and Y chromosome-bearing cells using flow cytometry. Seidel et al. describe staining the cells at a temperature between 30° C. and 40° C.

United States Patent Application Pub. No. 2003/0157475 Al (Schenk, Aug. 21, 2003) describes a method of cryopreserving sperm cells that have been sorted according to X or Y chromosome content. As noted therein, it is desirable to add a cryoprotectant to sperm cells before they are cryopreserved to protect the sperm cells during the cryopreservation process. For example, glycerol is one cryoprotectant that is commonly added to bovine sperm cells prior to cryopreservation. However, in order to obtain better protection from the cryoprotectant, it is desirable to wait for the cryoprotectant to equilibrate with the sperm cells before subjecting the sperm cells to temperatures below 0° C. During the equilibration period, the cryoprotectant penetrates the cell membrane to provide intracellular protection in addition to any extra-cellular protection provided by the cryoprotectant. Thus, the cryopreservation methods described in United States Patent Application Pub. No. 2003/0157475 A1 specify that an extender containing glycerol is added to the sperm cells after they have been cooled to about 5° C. Then the sperm cells and glycerol are allowed to equilibrate at 5° C. for anywhere between 1 and 18 hours before the sperm cells are subjected to lower temperatures. The disclosure recommends an equilibration period of between three and six hours in order to obtain the best results.

Unfortunately, the time and expense involved in a 3 to 6 hour equilibration period will have a negative impact on profitability of a commercial sperm sorting process. Furthermore, in the context of a commercial sperm sorting process, it is believed that the health of the sperm is generally improved by reducing the time between collection of the sperm and cryopreservation (other factors being equal). From this standpoint as well, it would be desirable to have access to cryopreservation technology that does not require a long equilibration period to obtain the optimal benefits of a cryoprotectant. Moreover, the known cryopreservation technology is reported to have a detrimental impact on sperm motility, which is indicative of decreased sperm fertility. Thus, there is a need for cryopreservation techniques that preserves sperm health compared to conventional techniques.

SUMMARY OF THE INVENTION

This invention is directed to an improved system (methods and apparatus) for analyzing, classifying and sorting particles based on one or more desired characteristics; the provision of such a system which, in one embodiment, uses flow cytometry to accurately isolate and sort cells by DNA content; the provision of such a system which, in certain embodiments, incorporates sorting protocols which enable the output of the system to be controlled as a function of one or more factors, including the purity of the desired sorted population of particles, the rate at which the desired particle population is collected, the loss of desired particles not sorted into the desired population, and other factors; the provision of such a system which, in one embodiment, operates at high-speed to provide sex sorted sperm for commercial use by the animal production industry; the provision of such a system which can be used to sort cells without significant detrimental effect on the cells, including the motility of sperm cells; the provision of a system that can be used to preserve sorted sperm cells until they are needed with minimal detrimental effect on the cells, including, the motility of the cells, the provision of such a system which, as it relates to the production of sexed sperm, incorporates techniques which increase the speed and accuracy of the classification and sorting of the sperm cells; the provision of a flow cytometry system which uses epi-illumination optics to detect various characteristics of particles to be analyzed and, optionally, sorted; the provision of such an epi-illumination flow cytometry system which is economical to manufacture; the provision of a system which, in one embodiment, incorporates multiple flow cytometry units which share an integrated platform for classifying and (optionally) sorting particles, such as cells in general and sperm cells in particular, at high rates of production; the provision of such a multi-channel system which share common components and systems to reduce variations between the channels for more efficient operation; and the provision of such a sorting system which, in one embodiment, incorporates protocols which enable a sample to be quickly tested to determine the quality of the sample so that the profitability of further sorting can be evaluated.

In addition, this invention is directed to an improved system (methods and apparatus) for digitally processing signals representing fluorescence; the provision for such a digital system, in one embodiment, for detecting analog to digital converted-pulses as a function of background characteristics; the provision for such a digital system, in one embodiment, for initializing discrimination parameters; the provision for such a digital system, in one embodiment, for detecting digital information corresponding to waveform pulses; the provision for such a digital system, in one embodiment, for digital information analysis including feature extraction; the provision for such a digital system, in one embodiment, for classifying pulses and defining decisions boundaries; the provision for such a digital system, in one embodiment, employing a droplet break-off sensor to control transducer amplitude; and the provision for using such a digital system, in one embodiment, to distribute and collect cells for commercial distribution.

Further, this invention is directed an improved comprehensive system (apparatus and methods) for commercial processing of animal semen from the time a semen sample is collected from a male animal through cryopreservation of a sperm sample containing a greater percentage of a sperm having a desired chromosome characteristic than exists in the collected semen; the provision of such a system, in one embodiment, that allows efficient processing of commercial quantities of viable gender enriched sperm; the provision of such a system that allows, in one embodiment, adjustment of the system to counter day-to-day and animal-to-animal variations in the semen characteristics; the provision of such a system that, in one embodiment, allows production of about 18,000,000 gender enriched sperm per hour by a single flow cytometry unit at 85% purity; and the provision of such a system that allows, in one embodiment, complete processing of a batch of semen (e.g., the amount of semen collected from a male animal) to yield viable sperm samples having a desired gender characteristic at 85% purity with less than 10% loss of collected sperm having the desired gender characteristic in about 1 hour of processing time.

In general, this invention is directed to the apparatus and methods set forth in the claims of this application.

Other objects and features of this invention will be in part apparent and in part pointed out hereinafter.

BRIEF DESCRIPTION OF THE DRAWINGS

FIG. 9 is a side view of the nozzle body shown in FIG. 8 showing a series of cutting planes (A-A through H-H and J-J through K-K) through the nozzle body;

FIGS. 9A-9H and 9J-9K are sectional views of the nozzle body shown in FIGS. 8 and 9 along the corresponding planes (A-A through H-H and J-J through K-K) of FIG. 9;

FIG. 18 is a side cross sectional view of one embodiment of a nozzle system including a baffle showing a series of cutting planes (A-A through E-E) through the nozzle and baffle;

FIGS. 18A-18E show the cross sectional flow areas at various points in the nozzle system shown in FIG. 18;

FIG. 19 is a cross sectional view similar to FIG. 12 taken through a nozzle having a baffle plate that is perpendicular to the longitudinal axis of the nozzle;

FIGS. 56-59 show fluorescence histograms and scatter plots of peak vs. area for sperm nuclei and live sperm cells;

—FIG. 60 shows raw data and FIG. 61 shows model curves generated by one embodiment of an iterative algorithm of the present invention based on the data shown in FIG. 60

—FIG. 62 shows raw data and FIG. 63 shows model curves generated by one embodiment of an iterative algorithm of the present invention based on the data shown in FIG. 62;

FIG. 85 is a schematic diagram of one embodiment of a collection system of the present invention;

FIG. 86 is a front elevation of an intercepting device of the collection system shown in FIG. 83;

FIG. 87 is a side elevation of an intercepting device of the collection system shown in FIG. 83;

FIG. 96-98 are schematic diagrams illustrating the steps in one embodiment of a filtration method of the present invention;

Figure 1:
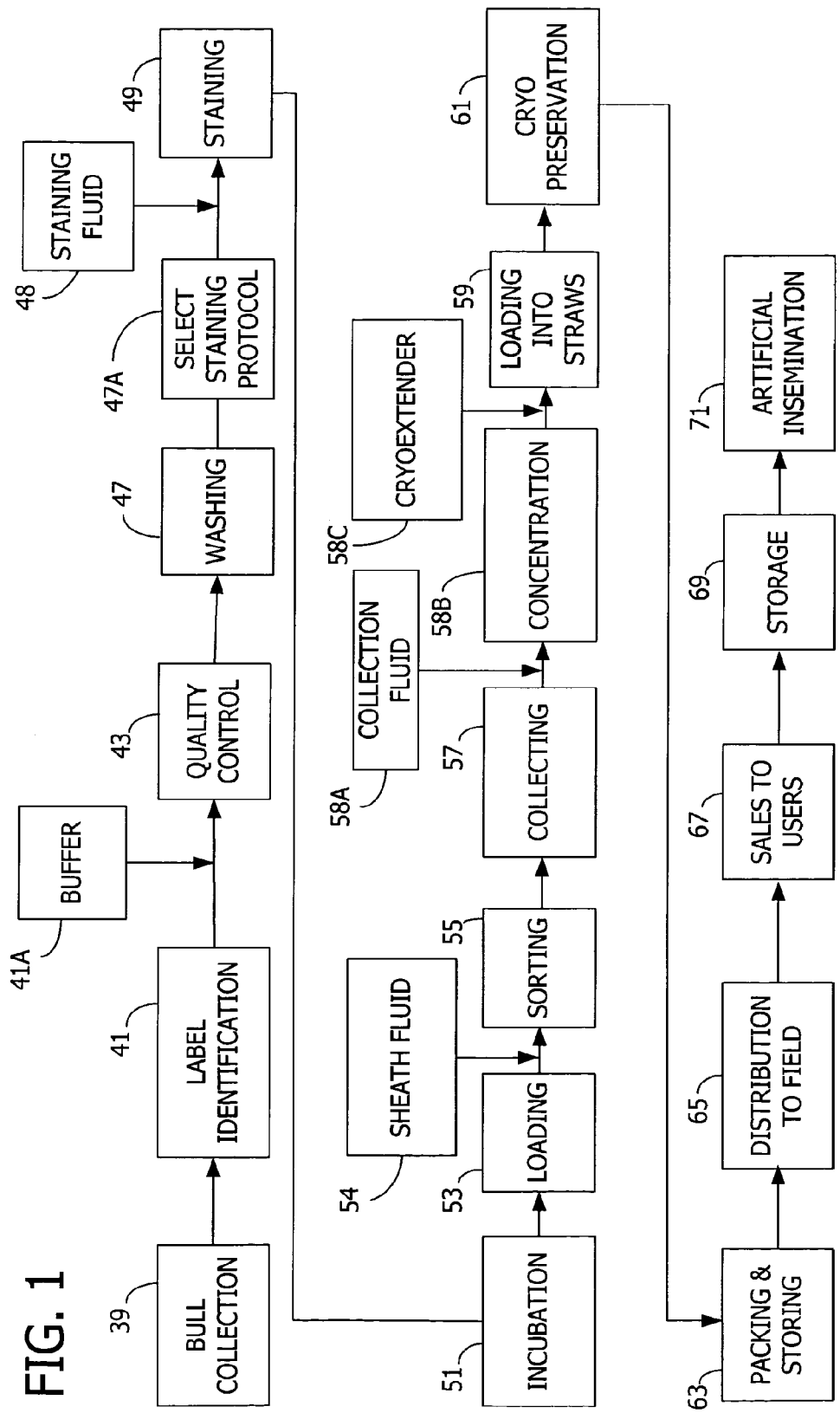
FIG. 1 is a work flow diagram for an exemplary sperm sorting process of the present invention.

Corresponding parts are designated by corresponding reference numbers throughout the drawings. A parts list with associated reference numerals for each part follows. The parts list is provided with section headings generally corresponding to section headings in the specification to facilitate use of the parts list. Generally, each section of the parts list provides a reference numeral for the parts that are introduced for the first time in the corresponding section of the Detailed Description.

| Parts List with Associated Reference Numerals for Each Part | |
|---|---|
| General Overview | |
| 39 | Semen Collection |
| 41 | Label Semen |
| 41A | Add Buffer |
| 43 | Quality Control |
| 47 | Washing |
| 48 | Staining Fluid |
| 49 | Staining |
| 51 | Incubation |
| 53 | Load into Sample Introduction Device of Flow Cytometer |
| 54 | Add Sheath Fluid Through Flow Cytometry |
| 55 | Sorting |
| 57 | Collecting Sorted Sperm |
| 58A | Add Collection Fluid |
| 58B | Concentrate Sperm Cells |
| 58C | Add Cryoextender |
| 59 | Load Sorted Sperm into Straws |
| 61 | Cryopreservation |
| 63 | Packing in Liquid Nitrogen |
| 65 | Distribution |
| 67 | Sales |
| 69 | Storage |
| 71 | Artificial Insemination |
| Flow Cytometry | |
| 1 | System (Overall) |
| 3 | Supply of Carrier Fluid |
| 7 | Supply of Sheath Fluid |
| 9 | Flow Cytometry Apparatus Having Sorting Capabilites |
| 15 | Fluid Delivery System |
| 17 | Carrier Fluid |
| 19 | Sheath Fluid |
| 21 | Stream of Fluid |
| 23 | Stream of Particles |
| 25 | Beam of Electromagnetic Radiation |

| Parts List with Associated Reference Numerals for Each Part | |
|---|---|
| 31 | Electromagnetic Radiation Emission from Particles |
| 33 | Droplets |
| 35 | Particles Contained in Droplets |
| Flow Cytometry Apparatus (Single Channel) | |
| 101 | Nozzle System |
| 103 | Nozzle Orifice |
| 105 | Transducer |
| 107 | Droplet Break-off |
| 109 | Optics System |
| 115 | Interrogation Location |
| 117 | Photodetector |
| 119 | Sorting System |
| 123 | First Different Group or Population of Droplets |
| 125 | Second Different Group or Population of Droplets |
| 2201 | Collection System |
| 131 | Processor |
| Nozzle System | |
| 133 | Cylindrical Flow Body |
| 135 | Central Longitudinal Bore |
| 137 | Nozzle |
| 139 | Funnel-shaped Nozzle Body |
| 141 | Passage Through Nozzle Body |
| 145 | Internally Threaded Counterbore |
| 149 | Threaded Projection or Stud |
| 155 | 0-ring Seal |
| 157 | Conduit (Tubular Needle) |
| 167 | Annular Space (Gap) |
| 173 | Radial Bore in Flow Body (Sheath Fluid) |
| 183 | Second Radial Bore (Additional Sheath Fluid) |
| 189 | Central Core of Carrier Fluid |
| 191 | Outer Co-axial Sheath of Fluid |
| Cell Orientation | |
| 201 | Bovine Sperm Cell |
| 205 | Paddle-shaped Head |
| 207 | Flat Wide Opposite Faces |
| 209 | Narrow Edges |
| 211 | Sperm Equator |
| 213 | Nucleus |
| 215 | Tail |
| 217 | Nucleus Length |
| 219 | Head Length |
| 221 | Head Width |
| 223 | Overall Length |
| 225 | Localized Region Within Nucleus |
| 227 | Direction of Stream Flow |
| 229 | Angular Envelope in Which Light Beam Strikes Wide Face |
| R1 | Angular Range |
| P | Plane |
| Nozzle Design | |
| 231 | Interior of Nozzle Body |
| 233 | Interior Surface of Nozzle Body |
| 235 | First Axially Tapered Region |
| 237 | Second Axially Tapered Region |
| 239 | Third Axially Tapered Region |
| 247 | Longitudinal Axis of Nozzle |
| 249 | Fourth Region Interior of Nozzle |
| 251 | Axial Length of Fourth Region |
| 255 | Orifice Member |
| 257 | Counterbore at Front End of Nozzle |
| 259 | First Torsional Zone |
| 261 | Second Torsional Zone |
| 263 | Surface of First Torsional Zone |
| 267 | Surface of Second Torsional Zone |
| 271 | Torsional Forces |
| 273 | Axial Length of First Torsional Zone |
| 275 | Axial Length of First Tapered Region |
| 277 | Axial Length of Second Tapered Region |
| 279 | Axial Length of Second Torsional Zone |
| 309 | Conical Upstream Surface of Orifice Member |
| 315 | Cylindrical Downstream Surface of Orifice Member |
| 317 | Axial Length of Conical Upstream Surface |
| 327 | Axial Length of Downstream Surface |

| Parts List with Associated Reference Numerals for Each Part | |
|---|---|
| Orienting Baffle | |
| 2001 | Orienting Baffle |
| 2003 | Baffle Plate |
| 2005 | Baffle Holder |
| 2007 | Upstream Leg |
| 2009 | Downstream Leg |
| 2015 | Line of Intersection |
| 2017 | Central Axis of Nozzle Body |
| 2019 | Curved Edge of Upstream Leg |
| 2025 | Distance Lower Leg Extends Downstream |
| 2027 | Overall Length of Baffle Holder |
| 2029 | Exterior Diameter of Baffle Holder |
| 2031 | Interior Diameter of Baffle Holder |
| 2033 | Distance Between Line of Intersection and Center of Nozzle |
| 2035 | Upstream End of Baffle |
| 2037 | Inclined Surface of Baffle Holder |
| 2039 | Side Edges of Downstream Leg |
| 2041 | Downstream Edge of Downstream Leg |
| 2049 | Gap Between Baffle Plate and Baffle Holder |
| 2051 | Inside surface of Baffle Holder |
| 2053 | Volume Behind Baffle Plate |
| 2055 | Interior Volume of Nozzle |
| 2057 | Longitudinal Axis of Cylindrical Baffle Holder |
| 2059 | Line Through Major Axis of Ellipse D |
| 2061 | Distance Between Injection Needle and Baffle |
| 2067 | Downstream End of Baffle Holder |
| 2069 | Contact Points Between Baffle Holder and Nozzle |
| 2071 | 0-Rings |
| 2077 | Downstream End of Nozzle Holder (Boss) |
| 2079 | Interior Diameter of Boss |
| 2081 | Portion of Sheath Fluid Between Core Stream and Nozzle Surface |
| 2087 | Cross Section Upstream (A) |
| 2089 | Cross Section at Baffle (B) |
| 2091 | Cross Section at Baffle (C) |
| 2093 | Cross Section at Baffle (D) |
| 2094 | Cross Section Downstream of Baffle (E) |
| 2097 | Perpendicular Baffle System |
| 2095 | Air Bubble |
| 2099 | Perpendicular Baffle Plate |
| 2101 | Curved Edge of Perpendicular Baffle Plate |
| 2103 | Straight Edge of Perpendicular Baffle Plate |
| 2105 | 0-ring |
| 2107 | Annular Shoulder (Shelf) in Nozzle |
| 2109 | Outer Diameter of Sample Injection Needle (Conduit) |
| 2151 | Nozzle System Having an Offset Sample Introduction Conduit |
| Nozzle Mounting and Adjustment | |
| 331 | Nozzle Mount |
| 333 | First Linear Stage |
| 337 | Second Linear Stage |
| 339 | X Axis |
| 341 | Y Axis |
| 343 | Third Rotational Stage |
| 345 | Z Axis |
| 347 | Fixed First Stage Member (Not Shown) |
| 349 | Frame for First Fixed Stage Member |
| 355 | Movable First Stage Member |
| 357 | Actuator (Micrometer) for First Stage |
| 359 | Fixed Second Stage Member |
| 361 | Movable Second Stage Member |
| 363 | Actuator (Micrometer) for Second Stage |
| 365 | Fixed Third Stage Member |
| 371 | Movable Third Stage Member |
| 373 | Actuator (Micrometer) for Third Stage |
| 375 | Generally Upward Direction of Stream Containing Cells |
| 377 | Angle of Upward Direction |
| Transducer and Droplet Formation | |
| 379 | Collar |
| 381 | Piezoelectric Element (Not Shown) |
| 383 | Terminals |
| D | Diameter of Stream |

| Parts List with Associated Reference Numerals for Each Part | |
|---|---|
| Break-off Sensor | |
| 389 | Break-off Sensor |
| 391 | Microprocessor |
| 393 | Light Source |
| 395 | Linear Photoarray (Photodiodes) |
| 401 | Lens for Droplet Break-off Sensor |
| 405 | Current to Voltage Op-amp Circuits |
| 407 | Track/hold Amplifiers |
| 409 | Sinewave Generator (Track/hold Signal) |
| 411 | A/D Converter |
| 412 | Camera System |
| 413 | Strobe |
| 414A | Mask |
| 414B | Slit-Shaped Opening in Mask |
| Epi-illumination Optics System | |
| 415 | Epi-illumination System |
| 417 | Epi-illumination Instrument |
| 419 | Longitudinal Optical Axis |
| 425 | Beam Spot |
| 427 | Axis of Focused Illumination Beam |
| 429 | Rectangular Base |
| 431 | Reflecting Filter |
| 435 | Laser or Arc-lamp |
| 437 | Conditioning Lens Assembly |
| 439 | Opening in |
| 441 | Side Wall of a Dichroic Chamber |
| 443 | Dichroic Chamber |
| 445 | Retaining Ring |
| 447 | Neutral Density Filter |
| 449 | Cylindrical Lens |
| 455 | Lens Holder |
| 457 | Jam Nut |
| 459 | Elliptical Cross Section of Beam Spot |
| 461 | Clips for Reflecting Filter |
| 463 | Filter Holder |
| 465 | Angular Face of Filter Holder |
| 467 | Openings in Filter Holder |
| 469 | Linear Stage for Filter Holder |
| 471 | X Axis |
| 473 | Outrigger |
| 475 | Actuator for Linear Stage |
| 477 | Dichroic Filter |
| 479 | Clips for Dichroic Filter |
| 485 | Frame for Dichroic Filter |
| 487 | Forward Direction |
| 489 | Longitudinal Optical Axis of the Optical Instrument |
| 491 | Focusing Lens Assembly |
| 497 | Fluorescent Pulse Waveform or Signal Emitted by Cell |
| 498 | Excitation Spatial Function |
| 501 | Microscope Adapter |
| 503 | Opening in Front Wall of Dichroic Chamber |
| 505 | Front Wall of Dichroic Chamber |
| 507 | Focusing Barrel |
| 509 | Lens Mount Barrels |
| 511 | Focusing Lens |
| 513 | Rearward Direction |
| 515 | Telescoping Focus Adjustment |
| 517 | Collimated Emitted Light |
| 519 | Filtering System |
| 521 | Emission Filter |
| 523 | Emission Filter Holder |
| 525 | Opening in Back Wall of Dichroic Chamber |
| 527 | Back Wall of Dichroic Chamber |
| 529 | Alignment Pellicle Assembly |
| 531 | Slider of Alignment Pellicle |
| 533 | Rail for Filter Assembly Components |
| 535 | Filter Holder for Alignment Pellicle |
| 539 | Pellicle Filter Element |
| 541 | Clips for Securing Filter Element to Filter Holder |
| 543 | Angle for Alignment Pellicle Relative to Optical Axis |
| 545 | Fasteners for Securing Slider to Base |
| 547 | Parallel Slots in Base |
| 549 | Aspheric Lens |
| 551 | Holder for Aspheric Lens |
| 553 | Frame for Aspheric Lens |
| 557 | Fasteners for Aspheric Lens |

| | Parts List with Associated Reference Numerals for Each Part |
|---|---|
| 559 | Spatial Filter |
| 561 | Aperture Plates |
| 563 | Frame for Spatial Filter Plates |
| 567 | Vertical Slit |
| 571 | Horizontal Slit |
| 573 | Aperture |
| 575 | Vertical Dimension |
| 577 | Horizontal Dimension |
| 579 | Collection Volume |
| 583 | Plate Holder |
| 587 | Fasteners for Plate Holder |
| 589 | Backing Member for Aperture Plates |
| 449A | Adjustable Mounting Assembly |
| 449B | Slots |
| 449C | Slots |
| 450 | Epi-illumination that Reflects Fluorescence Emissions |
| 451 | Dichroic Filter |
| | Photodetector |
| 591 | Mounting Plate for Photodetector |
| 595 | Fasteners for Photodetector |
| | Angle of Beam Incidence |
| 605 | Distance Between Interrogation Location and Nozzle Orifice |
| 609 | Beam Axis |
| A | Angle of Incidence |
| | Focused Beam Spot |
| L1 | Length along Major Axis |
| W1 | Width along Minor Axis |
| | Sorting System |
| 627 | Charging Device |
| 629 | Charged Deflector Plates |
| 631 | Charging Element |
| 633 | Opening in Charging Element |
| 635 | Power Supply for Deflector Plates |
| 5001 | Adjustable Mounting Assembly |
| 5003 | Mounting Assembly Adjustment Board |
| 5005 | Mounting Assembly Backing |
| 5007 | Fasteners |
| 5009 | Slots |
| 5011 | Translation Axis |
| 5013 | Translation Axis |
| 5015 | Mounting Assembly Adjustment Board |
| 5017 | Fasteners |
| 5019 | Slots |
| 5021 | Fixed Support |
| 5023 | Fasteners |
| 5025 | Spring |
| | Automat Sort Calibration |
| 4201 | Calibration System |
| 4203 | Epl-Illumination Sensor |
| 4205 | Fiber Optic Cable |
| 4207 | Dichroic Filter |
| 4209 | Lens System |
| 4211 | Fluorescent Emission from Particle in Droplet |
| 4213 | Photodetector |
| 4215 | Beam Stop |
| | Sort System Fault Correction |
| 5047 | Debris Removal System for Charging Element |
| 5049 | Debris Removal System for Deflector Plates |
| 5051 | Support for Charging Element |
| 5053 | Vacuum Passage |
| 5055 | Vacuum Line |
| 5057 | Opening Adjacent Charging Element |
| 5058 | Fitting |
| 5059 | Compressed Gas Line |
| 5061 | Manifold |
| 5063 | Air Passages |
| 5064 | Openings |
| 5065 | Fitting |
| 5066 | Side of Deflector Plate |

| | Parts List with Associated Reference Numerals for Each Part |
|---|---|
| | Protection of Sorted Sample |
| 4033 | Collection Vessel |
| 4041 | Contamination Prevention Mechanism |
| 4043 | Pneumatic Actuator |
| 4045 | Swing Arm |
| 4047 | End of Swing Arm |
| | Fluid Delivery System |
| 645 | Syringe Pump |
| 647 | Flow Line from Pump to Carrier Supply |
| 649 | Vessel for Containing Supply of Carrier Fluid |
| 651 | Line from Pump to Injection Needle |
| 657 | Supply Line from Syringe Pump to Needle |
| 659 | Variable Speed Motor |
| 661 | Second Vessel - for Supply of Sheath Fluid |
| 667 | Supply Line for Connecting Sheath Fluid to Radial Bore in Nozzle |
| 669 | Control Valve in Supply Line |
| 671 | Gas Pressure System for Sheath Fluid |
| 675 | Source of Pressurized Gas |
| 679 | Air Line for Pressurized Gas |
| 681 | Regulator for Controlling Pressure Supplied to Sheath Fluid Tank |
| 683 | Two-way Valve in Air Line |
| | Control |
| 689 | A/D Converter |
| 693 | Relative Beam Intensity Experienced by Point Moving Through Beam Spot |
| 695 | Relative Emitted Pulse Intensity From Sperm Traversing Beam Spot |
| d | Distance Between Nozzle and Droplet Break-off Location |
| | Signal Processing |
| 701 | Output Signal From Photodetector |
| 703 | Droplet Generation Clock Signals |
| 705 | Digital Signal Processing (Digital Cell Analyzer) |
| 707 | Digital Signal from A/D |
| 735 | PC/Computer Terminal |
| 737 | Master Clock (128 × Clock Signal) |
| 739 | Data Acquisition (HH1') |
| 741 | Initializing Detection Parameters (HH1) |
| 745 | Initializing Discrimination Parameters (HH2) |
| 747 | Digital Pulse Detection (HH3) |
| 749 | Digital Pulse Analysis - Feature Extraction (HH4) |
| 753 | Pulse Area (HH5) |
| 755 | Pulse Peak (HH6) |
| 757 | Pulse Discrimination (HH7) |
| 759 | Sorting (HH8) |
| 761 | Drift Analysis (HH9) |
| 763 | Decision Boundary for Bayes Rules |
| 769 | Initialize |
| 771 | System Check |
| 773 | User Interaction |
| 775 | Retry (Up to Three Times) |
| 777 | Flush |
| 779 | Bead Quality Control |
| 781 | Aspirate Sample |
| 783 | Sample Quality Control |
| 785 | Start Sample |
| 787 | Sort On |
| 789 | Sample Complete |
| 791 | Continue Sample |
| 793 | Sort Off |
| 795 | X/Y Discrimination Optimum |
| 797 | Set X/Y Discrimination |
| 799 | Discrimination OK |
| 801 | Rate Optimum |
| 803 | Set Syringe Rate |
| 805 | Rate OK |
| 807 | System Check |
| 809 | System Reset |
| 811 | System OK |
| 813 | Exemplary Overall Operational Flow |
| 825 | Integrator |
| 827 | Width/Area Comparator |
| 829 | Dynamic Threshold Calculator |

-continued

Parts List with Associated Reference Numerals for Each Part

| | |
|---|---|
| 831 | Pulse Discrimination |
| 833 | JTAG Port I/O |
| 837 | Window Comparator (Area) |
| 839 | Pulse Width and Trigger Logic |
| 841 | Sort Decision |
| 843 | I/O Controllers |
| 845 | Slave Controllers |
| 847 | Sort Controller Board |
| 849 | USB |
| 851 | DSP Board SDRAM |
| 853 | Sort Signal |
| 854 | Low-Pass Filter |
| 855 | I/O Board SDRAM |
| 857 | Processor I/O |
| 859 | Peripheral I/O Bus |
| 861 | Sort Pulse Generator |
| 863 | Data Management Processor |
| 865 | Pulse Detection Processor |
| 867 | Feature Extraction Processor |
| 873 | Sort Processor |
| 875 | DSP Board RAM |
| OL | Inverse Relationship Between Coincident Droplets in Usable Population Compared to Coincident Droplets in Unusable Population |
| P1 | Point on Line OL Corresponding to 85% Purity |
| LL | Point on Line OL Corresponding to 60% Collection of Desired Particles |
| OR | Operating Range (Segment of OL Between P1 and LL) |
| 6000 | Raw Data |
| 6001 | 1st Population of Non-aligned Cells |
| 6003 | 2nd Population of Non-aligned Cells |
| 6005 | Aligned Y Population |
| 6007 | Aligned X Population |
| 6010 | Raw Data |
| 6011 | Population of Non-aligned Cells |
| 6015 | Aligned Y Population |
| 6017 | Aligned X Population |
| Multi-channel System | |
| 1001 | Multi-channel System |
| 1003 | Flow Cytometry Units |
| 1005 | Common Particle Supply |
| 1007 | Common Source of Electromagnetic Radiation |
| 1009 | Common Housing |
| 1011 | Common Input for Control |
| 1019 | Common Output |
| 1021 | Common Fluid Delivery System |
| 1023 | Common Temperature Control System |
| 1025 | Common Power Source |
| 1027 | Common Waste Recovery System |
| 1029 | Common Deflector Plate System |
| 1031 | Common Cleaning System |
| Common Housing | |
| 1069 | Base |
| 1071 | Two Side Walls |
| 1073 | Lower Pair of Shoulders |
| 1075 | Lower Cover Panel |
| 1077 | Front of Housing |
| 1081 | Upper Pair of Shoulders |
| 1083 | Upper Cover Panel |
| 1085 | Rear of Housing |
| 1087 | Framework for Mounting Multiple Cytometry Units |
| 1089 | Cross Bar Affixed to Side Walls of Housing (For Attaching Nozzle Mounts) |
| 1093 | Angled Mounting Plate Extending Between Side Walls |
| Common Fluid Supply | |
| 1105 | Pump for Carrier Fluid |
| 1107 | Common Supply of Carrier Fluid |
| 1115 | Gas Pressure System for Sheath Fluid |
| 1117 | Common Supply of Sheath Fluid |
| 1121 | Manifold System |
| 1123 | Vessel Containing Common Supply of Carrier Fluid |
| 1125 | Holder for Vessel |
| 1133 | Holding Block |
| 1135 | Cavity for Receiving Vessel |
| 1137 | Second Cavity for Buffer Material |
| 1139 | Vessel for Buffer Material |
| 1141 | Syringe Pump |
| 1147 | Supply Line from Syringe Pump to Manifold |
| 1149 | Three-way Valve Controlling Carrier and Buffer Fluid |
| 1155 | Vessel for Common Supply of Sheath Fluid |
| 1157 | Supply Line from Sheath Fluid Vessel to Manifold |
| 1161 | Source of Pressurized Gas |
| 1163 | Gas Line |
| 1165 | Regulator in Gas Line |
| 1167 | Two-way Valve for Gas Line Between Gas Source and Sheath Fluid Tank |
| 1169 | Gas Line for Pressurizing a Supply of Cleaning Solution |
| 1173 | Tank for Cleaning Solution |
| 1175 | Two-way Valve for Gas Line for Cleaning Solution |
| 1177 | Manifold |
| 1179 | Laminated Block |
| 1181 | Passages |
| 1185 | Fluid Flow Circuit |
| 1189 | Inlets Connected to Syringe Pump |
| 1191 | Inlets Connected to Supply of Sheath Fluid |
| 1193 | Outlets for Carrier Fluid and Sheath Fluid |
| V1-V6 | Valves for Controlling Flow Through Manifold Passages |
| 1203 | Frame Member (For Attaching Manifold Block) |
| 1205 | Fittings Threaded into Block |
| 1207 | Sample Reservoir |
| V1A-V1D | Two-way Valves (For Controlling Flow of Sample Fluid to Nozzles) |
| 1217 | Needle of Sample Reservoir |
| 1221 | Waste System |
| 1223 | Waste Tank (Receptacle) |
| 1225 | Mechanism Such as Vacuum Pump (For Generating Vacuum) |
| 1227 | Waste Lines (Connecting Valves V1A-V1D to Waste Tank) |
| 1233 | Hydrophobic Filter (In Line Connecting Waste Tank and Vacuum Pump) |
| 1235 | Fluid Circuit for Sheath Fluid |
| V2A-V2D | Two-Way Valves (For Controlling Flow of Sheath Fluid to Nozzles) |
| 1241 | Sheath Supply Line |
| 1247 | Waste Lines Connecting Sheath Fluid Flow Circuitry to Waste Tank |
| Common Power Supply and Controls | |
| 1249 | Common Power Supply |
| 1251 | Common Power Delivery Systems |
| 1253 | Common Input (GUI) |
| 1255 | Common Output (To Microprocessor) |
| Common Temperature Control | |
| 1257 | Temperature Control System |
| 1259 | Fluid Flow Circuit (For Temperature Control) |
| 1263 | Fluid Passages (For Temperature Control in Holding Block) |
| 1265 | Control Unit |
| 1269 | Fluid Passages (For Temperature Control in Manifold) |
| V6 | Shut off Valve |
| Common Light Beam and Beam Splitting System | |
| 1270 | Beamsplitter |
| 1270A | First Beam from Beamsplitter |
| 1270B | Second Beam from Beamsplitter |
| 1271 | Second Beamsplitter |
| 1271A | First Beam from Second Beamsplitter |
| 1271B | Second Beam from Second Beamsplitter |
| 1272 | Third Beamsplitter |
| 1272A | First Beam from Third BeamSplitter |
| 1272B | Second Beam from Third Beamsplitter |
| 1273 | Beam Guidance System |
| 1279 | Lower Filter Assembly |
| 1281 | Upper Mirror Assembly |
| 1285 | Base (For Lower Filter Assembly) |
| 1289 | Stage (For Lower Filter Assembly) |
| 1291 | Mechanism for Moving Stage (Micrometer) |
| 1293 | Tiltable Platform on the Stage |
| 1295 | Mirror (On Platform) |
| 1297 | Base (For Upper Mirror Assembly) |
| 1299 | Stage (For Upper Mirror Assembly) |
| 1301 | Tiltable Platform (For Upper Mirror Assembly) |
| 1303 | Mirror (For Upper Mirror Assembly) |
| 1305 | Mechanism for Moving Upper Stage |

-continued

Parts List with Associated Reference Numerals for Each Part

| | |
|---|---|
| 1309 | Target Plates (Affixed to Side Wall of Housing) |
| 1311 | Vertically Aligned Holes (In the Target Plates) |
| 1315 | 1st Reflecting Filter |
| 1317 | 2nd Reflecting Filter |
| 1319 | 3rd Reflecting Filter |
| 1321 | 4th Reflecting Filter |
| | Common Deflector Plates |
| 1331 | Two Common Deflector Plates |
| 1333 | Frame (For Mounting Common Deflector Plates on Housing) |
| | Modular Multi-Channel System |
| 4001 | Multi-Channel System |
| 4009 | Modular Cytometry Unit |
| 4011 | Housing for Modular Unit |
| 4013 | Common Housing |
| 4015 | Laser |
| 4017 | Beam Splitting and Guidance System |
| 4021 | Hole for Laser to Enter Modular Housing |
| 4023 | Plate to Cover Exit Hole |
| 4025 | Collection System for System |
| | Capillary Tube Nozzle System |
| 1335 | Capillary Tube Nozzle System |
| 1337 | Capillary Tube |
| 1341 | Chamber Filled with Light-transmitting Medium |
| | Alternative Sorting Systems |
| 1351 | Photodamage Sorting System |
| 1353 | Second Laser |
| 1355 | Collection Receptacle |
| 1357 | Fluid Switching System |
| 1359 | Fluid Switching Device |
| 1361 | Capillary Branch to First Collection Vessel |
| 1365 | Capillary Branch to Second Collection Vessel |
| 1367 | Transducer (For Creating Pressure Waves for Selectively Controlling Direction of Fluid Flow) |
| 1369 | Capillary Tube on End of Nozzle |
| 1371 | Droplet Interference Stream Sorting System |
| 1373 | High-Speed Droplet Interference Stream |
| 1375 | Droplet Generation System for High-Speed Droplet Stream |
| 1377 | High-Speed Nozzle System |
| 1379 | High-Speed Fluid Stream |
| 1381 | Transducer for Droplet Interference Stream Generation |
| 1383 | High-Speed Droplets |
| 1387 | Electric Deflection Plate for High-Speed Droplet Deflection |
| 1389 | Uncharged Droplets |
| 1391 | Charged Droplets |
| 1397 | Diverted Segment of Fluid Stream |
| 1399 | Intersection of High-Speed Droplet Stream with Coaxial Fluid Stream |
| 1403 | Collection Capillaries |
| | Collection System |
| 2201 | Collection System |
| 2203 | Intercepting Device |
| 2205 | Impact Surface |
| 2207 | Collection Vessel |
| 2211 | Droplet Entryway |
| 2213 | Bulb of Pipette |
| 2215 | Pipette |
| 2217 | Inside Wall of Pipette |
| 2225 | Guide Tube |
| 2227 | Collection System Frame |
| 2229 | Circular Holder |
| 2231 | Set Screw for Intercepting Device Height |
| 2233 | Mounting Plate |
| 2235 | Set Screws for Lateral Adjustment |
| 2241 | Lateral Slot |
| 2243 | Tray for Holding Collection Vessels |
| 2245 | Exit Window |
| 2247 | First Intercepting Device |
| 2249 | Second Intercepting Device |
| 2265 | Stray Droplets |
| | Collection Fluid |
| 2301 | Collection Fluid |
| | Filtration |
| 2401 | Filter |
| 2403 | Collection Vessel for Filtration |
| 2405 | Concentrated Slurry Containing Sperm Cells |
| 2409 | Syringe Mechanism |
| 2411 | Cannula Filter |
| 2413 | Resuspension fluid |
| 2419 | Second Container |
| 2421 | Syringe for Filtration Experiment |
| 2423 | Sample for Filtration Experiment |
| 2425 | Filter for Filtration Experiment |
| 2427 | Vacuum Pump for Filtration Experiment |
| 2431 | Syringe for Filtration Experiment II |
| 2433 | Sample for Filtration Experiment II |
| 2435 | Filter for Filtration Experiment II |
| 2437 | Filter Holder for Filtration Experiment II |
| | Cryopreservation |
| 2501 | Adjust Concentration |
| 2503 | Add Cryoprotectant |
| 2505 | Add Protein Source |
| 2507 | Load in Straws |
| 2509 | Cool to Holding Temperature |
| 2511 | Maintain at Holding Temperature |
| 2513 | Cool to Temperature Approaching Critical Zone |
| 2515 | Cool Through Range of Ice Crystal Formation |
| 2517 | Immerse in Liquid Nitrogen |
| | Common Collection System |
| 2801 | Common Collection System |
| 2803 | Common Frame for Intercepting Devices |
| 2805 | Waste Trough |
| 2807 | Tray for Collection Vessels |
| | Pulsed Laser System |
| 3001 | Pulsed Laser |
| 3003 | Laser Pulse Sensor |
| 3005 | Laser Pulse |
| 3007 | Fluorescence Pulse Lifetime Decay |
| 3009 | Digital Sample |

DETAILED DESCRIPTION OF EMBODIMENTS

The embodiments described below relate to collection and processing of animal semen, particularly to processing semen from a domestic animal to sort the sperm cells according to a specified DNA characteristic (e.g., X/Y chromosome content to preselect the gender of offspring). A number of inventive technologies are combined to achieve the results described below. However, it will be understood that the inventive technologies described herein may be applied to other applications without deviating from the scope of this invention.

General Overview

FIG. 1 is a work flow diagram providing an overview of the steps in one exemplary process of the present invention. The process starts with collection of neat semen samples from one or more male animals (e.g., bulls) at step 39. The semen samples are labeled for identification at step 41, contacted with a buffer, at step 41A and transported to a processing facility. In addition to the buffer, additives may also be added at step 41A, including, for example, an energy source, a protein source, an antibiotic, and/or a composition which regulates oxidation/reduction reactions intracellularly and/or extracellularly. An optional quality control test may be performed at step 43 to insure that the quality of each sample (e.g., sperm motility) is sufficient to indicate that the final product is likely to meet minimal quality criteria. An optional washing step may be performed at step 47. At step 47A the staining protocol that will be used for processing is selected by using various staining protocols to stain aliquots of the sample and then analyzing the sortability of each aliquot to identify a desired staining protocol for that particular sample. Staining according to the selected staining protocol is performed at step 49 by adding a staining fluid 48 containing a chemical dye (e.g., a DNA selective fluorescent dye) to each sample. In addition to the staining fluid, additives may also be added at step 48, including, for example, an energy source, a protein source, an antibiotic, and/or a composition which regulates oxidation/reduction reactions intracellularly and/or extracellularly. The samples are incubated at step 51 to allow for uptake of the dye by the sperm. Then a sample is loaded into the sample introduction device of a flow cytometer at step 53. The sample fluid is introduced into the flow cytometer along with a sheath fluid at step 54. In addition to the sheath fluid, additives may also be added at step 54, including, for example, an energy source, a protein source, an antibiotic, and/or a composition which regulates oxidation/reduction reactions intracellularly and/or extracellularly. At step 55 the flow cytometer sorts the sperm cells according to a specified DNA characteristic, as will be described below. As the sorted sperm cells are collected by the collection system of the flow cytometer at step 57, they are added to a collection vessel that contains a collection fluid or cryoextender at step 58A. In addition to the collection fluid, additives may also be added at step 58A, including, for example, an energy source, a protein source, an antibiotic, and/or a composition which regulates oxidation/reduction reactions intracellularly and/or extracellularly. By this time the sperm cells are in a solution that has been diluted by the various fluids added throughout the process. Accordingly, the population of sperm cells having the desired DNA characteristic are concentrated at step 58B for use in commercial artificial insemination. A cryoextender is added to the concentrated sorted sperm cells at step 58C. In addition to the cryoextender, additives may also be added at step 58C, including, for example, an energy source, a protein source, an antibiotic, and/or a composition which regulates oxidation/reduction reactions intracellularly and/or extracellularly. The sperm cells are then packed in tubular containers (referred to in the breeding industry as "straws") at step 59 and cryopreserved at step 61. The cryopreserved sperm are packed for storage in liquid nitrogen at step 63. The cryopreserved sperm are then distributed through a commercial distribution system at step 65 and sold to animal breeders at step 67. The animal breeders may store the cryopreserved sperm at step 69 until they are ready to use the sperm to artificially inseminate a female animal (e.g., cow) at step 71. As will be discussed below, one embodiment of the present invention involves temperature control through substantially the entire process. Likewise, completion of the various steps within defined time limits is one aspect of another embodiment of the present invention. This overall process is only one example of how the present invention can be used, and it will be understood that some of the aforementioned steps can be deleted and/or others added. The sorted sperm cells can also be used for microinjection or other in vitro fertilization, followed by embryo transplant into a recipient female animal.

The steps of the overall process incorporating advances of the present invention are described in detail below. While a particular process described is in the context of sorting animal sperm (e.g., bovine sperm), it will be understood that the various aspects of this invention are more generally applicable to any type of sperm (equine, porcine, and others), even more generally to any type of cells, and even more generally to any type of particles, organic and inorganic, including latex particles, magnetic particles, chromosomes, sub-cellular elements, protoplasts, and starch particles. These particles generally fall within a size range of 0.5 to 200 microns, but the technology of this invention is not limited to this range.

Sample Collection and Dilution

Sample Collection

The sperm sample to be sorted may be a freshly collected sample from a source animal, such as bovine, equine, porcine, or other mammalian source, or a thawed, previously cryopreserved sample. Moreover, the sample may be a single ejaculate, multiple pooled ejaculates from the same mammal, or multiple pooled ejaculates from two or more animals.

Various collection methods are known and include the gloved-hand method, use of an artificial vagina, and electro-ejaculation. The sperm are preferably collected or quickly transferred into an insulated container to avoid a rapid temperature change from physiological temperatures (typically about 35° C. to about 39° C.). The ejaculate typically contains about 0.5 to 15 billion sperm per milliliter, depending upon the species and particular animal.

Regardless of the method of collection, an aliquot may be drawn from the sperm sample and evaluated for various characteristics, such as for example, sperm concentration, sperm motility, sperm progressive motility, sample pH, sperm membrane integrity, and sperm morphology. This data may be obtained by examination of the sperm using, for example, the Hamilton-Thorn Motility Analyzer (IVOS), according to standard and well known procedures (see, for example, Farrell et al. *Theriogenology* (1998) 49(4): 871-9; and U.S. Pat. Nos. 4,896,966 and 4,896,967).

Dilution

The sperm sample may be combined with a buffer (in the form of a solid or solution) to form a sperm suspension. Among other things, the buffer may enhance sperm viability by buffering the suspension against significant changes in pH or osmotic pressure. Generally, a buffer is non-toxic to the cells and is compatible with the dye used to stain the cells. Exemplary buffers include phosphates, diphosphates, citrates, acetates, lactates, and combinations thereof. Presently preferred buffers include TCA, TEST, sodium citrate, HEPES, TL, TES, citric acid monohydrate, HEPEST (Gradipore, St. Louis, Mo.), PBS (Johnson et al., *Gamete Research*, 17:203-212 (1987)), and Dulbecco's PBS (Invitrogen Corp., Carlsbad, Calif.).

One or more buffers may be combined together or with additives as discussed below to form a buffered solution, and the buffered solution combined with the sperm sample to form a sperm suspension. A buffered solution may also contain one or more additives, as described in greater detail below. Exemplary buffered solutions are described in Table I. Preferred buffered solutions include a solution comprising 3% TRIS base, 2% citric acid monohydrate, and 1% fructose (w/v) in water at a pH of about 7.0, a solution designated as TCA #1 in Table I, and a solution designated as TCA #2 in Table I.

TABLE I

Buffered Solutions

| COMPONENTS | TCA#1 | TCA#2 | TEST | Na Citrate | HEPES | TL |
|---|---|---|---|---|---|---|
| Sodium chloride (NaCl) | | | | | 7.6 g | 5.84 g |
| Potassium chloride (KCl) | | | | | 0.3 g | 0.23 9 |
| Sodium bicarbonate (NaHCO3) | | | | | | 2.1 g |
| Sodium phosphate monobasic (NaH2PO4—H2O) | | | | | | 0.04 g |
| (+)-2-hydroxyproprionic acid (Na Lactate) | | | | | | 3.68 ml |
| Magnesium chloride (MgCl2) | | | | | 0.1 g | 0.08 g |
| N-(2-hydroxyethyl)piperazine-N'-(2-ethansulfonic acid) (HEPES) | | | | | 2.38 g | 2.38 g |
| tris(hydroxymethyl)amimonethane (TRIS base) | 30.3 g | 32.02 g | 10.28 g | | | |
| Citric Acid Monohydrate | 15.75 g | 18.68 g | | | | |
| Na Citrate Dihydrate | | | | 29 g | | |
| 2-[(2-hydroxy-1,1-bis[hydroxymethyl] ethyl) aminoethanesulfonic acid (TES) | | | 43.25 g | | | |
| Fructose | 12.5 g | 2.67 g | | 10 g | 2.52 g | |
| D-Glucose | | | 2 g | | | |
| Steptamycin | | | 0.25 g | | | |
| Penicillin-G | | | 0.15 g | | | |
| Water | 1 liter | 1 liter | 1 liter | 1 liter | 1 liter | 1 liter |
| Target pH | 7.35 | 7.35 | 7.35 | 7.35 | 7.35 | 7.35 |
| Target osmolality (milliosmols/kg H2O) | ~314 | ~300 | ~302 | ~316 | ~298 | ~296 |

Alternatively, the sperm may be combined with a metabolic inhibitor to form an inhibited sperm suspension. Metabolic inhibitors cause the sperm cells to emulate sperm cells of the epididymis of a mammal, such as for example a bull, by simulating the fluid environment of the epididymis or epididymal tract of the mammal. Such an inhibitor would reduce or inhibit the motility and metabolic activity of the sperm. Exemplary inhibitors of this class include carbonate based inhibitors, such as for example those disclosed in Salisbury & Graves, J. Reprod. Fertil., 6:351-359 (1963). A preferred inhibitor of this type comprises $NaHCO_3$, $KHCO_3$, and $C_6H_8O_7 \cdot H_2O$. A more preferred inhibitor of this type comprises 0.204 g $NaHCO_3$, 0.433 g $KHCO_3$, and 0.473 g $C_6H_3O_7 \cdot H_2O$ per 25 mL of purified water (0.097 moles/L of $NaHCO_3$. 0.173 moles/L of $KHCO_3$, 0.090 moles/L $C_6H_8O_7 \cdot H_2O$ in water).

In addition to a buffer, the sperm suspension may also contain a range of additives to enhance sperm viability or motility. Exemplary additives include energy sources, protein sources, antibiotics, and compositions which regulate oxidation/reduction reactions intracellularly and/or extracellularly. One or more of these additives may be introduced into the buffer or buffered solution before the formation of the sperm suspension or, alternatively, may be separately introduced into the sperm suspension.

One or more energy sources may be added to minimize or inhibit the sperm cells from oxidizing intracellular phospholipids and other cellular components. Exemplary energy sources include monosaccharides, such as fructose, glucose, galactose and mannose, and disaccharides, such as sucrose, lactose, maltose, and trehalose, as well as other polysaccharides. For example, the resulting sperm suspension may include about 1% (w/v) to about 4% (w/v) of the energy source(s). If included, the energy source is preferably fructose and the sperm suspension contains about 2.5% (w/v).

To minimize dilution shock, provide support to the cells, or disperse the cells throughout the suspension, a protein source may also be included in the buffer, buffered solution, or sperm suspension. Exemplary protein sources include egg yolk, egg yolk extract, milk (including heat homogenized and skim), milk extract, soy protein, soy protein extract, serum albumin, bovine serum albumin, human serum substitute supplement, and combinations thereof. Albumin, and more particularly bovine serum albumin (BSA), is a preferred protein source. For example, if included, BSA may be present in the sperm suspension in an amount of less than about 5.0% (w/v), preferably less than about 2% (w/v), more preferably less than about 1% (w/v), and most preferably in an amount of about 0.1% (w/v).

The use of a protein source, such BSA, alone may initiate the process of capacitation in a percentage of the sperm cells in the suspension. It is preferred that this process take place in the female reproductive tract. Therefore, in order to inhibit the initiation of capacitation during dilution, as well as during the subsequent staining and sorting, an alternative protein source or a protein substitute may be included in the sperm suspension. The alternative protein source or protein substitute possess the advantageous effects of a typical protein source, such as BSA, in addition to the ability to inhibit the initiation of capacitation in a larger percentage of the cells in the sperm suspension. Examples of alternative protein sources include human serum substitute supplement (SSS) (Irvine Scientific, Santa Ana, Calif.) and cholesterol enhancer BSA, while an example of a protein substitute includes a polyvinyl alcohol, such as for example, a low to medium viscosity polyvinyl alcohol generally of a molecular weight of about 30,000 to about 60,000. Generally, if included, these compositions will be present in the same amounts as disclosed above with respect to BSA, with the total albumin content of the buffer or buffered solution generally not exceeding about 5.0% (w/v).

An antibiotic may be added to the sperm suspension in order to inhibit bacterial growth. Exemplary antibiotics include, for example, tylosin, gentamicin, lincomycin, spectinomycin, Linco-Spectin® (lincomycin hydrochloride-spectinomycin), penicillin, streptomycin, ticarcillin, or any combination thereof. The antibiotics may be present in a concentration of about 50 ☐g to about 800 ☐g per ml of semen, regardless of whether the semen is neat, buffered, or contains additional substances, such as for example, any of the additives mentioned herein. The Certified Semen Services (CSS) and National Association of Animal Breeders (NAAB) have promulgated guidelines regarding the use of antibiotics with respect to sperm collection and use.

A composition which regulates oxidation/reduction reactions intracellularly and/or extracellularly may also be included in the sperm suspension. Such a composition may provide a protective effect to the sperm cells, such as for example by maintaining sperm viability or progressive motility. Examples of such a composition include, for example, pyruvate, vitamin K, lipoic acid, glutathione, flavins, quinones, superoxide dismutase (SOD), and SOD mimics. If included in the sperm suspension, such a composition may be present in a concentration sufficient to effect the protective effect without detrimentally affecting sperm health. Exemplary concentration ranges include from about 10 µM to about 50 mM depending upon such factors as the particular composition being used or the concentration of sperm in the suspension. For example, pyruvate may be present in the sperm suspension in a concentration from about 1 mM to about 50 mM, preferably from about 2.5 mM to about 40 mM, more preferably from about 5 mM to 25 mM, even more preferably from about 10 mM to 15 mM, still more preferably about 15 mM, and most preferably about 10 mM. Vitamin K may be present in the sperm suspension in a concentration from about 1 µM to about 100 µM, preferably from about 10 µM to about 100 µM, and more preferably about 100 µM. Lipoic acid may be present in the sperm suspension in a concentration from about 0.1 mM to about 1 mM, preferably from about 0.5 mM to about 1 mM, and more preferably about 1 mM.

Staining of the Cells to be Sorted

Generally, sperm cells may be stained by forming a staining mixture comprising sperm cells, a buffer, and a dye. The sperm cells may be derived from a freshly obtained semen sample, as discussed above with respect to sample collection and dilution, or from a thawed cryopreserved semen sample.

If the semen sample is a thawed, previously cryopreserved sample, the sperm are preferably thawed immediately prior to staining. Generally, a straw or other cryopreservation vessel containing the frozen sperm may be placed in a water bath, the temperature of which is preferably in excess of the glass transition temperature of the sperm cell membrane (i.e., about 17° C.), but not so great as to adversely impact sperm health. For example, frozen sperm may be thawed by immersing the cryopreservation vessel in a water bath maintained at a temperature of about 17° C. to about 40° C. for a period of about 30 seconds to about 90 seconds.

Once obtained, the sperm cells may be introduced into the staining mixture in the form of neat semen or in the form of a suspension derived therefrom, e.g., a sperm suspension as discussed above with respect to sample collection and dilution.

The dye may be in the form of a neat solid or a liquid composition. The dye may also be dissolved or dispersed in an unbuffered liquid to form a dye solution. Alternatively, the dye may be in the form of a dye suspension comprising a dye and a buffer or buffered solution that is biologically compatible with sperm cells. A range exemplary buffers and buffered solutions are discussed above with respect to sample collection and dilution. For example, among the buffers which may be used is a TCA buffer solution comprising 3% TRIS base, 2% citric acid monohydrate, and 1% fructose in water at a pH of about 7.0, or a carbonate-based inhibitor solution comprising 0.204 g $NaHCO_3$, 0.433 g $KHCO_3$, and 0.473 g $C_6H_8O_7 \cdot H_2O$ per 25 mL of purified water (0.097 moles/L of $NaHCO_3$, 0.173 moles/L of $KHCO_3$, 0.090 moles/L $C_6H_8O_7 \cdot H_2O$ in water). Thus, for example, a staining mixture may be formed by combining neat semen with a dye. Alternatively, the staining mixture may be formed by combining neat semen with a buffer or buffered solution and a dye. Additionally, the staining mixture may be formed by combining a sperm suspension with a dye.

The staining mixture may be formed by using one or more UV or visible light excitable, DNA selective dyes as previously described in U.S. Pat. No. 5,135,759 and WO 02/41906. Exemplary UV light excitable, selective dyes include Hoechst 33342 and Hoechst 33258, each of which is commercially available from Sigma-Aldrich (St. Louis, Mo.). Exemplary visible light excitable dyes include SYBR-14, commercially available from Molecular Probes, Inc. (Eugene, Oreg.) and bisbenzimide-BODIPY® conjugate 6-{[3-((2Z)-2-{[1-(difluoroboryl)-3,5-dimethyl-1H-pyrrol-2-yl]methylene}-2H-pyrrol-5-yl)propanoyl]amino}-N-[3-(methyl{3-[({4-[6-(4-methylpiperazin-1-yl)-1H,3'H-2,5'-bibenzimidazol-2'-yl]phenoxy}acetyl)amino]propyl}amino)propyl]hexanamide ("BBC") described in WO 02/41906. Each of these dyes may be used alone or in combination; alternatively, other cell permeant UV and visible light excitable dyes may be used, alone or in combination with the aforementioned dyes, provided the dye does not detrimentally affect the viability of the sperm cells to an unacceptable degree when used in concentrations which enable sorting as described elsewhere.

The preferred concentration of the DNA selective dye in the staining mixture is a function of a range of variables which include the permeability of the cells to the selected dye, the temperature of the staining mixture, the amount of time allowed for staining to occur, and the degree of enrichment desired in the subsequent sorting step. In general, the dye concentration is preferably sufficient to achieve the desired degree of staining in a reasonably short period of time without substantially detrimentally affecting sperm viability. For example, the concentration of Hoechst 33342, Hoechst 33258, SYBR-14, or BBC in the staining mixture will generally be between about 0.1 µM and about 1.0 M, preferably from about 0.1 µM to about 700 µM, and more preferably from about 100 µM to about 200 µM. Accordingly, under one set of staining conditions, the concentration of Hoechst 33342 is preferably about 100 µM. Under another set of staining conditions, the concentration of Hoechst 33342 is about 150 µM. Under still another set of staining conditions the concentration is preferably about 200 µM.

In addition to buffer, other additives may be included in the staining mixture to enhance the viability or motility of the sperm; these additives may be provided as part of the sperm source, the dye source, or separately to the staining mixture. Such additives include energy sources, antibiotics, compositions which regulate oxidation/reduction reactions intracellularly and/or extracellularly, and seminal plasma, the first three of which are discussed above with respect to sample collection and dilution, and the last of which is discussed below with respect to collection fluids. Such additives may be added during the staining techniques in accordance therewith.

In particular, it has been observed that the inclusion of a composition which regulates oxidation/reduction reactions intracellularly and/or extracellularly in the staining mixture may help to maintain sperm viability at elevated staining temperatures, at elevated dye concentrations, at increased staining periods, or any combination thereof. Examples of these compositions and the use of the same are discussed above with respect to buffers and diluents. Such compositions may be added during the staining techniques in accordance therewith.

The staining mixture may be maintained at any of a range of temperatures; typically, this will be within a range of about 4° C. to about 50° C. For example, the staining mixture may be maintained at a "relatively low" temperature, i.e., a temperature of about 4° C. to about 30° C.; in this embodiment, the temperature is preferably from about 20° C. to about 30°

C., more preferably from about 25° C. to about 30° C., and most preferable at about 28° C. Alternatively, the staining mixture may be maintained within an "intermediate" temperature range, i.e., a temperature of about 30° C. to about 39° C.; in this embodiment, the temperature is preferably at about 34° C. to about 39° C., and more preferably about 37° C. In addition, the staining mixture may be maintained within a "relatively high" temperature range, i.e., a temperature of about 40° C. to about 50° C.; in this embodiment, the temperature is preferably from about 40° C. to about 45° C., more preferably from about 40° C. to about 43° C., and most preferably at about 41° C. Selection of a preferred temperature generally depends upon a range of variables, including for example, the permeability of the cells to the dye(s) being used, the concentration of the dye(s) in the staining mixture, the amount of time the cells will be maintained in the staining mixture, and the degree of enrichment desired in the sorting step.

Uptake of dye by the sperm cells in the staining mixture is allowed to continue for a period of time sufficient to obtain the desired degree of DNA staining. That period is typically a period sufficient for the dye to bind to the DNA of the sperm cells such that X and Y chromosome-bearing sperm cells may be sorted based upon the differing and measurable fluorescence intensity between the two. Generally, this will be no more than about 160 minutes, preferably no more than about 90 minutes, still more preferably no more than about 60 minutes, and most preferably from about 5 minutes to about 40 minutes.

Accordingly, in one embodiment, a staining mixture is formed comprising sperm cells and a dye in a concentration from about 100 µM to about 200 µM, and the staining mixture is held for a period of time at a temperature of about 41° C. In another embodiment, the staining mixture further comprises pyruvate in a concentration of about 10 mM, vitamin K in a concentration of about 100 µM, or lipoic acid in a concentration of about 1 mM.

In still another embodiment, a staining mixture is formed comprising sperm cells and a dye in a concentration from about 100 µM to about 200 µM, and the staining mixture is held for a period of time at a temperature of about 28° C. In another embodiment, the staining mixture comprises pyruvate in a concentration of about 10 mM, vitamin K in a concentration of about 100 µM, or lipoic acid in a concentration of about 1 mM.

In yet another example, a staining mixture is formed comprising sperm cells, a metabolic inhibitor comprising 0.204 g $NaHCO_3$, 0.433 g $KHCO_3$, and 0.473 g $C_6H_8O_7 \cdot H_2O$ per 25 mL of purified water (0.097 moles/L of $NaHCO_3$, 0.173 moles/L of $KHCO_3$, 0.090 moles/L $C_6H_8O_7 \cdot H_2O$ in water), and a dye in a concentration from about 100 µM to about 200 µM, and the staining mixture is held for a period of time at a temperature of about 28° C. In another embodiment, the staining mixture is held for a period of time at a temperature of about 41° C.

Sheath Fluid

To sort the sperms cells, the stained cells are introduced as a sample fluid into the nozzle of a flow cytometer as described below. As part of the process, the sample fluid is typically surrounded by a sheath fluid. The sheath fluid permits the sperm cells in the sample fluid to be drawn out into a single file line as discussed below. The sheath fluid is collected along with the sperm cells by the collection system of the flow cytometer and therefore forms part of the post-sort environment for the sperm cells. Thus, it is desirable that the sheath fluid provides a protective effect to the cells upon contact of cells by the sheath fluid.

The sheath fluid generally comprises a buffer or buffered solution. Examples of buffers and buffered solutions and illustrative concentrations of the same that may be used in the sheath fluid are disclosed above with respect to sample collection and dilution. In a particular embodiment, the sheath fluid comprises 0.96% Dulbecco's phosphate buffered saline (w/v), 0.1% BSA (w/v), in water at a pH of about 7.0.

Optionally, the sheath fluid may also contain a range of additives that are beneficial to sperm viability or motility. Such additives include, for example, an energy source, a protein source, an antibiotic, a composition which regulates oxidation/reduction reactions intracellularly and/or extracellularly, an alternative protein source, and polyvinyl alcohol. Each of these additives, and examples of the same, is discussed above with respect to sample collection and dilution. Such additives may be added to the sheath fluid in accordance therewith.

The sheath fluid may optionally be filtered prior to the sorting step. Contaminants that may be present in the sheath fluid, such as non-soluble particulates, may interfere with sorting. Therefore, the sheath fluid may be filtered prior to its introduction into a flow cytometer. Such filters and methods of using the same are well known in the art. Generally, the filter is a membrane of about 0.1 microns to about 0.5 microns, preferably about 0.2 microns to about 0.3 microns, and more preferably about 0.2 microns.

The stained cells may be introduced into the sheath fluid at any time subsequent to staining. Typically, a stream of the stained cells in the sample fluid is injected into a stream of sheath fluid within the nozzle of the flow cytometer. Initially, there is substantially no contacting of the sample fluid and the sheath fluid due to laminar flow of the fluids as discussed in more detail below. It is desirable that the sample fluid and the sheath fluid remain as substantially discrete flowing streams until after the particles (e.g., the stained sperm cells) in the sample fluid have been analyzed. At some point, however, the sheath fluid and the cells of the sample fluid come in contact with one another. For instance in a droplet sorting flow cytometer (discussed below) the sheath fluid and sample fluid begin contacting one another as droplets are being formed downstream of the interrogation location.

At the time of the introduction of the stained cells and the sheath fluid, both the stained cells and the sheath fluid may be at a temperature from about 4° C. to about 50° C. The sheath fluid and the stained cells may be at the same or at different temperatures, with either being at a higher temperature than the other. Accordingly, in one embodiment, at the time of the introduction of the stained cells and the sheath fluid, both the cells and the sheath fluid are at the same temperature; for example, at a "relatively low" temperature, such as for example at about 5° C. to about 8° C.; at an "intermediate" temperature, such as for example at about 25° C. to about 30° C.; or at a "relatively high" temperature, such as for example at about 40° C. to about 43° C. In another embodiment, the stained cells are at a higher temperature than the sheath fluid, such as for example, the cells being at about 40° C. to about 43° C. and the sheath fluid being at about room temperature or at about 5° C. In yet another embodiment, the stained cells are at a lower temperature than the sheath fluid.

Flow Cytometry

Figure 2:
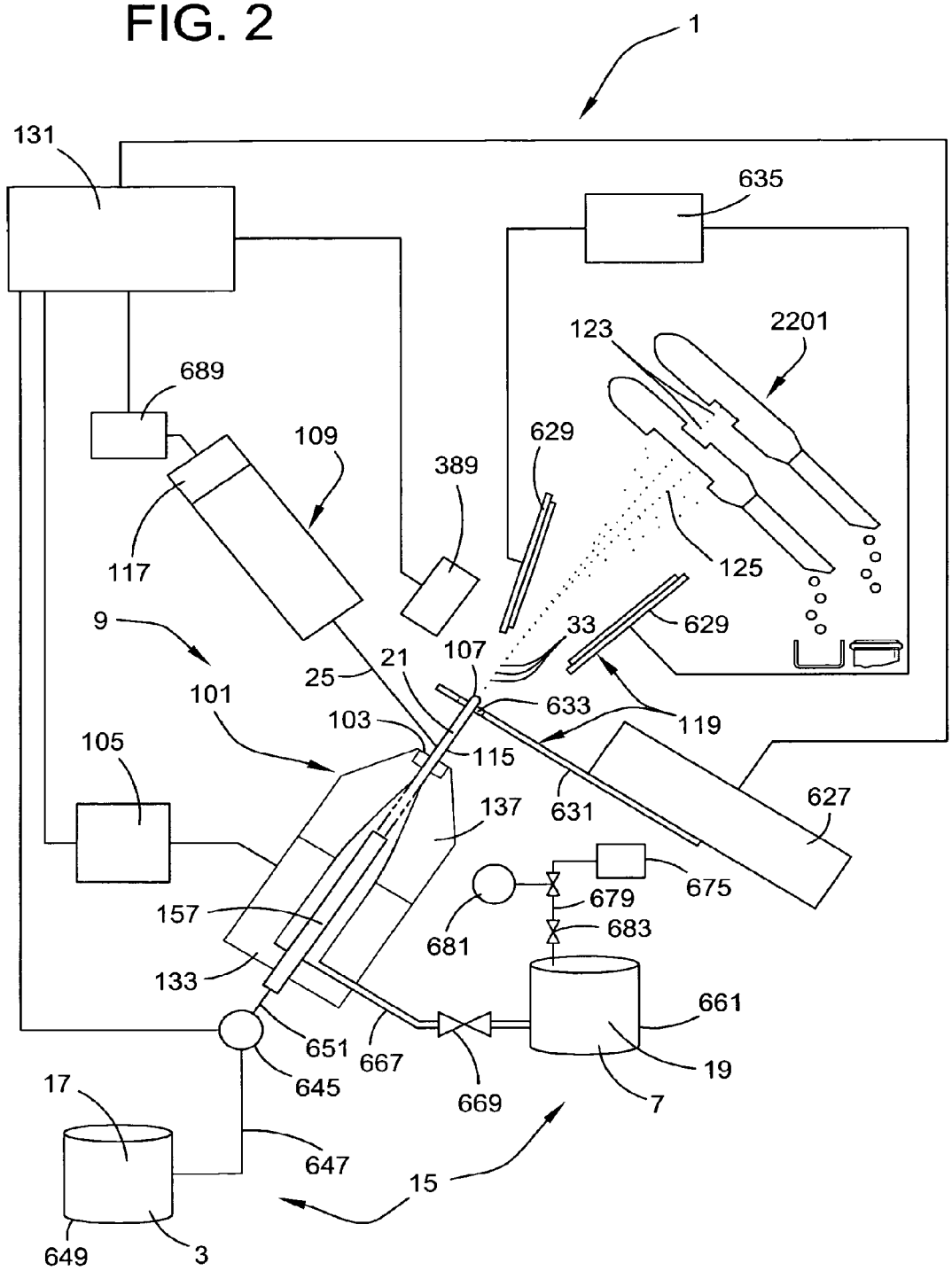
FIG. 2 is a schematic diagram of a one embodiment of a flow cytometry droplet sorting system of the present invention.
Figure 3:
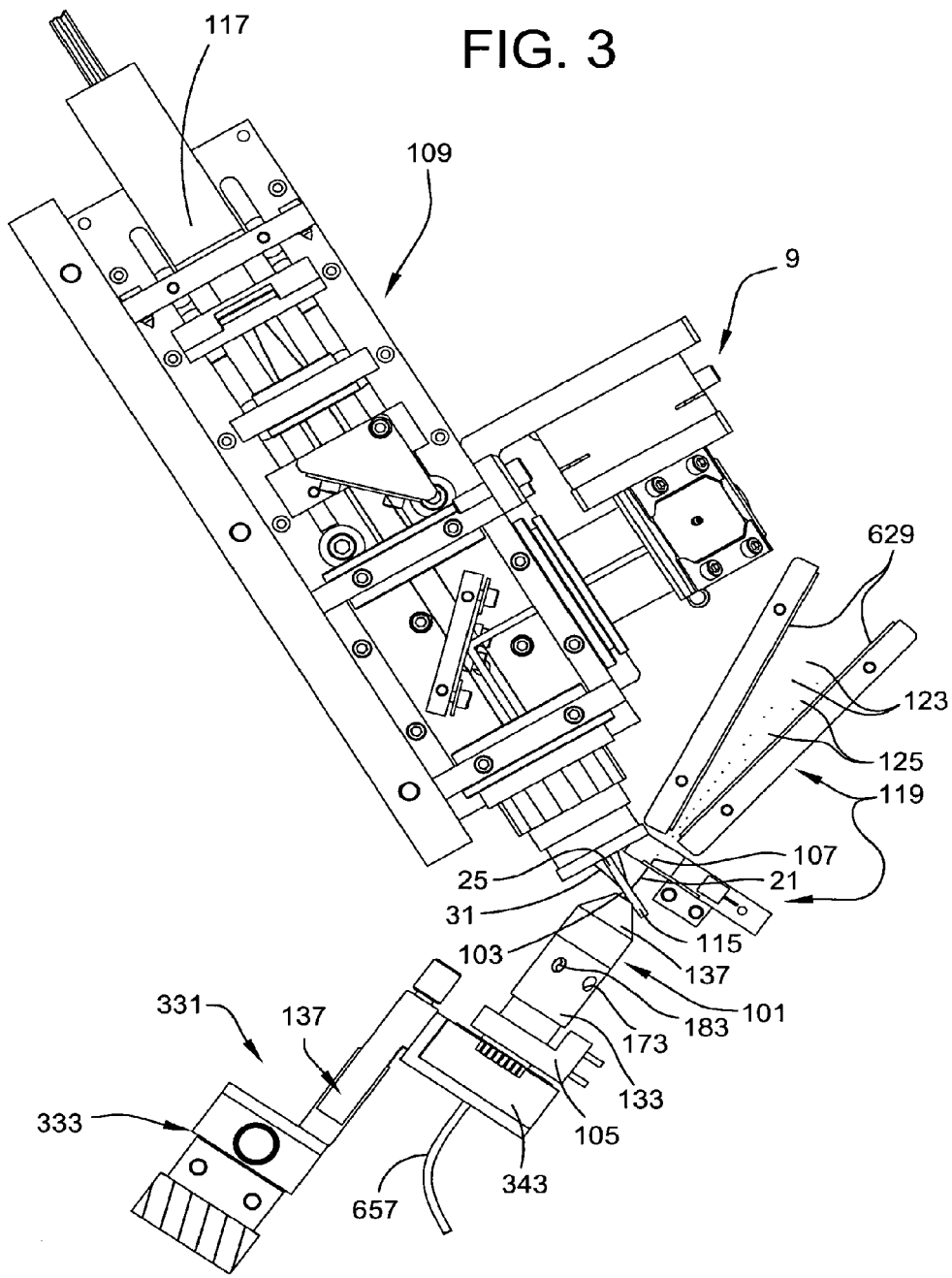
FIG. 3 is a side view of a portion of one embodiment of a flow cytometry apparatus of the present invention for droplet sorting showing an epi-illumination optic assembly focusing an excitation beam on an upward moving fluid stream generated by a nozzle system.

One embodiment of the present invention employs inventive technologies in flow cytometry to analyze and sort the sperm cells. Referring now to FIGS. 2 and 3, one embodiment of a flow cytometry system of the present invention is designated in its entirety by the reference numeral 1. As will appear, the flow cytometry system 1 is useful for classifying and sorting particles, such as sperm cells, according to selected characteristics. In general, the system 1 comprises a supply 3 of carrier fluid 17 containing particles to be sorted, a supply 7 of sheath fluid 19, flow cytometry apparatus having sorting capabilities, generally designated 9, and a fluid delivery system 15 for delivering the carrier 17 and sheath fluids 19 from respective supplies 3, 7 under pressure to the flow cytometry apparatus 9. The flow cytometry apparatus 9 is adapted for receiving the carrier 17 and sheath 19 fluids, for combining the fluids 17, 19 to create a stream of pressurized fluid 21, for directing the stream 21 carrying the particles through a focused beam of electromagnetic radiation 25 (e.g., UV laser light), and for analyzing the electromagnetic radiation 31 (e.g., fluorescent light) emitted by particles passing through the focused beam 25. The apparatus 9 also functions to break the stream 21 up into droplets 33 containing particles to be evaluated, and to sort the droplets 33 based on the aforesaid measurements according to one or more characteristics of the particles contained in the droplets 33. While this invention may be used to analyze and preferably sort any type of particle, it has particular application to sorting cells according to one or more desired characteristics of the cells (e.g., size, DNA content, shape, density, gene sequence, etc.). This invention is especially suited for sorting animal sperm cells for commercial use by the animal production industry for in vivo or in vitro artificial insemination, as discussed in more detail below.

Single-Channel Sorting Apparatus and Method
Flow Cytometry Apparatus

The flow cytometry apparatus 9 shown in FIG. 3 comprises a nozzle system, generally designated 101, for delivering a fluid stream 21 containing particles (e.g., stained sperm cells) through a nozzle orifice 103 under pressure with the cells substantially in single file and, in the case of sperm cells, with asymmetric heads of the sperm cells substantially in a desired orientation which will be described. As in conventional flow cytometry droplet sorting systems, a transducer 105 is provided opposite the nozzle orifice 103 for introducing acoustical energy into the fluid stream 21 which causes the stream 21 to break into droplets 33 containing individual cells at a "droplet break-off" location 107 spaced from the nozzle orifice 103. The system 1 also includes an optics system, generally designated 109, for focusing a beam of electromagnetic radiation 25 (e.g., 350-700 nm UV or visible laser light) on the fluid stream 21 at an "interrogation" location 115 which, in the described embodiment, is between the nozzle orifice 103 and the droplet break-off location 107. Thus, the described embodiment is a jet-in-air system. In other embodiments, the interrogation location 107 could be inside the nozzle orifice 103 or upstream from the orifice 103. In any event, the cells are adapted to pass through the beam of light 25 at the interrogation location 107, resulting in excitation of a chemical stain (or other reporting medium) in the cells to cause fluorescence emissions 31 having a wavelength different from that of the beam 25 (e.g., if the illumination light 25 has a wavelength of about 350 to 370 nm, the fluorescent emissions 31 may have a wavelength of about 460 nm). A photodetector 117 is operable to detect these emissions 31 and to convert them into electrical signals which are processed and used to classify the cells according to selected characteristics, such as the X/Y chromosome content of sperm cells. The flow cytometry apparatus 9 further comprises a sorting system, generally designated 119, for sorting the droplets 33 into different groups or populations (e.g., two populations 123, 125) according to the classification of the cells contained in the droplets 33 and a collection system, generally designated 2201 (FIG. 2), for collecting the droplets 33 and maintaining the segregation of the different populations 123, 125.

Operation of the system 1 is controlled by a processor 131, such as microprocessor or other digital or analog control and/or processor, or combinations thereof, which controls the various functions of the components of the system 1 in a manner to be described. Significantly, the processor 131 is also responsive to particle analysis information to control the output of the system 1 based on selected control and sorting strategies involving different parameters, including the desired purity of one of the sorted populations of particles, the acceptable quantity (or percentage) of desired particles one of the populations as compared to the quantity (or percentage) of desired particles in one or more of the other populations, and other parameters, as will be discussed later.

The various components of the system 1 are described in detail below.

Nozzle System

Figure 4:
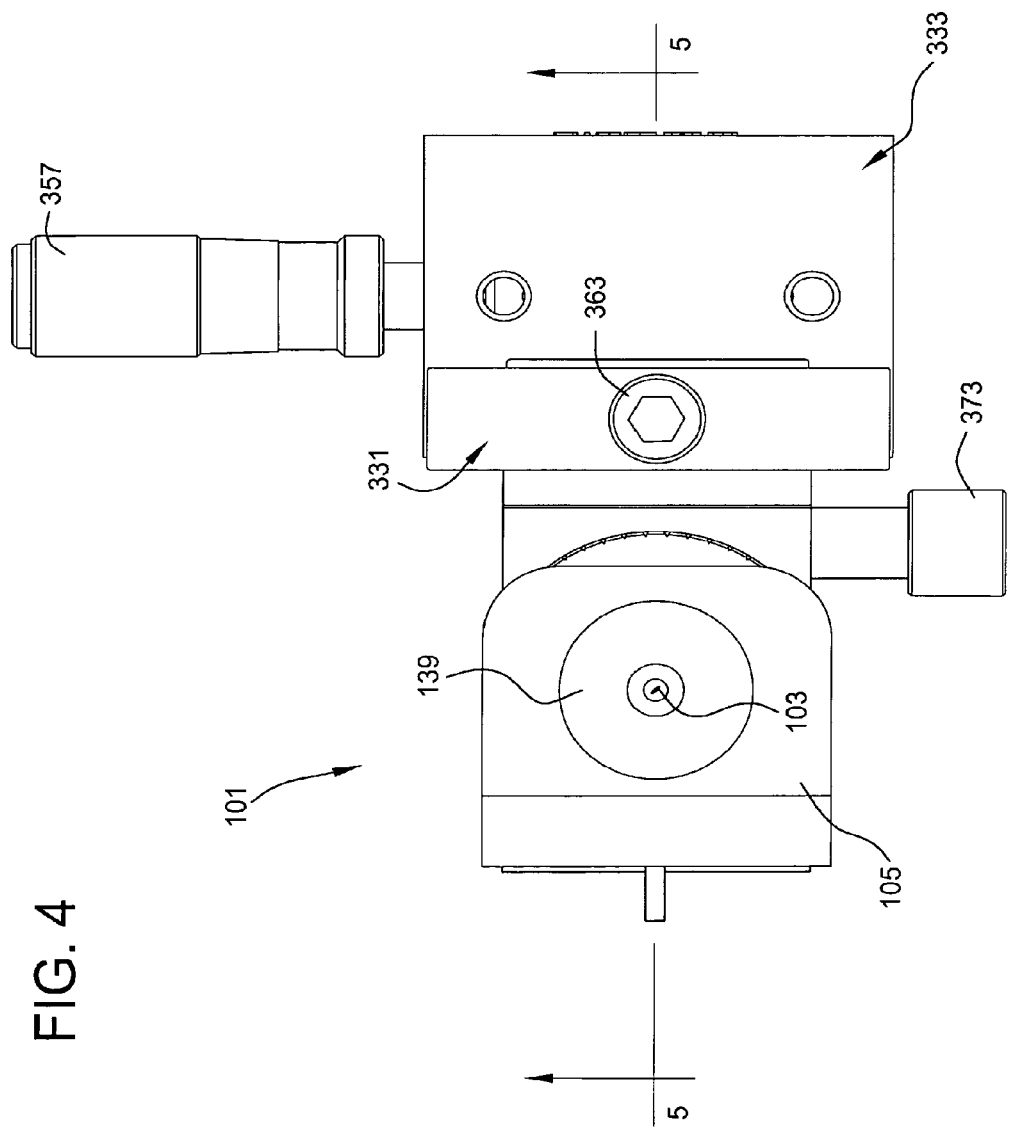
FIG. 4 is an end view of one embodiment of a nozzle and nozzle holder of the present invention.
Figure 5:
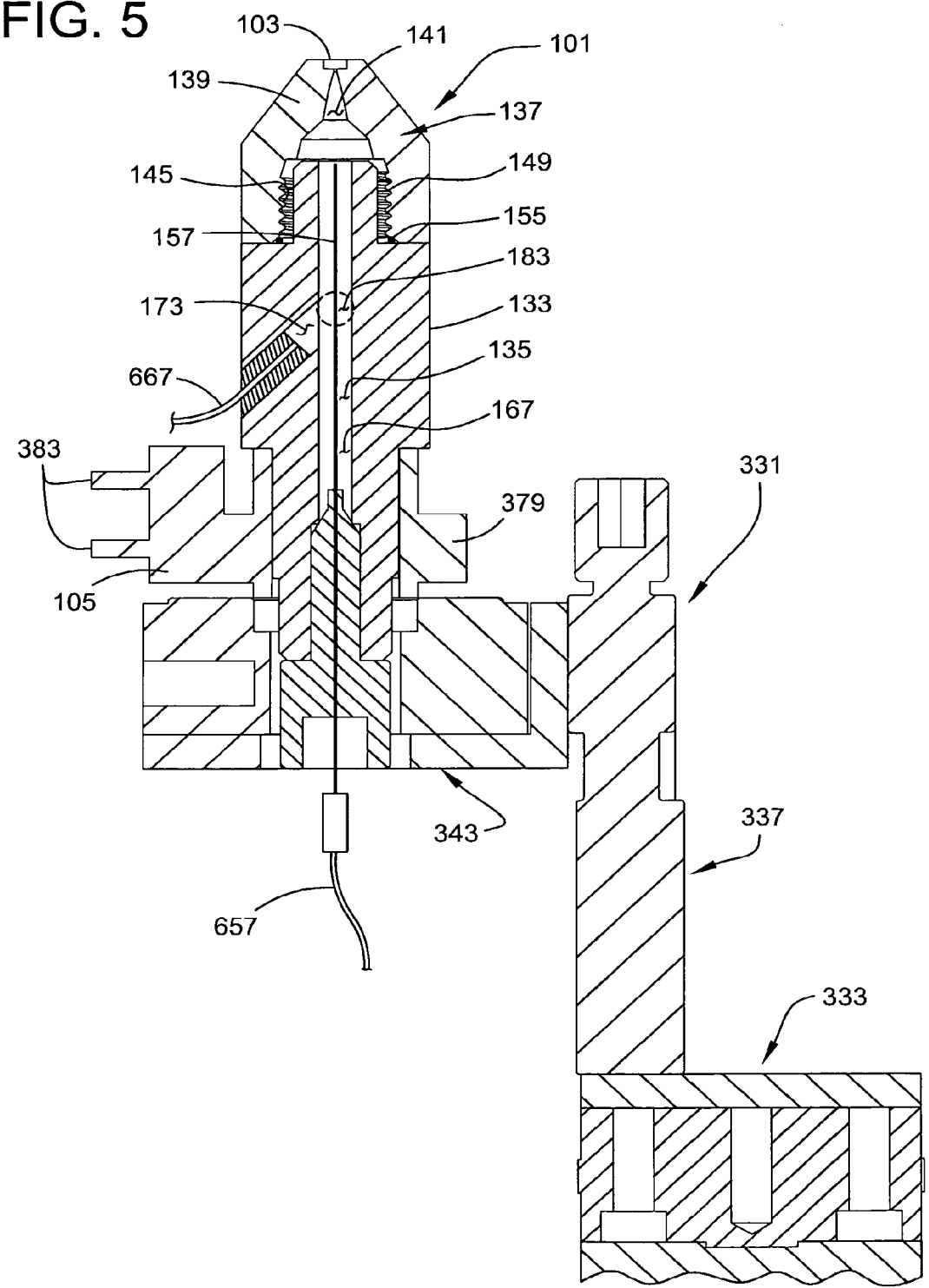
FIG. 5 is a sectional view of the nozzle and nozzle holder of FIG. 4 taken through cutting plane 5-5 on FIG. 4.

Referring to FIGS. 4 and 5, the nozzle system 101 comprises, in one exemplary embodiment, a generally cylindrical flow body 133 having a central longitudinal bore 135 through it, and a nozzle 137 on the flow body 133 having a funnel-shaped nozzle body 139. A passage 141 extends through the nozzle body 139 co-axial with the bore 135 in the flow body 133 and terminates in the aforementioned nozzle orifice 103 at the forward end of the nozzle 137. The nozzle body 139 has an internally threaded counterbore 145 at its rearward end for threadably receiving a threaded projection or stud 149 at the forward end of the flow body 133 to removably connect the nozzle 137 to the flow body 133, the connection being sealed by an O-ring seal 155. It will be understood that the nozzle can be removably connected to the flow body in other ways or, alternatively, the parts could be integrally formed as one piece.

Particles are delivered to the nozzle 137 by means of a conduit 157 positioned co-axially in the bore 135 of the flow body 133. The outside diameter of the conduit 157 is less than the inside diameter of the bore 135 so that an annular space 167 is formed around the conduit 157. In one particular embodiment, the conduit 157 is a tubular needle (e.g., a 16-ga. needle having an inside diameter of 0.01 in.) having a front end which extends into the counterbore 145 at the back of the nozzle 137. The back end of the conduit 157 is connected to the fluid delivery system 15 for delivery of carrier fluid 15 (e.g., a staining mixture containing sperm cells) to the conduit 157. The annular space 167 surrounding the conduit 157 is connected by means of a radial bore 173 in the flow body 133 to the fluid delivery system 15 for delivery of sheath fluid 19 into the annular space 167. As shown in FIGS. 3 and 5, an optional second radial bore 183 may be provided in the flow body 133 connecting the annular space 167 to another line (not shown) for supply of additional sheath fluid 19 to the nozzle 137.

As in conventional flow cytometry systems, sheath fluid 19 is introduced into the annular space 167 surrounding the conduit 157. The velocity of the sheath fluid 19 as it flows past the tip of the conduit 157 is much higher that the velocity of the carrier fluid 17 exiting the conduit 157, so that the carrier fluid 17 and cells (e.g., sperm cells) contained therein are accelerated by the sheath fluid 19 toward the orifice 103 of the nozzle 137. This acceleration functions to space the cells out generally in a single file arrangement for separate analysis by the optics system 109. The sheath fluid 19 surrounds the carrier fluid 17, resulting in the fluid stream 21 having a central core 189 of carrier fluid 17 and an outer co-axial sheath 191 of sheath fluid 19 surrounding the central core 189

Figure 6:
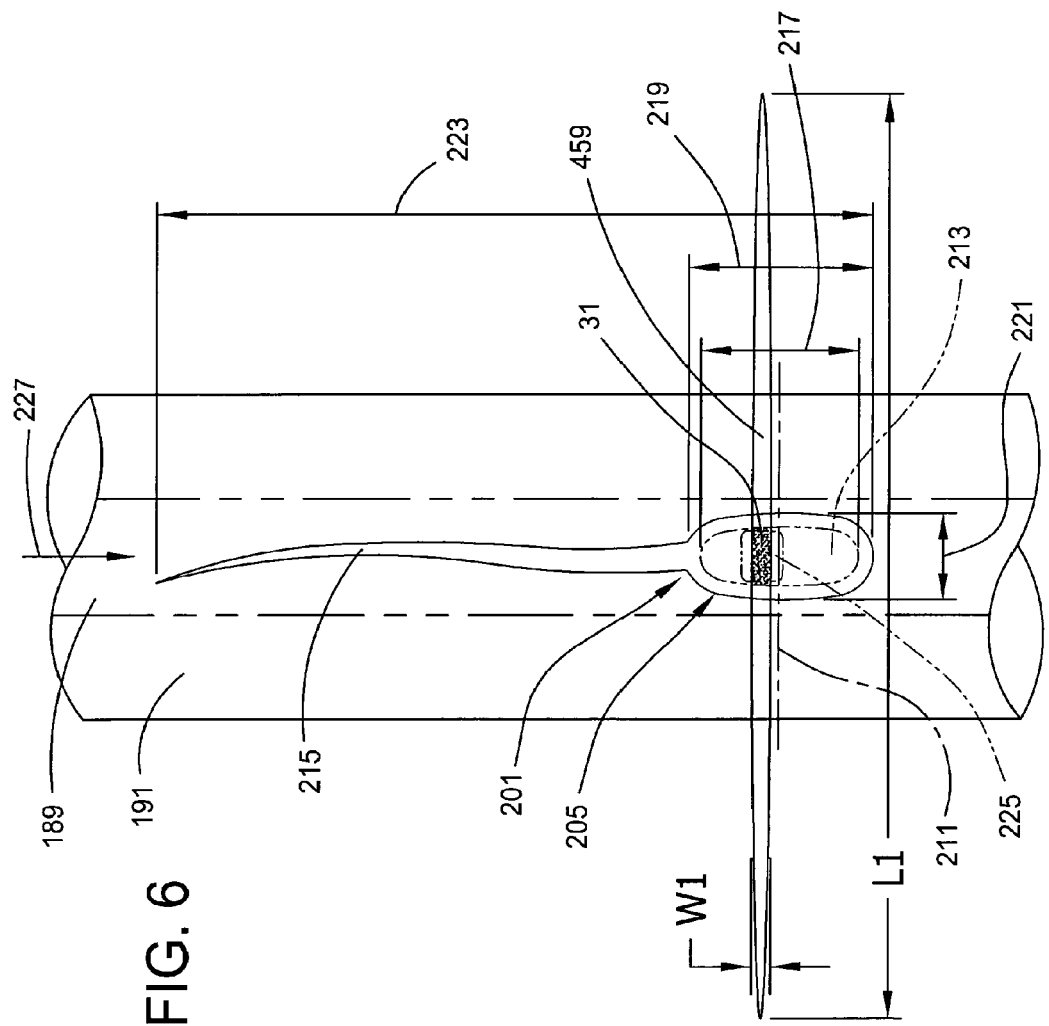
FIG. 6 is a schematic diagram of a sperm cell entrained in a fluid stream being interrogated by an elliptically shaped beam spot according to one embodiment of the present invention.

(see FIG. 6). As will be understood by those skilled in flow cytometry, the laminar flow and hydrodynamic focusing of the central core 189 tends to confine the particles to the core 189, with little mixing of the sheath 19 and carrier fluids 17 in the nozzle 137. Further, the central core 189 remains essentially intact within the sheath 191 as the stream 21 moves through the nozzle system 101, until such time as droplets 33 are formed at the break-off location 107. This type of co-axial flow is particularly suited for flow cytometry, because the particles to be analyzed are confined within the relatively narrow core 189 of the stream. As a result, a beam of light 25 focused on the center or core 189 of the stream 21 will illuminate the particles so that they may be analyzed substantially one at a time. By confining the core 189 within a sufficiently narrow diameter, one can obtain more uniform illumination of the particles in the core fluid 189. For good analytical results, the diameter of the core containing the particles should desirably be within a range of 7 to 20 microns, and more desirably within a range of 7 to 14 microns. The diameter of the core stream 189 can be increased or decreased by adjusting the rate of delivery of the carrier fluid 17 relative to the rate of delivery of the sheath fluid 19.

Cell Orientation

For optimizing analytical results, it is desirable that particles having asymmetric shapes be in a desired orientation when they pass through the light beam from the optics system. As is known to those skilled in the art, fluorescence emissions from asymmetric particles tend to anisotropic (i.e., the intensity of the emissions are not uniform in all directions). As used herein, the term "desired orientation" means an orientation which allows the processing system to discriminate between cells having different characteristics with an accuracy in a range of 70% to 100%, more desirably in a range of 80% to 100%, still more desirably in a range of 90% to 100%, and most desirably 95% or greater.

Figure 7:
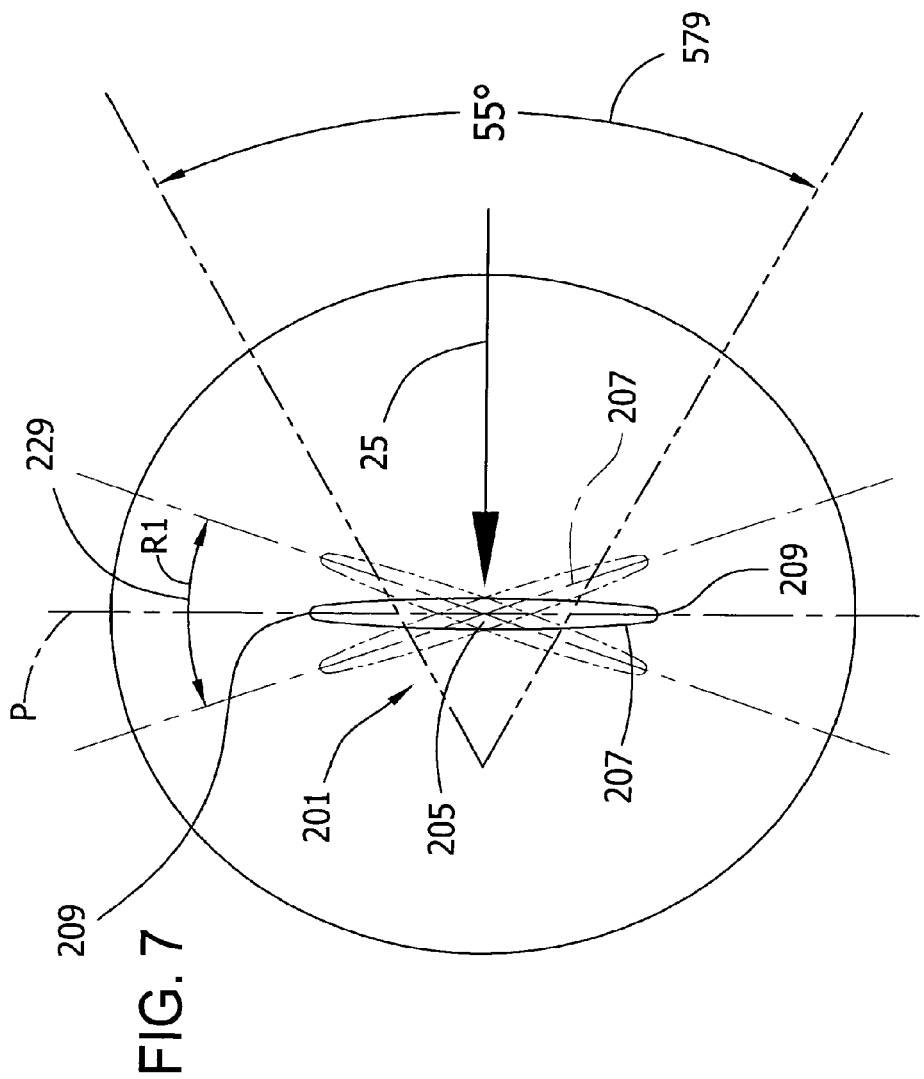
FIG. 7 is a schematic diagram showing the angular envelope for the desired orientation of a sperm cell in which the light beam from the optics system will strike a wide face of the cell generally broadside.

To illustrate the point, a bovine sperm cell 201 is illustrated in FIGS. 6 and 7. Typically, the cell has a paddle-shaped head 205 with relatively flat wide opposite faces 207 and narrow edges 209, a nucleus 213 in the head 205 containing the chromatic DNA mass of the cell, and a tail 215 extending from the head 205 providing the motility necessary for effective fertilization. The average bovine sperm cell 201 has a head length 219 of about 8 µm, a head width 221 of about 4 µm, and an overall length 223 from the front of the head to the end of the tail of about 100 µm. In the average bovine sperm cell 201, the nucleus 213 occupies most of the head volume and is only slightly smaller than the sperm head 205. Thus, the nucleus length 217 is almost equal to the head length 219, again being about 8 µm in length. It has been observed that in the bovine the X/Y chromosomes of the sperm cells 201 are localized in a region of the nucleus 225 (FIG. 6) below and immediately adjacent the longitudinal midline or equator 211 or center of the head 205. More specifically, this sub-equatorial region 225 extends no more than about 20% of the nucleus length 217 on the lower half (toward the tail 215) of the nucleus 213, even more specifically no more than about 10-15% of the nucleus length 217 on the lower half of the nucleus 213, and still more specifically no more than about 1.0-1.5 µm below the equator 211 of the nucleus 213.

When sperm cells pass through the excitation beam 25, it is desirable that the cells be substantially in single file and that the head 205 of the each cell 201 be substantially similarly oriented to reduce orientation variability from cell to cell and thus provide for a more uniform measurement of the cells. It is also desired that the cells have an orientation which will enable accurate discrimination between X and Y cells. Desirably, this orientation is one where the length of the sperm cell 201 is generally aligned with the direction of stream flow 227 (either head leading (shown FIG. 6) or head trailing) and where the head 205 of the sperm cell 201 is rotated on its longitudinal axis so that the head 205 falls within an angular envelope 229 in which the light beam 25 from the optics system 109 will strike a wide face 207 of the cell 201 generally broadside, as shown schematically in FIG. 7, rather than a narrow edge 209 of the cell. Preferably, the envelope 229 defining the desired orientation is generated by rotation of a sperm cell 201 through an angular range of R1 relative to a plane P which is generally perpendicular to the incoming light beam 25, as viewed in a cross section taken transversely through the stream 21. The range R1 is preferably 0 to 90 degrees, more preferably 0 to 60 degrees, and even more preferably 0 to 30 degrees. The nozzle of the present invention is configured to achieve this desired orientation with an accuracy of up to 90% or more.

The tolerance for sperm orientation (i.e., the size of the envelope 229 defined by angular range R1) is related to the numerical aperture of the lens used to collect fluorescence emissions 31 from the sperm cells. In the embodiment shown FIG. 7, for example, the optics system 109 has a fluorescence emission 31 detection volume 579 defined by a solid angle of 55 degrees. When the rotational orientation of a sperm head 205 is outside the envelope 229 defined by R1 as the sperm moves through the beam 25, a relatively stronger fluorescence emission 31 from an edge 209 of the sperm head 205 will be collected by the optic system 109, preventing the processor 131 from correlating the intensity of the fluorescence emission 31 with the X/Y chromosome content of the sperm cell 201. However, the optics system 109 does not collect the relatively stronger fluorescence emissions 31 from the narrow edge 209 of the sperm heads 205 as long as the rotational orientation of a sperm head 205 is within the envelope 229 as it passes through the interrogation location 115. Thus, in the embodiment shown FIG. 7, the orientation of the sperm cell does not result in collection of the relatively stronger edgewise fluorescence emissions as long as the narrow edges 209 of the sperm head 205 are confined within angle R1. The solid angle of the collection volume 579 can be decreased by using a lens with a smaller numerical aperture, thereby increasing angle R1 and the tolerance for poorly oriented sperm. However, this also decreases the number of photons that can be collected by the optics system 109, which can impact the measurement of fluorescence emissions 31 by reducing the intensity of the emissions 31 detected by the photodetector. Likewise, if the optics system 109 collects fluorescence emissions 31 with a high numerical aperture lens to obtain a stronger intensity of the fluorescence emissions detected by the photodetector, then the tolerance for sperm orientation decreases. Thus, in designing a system of the present invention, one needs to strike a balance between the tolerance for sperm orientation and the numerical lens aperture. The optimal balance will depend on the orienting capabilities and optical sensitivity of the system. In one desirable embodiment, for example, a lens having a numerical aperture 0.65 is used.

Nozzle Design

Figure 8:
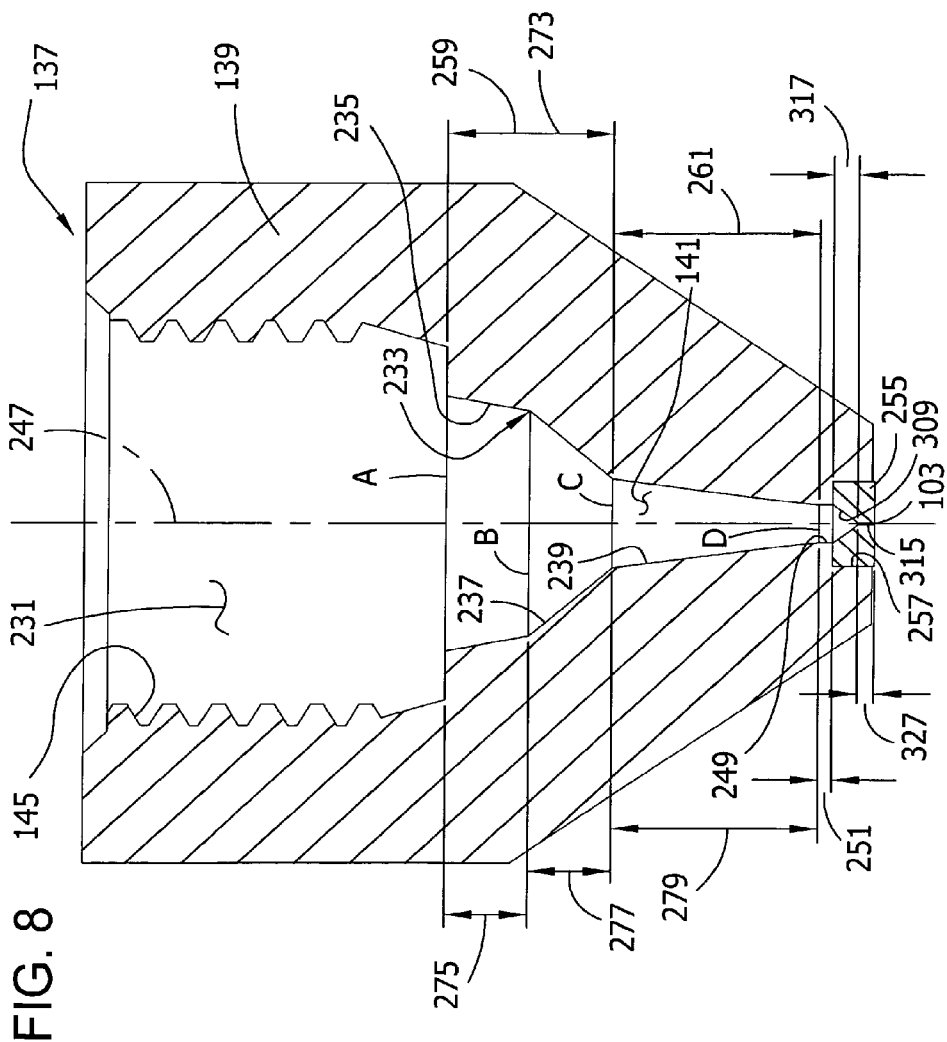
FIG. 8 is a cross sectional view of one embodiment of a nozzle body of the present invention.
Figure 9C:
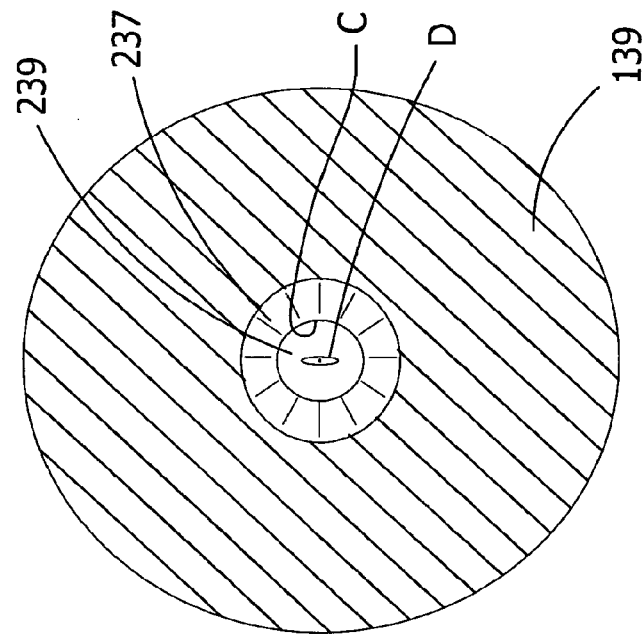
Figure 9D:
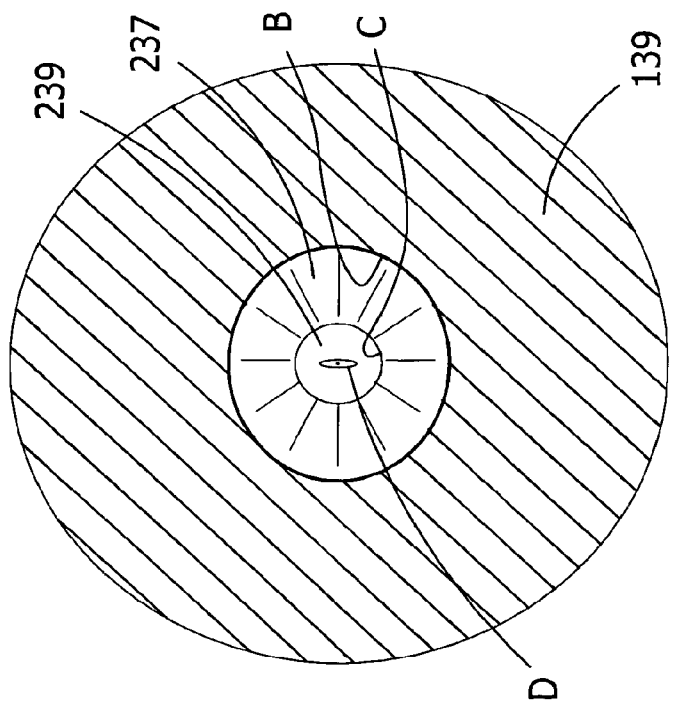
Figure 9E:
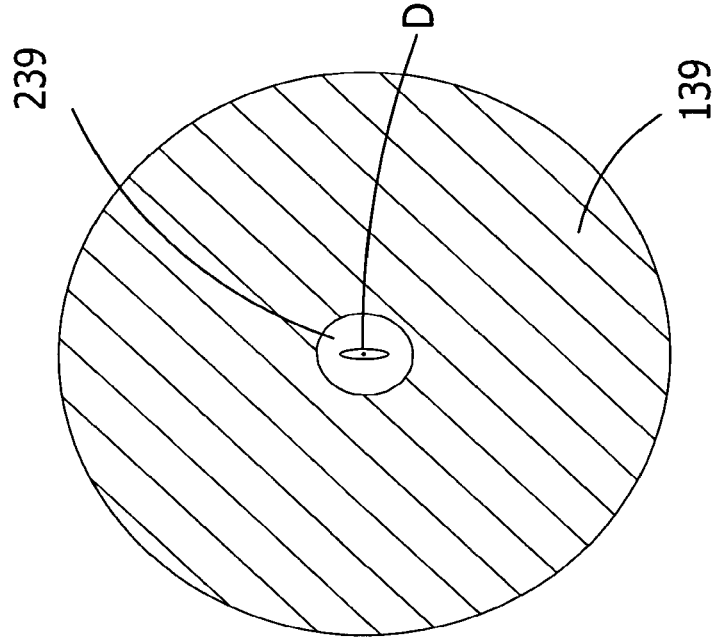
Figure 9F:
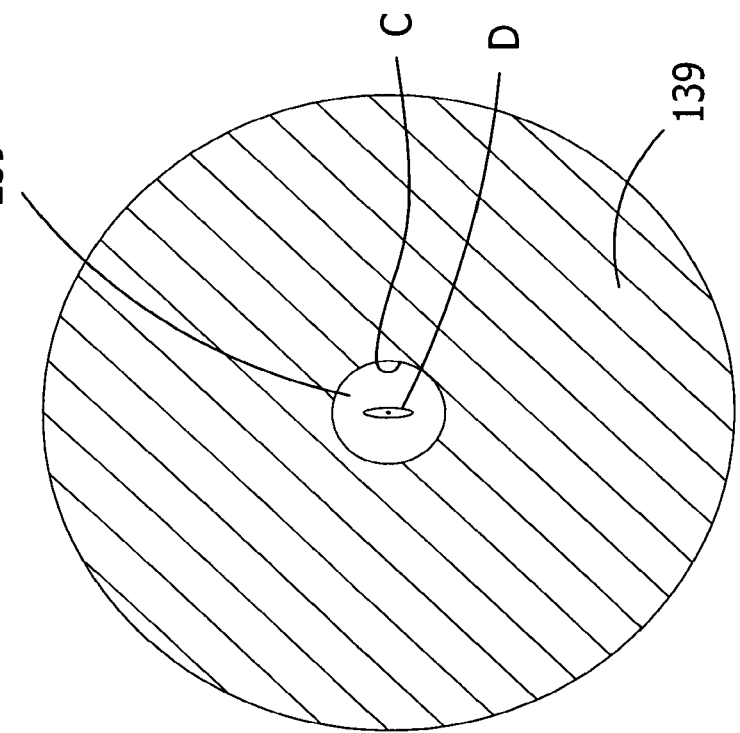
Figure 9H:
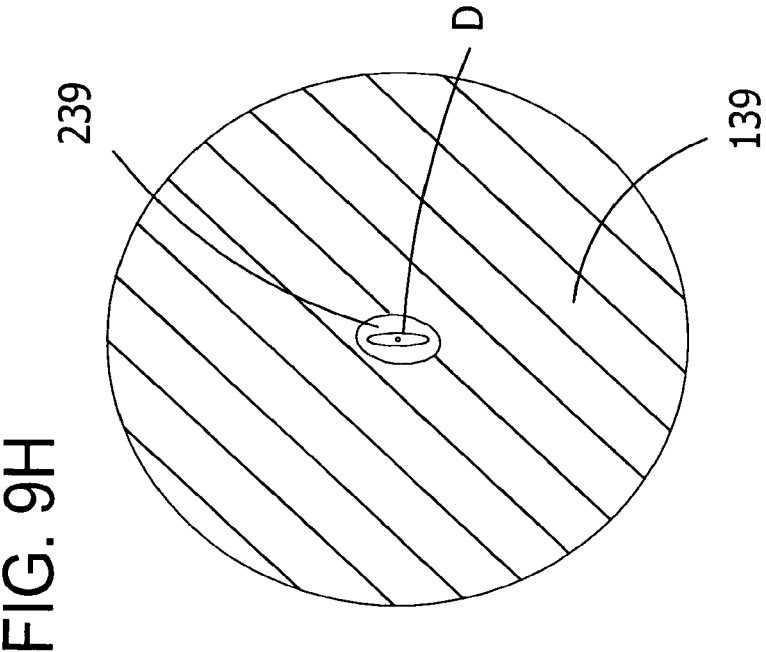
Figure 9G:
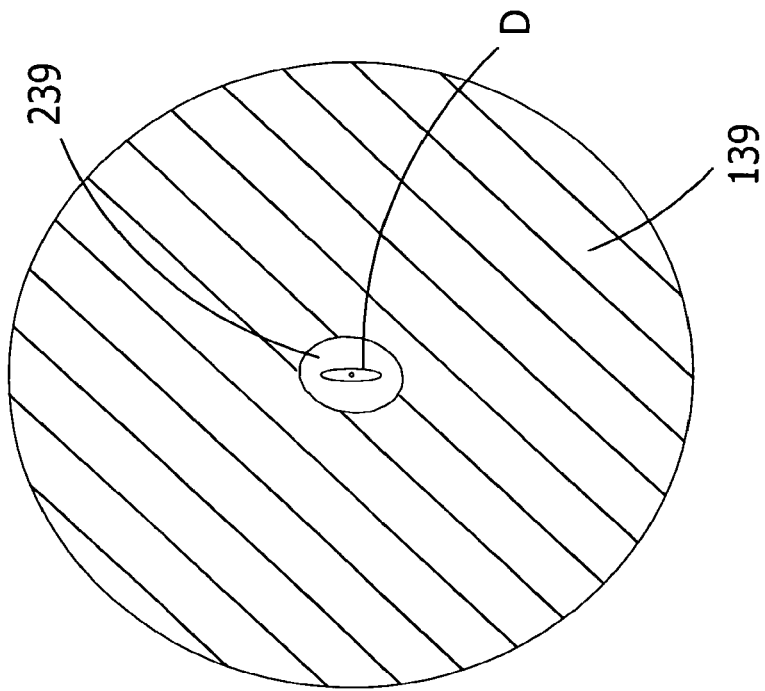
Figure 9K:
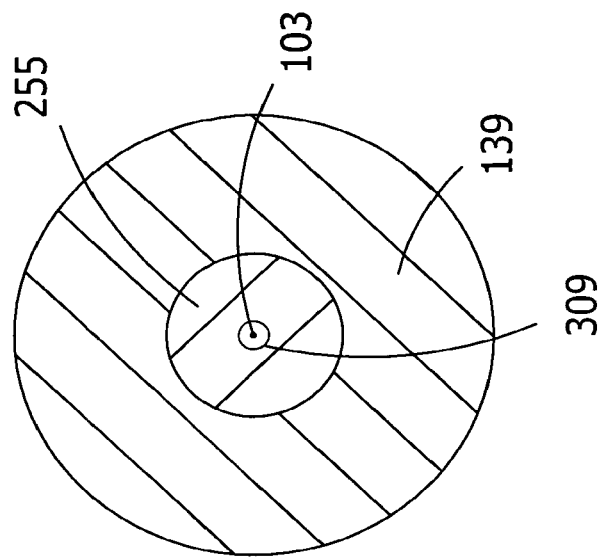
Figure 9J:
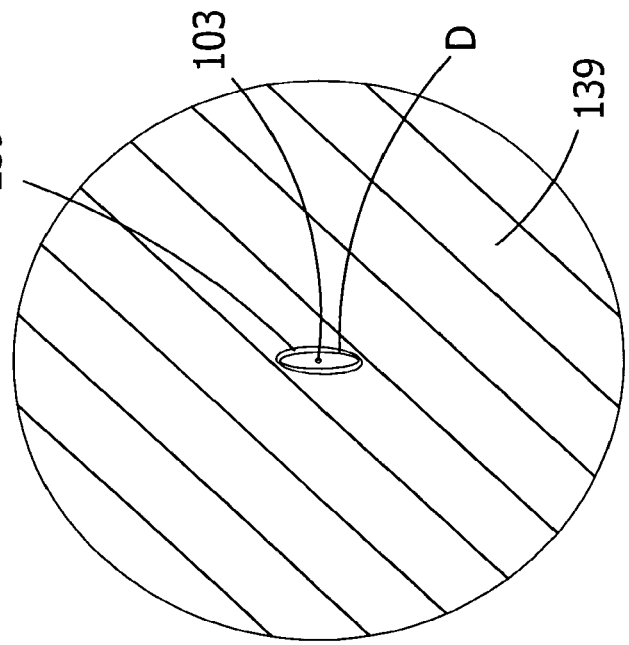
Figure 10:
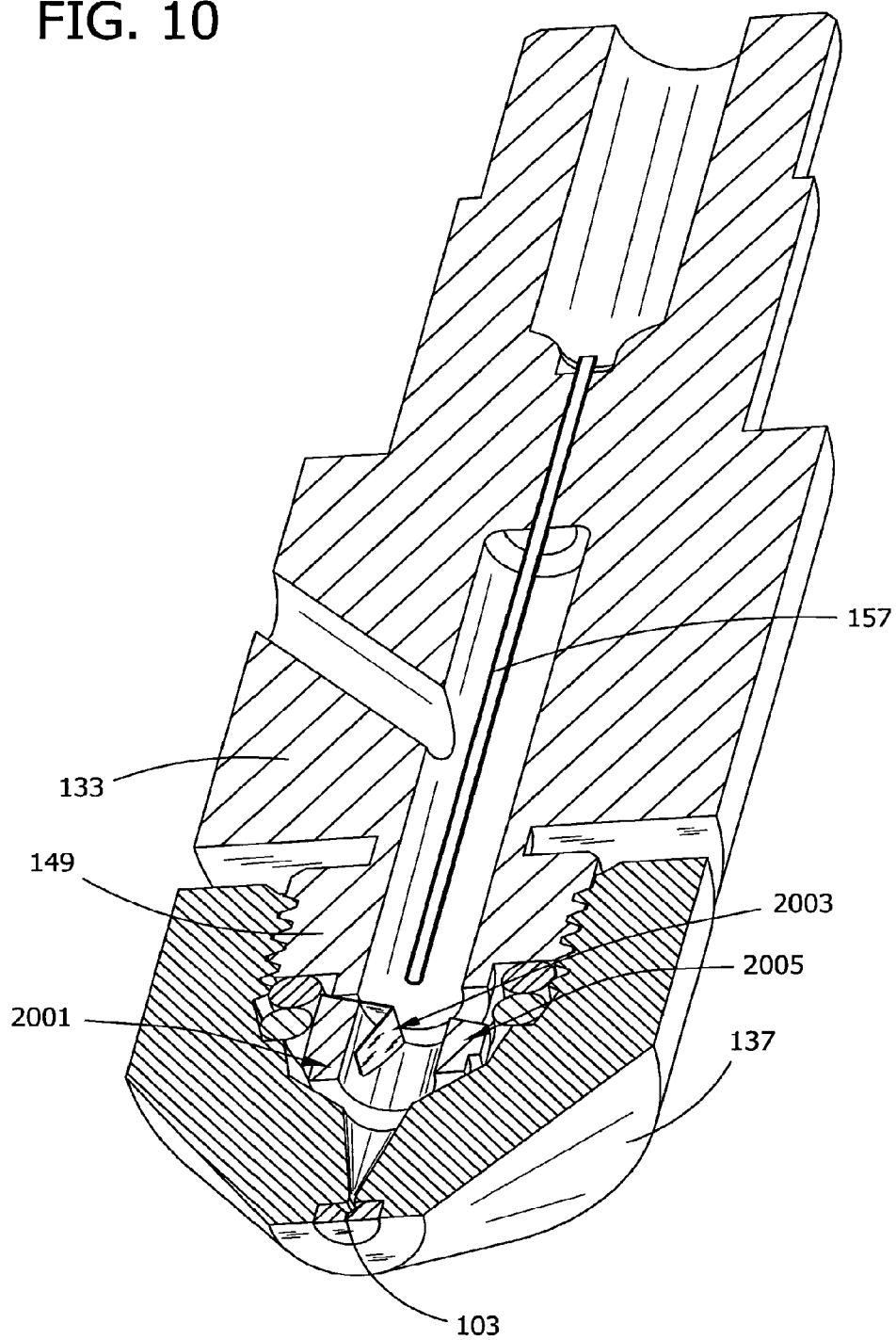
FIG. 10 is a perspective view of a cross section of one embodiment of a nozzle system having an orienting baffle in the nozzle.

In one embodiment, as shown in FIGS. 8 and 9, the interior 231 of the nozzle body 139 downstream from the counterbore 145 has an interior surface 233 comprising first, second and third axially tapered regions 235, 237, 239 for progressively accelerating the speed of the fluid stream 21 in a downstream direction toward the nozzle orifice 103. As noted previously, this acceleration functions to space the particles (e.g., cells) in the stream 21 so they assume a generally single file formation so they can be analyzed substantially one particle at a time. At least two of these regions, and preferably all three 235, 237, 239, have generally elliptical (oval) shapes in cross sections taken at right angles to the longitudinal axis 247 of the nozzle 137, as is shown in FIGS. 9A-9H and FIGS. 9J-9K. The interior surface 233 of the nozzle body 139 also has a fourth region 249, not tapered, downstream from the first three regions 235, 237, 239 and immediately upstream of the nozzle orifice 103 which, in one embodiment, is formed in a separate orifice member 255 secured in a counterbore 257 at the front of the nozzle body 139. In one embodiment, the generally elliptical cross sectional shapes of the first 235 and second 237 regions are oriented in substantially the same direction to define a first torsional zone 259, and the generally elliptical cross sectional shape of the third region 239, constituting a second torsional zone 261, is oriented at an angle (e.g., about 90 degrees) relative to the generally elliptical cross sectional shapes of the first 235 and second 237 regions. The orientation is such that the interior surface 233 of the nozzle body 139 applies torsional forces to the fluid stream 21 and thereby tends to orient the sperm cells 201 in the aforestated desired orientation as they pass through the nozzle orifice 103. Preferably, the first torsional zone 259 has an axial length 273 of 3.0-4.5 mm, preferably about 3.6 mm, and the first 235 and second 237 tapered regions making up the zone 259 have approximately equal axial lengths 275, 277 (e.g., about 1.8 mm). The second torsional zone 261 has an axial length 279 of 3.5-5.0 mm, preferably about 4.45 mm. The fourth region 249 is preferably generally cylindrical in shape. Each generally cross-sectional elliptical shape A-D (FIG. 8) at the boundaries of the first 235, second 237 and third 239 regions has a major axis diameter and a minor axis diameter, exemplary dimensions of which are shown in FIG. 8 and Table 1 below.

TABLE 1

| Ellipse | Major Axis Diameter (mm) | Minor Axis Diameter (mm) | Ratio |
|---|---|---|---|
| A | 7.0 | 6.0 | 1.2 |
| B | 6.1 | 5.3 | 1.15 |
| C | 2.1 | 2.1 | 1 |
| D | 0.9 | 0.2 | 1.45 |

It will be understood that the above dimensions are exemplary, and that other dimensions and shapes may also be suitable. Functionally, the changes in the ratios between the major and minor diameters, and the different orientations of the elliptical shapes of the regions, create side forces which act on each cell 201 and apply a torsional force 271 tending to rotate the cell 201 on its longitudinal axis so that its wide faces 207 align with the minor axis in the first torsional zone 259 and as the cell is gently twisted (e.g., 90 degrees) to align with the minor axis of the second torsional zone 261. Each of the tapered surfaces 235, 237, 239 also serves to accelerate the stream 21 (and cells) flowing through the nozzle 101. In one embodiment, the acceleration increases more gradually in the first 235 and third 239 regions and more rapidly in the second region 237. Again by way of example, the taper of the first region 235 may range from about 11-14 degrees; the taper in the second region 237 may range from about 42-48 degrees; and the taper in the third region 239 may vary from about 8-12 degrees. The nozzle body 139 is formed from a suitable material such as molded plastic (ABS) or metal.

The orifice member 255 (FIG. 8) is preferably formed from a hard, wear resistant material, such as sapphire, which is capable of being machined or otherwise formed with precise dimensions. The orifice member 255 itself has, in one embodiment, a conical upstream surface 309 of generally circular cross section which decreases in diameter from about 0.92 mm to about 0.060 mm and has an axial length 317 of about 0.54 mm and a taper angle of about 39 degrees. The orifice member 255 also has a generally cylindrical downstream surface 315 with a diameter of about 0.060 mm and an axial length 327 of about 0.36 mm. These dimensions are exemplary only, and it will be understood that the orifice member 255 may have other sizes and shapes. For example, the shape of the upstream surface 309 may be generally elliptical (oval) in cross section, and the diameter of the orifice 103 at the downstream end of the nozzle 137 may range from 40 to 100 microns or more. It is desirable that the size of the orifice 103 be such that the cells exiting the nozzle 101 are substantially in single file formation within the core 189 of the stream 21 and substantially in the desired orientation, as described previously. For example, in the case of sperm cells an orifice 103 having a diameter of about 60-62 microns at the downstream end has been found to be suitable. Preferably, the nozzle orifice 103 serves to further accelerate the stream 21 and to shape and size the stream 21 for optimum cell spacing, cell orientation and droplet 33 formation, as will be described.

The velocity of the cells as they exit the nozzle 137 will depend on various factors, including the pressure at which sheath fluid 19 is introduced into the nozzle system 101. At a pressure of 20 psi, the cells will exit the nozzle orifice 103 of the above embodiment at a velocity of about 16.6 m/s as a generally cylindrical stream 21 containing cells which are substantially similarly oriented at the core 189 of the stream 21. At a sheath pressure of 30 psi, the cell velocity will be about 20.3 m/s. At different sheath fluid 19 pressures, the velocity of the stream 21 will vary.

Introduction of Core Stream to Torsional Zone

Improved orientation of particles may be obtained by altering the flow of the fluid stream 21 through an orienting nozzle so that the core stream 189 containing the particles to be oriented (e.g., sperm cells) is directed along a flow path, at least a portion of which is offset from the center of the nozzle so that the particles are subjected to the hydrodynamic orienting forces generated by a nozzle while they are at a location that is offset from the center of the nozzle. Directing the core stream 189 along an offset flow path may also improve orientation of particles in a traditional nozzle (i.e., one that does not have any torsional zones). In many nozzles, one can determine that a given position is offset from the center of the nozzle because it is displaced from a longitudinal axis of the nozzle. One can also recognize that a particular position is offset from the center of a nozzle because it is displaced from the geometric center of a cross sectional area of the nozzle through which the fluid stream flows.

A number of techniques may be used to direct the core stream 189 along a flow path that is offset from the center of the nozzle. For example, an orienting baffle may be positioned in the nozzle to deflect the core stream to one side of the nozzle. Similarly, the conduit 157 for introducing the core stream 189 containing the sample particles may be relocated from the traditional center of the nozzle to an offset location. Furthermore, it is contemplated that an offset sample introduction conduit 157 may be used in combination with an orienting baffle. Exemplary embodiments of use of an orienting baffle and use of an offset sample introduction conduit are discussed below.

The improved orientation of particles (e.g., sperm cells) achieved by use of an orienting baffle and/or offset sample introduction conduit 157 may be due to a number of factors. One factor is that the deflection of the core stream 189 and/or a change in the size and shape of the cross sectional flow area results in application of hydrodynamic forces that tend to orient asymmetric particles. (Kachel, at al., Histochemistry and Cytochemistry, 25(7): 774-80 (1977)). Another factor is that it has been found that asymmetric particles (in particular sperm cells) tend to orient as they flow in a fluid stream in close proximity to a solid surface. Thus, by directing the core stream 189 so that it is in close proximity to the interior surface of a nozzle or a baffle surface one can obtain improved orientation of the particles. Furthermore, a baffle and/or offset sample introduction conduit can be used in conjunction with an orienting nozzle which applies additional orienting forces (e.g., torsional forces) to the asymmetric particles. In that case, the baffle can operate to direct the fluid stream so that the core stream containing the particles to be oriented flows along a path that is offset from the center of the nozzle while the particles are subjected to the torsional forces generated by one or more of the torsional zones.

Orienting Baffle

Figure 11:
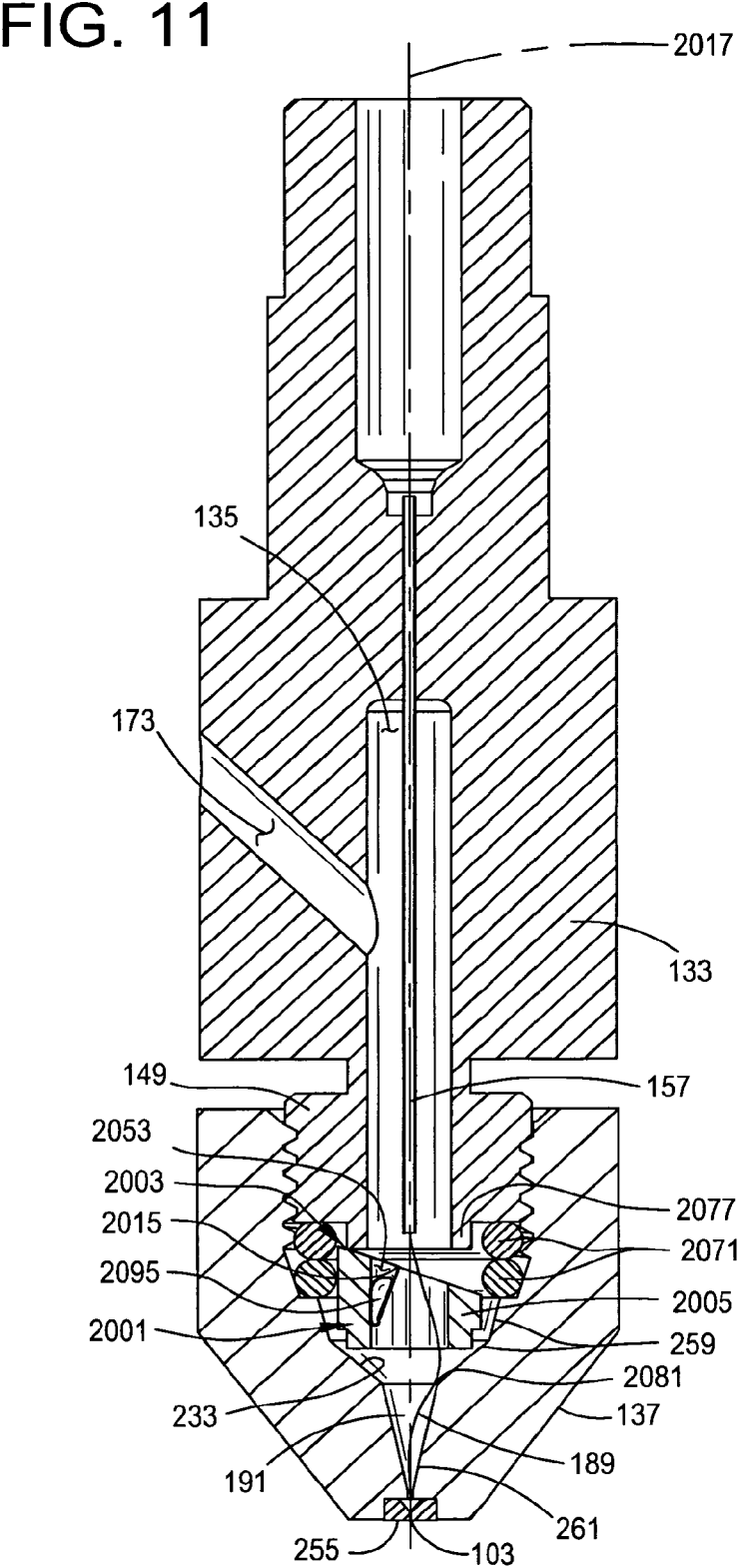
FIG. 11 is a cross sectional view of the nozzle system shown in FIG. 10.
Figure 12:
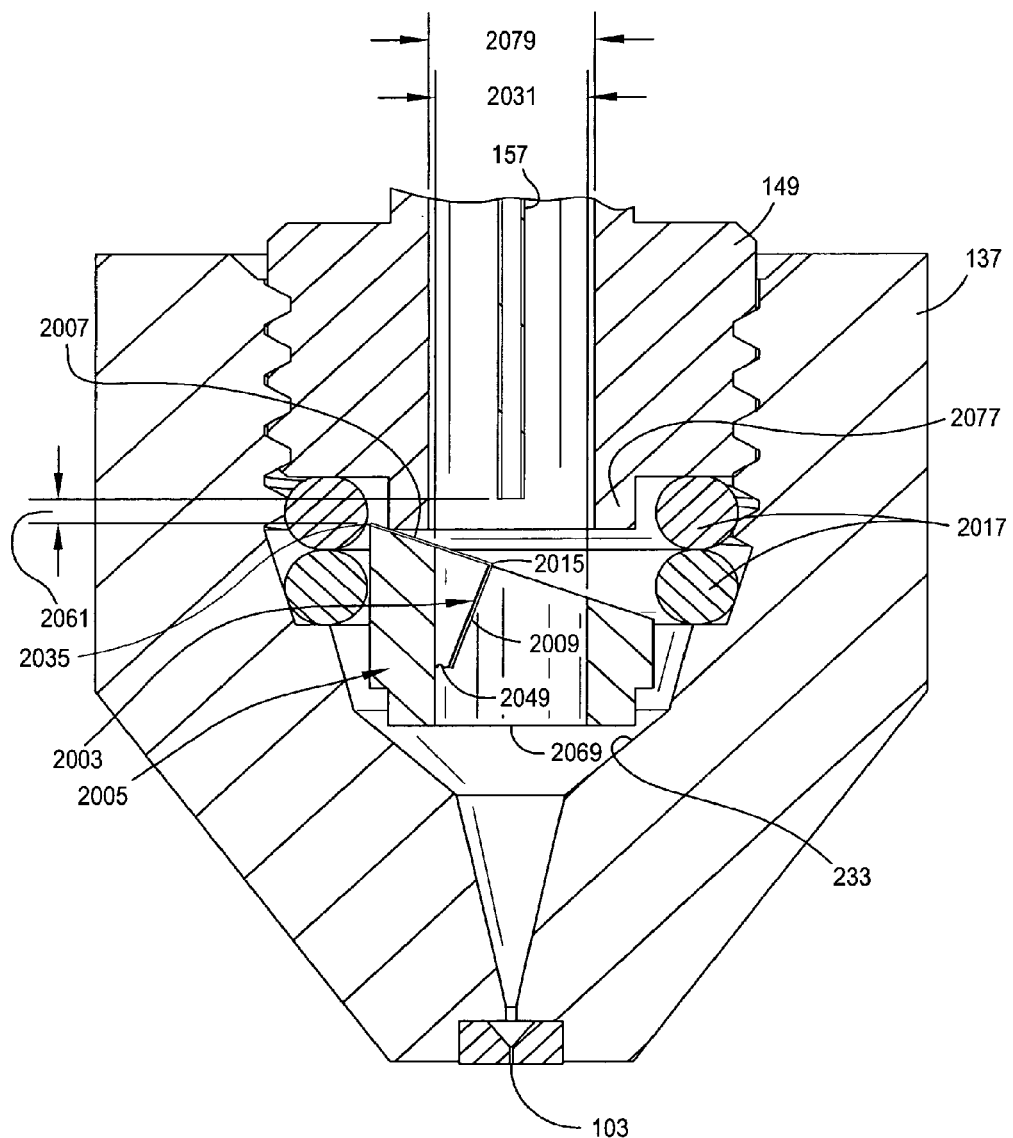
FIG. 12 is an enlarged partial cross sectional view of a portion of the nozzle system shown in FIGS. 10 and 11.
Figure 13:
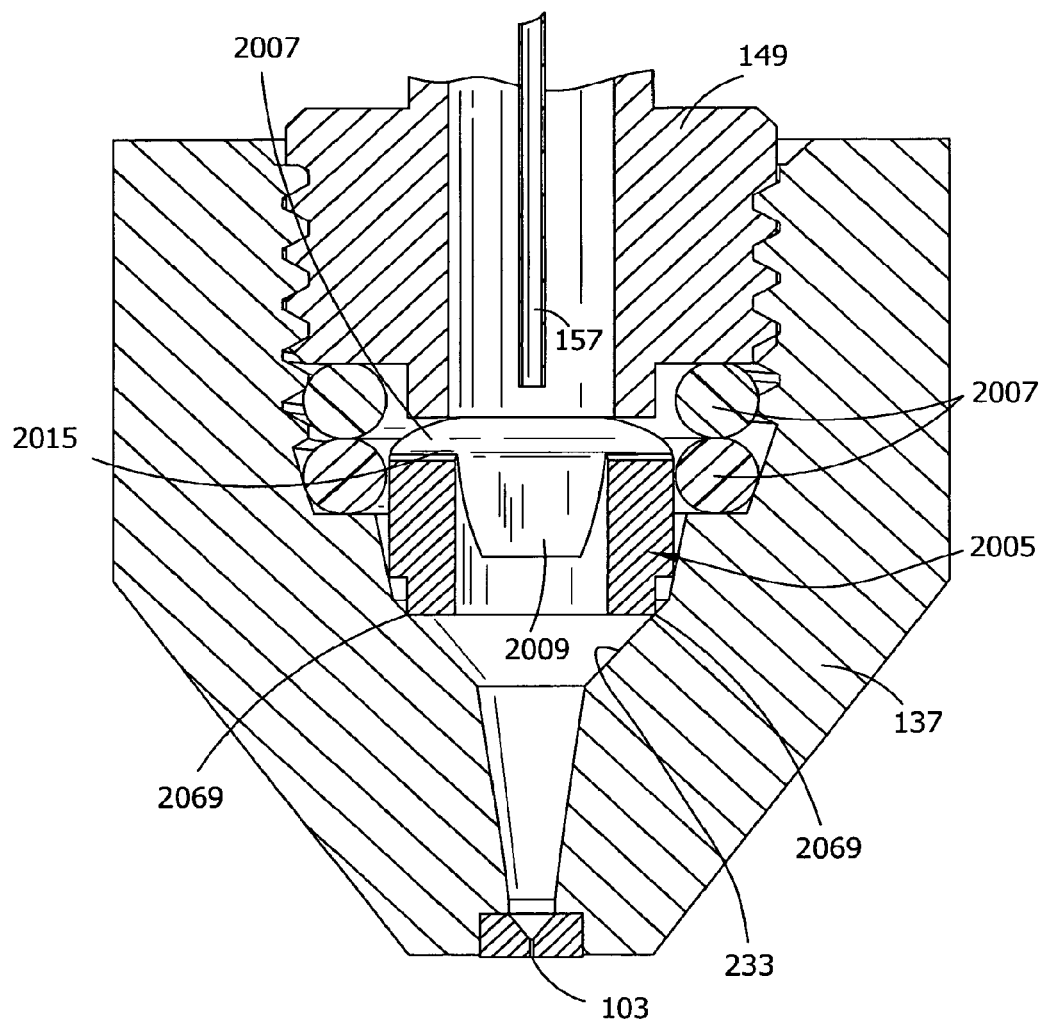
FIG. 13 is an enlarged partial cross sectional view similar to the view shown in FIG. 12, but taken from a direction that is perpendicular to the viewing direction in FIG. 12.
Figure 14:
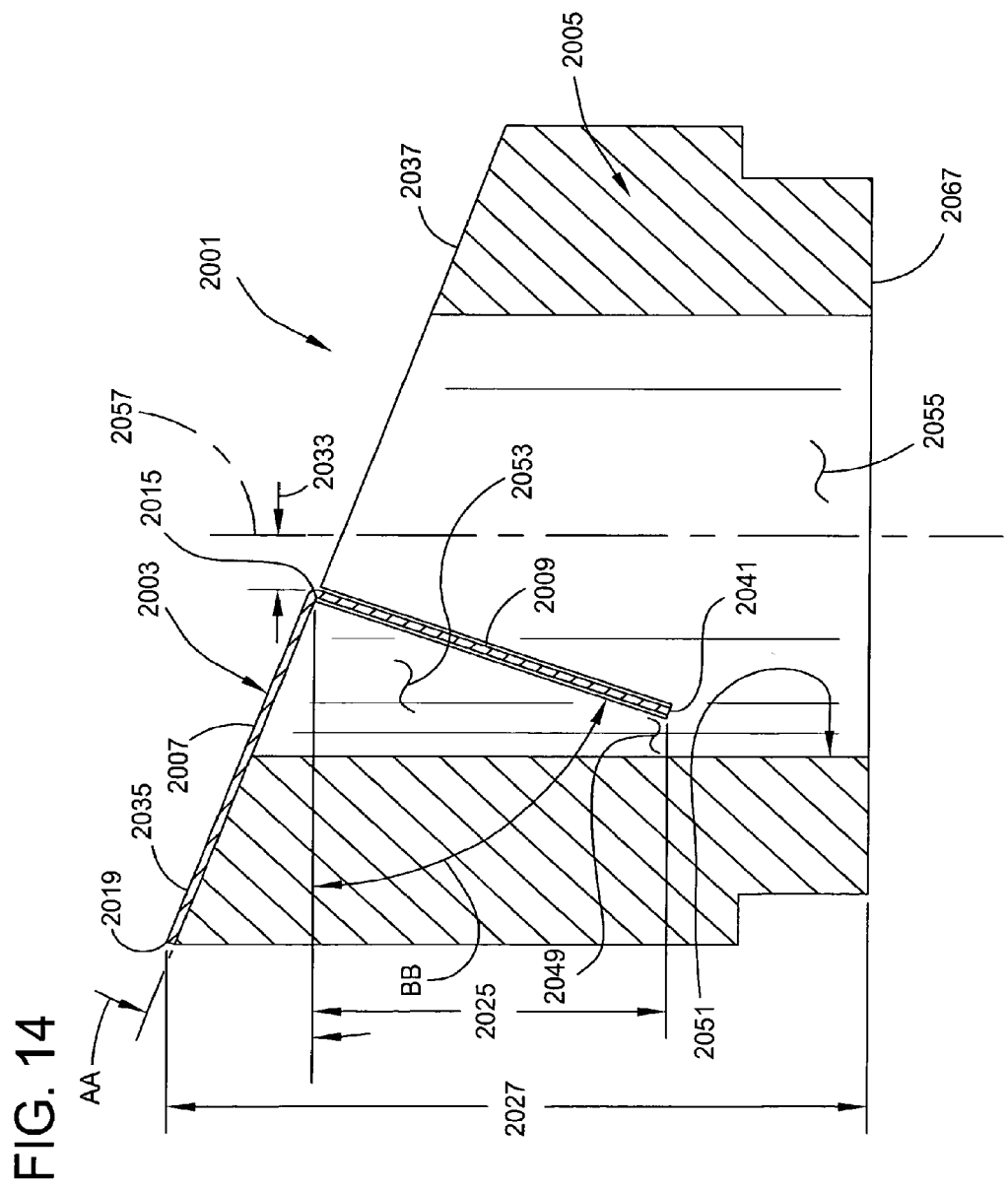
FIG. 14 is a side view of one embodiment of baffle holder holding a baffle plate.
Figure 15:
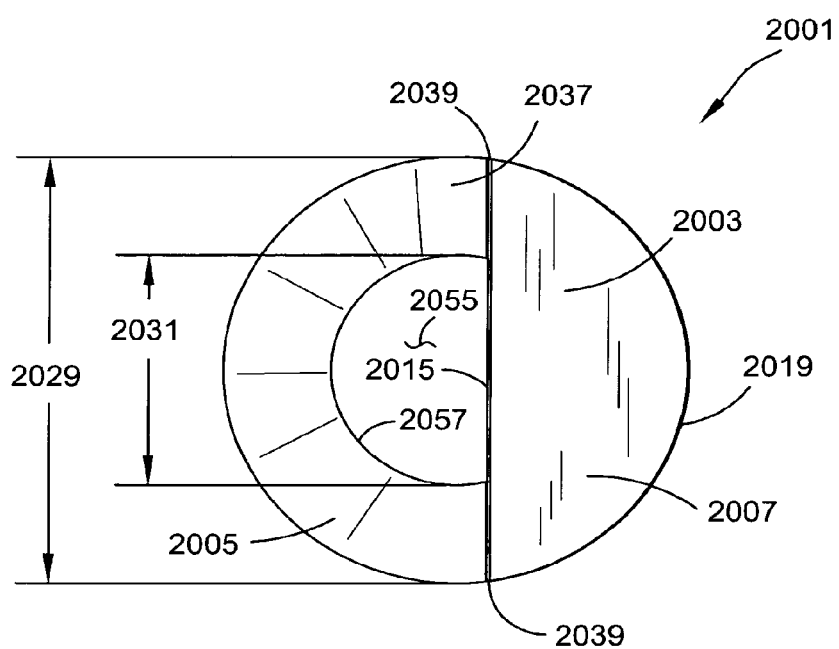
FIG. 15 is a top view of the baffle holder and baffle plate shown in FIG. 14.

FIGS. 10-13 show one exemplary orienting baffle, generally designated 2001, positioned in the orienting nozzle 137 described above. However, the baffle 2001 could be used in conjunction with a different nozzle, including a non-orienting nozzle, without departing from the scope of this invention. The baffle 2001 is positioned in the nozzle upstream from the orifice 103 and downstream from the sample injection needle 157. Referring to FIGS. 14 and 15, the baffle comprises a baffle plate 2003 that is held in place by a baffle holder 2005. In the embodiment shown, the baffle plate 2003 is generally L-shaped and constructed of a substantially rigid, durable and corrosion-resistant material (e.g., stainless steel). The L-shaped plate 2003 has an upstream leg 2007 and a downstream leg 2009, which are desirably substantially perpendicular to each other (e.g., within about 5 degrees of being perpendicular). In the exemplary embodiment shown in the drawings, the two legs 2007, 2009 of the L-shaped plate 2003 intersect at a line 2015 that is perpendicular to the longitudinal axis 2017 of the nozzle 137 (FIG. 11). As shown in FIG. 14, the line of intersection 2015 is also spaced a short distance 2033 (e.g., about 0.3 mm) away from the longitudinal axis 2057 of the baffle holder 2005. The upstream leg 2007 of the L-shaped plate 2003 extends from the line of intersection 2015 away from the longitudinal axis 2017 of the nozzle 137 all the way to the edge of the baffle holder 2005, as shown in FIG. 15. Thus, the upstream leg 2007 is formed with a curved edge 2019 that closely matches the shape of the baffle holder 2005. As shown in FIG. 14, the upstream leg 2007 is inclined at an angle AA of about 15-25 degrees from perpendicular to the longitudinal axis 2057 of the baffle holder 2005. The downstream leg 2009 of the L-shaped plate 2007 extends downstream from the line of intersection 2015 of the two legs 2007, 2009 a distance 2025 of about 2.0-2.5 mm at an angle BB that is in the range of about 60-80 degrees from perpendicular to the longitudinal axis 2057 of the baffle holder 2005.

The baffle holder 2005 is sized and shaped to fit inside the nozzle 137, as shown in FIGS. 10-13. The baffle holder 2005 is preferably made of a moldable material (e.g., polypropylene) although the baffle holder 2005 may be constructed from other materials without departing from the scope of the present invention. The baffle holder 2005 used in the exemplary embodiment, shown in FIGS. 14 and 15, is generally shaped as a hollow cylindrical shell about 4.0-4.5 mm in overall length 2027. The baffle holder 2005 has an exterior diameter 2029 of about 5-6 mm and an interior diameter 2031 of about 2.5-3.5 mm. If the baffle holder 2005 is to be molded, a minor draft (not shown) can be provided on the surfaces of the holder 2005 (e.g., to allow the baffle holder to be easily removed from an injection molding machine). The upstream end 2035 of the exemplary baffle holder 2005 has an inclined surface 2037 which is inclined at the same angle AA as the upstream leg 2007 of the L-shaped plate 2003. The upstream leg 2007 of the L-shaped plate 2003 abuts against and is supported by the inclined surface 2037 of the baffle holder 2005. The side edges 2039 (FIG. 15) of the downstream leg 2009 of the L-shaped plate 2003 are partially embedded (e.g., received in slots) in the baffle holder 2005 to hold the baffle plate 2003 in a position in which the downstream leg 2009 spans generally from one side of the baffle holder 2005 to the other. The downstream edge 2041 of the downstream leg 2009 in the exemplary embodiment forms a straight line which is generally perpendicular to the longitudinal axis 2057 of the baffle holder 2057. There is a gap 2049 (FIG. 14) between the downstream edge 2041 of the downstream leg 2009 and the interior cylindrical surface 2051 of the baffle holder 2005. The gap 2049 provides fluid communication between a volume 2053 defined by the legs 2007, 2009 of the L-shaped plate 2003 and the interior cylindrical surface 2051 of the baffle holder 2003 and the rest of the interior volume 2055 of the nozzle 137.

Figure 16:
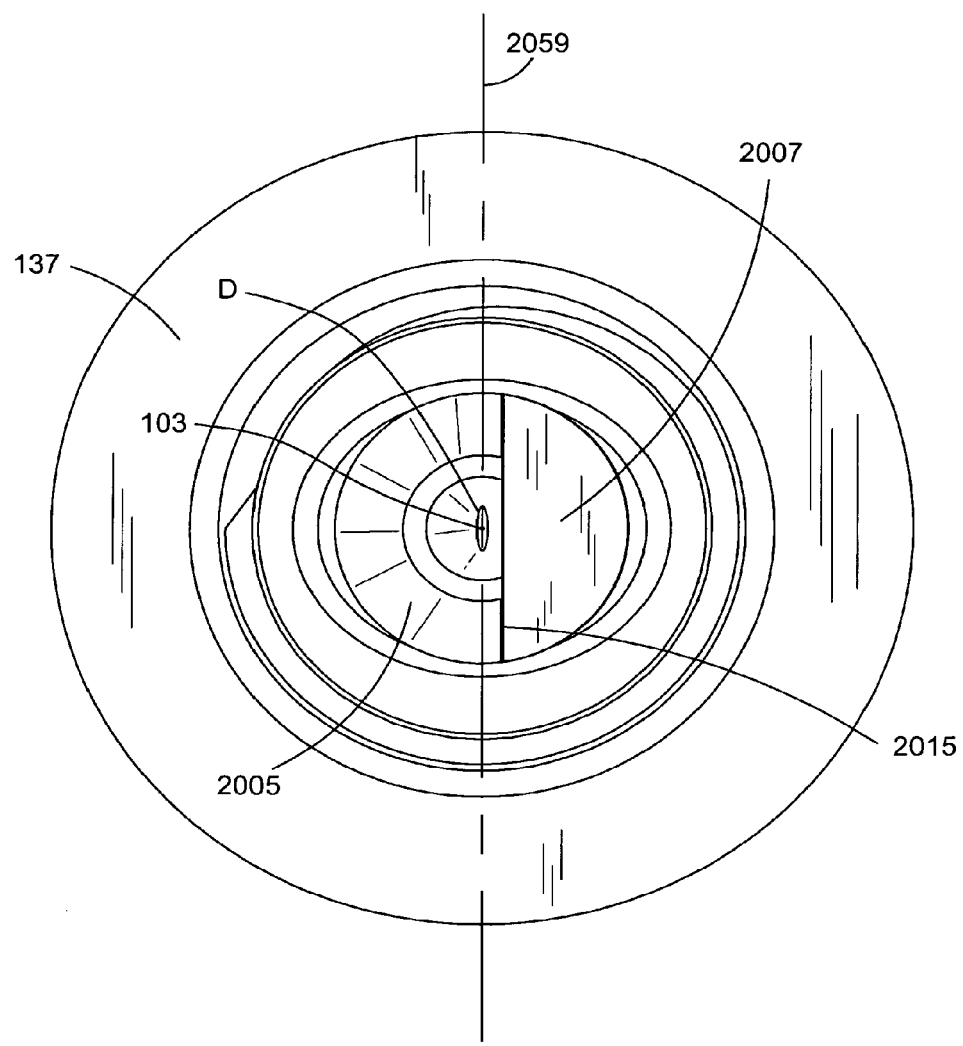
FIG. 16 is a top view of one embodiment of a baffle holder rotationally oriented in a nozzle so that the legs of the baffle plate intersect in a line that is parallel to the major axis of ellipse D in the nozzle.
Figure 17:
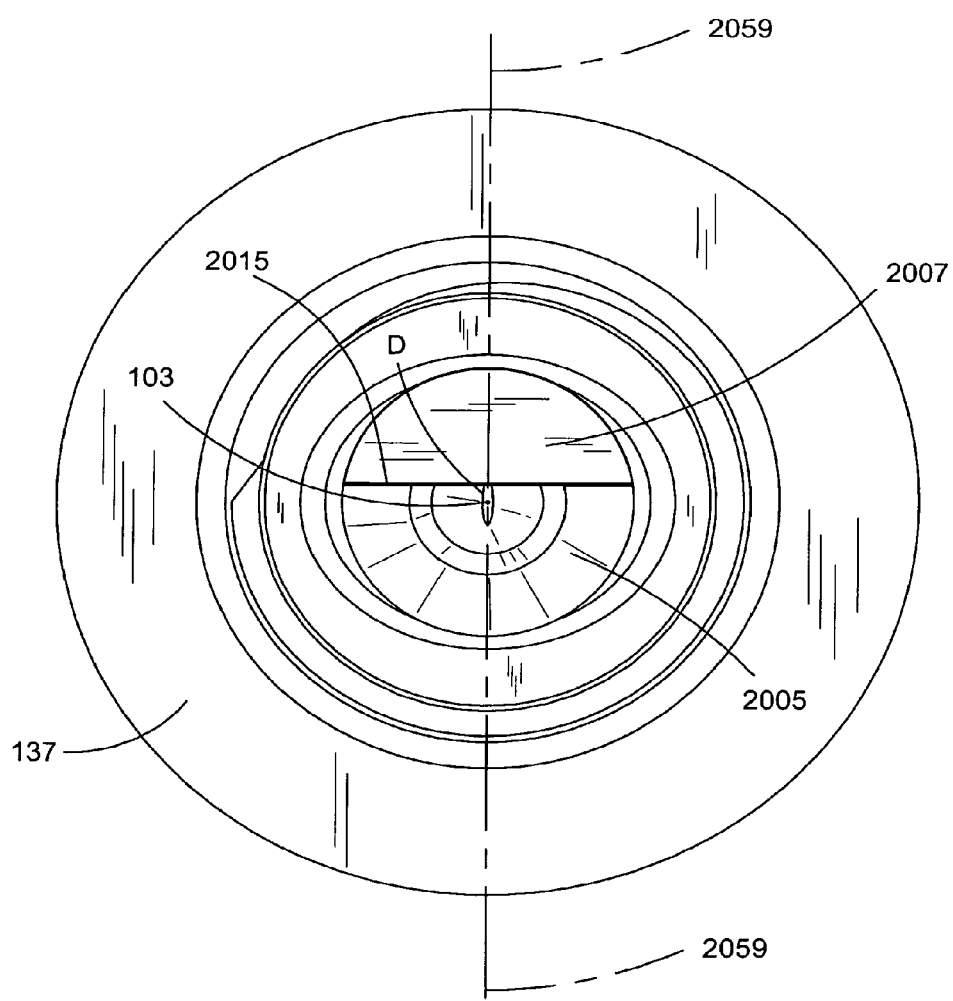
FIG. 17 is a top view of one embodiment of a baffle holder rotationally oriented in a nozzle so that the legs of the baffle plate intersect in a line that is perpendicular to the major axis of the ellipse D in the nozzle.

The baffle holder 2005 is desirably positioned inside the nozzle with the longitudinal axis 2057 of the baffle holder 2005 generally aligned with the longitudinal axis 2017 of the nozzle 137 so that it holds the L-shaped plate 2003 in the position described above. Desirably, the exemplary baffle plate 2003 is rotationally oriented so that the line of intersection 2015 of the two legs 2007, 2009 of the plate 2003 is parallel to a line 2059 running through the major axis of ellipse D, as shown in FIG. 16. However, the exemplary baffle 2001 also performs well when the intersection 2015 of the two legs 2007, 2009 of the L-shaped plate 2003 is perpendicular to the line 2059 running through the major axis of ellipse D, as shown in FIG. 17. Furthermore, the baffle may have any rotational orientation without departing from the scope of this invention. As shown in FIG. 12, the sample injection needle 157 in the exemplary embodiment is desirably a distance 2061 of about 0.25-1.0 mm upstream from the most upstream portion 2035 of the baffle 2001. More desirably, the sample injection needle 157 is about 0.55-0.65 mm upstream from the most upstream portion 2035 of the baffle 2001.

The baffle holder 2005 may be held in a desired position relative to the nozzle in any number of ways. Referring to FIG. 14, the downstream end 2067 of the baffle holder 2005 is stepped so that it fits farther downstream in the nozzle 137. The stepped downstream end 2067 of the holder 2005 is circular in shape and abuts against the elliptically shaped interior surface 233 of the nozzle 137. Thus, the contact between the interior surface 233 of the nozzle 137 and the baffle holder 2005 is generally limited to two points 2069, as shown in FIG. 13. A pair of O-rings 2071 are positioned around the baffle holder 2005 between the nozzle 137 and the threaded projection 149 of the flow body 133 (FIGS. 11-13) and seal the nozzle system 101 against leakage. The O-rings 2071 may be made of Viton®, or any other similar materials. The two O-rings 2071 are compressed as the nozzle 137 is screwed onto the threaded projection 149 to provide a fluid-tight seal. Two O-rings 2071 are used in the exemplary embodiment because a single O-ring cannot be compressed within the space between the nozzle 137 and the flow body 133 due to the length 2027 of the baffle holder 2005. Any number of O-rings or a different type of seal could be used without departing from the scope of the present invention, provided that the number of O-rings or other type of seal is selected so that there will be a fluid-tight seal when the nozzle 137 is screwed onto the flow body 133. This will depend on a number of factors, including the size and shape of the nozzle 137, flow body 133, baffle holder 2005, and O-rings 2071 as well as the type of seal. The O-rings 2071 also help hold the baffle holder 2005 in the desired position. The O-rings 2071 occupy the space around the baffle holder 2005, thereby restricting side-to-side movement of the baffle holder 2005 inside the nozzle 137. Frictional forces between the O-rings 2071 and the baffle holder 2005 also resist rotational movement of the baffle holder 2005.

When the nozzle 137 is tightened on the flow body 133 as shown in FIG. 12, the downstream end 2077 of the threaded projection 149 from the flow body 133, in the form of a boss in this embodiment, is approximately even with the most upstream portion 2035 of the baffle 2001. As a result, the baffle holder 2005 is held axially captive between the flow body 133 (at the upstream end 2035 of the baffle holder 2005) and the interior surface 233 of the nozzle 137 (at the downstream end 2067 of the baffle holder 2005). Other retaining mechanisms may be used. In the embodiment shown in the drawings, the interior diameter of the boss 2079 (FIG. 12) at the downstream end of the threaded projection 149 is roughly equal to the internal diameter 2031 of the baffle holder 2005.

Those skilled in the art will recognize that the flow through the nozzle system 101 remains laminar notwithstanding the baffle 2001 because the small cross sectional area through which the fluids must flow results in a low Reynolds number for the flow. As is shown in FIG. 11, the baffle deflects the core stream 189 and sheath stream 191 away from the central longitudinal axis 2017 of the nozzle 137 and toward an interior surface 233 of the nozzle 137. In one embodiment, the core stream 189 also flows very close to the interior surface 233 of the nozzle 137 as the core stream 189 passes between the transition between the first 259 and second 261 torsional zones. However, a portion 2081 of the sheath fluid stream 191 remains between the core stream 189 and the interior surface 233 of the nozzle 137 so the particles in the core stream 189 do not actually impact or contact the interior surface 233 of the nozzle 137. Farther downstream in the nozzle 137, the hydrodynamic forces push the core stream 189 back toward the center of the nozzle 137 (e.g., in alignment with the longitudinal axis 2017 of the nozzle 137).

Figure 18D:
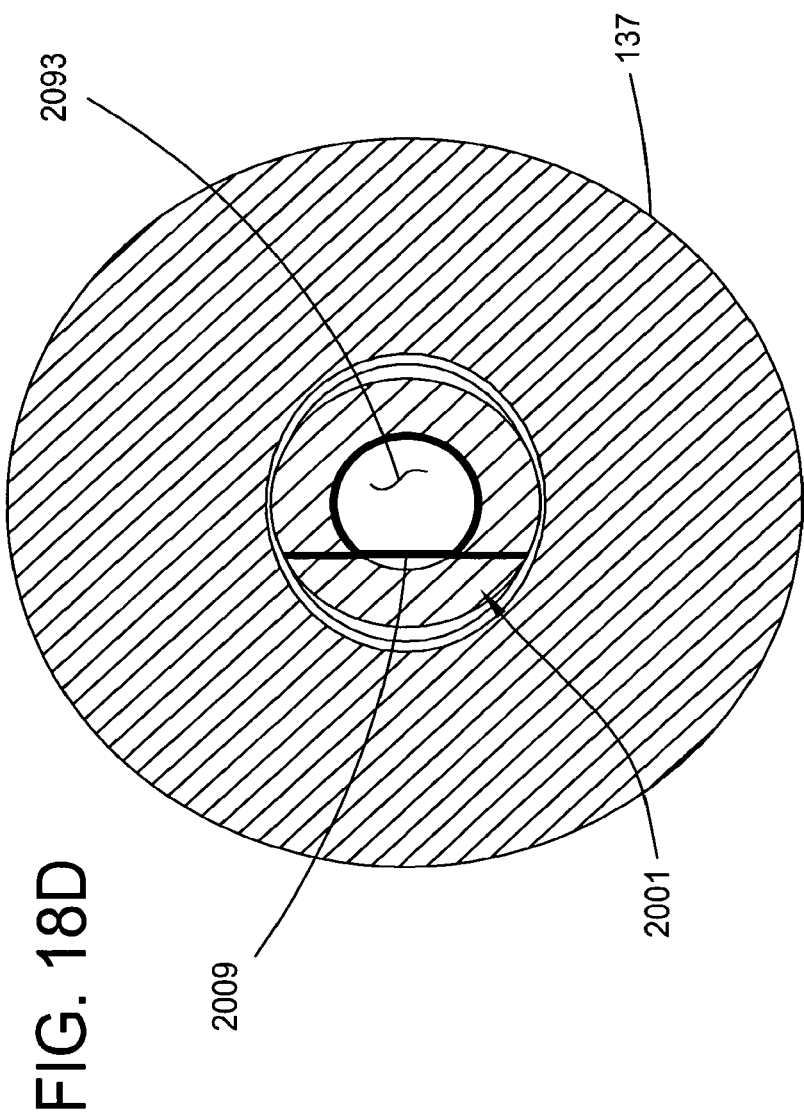
Figure 18E:
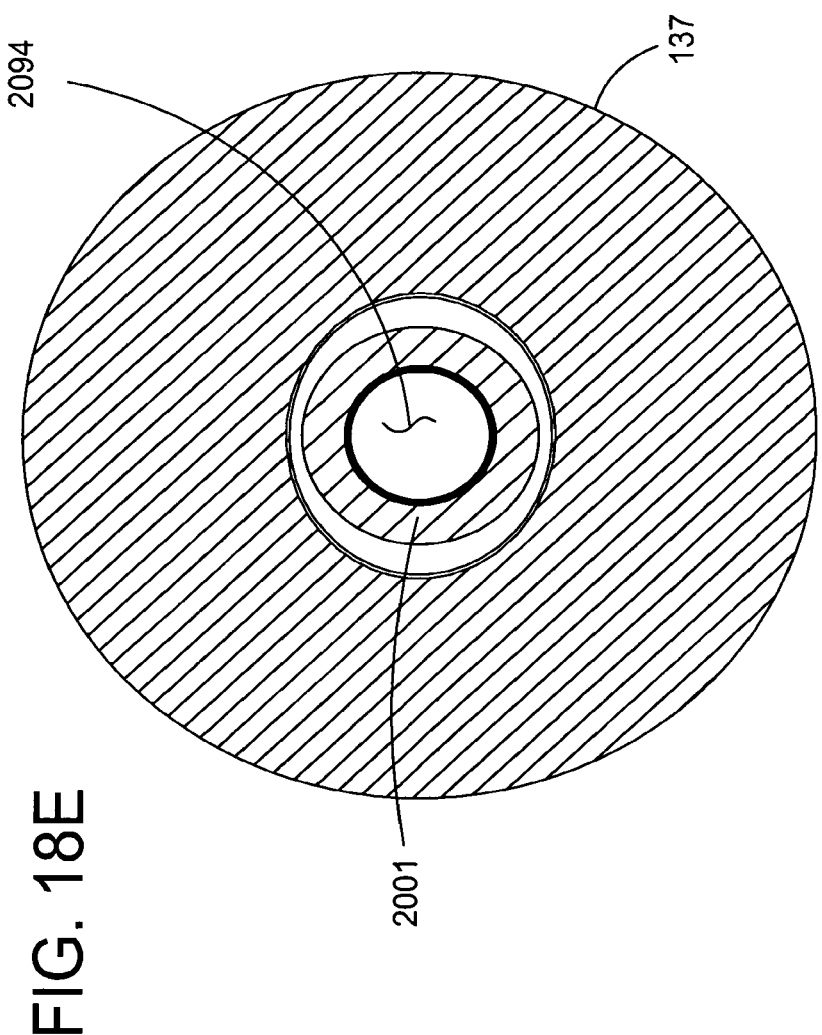

Referring to FIGS. 18A-18E, the baffle 2001 changes the shape and reduces the size of the cross sectional flow area in the nozzle 137. (For the sake of clarity, FIGS. 18A-18E do not show any nozzle structure downstream from the baffle. The flow area in each of the FIGS. 18A-18E is outlined in bold for clarity.) Upstream from the baffle 2001 (FIG. 18A), the cross sectional flow area 2087 is generally circular or elliptical. At the upstream end 2035 of the baffle 2001, the flow area begins to change from a circular shape to a generally semi-circular shape 2089 at the intersection 2015 of the legs 2007, 2009 of the baffle plate 2003 (FIG. 18B), although other shapes may be suitable. There the cross sectional flow area 2089 is smaller than the flow area 2087 upstream from the baffle. FIG. 18C illustrates the flow area 2091 as fluid flows through a part of the baffle holder 2005, and FIG. 18D illustrates the flow area 2093 farther downstream at the downstream end 2041 of the downstream leg 2009 of the baffle plate 2003. It will be observed that flow area 2093 is somewhat larger than flow area 2091 due to the angular orientation of the downstream leg 2009 of the baffle plate 2003. Downstream from the baffle plate 2003 (FIG. 18E) the flow area 2094 through the baffle corresponds the shape of the interior surface 2051 of the baffle holder 2005, which is circular in the illustrated embodiment.

(Other shapes may be suitable.) Downstream from the baffle holder 2005 the torsional zones 259, 261 of the nozzle 137 desirably provide torsional forces as discussed above.

As shown in FIG. 11, it has been observed that one or more air bubbles 2095 may become trapped in the volume 2053 between the downstream leg 2009 of the L-shaped plate 2003 and the baffle holder 2005. Furthermore, a portion of a bubble 2095 may extend through the gap 2049 between the edge 2041 of the downstream leg 2009 and the baffle holder 2005. Thus, the air bubble(s) 2095 can occupy a portion of the cross sectional flow area downstream of the downstream leg 2009 of the L-shaped plate 2003, perhaps affecting the flow of fluid through the nozzle 137. The exemplary baffle 2001 has been found to work well both with and without the air bubble(s) 2095. Thus, a baffle can be used to orient sperm cells without involvement of any bubbles without departing from the scope of the present invention.

Figure 20:
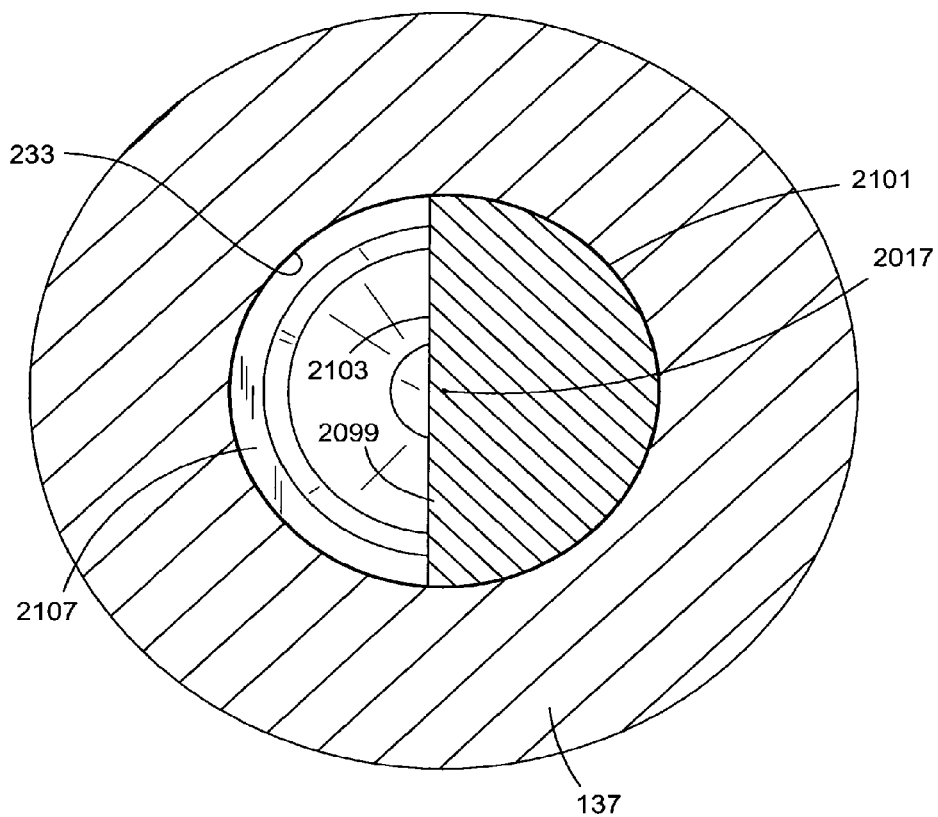
FIG. 20 is a cross sectional view of the nozzle shown in FIG. 19 taken through the cutting plane 20-20 shown on FIG. 19.

Another exemplary orienting baffle, generally designated 2097, is shown in FIGS. 19 and 20. The baffle 2097 comprises a flat generally semi-circular baffle plate 2099 in the orienting nozzle 137 discussed above. The baffle plate 2099 is positioned in the nozzle 137 downstream of the sample introduction conduit 157 and generally perpendicular to the longitudinal axis 2017 of the nozzle 137. The baffle plate 2099 has a curved edge 2101 that generally matches the curvature of the interior surface 233 of the nozzle 137 so that there are no large gaps between the curved edge 2101 of the baffle plate 2099 and the interior surface 233 of the nozzle 137. The baffle plate 2099 also has a straight edge 2103 that extends a short distance past longitudinal axis 2017 of the nozzle 137 so that it is approximately aligned with the outer diameter 2109 of the sample introduction conduit 157. The baffle plate 2099 is held in position by friction resulting from compression of the baffle plate 2099 between an o-ring seal 2105, which is similar to the o-ring seals 2071 described in connection with the L-shaped baffle 2001 above, and an annular shoulder or shelf 2107 formed on the interior of the nozzle 137. As shown in FIG. 19 the orienting baffle 2099 operates by deflecting the fluid stream so that the core stream 189 containing the particles to be analyzed is offset from the central longitudinal axis 2017 of the nozzle 137 along a portion of its flow path. For example, the core stream 189 may be directed along a flow path that is offset from the longitudinal axis 2017 of the nozzle 137 as it flows through the first torsional zone 259, as well as at least a portion of the second torsional zone 261. Consequently, the particles (e.g., sperm cells) are subjected to the torsional forces generated by the torsional zones 259, 261 while they are in a position that is offset from the central longitudinal axis 2017 of the nozzle 137.

Those skilled in the art will recognize that substantial changes may be made to the exemplary baffles 2001, 2097 described above without departing from the scope of the present invention. All that is required is that the baffle be configured to deflect the core stream 189 and sheath stream 191 toward an interior surface of the nozzle or to cause the core 189 and sheath stream 191 to flow through a cross sectional area that changes in size and/or shape. Further, it is understood that the orienting baffle structure may be integrally formed with the nozzle or integrally formed with the nozzle and flow body without departing from the scope of the present invention.

Offset Sample Introduction Conduit

Figure 21:
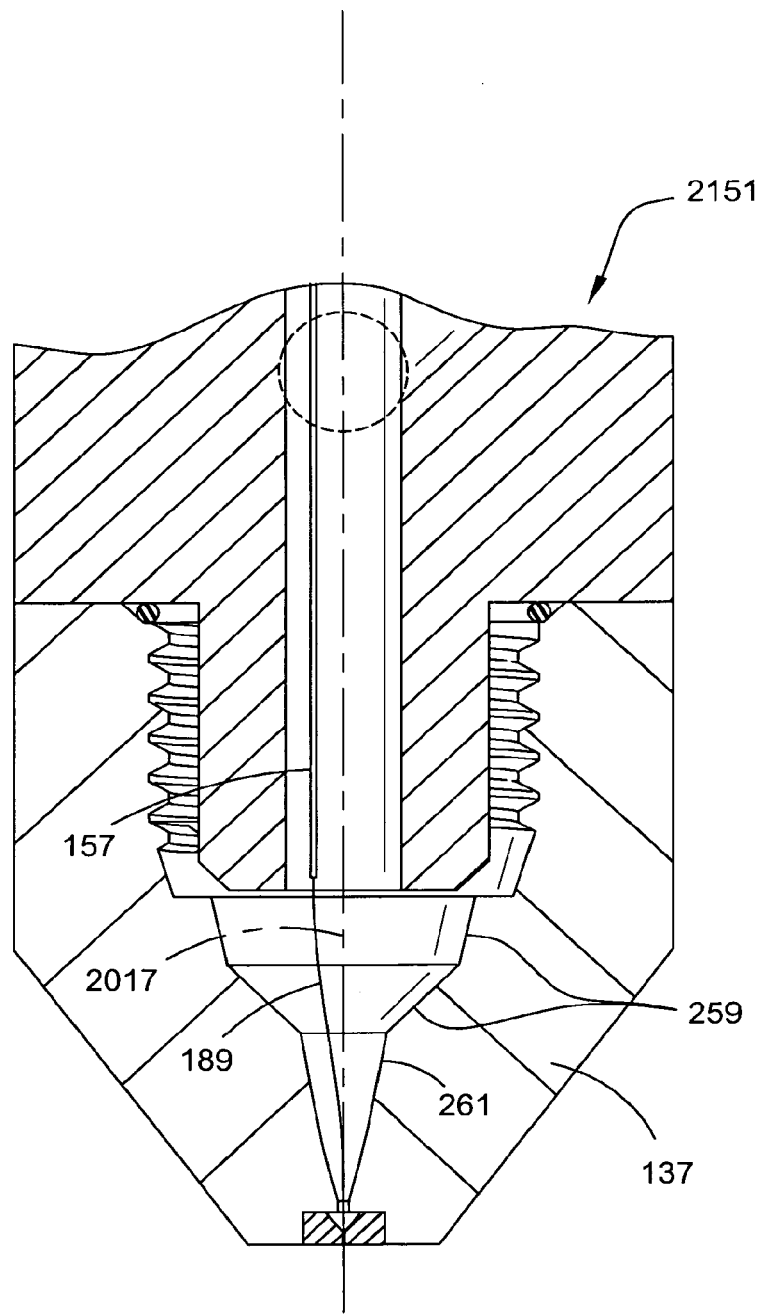
FIG. 21 is a cross sectional view similar to the cross sectional view of FIG. 18 showing a nozzle system having a sample introduction conduit at an offset location.

The core stream 189 may be directed along a flow path that is offset from the central longitudinal axis 2017 of the nozzle 137 by repositioning the sample introduction conduit 157 from its traditional position at the center of the nozzle 137 to an offset position. For example, FIG. 21 shows an exemplary offset sample introducing nozzle system 2151 having an offset sample introduction conduit 157. Except as noted, the nozzle system 2151 is substantially the same as the nozzle system 101 shown in FIGS. 4 and 5. The significant difference is that the sample introduction conduit 157 has been moved away from the center of the nozzle 137 so that it is no longer aligned with the nozzle's longitudinal axis 2017. Thus, the core stream 189 is directed into the torsional zones 259, 261 of the orienting nozzle 137 along a flow path that is offset from the longitudinal axis 2017. Although the exemplary nozzle system 2151 shown in FIG. 21 uses the exemplary orienting nozzle 137 describe above, it is contemplated that offset sample introduction conduit 157 could be used with a different orienting nozzle or a non-orienting nozzle to orient particles in the core stream 189.

Nozzle Mounting and Adjustment

Figure 22:
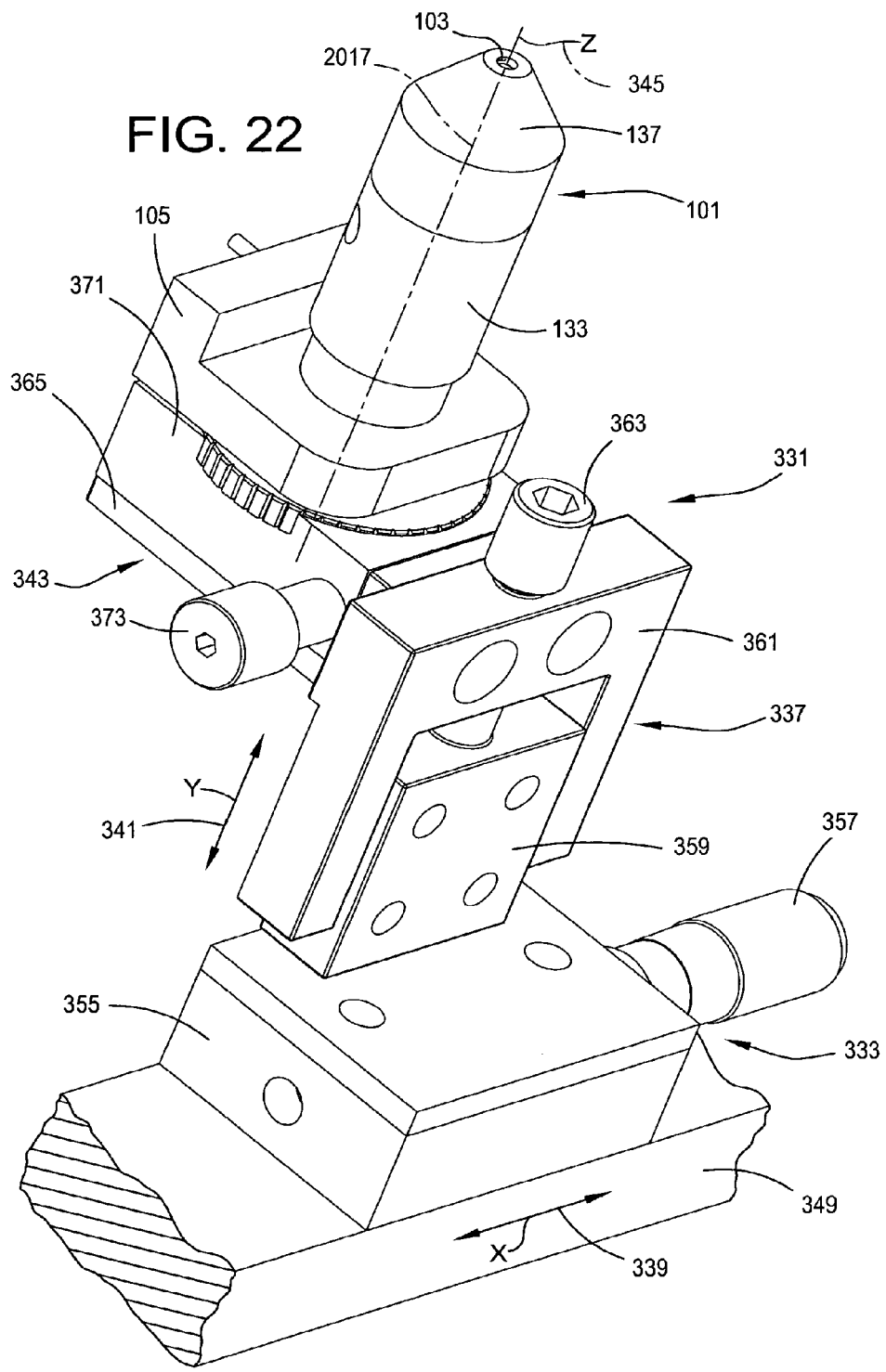
FIG. 22 is a perspective view of one embodiment of a nozzle system mounted on a nozzle mount of the present invention.

The flow body 133 and nozzle 137 are mounted in a selected orientation and position by means of a nozzle mount, generally designated 331. In one embodiment (FIG. 22), the mount 331 comprises a plurality of stages, including first and second linear stages 333, 337 providing linear adjustment of the flow body 133 and nozzle 137 along X and Y axes 339, 341, respectively, and a third rotational stage 343 providing rotational adjustment about a Z axis 345 corresponding to the longitudinal axis 2017 of the flow body 133 and nozzle 137. These stages 333, 337, 343 may be conventional in design, suitable stages being commercially available, for example, from Newport Corporation of Irvine Calif. In particular, the first linear motion stage 333 comprises a fixed first stage member (not shown) mounted on a frame 349, a movable first stage member 355 slidable on the fixed first stage member along the X axis 339, and an actuator 357, e.g., a micrometer, for precisely moving the movable first stage 355 member to a selected X-axis position. The second linear motion stage 337 comprises a fixed second stage member 359 mounted on the movable first stage member 355, a movable second stage member 361 slidable on the fixed second stage member 359 along the Y axis 341, and an actuator 363, e.g., a micrometer, for precisely moving the movable second stage member 361 to a selected Y-axis position. The rotational (third) stage 343 comprises a fixed third stage member 365 mounted on the movable second stage member 316, a movable third stage member 371 rotatably mounted on the fixed third stage member 365 for rotation about the Z-axis 345, and an actuator 373, e.g., a micrometer, for precisely rotating the movable third stage member 371 to a selected angular position relative to the Z-axis 345. The three-axis adjustment provided by these stages 333, 337 343 allows the nozzle 137 and the fluid stream 21 exiting the nozzle orifice 103 to be precisely positioned relative to the optics system 109. Rotation of the nozzle 137 about the Z-axis 345 is particularly helpful because it enables the stream 21 exiting the nozzle 137 to be rotated to bring the cells (e.g., sperm cells) oriented by the nozzle 137 into a position in which the light beam 25 from the optics system 109 will fall on the desired surfaces of the cells (e.g., the flat faces 207 of sperm heads 205), as illustrated schematically in FIG. 23. Other nozzle mounts may be suitable. For example, a 4-axis nozzle mounting system can also be used, providing linear adjustment along X, Y and Z axes and rotational adjustment along the Z axis. Further, it may be desirable to use one or more stages having an automated alignment feature, such as a servo or stepper motor controlled microtranslation stage (e.g., part number M-110.2DG from Polytech PI, Inc. of Auburn, Mich.).

Figure 36:
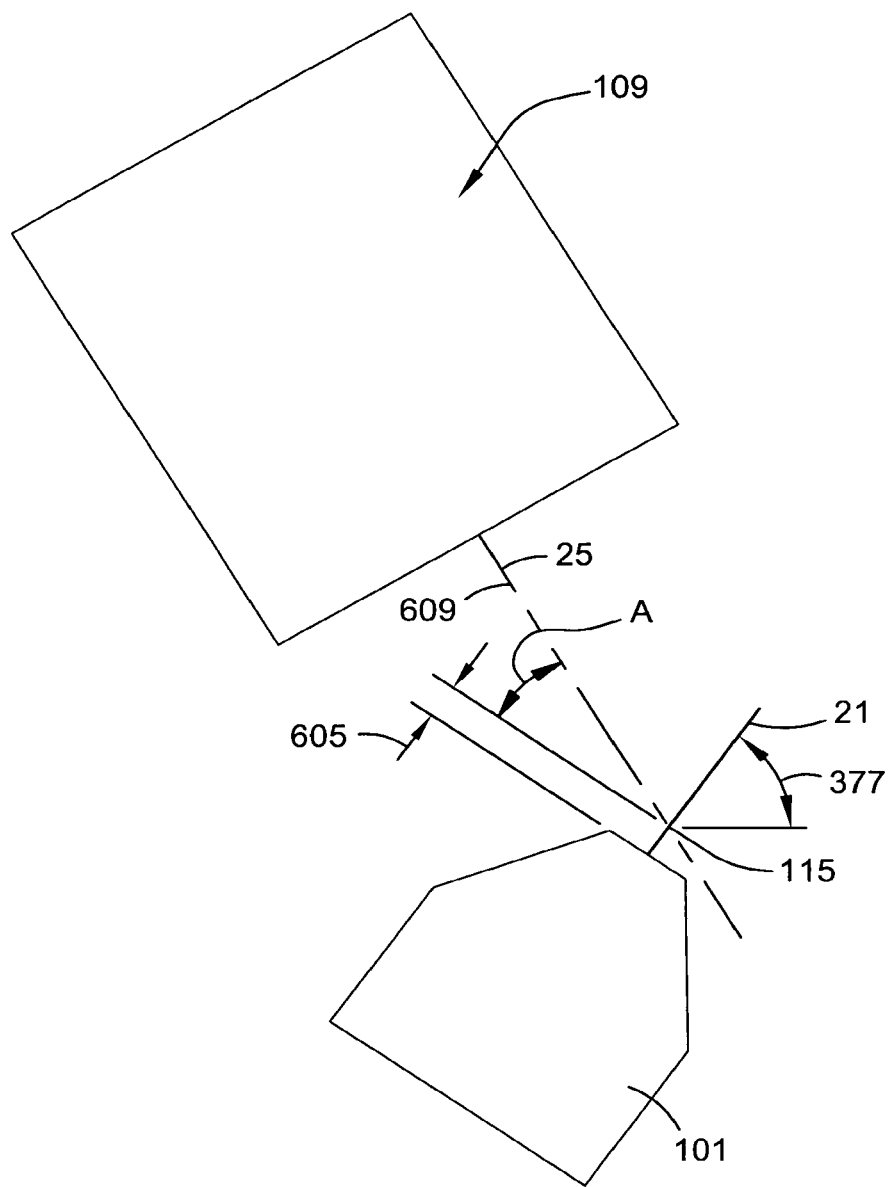
FIG. 36 is a schematic diagram of an interrogation location of one embodiment of the present invention showing a laser beam focused on a fluid stream downstream of the nozzle at a skewed angle of incidence.

In one embodiment shown schematically in FIG. 36, for example, the nozzle 137 is oriented to direct a stream 21 containing cells to be analyzed in a generally upward direction. The angle 377 between the direction of the fluid stream 21 and horizontal is preferably in the range of 5 to 85 degrees, more preferably in the range of 15 to 75 degrees, even more preferably about 30 to 65 degrees, still more preferably about 45 to 60 degrees, and most preferably about 50 to 55 degrees. This orientation is advantageous in that any air trapped in the nozzle system 101 is readily removed. Also, the velocity of the fluid stream 21 decreases gradually under the force of gravity prior to collection of the droplets 33. A more gradual deceleration of the droplets 33 is believed to be less stressful to the cells being analyzed which, in the case of sperm cells, can result in higher motility of the sorted sperm after collection. Of course, in other embodiments of the present invention, the nozzle 101 is positioned so that the fluid stream 21 has a substantially downward velocity when it exits the orifice 103 as is conventional for jet-in-air cytometers.

Optionally, components of the nozzle system 101 such as the flow body 133 and nozzle 137 are coated with a non-reflective, non-emissive material (e.g., a dull dark paint or epoxy which does not emit light when subjected to UV laser light) to reduce any reflected and/or emitted light off these elements 133, 137 which might otherwise cause signal noise or have other adverse effects on the optics system 109.

Transducer and Droplet Formation

Figure 24:
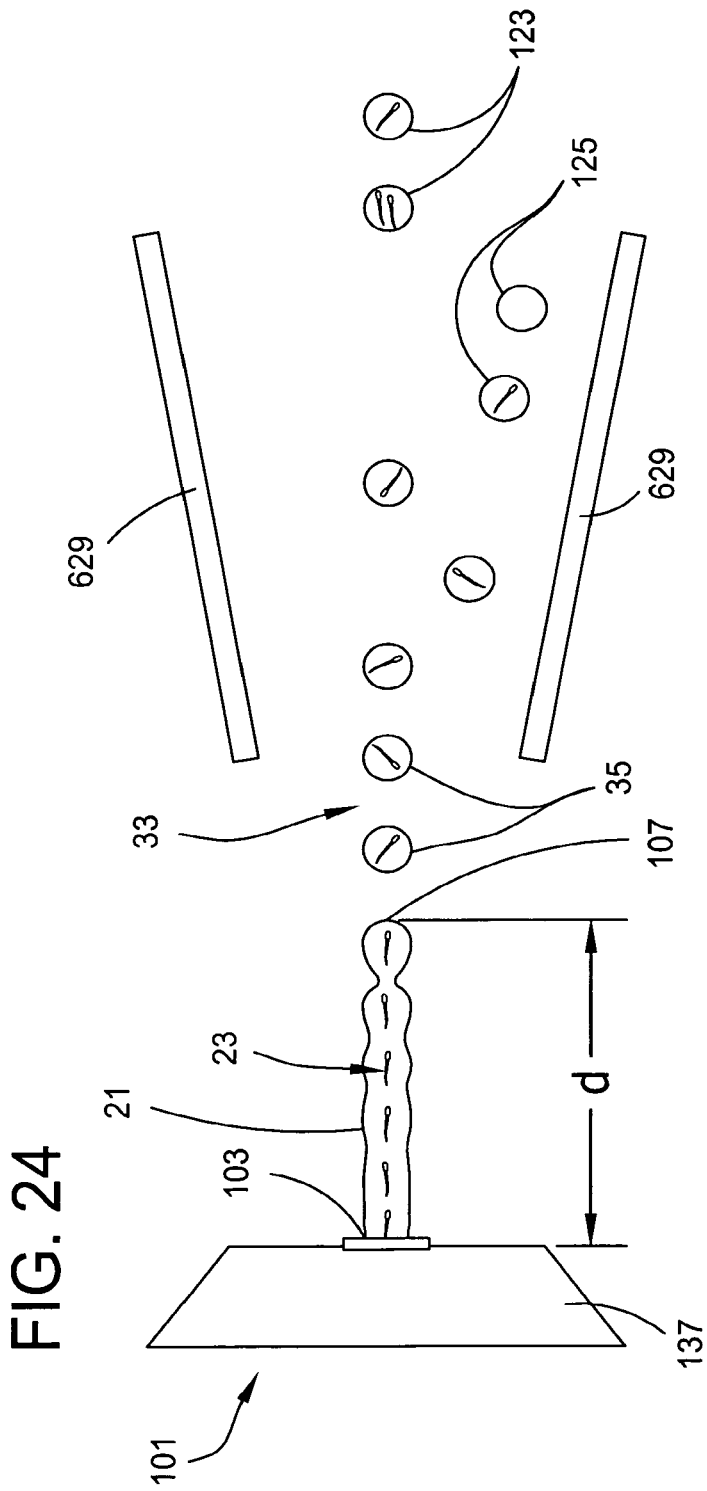
FIG. 24 is a schematic diagram showing the droplet break-off location downstream from the nozzle according to one embodiment of the present invention.

The transducer 105 for introducing energy into the fluid stream 21 comprises, in one embodiment, a collar 379 containing a piezoelectric element (not shown) secured around the flow body 133 of the nozzle system 101 (FIGS. 3-5). The transducer is of conventional design, such as is available from Beckman Coulter, Inc. as part No. 6858368. The transducer has terminals 383 for connection to a suitable source of acoustical energy so that energy can be delivered to the fluid stream 21 at a frequency which will cause it to break into droplets 33 at the droplet break-off location 107 downstream from the nozzle 137 a distance d (FIG. 24). As will understood by those skilled in flow cytometry, the characteristics of the droplet formation are governed by the following Equation 1:

$$(V=f\lambda)$$  Equation 1 where V is the velocity of the stream 21; f is the frequency applied to the fluid stream 21 through the nozzle 137; and λ is the "wave length" or distance between the droplets 33. It is a known principle of flow cytometry that droplets 33 will form in a regular pattern with the distance between droplets 33 being 4.54 times the diameter of the stream 21. Since the diameter D of the stream 21 close to the nozzle 137 generally corresponds to the diameter of the nozzle orifice 103 at its downstream end, the frequency at which the stream 21 (and nozzle 137) must be vibrated to form the droplets 33 can be easily calculated using the following Equation 2:

$$(f=V/4.54D)$$  Equation 2

The transducer 105 may be operated to generate in the range of 30,000-100,000 droplets 33 per second. For example, the transducer 105 may generate 50,000-55,000 droplets per second. Assuming the frequency is 55,000 cycles per second (55 kHz), and further assuming that the concentration of cells in the stream 21 is such that cells exit the nozzle 137 at a substantially matching rate of 55,000 cells per second, then there will be, on average, one cell per droplet 33. (In reality, some droplets 33 will contain no cells, some will contain one cell, and some will contain more than one cell.) Of course, any of various factors can be changed to vary this average, including a change in frequency (f), stream 21 (orifice 103) size (D) and stream 21 velocity (V). Ideally, these factors should be such as to reduce the amount of stress imparted to the cells during the course of the process, especially in the case of sperm cells where the preservation of motility is important.

Break-Off Sensor

Referring to FIG. 2, a break-off sensor 389 may be employed to determine the location (e.g., break-off location 107) at which the stream 21 begins to form free droplets 33. The break-off location 107 will vary depending on several factors including stream 21 viscosity, surface tension of the fluid and the amplitude of vibration of the transducer 105. By monitoring the break-off location 107, the amplitude of the transducer 105 may be varied to maintain the break-off location 107 within a given range so that the time at which each droplet 33 breaks off can be more accurately predicted by the microprocessor 131. This allows the microprocessor 131 to accurately control the electrical charge of the droplet 33 which is accomplished by selectively controlling the charge of the stream 21. Since the charge of the droplet 33 will be the same as the charge of the stream 21 immediately before droplet 33 formation, the microprocessor 131 controls the sorting of the droplets 33 by selectively charging the stream 21, as noted below.

In general, a break-off sensor is for use with any continuous stream of fluid which is breaking into droplets at a break-off location. (In the embodiment of FIG. 2, the break-off sensor 389 is located downstream from the nozzle 137 and interrogation location 115.) One exemplary break-off sensor 389 is shown schematically in FIG. 25. A light source 393 is positioned on one side of the stream 21 to illuminate the stream 21 within the given range at which the break-off location 107 will be maintained. A linear photoarray 395 positioned on the other side of the stream 21 is adapted to be oriented along an axis substantially parallel to the stream 21. As a result, the photoarray 395 detects light from the light source 393 which passes through the droplets 33 and provides output signals corresponding to the detected light.

Figure 25:
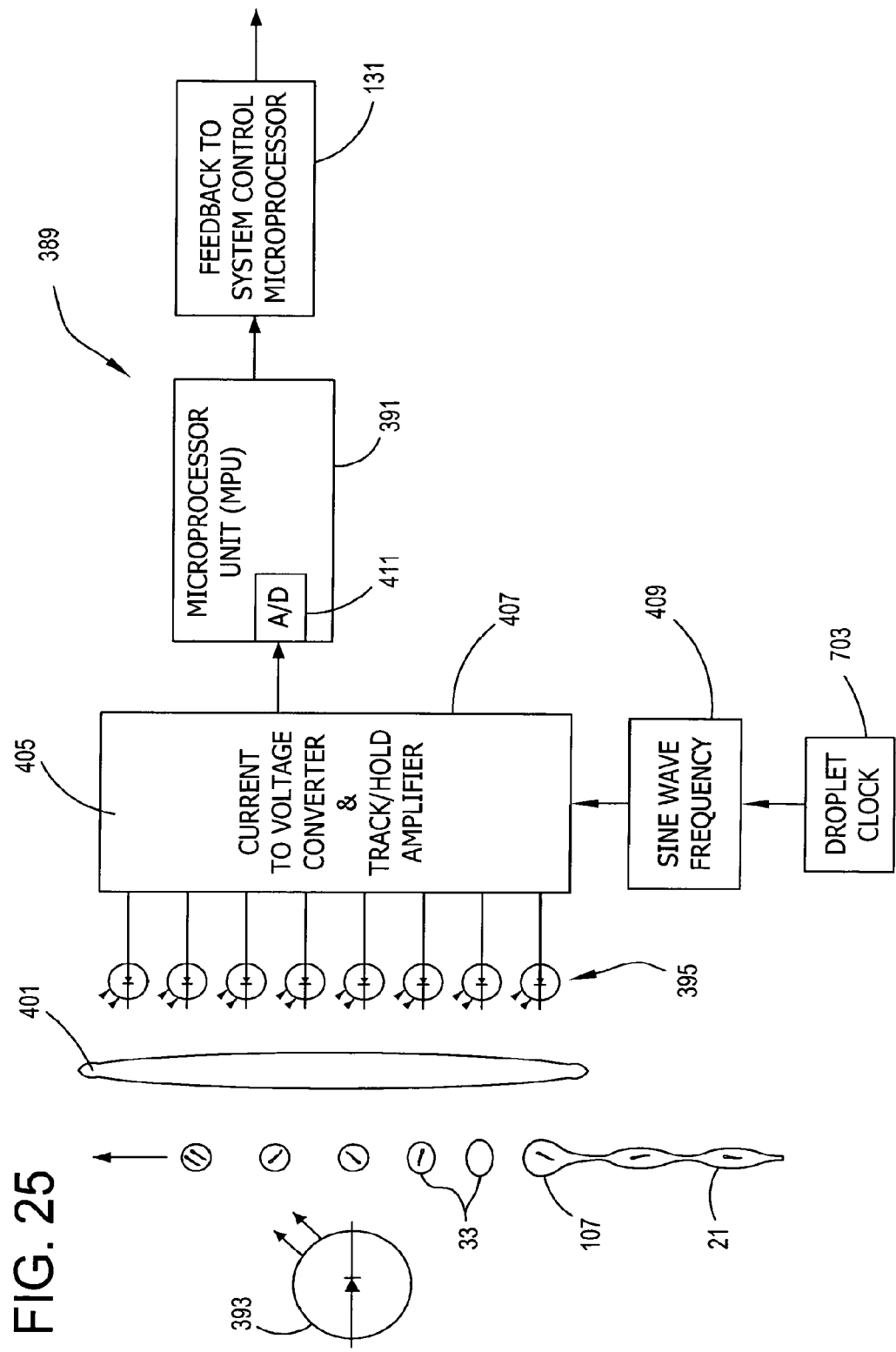
FIG. 25 is a schematic diagram of one embodiment of a break-off sensor system of the present invention.

The output signals are processed to determine the position of the break-off location 107. For example, the output signals may be digitized and provided to the processor 131 for processing. Alternatively, as shown in FIG. 25, the light source 393 may be an LED or other source which generates a near-infrared portion of the visible spectrum. The light passing between the droplets 33 is magnified by a lens 401 and directed toward an 8 by 1 linear array of photodiodes 395. Each photodiode generates a current that is proportional to the light intensity impinging thereon. This current is fed into 8 current to voltage op-amp circuits 405. The output voltage from the op-amps is AC coupled into 8 track/hold amplifiers 407. The track/hold signal 409 used by the amplifiers is taken from the transducer 105. The output from the track/hold amplifier is fed into the A/D converter 411 of a microprocessor unit (MPU) 391. The digital values computed by the MPU 391 will be provided to the system control microprocessor 131. A lookup table and/or algorithm may be used by the system control microprocessor 131 to convert between break-off location 107 drift and voltage adjustment to the transducer 105. Alternatively, the output from the MPU 391 may be an analog signal such as a DC voltage having an amplitude corresponding to a change in the amplitude of vibration of the transducer 105. The dc voltage can be applied to the high voltage amplifier input driving the droplet transducer 105 to vary the amplitude of vibration. Thus, such a processor 391 would constitute a control for receiving the output signal from the photoarray 395 and providing a location signal corresponding to a location of the break-off location 107. Such a processor 391 would also constitute a control for receiving the output signal indicative of the position of the break-off location 107 of the droplets 33 and varying operation of the transducer 105 as a function of the position of the location 107.

Figure 26:
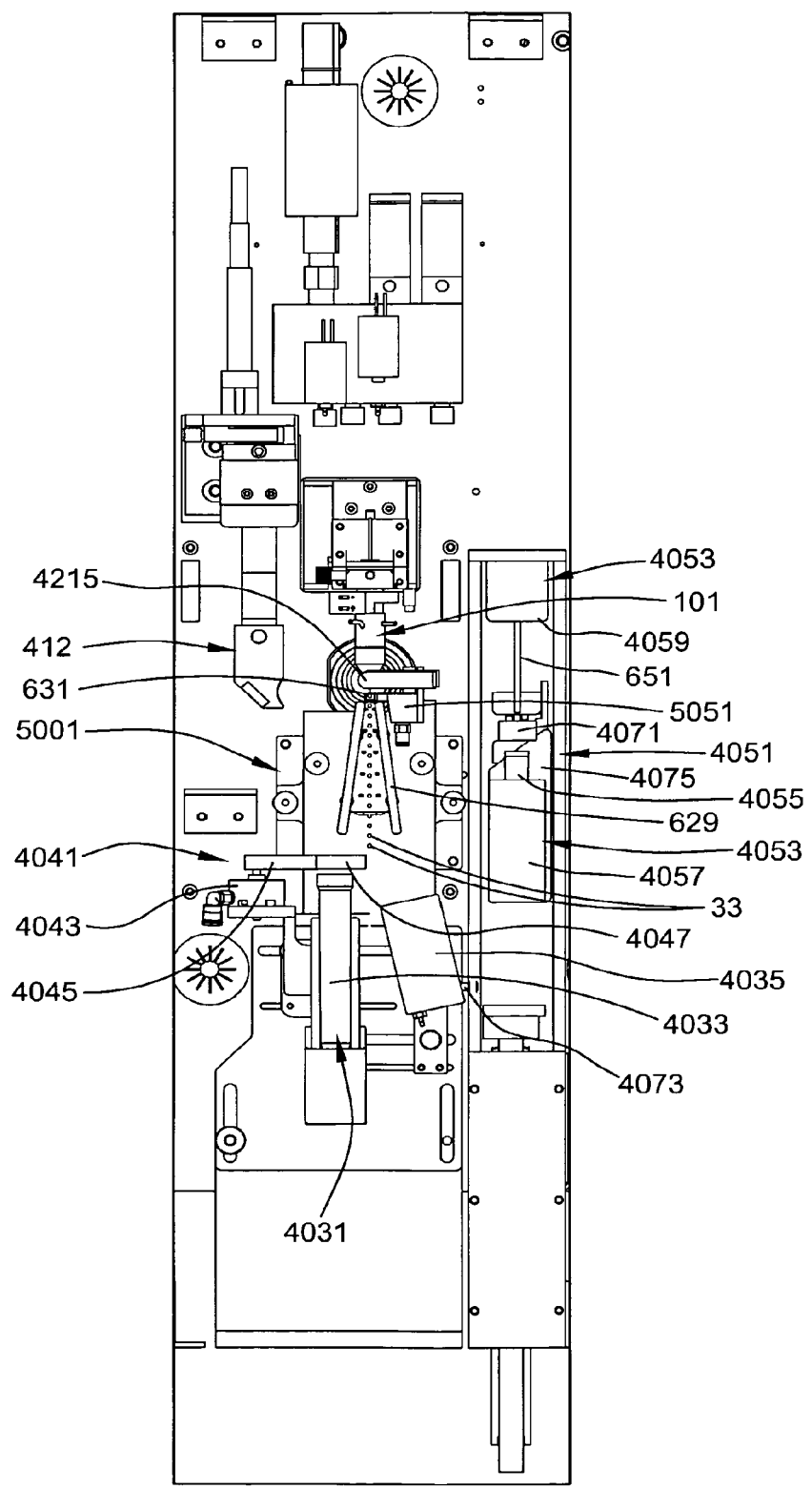
FIG. 26 is a front elevation of one flow cytometry system of the present invention.
Figure 27:
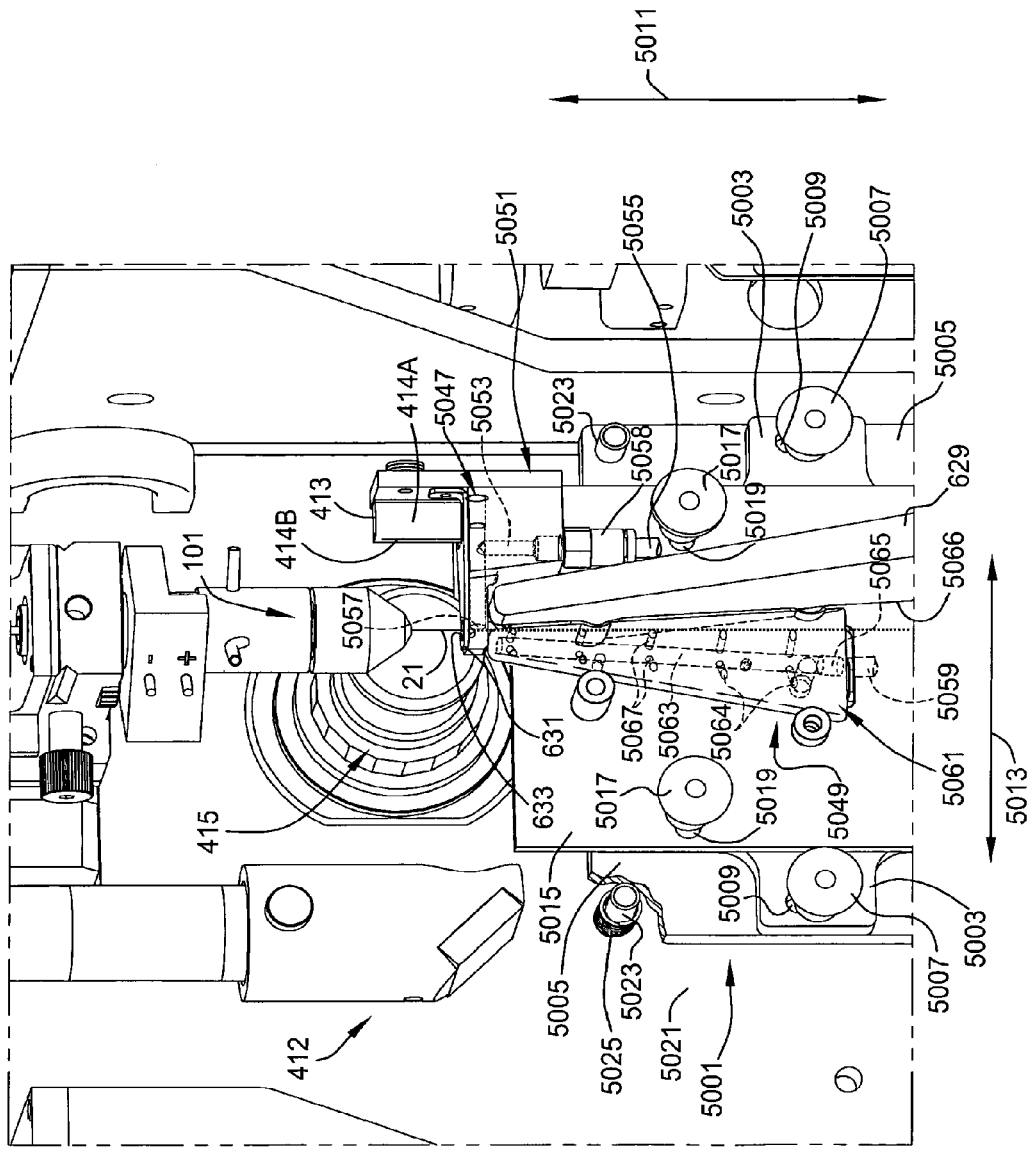
FIG. 27 is an enlarged perspective view of a portion of the system shown in FIG. 26 with parts of the system removed for clarity.
Figure 28:
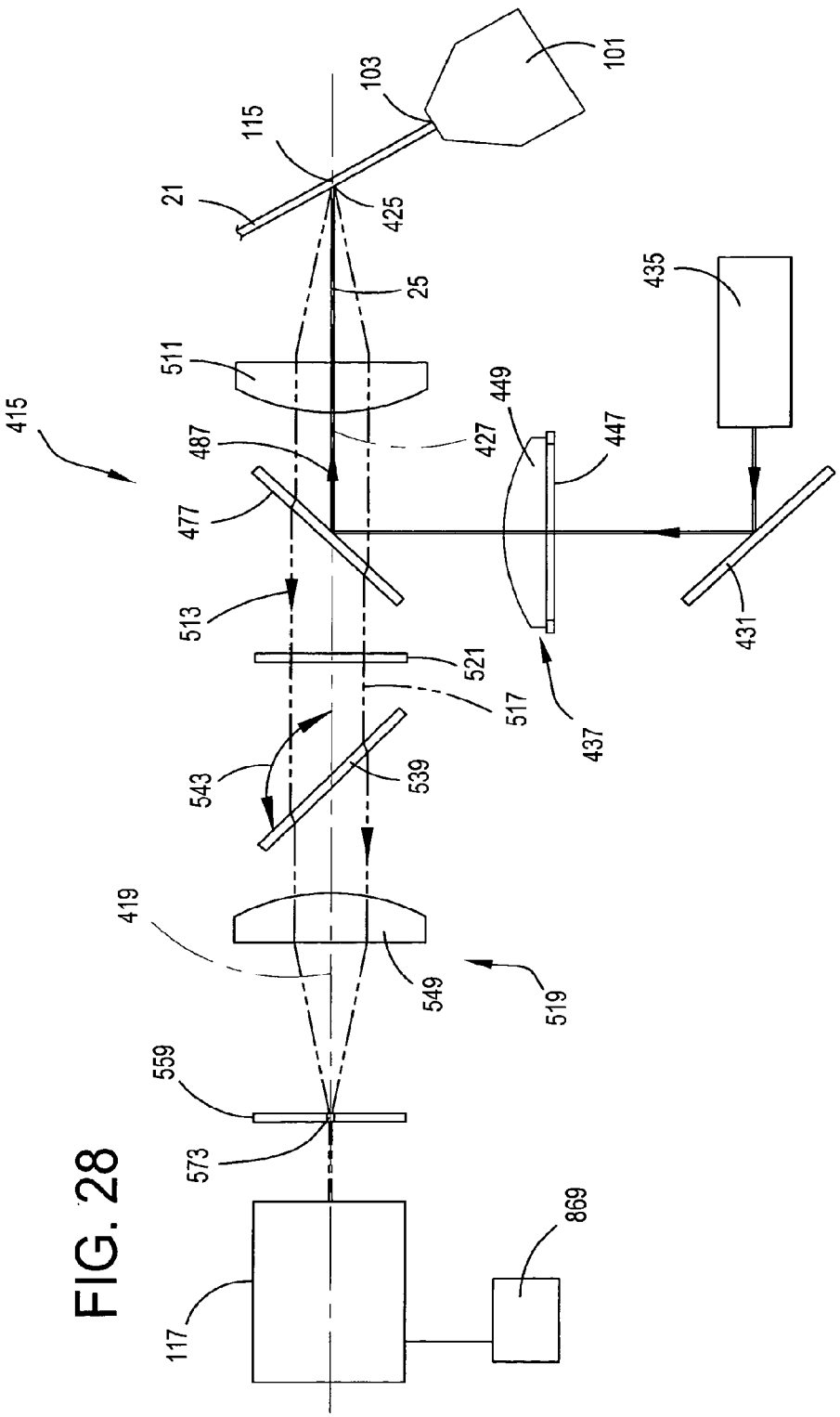
FIG. 28 is a schematic diagram of one embodiment of an epi-illumination optics system of the present invention.
Figure 29:
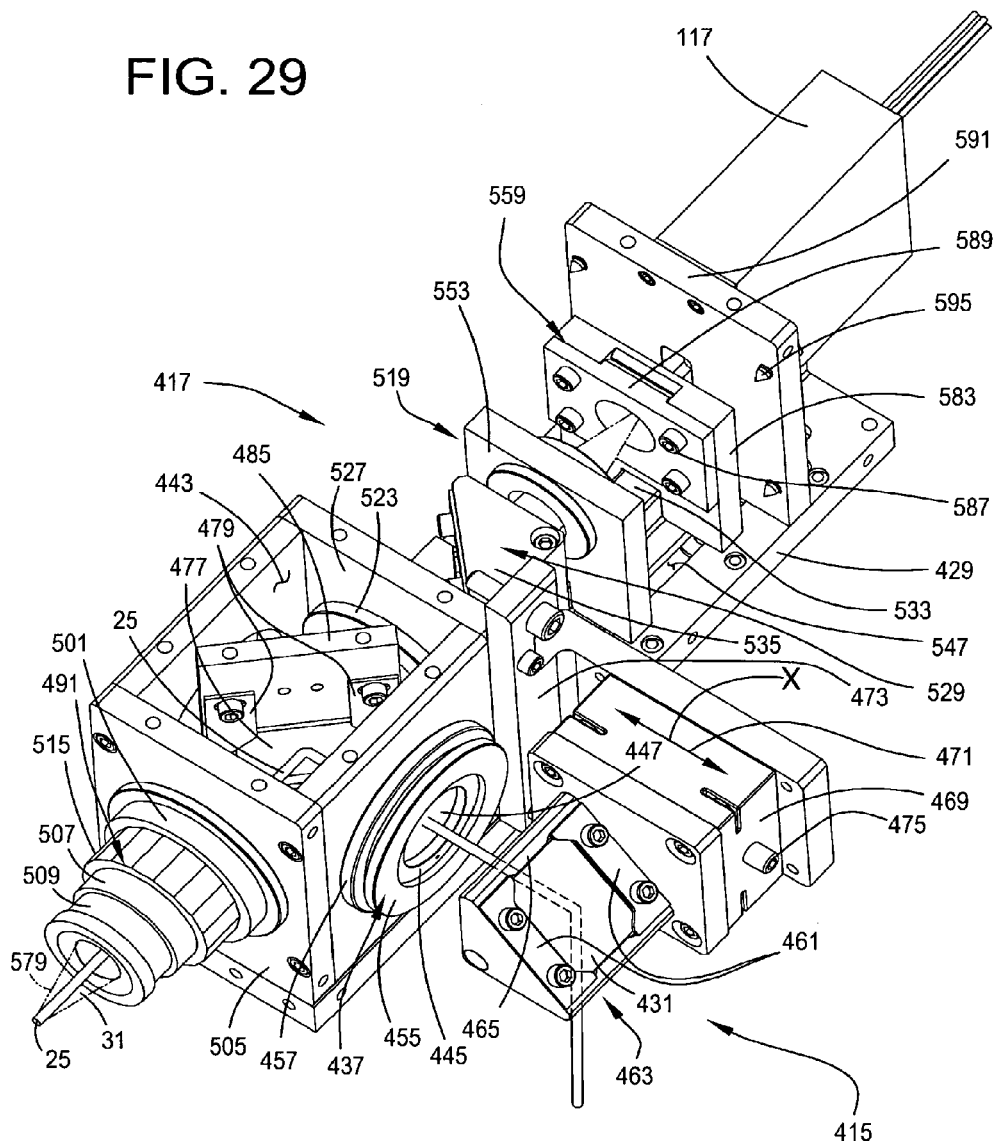
FIG. 29 is a perspective view of one embodiment of an epi-illumination optics system of the present invention.
Figure 30:
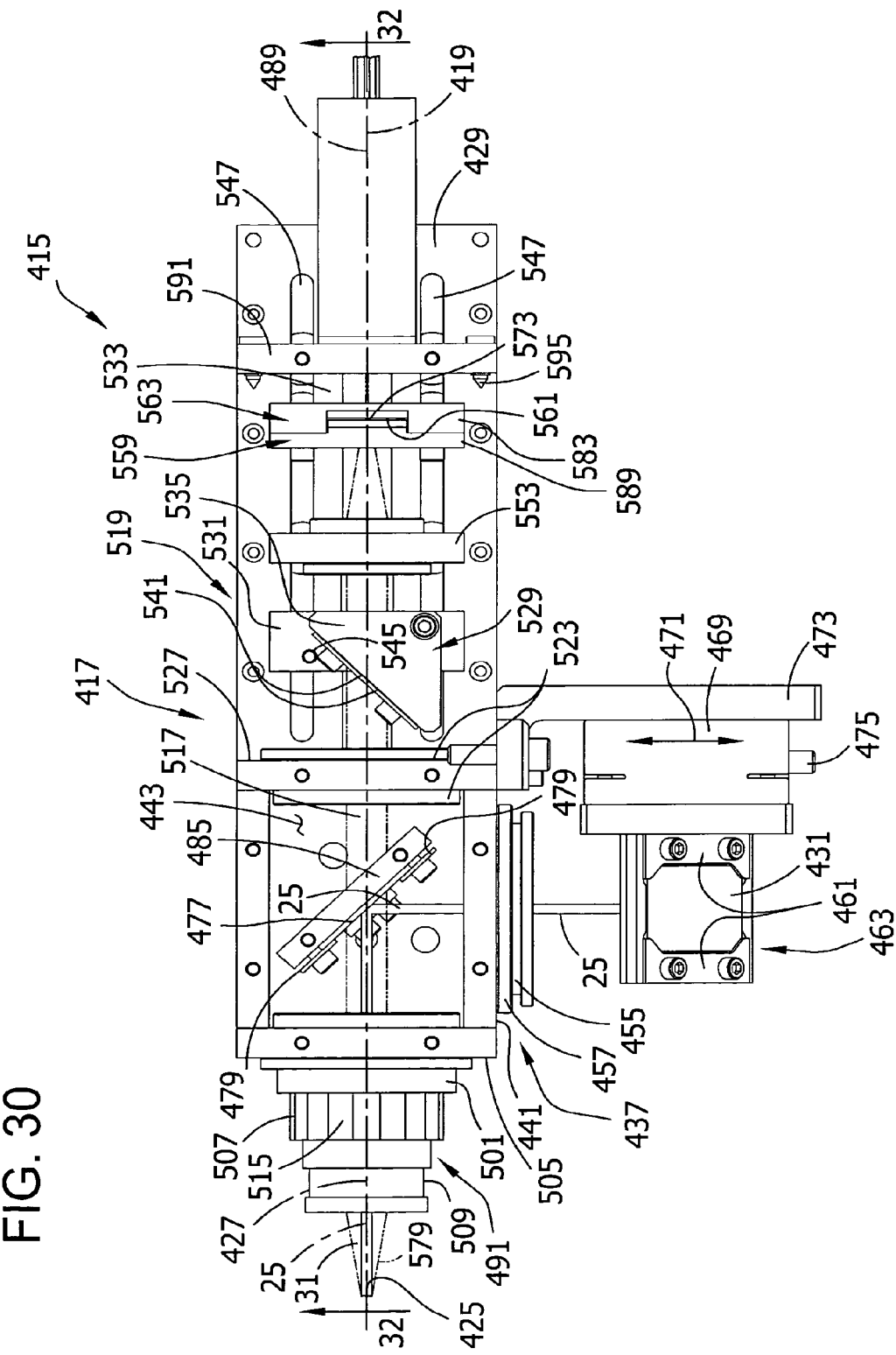
FIG. 30 is a side view of the epi-illumination optics system shown in FIG. 29.
Figure 31:
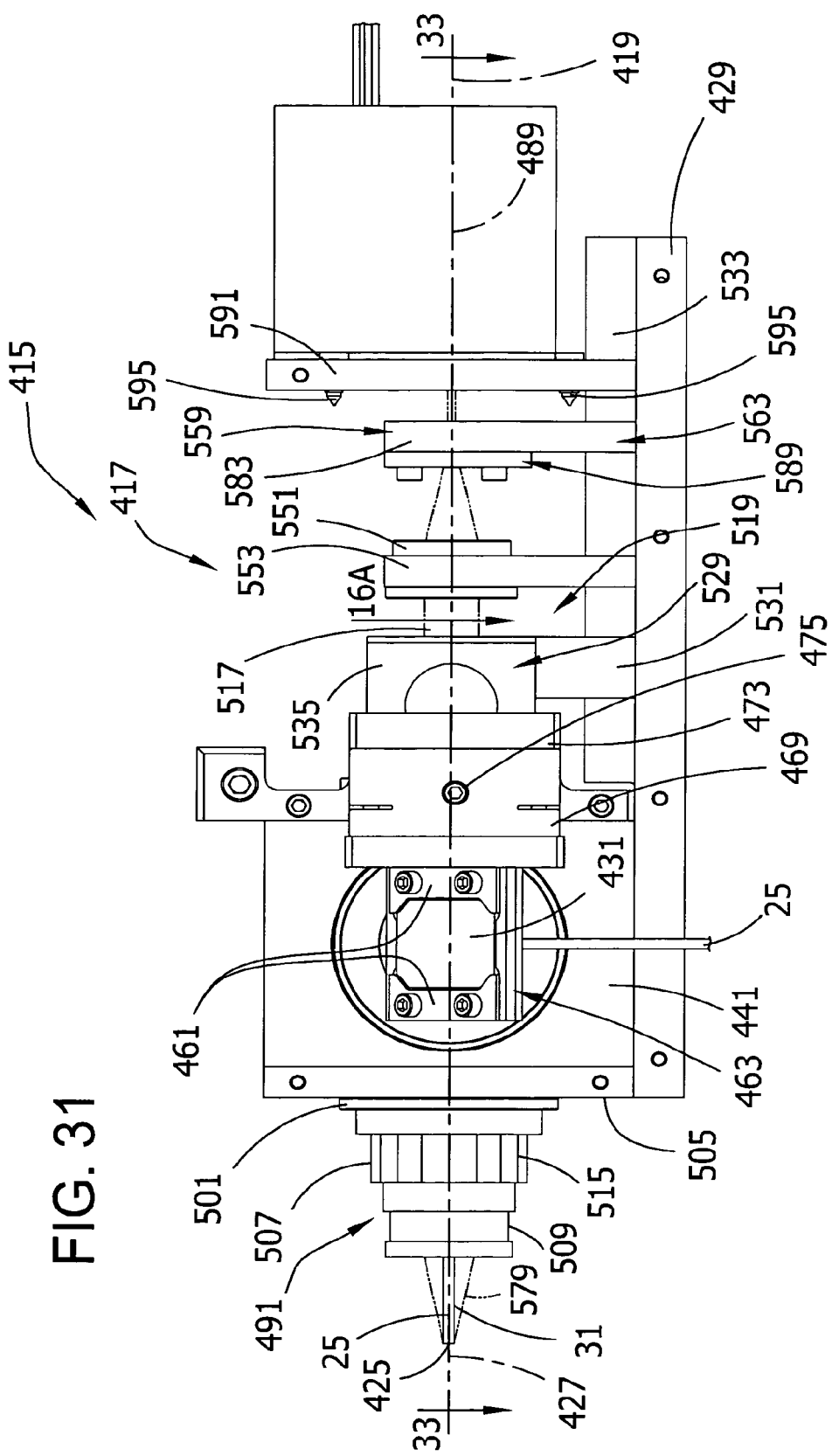
FIG. 31 is a top view of the epi-illumination optics system shown in FIGS. 29 and 30.

Alternatively, as is well known to those skilled in the art, a video camera and strobe light may be used to monitor and control the droplet break-off location. Thus, as shown in FIGS. 26-27, a video camera system 412 and strobe 413 may be provided to monitor the break-off location 107. It is desirable to place the strobe 413 behind a mask 414A (e.g., a cover with a small slit-shaped opening 414B) to limit the amount of light produced by the strobe 413 that enters the optics system 109 (FIG. 27).

Epi-Illumination Optics System

The optics system 109 is adapted for focusing a beam of electromagnetic radiation 25 (e.g., a laser beam) on the fluid stream 21 as a beam spot, so that the cells to be analyzed pass through the spot. The beam 25 may be laser light in the visible or ultraviolet portion of the spectrum, for example, having a wavelength of about 350-700 nm, although other wavelengths may be used. The wavelength of the laser light may be selected so that it is capable of exciting a particular fluorochrome used to analyze particles. If the optics system 109 is used to analyze sperm cells stained with Hoechst 33342, for instance, the wavelength may be selected to be in the range of about 350-370 nm. The power output of the laser may vary between 50 and 300 mW. Sperm cells may be analyzed using a 200 mW laser, for example. Referring to FIGS. 28-34, the system 109 is an epi-illumination system 415 comprising an instrument, generally designated 417, having a longitudinal optical axis 419. As used herein, the term "epi-illumination" means an optics system where at least some of the fluorescence emissions from cells passing through the beam spot are directed back through the optical instrument along the same axis as the focused beam 25, but in the opposite direction. This type of system is advantageous in that only one set of optics is required, including only one photodetector 117, unlike conventional systems which detect forward and side fluorescence and which use two or more photodetectors. However, it will be understood that while an epi-illumination system is preferred, many of the aspects of this invention can be applied regardless of the type of optics system used.

In one embodiment, the epi-illumination instrument 417 comprises a rectangular base 429 supporting a plurality of optical elements. These optical elements are described below, with specific examples of relevant dimensions, focal lengths, and part numbers. As will be understood by those skilled in the art, this information is exemplary only, and alternative optical elements can be used without departing from the scope of this invention.

Referring to FIGS. 28-34, the optical elements include a reflecting filter 431 which reflects a collimated beam 25 of light from a laser or arc lamp 435, for example, through a conditioning lens assembly 437 mounted in an opening 439 in a side wall 441 of a dichroic chamber 443 extending up from the base 429. In this particular embodiment, the conditioning lens assembly 437 comprises a retaining ring 445, neutral density filter 447, cylindrical lens 449, lens holder 455 and jam nut 457. The cylindrical lens 449 introduces a one-dimensional divergence into the beam 225 and directs it toward optical elements (described below) which shape the beam to have a desired cross sectional shape 459, preferably generally elliptical. By way of example, the cylindrical lens 449 may be a plano-convex lens having a focal length of 16 mm. A beam expander (not shown) can optionally be installed in the instrument 417 to allow adjustments to be made to the shape of the elliptical beam spot 459.

Figure 23:
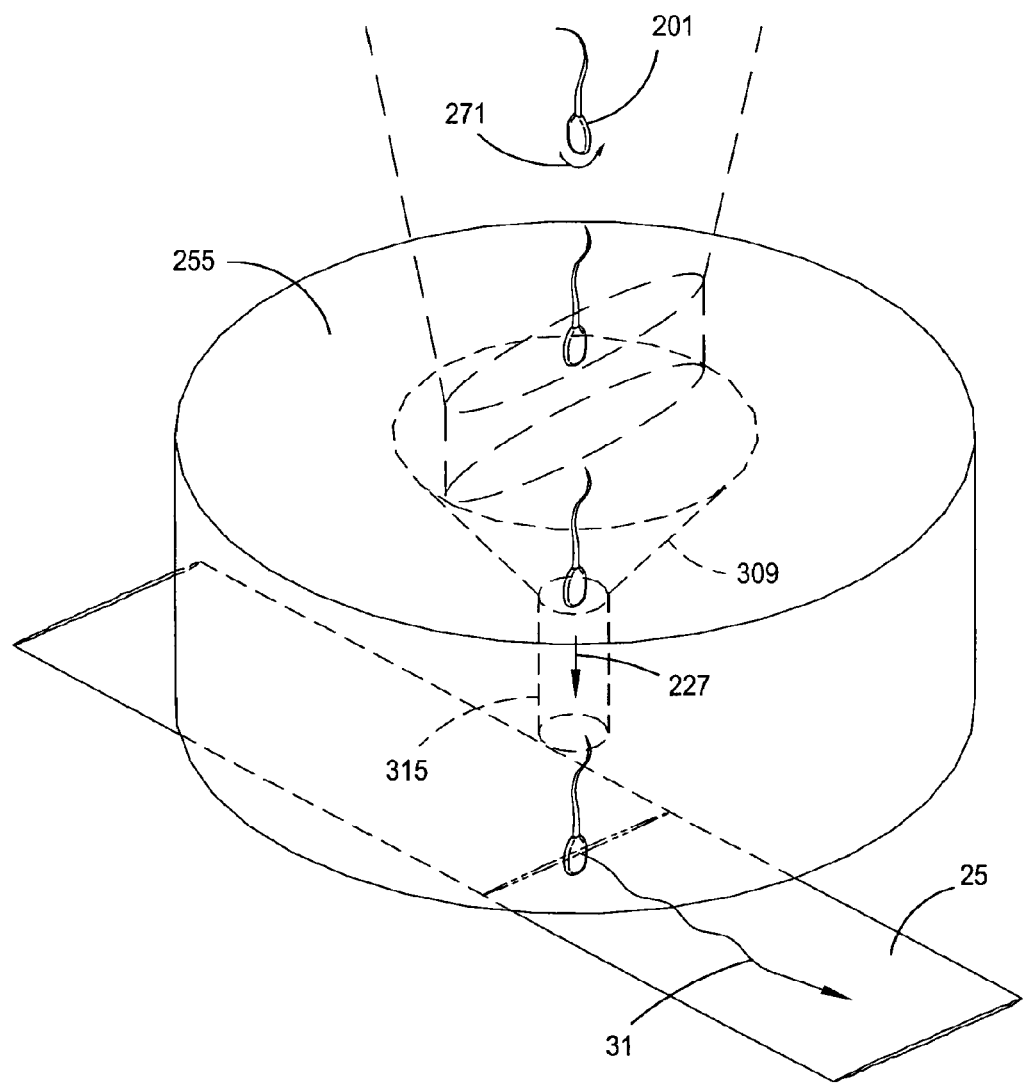
FIG. 23 is schematic diagram of a plurality of aligned sperm cells being rotationally oriented as they pass through an orifice member of the present invention toward the interrogation location.

The reflecting filter 431 is mounted by clips 461 on the angular face 465 of a filter holder 463 which has openings 467 in it to permit the beam 25 to reflect off the filter 431 toward the optics of the instrument 417. The holder 463 is fastened to a linear stage 469 movable along an X-axis 471 relative to an outrigger 473 secured to the base 429 and dichroic chamber 443, the stage 469 being movable by suitable means 475 (e.g., a micrometer) to precisely locate the holder 463 and reflecting filter 431 to reflect the beam 25 into the instrument 417 at the proper location. A dichroic filter 477 is held by clips 479 on a frame 485 mounted in the dichroic chamber 443 and functions to reflect the shaped beam 25 in a forward direction 487 along an axis 489 which, in this particular embodiment, corresponds to the longitudinal optical axis 419 of the instrument. The beam 25 passes through a focusing lens assembly 491 which focuses the beam 25 on the fluid stream 21 as a beam spot having the aforementioned generally elliptical shape 459 (FIG. 6) with the major axis of the ellipse extending generally perpendicular to the direction of flow 227 of the stream 21. As each cell passes through the beam spot 459, the fluorescing dye (or other reporting agent) in the cell is activated to emit fluorescent light 31 (FIG. 23). In the case of sperm cells stained with a DNA selective fluorescing dye, X cells have more DNA than Y cells, include more fluorescing dye, and emit a stronger signal than Y cells (e.g., 3.8%), which provides a basis for discriminating and sorting cells, as will be described. The focusing lens assembly 491 includes, in one embodiment, a microscope adapter 501 mounted in an opening 503 in a front wall 505 of the dichroic chamber 443, a focusing barrel 507, a pair of lens mount barrels 509, and the lens 511 itself, which may be a 12.5 mm diameter, plano-convex lens with a focal length of 16 mm, available from Oriel Corporation as part number 41209, and is anti-reflective coated for light having a wavelength in the range of 340-550 nm. The lens 511 may be made of fused silica. Other focusing lenses may also be suitable, such as an infinity-corrected fluorescence microscope objective. The focusing lens assembly 491 has a conventional telescoping focus adjustment 515 to focus the elliptically-shaped beam spot 459 on the core 189 of the stream 21.

The outgoing fluorescent light 31 emitted by the cells as they pass through the beam spot 459 is of a different (longer, due to the Stoke's shift principle) wavelength than the incoming laser light 25. Some of the fluorescence emissions 31 are transmitted in a rearward direction 513 along the incoming beam axis back through the focusing lens 511 which collects and collimates the fluorescence emission 31. The collimated fluorescence emissions 517 pass in a rearward direction from the lens 511 to the dichroic filter 477, which transmits the fluorescence emission 517. By way of example, the dichroic filter 477 may be a filter available from Omega Optical as part number XF2001, 400DCLP.

The optics system 415 includes a filtering system 519 positioned rearward of the dichroic filter 477 along the optical axis 419 of the instrument 417. In one embodiment, the filtering system 519 includes an emission filter 521 in a holder 523 mounted in an opening 525 in a back wall 527 of the dichroic chamber 443. The emission filter 521 attenuates any laser light scatter or other undesired electromagnetic radiation that is transmitted through the dichroic filter 477. By way of example and not limitation, the emission filter 521 can be a thin film, long-pass filter adapted to transmit more than 90% of light having a wavelength greater than 408 nm, as is available from Omega Optical as part number XF3097. An alignment pellicle assembly 529 is spaced rearwardly along the optical axis 419 from the emission filter. This assembly includes a slider 531 movable on a rail 533 extending longitudinally of the base 429 parallel to the longitudinal optical axis 419 of the instrument 417, a filter holder 535 secured to the slider 531, a pellicle filter element 539, and clips 541 for securing the pellicle filter element 539 to the filter holder 535 at an angle 543 relative to the optical axis 419 of the instrument 417. The pellicle filter element 539 has the same thickness as the dichroic filter 477 and functions to translate the collimated fluorescence emission 517 back onto the optical axis 419 of the instrument 417. Fasteners 545 extending up through parallel slots 547 in the base 429 on opposite sides of the rail 533 secure the slider 531 to the base 429 in the desired position along the optical axis 419. Spaced to the rear of the alignment pellicle assembly 529 is an aspheric lens 549 held by a holder 551 mounted in a frame 553 which is also slidable on the rail 533 and secured in selected position by suitable fasteners 557. The aspheric lens 549 focuses the collimated fluorescence emission 517 onto a spatial filter, generally designated 559, which filters out reflection or emission from sources other than the cells to be analyzed. The aspheric lens 549 may be, for example, an 12.5 mm diameter aspheric lens having a focal length of 15 mm, as is available from Oriel Corporation. The lens 549 is preferably anti-reflective coated for visible emission wavelengths but made of a material (e.g., flint glass) which further attenuates transmission of laser light scatter.

Figure 34:
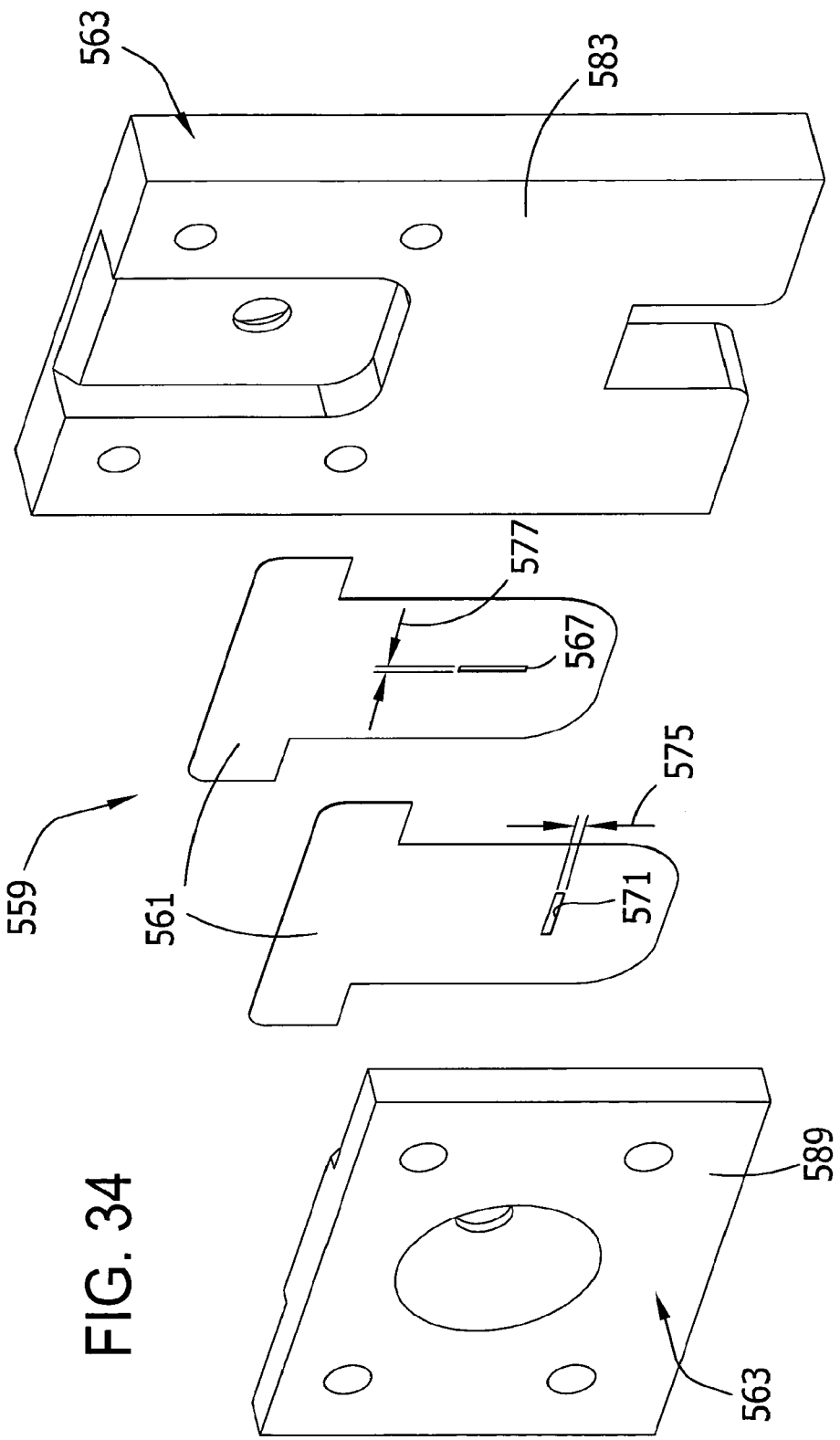
FIG. 34 is a perspective view showing only elements of the optical filtering system that are rearward of the dichroic filter of the epi-illumination optics system shown in FIG. 29.

As shown in FIG. 34, the spatial filter 559 comprises, in one embodiment, a pair of aperture plates 561 releasably held by a frame 563 mounted on the base 429 of the instrument 417. Each of the plates 561 has a slit 567, 571 therein, one slit 567 preferably being generally vertical and the other 571 preferably generally horizontal, the arrangement being such that the slits 567, 571 intersect to form an aperture 573. In one embodiment, the aperture 573 is generally rectangular in shape and has a vertical dimension 575 of 100 microns and a horizontal dimension 577 of 500 microns. The size and shape of the aperture 573 may vary (or even be adjusted by changing aperture plates), so long as it functions to remove reflections and light from any source other than the collection volume 579. The frame 563 holding the aperture plates 561 preferably has two parts, namely, a plate holder 583 slidable on the rail 533 of the base 429 and secured in selected position by fasteners 587, and a backing member 589 for securing the aperture plates 461 in position on the plate holder 583.

In one embodiment, the smaller (vertical) dimension 575 of the aperture 573 in the spatial filter 559 is sized (or adjusted) to enable use of a "slit scanning" technique to evaluate the cell. This technique is described in more detail in the "Focused Beam Spot" section of this specification.

Figure 35:
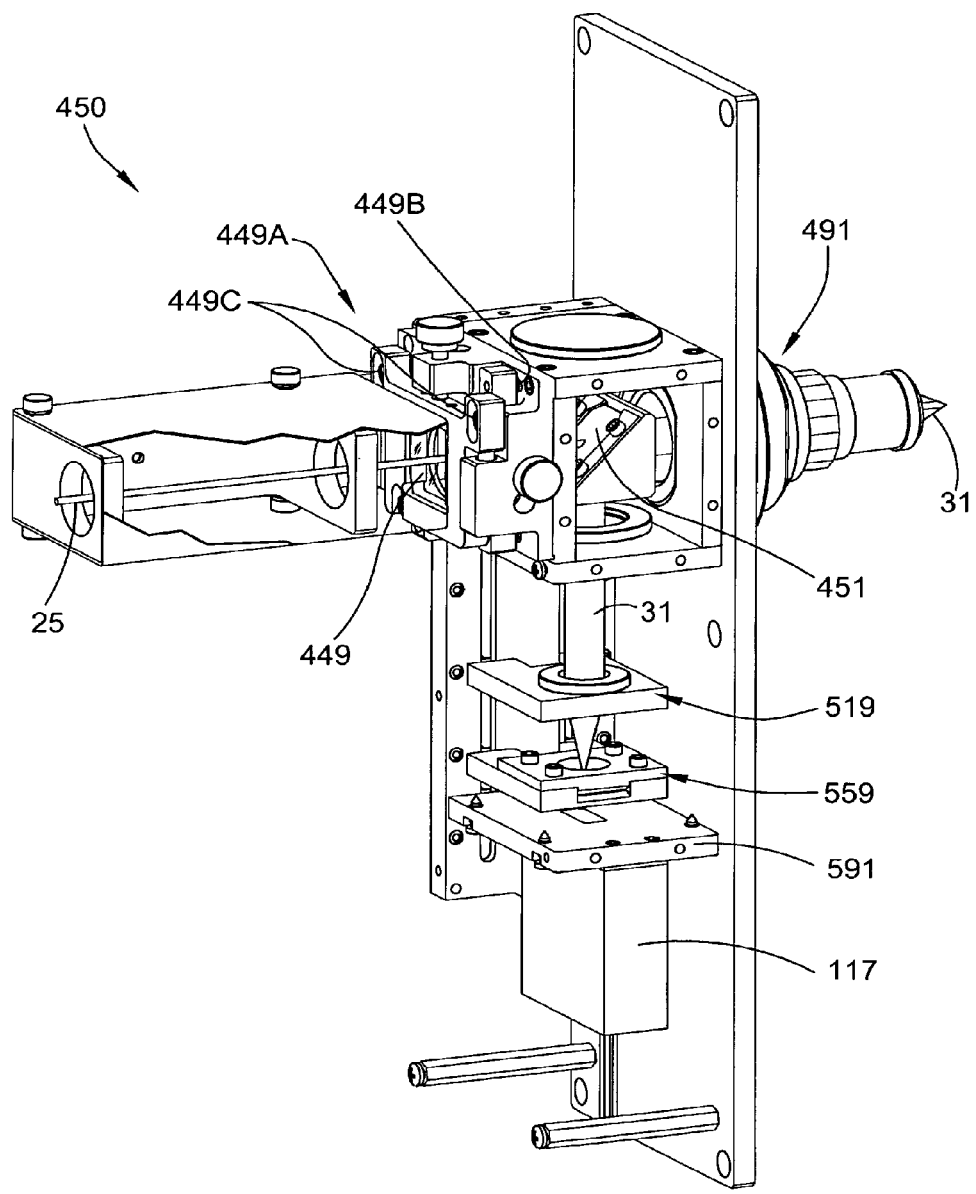
FIG. 35 is a perspective view of another epi-illumination optics system of the present invention including translational adjustment of the cylindrical lens.

Another embodiment of an epi-illumination optics system, generally designated 450, is shown in FIG. 35. This embodiment is substantially the same as the embodiment shown in FIGS. 28-34, except as noted. One significant difference is that the dichroic filter 477 has been replaced with a different dichroic filter 451 that transmits (rather than reflects) the illumination beam 25 and reflects (rather than transmits) the fluorescent emissions 31. Also, because the fluorescence emissions 31 are reflected by the dichroic filter 451 rather than transmitted, there is no need for an alignment pellicle 539 in this embodiment of an epi-illumination optics system 450. Thus, the epi-illumination system 450 is just one example of how the optics system can be reconfigured if desired without departing from the scope of this invention.

Further, the cylindrical lens 449 is mounted on an adjustable mounting assembly 449A. The mounting assembly 449A allows two-axis translational movement of the cylindrical lens 449 in a plane perpendicular to the illumination beam 25. Releasable fasteners (e.g., screws (not shown))

extend through slot-shaped holes 449B (only one of which is visible on FIG. 35). Release of the fasteners allows translational movement of the lens 449 in a first direction perpendicular to the beam 25. Similar fasteners (not shown) extend through slot-shaped holes 449C, allowing translational movement of the lens 449 in a second direction perpendicular to the first direction. This allows minor adjustment of the relative positions of the cylindrical lens 449 and beam 25 so that the intersection of the beam 25 and lens 449 can be moved across the surface of the lens 449, thereby causing slight changes to the focusing provided by the cylindrical lens 449. Once the lens 449 is in the desired position, the fasteners can be tightened to hold it there.

Photodetector

Figure 32:
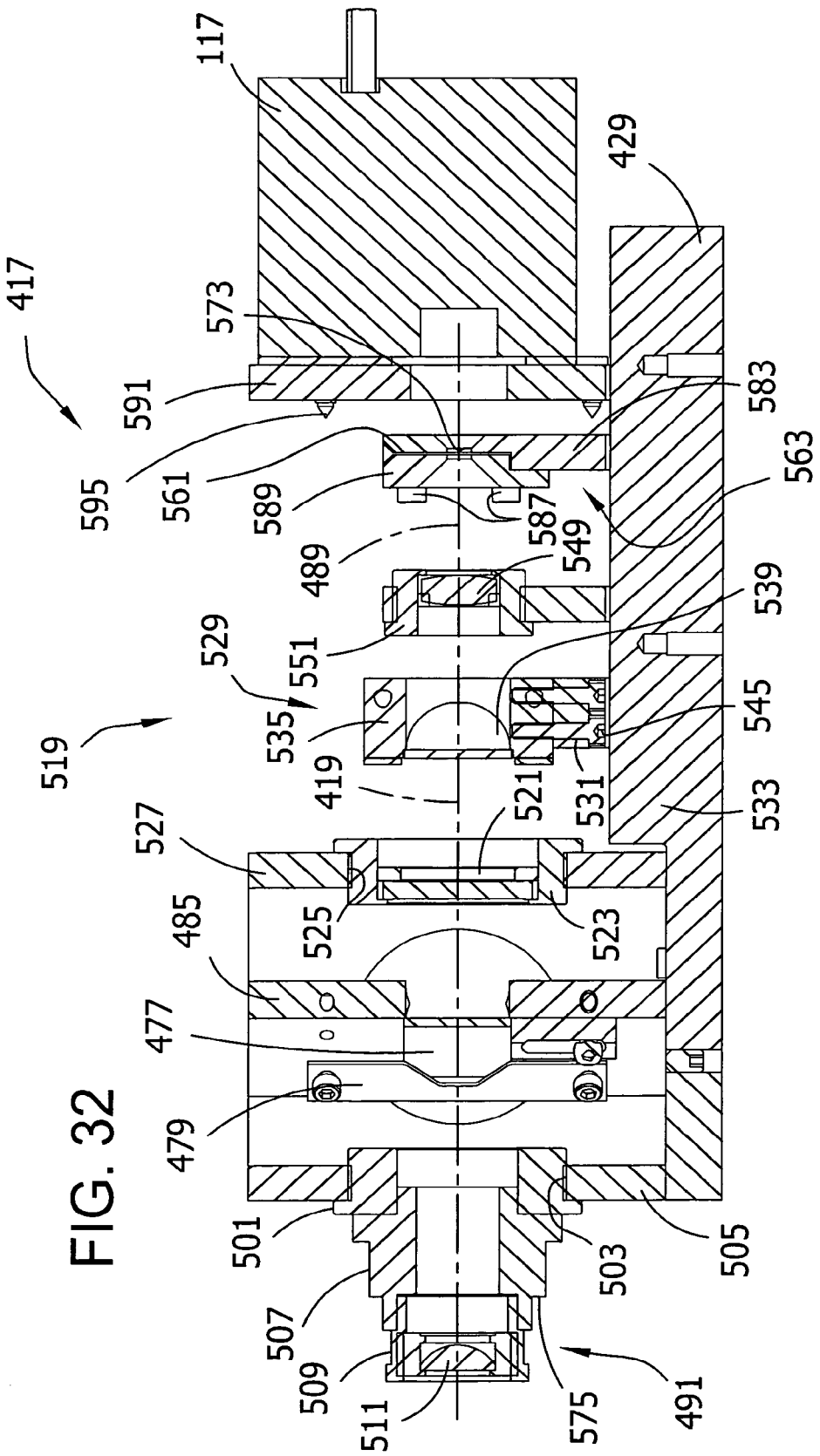
FIG. 32 is a sectional view of the epi-illumination optics system along the plane 32-32 of FIG. 30.
Figure 33:
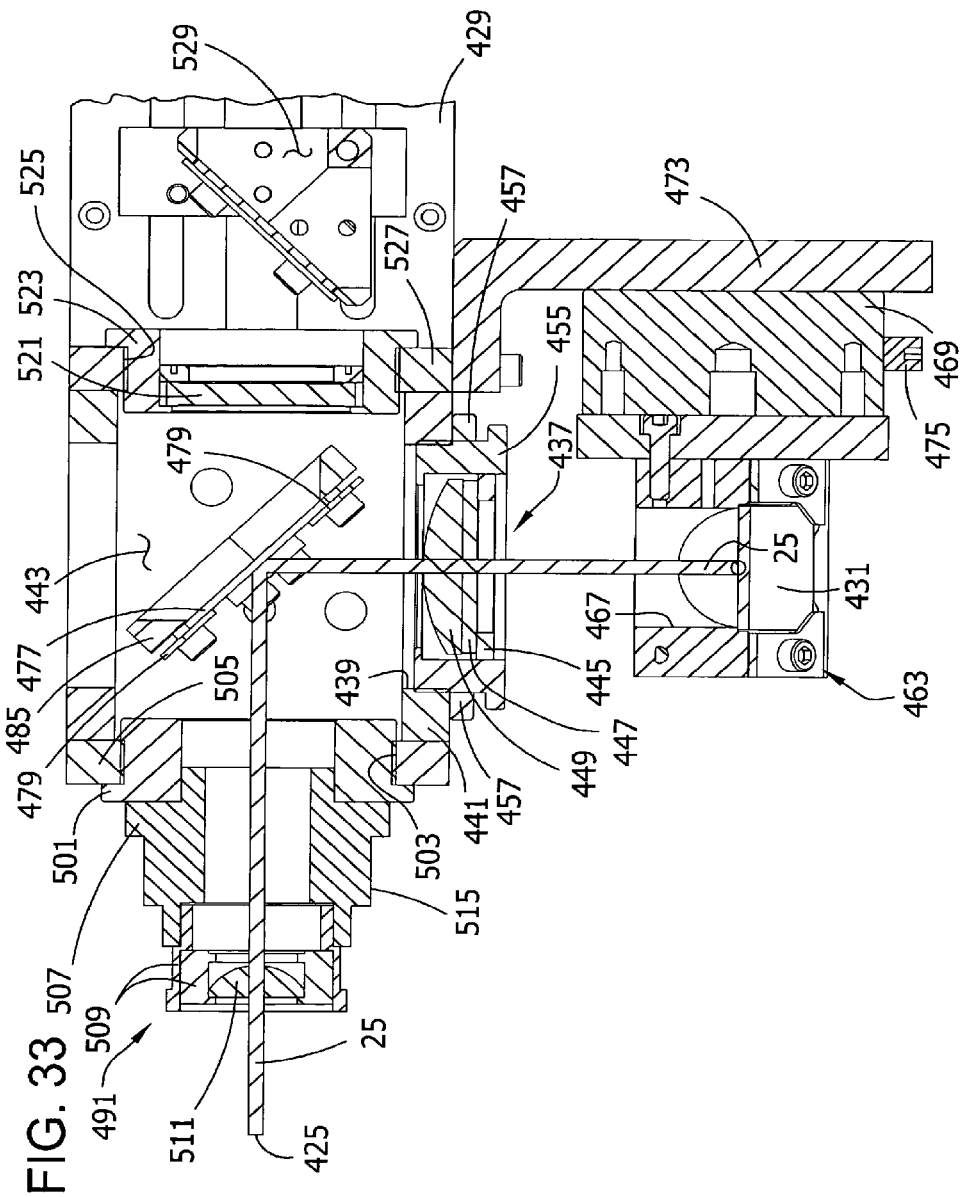
FIG. 33 is a sectional view of a portion of the epi-illumination optics system along the plane 23-33 of FIG. 31.

The emitted fluorescence passing though the spatial filter 559 falls upon a photodetector 117 fastened to a mounting plate 591 slidable on the rail 533 of the base 429 at the rear of the epi-illumination instrument 417 and securable in fixed position by fasteners 595 (FIG. 32). The photodetector 117 detects the fluorescent emissions 31 and converts them into electrical signals which can be processed to analyze the desired characteristics of the cells, as will be described in more detail later. The photodetector 117 may be a conventional device, such as a photodetector available from Hammamtsu. The photodetector 117 preferably includes a preamplifier and PMT gain which is optimized for emission intensity produced by the epi-illumination system for the particular stained cells being analyzed.

In general, the PMT gain is optimized when between about 200 and 2000 volts are applied to the vacuum tube. In the case of detecting fluorescent emissions from Hoechst 33342, for instance, the PMT gain is optimized when between about 400-800 volts are applied to the vacuum tube. One particularly desirable photodetector includes a PMT having a spectral range of 185-830 nm (530 nm peak), a 0.01 mA maximum average anode current, a cathode radiant sensitivity of 70 mA/W typical, a cathode luminous sensitivity of 140 µA/lm, anode luminous sensitivity of 300 A/lm, max anode dark current of 1 nA (0.1 nA typical), and a 1.4 nanosecond risetime. The PMT is DC coupled amplifier demonstrating a flat gain to >37 MHz, having a 1 V peak output into a 50Ω load and a recovery time of less than 400 nanoseconds. It is also desirable for the amplifier to allow high voltage adjustment for compensation of PMT efficiency variations without decreasing the signal-to-noise ratio to less than 800 dB.

Angle of Beam Incidence

FIG. 36 schematically illustrates one desirable orientation of the intersection of the light beam and the fluid stream. Several points are of note. As shown, the light beam 25 is focused on the stream 21 at a location 115 that is only a short distance 605 from the exit orifice 103 of the nozzle 137, preferably less than 1.0 mm, or even inside the nozzle 137, so that the cells pass through the spot 459 while they are still substantially in desired orientation, as previously described. This is particularly important for cells which are mobile in the fluid stream 21, including sperm cells.

Another point of note is that the beam 25 of this embodiment may be directed toward the fluid stream 21 along a beam axis 609 which intersects the fluid stream 21 at an angle of incidence A which is skewed (off 90 degrees) relative to a longitudinal axis of the fluid stream 21, as viewed from a side of the stream 21 (see FIG. 36). When sorting certain particles, it has been found that better discrimination of the different types of particles may be obtained by illuminating the stream 21 at an angle of incidence other than 0°. Sperm nuclei, for instance, are desirably illuminated at an angle of incidence A that is in the range of 5 to 45 degrees, more preferably in the range of 15 to 30 degrees, and even more preferably in the range of 18 to 24 degrees. Other particles (e.g., live sperm cells) are easier to interrogate when the light beam 25 is generally perpendicular to the fluid stream 21 (i.e., when angle A is about 0°). Thus, it is contemplated that angle A may be any angle without departing from the scope of this invention.

The proper selection of angle A results in improved signal to noise discrimination in certain particles and thus more accurate discrimination based on different characteristics of those particles (e.g., sperm nuclei with X and Y chromosomes sperm cells). This improvement may be due to a number of factors, including reduced laser light scatter entering the focusing lens 511. Because the focused beam spot 459 is preferably wider than the stream 21, a diffraction pattern is created at the intersection 115 of the beam 25 and the stream 21. When angle A is greater than about 12 degrees, the reflected diffraction pattern does not fall on the lens 511. Another factor may be that the skewed angle A allows the beam 25 to be focused very close to the nozzle orifice 103, so that the nozzle body 139 does not interfere with the lens 511. Relatedly, the cells are more uniformly aligned closer to the nozzle 137, so that focusing the beam spot 459 closer to the nozzle 137 results in an improved signal. Further, the more "head on" profile of the cell presented to the lens 511 (beam 25) at the skewed angle A reduces the variation of total fluorescence intensity caused by any misalignment of the cells. In this regard, in the case of sperm cells it is preferable that the beam 25 fall on one of the wide faces 207 of each sperm cell 201, as discussed above, and that the nozzle 101 and optics system 109 be positioned to achieve this result.

While a skewed angle of incidence A is believed to be beneficial in sorting some particles, it is contemplated that the angle of intersection between the beam axis and the stream may be 90 degrees or any skewed angle without departing from the scope of this invention. It is also expected that the optimal angle of incidence may vary widely depending on the properties of the particular particles being analyzed.

Focused Beam Spot

Referring to FIG. 6, the focused beam spot of one embodiment is shown as having a generally elliptical (oval) shape 459 with a length L1 along a major axis extending generally at right angles to the direction of fluid stream flow 227 and a width W1 along a minor axis extending generally parallel to the direction of fluid stream flow 227. In one embodiment, the width W1 is less than the length of the head of the sperm cell 219, and even more preferably less than the length of the region 225 containing the chromatic DNA mass of the cell, which in the case of a bovine sperm cell 201 has a length of less than about 1 µm. For a stream 21 having sheath stream 191 that is about 60 µm in diameter and a core stream 189 containing bovine sperm cells 201, an exemplary length L1 is about 80 µm and an exemplary width W1 is about 1.5 µm. By focusing the beam spot 459 to a width W1 which is less than the length of the head 205 of the sperm cell 201, or any other cell or particle being analyzed, and even more preferably less than the diameter of the DNA region 225 of the head 205 of the sperm cell 201, greater signal resolution is achieved, as will be understood by those familiar with "slit scanning" techniques. This is a technique by which a beam 25 is narrowed to have a width less than the length of a cell (i.e., the dimension of the cell in the direction of stream flow) so that as the cell moves through the narrow beam, photon emissions 31 from the cell are measured over the length of the cell, as will be discussed later. In this way, information can be obtained about variations in structure, including DNA material, along the length of the cell. The slit-scanning technique is also helpful in identifying "coincident" cells, that is, cells which are overlapping or very close together.

As mentioned previously, slit scanning can also be carried out by sizing the aperture 573 of the spatial filter 559 to have a vertical dimension 575 such that only a portion of the light emitted from a cell, corresponding to a fraction of the cell length in the direction of stream flow, passes through the aperture to the photodetector 117. Further, signal resolution can be optimized by adjusting the width of the beam and/or the size of the aperture of the spatial filter to work together to provide a beam spot that is suitably shaped for slit scanning.

One way to adjust the shape of the beam spot 459 is by changing to a different cylindrical lens and/or by making an adjustment to a beam expander in the optics system 109. Further any method of shaping the beam 25 to form an elliptically shaped beam spot 459 is contemplated as being within the scope of the present invention. Beam spots of other shapes and sizes may also be used and are contemplated as falling within the scope of this invention.

Sorting System

FIG. 2 illustrates an exemplary embodiment of the sorting system 119. The sorting system 119 comprises an electrostatic charging device 627 for charging and/or not charging the droplets 33 depending on the classification of the particles contained in the droplets 33 (e.g., the X/Y chromosome content of sperm cells), and a pair of electrostatic charged deflector plates 629 for sorting the droplets 33 into different groups 123, 125, according to their charge. It is desirable to coat the deflector plates 629 with a dull, low-emissive coating (e.g., epoxy or paint) to limit light reflected or emitted by the deflector plates 629. The deflector plates 629 may be charged by any suitable power supply 635. It is generally desirable for the electrical potential between the two fully charged deflector plates 629 to be in the range of 2000-4000 volts. However, the electrical potential between the deflector plates 629 may be anywhere between about 1000 and 6000 volts.

The charging device 627 comprises a charging element 631 having an opening 633 therein through which the stream 21 passes at a location near the droplet break-off location 107 (e.g., within five droplet lengths or closer). It is desirable to mount the charging element 631 with a mechanism that facilitates adjustment of the position of the charging element 631 with respect to the droplet break-off location 107. As shown in FIGS. 26 and 27, for example, the charging element 631 and deflector plates 629 may be attached to an adjustable mounting assembly 5001 that allows three-axis translation and tilt adjustment of the charging element 631 and deflector plates 629 with respect to the nozzle system 101. For translation along an axis 5011 parallel to the stream 21, the mounting assembly 5001 includes a board 5003 fastened to a backing 5005 by releasable fasteners 5007 passing through slots 5009 in the board 5003, the slots 5009 being oriented generally parallel to axis 5011. For translation in an axis 5013 perpendicular to the stream 21, a second adjustment board 5015 is fastened to the first board 5003 by releasable fasteners 5017 passing through slots 5019 in the second adjustment board 5015, the slots 5019 being oriented generally parallel to axis 5013. The charging element 631 and deflector plates 629 are secured to the second adjustment board 5015. Thus, by releasing the fasteners 5007 and/or 5017, one can adjust the position of the charging element 631 and deflector plates relative to the nozzle system 101 in a plane parallel to the fluid stream 21 and then tighten the fasteners 5007 and/or 5017 to secure the mounting assembly 5001.

For translation along a third axis perpendicular to the first two axes 5011, 5013, the backing 5005 is fastened to a fixed support 5021 by adjustable fasteners 5023 (e.g., threaded bolts screwed into tapped holes in the fixed support 5021). In one embodiment, each adjustable fastener 5023 passes through a spring 5025 positioned between the backing 5005 and the fixed support 5021. The amount of compression of any spring 5025 can be adjusted by tightening or loosening the respective fastener 5023. Adjusting the compression of all springs 5025 in the same amount results in translation along the third axis. The mounting assembly 5001 can be tilted in virtually any direction by changing the relative compression of one or more of the springs 5025 with respect to one or more other springs 5025.

In this exemplary embodiment, the relative positions of the charging element 631 and deflector plates 629 remain fixed with respect to one another because they are all fastened to the same adjustment board 5015. This prevents adjustment of the mounting assembly 5001 from affecting alignment of the changing element 631 with respect to the deflector plates 629.

The charging element 631 is connected to a suitable electrical circuit (e.g., a 90 volt selectively charging circuit) under the control of the processor 131 and coupled to a power supply for applying an electrical charge to the charging element 631. The circuit is used to charge or not charge the stream 21 immediately prior to the formation of a droplet 33 at the break-off location 107 depending on whether the droplet 33 contains a particle having the desired characteristics (e.g., at least one live X-chromosome sperm cell). The charging element 631 is positioned electrostatically near the stream 21 or near the droplets 33 formed from the stream 21 for providing an electrical reference with respect to the electrostatic polarity of the stream 21. The droplets 33 carry the same charge as the stream 21 at the instant the droplet 33 breaks from the stream 21. The charged or uncharged droplets 33 then pass between the deflector plates 629 and are sorted by charge into collection vessels 2207 of the collection system 2201. While sorting produces two groups or populations of droplets 123, 125 in FIG. 2, the particles may be separated into any number of populations from 1 to N sorted by placing different charges on the droplets 33 in respective groups, any by supplying the appropriate number of collection vessels, each being positioned to collect a different population of droplets.

Automated Drop Delay Calibration

In the sorting system 119 described above, the processor 131 must estimate the time it takes for a particle to move from the interrogation location 115 to the droplet break-off location 107 so that the charge (or lack of charge) to be applied to the droplet 33 containing that particle is applied when the particle is in the last attached droplet 33 at the break-off location 107. If the delay setting used by the processor 131 is wrong, the droplets 33 will not be sorted according to their contents. Similarly, if the application of electrical charges to the droplets 33 is even slightly out of phase with droplet 33 formation this can degrade sorting because none of the droplets 33 will be fully charged and droplets 33 that are supposed to have neutral charge will carry a small positive or negative electrical charge. This will alter the paths of the droplets 33 through the electric field between the deflection plates 629.

The best way to verify that the processor 131 is using the appropriate delay setting or to adjust the drop delay setting (i.e., calibrate the system's 9 drop delay setting), is to sort a number of droplets 33 and examine the results. By incrementally varying the delay setting and monitoring the results, one can select the optimal delay setting. Traditionally, this sort calibration is performed manually. Recently, automated calibration systems have been designed to sample or examine the contents of the droplets in the sorted droplet streams and automatically adjust the delay setting without human intervention. For example U.S. Pat. Nos. 6,372,506 (Norton) and 5,643,796 (van den Engh), which are hereby incorporated by reference, both disclose automated sort calibration systems. The purported advantages of these systems are that they are less labor intensive and are capable of verifying the delay setting throughout the sorting process rather than just during initial set up. The drawbacks are that they are cumbersome and take up valuable space unnecessarily.

(i) Epi-Illumination Sensors

Figure 37:
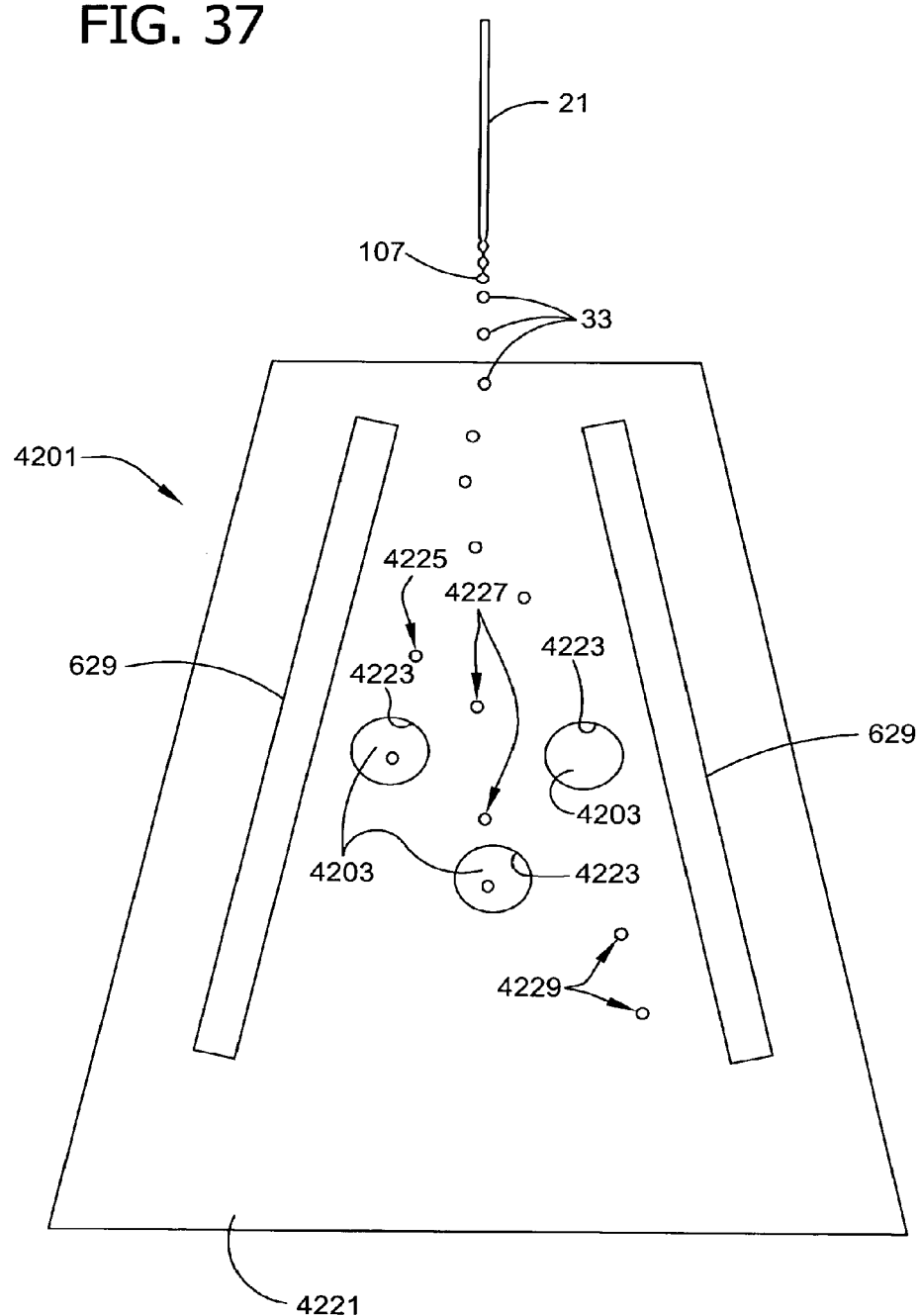
FIG. 37 is a schematic diagram of one embodiment of a sort calibration system of the present invention.
Figure 38:
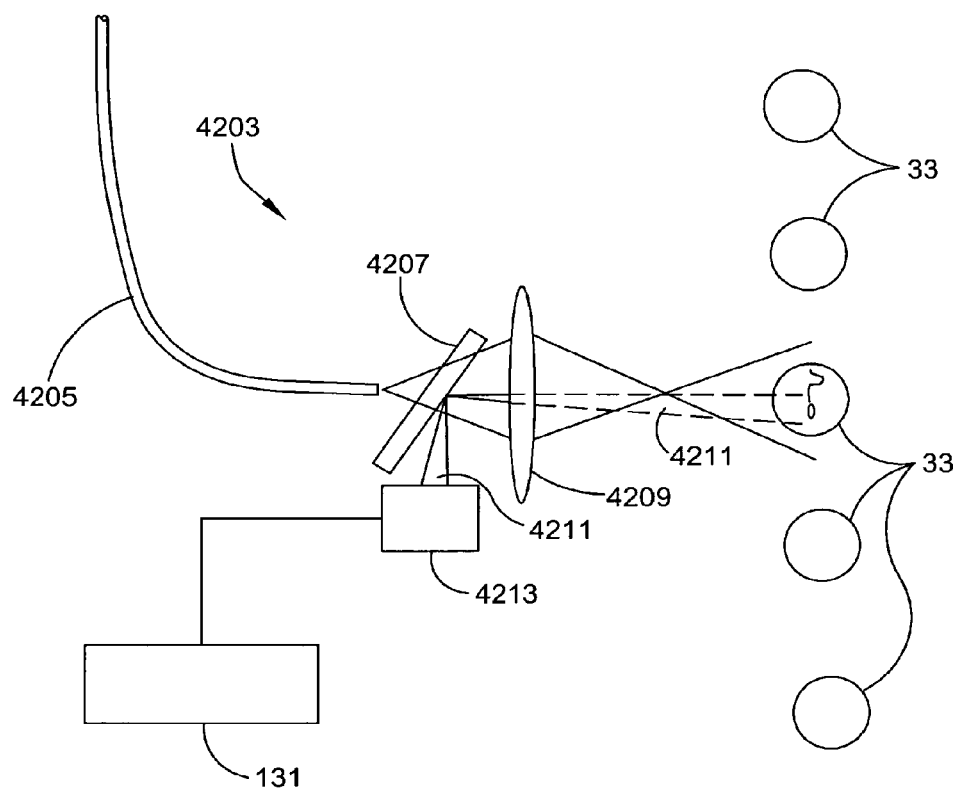
FIG. 38 is a schematic diagram of one embodiment of an epi-illumination sensor for use with the sort calibration shown in FIG. 37.

Referring to FIG. 37, an automated continuous calibration system 4201 of the present invention for a fluorescence activated droplet sorting cytometry system comprises one or more epi-illumination sensors 4203 positioned to sense the contents of droplets 33 to verify the delay setting for droplet charging. Referring to FIG. 38, each epi-illumination sensor includes a light source (not shown), a fiber optic cable 4205, a dichroic filter 4207, a lens system 4209, a photodetector 4213, and a control system. In one exemplary embodiment, the processor 131 serves as the control system, but other processors or controls could be used instead.

The light source may be a low-power solid state laser dedicated solely to the automated calibration system 4201. Alternatively, a beamsplitter (not shown) may be used to divert a portion (e.g., about 5%) of the energy in the beam 25 used for interrogation of particles in the fluid stream 21 to one or more epi-illumination sensors 4203. Similarly, the fiber optic cable 4209 can be positioned in a beam stop 4215 (FIG. 26) to gather light from beam 25 after it passes through the interrogation location 115. The light from the light source must include light having a wavelength capable of exciting fluorescent molecules in the particles being sorted, thereby causing fluorescence emissions 4211 from the particles. If the particles are stained with Hoechst 33342, for instance, the light source can provide light having a wavelength of about 350 nm, about 407 nm or any other wavelength capable of exciting the Hoechst 33342 molecules.

The fiber optic cable 4205 extends from the light source to a location downstream of the interrogation location 115. For example, in the exemplary embodiment the fiber optic cable 4205 leads to a location adjacent the trajectory of one of the droplet streams as it moves through the electric field between the deflector plates 629. The dichroic filter 4207 is positioned in front of the end of the fiber optic cable 4205. The dichroic filter 4207 transmits light having the spectral characteristics of the light conducted by fiber optic cable 4205, but reflects light having the spectral characteristics of the fluorescence emissions 4211. Thus, the dichroic filter 4207 may have the same specifications as the dichroic filter 477 describe above in connection with the epi-illumination optics instrument 417. The focal length of the lens system 4209 is selected based on the expected distance of the sensor 4203 from the droplets 33 so that the illumination/detection volume of each sensor 4203 is about equal to the volume of the droplets 33.

Referring to the exemplary embodiment shown in FIG. 37, an epi-illumination sensor 4203 is positioned adjacent the trajectory of each of the three sorted droplet streams 4225, 4227, 4229 to sense the contents of droplets 33 in a respective stream. The cytometer system 9 includes an electrically insulated support 4221 for mounting the two deflection plates 629. The support has three holes 4223, one adjacent the trajectory of each sorted droplet stream 4225, 4227, 4229. An epi-illumination sensor 4203 is positioned at each hole 4223 to observe droplets 33 in one of the droplet streams 4225, 4227, 4229 through the respective hole 4223. This compact configuration takes up relatively little space and keeps components of the calibration system 4201 out of the way, providing better access to other parts of the cytometer 9.

If a droplet containing a fluorescent particle passes through the illumination/detection volume of the sensor 4203, this will result in a flash of fluorescence emissions 4211, some of which will be collected by the lens system 4209 and reflected off from the dichroic filter 4207 to the photodetector 4213. Signals from the photodetector 4213 are provided to the processor 131. Based on the signals received from the photodetectors 4213, the processor 131 can determine the contents of the droplets 33 in each of the sorted droplet streams 4225, 4227, 4229.

If a sensor 4203 fails to detect a flash of fluorescence emission 4211 when the processor 131 expects a droplet 33 containing a fluorescent particle to pass by that sensor 4203, the processor 131 can use that information to adjust the delay setting or adjust the location of the droplet break-off location 107. Likewise, the processor 131 can make an adjustment if a sensor 4203 detects a fluorescence emission 4211 when the processor 131 does not expect a droplet 33 containing a particle to be passing by the sensor 4203. Furthermore, the processor can compare the relative frequency of fluorescent emissions 4211 from the sorted streams 4225, 4227, 4229 to see if the frequency of detected fluorescent emissions 4211 matches the expected frequency. The processor 131 can also adjust the amplitude of the charge applied to the charging element 631 to increase or decrease the amount by which a sorted stream 4225, 4229 is deflected to maximize the intensity of the detected fluorescence emissions 4211. This will maintain the alignment of the trajectory of the deflected droplet streams 4225, 4229 so the droplets pass directly through the collection volume of the epi-illumination sensor. Because the sensors 4203 are positioned to observe the streams 4225, 4227, 4225 as they move through the electrical field between the deflector plates 629, the calibration system has a shorter response time than it would if it observed the streams 4225, 4227, 4229 in the freefall area downstream of the deflection plates.

(ii) Empty Droplet Test Stream

One sensitive indication of the quality of the calibration can be arranged by creating and monitoring a calibration test stream that contains substantially only empty droplets 33. Referring to the sort calibration system 4201 shown FIG. 37, droplets 33 containing desired particles are sorted into stream 4225 and droplets 33 containing any other particles and most of the empty droplets 33 are sorted into stream 4229 (i.e., the waste stream). The test stream 4227 is created by applying a neutral charge to at least a fraction (e.g., 1 out of every 10) of the empty droplets 33. Many droplets 33 that are considered "empty" for traditional sorting purposes are actually droplets 33 for which there is a low probability that the droplet 33 contains a particle, based on the arrival time of particles at the interrogation location 115 and estimated droplet formation boundaries in the fluid stream 21. These "empty" droplets should not be sorted into the test stream 4227 because this would inevitably result in detection of some particles in the test stream 4227.

Instead, for the test stream 4227 the processor 131 should select only droplets 33 that the processor 131 believes have substantially zero probability of containing a particle in order to create a substantially particle-free test stream 4227. The probability that any randomly selected droplet 33 contains a cell is known and is approximately the average cell analysis rate divided by the droplet generation rate. This means that by monitoring the rate of mis-sorts in the test stream 4227 it is possible to estimate fractional adjustment of the phase relationship of droplet charging needed to match the phase of droplet 33 formation. For example the processor 131 may select droplets that it estimates have about 15% or lower probability of containing a particle, about 10% or lower probability of containing a particle, about 5% or lower probability of containing a particle, about 1% or lower probability of containing a particle, about 0.1% or lower probability of containing a particle, about 0.01% or lower probability of containing a particle, about 0.001% or lower probability of containing a particle, or about 0.0001% or lower probability of containing a particle. The probabilistic cutoff for substantially zero probability may be selected based on sort-speed, tolerance for impurity, or other sort parameters, with the cutoff including higher probabilities that a droplet will include a particle for high-speed sorting or when there is more tolerance for impurity.

Failure of the processor 131 to create a substantially particle-free test stream 4227 (i.e., a test stream 4227 in which the ratio of droplets 33 containing particles to the total number of droplets 33 agrees with the probabilistic cutoff used to select droplets 33 for the test stream 4227), as indicated by detection of more than a threshold number of droplets 33 containing particles in the test stream 4227, is a definitive indication of sub-optimal sorting and prompts the processor 131 to adjust the drop delay setting. The threshold level is determined in relation to the probabilistic cutoff used to select droplets 33 for the test stream 4227 and the total number of droplets 33 selected for the test stream 4227. Ideally, some droplets 33 can be selected for the test stream 4227 even though one or more particles in the fluid stream 21 are relatively close to an estimated drop formation boundary for the respective droplet 33 to make the system 4201 more sensitive to slightly sub-optimal drop delay settings.

Of course, the sort calibration system could apply a non-neutral charge to and deflect droplets selected for the test stream, without departing from the scope of this invention. The relative order of the streams 4225, 4227, 4229 could also be rearranged without departing from the scope of this invention, although interposing the test stream 4227 between the waste stream 4225 and the stream of desired particles 4229 (as shown in the exemplary embodiment) reduces the risk of crossover contamination of the sorted sample by the waste stream. Further, if the particles do not emit fluorescent light, different sensors can be used to detect any scattered light caused by particles in the test stream without departing from the scope of this invention.

(iii) Impact of Sort Calibration System

In one embodiment of the invention, the automated calibration system 4201 is operable to automatically determine and set the phase relationship between droplet formation and droplet charging to within about 5% of the optimal phase (i.e., within +/− about 18 degrees. In another embodiment the system 4201 is operable to automatically determine and set the phase relationship to within about 1% of the optimal phase (i.e., within +/− about 3.6 degrees)). In another embodiment, the calibration system 4201 is operable to continuously monitor a high-speed droplet sorting system and automatically maintain the phase relationship within about 10% of the optimal phase (i.e., within +/− about 36 degrees). In still another embodiment, the system 4201 is operable to continuously monitor a high-speed droplet sorting system and automatically maintain the phase relationship without about 3% of the optimal phase (i.e., within +/−10.8 degrees).

Sort System Fault Correction

From time to time, a droplet 33 will stray from its normal trajectory and hit the charging element 631 or the deflector plates 629. If one or more droplets 33 hit the charging element 631, the charging element 631 may not be able to charge droplets 33 properly. Further, the normal droplet 33 trajectory through the charging element 631 can become obstructed causing even more droplets 33 to accumulate on the charging element 631. Also, if stray droplets 33 strike a deflector plate 629, they can distort or otherwise disrupt electrical field lines between the deflector plates 629, thereby changing the trajectory of the sorted droplet steams 123, 125.

Thus, it is desirable to have a debris removal system to remove debris from the charging element 631 and/or the deflector plates 629. In one exemplary embodiment, shown FIGS. 26 and 27, the system 9 includes a debris removal system 5047 for the charging element 631 and a debris removal system 5049 for the deflector plates 629.

Referring to FIG. 27, the charging element 031 is held in position by a support 5051 secured to board 5015 of the adjustable mounting assembly 5001. A vacuum passage 5053 (shown in phantom) extends through the support 5051 to an opening 5057 adjacent the charging element 631. The vacuum passage 5053 is connected to a suitable vacuum source (not shown) by a vacuum line 5055 attached to a fitting 5058 on the support 5051. Suitable controls are provided for selectively applying a vacuum in the passage 5053 to vacuum any undesired material (e.g., stray droplets 33) off the charging element 631 and restore proper function of the charging element 631.

Relatedly, as shown in FIG. 27, a manifold 5061 fastened to the mounting assembly 5001 has a network of air passages 5063 therein (shown in phantom) connected via an air line 5059 and fitting 5065 to a source of compressed air or other gas (not shown). The passages 5063 have openings 5064 positioned along a side 5066 of each deflector plate 629 and the portions 5067 of the passages 5063 leading to the openings 5065 are oriented so compressed air blown through the manifold 5061 will clear any stray droplets 33 or other debris off the deflector plates 629. Any material blown off the deflector plates 629 will hit a cover panel (not shown) and drain into a suitable waste collection device (not shown).

In one embodiment, if the processor or other sensor determines that stray droplets 33 have hit the charging element 631 or deflector plates 629, as indicated by the sort calibration system described above for example, the processor can automatically initiate a fault correction procedure or mode, which can include applying a vacuum to passage 5053 to vacuum material from the charging element 631 and/or sending compressed gas through passages 5067 to blow material off the deflector plates 629.

Protection of Sorted Sample During Fault Mode

One embodiment of the system 9 also includes a contamination prevention mechanism 4041 (FIG. 26), which can be activated by the processor 131 to limit or prevent contamination of the sorted sample any time the sorting system is in the fault correction mode. The contamination prevention mechanism includes a pneumatic actuator 4043 operable to selectively move a swing arm 4045 between a shielding position (shown FIG. 26) and a non-shielding position (not shown). In the shielding position, the end 4047 of the swing arm 4045 covers the opening of the collection vessel 4033, thereby preventing collection of droplets 33 by the collection vessel 4033. In the non-shielding position, the collection vessel 4033 is uncovered. Normally, the swing arm 4045 is in the non-shielding position, but the processor 131 causes the actuator 4043 to move the swing arm 4045 into the shielding position any time the processor 131 determines that there is a risk of contamination (e.g., the nozzle system 101 becomes clogged, the droplet break-off location 107 becomes unstable, or stray droplets 33 have hit the charging element 631 or deflector plates 629). The end 4047 of the swing arm 4045 is trough-shaped to drain any fluid collected by the swing arm 4045 into the waste container 4035.

Fluid Delivery System

The system 1 described above is capable of effectively producing quantities of particles (e.g., X-sperm cells) sorted by selected characteristics. The rate of production can be increased or decreased by varying the rates at which the fluid delivery system 15 (FIG. 2) delivers carrier fluid 17 and sheath fluid 19 to the nozzle 137. In one embodiment, the fluid delivery system includes a syringe pump 645, one example of such a pump being MICROLAB® Model PSD/3 available from Hamilton Company. The pump 645 is operable to deliver carrier fluid 17 to the nozzle 137 at a rate of about 20 µl/min. In general, the pump 645 should be operable to deliver sample fluid 17 to the nozzle 137 at a rate in the range of 10-50 µl/min. The pump 645 is connected by a flow line 647 to the supply 3 of carrier fluid 17, which may be a suitable vessel 649 containing a volume of material to be analyzed and sorted. Where the temperature of the particles being analyzed is a factor, as in the case of sperm cells, for example, the temperature of the vessel 649 may be controlled by a suitable temperature control system, such as heating/cooling bath (not shown). The syringe pump 645 is movable through an intake stroke to aspirate carrier fluid from the supply vessel and through a discharge stroke to dispense carrier fluid 17 through a supply line 651 to the injection needle 157 of the nozzle system 101. The pump 645 is preferably driven by a variable speed motor (not shown) under the control of the processor 131. By way of example, the pump 645 may be driven by a stepper motor which operates at selectively variable rates to pump carrier fluid 17 to the needle 159 at rates necessary to obtain the desired throughput. Other types of fluid delivery devices can be used instead of a syringe pump. To provide just one example, the vessel 649 can be pressurized by a pressurized gas source without departing from the scope of the invention. Furthermore, it is desirable to keep the lines 647, 651 as short as is practically possible because the line environment is not conducive to the health of sensitive cells (e.g., sperm cells) that may be in the carrier fluid 17.

The supply 7 of sheath fluid 19 comprises a second vessel 661, e.g., a tank in FIG. 2, holding an appropriate volume of sheath fluid 19 connected to the radial bore 173 in the flow body 133 of the nozzle system 101 by a supply line 667 having a control valve 669 therein. In the embodiment of FIG. 1, the sheath fluid vessel 661 is pressurized by a gas pressure system 671 comprising a source 675 of pressurized gas (e.g., air or other gas, such as nitrogen) communicating with the tank 661 via an air line 679 having a regulator 681 in it for controlling the pressure supplied to the tank 661. A two-way valve 683 in the air line 679 is movable between a first position establishing communication between the tank 661 and the gas source 675 and a second position venting the tank 661. The gas pressure regulator 681 is a conventional regulator preferably under the control of the processor 131. By controlling the tank 661 pressure, the pressure at which sheath fluid 19 is delivered to the flow body 133 may also be controlled. This pressure may range from 16 to 100 psi, more preferably from 10 to 50 psi, even more preferably 15 to 40 psi, and even more preferably from about 20 to 30 psi. The pressure at which the sheath fluid 19 is supplied to the flow body 133 can be controlled in other ways without departing from the scope of the invention.

In one embodiment, shown FIG. 26 the fluid delivery system 15, includes a sheath fluid tank (not shown) and a sample station 4051. The sample station includes a two-part pressure container 4053 adapted to hold a sample tube 4055. The bottom section 4057 of the pressure container is moveable up and down relative to the upper section 4059 of the pressure container 4053 between an open position (shown FIG. 26), in which the sample tube 4055 may be loaded or unloaded, and a closed position (not shown) in which the two parts 4057, 4059 of the pressure container 4053 come together to form a seal to contain pressurized gas used to pump carrier fluid 17 from the sample tube 4055 to the nozzle system 101.

Figure 119:
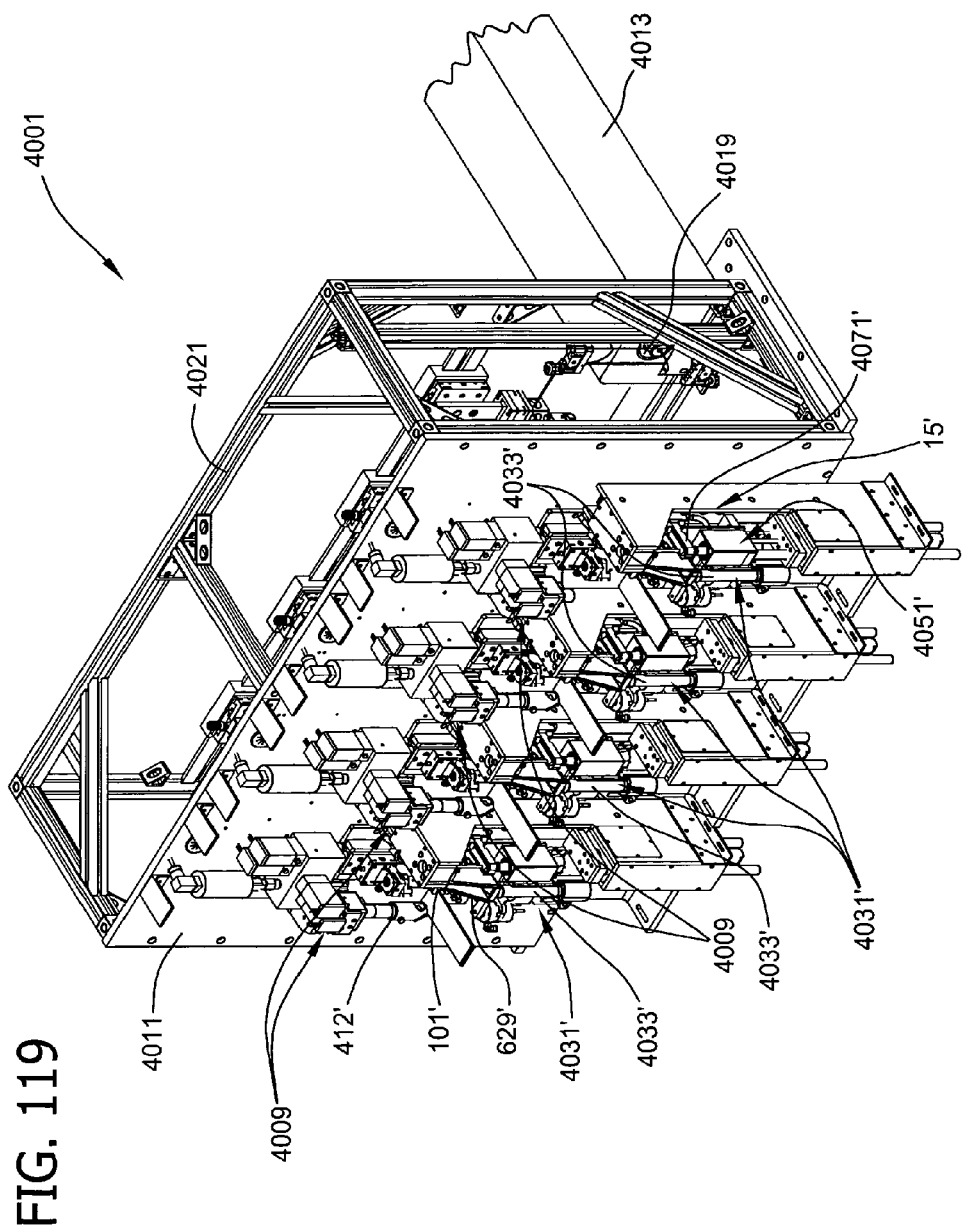
FIGS. 119 and 120 are perspective views of another multi-channel system of the present invention.

When the pressure container is open a spring-biased swing arm 4071 moves to a position beneath the line 651 that delivers carrier fluid 17 to the nozzle system 101 (See also FIG. 119 #4071'). The swing arm 4071 is trough-shaped and adapted to collect fluid backflushed through the line 651 and to drain the backflushed fluid to the waste container through port 4073. As the pressure container 4053 moves from its open position to its closed position, a cam plate 4075 attached to the bottom section 4057 of the pressure container 4053 moves the swing arm 4071 against its spring bias to clear the area between the two sections 4057, 4059 and allow the pressure container 4053 to close.

Control

Figure 39:
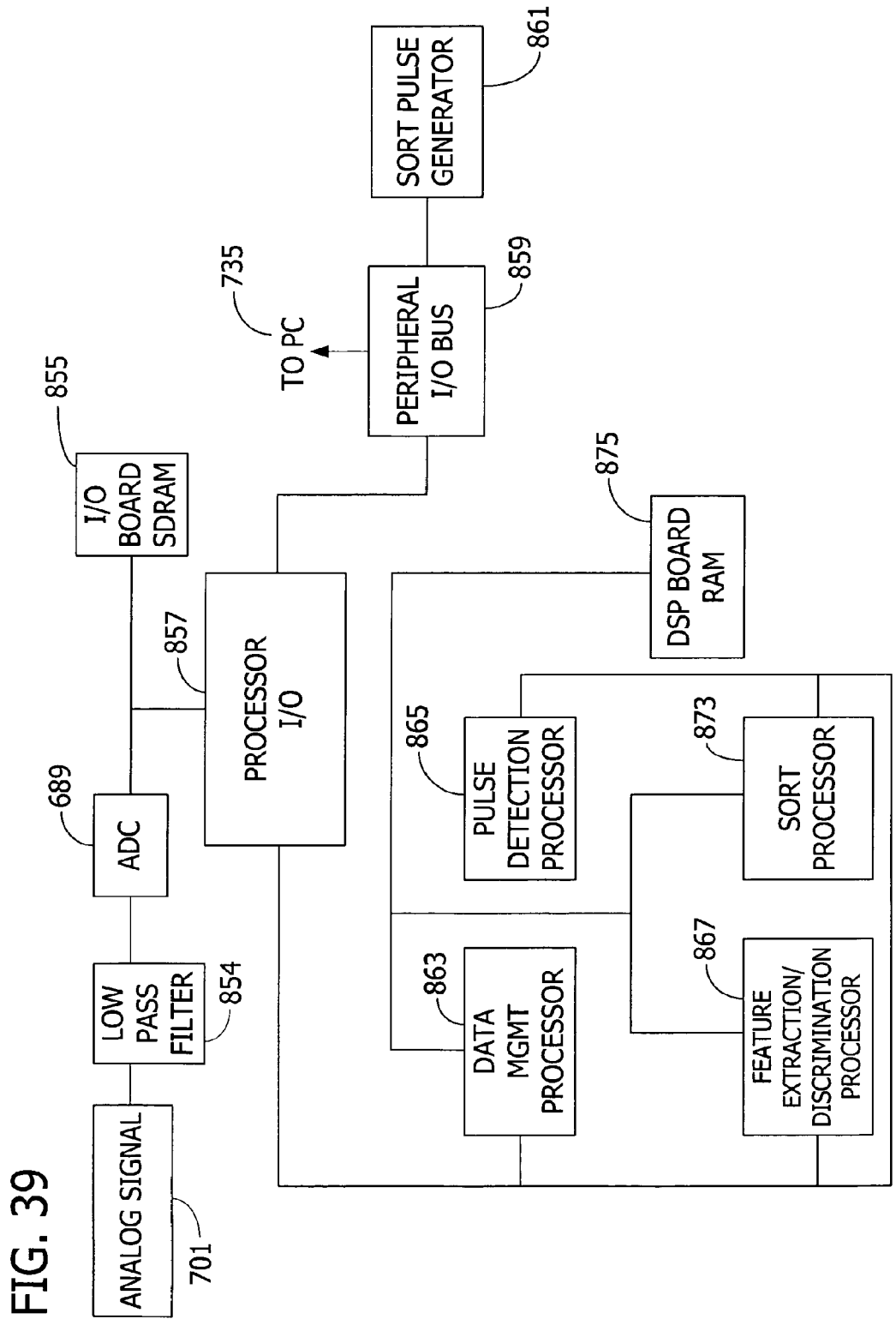
FIG. 39 is a block diagram of one embodiment of a digital cell analyzer (DCA) and processor controller according to the invention.

Referring again to FIG. 2, the microprocessor 131 (or other digital or analog control and/or processor, or combinations thereof) controls the operation of the system 1. As noted below with regard to FIG. 39, the microprocessor may be implemented as a system control processor and four processors for handling signal processing. Alternatively, some or all functions may be integrated into one or more processors. For example, the system control microprocessor (see FIG. 36) may be implemented by using one of the four signal processing processors. In addition, as noted below, the signal processing may be implemented by an analog circuit (e.g., an analog cell analyzer as shown in FIG. 39) or a combination of analog and digital circuitry.

The microprocessor 131 provides output signals to control the fluid delivery system 15 (noted below) in response to input signals received from the epi-illumination system 415, provides output signals to control the transducers 105 in response to input signals received from the break-off sensors 389, and provides output signals to control the sorting system 119 (noted below) in response to input signals received from the epi-illumination system 415. The microprocessor 131 may provide output signals to other parts of the cytometry system 9 as noted elsewhere herein. Further, the microprocessor 131 may be adapted to process information and provide output signals in real time. Broadly speaking, the term "real time" refers to operations in which the operation of the processor 131 matches the human perception of time or those in which the rate of the operation of the processor 131 matches the rate of relevant physical or external processes. In one context, the term "real time" can indicate that the system reacts to events before the events become obsolete.

In general, electrical signals from the epi-illumination system 415 are converted to digital information by an A/D converter 689 which supplies the corresponding digital information to the microprocessor 131. In response to the information, the microprocessor 131 controls a sorting system 119 and a fluid delivery system 15, both described above.

The electrical signals output from the photodetector 117 of the epi-illumination system 415 are time-varying analog voltage signals indicative of the amplitude of the emitted fluorescence 31 at any instant in time generated by each cell as it is illuminated by the laser beam 25. Thus, the analog signals (also referred to as analog output) are in the shape of time-varying waveform pulses 497 as illustrated schematically in FIGS. 52 and 53. In general a waveform pulse 497 is defined as a waveform or a portion of a waveform containing one or more pulses or some portion of a pulse. Thus, the amplitude of each waveform pulse 497 at any instant in time represents the relative rate of photon emission 31 of each cell at that instant in time as the cell passes through the laser beam 25. X chromosome bovine sperm cells have a higher DNA content than Y chromosome bovine sperm cells (e.g., about 3.8%). As a result, live X cells labeled with a fluorescent stain as noted above will produce a different waveform pulse 497 than pulses from any other labeled cells. By analyzing the pulses 497 as noted below (see Signal Processing, Slit Scanning, and Critical Slope Difference), each cell can be identified as an X cell or not identified as an X cell (~X). In general, as used herein, X cells refers to live X cells, Y cells refers to live Y cells and ~X cells refers to the combination of live Y cells and cells which otherwise produce a detectable fluorescence emission 31 but which cannot be identified with a reasonable probability as being live X cells.

The timing of each waveform pulse 497 indicates the position of each cell in the stream 21. Since the rate at which the sheath fluid 19 is being delivered through the nozzle 137 remains constant, and since the distance d (in FIG. 25) between the nozzle 137 and the droplet break-off location 107 is known, the position of each droplet 33 is known and the cells, if any, within each droplet 33 are known. Thus, the microprocessor 131 can calculate the instant at which each forming droplet passes through the charging collar 631 and can control the polarity of the collar 631 and thus control whether a droplet 33 is charged for deflection by the charging elements 631 of the sorting system 119. Since the microprocessor 131 knows the droplet formation rate and identifies the cells within a droplet as X or ~X, the microprocessor 131 knows the cell content of each droplet 33 and keeps track of (or enumerates) the number of cells in each population 123, 125. Depending on the sort strategy, see below, the microprocessor 131 determines which droplets 33 are charged for deflection and which droplets 33 are not charged so that they are not deflected.

Signal Processing

A. Digital Sampling Introduction

Figure 43:
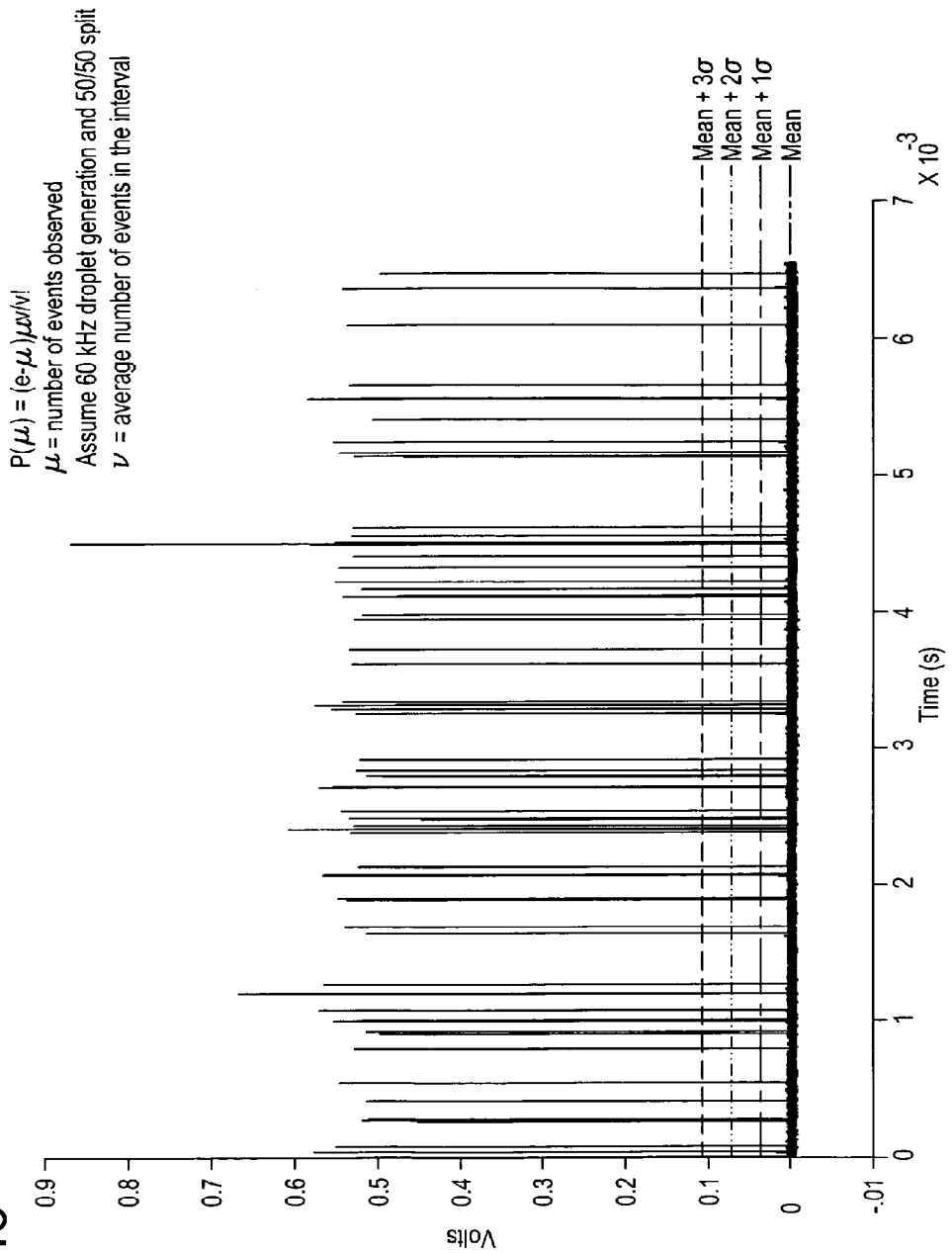
FIG. 43 is a graph illustrating a stream of waveform pulses from a photodetector output detecting fluorescent pulses from cells streaming at an average rate of 10,000 cells/second.
Figure 44:
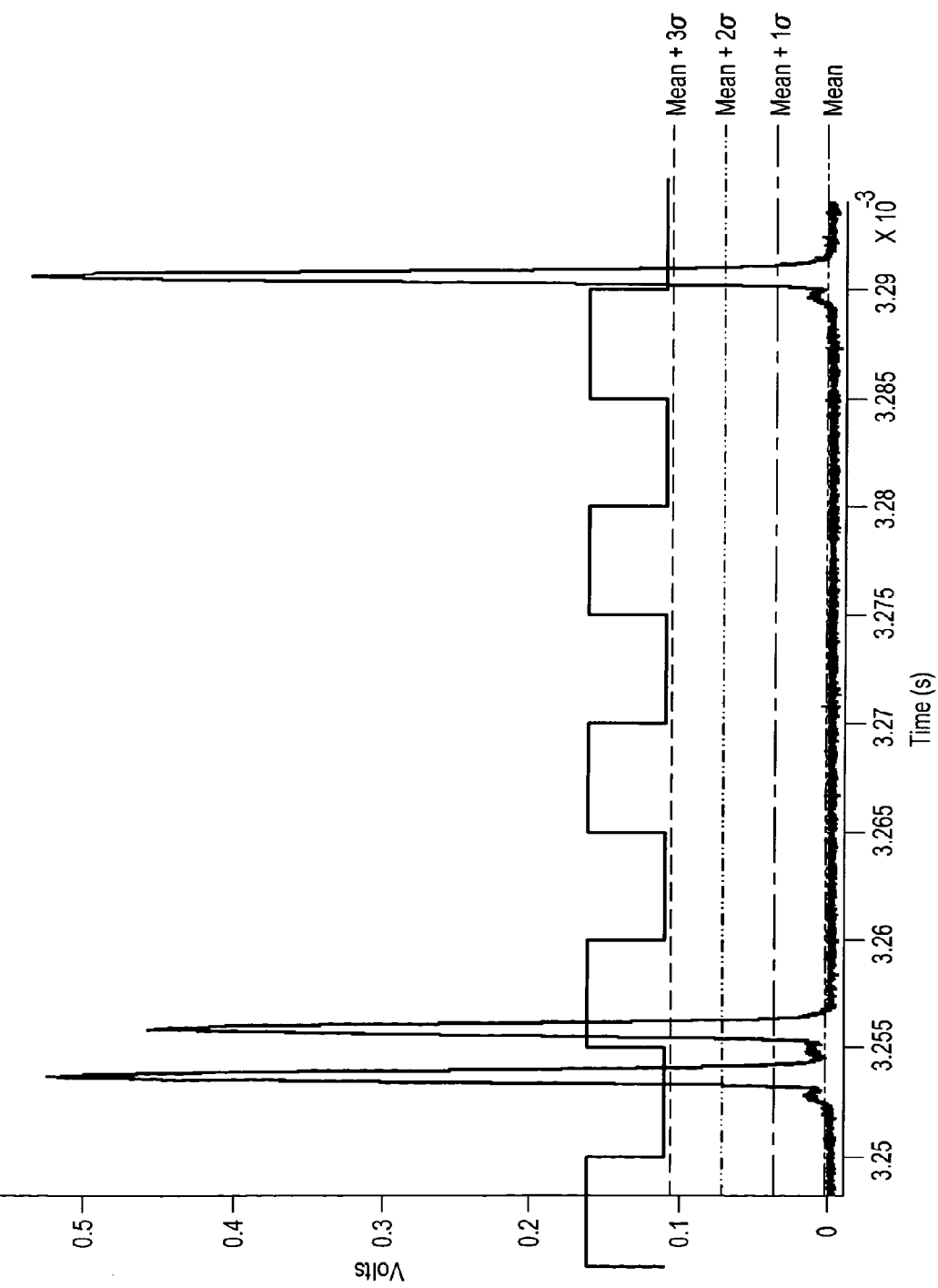
FIG. 44 is an exploded view of FIG. 43 illustrating the stream from a photodetector output detecting three fluorescent pulses from three cells streaming at an average rate of 10,000 cells/second; a square wave of a 100 MHz droplet clock has been superimposed on the illustration to show the synchronization between the three pulses and the square wave pulses of the droplet clock.
Figure 45:
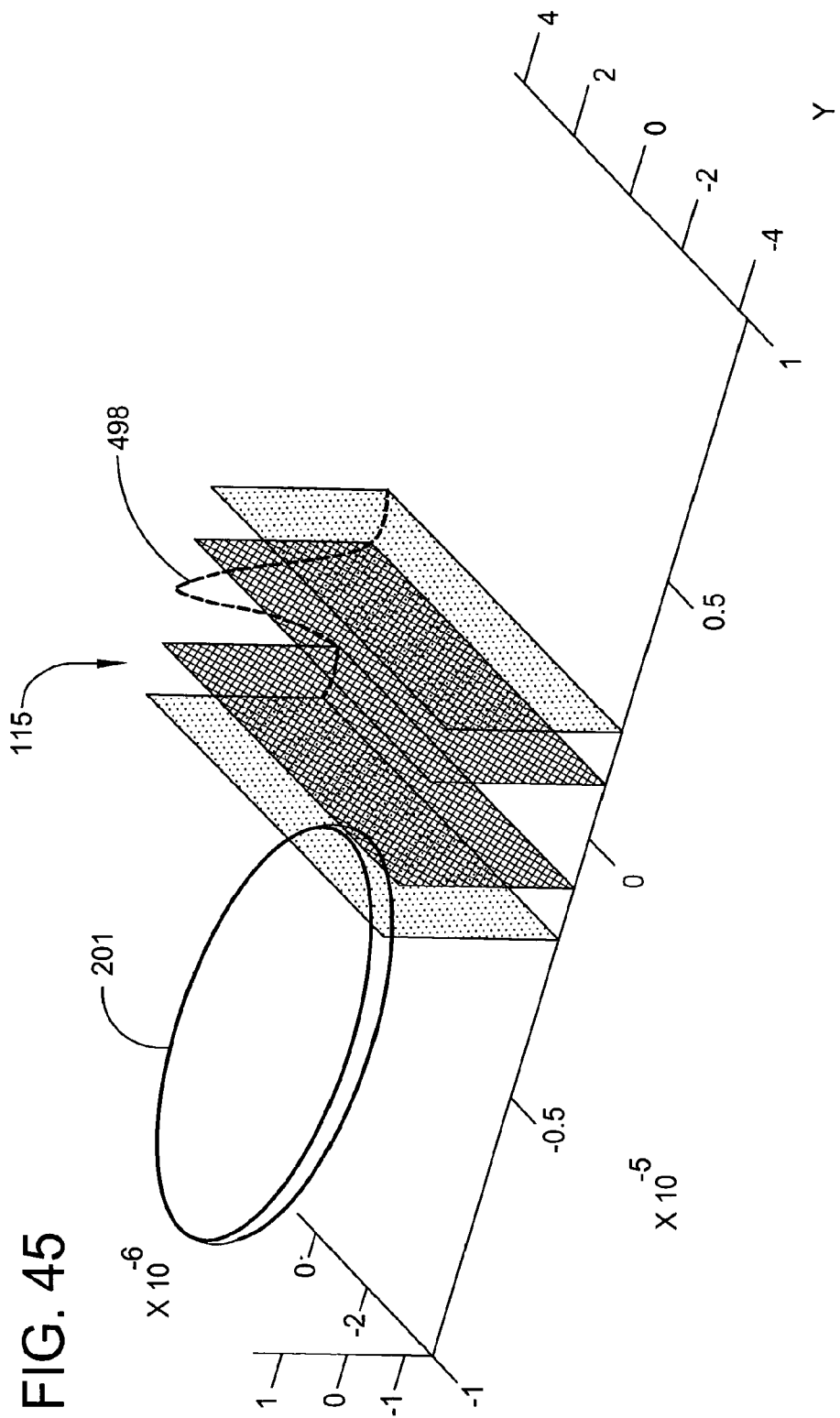
FIGS. 45-48 illustrate movement of a sperm cell relative to a laser beam spot having a narrow width.
Figure 46:
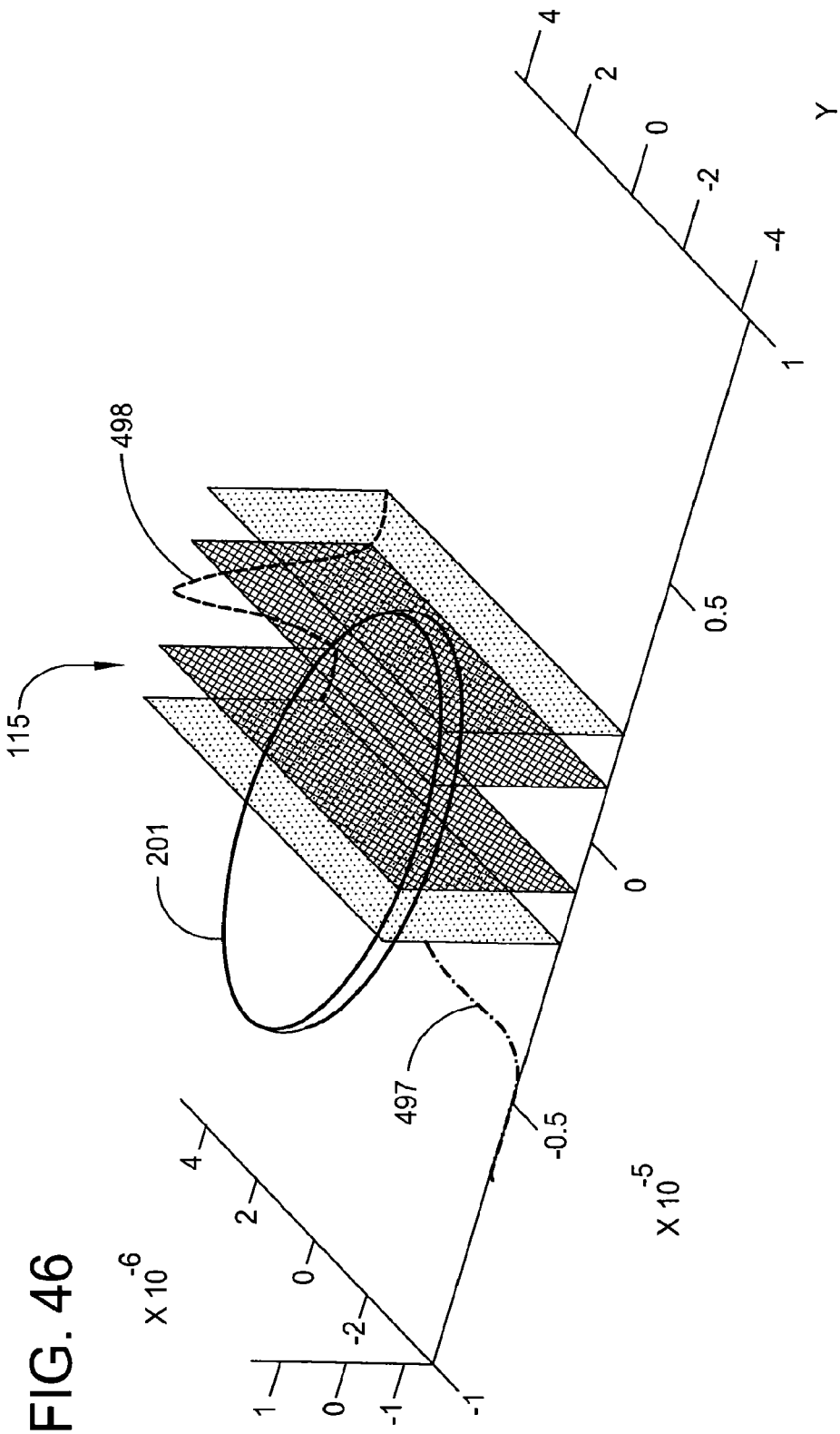
Figure 47:
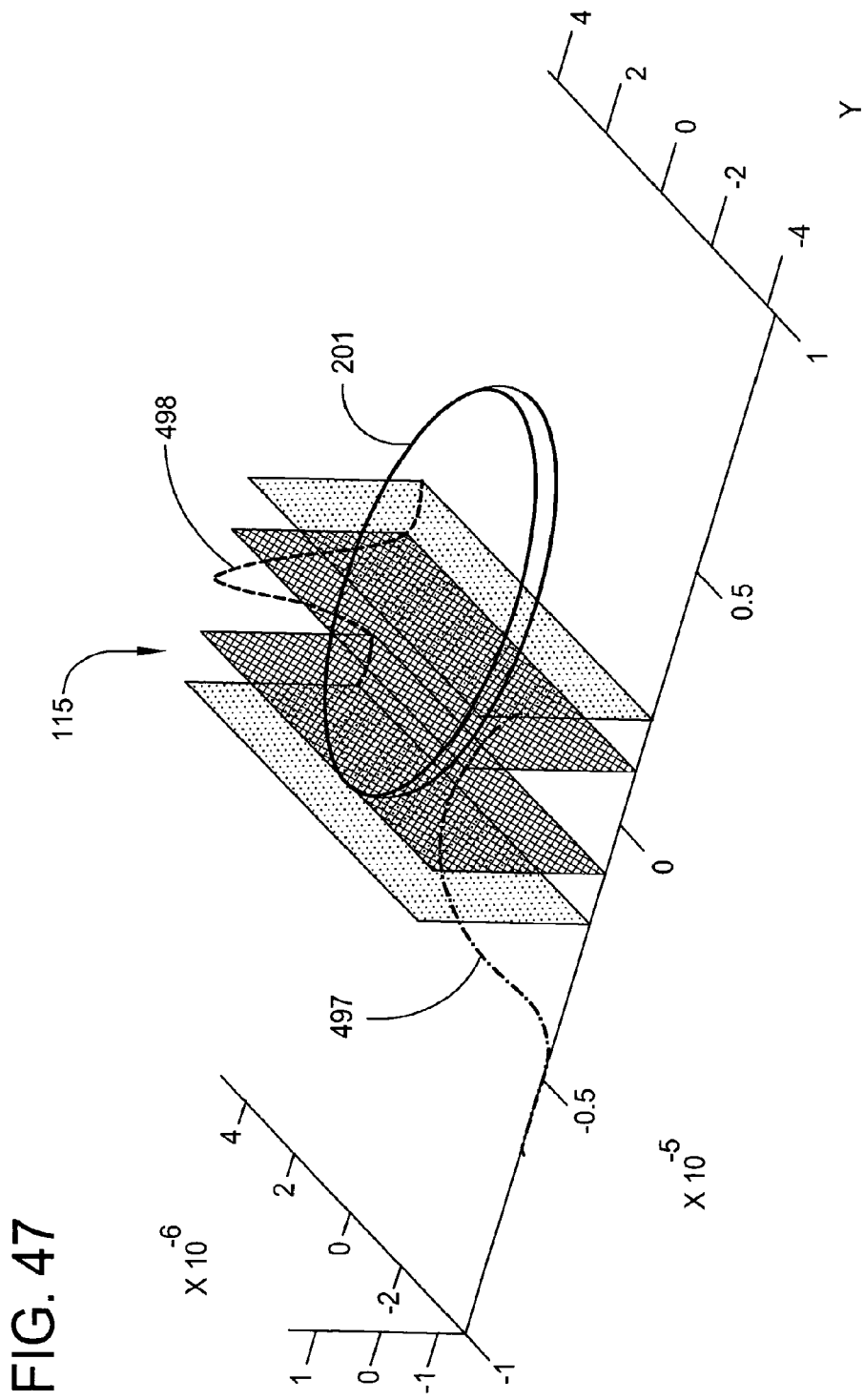
Figure 48:
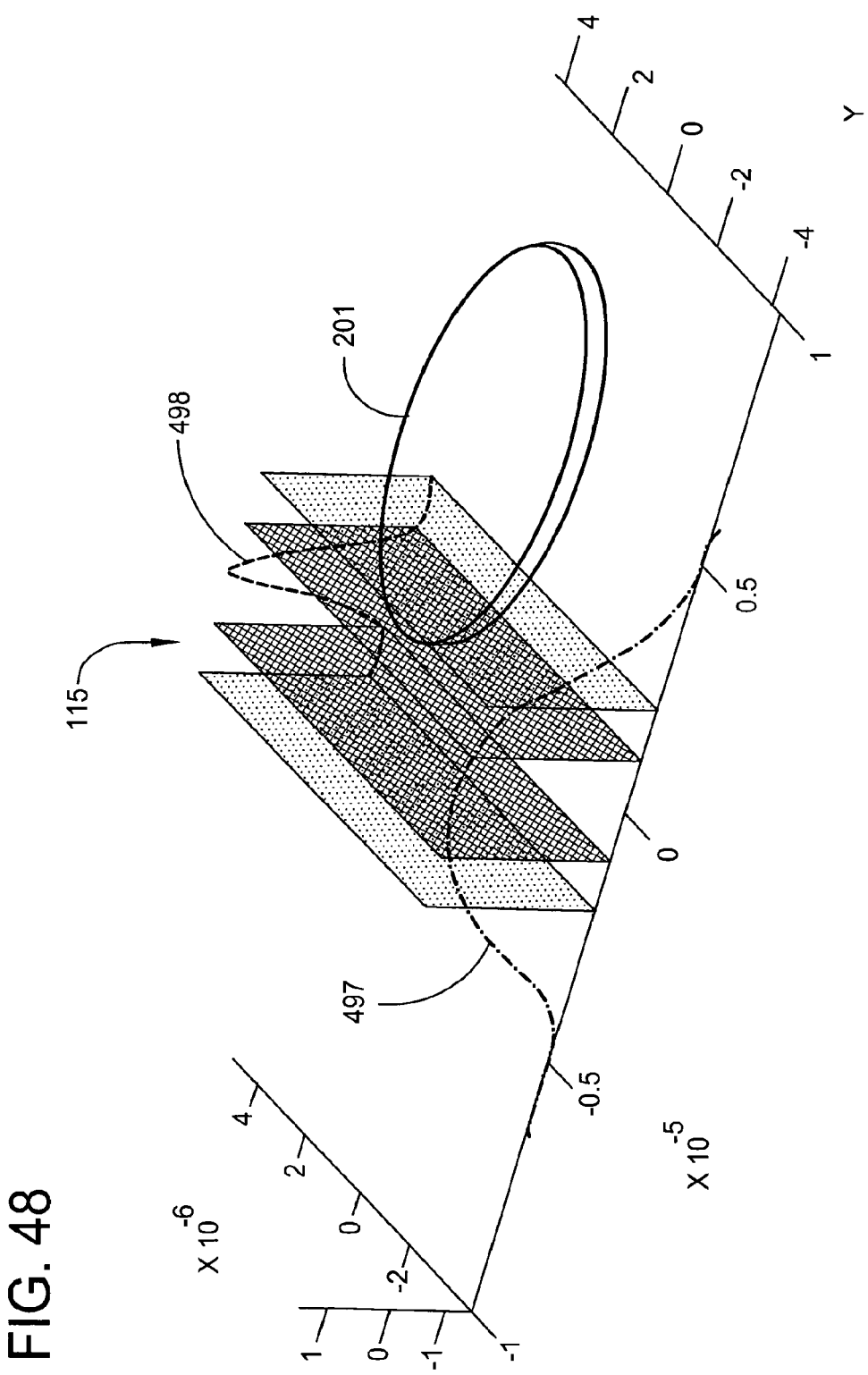

As previously described, the interaction between the laser beam 25 and the particle produce a "pulsed" photon emission 31 (e.g., a fluorescence emission) that is captured by the collection lens 511 of the optics system 109 and delivered to a photodetector 117. The photodetector 117 converts the photon energy at any instant in time to an analog voltage output of time-varying amplitude. This output is a series of waveform pulses 497 (FIGS. 43 and 44) which contain many features that can be used to discriminate among populations of particles. Among these features are the total photon emission, the rate of photon emission as a function of the particle's spatial transit through the laser beam, the maximum rate of photon emission during the transit, the average rate of photon emission during the transit, and the time required for transit. The combination of laser beam geometry 459, particle size, distribution of the emission source through the particle volume and particle velocity determine the frequency spectrum of waveform pulse 497. For the system 1 used with bovine semen described previously it has been determined that each cell 201 produces a waveform pulse 497 of between 800 ns and 1200 ns in duration. It has also been determined that as a function of frequency, more than 97% of the power in the waveform pulse 497 is delivered at frequencies below 30 MHz. This frequency spectrum will be discussed later as it related to the Nyquist sampling theorem. Taken together these waveform pulses 497 form an output signal 701 from the photodetector 117 that is a continuous, time varying, signal that represents the transit of the particle stream through the apparatus. In addition to features of individual pulses that are used to discriminate among populations, the time varying signal provides a precise record as to the relative spacing (time and position) among the individual particles that pass through the apparatus and relative velocity of the particles moving through the apparatus. This precise time, position and velocity record can be synchronized with the droplet generation clock signals 703 as shown in FIG. 44 to determine which particles are members of a particular droplet 33 formed by the droplet generation apparatus 105. This information can be used as the basis for determining "coincidence" or the occurrence of a desired and undesired particle in a single droplet 33. The ability to accurately determine the number and classification of each particle in a droplet 33 allows for accurate, efficient sorting.

Figure 72:
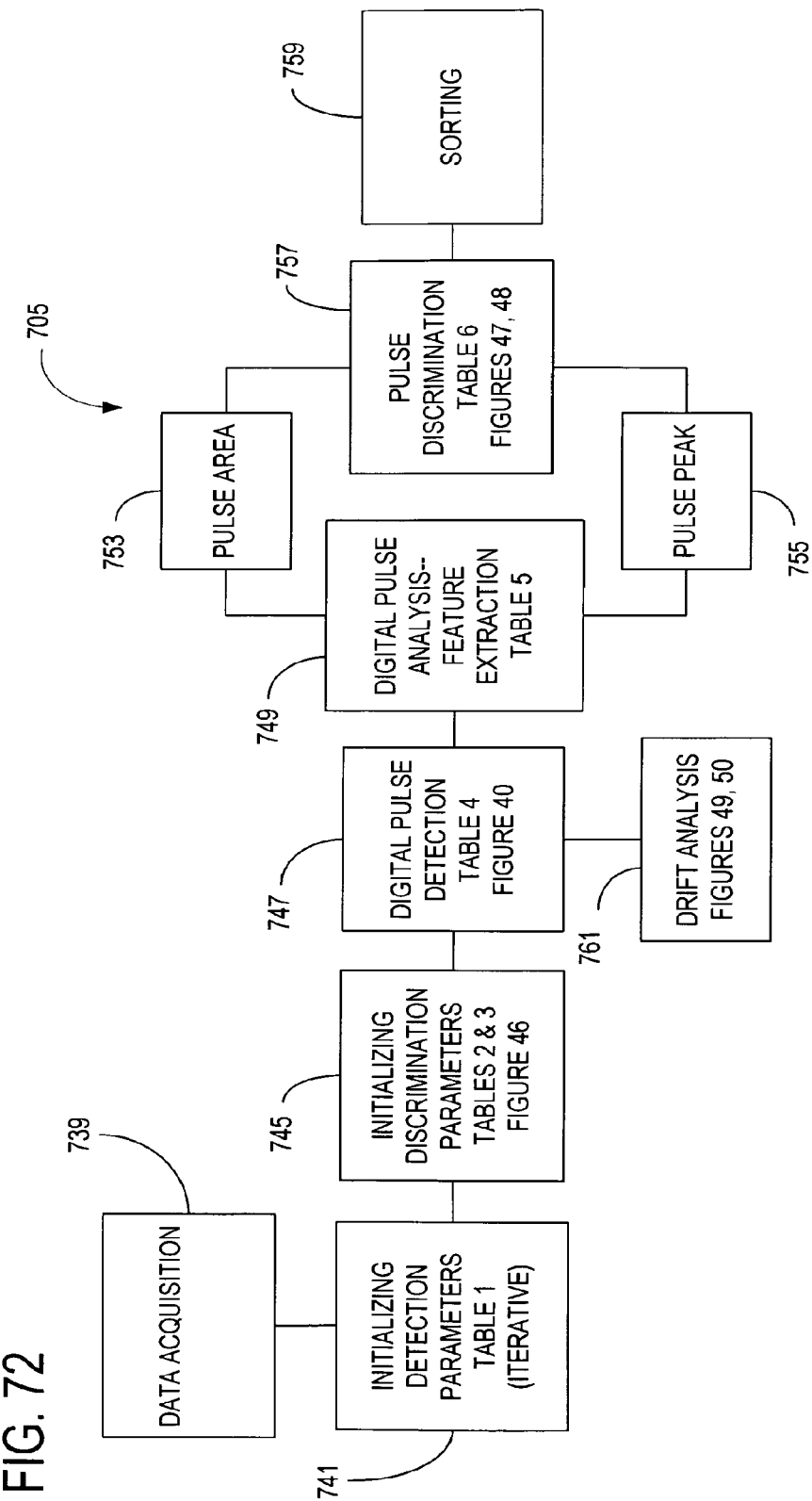
FIG. 72 is a work flow diagram of one embodiment of digital signal processing of the present invention.

Digital signal processing 705 as illustrated in FIG. 72 may be employed to analyze detection of fluorescence pulses 31 as indicated by synchronously sampled output signals 701 from the photodetector 117. This processing would be implemented in pulse analysis software employing instructions and/or algorithms, as noted herein. The time-varying analog output signal 701 of the photodetector 117 is provided to an A/D (analog/digital) converter 689 which synchronously samples it. Synchronously sampling means sampling to produce digital information corresponding to the analog output. Synchronously sampling is also referred to as continuously sampling or streaming acquisition. As noted below, the sampling rate depends on the frequency spectrum of the analog output.

Converter 689 provides an output including digital information 707 which is provided to the microprocessor 131 or other digital analysis device which executes the pulse analysis software to analyze the digital information 707. In general, the pulse analysis software would include digital pulse detection HH3, pulse feature extraction HH4 and pulse discrimination HH7.

B. Sampling Frequency & Signal Frequency Spectrum

The signal output 701 from the PMT 117 is captured by a high speed analog to digital converter 689 (ADC) that samples the output 701 continuously at a frequency of 105 MHz. It is well understood that when sampling a time varying signal it is necessary for the sampling frequency to be at least twice the maximum frequency contained in the signal being sampled. This is known as the Nyquist sampling theorem. For this reason the output signal 701 from the PMT 117 is first sent through a 40 MHz low-pass filter 854 (see FIG. 39) to ensure that the maximum frequency contained in the signal 701 is under the 52.5 MHz limit imposed by the sampling rate. It is important to note that the optical 109, fluidic 15 and detection systems of the apparatus 1 have been tuned to produce a pulse waveform 497 having optimum frequency characteristics for sampling at the 105 MHz rate. The sampling rate may be varied between about 25 and 200 MHz without departing from the scope of the present invention.

C. Pulse Processing

Pulse processing takes place in four (4) TigerSharc DSP processors that share memory and are connected to one another by high-speed parallel ports. As illustrated in FIG. 39, the four processors are: 1) a data management processor 863 which receives data from a high-speed ADC 689 which digitizes the output signals 701 from the photodetector 117; 2) a pulse detection processor 865 which detects the waveform pulses 497 represented by the digital information; 3) a feature extraction and discrimination processor 867 which extracts features from the detected pulses 497 and discriminates the pulses 497 based on the extracted features; and 4) a sort processor 873 which determines a sort classification for each pulse 497 based on the extracted features and the discrimination, which determines sort decisions for the corresponding cells and droplets 33 and which is synchronized with droplet formation 105. In general a processor 863, 865, 867, 873 completes a task and sets a "flag" so that companion processors know there is data available to process.

Each processor 863, 865, 867, 873 runs independently of the others, maximizing the overall throughput because they do not interrupt each other. Thus, any processor 863, 865, 867, 873 may be capable of performing any function and one or more processors or functions may be combined into a single processor or spread out over a plurality of processors. The processor 863, 865, 867, 873 labels as used above and this application are used for convenience only and are not intended to be limiting in any way.

All four processors 863, 865, 867, 873 are linked to a DSP board SDRAM 851 for exchanging information and are linked to a processor input/output (I/O) 857 for synchronization and communication with a peripheral I/O bus 859 connected to the PC 735 and the sort pulse generator 861. The processor I/O 857 may be implemented by two or more SharcFIN I/O processors connected by a communication link. Sort signals 853 are provided to the PC 735 via the peripheral I/O bus 857 and are used to control the sort pulse generator 861 controlling the charging of droplets 33.

The processor I/O 857 receives the output 707 from the analog/digital converter (ADC) 689, e.g., Bitware Corp. 105 MHz/2-channel, 14 bit capable of 105 MHz/1-channel sustained. The ADC 689 is connected to the photodetector 117 output for converting its time varying analog output signals 701 into digital information 707 and is also connected to an I/O board SDRAM 855 for storing the blocks of digital information from the ADC 689.

In general, the analog output signals 701 from the photodetector 117 are indicative of characteristic A or characteristic B (e.g., X or ~X). The A/D converter 689 converts the analog output signals 701 from the photodetector 117 of the flow cytometry system 1 into corresponding digital information 707. The processors 863, 865, 867, 873 analyze and classify the digital information 707 and provide a sorting signal to the sorting system 119 as a function of the detected and classified digital information.

D. Data Acquisition

As previously stated, the signal output 701 from the photodetector 117 is captured by a high speed analog to digital converter (ADC) 689 that samples the output continuously at a frequency of 105 MHz. Data (digital information 707) are transferred immediately into high-speed memory blocks (I/O Board SDRAM) 855 which serve to buffer the incoming data. These memory blocks 855 are organized in a manner to maintain the integrity and sequence of the data stream 707. These memory blocks 855 are also accessible by the digital signal processing (DSP) processors 863, 865, 867, 873 by direct memory access (DMA). In this manner the processors 863, 865, 867, 873 can access the incoming data 707 without interrupting the ADC 689. This facilitates efficient transfer of data 707 to these processors 863, 865, 867, 873 for feature extraction, analysis and sort classification. Throughout this process, the data management processor 863 keeps the pulse samples 707 in order and time indexed (relative to the master clock 737, which is 128 times the droplet 33 frequency) to preserve their reference to "real time" or the actual time that the cell passed through the laser beam 25. The ADC 689 ping-pongs back and forth between two inputs, continuously sampling the time varying analog output signals 701 including the waveform pulses 497 and converting them into digital information 707 which is provided in blocks 855 to the I/O Board SDRAM under the control of the data management processor 863. Processor 863 assembles the information 707 into a continuous stream.

E. Initializing Detection Parameters

In order effectively distinguish over background noise, the digital pulse detection software 747 should be provided with information indicating signal background second order statistics, i.e. knowledge of the behavior of the output voltage signal 701 from the photodetector 117 when there is no fluorescence pulse 497. These statistics can be learned by software for initializing detection parameters 741 in an unsupervised manner during the initialization period immediately following startup of the system 1. In general, a pulse may be defined as 2 or 3 standard deviations from the background level.

Due to the possibility that introduction of the carrier fluid 17 into the sheath fluid stream 191 may cause a change in background fluorescence emission, the carrier fluid 17 should be present for the initialization of the detection parameters. Simple computation of the second order statistics of a time sequence of output voltage signal values may overestimate the standard deviation of the background (due to the possible presence of fluorescence pulses 497 in the sequence). An iterative procedure is therefore preferred to gradually eliminate this effect. The pulse detection software 747 accomplishes this by computing the statistics of the total signal 701 (background+pulses), using these values to apply pulse detection logic, re-computing the signal statistics without samples detected to be within pulses, and repeating this procedure until the background statistic estimates converge (or a fixed maximum number of iterations occurs). By evaluating the background with cells present, a more accurate indication of the expected correct pulse 497 amplitude can be determined. Table II summarizes the detection initialization procedure for determining detection parameters for use by the pulse detection software.

TABLE II

Initialization of pulse detection algorithm parameters.

| | |
|---|---|
| Algorithm: | Initializing detection parameters |
| Input: | vector of floats PMTvolts; float statWindowSize, integer maxIterations |
| Output: | float bckgrndMean; float bckgrndSTD |
| Procedure: | |
| 1. | Initialize background vector bckgrnd to last statWindowSize samples of PMTvolts vector and numIterations, lastSampleMean, and lastSampleSTD to zero:<br>    bckgrnd = PMTvolts[ 1 to statWindowSize]<br>    lastSampleMean = 0<br>    lastSampleSTD = 0<br>    numIterations = 0 |
| 2. | Compute sample mean and sample standard deviation of bckgrnd and increment iteration counter: |

TABLE II-continued

Initialization of pulse detection algorithm parameters.

$$sampleMean = \frac{sum(bckgrnd)}{statWindowSize}$$

$$sampleSTD = \frac{sum(bckgrnd - sampleMean)^2)}{statWindowSize}$$

numIterations = numIterations + 1
3.    Check for convergence or exceeding maximum number of iterations:
        exitFlag = ( (sampleMean − lastSampleMean) < eps ∧
        (sampleStd − lastSampleStd < eps)) ∨
        (numIterations > maxIterations)
        If exitFlag is true, go to step 6 (else continue with step 4).
4.    Apply pulse detection algorithm, obtaining vectors of pulse samples and
        new estimate of background samples:
        [pulse, bckgrnd] = pulse_detect(bckgrnd , sampleMean, sampleSTD)
5.    Record statistics estimates from this iteration and repeat
        lastSampleMean = sampleMean
        lastSampleSTD = sampleSTD
        Go to step 2.
6.    Set background statistics estimates to sample statistics and exit:
        bckgrndMean = sampleMean
        bckgrndSTD = sampleSTD In general, the A/D converter 689 converts the analog output signals 701 from the photodetector 117 into corresponding digital information 707 indicative of characteristic A or characteristic B (e.g., X or ~X). The digital signal processor 865 determines background characteristics of the time-varying output signals 701 from the digital information 707 corresponding thereto, detects waveform pulses 497 from the digital information 707 as a function of the determined background characteristics, and provides a sorting signal 853 to the sorting system 119 as a function of the detected pulses 497.

F. Initial Discrimination Parameters

Similar to the detection parameters (and subsequent to their initialization as shown in Table II), parameters for use in a discrimination algorithm may be initialized in an unsupervised fashion. Unlike the detection algorithm parameters, however, an iterative procedure is not necessary. In this case, software for initializing the discrimination parameters 745 detects a preset number (e.g., 100,000) of fluorescence pulses 497, computes the features to be used for discrimination for each detected pulse 497, and uses a clustering procedure (see Table II for a summary of candidate clustering procedures) to assign these pulses 497 to populations of interest (e.g. X, ~X).

TABLE 2

Summary of clustering approaches being considered for use in discrimination algorithm parameter initialization.

| Algorithm Name | Algorithm Approach |
|---|---|
| k-Means | Iterative (local) minimization of sum of squared distance (Euclidean or Mahalanobis) between points within each population [1] |
| Fuzzy k-Means | Expectation-Maximization of (Gaussian) mixture model [2] |
| Agglomerative Hierarchical | Merging of "nearest" clusters (starting with each data point as its own cluster) until desired number of clusters is reached. Various measures for determination of "nearest" clusters include distance between closest points, distance between furthest points, distance between cluster means, and average distance between points. [1] |

Figure 73:
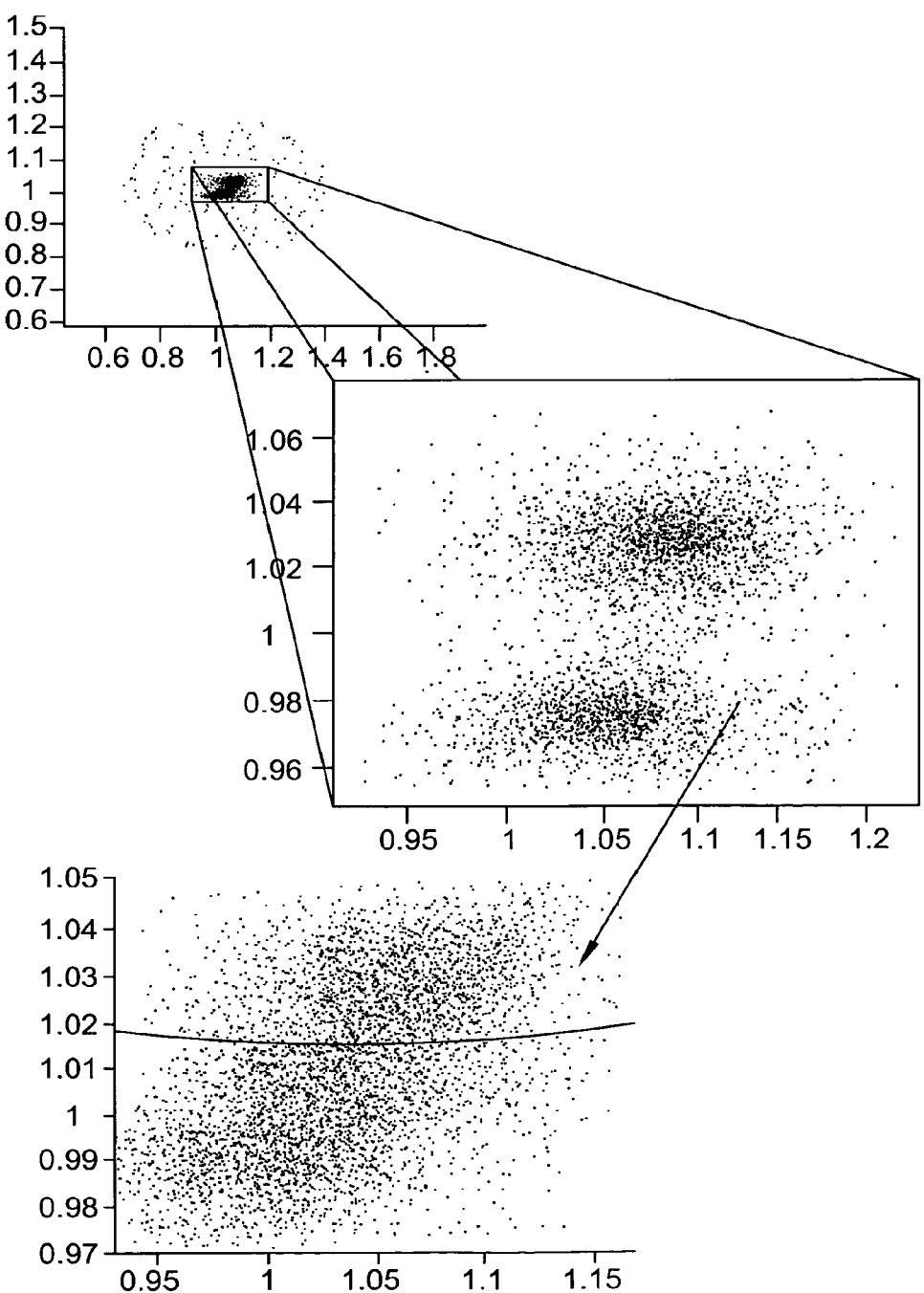
FIG. 73 is an example of a k-Means clustering strategy that may be employed according to one embodiment of the present invention.

FIG. 73 contains an example of the results of application of a k-means clustering procedure to define population 1 and population 2 based on statistics of distribution. The second order statistics of these populations are then used to set the parameters necessary for discrimination (the coefficients of a $1^{st}$ or $2^{nd}$ order polynomial decision function). Table IV summarizes the discrimination initialization procedure.

TABLE IV

Initialization of discrimination algorithm parameters.

Algorithm:   Initializing discrimination parameters
Input:   Matrix of floats detectedPulseData, vector of floats popPriorProbabilities
Output:   For each class population i: matrix of floats $W_i$, vector of floats $w_i$, float $w_{i0}$
Procedure:

1.    Compute feature values from detected pulses
        (n values per pulse, where n is dimensionality of feature space):
        featureValues = feature extract(detectedPulseData)
2.    Cluster feature values in feature space to obtain population memberships
        populations = cluster( featureValues)
3.    Compute $2^{nd}$ order statistics of populations:
        (for i = 1 to m, where m is number of populations/classes)
          (for j = 1 to n, where n is dimensionality of feature space)

$$popMean_i[j] = \frac{sum(featureValues[populations_i, j])}{\# \text{ of samples in populations}_i}$$

TABLE IV-continued

Initialization of discrimination algorithm parameters.

(for k = 1 to n, where n is dimensionality of feature space)
tmpVal[j , k] = (featureValues[populations$_i$ , j] − populationMean$_i$[j]) ·
(featureValues[populations$_i$ , k] − populationMean$_i$ [k])

$$popConvariance_i[j, k] = \frac{sum(tmpVal[j, k])}{\text{\# of samples in populations}_i}$$

4. Compute polynomial discriminant function coefficients:
(for i = 1 to m, where m is number of populations/classes)
$W_i = -\frac{1}{2} \cdot popCovarinace_i^{-1}$
$w_i\ popCovarinace_i^{-1} \cdot popMean_i$
$w_{io} = -\frac{1}{2} \cdot \ln(|popCovaricnce_i|) -$
$\frac{1}{2} \cdot popMean_i^T \cdot popCovariance_i^{-1} \cdot popMean_i +$
$\ln(popPriorPtobabilities_i)$ In general, the A/D converter 689 converts the analog output signals 701 from the photodetector 117 into corresponding digital information 707 indicative of characteristic A or characteristic B (e.g., X or ~X). The digital signal processor 867 generates initial discrimination parameters corresponding to the digital information 707, discriminates the digital information as a function of the initial discrimination parameters, and provides a sorting signal 853 to the sorting system 119 as a function of the discriminated digital information.

G. Digital Pulse Detection

The first processing step is pulse detection performed by pulse detection processor 865 to determine whether a particular waveform is a waveform pulse 497 corresponding to a fluorescence emission 31 of a cell. The processor 865 executes a pulse detection algorithm which identifies sample sets that are likely to represent either particles targeted for sorting into a population or particles targeted to be avoided because they are potential contaminants to a population. In the case of bovine sperm sorting, a dye is added to quench the emission 31 of non-viable cells, causing their associated pulse intensities to be ~⅓ the intensity of a live cell. Nonviable cells are not considered as sorting targets or potential contamination. They are not considered detected pulses 497. Pulses 497 from live cells are detected by monitoring the intensity of samples for a successive number of samples that rise above the background levels. Once this level crosses a statistically determined threshold the processor 865 jumps to a later time that is approximately 75% of the expected pulse 497 width for a live cell. If the level is still above the threshold, the series of samples are considered to be a pulse 497. Samples from detected pulses 497 are moved to a block of memory used by the feature extraction processor 867.

A statistical anomaly detection approach is one embodiment which may be employed by digital pulse detection software 747 although it is contemplated that other approaches for identifying and/or isolating digitized pulses 497 may be used. Essentially, digital samples 707 of the output voltage signals 701 from the photodetector 117 detecting fluorescence which are statistically anomalous from the background are considered to part of a pulse 497. For additional robustness (to minimize noise detections), additional temporal criteria may be included.

Figure 49:
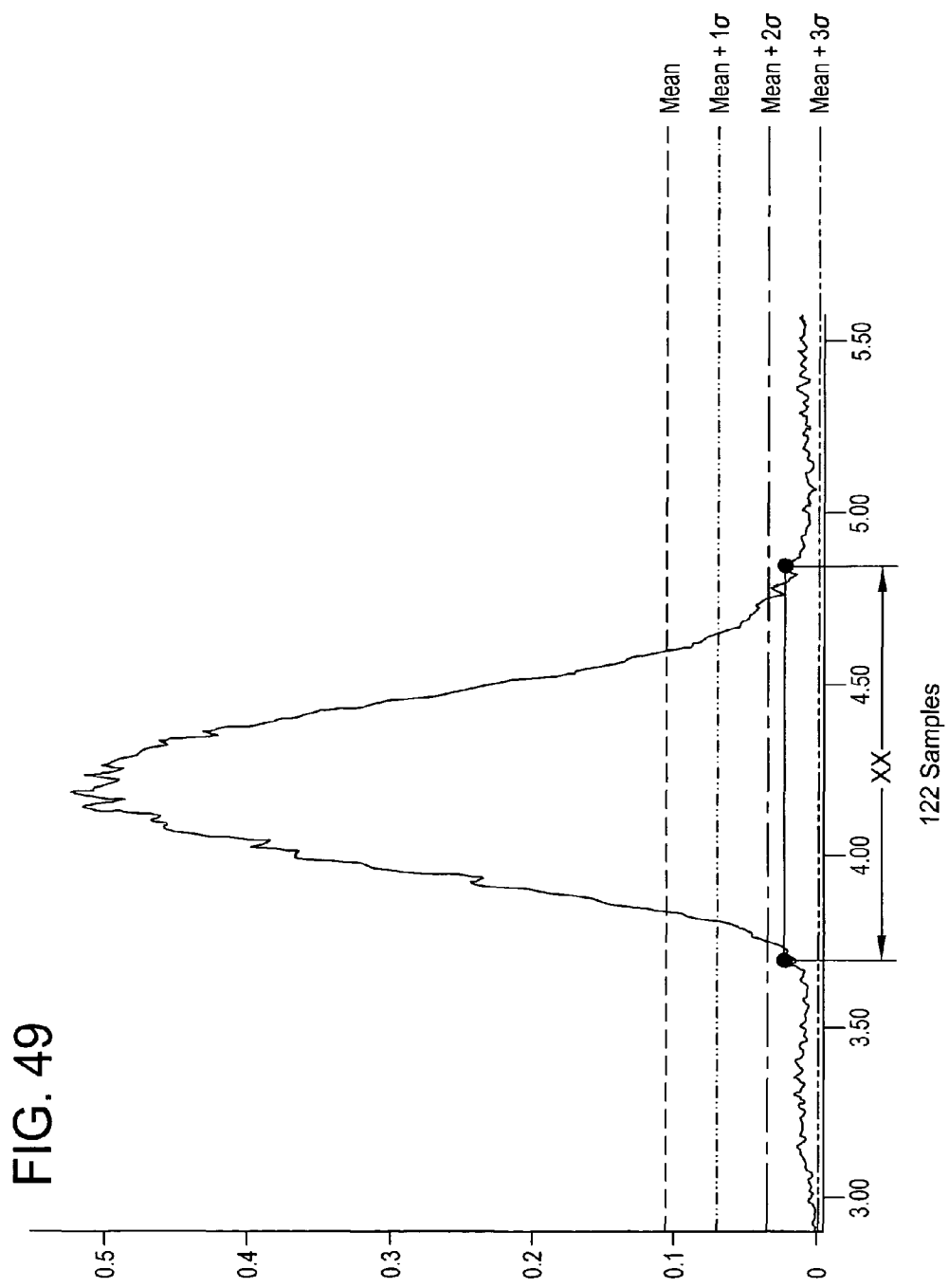
FIG. 49 is an exemplary illustration of the digital information corresponding to a time-varying analog output from a photodetector detecting a single fluorescence pulse based on 122 samples at a 105 MHz continuous sampling rate.

Pulse detection proceeds as follows. When the voltage output signal 701 from the photodetector 117 is not a pulse, the Mahalanobis distance from the background of incoming samples 707 of the signal 701 is computed and compared with a preset threshold. If the distance of a given sample exceeds the threshold, it is considered to be the potential start of a pulse 497, and the pulse detection software begins to buffer the incoming samples. If the next predetermined number of samples (e.g., 25) also exceed the threshold, a pulse 497 is considered to have started and buffering continues until the pulse end criteria are met; otherwise, the buffer is reset and checking for the start of a pulse resumes. While in a pulse 497, if a sample is below the threshold, then it is considered to be the potential end of a pulse and the buffer location is recorded (but sample buffering continues). If the next predetermined number of samples (e.g., 25) are also below threshold, the pulse 497 is considered to have ended and the pulse 497 consists of the buffered samples up to the recorded location. Table V summarizes the pulse detection algorithm, and FIG. 49 provides an illustration of the results of pulse detection on a digitally acquired fluorescence pulse 497.

TABLE V

Summary of digital fluorescence pulse detection.

Algorithm: Digital fluorescence pulse detection
Input: vector of floats digSamples, float bkgrndMean, float bkgrndSigma, float pulseStartThresh, float pulseEndThresh, integer numStartSamples, integer numEndSamples
Output: vector of floats pulseBuffer
Procedure:

1. Initialize inPulseFlag = 0, pulseStartCount = 0, pulseEndCount = 0
2. For each sample in digSamples, compute Mahalanobis distance from background:

$$mhDist[i] = \frac{(digSample[i] - bkgrndMean)}{bkgrndSigma}$$

TABLE V-continued

Summary of digital fluorescence pulse detection.

3. If inPulseFlag is not set, go to step 4, else go to step 6.
4. If mhDist > pulseStartThresh, place sample in pulseBuffer, increment pulseStartCount, and go to step 5; else set pulseStartCount = 0, go to step 2.
5. If pulseStartCount > numStartSamples, set inPulseFlag and go to step 2.
6. If mhDist < pulseEndThresh, place sample in pulseBuffer, set lastPulseSample to current buffer position, increment pulseEndCount, and go to step 7; else set pulseEndCount to zero and go to step 2.
7. If pulseEndCount is greater than numEndSamples, return pulseBuffer[ 1 to lastPulseSample] and exit.

In general, the A/D converter 689 converts the analog output signals 701 from the photodetector 117 into corresponding digital information 707 indicative of characteristic A or characteristic B (e.g., X or ~X). The digital signal processor 865 analyzes the digital information and processor 873 provides a sorting signal 853 to the sorting system 119 as a function of the detected digital information.

H. Feature Extraction and Discrimination

The next processing step is feature extraction performed by the feature extraction and discrimination processor 867. This processor responds to flags set by the pulse detection processor 865. Samples from detected pulses are placed in memory shared with the feature extraction processor 867. Features such as area, pulse width, pulse height, Gaussian correlation coefficient and/or other features are determined for each pulse 497. In some cases pulses 497 are determined to be "doublets" or invalid and features are not extracted. For the case of bovine sperm 201 features are only extracted for pulses 497 that have the general amplitude and width of a live X or Y cell. Typically, the pulse amplitude for a live sperm cell is in the range of about 700-900 mV, although this range may be as wide as 500-1000 mV. Once the features are extracted they are compared to the feature spaces defined for the population(s) selected for sorting. If the features match the feature spaces identified for sorting, then processor 867 sets a flag indicating a positive sort command to the sort processor 873. In general, the classification of a particular cell is made by the discrimination processor 867 and the sort decision is made by the sort processor 873.

Digital information 707 representing fluorescence emissions 31 (and thus the characteristics of corresponding cells which created them) are discriminated by software 757 based on specific features or characteristics which exhibit distinguishably different statistical behavior in feature space (the n-dimensional orthogonal space formed by n features as the axes) for the different populations of interest. Therefore, the first step in analyzing digital information 707 for the purposes of discrimination is computation of these features, a process called feature extraction performed by pulse analysis software 749 executed by the processor 867. Table VI lists the several candidate features which software 749 may use for this application. One or more of these features will be selected to form the feature space for classification. It should be noted that there are additional features providing enhanced separation so that this list is exemplary, not comprehensive. For example, the software 749 may employ a subroutine 753 to determine pulse 497 area and/or may employ a subroutine 755 to determine pulse 497 peak.

TABLE VI

Summary of candidate features currently being considered for use in digital pulse analysis relating to feature extraction.

| Feature Name | Feature Description |
|---|---|
| Pulse Area | Approximated by sum (or average) of pulse samples |
| Pulse Peak | Maximum value of pulse samples |
| Pulse "Inner" Area | Sum (or average) of inner TBD samples of pulse (centered on pulse mean) |
| Pulse Width | Number of samples in pulse. |
| Pulse "Gaussianity" | MSE or correlation coefficient of pulse with a Gaussian shape with the same $2^{nd}$ order statistics. |
| Pulse "Lagging Peak" | Pulse value at TBD samples past peak (or mean) |
| Critical Slope Difference (CSD) | Slope of pulse at a point along the pulse at which the difference between the first derivative of a pulse produced by particles having characteristic A and the first derivative of a pulse produced by particles having characteristic B is at or near a maximum |

I. Slit Scanning

In general, the elliptical spot 459 provided by the illumination system 109 measures the relative DNA content differences in cells. Resolution can be improved further by analyzing the fraction of the pulse 497 of the fluorescence emission 31 detected by the photodetector 117 more likely to contain characteristics which are being evaluated. A biological phenomenon of certain cells (e.g., bovine sperm cells) is the localization of the X/Y chromosomes in a sub-equatorial region 225 which is immediately adjacent the longitudinal midline or equator or center of the nucleus 213 of the cell 201 and which has a length of about 1 μm. (See FIG. 6). In fact, the X/Y chromosomes are not necessarily centered in the nucleus 213. Thus, resolution can be improved by converting the time-varying analog output 701 of the photodetector 117 into digital information 707 and analyzing a portion of the digital information corresponding to the fraction of the pulse 497 of the fluorescence emission 31, e.g., corresponding to the light emitted from the circumequatorial region 225 such as such as 20-60% and particularly 20-30% of the waveform pulse centered around the pulse 497 peak.

As noted above, slit scanning can be employed to obtain the fluorescence measurement from a portion of each cell's chromatin rather than from the chromatin as a whole. The elliptical spot 459 provided by the epi-illumination system 415 noted above measures the relative DNA content differences in cells from specific sections of the chromatin, so that the resolution of X cells and ~X cells relative to one another is improved. As noted above, the slit scanning measurement technique is a fluorescence measurement approach that focuses the excitation beam 25 so that a dimension of the focused spot size 459 is much less than a cell diameter as shown in FIG. 6. In this way, the cell 201 is scanned by the laser beam 25 as the cell passes through the elliptically-shaped beam spot 459. The resulting waveform pulse 497 produced by the photodetector 117 output 701 detecting the fluorescence emission 31 resulting from slit scan illumination contains information about the localization of fluorescence along the length of the cell 201. As shown in FIGS. 45-48, as the cell 201 traverses the elliptically-shaped beam spot 459, the time-varying waveform pulses 497 (red/orange line) are the convolution of the relative beam intensity (blue line) and the relative emitted pulse intensity (which corresponds to the fluorescence emissions from stain excited by the elliptical spot as the cell traverses the beam and which varies because the fluorescence distribution along the axis of the cell varies).

Figure 53:
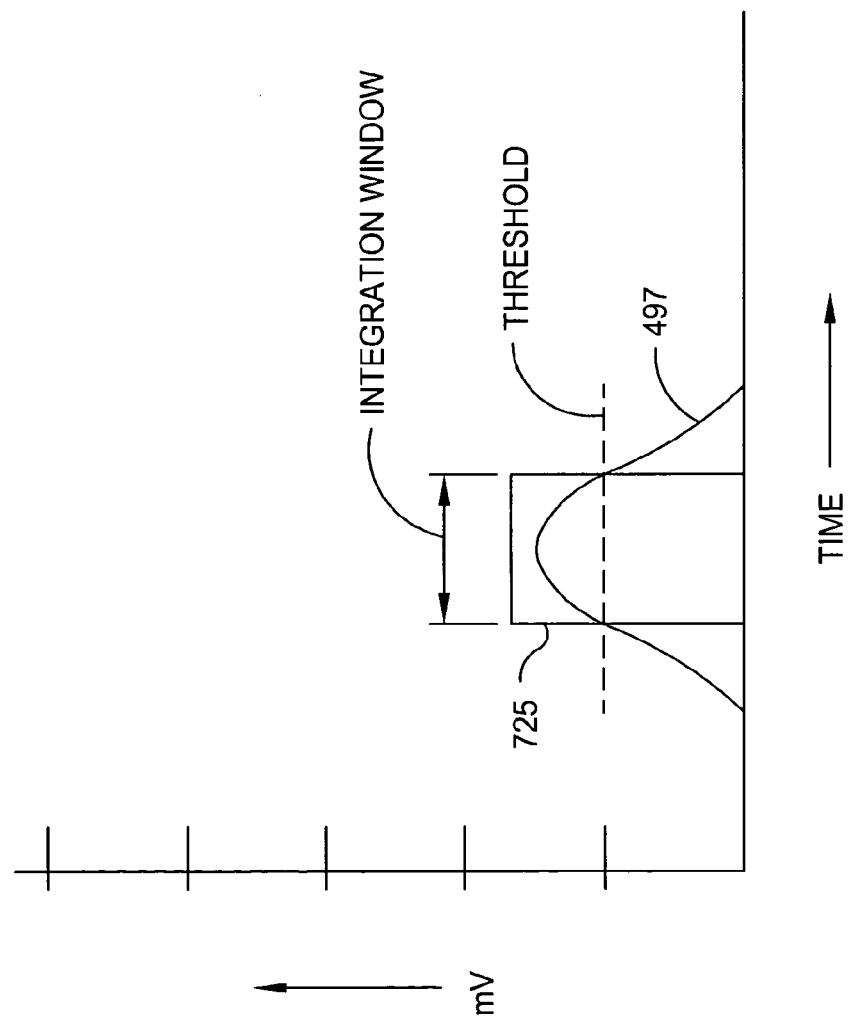
FIG. 53 is a schematic diagram of a pulse waveform showing a threshold and integration window that can be used for pulse analysis.
Figure 54:
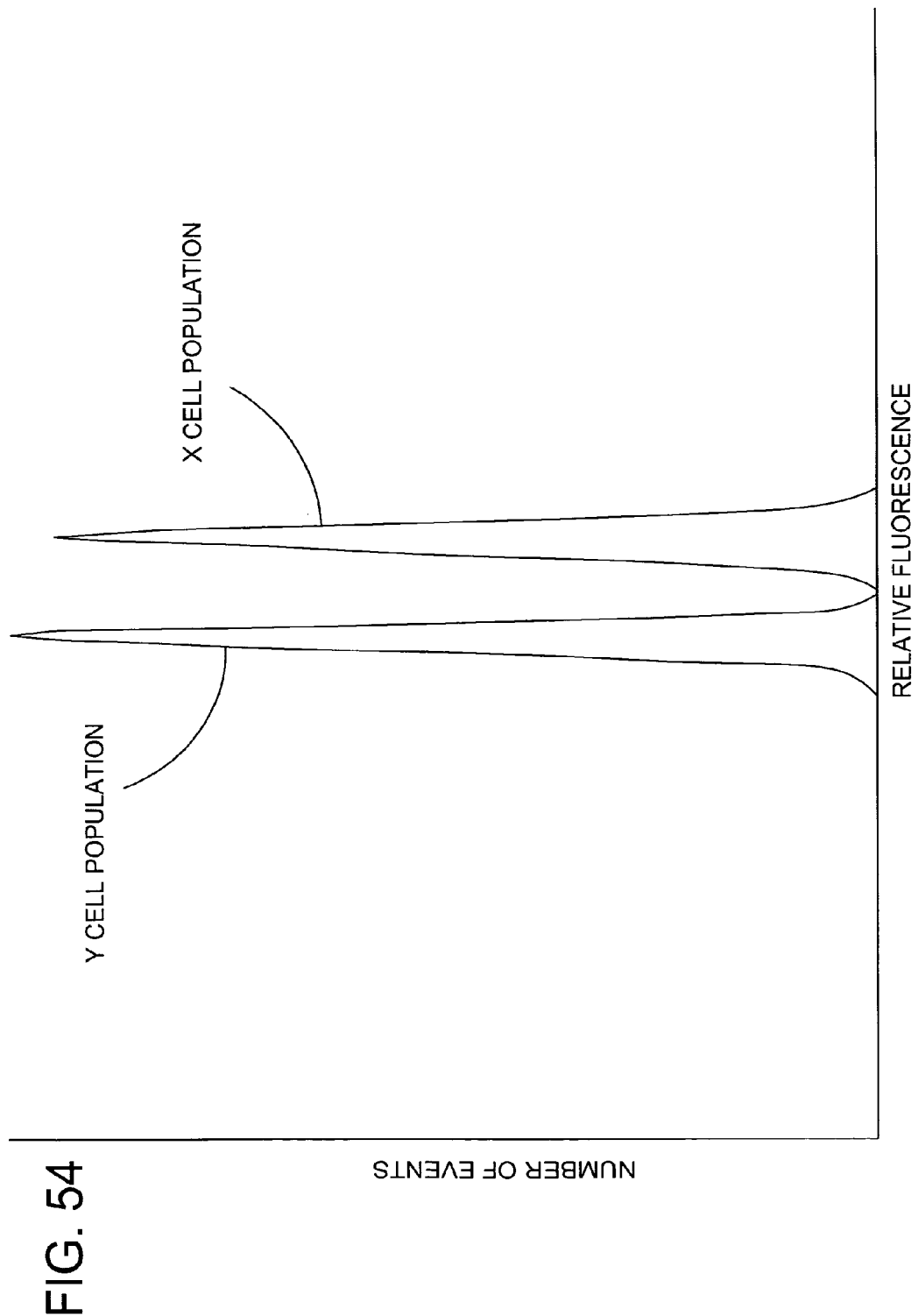
FIG. 54 is a histogram of a sample containing X and Y sperm cells showing the high resolution attainable with slit scanning techniques.
Figure 55:
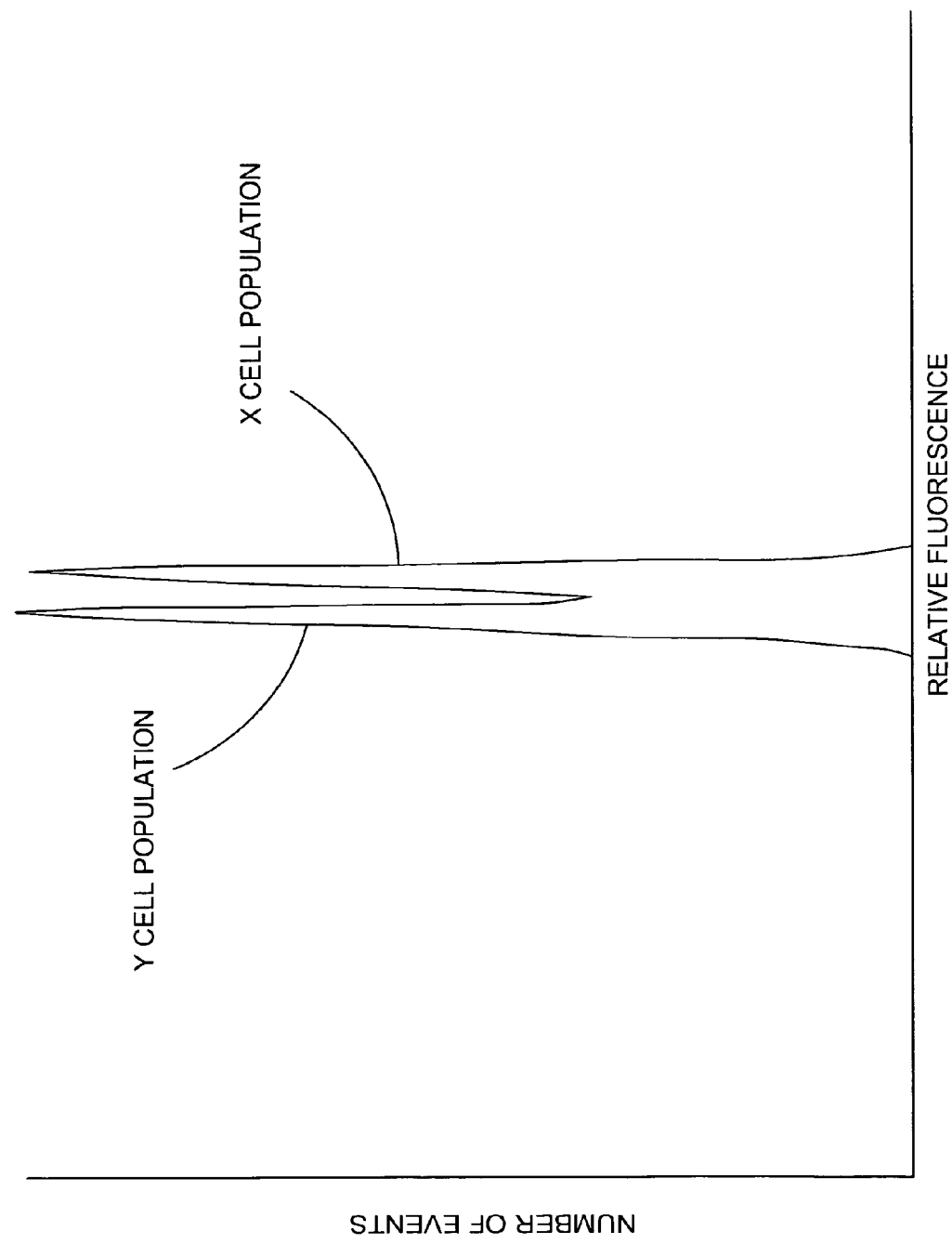
FIG. 55 is histogram of a sample containing X and Y sperm cells showing the relatively poor resolution attained with standard illumination.
Figure 59:
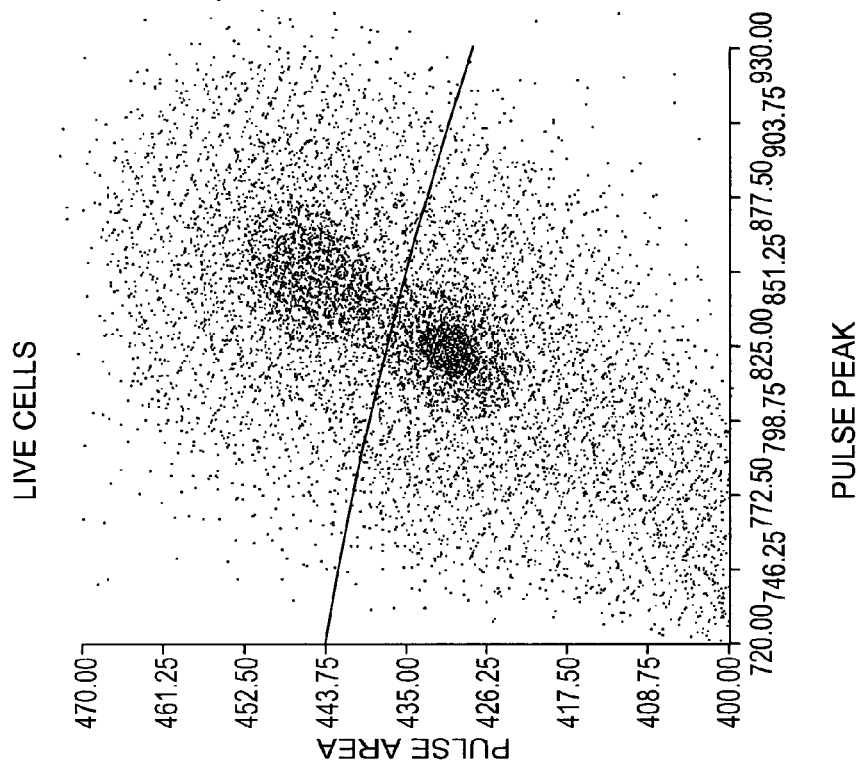
Figure 58:
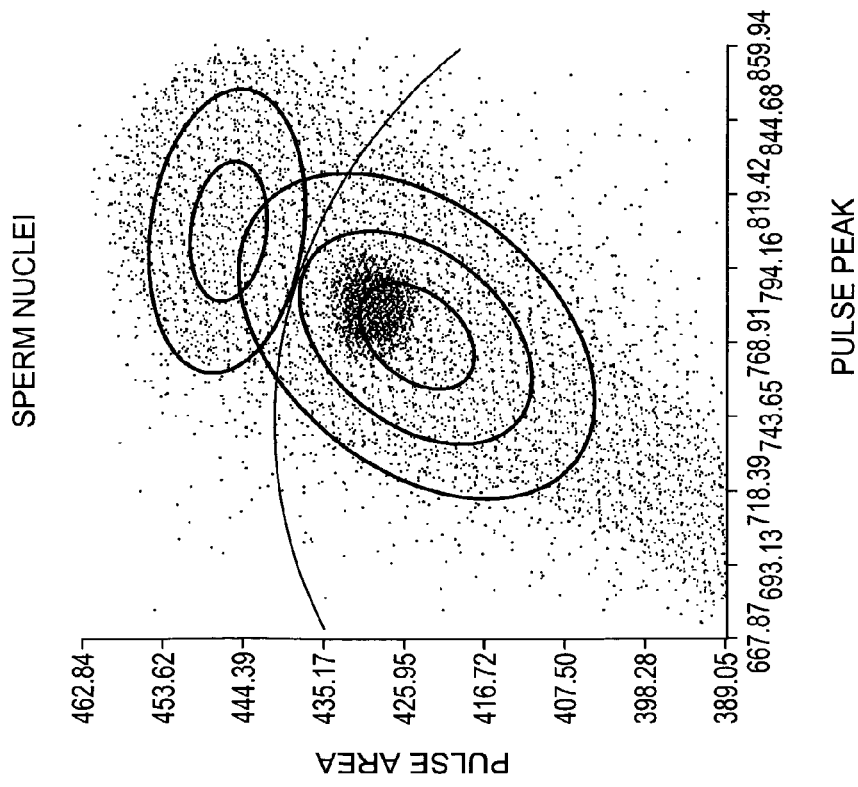

By illuminating only a fraction of the cell's chromatin at one time, the resulting time-varying analog output 701 from the photodetector 117 contains information specific to the localization of fluorescence within the chromatin along the longitudinal axis of the cell 201. Although the detected fluorescence emission 31 from slit scanning is less than the detected emission 31 from scanning by a beam 25 having a spot width comparable to the cell diameter, resulting in waveform pulses 497 from slit scanning having a lower pulse amplitude, the majority of difference between the X-chromosome bearing cells and the Y-chromosome bearing cells appears in the center 20-30% to 20-60% of the waveform pulse 497. If only the rectangular area 725 in FIG. 53 is considered for discriminating X-Y sperm cells, then a larger relative difference can be measured between the localized variation in DNA content within the section of chromatin that corresponds to the rectangular region 725 due to the presence of the X and Y chromosomes within that region as compared to the total DNA content of the cells. For example, bovine X-Y sperm cells have a difference in total DNA content of about 3.8%. The fluorescence emission 31 from the X and Y chromosomes will be contained in the rectangular region 725. If this rectangular region 725 accounts for 20% of the total waveform pulse 497 corresponding to a fluorescence emission 31, then a 14% difference in relative DNA content within the region will exist. By measuring the relative DNA content differences from specific sections of the chromatin, the resolution of X-Y sperm cell differentiation is improved (e.g., from 3.8% to 14%). FIG. 54 illustrates the resolution attainable using slit scanning illumination and processing the areas from only the center 20% of the pulse 497 (i.e., the rectangular region 725 of FIG. 53). The histogram of FIG. 54 allows a very high percentage (e.g., 98%) of the X chromosome bearing sperm and Y chromosome bearing sperm to be identified with a high degree of confidence (e.g., 95%). In comparison, the histogram of FIG. 55, which illustrates the resolution obtainable when using standard illumination techniques, shows that slit scanning offers a significant improvement over the results obtained using standard illumination techniques.

Two approaches which can be employed to obtain the area 725 of the center portion of the waveform pulse 497 as illustrated in FIG. 53 are digital signal processing (DSP) of digitized photodetector 117 time-varying analog output 701, as discussed in this section, or analog integration using an analog threshold trigger, as noted below. As noted herein, DSP processing involves continuously sampling the time-varying analog output 701 from the photodetector 117 to obtain digital information 707 corresponding to the output 701 and applying DSP algorithms to the digital information 707 to extract features, such as area size, from the digital information corresponding to the center portion 725 of the waveform pulse 497 which corresponds to the difference in DNA content due to the presence of an X or Y chromosome in different cells 201. As a simple example, the center 20% of the total area of each waveform pulse 497 would be determined by analyzing the digital information 707 corresponding thereto. The analysis would be used to generate a histogram such as illustrated in FIG. 53.

J. Pulsed Laser Scanning

In one embodiment, it is contemplated that the system 1 include a pulsed laser to illuminate the cells. In this embodiment, slit scanning (as described above) may or may not be employed. For example, a mode-locked solid-state laser can be used to emit a train of electromagnetic pulses having a pulse width (duration) of 1-100 picoseconds at a pulse frequency of about 50-150 MHz and at an average power output of about 100-500 milliwatts. One suitable laser is a Vanguard 350 mode-locked solid-state laser (available from Spectra-Physics, Mountain View, Calif. 94039), which is operable to emit a series of pulses about 12 picoseconds in width (duration) at a frequency of about 85 million pulses per second and at an average power of about 350 milliwatts. Because the 350 mW of power is delivered over extremely short bursts of only 12 picoseconds, the peak power output of such a laser is several hundred times (e.g., about 800 times) greater than the average power.

The output of such a laser can be described as quasi continuous wave (quasi-cw) because, for many applications, the pulse repetition rate is fast enough to approximate a continuous wave (cw) output. Indeed it is possible to operate the system as described above with a quasi-cw laser in much the same manner as one would operate with a cw laser. This provides certain advantages because solid-state lasers typically operate more efficiently, require less extensive cooling systems, and require less maintenance than most other lasers.

Figure 40:
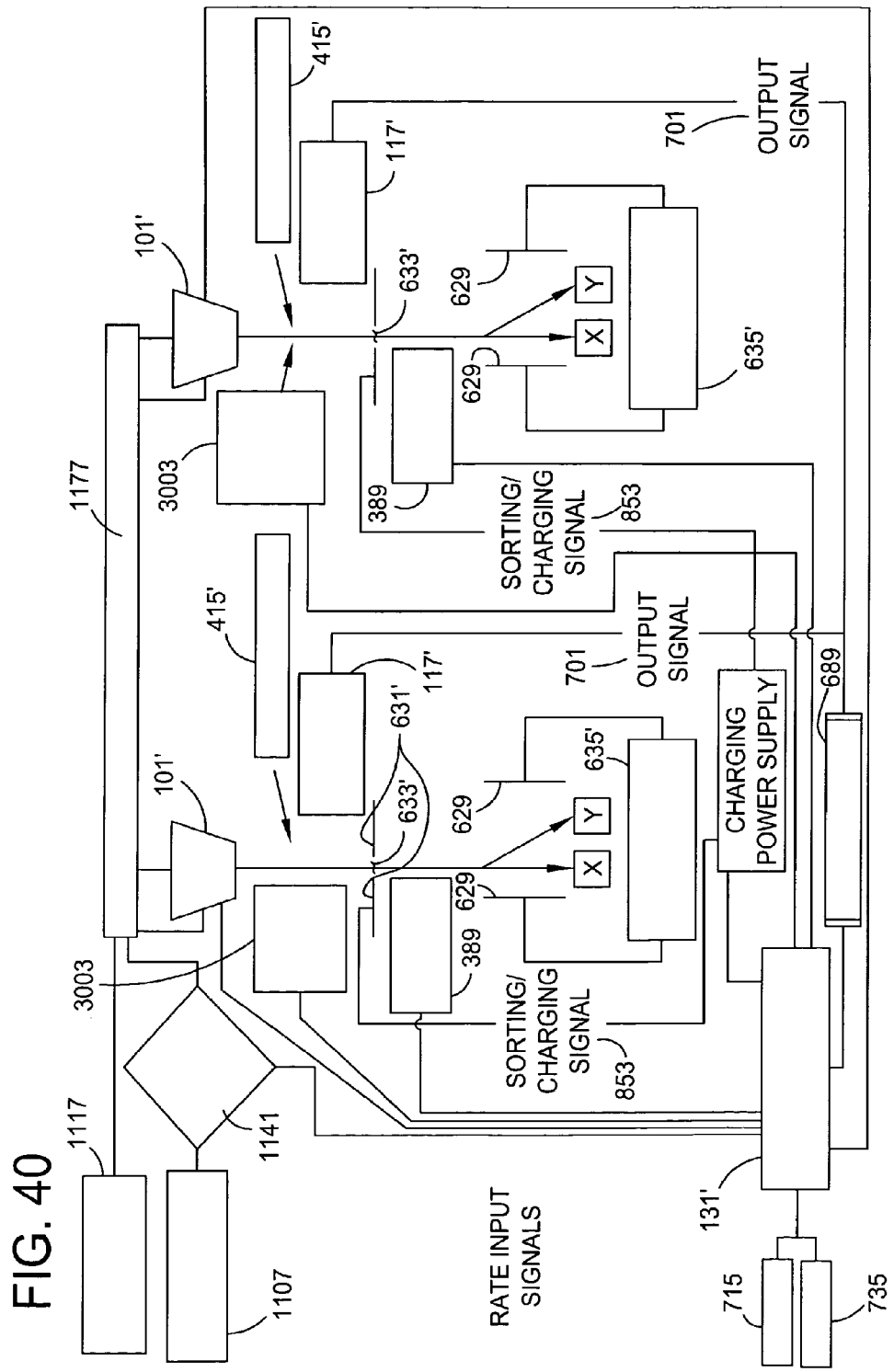
FIG. 40 is a schematic diagram of one embodiment of a multi-channel sorter of the present invention showing two channels.
Figure 41:
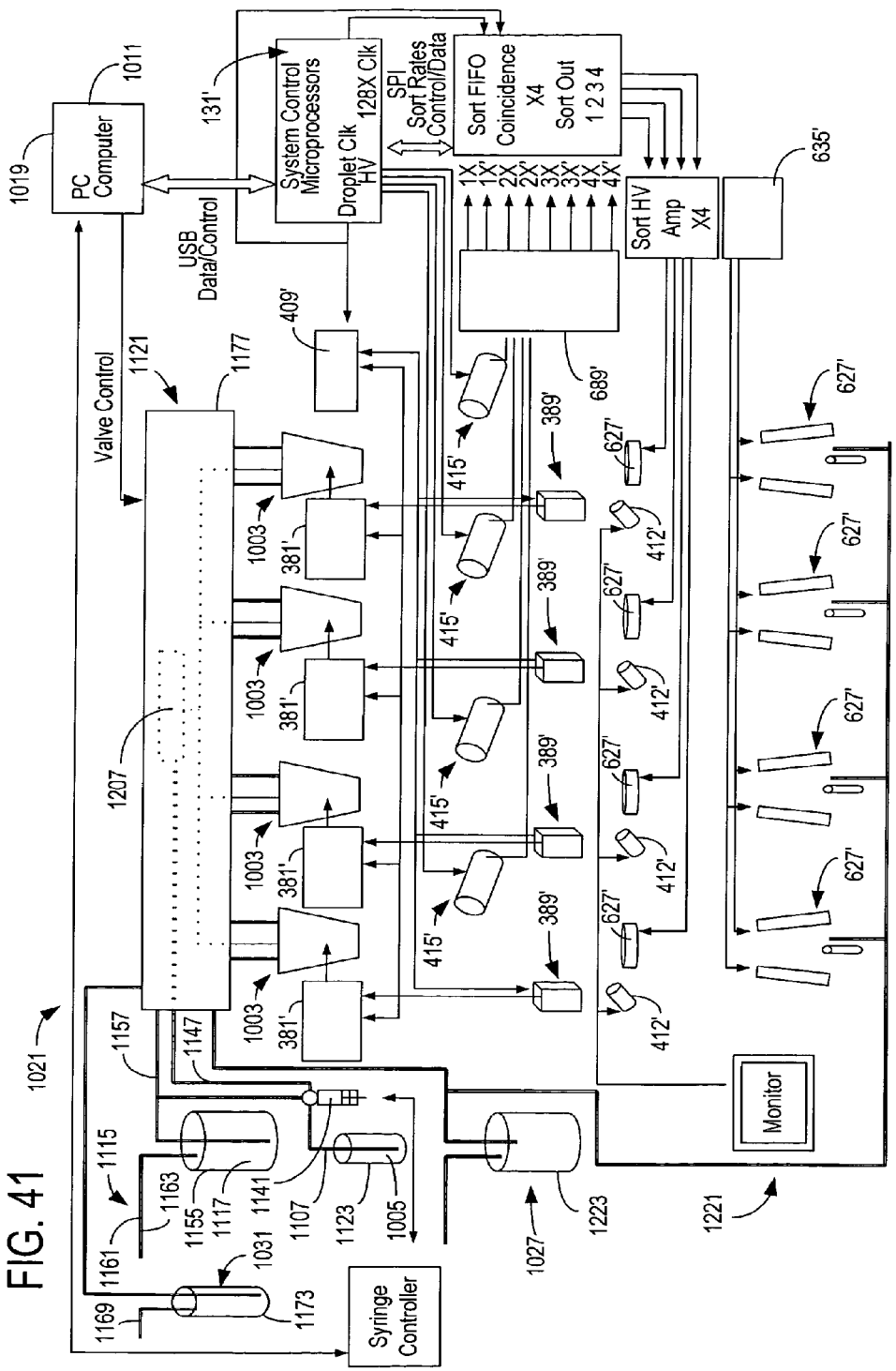
FIG. 41 is a work flow diagram of one embodiment of a multi-channel sorter of the present invention showing four channels.

A quasi-cw pulsed solid-state laser can also result in significantly improved signal-to-noise ratios using digital signal processing techniques. A timing circuit may be included and is operable to produce a timing signal indicative of the arrival of laser pulses at the interrogation location 115 (i.e., the area where the laser beam 25 illuminates the stream 21). For example, the timing circuit may be a laser pulse sensor 3003 as shown in FIG. 40 for detecting light corresponding to the laser pulse including scattered light generated by the interaction of each laser pulse with the fluid stream 21 and/or including light from the laser pulses. Alternatively, for lasers which may be triggered, a triggering signal may be provided to the microprocessor 131 and/or the A/D converter 689 to synchronize either or both to the laser pulses, as noted below with regard to FIG. 50. In either embodiment, the laser pulse timing would provide a clock signal for the system.

Figure 50:
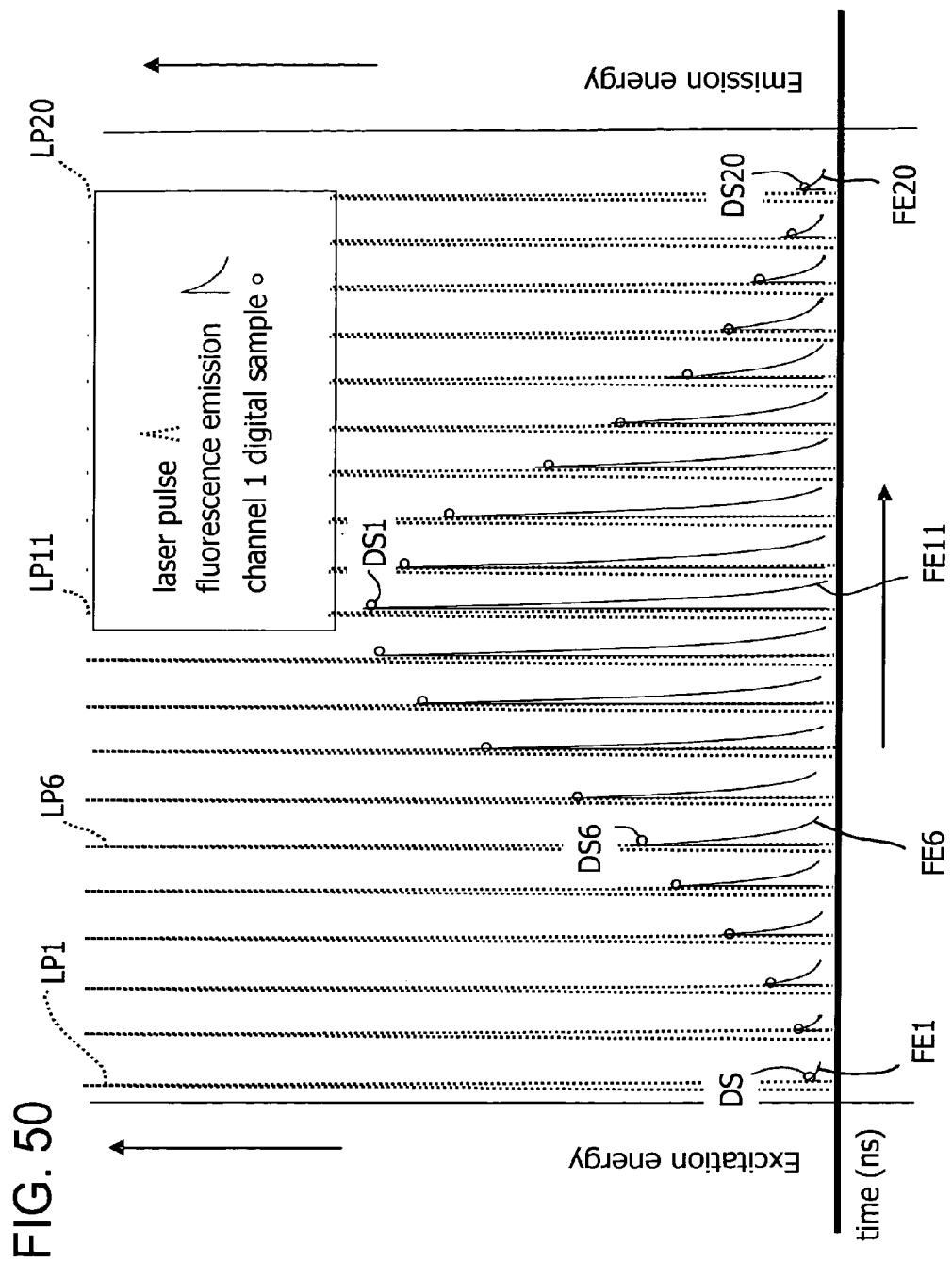
FIG. 50 is a schematic diagram illustrating the timing relationship between laser pulses, fluorescence emissions from a cell resulting from the laser pulses and the digital samples of the photodetector output in one embodiment of the invention.

Referring to FIG. 50, a timing diagram illustrates the timing relationship between the laser pulses LP, the fluorescence emissions FE from a cell as a result of repeated excitation by the laser pulses LP as the cell passes through the beam spot 459 and the digital samples DS of the photodetector output 701. As shown in FIGS. 45-49, as a cell passes through the laser beam spot 459 the fluorescence emission 31 varies depending upon the amount of illumination of the portion of the cell which generates the fluorescence emission 31. FIG. 50 illustrates twenty (20) laser pulses LP1-LP20 which impinge upon a cell as the cell passes through the interrogation zone 115 of a flow cytometer 1. Each laser pulse LP1-LP20 corresponds to a fluorescence emission FE1-FE20, respectively, which exponentially decays after substantially instantaneous excitation by the laser pulse.

Figure 51:
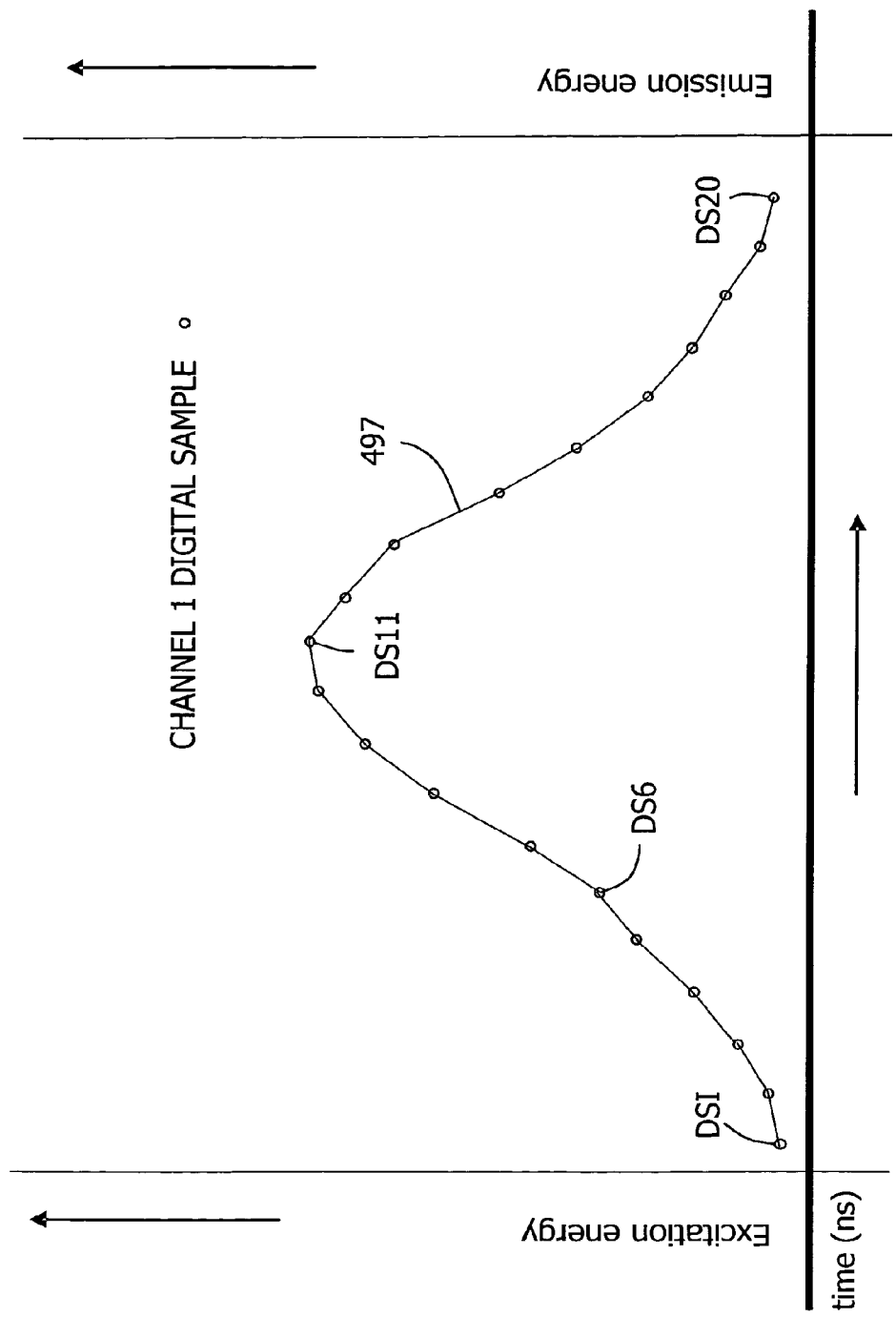
FIG. 51 is a schematic diagram illustrating how the digital samples shown in FIG. 50 form a pulse waveform.

In one embodiment, the microprocessor 131 controls the A/D converter 689 (see FIG. 40) so that the converter 689 samples the output signal 701 of the photodetector 117 at or near peak of each fluorescence emission FE1-FE20, as indicated by digital samples DS1-DS20, respectively. In other words, the timing circuit synchronizes the sampling rate of the A/D converter 689 with the fluorescence emissions FE1-FE20. The resulting digital signal produced by transit of a particle through the interrogation zone 115 is the functional equivalent of the digital signal that would have been produced by the digitization of a pulse waveform 497 from a continuous wave laser. As shown in FIG. 51, for example, by considering only the fluorescence intensity during the digital samples DS1-DS20 and disregarding fluorescence intensity drop-off between laser pulses LP1-LP20, the fluorescence intensity as a function of time is a pulse waveform 497. This permits feature extraction by the microprocessor 131 from the digital signal 707 generated by the pulsed laser in order to analyze the cell providing the fluorescence emissions FE1-FE20. In one embodiment, a more sensitive photodetector having relatively fast response time of about 2 nanoseconds or less may be used to more accurately detect the fluorescence emissions.

Thus, the pulsed laser provides advantages in a flow cytometry system 1 in that it is possible to use a lower power pulsed laser to obtain substantially the same analysis that would be obtained with a cw laser operating at an average power much higher than the average power of the pulsed laser. Further, the high peak power from a pulsed laser tends to saturate the fluorophores so that the fluorescence emissions are maximized thereby reducing the signal-to-noise ratio of the output signals of the photodetector. In other words, by using a laser pulse that contains much more energy than is required to saturate the fluorophore, variations in the output of the laser do not result in variations in the fluorescent emissions 31.

Those skilled in the art will recognize that there are many ways to cause a laser to emit a series of pulses. It is understood that other pulsed lasers, including other mode-locked lasers, Q-switched lasers, and cavity dumping lasers, could be used in place of the mode-locked laser discussed above without departing from the scope of this invention. Similarly, many other ways to time the digital sampling and process the resulting information will be apparent from the foregoing disclosure. For example, the digital sampling could be timed so there is a different delay (or no delay) between a laser pulse and a digital sample without departing from the scope of the invention. Likewise, the number of digital samples per pulse or the number of pulses that elapse between digital sampling can also be varied without departing from the scope of this invention.

K. Estimation of Population Characteristics

As noted above, flow cytometry can be used to discriminate X-bearing bovine sperm cells from Y-bearing bovine sperm cells based on their relative 3.8% difference in DNA content. Discrimination is achieved through analysis of characteristics of the time-varying signal 701 that is produced by the photodetector 117 used to record the fluorescence emission 31 as the stained cell passes though the interrogation location 115. This interaction is illustrated in FIGS. 45-48. FIGS. 45-48 illustrate how a pulse waveform 497 is generated by the fluorescence emissions 31 resulting from the interaction between the laser beam 25 and a stained sperm cell 201. The emission pulse 497 is the convolution integral of the excitation spatial function 498 and the emission spatial function of the cell 201. Characteristics of the fluorescence pulse waveform 497 are used to classify a cell as X, Y or undetermined. In one embodiment, X-Y discrimination relies on two pulse characteristics: peak pulse height and pulse area.

Figure 52:
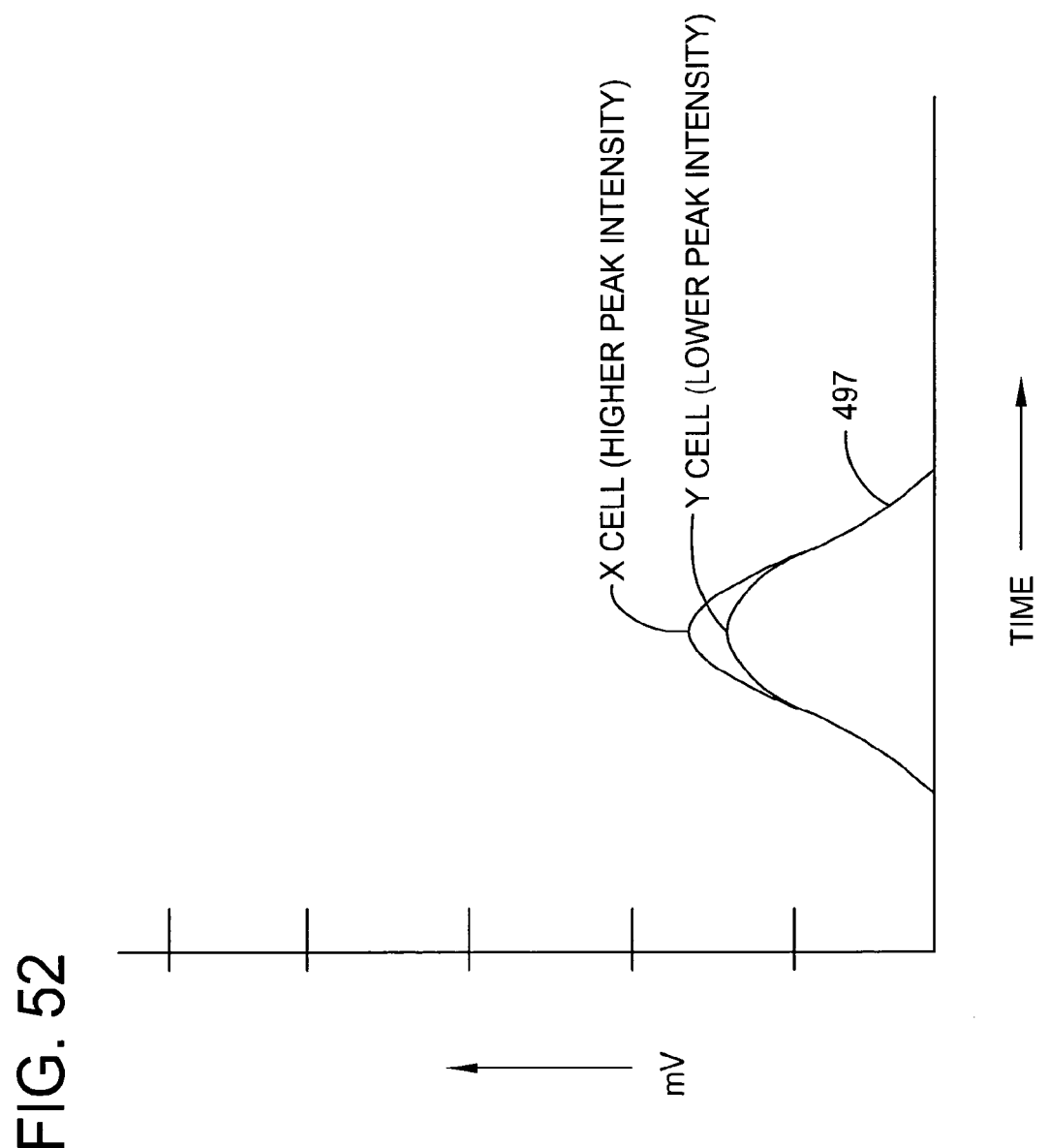
FIG. 52 is a schematic diagram of a pulse waveform from and X sperm cell synchronized with the pulse waveform of a Y sperm cell showing higher peak intensity in the pulse waveform for the X sperm cell.

These characteristics are illustrated on the example pulse that appears in FIGS. 52 and 53. FIGS. 52 and 53 are examples of pulses 497 from X-bearing and Y-bearing sperm cells. The pulses 497 were generated from a computer model that assumed excitation illumination with a laser beam 25 having an elliptically-shaped beam spot 459 having a 2 μm Gaussian beam waist W1 (FIG. 6) and that the DNA content difference was distributed uniformly across the center 20 percent of the cell 201. These assumptions are representative of slit scanning illumination of bovine sperm cells 201 having a localized DNA difference as discussed in more detail above. Integration of the pulses 497 results in a 3.8% average difference between the pulse 497 area for an X cell and the pulse 497 area for a Y cell.

It is possible to generate histogram and scatter plots of the pulse 497 peak and area characteristics for stained cells and nuclei. FIGS. 56-59 contain histograms of the pulse area characteristic for stained nuclei and live cells, plus scatter plots of the pulse 497 area and peak characteristics for stained nuclei and live cells. Some of the items that may limit live cell discrimination, and ultimately the cell sorting rate are evident in these plots. Notably, the live cell histogram of FIG. 57, and to a lesser extent the nuclei histogram of FIG. 56, have a left shoulder that is typical of fluorescence intensity histograms for mammalian sperm cells. It has been determined that the left shoulder is generated by one or more populations of slightly unaligned cells (i.e., cells that generate relatively weaker fluorescence emissions due to slight deviations from the optimal alignment, but that are not so far out alignment to cause the relatively brighter fluorescence emission 31 from the narrow edge 209 of the sperm head 205 to be collected by the optics system 109). Only about half of the X cells can be easily identified in the live cell area histogram. The rest overlap with the Y cell population and the non-aligned cell populations. Even when peak pulse height is added, as shown in the scatter plots in FIGS. 56-59, X-bearing cell classification may be significantly limited.

Figure 60:
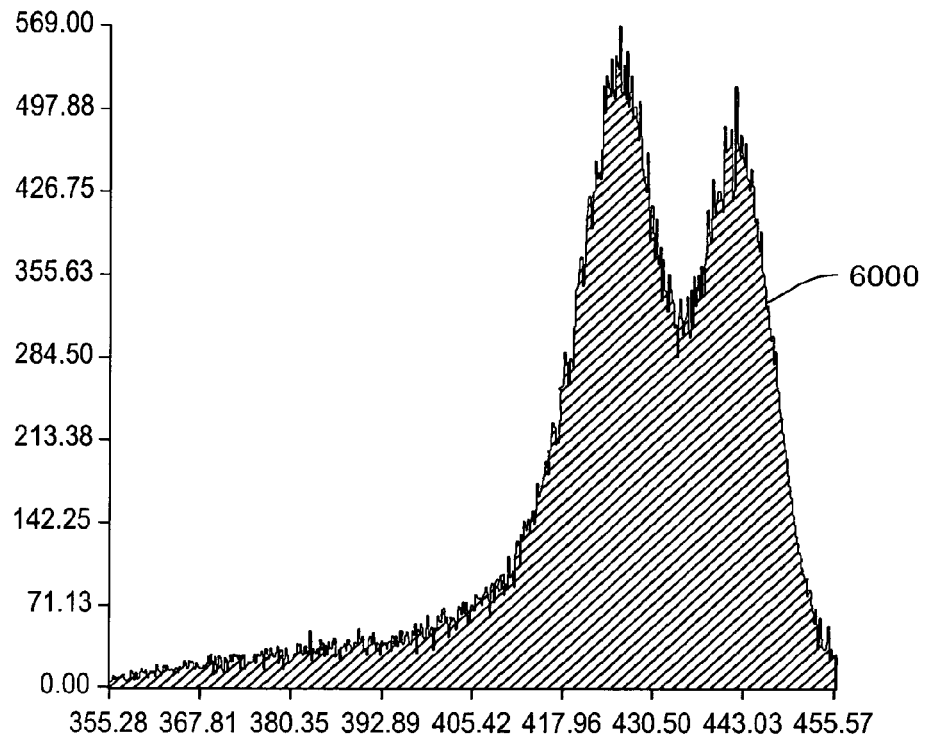
FIGS. 60-61 illustrate a four-component model of a fluorescence intensity histogram for sperm cells
Figure 61:
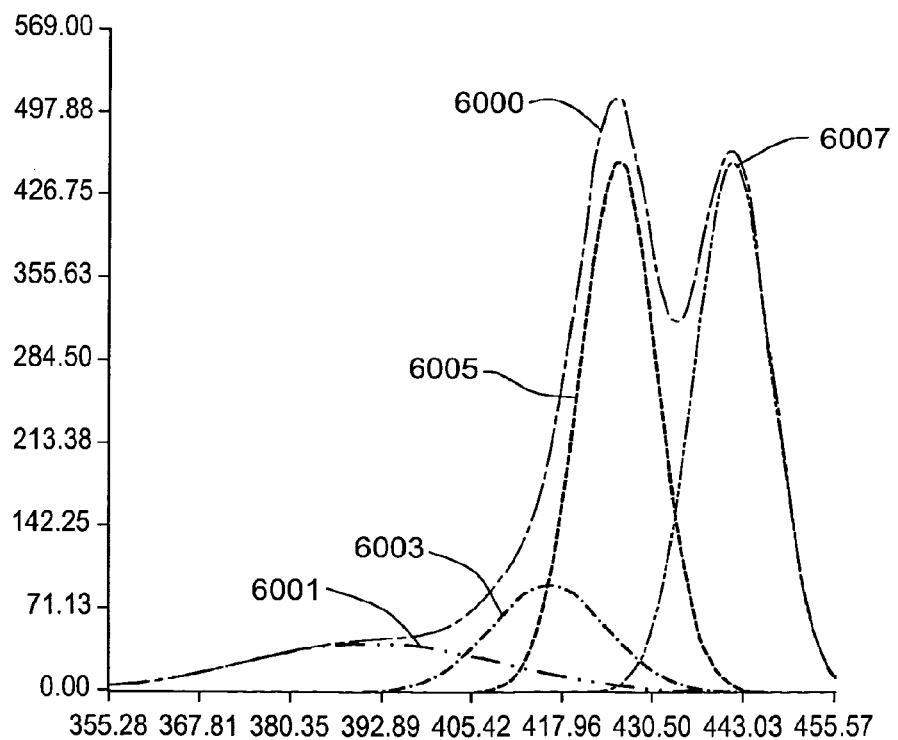

FIGS. 60-61 illustrate the overlap of the X and Y population distributions. In FIGS. 60-61, a four-component computer model has been applied to raw data 6000 (FIG. 60) to estimate population statistics for two populations of non-aligned cells (6001, 6003), aligned live Y cells (6005) and aligned live X cells (6007) (FIG. 61). It is desirable to discriminate the X and Y populations as a function of the coefficient of variation (CV) of the X and Y populations. For example, it is desirable to minimize the coefficient of variation (CV) of the X and Y populations in order to improve discrimination. In particular, when a population of sorted X cells is desired, it is desirable for the CV of the X cell population to be less than 1.5%, more desirably about 1.3%, and even more desirably less than 1.3%. Traditionally, the CV of a distribution of fluorescence intensity of sperm cells has been considered with respect to the distribution functions for only two populations (X and Y). Quality control with respect to CV has been limited to crude subjective estimation of the CV of the X and Y populations to decide whether continued analysis or sorting is worthwhile.

According to one embodiment of the present invention, one function of the microprocessor 131 is to provide an automated estimation of the CV of the X population using the four-component model illustrated in FIGS. 60-61. In order to estimate the CVs of the populations present in a feature (e.g. pulse area) distribution, it is necessary to estimate the $2^{nd}$ order statistics of the population distributions. This may be achieved by applying a model of a known form and finding the best fit of that model to the observed data.

Given the expectation of normally-distributed data, an approach consisting of Parzen Window based non-parametric density estimation (utilizing a Gaussian kernel function) followed by application of a Gaussian mixture parametric model has been chosen. Specifically, the four-component model illustrated in FIGS. 60-61 consists of a sum (or mixture) of four uni-variate Gaussian distributions, with these four components being the feature distributions corresponding to aligned X cells, aligned Y cells, and a two-component unaligned cell population. The parameters characterizing the model then are the population means (averages) (4), population standard deviations/variances (4), and prior probabilities (expected % of the overall distribution) (4). These 12 parameters can then be varied to achieve a best fit of the model to the observed data histogram. With the model component parameters thus estimated, an estimate of the CV of a population of interest (in particular, X cells) may be determined from the estimated population standard deviation and mean:

$$CV = \frac{\text{standard deviation}}{\text{mean}} \cdot 100\%$$

In order to reduce computational complexity, constraints have been placed on the model to reduce the dimensionality of the parameter space. In particular, the standard deviations of the model components corresponding to the aligned X and aligned Y populations have been constrained to be the same. Also, the aligned X and aligned Y components have been constrained to make up the same percentage of the overall mixture—thus the non-aligned populations are assumed 50% X cells and 50% Y cells.

Non-parametric density estimation is applied prior to model fitting to obtain an improved estimate of the total density function (being the sum of the component densities) underlying the raw histogram data. The specific technique applied is known as "Parzen Windows" (Duda, Hart, and Stork, 2001), here utilizing a Gaussian kernel or window function due to the assumed sum-of-Gaussian nature of the underlying density. The standard deviation of the Gaussian kernel is chosen to be 1% of the number of populated histogram bins; this value has been empirically observed to provide adequate but not excessive smoothing of the histogram. Each data point in the histogram then contributes a kernel function centered on the histogram bin containing the data point. The density estimate is then obtained as the sum of the kernel functions.

The methodology chosen for variation of the model parameters to achieve the best fit to the data is known as Expectation Maximization (See Duda R. O., Hart, P. E., and Stork, D. G., 2001, *Pattern Classification* 2$^{nd}$ Ed., John Wiley & Sons; and Moore, A., "Very Fast EM-based Mixture Model Clustering using Multiresolution kd-trees," in M. Kearns and D. Cohn, Eds., *Advances in Neural Information Processing Systems*, pages 543-549, 1999, Morgan Kaufman). The specific algorithmic implementation utilized is as follows:

1) Initial conditions for the model parameters are set. The top two local maxima in the Parzen density estimate are used as the initial Y and X mean locations (the initial amplitude of the maxima for both X and Y populations being estimated as the amplitude of the right peak). The initial X and Y population variance is estimated as the variance of the data to the right of the local minimum occurring between the left and right peaks relative to the right peak location. Also, the initial X and Y population prior probabilities are set as the percentage of all points falling to the right of this local minimum. The initial X and Y population Gaussian density estimates are then computed using these parameters and subtracted from the total Parzen density estimate. The mean and variance of the remaining data points are then computed and used to initialize the two-component unaligned population model as follows. The two population means are assumed (arbitrarily) to be 5% apart (2.5% above and below the overall unaligned mean). Given an (initial) assumption of equal priors and equal variances, then, the component variances are given by:

$$\sigma_{1,2}^2 = \sigma_{tot}^2 - \frac{1}{4}(\mu_2^2 - \mu_1^2)$$

where $\sigma^2$ is the variance and $\mu$ is the mean of the respective population.

2) Updated estimates of component population statistics (means, standard deviations, and priors) are computed using the Parzen density estimate. Each histogram bin location is weighted in the statistical computations by the Parzen density estimate in that bin. Additionally, each data point contributes to all component population statistic computations weighted by the degree to which that point is believed to belong to a given population, based on the current component population parameters. This degree of membership is determined as the ratio of a given component population (Gaussian) probability density value to the sum of all component population probability density values at the data point. Thus we have (for all data points x in the histogram, populations $c_p \in \{c_x, c_y, c_u\}$, and population parameter vector $\theta_p = [\mu_p, \sigma_p, P_p]$) population component memberships used in the computation of updated parameter estimates given by:

$$P(c_p | x, \theta_p) = P_p \cdot \frac{1}{\sigma_p \sqrt{2\pi}} \exp\left[-\frac{(x-\mu_p)^2}{2\sigma_p^2}\right]$$

$$\text{membership}(c_p | x, \theta_p) = \frac{P(c_p | x, \theta_p)}{\sum_{n \neq p} P(c_n | x, \theta_n)} \cdot \text{ParzenDensityEstimate}(x)$$

Updated means and variances are then computed using the Parzen density estimate values weighted by these membership values, with updated priors given by the average membership for each component population over all data points.

3) Parameter updating procedure continues until all parameters reach steady-state (i.e., stop changing significantly from one update iteration to the next (or a maximum allowed number of iterations occurs)).

As previously mentioned the aligned X and Y populations are constrained in this procedure to have the same variance and prior probability. This constraint is achieved by using the average of the X and Y variance and prior values computed via the above procedure at each iteration.

Alternatively, a similar modeling approach can be applied to a three-component model (FIGS. 62-63) in which the cells comprising the two unaligned populations 6001, 6003 in the four-component model are treated as a single Gaussian distribution 6011 rather than two distinct subpopulations. The non-aligned cells can be modeled as third Gaussian distribution (shown FIG. 63) having a mean and standard deviation determined by a best fit of the left shoulder and left major peak of the raw data 6010 (shown FIG. 62). The three-population model also has estimated statistics for the aligned Y Population 6015 and aligned X Population 6017. One advantage of the three-component model is that it requires only 9-dimensional parameter space (compared to 12-dimensional parameter space required for the four-component model). However, it has been found that the four-component model typically results in an estimated density function that more closely matches the raw data.

Those skilled in the art will recognize that a wide variety of statistical techniques can be used to estimate the characteristics of the aligned X and aligned Y populations. Thus, the four-component model, the three-component model, or other models may be implemented by any parametric or non-parametric computer algorithms to estimate the characteristics of the aligned X cell and/or aligned Y cell populations without departing from the scope of this invention.

L. CV-Based Selection of Staining Conditions

Several factors affect the efficiency of sorting stained cells within a population into enriched subpopulations of cells. Among these factors is the amount of differential fluorescence between the various subpopulations of cells within a stained population. Differential fluorescence is affected by dye uptake, which varies based upon staining factors, such as for example, the concentration of the stain, the length of the staining period, the temperature at which staining occurs, and the number and concentration of any additives that may be included with the stain or added to the staining mixture. Accordingly, adjustments to any or all of these factors may be made to increase the sorting efficiency (the rate at which cells may be sorted into at least one enriched subpopulation of cells with certain degree of purity and/or a minimal loss of desired cells) of the population of stained cells. Further, one can increase efficiency of a multi-sample sorting system by adjusting one or more of these factors for each sample, thereby countering any sample-to-sample variations. In the context of bovine sperm sorting, for example, sorting efficiency can be improved by adjusting one or more of the foregoing staining factors from one semen sample to the next to counter bull-to-bull variations or sample-to-sample variations within the same bull.

A determination of the coefficient of variation ("CV") for a given fluorescence emission characteristic of a population of cells to be sorted is one manner in which to determine if adjustments to the staining conditions could be made to achieve a desired sorting efficiency. For example, one may adjust the staining conditions as a function of the CV of any feature extracted from the pulse waveform generated by movement of a cell through the interrogation location, such as any feature indicative of total fluorescence intensity or peak fluorescence intensity (including total fluorescence intensity and peak fluorescence intensity). As previously discussed in greater detail, CV is an indicator of the homogeneity or consistency of a distribution of a measurable property or characteristic of a population, such as for example a fluorescence emission characteristic of a particular subpopulation of a given population. CV may be determined by dividing the standard deviation of the measured characteristic of a sample by the sample mean. CV can also be determined automatically by the flow cytometry system 9, such as by implementation of the iterative CV estimation algorithm discussed in detail above. The lower the CV, the greater the homogeneity or consistency of the distribution of the measured characteristic.

As applied to the staining and separation of sperm cells, the CV of a particular fluorescence emission characteristic for a sample of X and Y chromosome bearing sperm cells may be affected by the staining conditions. The concentration of the stain, the length of the staining period, the temperature of the staining mixture, and/or the number and concentration of additives affect the CV of a given fluorescence emission characteristic. Increasing the concentration of the stain, the length of the staining period, and the temperature of the staining mixture and/or decreasing the number and concentration of additives will generally lower the CV. Such conditions may be altered individually or in combination. In addition, if any one of these factors is such that it would tend to increase the CV of a fluorescence emission characteristic, such as for example, by shortening the staining time, then any one or more of the other conditions may be adjusted such that it counteracts the effect of the first, such as for example, by increasing the dye concentration, with the overall result being a decrease in the CV of the fluorescence emission characteristic to a level sufficient to achieve a desired sorting efficiency. Accordingly, by manipulating any one or any combination of these factors in this manner, the CV of a fluorescence emission characteristic of the X and Y chromosome bearing populations may be decreased to a value that enables sorting of the sperm sample into a subpopulation of gender enriched semen comprising a desired percent purity of X chromosome bearing cells.

Unfortunately, changes that tend to lower the CV of the X bearing sperm may have negative consequences such as increased cost or decreased sperm motility or fertility. For example, other things being equal it is desirable to use lower stain concentrations and shorter staining periods to minimize any harmful impact of the staining process on the sperm. With this in mind, one may predetermine a CV at which an acceptable sorting efficiency will be achieved. Thereafter, a fraction of the cell sample to be sorted is stained and subjected to flow cytometric analysis. A fluorescence emission characteristic of the fraction is determined, and the fraction is classified into subpopulations based upon the characteristic. The CV of the fluorescence characteristic is determined with respect to the cells of one of the subpopulations (an enriched subpopulation). If the CV of the fluorescence emission characteristic of the cells of the enriched subpopulation is equal to or less than the predetermined CV at which sorting is to occur, then the remainder of the cell sample is stained according to the conditions under which the fraction was stained. The sample is thereafter sorted, for example, according to the methods disclosed herein. If the CV of the particular fluorescence emission characteristic of the cells of the enriched subpopulation is greater than the predetermined CV at which sorting is to occur, then another fraction of the same sample is analyzed in a similar manner, but under staining conditions believed to achieve a yet lower CV. In such a situation, the CV may be lowered by, for example, increasing the length of the staining period, increasing the concentration of the dye, increasing the temperature at which the fraction is stained, or any combination thereof. This series of steps (i.e., removal of a fraction from the sample to be sorted, adjustment of the staining conditions, and a determination of the CV) is repeated until the CV of the particular fluorescence emission characteristic of the cells of the enriched subpopulation is determined to be equal to or lesser than the predetermined CV. Thereafter, the remainder of the sample is stained accordingly and may be sorted, for example, according to the methods disclosed herein. In a particular embodiment of the invention, the cell sample comprises a semen sample, and the cells of the enriched subpopulation comprise X chromosome bearing sperm cells.

Accordingly, one embodiment of the invention is a process for evaluating a set of conditions for staining a population of cells for sorting, the population comprising a first type and a second type of cell. The process comprises (a) staining a fraction of the population of cells with a fluorescent dye under a set of staining conditions; (b) exposing the stained cells to electromagnetic radiation as the stained cells are passed through an interrogation location of a flow cytometer at a rate, R; (c) determining a fluorescence emission characteristic of the exposed cells; (d) using the determined fluorescence characteristic to classify the cells into two or more sub-populations, one of the subpopulations being an enriched subpopulation of the first cell type; (e) determining a coefficient of variation for the fluorescence emission characteristic of the cells of the enriched subpopulation; and (f) determining whether to modify any staining condition under which the cells are to be stained or the rate, R, at which the stained cells are passed through the interrogation location of the flow cytometer. In another embodiment, another fraction of the population of cells is stained under a different set of staining conditions and steps (b) through (e) are repeated with that fraction. This process may be performed on two, three, four or any number of additional fractions. In another embodiment, multiple fractions of cells are drawn from the sample at the same time. Each fraction may be stained simultaneously, or each may be stained subsequent to the previous fraction being passed through the flow cytometer. In the former case, each fraction may be stained with its own unique set of staining conditions and step (f) may comprise using the respective CVs to determine a set of staining conditions to be used to stain additional cells. In the later instance, the staining conditions of the subsequently stained fractions may be altered according to the determination of step (f) with respect to a previously analyzed fraction. In one embodiment the process is repeated until the CV is determined to be about equal to or less than a specified CV (e.g., 1.3%).

Alternatively, once one has predetermined a CV at which an acceptable sorting efficiency will be achieved, the entire cell sample may be stained. A fraction of the cell sample is removed and subjected to flow cytometry analysis. A fluorescence emission characteristic of the fraction is determined and used to classify the cells into two or more sub-populations. The CV of the fluorescence characteristic is determined with respect to the cells of an enriched subpopulation. If the CV of the fluorescence emission characteristic of the cells of the enriched subpopulation is equal to or less than the predetermined CV at which sorting is to occur, then the remainder of the cell sample is thereafter sorted. If the CV of the particular fluorescence emission characteristic of the cells of the enriched subpopulation is greater than the predetermined CV at which sorting is to occur, then a second fraction from the same sample is analyzed in a similar manner and the CV of the same fluorescence characteristic is determined. The CV of the second fraction may be lowered by, for example, increasing the length of the staining period, increasing the concentration of the dye, or any combination thereof. This series of steps (i.e., removal of a fraction from the sample to be sorted and a determination of the CV) is repeated until the CV of the particular fluorescence emission characteristic of the cells of the enriched subpopulation is determined to be equal to or lesser than the predetermined CV. Thereafter, the remained of the sample may be sorted, for example, according to the methods disclosed herein. In a particular embodiment of the invention, the cell sample comprises a semen sample, and the cells of the enriched subpopulation comprise X chromosome bearing cells.

Accordingly, another embodiment of the invention is a process for evaluating a set of conditions for staining a population of cells for sorting, the population comprising a first type and a second type of cell. The process comprises (a) staining a fraction of the population of cells with a fluorescent dye under a set of staining conditions; (b) exposing the stained cells to electromagnetic radiation as the stained cells are passed through an interrogation location of a flow cytometer at a rate, R; (c) determining a fluorescence emission characteristic of the exposed cells; (d) using the determined fluorescence emission characteristic to classify the cells into two or more subpopulations, one of the subpopulations being an enriched subpopulation of the first cell type; (e) determining a coefficient of variation for the fluorescence emission characteristic of the cells of the enriched subpopulation; (f) determining whether to modify any staining condition under which the fraction of cells are to be stained or the rate, R, at which the stained cells are passed through the interrogation location of the flow cytometer; and (g) applying the modified staining condition to the remainder of the population of cells. In another embodiment, steps (a) through (f) are repeated at least once with at least one other fraction of the population of cells. Steps (a) through (f) may be repeated once, twice, three times, four times or a greater number of times. In another embodiment, multiple fractions of cells are drawn from the sample at the same time. Each sample may be stained simultaneously, or each may be stained subsequent to the previous fraction being passed through the flow cytometer. In the later instance, the subsequent staining of the fractions may be altered according to the determination of step (f) with respect to a previously analyzed. In still another embodiment, the process further comprises prior to step (g), selecting the modified staining condition that results in the lowest coefficient of variation for the fluorescence emission characteristic. In yet another embodiment, the process comprises the repetition steps (a) through (e) until the coefficient of variation for the fluorescence emission characteristic of at least one of the fractions is about 1.3% or less. In another embodiment of the invention, the process further comprises prior to step (g), selecting the modified staining condition that results in a coefficient of variation of about 1.3 or less.

In addition to performing such an analysis before sorting the entire sample as detailed above, a similar analysis may be performed while the staining and sorting of the sample is occurring in an effort to ensure that sorting efficiency is maintained. Accordingly, in another embodiment, the CV of a fluorescence emission characteristic of the cells of an enriched subpopulation of a fraction of a sample that has been previously stained, a portion of said sample which is in the process of being sorted, is determined as described above. Adjustments to the staining conditions under which these sample was stained are made according to the methods discussed above with respect to the presort adjustments.

The selection of a predetermined CV at which an acceptable sorting efficiency will be achieved is based upon several factors, including for example, the type of cell being sorted, the rate of sorting, and the degree of purity desired with respect to sorting of the population into enriched subpopulations. Generally, a CV is selected that will allow for sorting to the desired percent purity of the enriched subpopulation while minimizing the amount of time necessary to achieve the same, such as for example, by achieving an 85% degree purity of the enriched subpopulation while minimizing the length of the staining period. With these factors in mind, the CV of the fluorescence emission characteristic of the cells of an enriched subpopulation is generally between about 2.0% and about 1.0%, preferably between about 1.5% and about 1.0%, more preferably about 1.4%, and still more preferably about 1.3%.

M. Critical Slope Difference Feature Extraction

The microprocessor 131' with digital signal processing (DSP) illustrated in FIG. 40 employed as part of a cell sorter makes it possible to extract features of the time resolved fluorescence emission pulse, particularly features that cannot be easily or inexpensively obtained using analog technology. In particular, a pulse feature which exhibits non-linear properties and which significantly improves the separation and thus the resolution of particles A and B (e.g., improves the discrimination of live, aligned X sperm cells) is a feature referred to as critical slope difference (CSD). CSD is a quantification of the slope of the fluorescence emission pulse at a signal amplitude where the difference between the first derivative of a pulse produced by particle A (e.g., a X-bearing cell) and the first derivative of a pulse produced by particle B (e.g., a Y-bearing cell) approaches a maximum.

Functions that describe fluorescence emission pulses may be expressed in terms of signal amplitude as a function of time: y=x(t). Within the context of detecting CSD features, a function may be defined that describes the fluorescence emission pulses in terms of pulse duration time as a function of signal amplitude. This function may be referred to as an M function. The M function is obtained by transposing the fluorescence emission pulse function as shown below.

Figure 62:
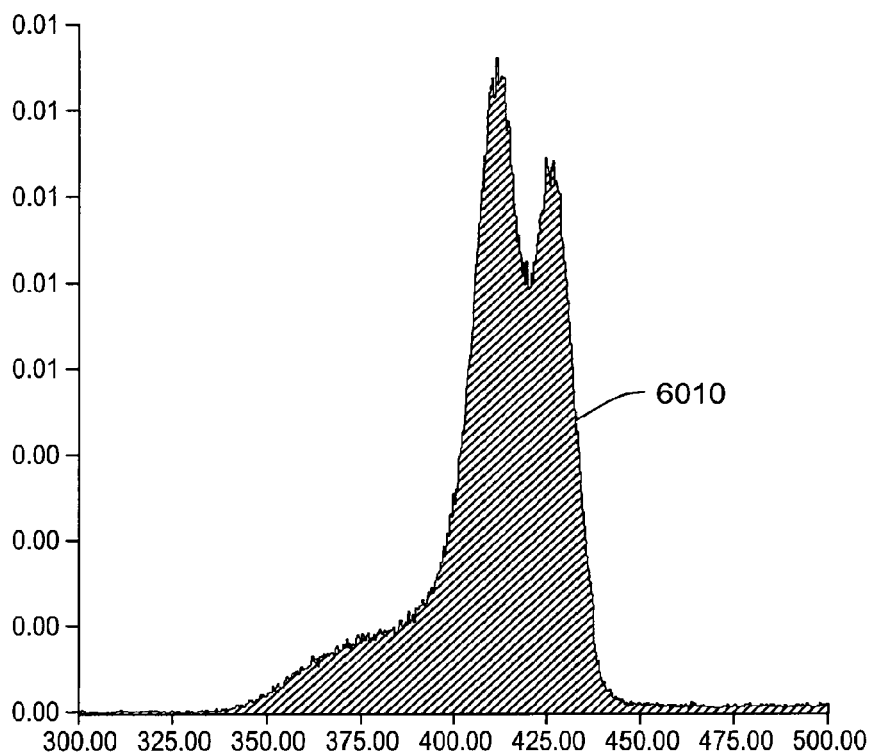
FIGS. 62-63 illustrate a three-component model of a fluorescence intensity histogram for sperm cells
Figure 63:
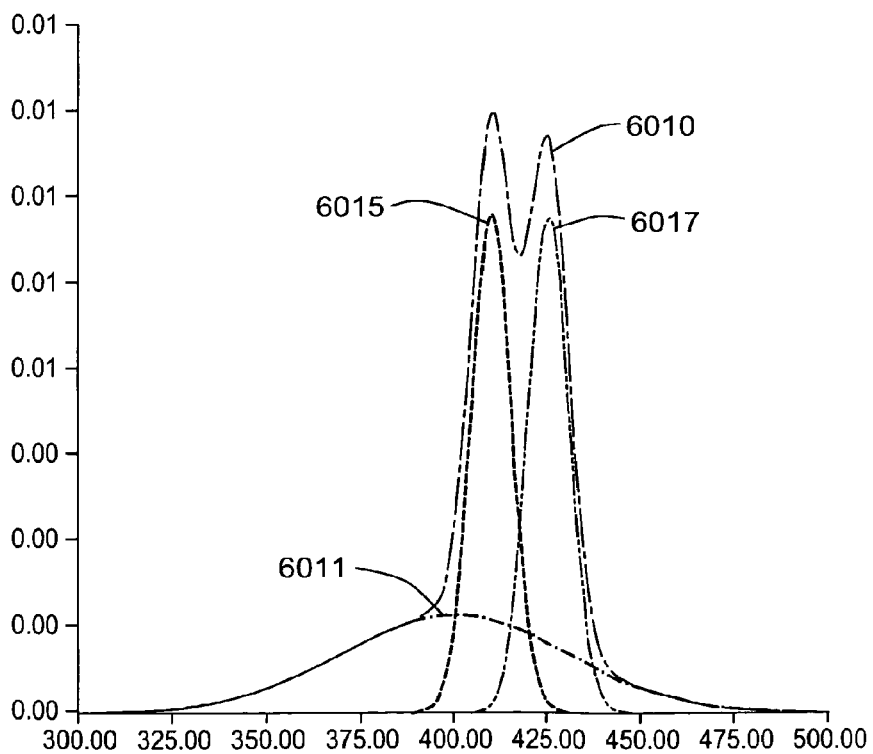
Figure 64:
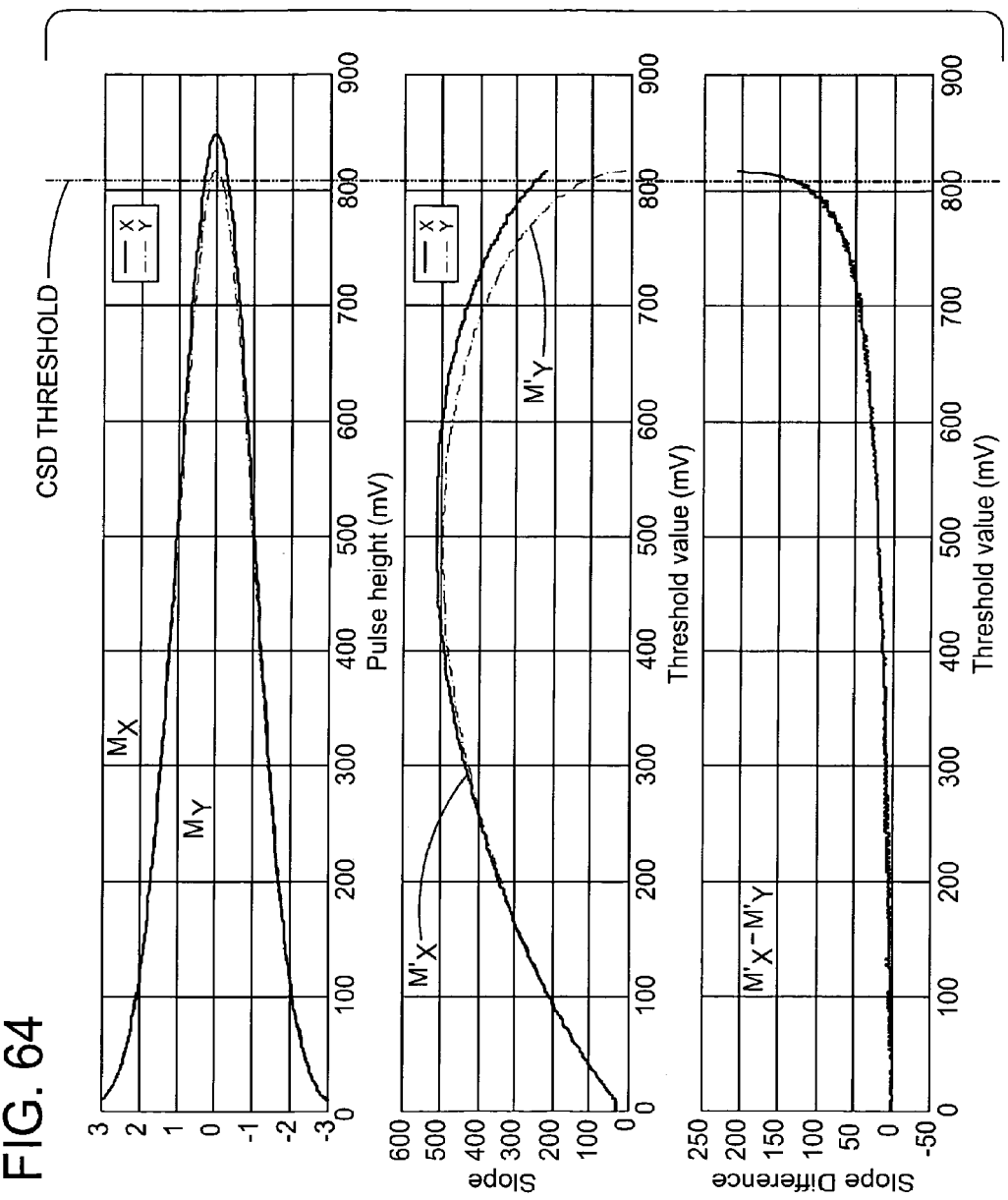
FIG. 64 illustrates the non-linear nature of the CSD feature; the top panel shows average M plots for X-bearing and Y-bearing sperm cells; the middle panel shows a graph of the first derivatives of these average M plots (i.e. M') for signal amplitude values less than the peak height of the average Y-bearing fluorescence emission pulse; and the bottom panel shows the difference between the first derivatives ($M'_x-M'_y$) as a function of signal amplitude.

Fluorescence Emission Pulse function: y=x(t)
  M Function: t=M(y)
  t=pulse duration
  y=signal amplitude Comparison of the M functions for typical X and Y bovine sperm cells illustrates the discriminating power of the CSD feature. The top panel of FIG. 64 shows average M plots for X-bearing and Y-bearing sperm cells. The middle panel in FIG. 64 shows a graph of the first derivatives of these average M plots (i.e. M') for signal amplitude values less than the peak height of the average Y-bearing fluorescence emission pulse. It can be seen in this plot that as signal amplitude approaches the average peak height of the Y-bearing pulse, the difference between the first derivatives ($M'_Y$ and $M'_X$) increases significantly. Plotted in the bottom panel of FIG. 64 is the difference between the first derivatives ($M'_X$–$M'_Y$) as a function of signal amplitude. The CSD feature quantifies the slope of M (M') for an individual pulse near the region where the maximum difference in first derivatives occurs (or the slope at a corresponding point on the fluorescence emission pulse function). For the purpose of discriminating X and Y bearing sperm cells, CSD is determined for each pulse at the point where the leading edge of the pulse intersects the CSD threshold, as shown in FIGS. 62-63. In some embodiments, CSD may depend upon the characteristics of the illuminating beam such as beam width whether the beam is continuous or pulsed. An algorithm for determining CSD is discussed below with regard to FIG. 65.

FIG. 64 illustrates that in some cases the CSD feature has a non-linear nature, such as in the case of sorting X-Y sperm cell populations. The difference between the derivatives ($M'_X$–$M'_Y$) increases as the CSD threshold approaches the peak of the Y pulse. The nonlinear characteristic of this difference places the mean value of the nonaligned cells and the aligned Y cells 45% lower than the mean value of the aligned X cells in the CSD feature space. The standard deviation in the CSD feature space of the aligned X cells is largely unaffected (i.e. similar to that seen in the peak or area feature spaces). It is this nonlinear, high gain nature of the CSD feature that increases the number of aligned X cells that can be accurately discriminated.

Figure 65:
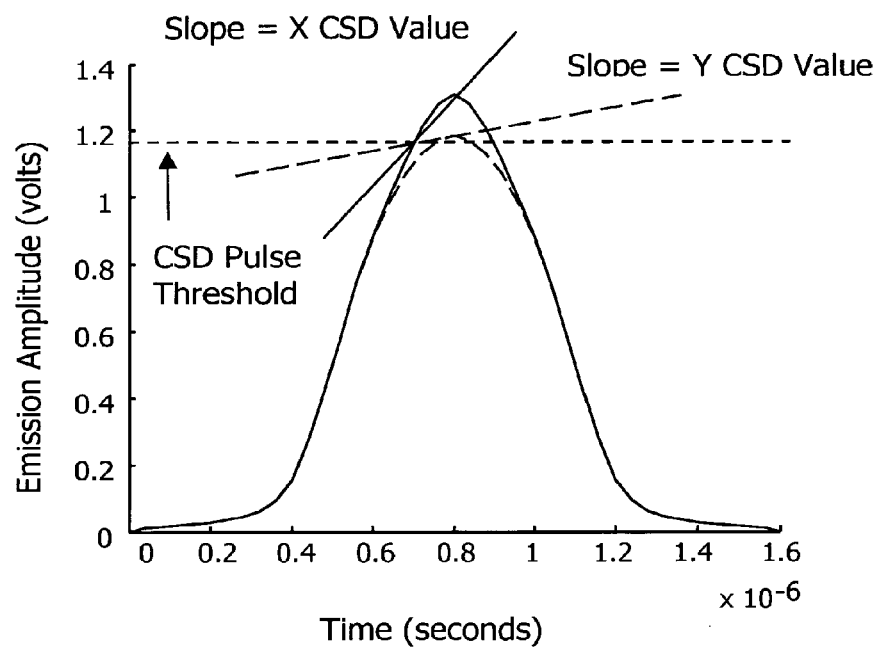
FIG. 65 illustrates one embodiment in which the CSD feature is the computed slope of a line that passes through two points on the fluorescence emission pulse.

One computationally efficient method for determining the CSD value for a given pulse is illustrated in FIG. 65. A CSD threshold may be determined as a function of a peak height of the fluorescence emission pulses. In particular, it may be determined based on the average peak height of the fluorescence emission pulses. The CSD threshold is maintained at a point where about 25% of the pulse peaks from live, aligned cells fall at or below the threshold. Therefore, the CSD threshold is adjusted dynamically during the sort based on a running peak height distribution (i.e., relative to an average peak height). For example, the threshold may be based on a weighted running average of peak height (with more recent measurements being given more weight than older measurements). The CSD value is the slope of a line that passes through two points on the pulse. These points are the CSD pulse threshold and the pulse peak. Thus, in this embodiment the CSD value is only an approximation of the slope of the pulse waveform 497 at the intersection of the leading edge of the pulse and the CSD threshold. However, other methods of computing the CSD value for a given pulse are readily apparent, some of which can provide more precise CSD values if desired.

In another embodiment, the CSD threshold is dynamically adjusted as a function of the CV of the CSD feature extraction for a subpopulation of particles. In the case of sorting sperm cells for example, by increasing the CSD threshold from a relatively low level (e.g., the pulse detection threshold) the CSD threshold will reach a level that results in a substantial increase in the CV of the CSD of the Y cells but is still low enough that the increase in the CV of the CSD for the X cells is significantly lower in comparison to the CV increase in the Y cells. This effect can be observed in the CSD distribution as a fanning out of one subpopulation in the overall CSD distribution. Good discrimination from the CSD feature can be achieved by maintaining the CSD threshold at this level.

It should be noted that the discriminating power of the CSD feature is enhanced by use of slit scanning approach to flow cytometry. The shape of the beam spot 459 can influence the shape of the pulse waveform 497. For example, by using a beam spot 459 having a relatively small width W1, a localized fluorescence difference in a sample particle (e.g., the localized fluorescent intensity difference resulting from localization of the X or Y chromosome in the central region 225 of a sperm nucleus 213) has a greater influence on the first order derivative of the pulse waveform. Accordingly, one embodiment of the present invention includes using the slit scanning techniques in combination with CSD feature extraction. Conversely, using a laser having a beam waist that is too large (e.g., equal to or greater than the diameter of the particles) may prevent effective use of the CSD feature to discriminate particles. The acceptable range for the width of the beam waist of the focused illumination beam will depend on a number of factors including the size and shape of the particles, the distribution of dye within the particles being analyzed, and the amount of difference between the typical waveform pulses for the particles to be discriminated. In the case of sperm cells, CSD feature extraction from waveform pulses 497 generated by excitation of bovine sperm cells 201 with a laser having a beam waist of less than 3 µm has worked well as indicated below. Of course, CSD feature extraction with any form of slit scanning discussed in the slit scanning section is considered to be within the scope of this aspect of invention.

Use of the CSD feature substantially increases the yield of the system, particularly in the case of sorting X-Y sperm cell populations because it allows collection of many more aligned X cells. Due to the overlap in the populations defined in peak vs. area or rise-time vs. area feature spaces, no more than about 70% of the aligned X cells can be discriminated with a certainty about or greater than 85%. When the CSD feature is used, 95% or more of aligned X cells can be discriminated, which significantly increases the percentage of live X cells that can be collected without reducing the purity of the population of collected X cells below a desired level of purity.

This is seen graphically in the live cell data shown in FIGS. 66-69. The non-linear nature of the CSD feature allows X cells to be isolated for sorting. The gross selection on CSD applied in the scatter plot shown FIG. 68 results in a 70% pure X area population. When bi-variate sort discrimination is applied in the area and CSD feature spaces (FIG. 68), >95% of the aligned X cells can be discriminated for sorting. The data in FIGS. 66-69 were collected at a total cell throughput of about 22,000 live cells per second on one channel of a four-channel cytometry system (see multi-channel system discussion below). Even with coincidence detection enabled (high purity), over 6,000 X cells per second were collected at a purity level of at least 85% purity.

Figure 67:
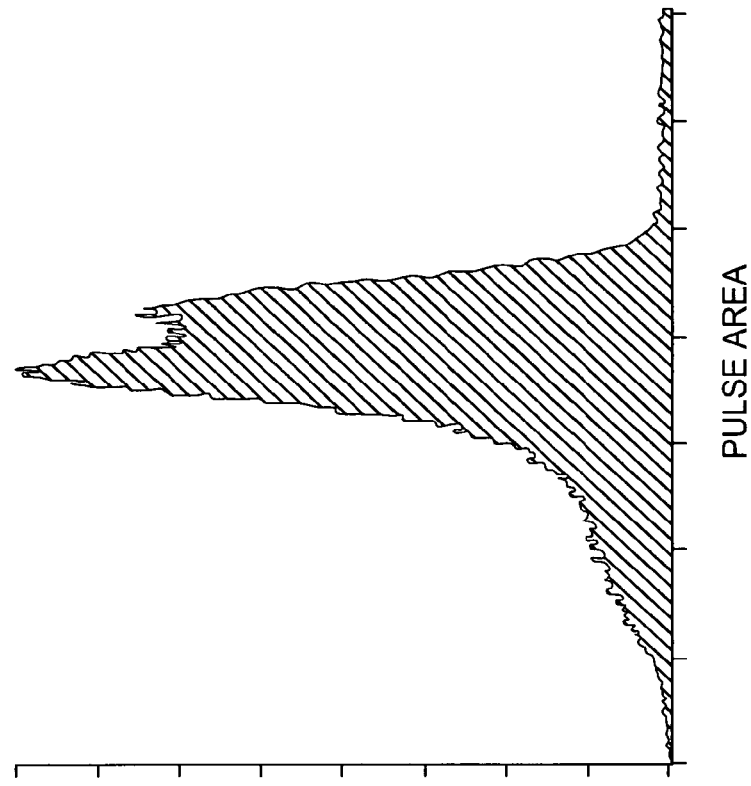
FIGS. 66-69 illustrate improved discrimination achieved by use of CSD feature extraction.
Figure 66:
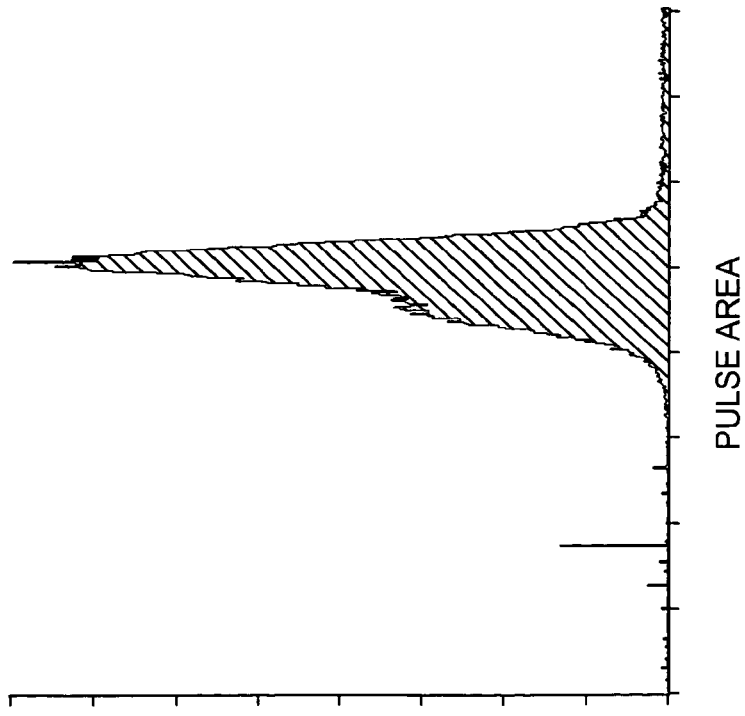
Figures 68, 69:
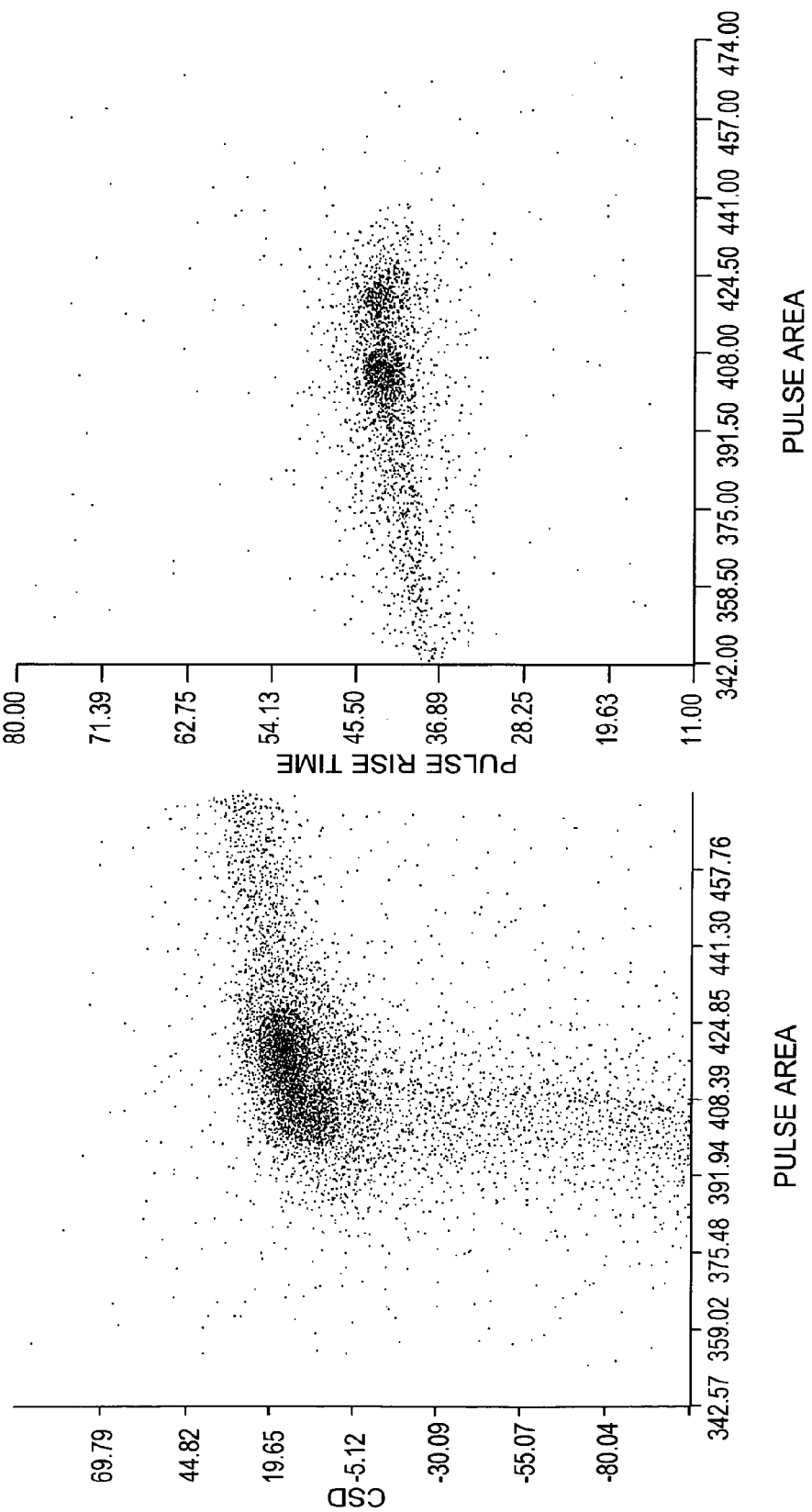

FIGS. 66-69 illustrate one advantage of the CSD feature when used to discriminate X-bearing and Y-bearing sperm cells. FIGS. 66 and 67 are histograms of the area feature of the fluorescence emission pulses for the feature space defined in the scatter plots shown FIGS. 68 and 69. In FIG. 68, the CSD feature has moved most of the non-aligned and aligned Y cells completely out of the display of the scatter plot. This leaves a 70% pure X population in the frame of the scatter plot, which is what is shown in the pulse area histogram in FIG. 66. Non-CSD discrimination is shown in the pulse area/rise time scatter plot shown in FIG. 69. Aligned X cells make up about 30% of the corresponding area histogram (FIG. 67). More than 95% of the aligned X cells can be collected at >85% purity using the CSD feature for discrimination. By comparison, no more than 70% of the aligned X cells can be discriminated using the traditional feature space on the right.

Figure 70:
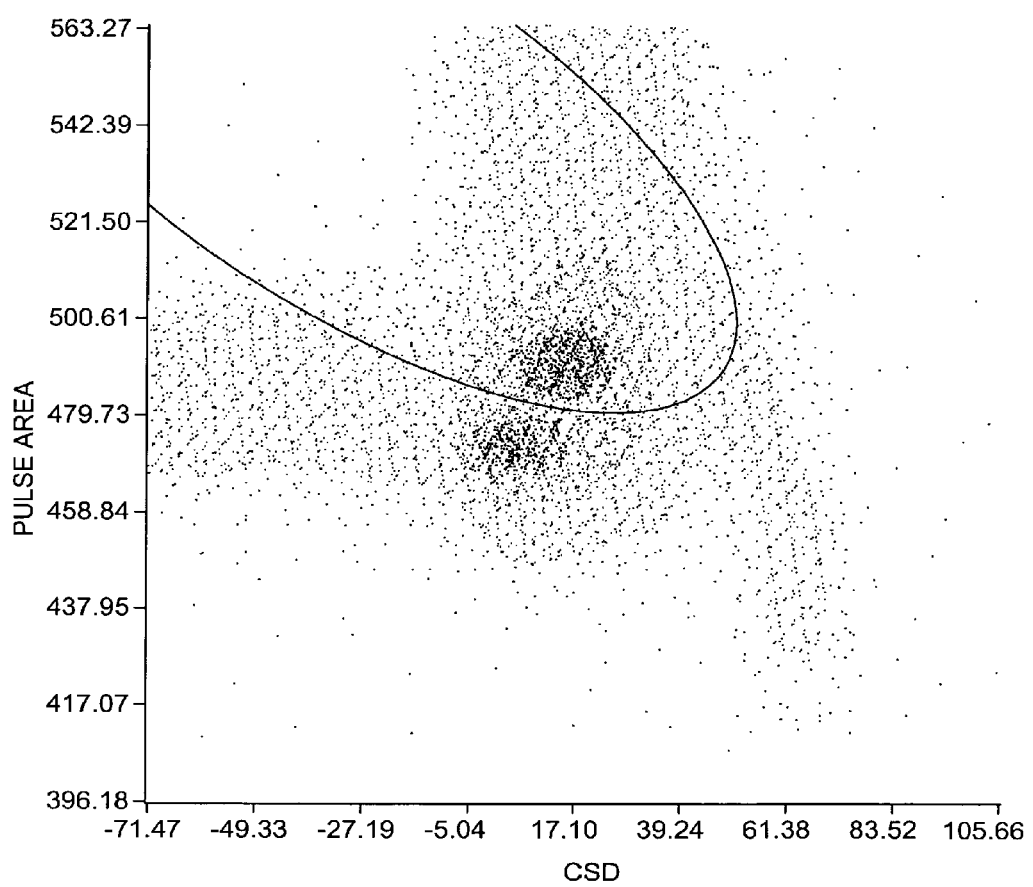
FIG. 70 illustrates a bi-variate sort region set on a scatter plot of CSD vs. pulse area scatter.

Several live cell sorts have been completed using the CSD vs. pulse area, bi-variate discrimination technique. FIG. 70 is an example of how a sort region set in this two dimensional feature space can be used to exclude non-aligned cells and Y cells. FIG. 70 illustrates a bi-variate sort region set on a scatter plot of CSD vs. pulse area scatter. Notice how the sort region drops lower on the area feature for high values of CSD (CSD increase from left to right and area increases from bottom to top) and moves higher on the area feature as CSD drops to lower values. The bi-variate sort region set on the above CSD vs. pulse area scatter plot was used to sort X cells at a sort decision rate >6000 X cells per second with a input live cell rate of 26,000 cells per second. Purity based on flow cytometry re-analysis was 87%.

The CSD feature makes possible a high yield, no-coincidence abort (i.e., coincident accept or high recovery) sorting strategy. In some embodiments, a pulse feature could provide nearly baseline separation and thus 100% accurate classification of live X and Y sperm cells. This condition would make it possible to sort cells at reasonably high rates without aborting droplets that contain both a cell classified as X and non-X (either unknown or Y). This sorting strategy is referred to as the high recovery or coincidence accept strategy. An experiment was performed to test this using the CSD feature. Coincidence accept sorts were performed with an input rate of 12,000 live X cells per second on one channel of a four-channel flow cytometer. 77% of the X cells were properly aligned, making 4,600 X cells per second potentially available for sorting. Under these conditions, 4,300 cells per second were sorted into the population of X cells. Subsequent purity analysis indicated a purity from this sort of >87% without correction for dead cells and 89% with correction for dead cells. A high purity, coincidence reject detection sort was performed immediately after this sort under the same conditions. A collection rate of 3200-3500 cells per second was observed. Purity analysis indicated a purity of 92% without correction for dead cells and a purity of 94% with dead cell correction.

The results of the above experiment indicate that at 12,000 live cells per second input, >92% of aligned X cells can be collected at a purity >85%. This is an indication that the CSD feature provides 95% accurate classification of all aligned X cells. Under these circumstances, yield from the cell sorter is limited primarily by correct cell alignment.

Figure 71:
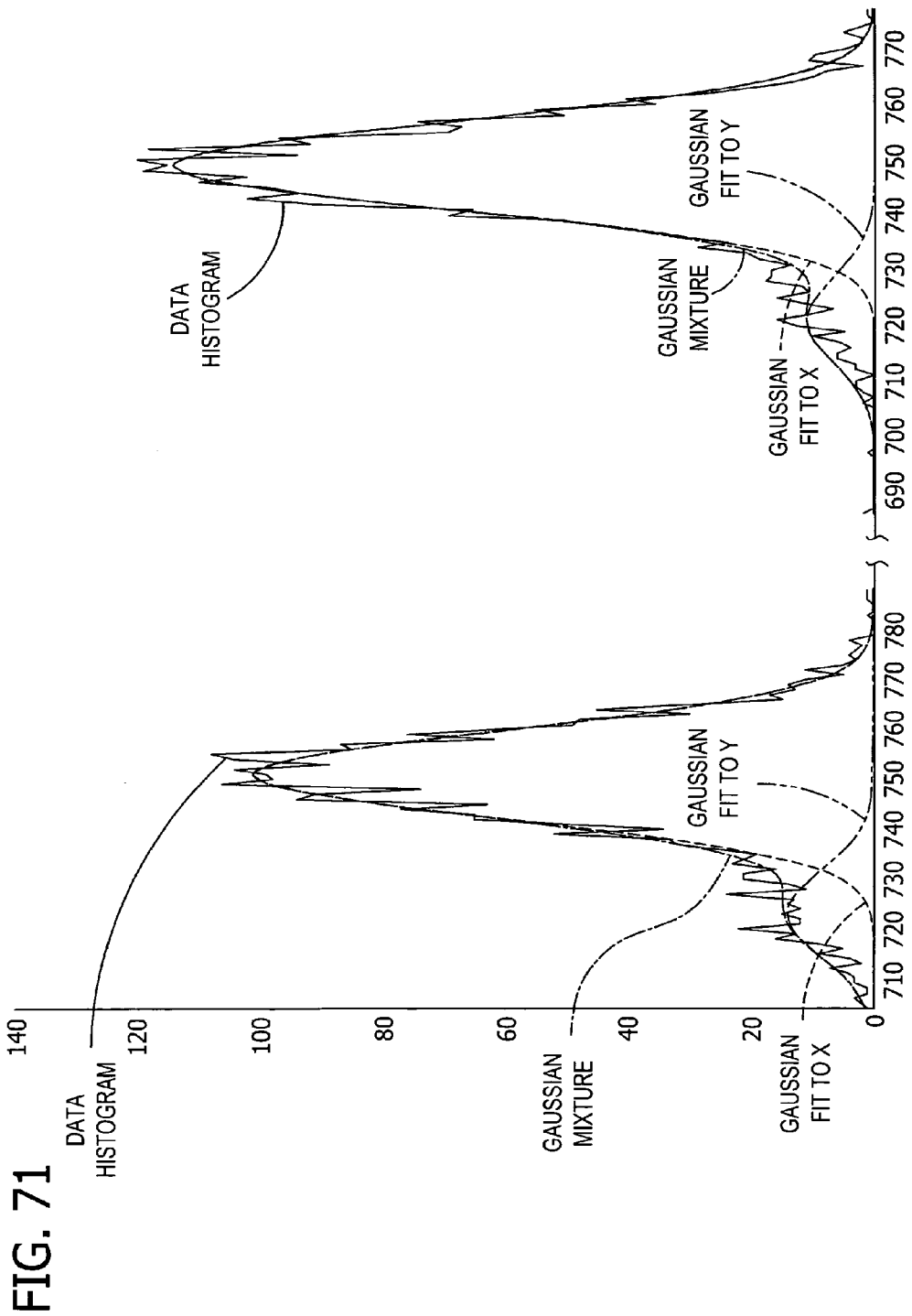
FIG. 71 illustrates one embodiment of flow cytometry re-analyses for a test in which the left panel corresponds to the high recovery/coincident accept sort strategy (no coincidence abort strategy) and the right panel corresponds to the high purity/coincident reject sort strategy (coincident abort strategy)

FIG. 71 illustrates one embodiment of flow cytometry re-analyses for a test in which the left panel corresponds to the high recovery/coincident accept sort strategy (no coincidence abort strategy) and the right panel corresponds to the high purity/coincident reject sort strategy (coincident abort strategy). The left panel (87% pure) was for an output of 4,400 X cells per second without coincidence aborts. The right panel was from a sort completed under the same conditions except droplets containing contaminating cells were aborted. Purity for this sort was about 92%. These sorts demonstrate that high recovery, no coincidence abort sorts are possible when the CSD feature is used for discrimination.

Use of the CSD feature is not limited to sorting of sperm cells or any particular species of sperm cells. As those skilled in the art will appreciate from the foregoing disclosure, the CSD feature can be adapted to improve discrimination between any groups of particles that generate signal pulses having different first order derivative characteristics regardless of the cause of the difference.

N. Discrimination

Once the features of the pulses have been extracted by pulse analysis software 749, discrimination (e.g., classification) of pulses is accomplished by pulse discrimination software 757 executed by processor 867 employing a logic application such as Bayes Minimum Risk decision rule. This rule is a modification of a Bayes Minimum Error decision rule that allows assignment (and adjustment for) differing costs associated with making different erroneous classification (e.g., discrimination) decisions.

Bayes Minimum Error computes the decision boundary 763 or decision surface as the surface of equal a posteriori probability between populations in feature space. For the case of (assumed) Gaussian probability distributions this surface is in general quadratic, although in certain conditions may be linear (or be able to be closely approximated by a hyperplane). The classification (e.g., discrimination) decision is made by first computing the a posteriori probabilities for a given point in feature space (generally from class-conditional probability densities and known/assumed a priori population probabilities using Bayes Rule) then choosing the class label as that of the population having the highest a posteriori probability.

Figure 74:
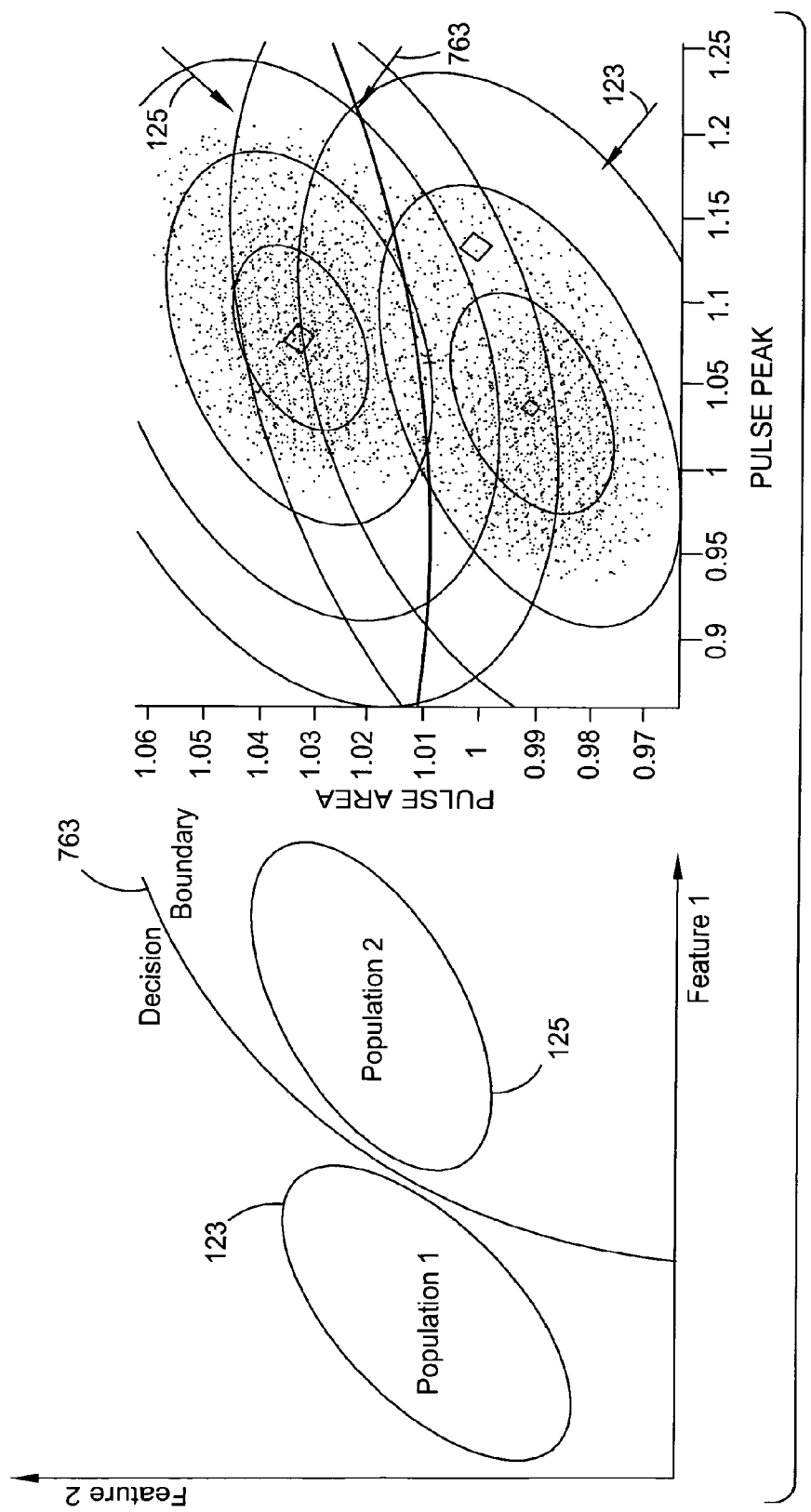
FIG. 74 is a conceptual illustration and graphical representation of application of a Bayes Minimum Error decision rule to pulse feature data as may be employed according to one embodiment of the present invention.

Bayes Minimum Risk includes a factor to allow adjustment of the decision boundary 763 in the case when it is desired to assign different costs for making different classification errors (e.g. it may be costlier to classify "Y" cells as "X" cells than vice versa). In this application, this allows a trade-off between sorted sample purity and recovery. In this decision rule, the "risk" of assigning each possible class label to a point in feature space is computed as the sum of the a posteriori probabilities of membership in each population times the cost associated with classifying as the current population given true membership in each other population. Table 6 summarizes the procedure for Bayes Minimum Error classification. Note that for multi-variate Gaussian densities, evaluation of Bayes rule to obtain the a posteriori probabilities may be reduced to evaluation of the quadratic function seen in Table VII, given that the coefficients W, w, and $w_o$ are as computed in the discrimination algorithm parameter initialization procedure given in Table 3. FIG. 74 shows a graphical example of classification by this procedure. The illustration on the left is a schematic illustration of the two populations 1 and 2 and the decision boundary 763 separating the populations. The histogram on the right shows two concentric sets of ellipses defining the X and Y regions, with the decision boundary 763 being a line defined by the intersection of the ellipses.

TABLE VII

Summary of digital fluorescence pulse classification (discrimination) by Bayes Minimum Error decision rule.

| | |
|---|---|
| Algorithm: | Bayes Minimum Error fluorescence pulse classification (discrimination) |
| Input: | vector of floats pulseFeatures, for each class population i: matrix of floats $W_i$, vector of floats $w_i$, float $w_{i0}$ |
| Output: | integer classLabel |
| Procedure: | |
| 1. | For each class/population i, compute value of discriminant function $g_i$: $g_i$ = pulseFeatures $^t \cdot W_i \cdot$ pulseFeatures + $w_i^t \cdot$ pulseFeatures + $w_{i0}$ |
| 2. | For each class/population i, compute value of risk function $risk_i$: Initialize $risk_i$=0, then for each class/population j: $risk_i$ = $risk_i$ + $cost_{ij}$ * $g_j$ |
| 3. | Find j s.t. $risk_j$ = min($risk_i$) ∀ i. Return classLabel = j and exit. |

Figure 75:
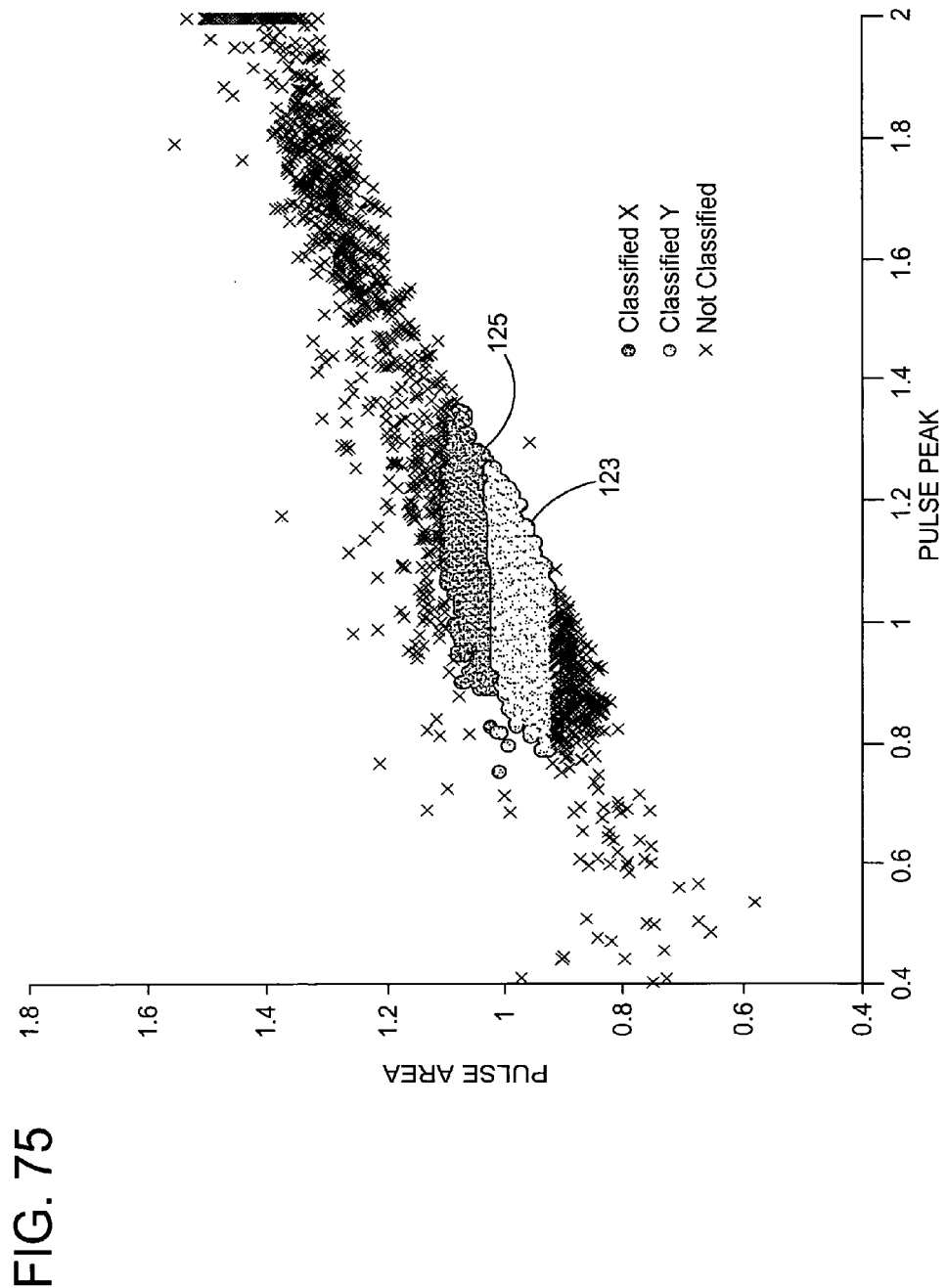
FIG. 75 is graphical representation of results obtained using a Bayes Minimum Error decision rule and Mahalonobis distance thresh holding as may be employed according to one embodiment of the present invention.

For additional robustness, an additional step is taken in the classification of digital fluorescence pulses. The Mahalanobis distance of a pulse in feature space from the population assigned via Bayes Minimum Error is computed, and if greater than a threshold, the pulse is labeled as "not classified" or some other appropriate indication that it is not likely a member of any known population. FIG. 75 illustrates the effect of this additional step, again using features computed from digitally acquired fluorescence pulse data.

In general, the A/D converter 689 converts the analog output signals 701 from the photodetector 117 into corresponding digital information 707 indicative of characteristic A or characteristic B (e.g., X or ~X). The digital signal processor 865 extracts features from the digital information and processor 873 provides a sorting signal 853 to the sorting system as a function of the extracted features.

O. Sort Classification and Droplet Synchronization

The fourth, sort processor 873 manages droplet classification, implements sorting strategy and delivers a sort trigger pulse 853 that is synchronized with the droplet selected for sorting. This processor 873 receives cell classification information from the discrimination processor 867 and relates that information to the droplet generation clock 703 (i.e. aligns the position of particles classified for sorting into a population with the formation of droplets). It determines if there is coincidence within a droplet and manages that coincidence based on pre-determined sort strategies. It maintains a FIFO of all cell classifications and droplet sort decisions that sets the correct delay between when the particle was observed in real time and when the particle arrives at the last attached droplet. It will produce a properly timed output pulse 853 of appropriate polarity and amplitude for each droplet selected for sorting.

In general, the A/D converter 689 converts the analog output signals 701 from the photodetector 117 into corresponding digital information 707 indicative of characteristic A or characteristic B (e.g., X or ~X). The digital signal processor 867 discriminates the digital information 707 as indicative of characteristic A or as indicative of characteristic B (e.g., X or ~X) and provides a sorting signal 853 to the sorting system 119 as a function of the discriminated digital information.

In general, the digital signal processors 863, 865, 867, 873 include instructions for detecting waveform pulses represented by the digital information, instructions for extracting features in the detected pulses and instructions for discriminating the detected pulses as a function of their extracted features. In addition, the processors include instructions for defining a decision boundary 763 discriminating between the extracted features representing characteristics A and the extracted features representing characteristic B. Further, the processors 863, 865, 867, 873 may optionally adjust the relative location of the decision boundary 763 with respect to the extracted features representing characteristic A and with respect to the extracted features representing characteristic B as a function of at least one of the following: (1) the purity of the at least one population with respect to either characteristic A particles or characteristic B particles, and (2) the quantity of characteristic A particles or characteristic B particles in the at least one population relative to the total quantity of characteristic A particles or characteristic B particles in the stream. For example, the processor may move the decision boundary 763 to include less of population 1 and more of population 2, or visa versa, based on the output of a particular sample or based on the desired output (e.g., as noted above with respect to the Bayes Minimum Risk decision rule to adjust the decision boundary for differing costs).

P. Drift Compensation

Given that over time the waveform pulses corresponding to the fluorescence emissions may vary or exhibit drift over time (due to staining variations, temperature change, sample age and/or other factors, for example), the system may optionally employ drift analysis software 761 (FIG. 72) defining dynamic thresholds which vary to compensate for any effects of drift. In particular, the pulse detection thresholds employed by software 747 may be adjusted for any slow variations in the signal background characteristics, and the discrimination algorithm of software 757 may adjust the decision boundary 763 (FIG. 74) to account for any drift in the populations in feature space.

Figure 76:
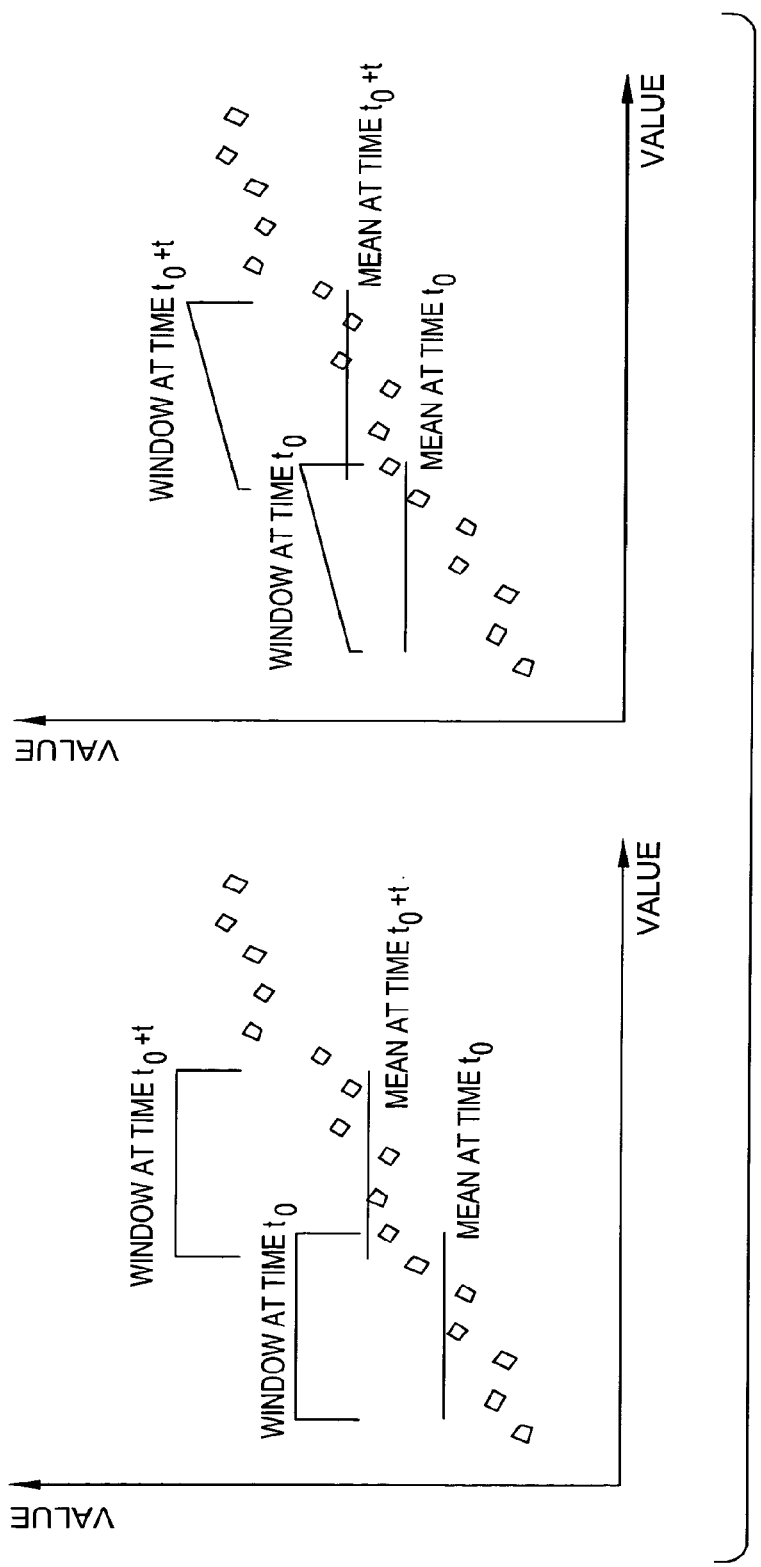
FIG. 76 is a conceptual illustration of moving window statistics to provide "forgetting" as may be employed according to one embodiment of the present invention.

In the case of the algorithm(s) employed by pulse detection software 747, the drift compensation software 761 accomplishes drift compensation by updating the background mean and standard deviation estimates based on sample statistics estimates computed within a moving window of a given length of samples (e.g., 10-100 samples) ending with the current sample. Given the (assumed) slow drift rate relative to the data acquisition frequency, the background statistics need not be updated every sample; rather, background statistic updates may occur periodically (e.g., every 6 seconds; see reference character 795 and FIG. 82). Additionally, the window may contain less than unity weighting to allow a "forgetting" rate to de-weight older samples relative to newer samples in the statistics computations. FIG. 76 illustrates the concept of statistic (mean) computation within a moving window without and with a "forgetting" rate.

Figure 77:
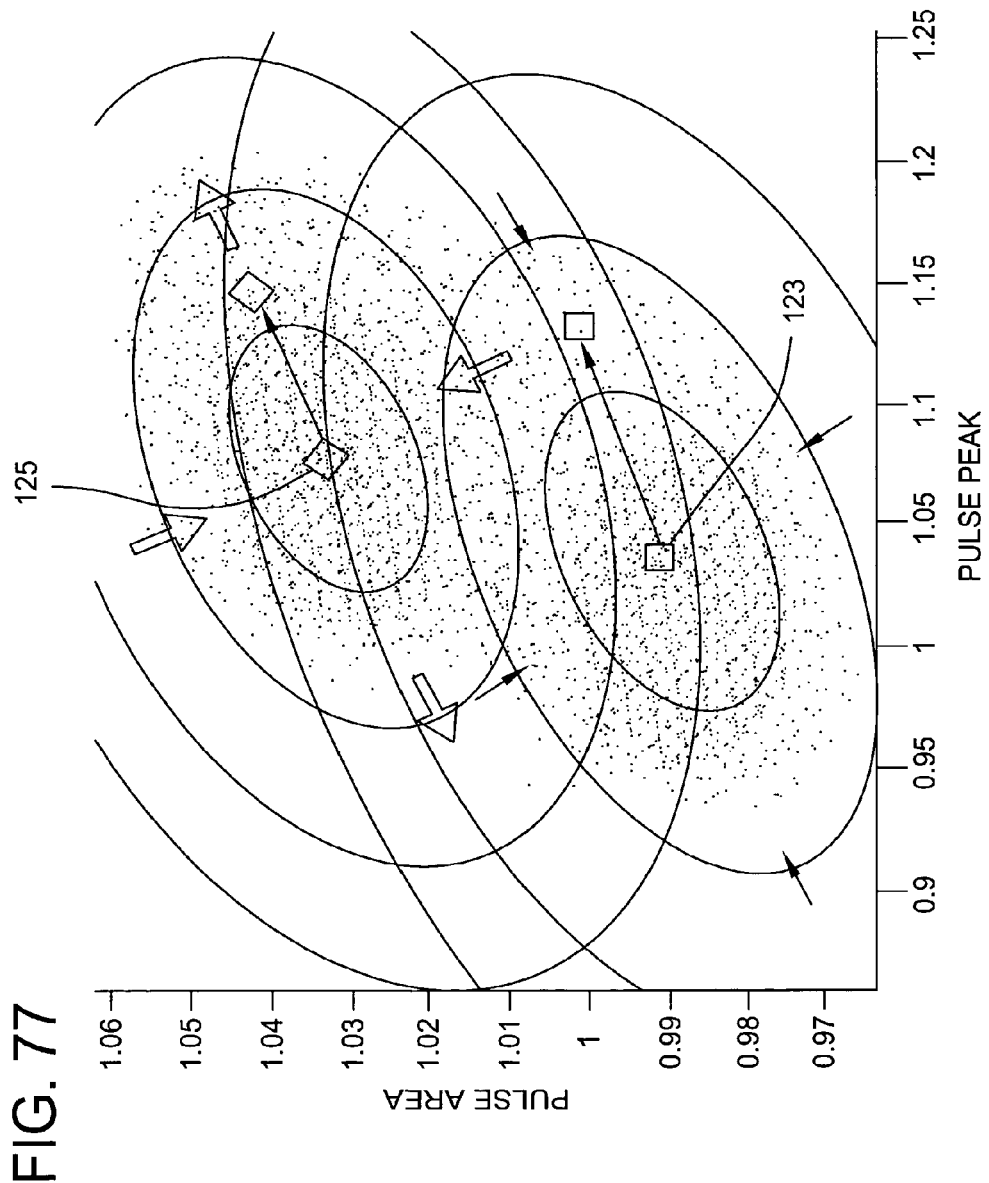
FIG. 77 is a graphical representation drift compensation as may be employed according to one embodiment of the present invention.

Similar to the detection algorithm drift compensation, the discrimination algorithm(s) employed by pulse discrimination software 757 achieve drift compensation by periodic updates of the $2^{nd}$ order statistics of the populations in feature space. In this case, however, only those feature values from pulses assigned to a given population are used to update the statistics of that population. Again, non-unity weighting may be used to include a "forgetting" rate. FIG. 77 shows a conceptual illustration of the effects of applying this technique to populations in feature space. FIG. 77 illustrates an example of drift compensation for population statistics in feature space. Yellow denotes population 1 (X), green population 2 (Y), diamonds the class mean estimates (with an exaggerated illustration of drift), and block arrows changes in the population covariance estimates reflected in deformation of the constant-sigma ellipses.

In general, the digital signal processor 863 employs a detection threshold for analyzing the digital information, which threshold is a function of a background mean estimate and a standard deviation of the sampled time-varying output signals computed within a moving window of samples ending with the current sample.

Q. Advantage of All Digital Techniques Over Analog Techniques

One of the main advantages for using an all digital system for sorting is that there is no "dead time" associated with the detection and analysis of a pulse. With analog systems there is always a finite "switching time" required for electronics to reset after the occurrence and detection of a pulse. This time is usually on the order of at least one microsecond. Since the digital system captures a continuous stream it really has no dead time.

Another advantage of a digital system is the ability to look forward and backward in time around a pulse classified for sorting. In general, the digital signal processing requires about five (5) droplet periods for analysis. Preferably, the time delay between droplet illumination 115 and droplet formation 107 is about seven (7) droplet periods. This allows the system to classify a particular particle based on the probability that it will contaminate the usable population as indicated by the features of the particular particle and based on the proximity of the particular particle to another classified particle. As an example, the sort processor 873 may reject a particle viewed as having a 50% probability of being a live X cell whereas the sort processor 873 may accept a particle viewed as having a 50% probability of being a live X cell when the particle is coincident with a second particle viewed as having a 95% probability of being a live X cell.

R. Analog Cell Analysis

Figure 42:
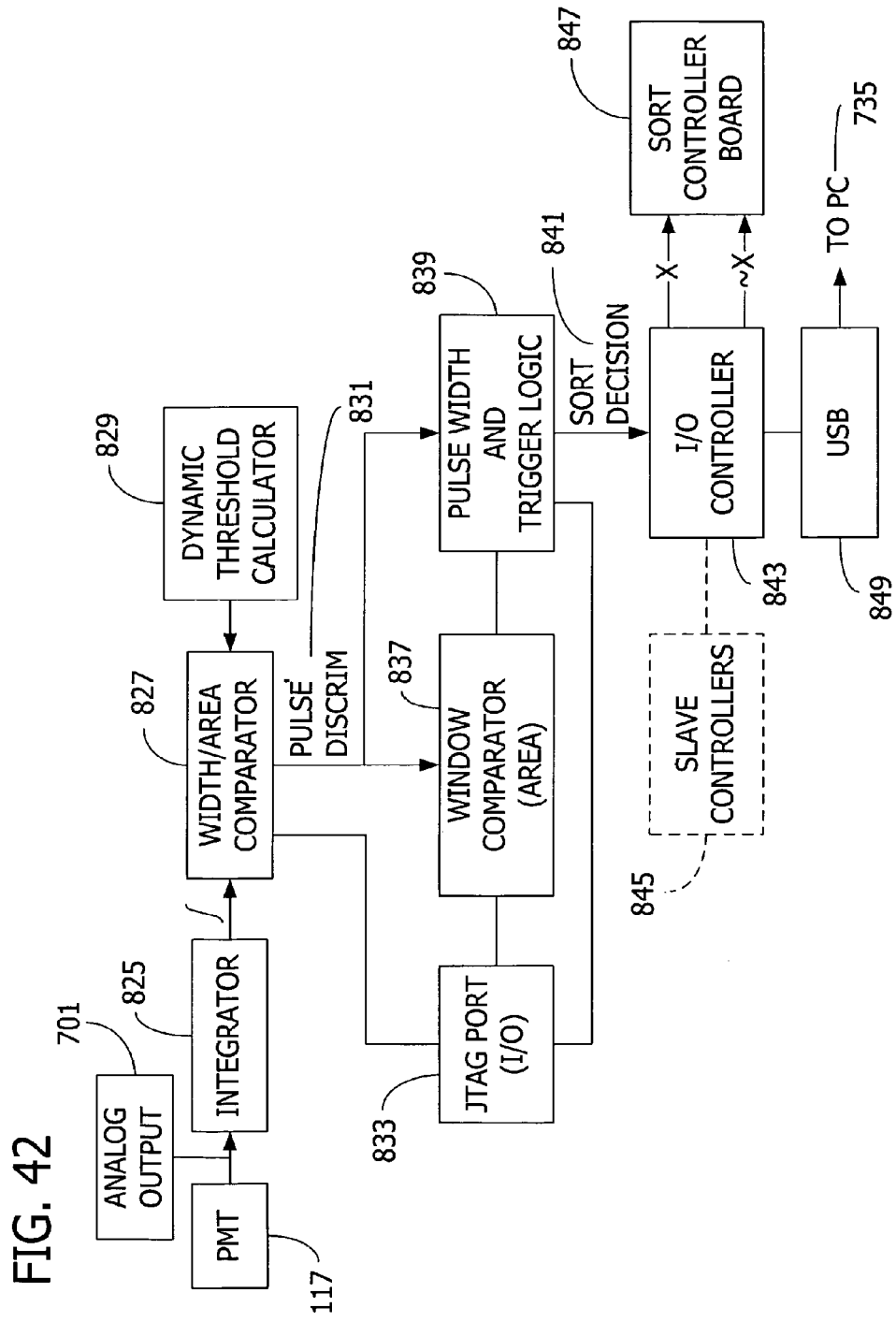
FIG. 42 is block diagram of one embodiment of an analog cell analyzer (ACA) according to the invention.

It is also contemplated that the time-varying output signals from the photodetector may be processed by analog circuitry 819, such as a field programmable gate array, which may be less expensive than a digital cell analyzer. FIG. 42 is a block diagram of one embodiment of an analog cell analyzer which may be employed as part of the system according to the invention. FIG. 53 graphically illustrates the analog analysis. A threshold is set to produce a trigger based on pulse height. The threshold opens an integration window which gates an analog integrator to accumulate charge. The window remains open either for a fixed period or until the pulse amplitude fall below the trigger threshold. In this way, only the area of the portion of the pulse within the integration window is used for relative fluorescence measurements.

Referring to FIG. 42, the output 701 of the photodetector 117 is supplied to an integrator 825 which integrates the output signal 701 in synchronization with the droplet clock 703. The integrated signal is provided to a width/area comparator 827 for comparing the level of the integrated signal to a threshold level defining a pulse (e.g., a pulse may be defined as an integrated signal with 40% of certain a certain threshold.). A dynamic threshold calculator 829 functions similarly to the drift compensation noted above in that monitors the integrated signal level and it varies the threshold level which the width/area comparator uses as a function of variations in the average integrated signal level.

The pulse discriminated signal is provided to a window comparator 837 to confirm that the pulse area is within an acceptable range. The pulse discriminated signal is also provided to a pulse width and trigger logic circuit 839 to confirm that the pulse width is within an acceptable range. If the area and width are acceptable, the logic provides a trigger signal to an I/O controller 843 which indicates the sort decision 841. Thus, the window comparator 837 and the pulse width and trigger logic 839 make the decision as to whether a cell should be classified as an X cell or a ~X cell.

The I/O controller 843 provides the sort decision 841 to the sort controller board 847 in the form of a X or ~X signal. The I/O controller 843 also includes a Universal Serial Bus (USB) interface 849 for connecting to the PC 735 and may have I/O port for connecting to slave controllers 845 of the other channels. The analog cell analyzer also includes a Joint Test Access Group (JTAG) port 833 for programming the width/area, comparator, the window comparator and the pulse width and trigger logic.

It is also contemplated that the analog cell analyzer may be employed simultaneously with the digital cell analyzer 705. For example, the analog analyzer may be used to adjust voltage thresholds used by the digital analyzer. On the other hand, the digital analyzer may be used to identify various features of the pulse and this feature information may be used to configure the analog cell analyzer, particularly if it is implemented with a gate array.

Control Strategies

In general, the microprocessor 131 is programmed to implement control and sorting strategies which are intended to optimize the efficiency of the system 1 in terms of throughput and/or loss of desirable particles to meet any cost requirements of the sorted product. This may involve, for example, balancing the need for high purity of at least one collected population and the need to recover at least a minimum percentage of desirable particles from the sample being sorted. Achieving such a balance is important, particularly in the context of commercial applications where cost and profitability are important considerations.

To this end, the microprocessor 131 implements a control strategy which is a series of instructions and/or algorithms that control system variables such as fluid delivery rate and/or sort parameters. The microprocessor also implements a sorting strategy which defines the decision process for determining how each particle or group of particles is sorted. Each particular control strategy may employ one or more sort strategies. Various sorting strategies may be used depending on such factors as the selected control strategy, the particle detection system and/or information relating to the particle distribution in the fluid stream.

Figure 78:
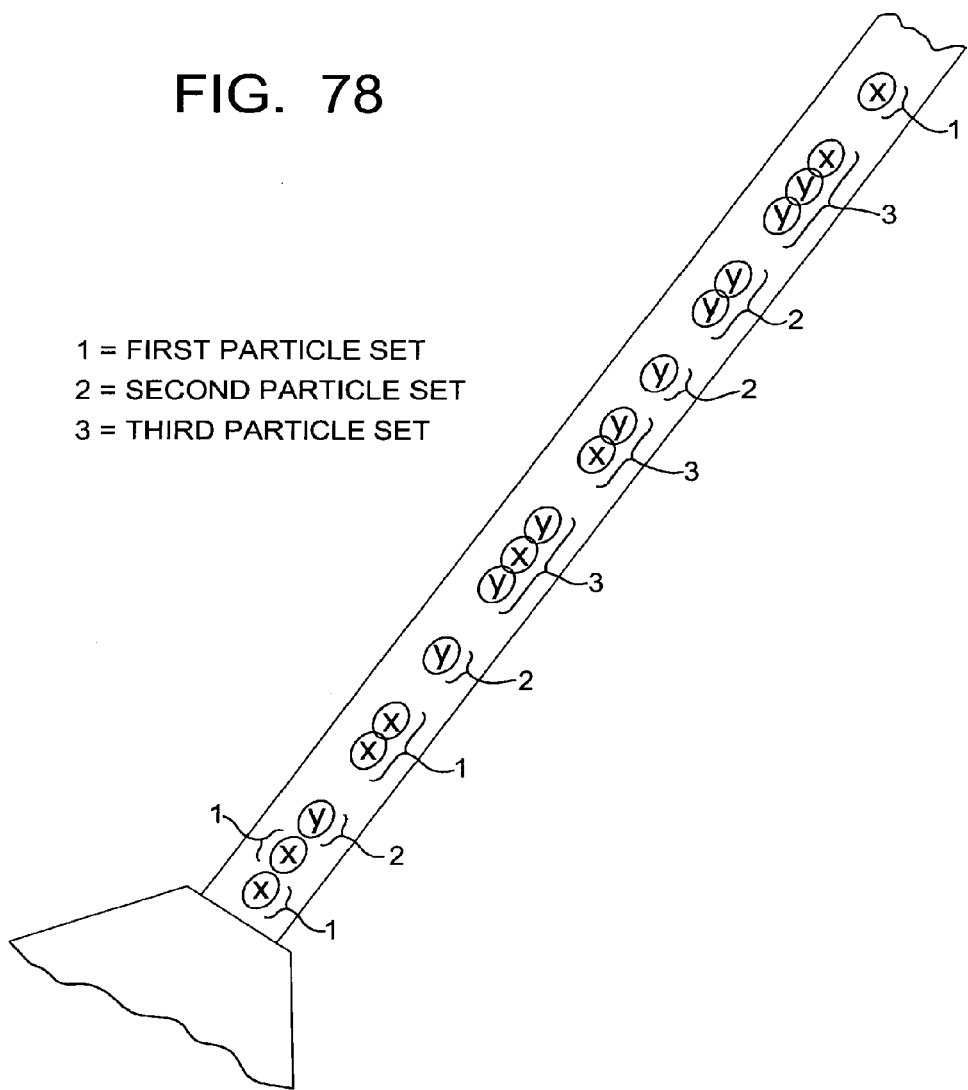
FIG. 78 illustrates a fluid stream containing an exemplary distribution of particles.

Regarding particle distribution, FIG. 78 illustrates a fluid stream containing an exemplary distribution of particles. In this particular example, the stream is formed by a nozzle similar to the nozzle described above and contains a mixture of particles having different characteristics A and B, e.g., X and Y sperm cells. As shown, the cells follow generally one after another in a series which can be viewed as comprising sequential sets of particles. These sets include first particle sets each comprising one or more particles having a characteristic A (e.g., indicating a live X sperm cell), second particle sets each comprising one or more particles having a characteristic B (e.g., indicating a Y sperm cell or, more generally, a sperm cell which is not a live X cell (~X), such as a Y cell, or a dead X or Y cell), and third particle sets each comprising two or more closely spaced particles at least one of which has characteristic A and at least one of which has characteristic B (e.g., one more X sperm cells and one or more ~X sperm cells). Third particle sets are also hereinafter referred to as "coincident" particle sets.

Whether a particular particle is considered as constituting a set by itself or part of another set will depend primarily on its spatial position and/or separation relative to adjacent particles. For example, in a droplet sorting system, the various particle sets will be defined by the particles in the droplets. In a photo-damage sorting system where a laser is used to ablate (kill or otherwise damage) selected particle sets to provide a collected population having a desired content, as discussed below in the "Photo-Damage Sorting" section, the various particle sets will be defined by the spatial proximity of the particles, i.e., whether the spatial separation between particles is sufficient to enable accurate classification of the particles and/or the ablation of one or more undesired particles by the laser without also ablating one or more desired particles. Similarly, in a fluid-switching sorting system where portions of the stream containing selected particles are diverted to provide a collected population having a desired content, as is discussed below in the "Fluid Switching Sorting" system, the various particle sets will be defined by the spatial proximity of the particles, i.e., whether the spatial separation between particles is sufficient to enable accurate classification of the particles and/or diversion of selected particles.

It will be observed from the foregoing that sort decision applied to the different particle sets may be varied, depending on the desired result or throughput of the system. For example, in a droplet sorting system, the sorting strategy used may depend on the treatment of "coincident" droplets, i.e., droplets containing third particle sets. In the handling of bovine sperm cells in a flow cytometry droplet sorting system and method as described herein, for example, to enhance the number of X sperm cells in at least one collected population, it may be desirable to use a strategy where each coincident droplet containing an X sperm cell is accepted and sorted as if it contained only X sperm cells, even though the droplet may also contain an ~X sperm cell (coincident accept strategy). On the other hand, to enhance the purity of X sperm cells collected in the stated population, it may be desirable to reject each coincident droplet containing a ~X sperm cell even though the same droplet may also contain an X sperm cell (coincident reject strategy). In general, as will be pointed out below, there are many control strategies which may be employed to maximize particle throughput and there are many sorting strategies that may by employed with each particular control strategy. The strategies can be applied to various sorting techniques using flow cytometry, such as droplet sorting, photo-damage sorting, and fluid-switching sorting. Further, the above strategies can be used to sort any type of particle according to any desired characteristic or characteristics of the particle.

According to one embodiment, the microprocessor controls the rate at which the fluid delivery system delivers the fluid containing the particles as a function of other variables of the system. For example, the microprocessor can the control the fluid delivery rate as a function of a desired output result. Since the microprocessor determines the identity of each particle and determines whether such is directed to at least one collected population, the microprocessor can determine and control the output result by varying the control strategy and/or by varying the sorting strategy. A desired output result may generally be defined as at least one of the following: (1) the purity of at least one collected population with respect to characteristic A particles or characteristic B particles ("high recovery"), and (2) the quantity of characteristic A particles in the stated population relative to the total quantity of characteristic A particles in the stream, or the quantity of characteristic B particles in the stated population relative to the total quantity of characteristic B particles in the stream ("high purity"). As another example, the system may employ a substantially constant fluid delivery rate and the microprocessor can the control the sort parameters as a function of a desired output result. In this latter example, the desired output result may generally be defined as a combination of (1) the purity of the particles in at least one collected population and (2) the quantity of desired particles available in the stream but not included in the stated population ("constant flow rate").

In general, it my be assumed that when sorting two populations an identified cell could have a 50/50 probability of being part of one population or the other. However, it is also contemplated that an unidentified cell may in fact have some other probability other than a 50/50 probability of being part of one population or the other. This other probability may be determined by empirical analysis or from other characteristics regarding the sample being sorted.

Several different control strategies are discussed in more detail below.

A. High Recovery Control Strategy

One type of control strategy may be referred to as a "high recovery" control strategy. The objective of this strategy is to maximize the number of desired particles sorted into the population of desired particles as long as the purity of that population is at or above an acceptable purity.

Pursuant to this strategy, the first particle sets described above are sorted into the population of desired particles because each of these sets contains one or more particles having a desired characteristic A. The third particle sets are also sorted into the population of desired particles (coincident accept) because each of these sets also contains one or more particles having a desired characteristic A, albeit accompanied by one more particles having characteristic B. On the other hand, the second particle sets are rejected (i.e., not sorted into the population of desired particles) because they do not contain a particle having the desired characteristic. To optimize throughput using this strategy, the microprocessor increases the fluid delivery rate as long as the purity of the collected population is at or above an acceptable level. Stated in the converse, the fluid delivery rate is increased as long as the probable level of contamination of the population of desired particles is at or below an acceptable level.

As an example, consider the use of a high recovery control strategy for sorting X and Y sperm cells in the fluid stream of FIG. 78. The desired result may be to sort all of the X cells into a population of X cells so long as the population remains at or above an acceptable purity, e.g., so long as $X/(X+Y)$ is greater than 85% or some other acceptable level. To obtain this result, the first particles sets are sorted into a population of X cells because they contain only one or more X cells. The third particle sets are also sorted into the population of X cells because they also contain one or more X cells, even though they may also contain a Y (or ~X) cell. The second particle sets are sorted into some other population because they do not contain one or more X cells. In this example, the rate at which the fluid delivery system delivers the fluid containing the cells to the nozzle would continue to be increased as long as the purity of the population of X cells is greater than 85%. Conversely, if the purity of the population of X cells falls below 85%, the fluid delivery rate is decreased.

Figure 79:
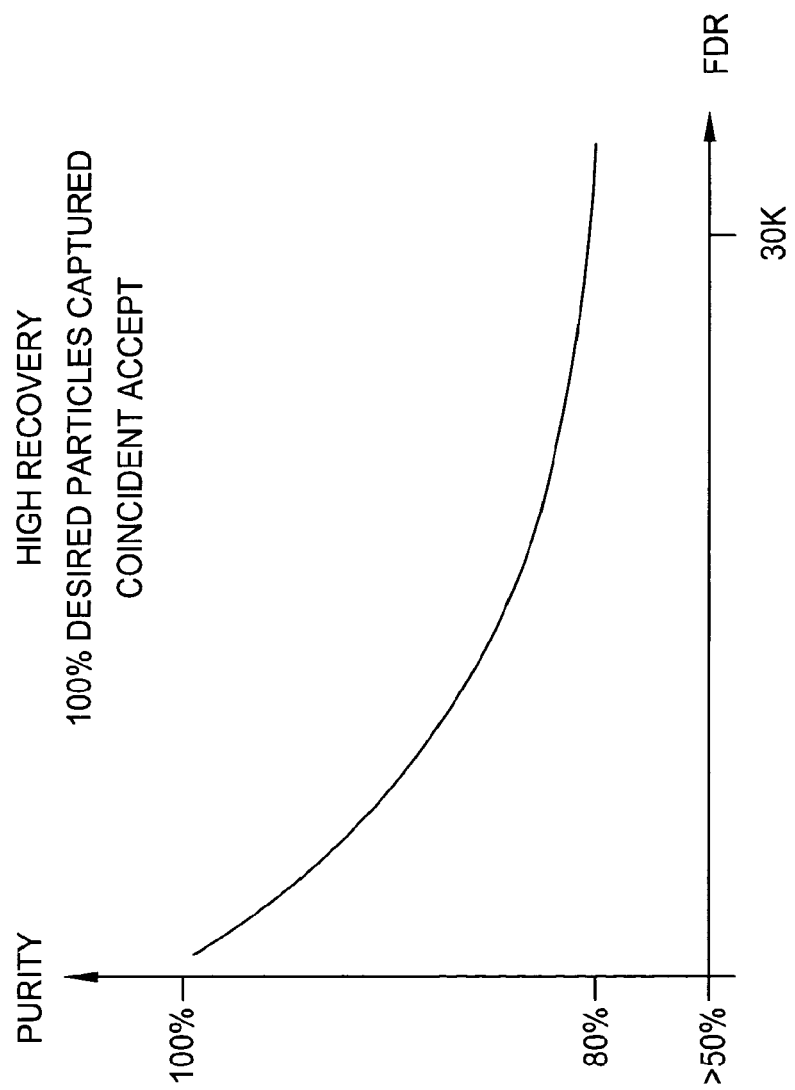
FIG. 79 is a graph showing purity as a function of fluid delivery rate with a coincident accept sort strategy.

In the context of a droplet sorting system, it is known from Poisson's equation that for any given droplet generation rate, the number of multiple-cell droplets will increase as the cell delivery rate increases. In other words, increasing the delivery rate of fluid containing the cells will increase the number of multiple-cell droplets. Therefore, if the coincident accept sorting strategy is used and coincident droplets containing third particle sets are sorted into the population of desired particles, increasing the fluid delivery rate will result in a decrease in the purity of the collected population because at higher fluid delivery rates more coincident droplets are being generated and collected. FIG. 79 illustrates this result for a two (2) particle fluid so that 100% of the desired particles are captured. As shown, at very low fluid delivery rates (FDR along x axis), the purity (y axis) of the resulting collected population is very high because very few coincident droplets containing third particle sets are being generated and collected. As the fluid delivery rate increases (FOR increases to the right along the x axis), the percentage of coincident droplets generated increases resulting in more coincident droplets being collected and reducing purity of the usable population (along the y axis). In the specific example illustrated, the fluid delivery rate is 30K particles/second at about 80% purity.

The results of using a high recovery strategy can be dramatic, as illustrated by a simple example where X and Y sperm cells are sorted using a droplet sorting process. Assume, for example that droplets are generated at a rate of 60 K/sec, and that sperm cells are delivered to the interrogation location at a rate of 30 K/sec. According to Poisson's equation, if all droplets containing X cells are sorted into the population of X cells, including coincident droplets containing X and Y cells, about 15,000 X cells will be collected every second. The collected population will include about 2,600 Y cells, reducing the purity of the population with respect to X cells to about 85.2%. However, the number of collected X cells (15,000) represents a substantial increase relative to a strategy where coincident droplets are not collected, as in the high purity strategy or mode discussed below. In the high purity mode, operating at a droplet frequency of 40 K/sec and cell delivery rate of 40 K/sec (10K cells/sec more than in the high recovery mode example above), only about 11,800 X cells are collected every second, or about 3,800 X cells less than in the high recovery strategy. Further, when the high purity strategy is used, about 9,200 X cells are lost or wasted because coincident droplets are not sorted into the population of X cells. Therefore, if less than 100% purity is acceptable, it may be desirable to use the high recovery mode to increase the number of X cells collected or, stated conversely, to decrease the number of X cells lost.

In summary, in the high recovery control strategy using the coincident accept sorting strategy, the particle delivery rate is inversely related to the purity of the collected population of desired particles (sometimes referred to as the "usable" population).

B. High Purity Control Strategy

A second type of control strategy may be referred to as a "high purity" control strategy. The objective of this strategy is to maintain the purity of the collected population with respect to particles having a desired characteristic at high level, so long as the quantity of desired particles in the collected population relative to the total number of desired particles available in the stream is at or above an acceptable quantity (i.e., so long as the quantity of desired particles in the stream which are not collected remains below an acceptable quantity). Pursuant to this strategy, the first particle sets described above are sorted into the population of desired particles because each of these sets contains one or more particles having a desired characteristic A, and because these sets contain no contaminating particles. On the other hand, the second and third particle sets are sorted into one or more "unusuable" populations (coincident reject) because they contain contaminating particles (i.e., characteristic B particles). To optimize throughput using this "high purity" strategy, the microprocessor increases the fluid delivery rate as long as the quantity of desired particles that are sorted into the usable population relative to the total number of desired particles available in the stream remains at or above an acceptable quantity.

As an example, consider the use of a high purity control strategy for sorting X and Y sperm cells in the fluid stream of FIG. 78. The desired result may be to sort all of the X cells in a into a population of X cells so long as the quantity of X cells collected from the stream remains at or above an acceptable quantity, e.g., at least 60%. To obtain this result, the first particles sets are sorted into the usable population because they contain only one or more X cells. On the other hand, the second and third particle sets are sorted into one or more unusable populations because they contain one or more contaminating (~X) cells. In this example, the rate at which the fluid delivery system delivers the fluid containing the cells to the nozzle would continue to be increased as long as the quantity of X cells collected in the usable population as a percentage of the total available quantity of X cells that have been sorted remains at or above 60%. Conversely, if the quantity of X cells not collected in the usable population rises above 40% of the total number of available X cells that have been sorted, the fluid delivery rate is decreased.

As noted above in the context of a droplet sorting system, it is known that increasing the fluid delivery rate will increase the number of multiple-cell droplets, and thus the number of coincident droplets containing third particle sets. Since coincident droplets are not sorted into the population of collected X cells when using a coincident reject sorting strategy, this means that increasing the fluid delivery rate will result in a increase in the quantity of live X cells lost to the unusable population.

Figure 80:
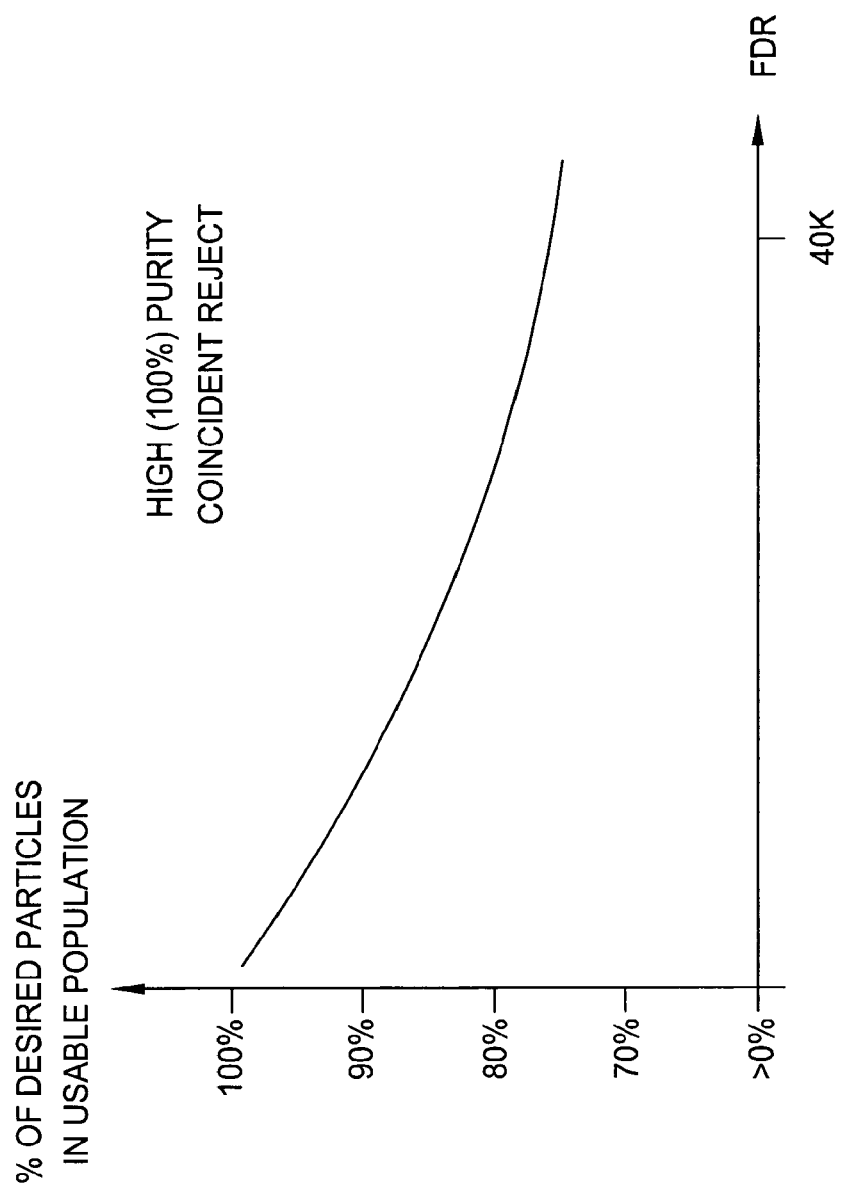
FIG. 80 is a graph showing the percentage of desired particles successfully sorted into the usable population as a function of fluid delivery rate with a coincident reject sort strategy.

FIG. 80 illustrates this result for a two (2) particle fluid so that the usable population has 100% purity of desired particles. As shown, at very low fluid delivery rates (FDR along x axis), the percentage of desired particles in the usable population is very high because very few coincident droplets are being generated and rejected. As the fluid delivery rate increases (FDR increases to the right along the x axis), the percentage of coincident droplets containing third particle sets increases and more such sets are rejected. This reduces the quantity of desired particles that are sorted into the usable population relative to the total quantity of desired particles available in the stream (i.e., the percentage of desired particles from the stream which are collected in the usable population). In the specific example illustrated, the fluid delivery rate is about 40 K particles/second and about 75% of the desired particles are sorted into the usable population.

In summary, in the high purity control strategy implementing the coincident reject sorting strategy, the particle delivery rate is inversely related to the percentage of desired particles in the collected population (i.e., high purity of desired particles in the usable population).

C. Constant Flow Rate Control Strategy

A third type of control strategy may be referred to as a constant flow rate control strategy. In this strategy, the microprocessor maintains the fluid delivery rate constant (or within a constant range) and varies the percentage of collected (or rejected) coincident droplets as long as the purity of at least one collected population is at or above an acceptable level and as long as the quantity of desired particles in that population is at or above an acceptable quantity relative to a total quantity of desired particles that have been processed. Stated in the converse, the fluid delivery rate is constant and the percentage of accepted (or rejected) coincident droplets varies as long as the probable level of contamination of the usable population is at or below an acceptable level of purity and as long as the probable quantity of desired particles that is lost to a population other than the stated (usable) population is at or below an acceptable quantity.

As an example, consider the use of a constant flow rate control strategy for sorting the fluid stream shown in FIG. 78. The desired result may be to sort X sperm cells into a usable population having a purity of at least 85% and to collect at least 60% of the X cells in the stream so that no more than 40% of the X cells are sorted into the unusable population. In this example, the rate at which the fluid delivery system delivers the particles would be maintained constant and the percent of collected or rejected third particle sets (coincident sets) would be varied as long as the purity of the usable population with respect to X cells is equal to or greater than 85%, and as long as the percentage of X cells sorted into the unusable population is less than 40% so that the percentage of desired particles sorted into the usable population is equal to or greater than 60% (variable coincident accept sorting strategy). As the percentage of accepted third particle sets increases, the purity of the usable population decreases, but the quantity of desired particles (e.g., X cells) sorted into the unusable population decreases. Conversely, as the percentage of accepted third particle sets decreases, the purity of the usable population increases, but the quantity of desired particles (e.g., X cells) that are sorted in the unusable population increases.

As noted above, it is known from Poisson's equation that the number of multiple-cell droplets (and thus the number of coincident droplets containing third particle sets) is constant for a constant fluid (cell) delivery rate. Since the number of coincident droplets is constant in this control strategy, the percentage of coincident droplets sorted into the usable population will impact both the purity of the usable population and the quantity of X cells that are wasted by being sorted into an unusable population. This is because the percent of unwanted Y (or ~X) cells in coincident droplets which are accepted and sorted into the collected unusable population is inversely related to the percent of X cells in coincident droplets which are rejected and thus not sorted into the collected usable population.

Figure 81:
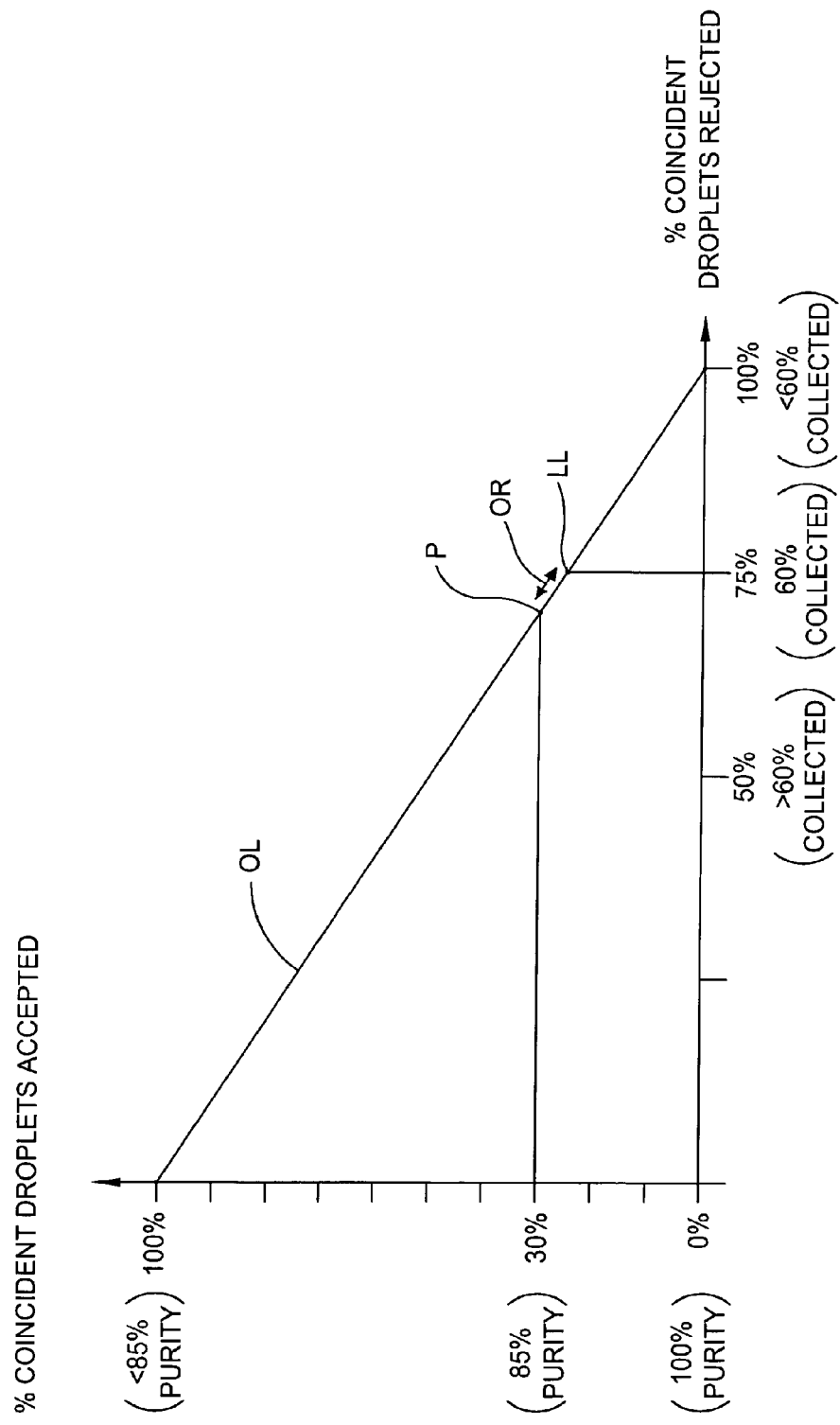
FIG. 81 is a graph showing the inverse relationship between the percentage of coincident droplets accepted for sorting into a population of desired particles compared to the percentage of coincident droplets rejected for sorting into that population.

FIG. 81 illustrates the constant fluid delivery rate control strategy in a flow cytometry droplet sorting system and method as described herein implementing a variable coincident reject sorting strategy for a two (2) particle fluid. As shown, line OL illustrates the inverse relationship between the percentage of rejected coincident droplets (x axis) compared to the percentage of accepted coincident droplets (y axis). When there is a very low percentage of accepted coincident droplets, there is a very high percentage of rejected coincident droplets. Conversely, when there is a very high percentage of accepted coincident droplets, there is a very low percentage of rejected coincident droplets. Line OL illustrates this inverse relationship and represents the operating line of the variable coincident accept sorting strategy at a given constant particle flow rate. At point P in FIG. 81 along operating line OL, the purity of the usable population is a given percentage depending on particle flow rate, e.g., 85% purity. As the percentage of accepted coincident droplets increases (to the left and upward) along operating line OL, the number of undesired particles that are sorted into the usable population increases and the purity drops below 85%, which may be unacceptable. As the percentage of accepted coincident droplets decreases (to the right and downward) along operating line OL, the purity goes above 85% and is acceptable.

At point LL along operating line OL, 75% of the coincident droplets are rejected (i.e., sorted into the unusable population) so that the percentage of desired particles that are wasted by being sorted into the unusable population is a given percentage based on the particle delivery rate, e.g., 40%. As the percentage of rejected coincident droplets increases (to the right and downward) along operating line OL, the percentage of desired particles that are sorted into in the usable population decreases (e.g., to <60%), which may be unacceptable. As the percentage of rejected coincident droplets (to the left and upward) along operating line OL, the percentage of desired particles sorted into the usable population increases (e.g., to >60%) and is acceptable. Thus, according to this aspect of the invention for a constant flow rate control strategy implementing a variable coincident accept sorting strategy, the microprocessor may operate the system so the percentage of accepted and rejected coincident droplets varies in an operating range between point P1 and LL as indicated by arrow OR. Note that operating range OR may encompass more or less of the operating line, depending on the level of tolerance for impurity and loss of desired particles to the unusable population.

In summary, in the constant flow rate control strategy using the variable coincident accept sorting strategy, the percentage of third particle sets which are accepted is inversely related to the purity of the usable population and inversely related to the quantity of desired particles wasted by being sorted to a unusable population.

D. Summary of Control Strategies

The following Table summarizes the control strategies noted above.

| CONTROL STRATEGY | HIGH RECOVERY | HIGH PURITY | CONSTANT FLOW RATE |
| --- | --- | --- | --- |
| Controlled parameter | Fluid delivery rate | Fluid delivery rate | Sort parameters |
| Controlling parameter: | Purity of population | Quantity of desired particles in population | Purity of population AND Quantity of desired particles in population |
| Sorting strategy | Coincident accept | Coincident reject | Variable coincident accept |
| X/Y Sorting strategy | Collect X droplets and X+~X droplets; reject ~X droplets | Collect X droplets; reject X+~X droplets and ~X droplets | Collect X droplets; vary percentage of collected X+~X droplets; reject ~X droplets |
| Definition | The fluid delivery rate is increased as long as the purity of the population with respect to X particles is at or above an acceptable level | The fluid delivery rate is increased as long as the quantity of desired particles in the usable population relative to the total quantity of X particles in the stream is at or above an acceptable quantity | The percentage of coincident droplets in the population is increased as long as the purity of the population with respect to X particles is at or above an acceptable level; to continue operation, the quantity of desired particles in the usable population relative to the total quantity of X particles in the stream must be at or above an acceptable quantity |

| CONTROL STRATEGY | HIGH RECOVERY | HIGH PURITY | CONSTANT FLOW RATE |
| --- | --- | --- | --- |
| Converse Definition | The fluid delivery rate is increased as long as the probability of contamination of the usable population is at or below an acceptable level of purity | The fluid delivery rate is increased as long as the probability of loss of the quantity of desired particles in an unusable population is at or below an acceptable quantity | The fluid delivery rate is increased as long as the probability of contamination of the usable population is at or below an acceptable level of purity AND as long as the probability of loss of the quantity of desired particles in the unusable population is at or below an acceptable quantity |
| Desired result | > minimum acceptable purity; e.g., >85% purity | >minimum acceptable quantity; e.g., >60% of desired particles captured (<40% of desired particles lost) | > minimum acceptable purity and >minimum acceptable quantity; e.g., >85% purity and >60% of desired particles captured (<40% of desired particles lost) |

Relatedly, a sorted sample obtained using one of the above control strategies can be combined with a second sample to obtain a final (e.g., commercial) sample having the desired characteristics. For example, a sample sorted according to the high purity strategy to produce a 100% pure population can be combined with a population of the same volume sorted to 80% purity to produce a final sample having a purity of 90%. Or in the case of animal sperm sorted to a high purity, an aliquot amount of the sorted sperm can be combined with an aliquot amount of unsorted sperm to produce a final sample of desired purity at lower cost than sorting the entire amount of sperm using any of the above sorting methods.

The above description of the control strategies assumes accurate identification and sorting of each droplet including each coincident droplet. In practice, 100% accuracy is not possible for any number of reasons. In order to minimize contamination, therefore, it may be desirable to reject particles which cannot be classified with certainty as belonging to the desired population. On the other hand, if certain particles can be identified and classified as being in the desired population within a certain selected probability (e.g., greater than 50% in the case of sperm cells), it may be desirable to classify the particles as belonging to the desired population so that they are not lost to the unusable population. Thus, as discussed earlier, particles such as sperm cells may be accepted or rejected for sorting into a population of desired cells based on the probability that such particles belong in the usable population.

The terms "usable" and "unusable" as used in the above table and this application are used for convenience only and are not intended to be limiting in any way. Thus, a "usable" population includes any "first" population, regardless of how or whether it is used, and an "unusable" population includes any "second" population different from the usable population, regardless of how or whether it is used. Similarly, a "desired" population means any population which is sorted according to selected particle characteristics.

The microprocessor and its signal processing software constitutes a system for processing the electrical signals from the photodetector to classify particles (e.g., particles in general and sperm particles in particular) according to characteristics of the particles and to obtain information relating to the distribution of the particles as described above with respect to FIG. 78. Furthermore, the microprocessor constitutes a control system responsive to the signal processing software for varying the rate at which the fluid delivery system delivers particles to the nozzle system as a function of the obtained information relating to the distribution of the particles. Furthermore, the microprocessor constitutes a control system responsive to the signal processing software for varying the sorting strategy as a function of the obtained information relating to the distribution of the particles.

In general, the microprocessor constitutes a control system responsive to information received from the flow cytometry apparatus for controlling the sorting system to vary its sorting strategy or for controlling the fluid delivery system. In other words, the microprocessor is capable of operating in a first mode to vary the sorting strategy, is capable of operating in a second mode for controlling the fluid delivery system, is capable of operating in a third mode to vary the sorting strategy and for controlling the fluid delivery system, and may be capable of operating in other modes. When operating in the first or third mode, the microprocessor is capable of varying the rate at which fluid is delivered as a function of at least one of the following: (1) the purity of the at least one population with respect to either characteristic A particles or characteristic B particles, and (2) the quantity of characteristic A particles or characteristic B particles in the at least one population relative to the total quantity of characteristic A particles or characteristic B particles in the stream.

Collection System

A collection system is needed to collect the droplets after they pass between the deflector plates. The collection system for a conventional cytometer may be no more than collection vessels disposed to catch the droplets in the various droplet streams after they pass between the deflection plates. Similar conventional collection systems can be used in some embodiments of the present invention.

However, it may be difficult to use a conventional collection system in embodiments of the present invention in which the nozzle is oriented to direct the fluid stream at an upward angle, thereby giving the droplets a horizontal velocity component. One issue is that the droplets would travel some horizontal distance along their arched trajectories before they begin downward movement that would be suitable for landing in a collection vessel. For example, if the nozzle is pointed upward at a range of 45° to 60° and the droplets exit at a velocity between 15 m/s and 20 m/s, the droplets will be a horizontal distance of several meters away from the nozzle before they reach the apex of their trajectories and begin downward movement. Thus, a good deal of lab space would be occupied by the droplet streams. Furthermore, at a range of several meters it could also be difficult to make sure the droplets land in the proper collection vessels. The trajectories of the droplet streams can change whenever one or more operating conditions for the cytometer change (e.g., adjustment to the fluid delivery rate resulting in a change in the fluid velocity at the nozzle orifice). Changes in the trajectories of the droplet streams will be magnified by the distance that the droplets travel. Thus, changes in the trajectories that do not result in an appreciable change in droplet location at a point relatively near the nozzle could result in a significant change in location of the droplets at a location that is farther away from the nozzle. As discussed above, some embodiments of the present invention employ feedback to the droplet formation and/or sample fluid delivery systems that could result in droplet streams that constantly alter their trajectories. One may also want to vary the pressure at which the sheath fluid is delivered to the nozzle. Air currents, temperature variations, and humidity variations could also alter the trajectories of the droplet streams. Any factor that could change the trajectory of the droplet streams could also require the collection vessels to be repositioned so the droplets land in the appropriate collection vessels. In contrast, the trajectories of droplets streams in a conventional cytometer having a downward pointing nozzle are less susceptible to variation. For example, the fact that the droplet streams have a substantially downward initial velocity means that variation in fluid velocity at the orifice does not result in any significant variation in the trajectories. Furthermore, the collection vessels are relatively close to the nozzle which makes the collection system more tolerant to trajectory variations in the droplet streams.

Figure 83:
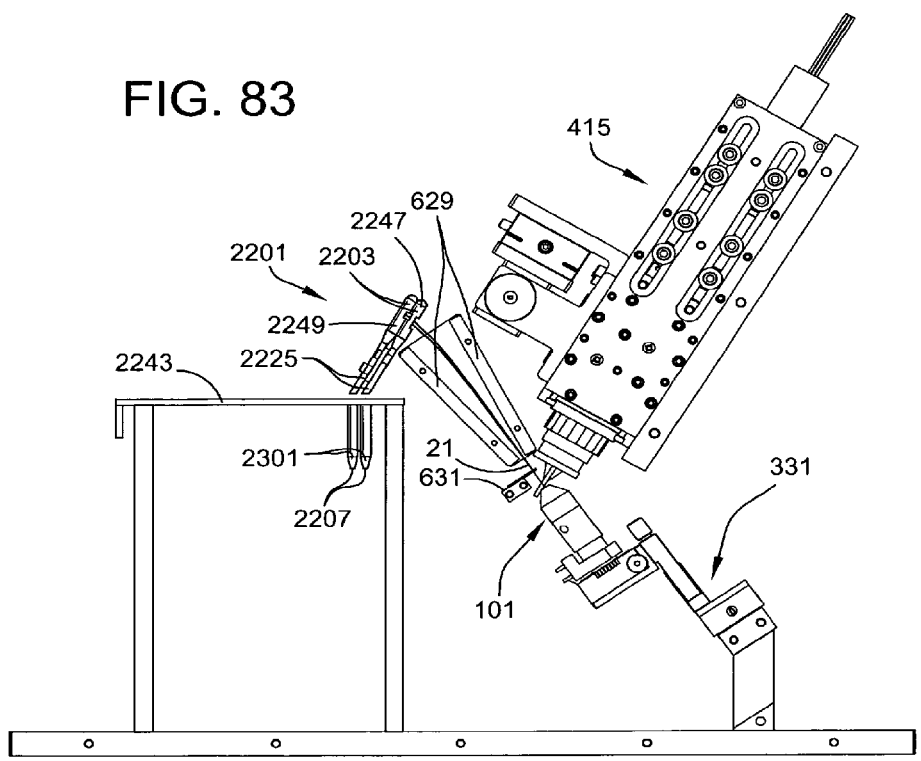
FIG. 83 is a side elevation of a cytometer oriented to produce a stream of droplets having a horizontal velocity component and a collection system to collect the droplets.
Figure 84:
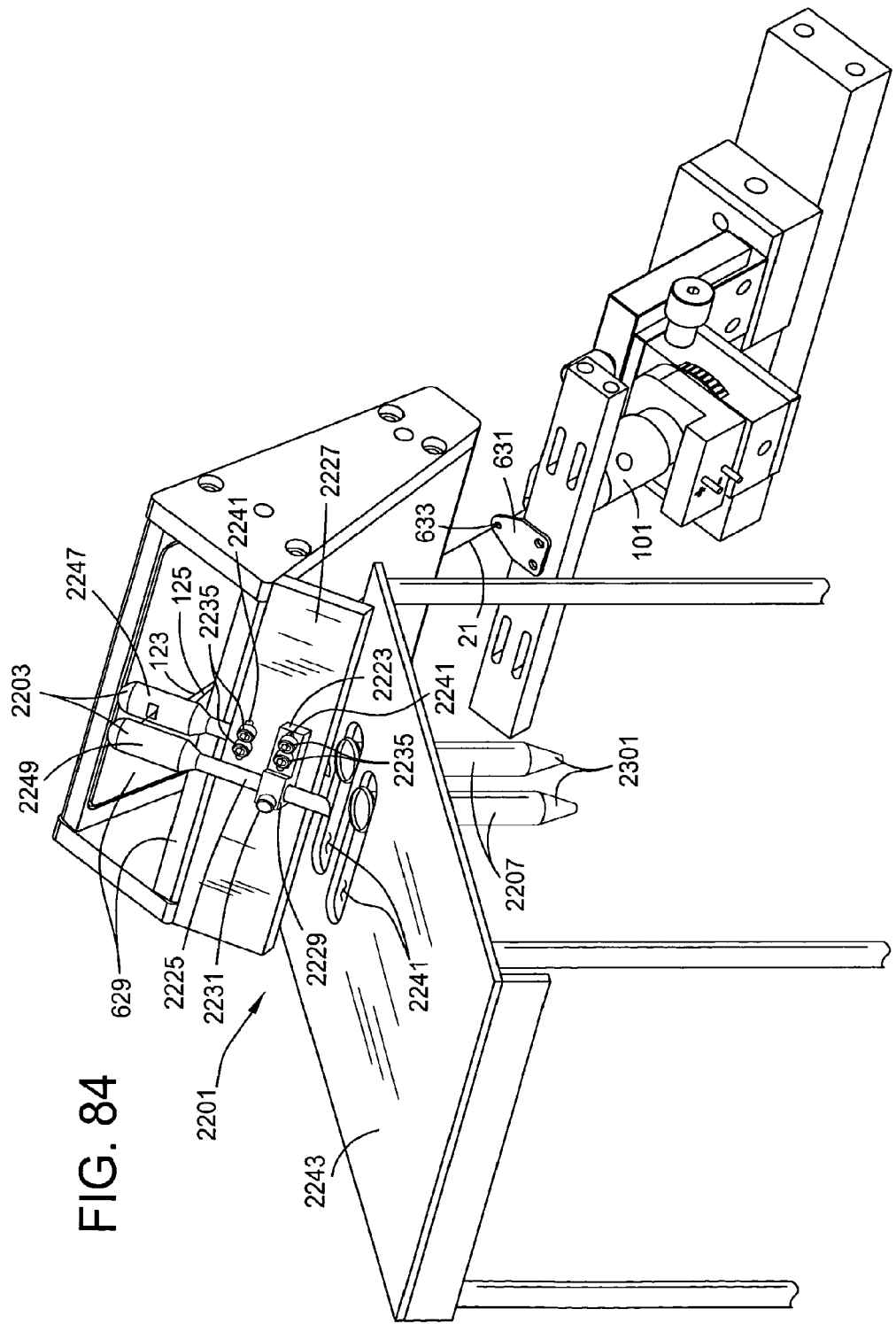
FIG. 84 is an enlarged perspective view of the collection system shown in FIG. 83 shown relative to the nozzle system and deflector plates.

FIGS. 83-85 show one embodiment of a collection system, generally designated 2201, that may be used to collect sorted droplets in a system of the present invention. The collection system is particularly suited for collection of droplets 33 when the cytometer nozzle system 101 is oriented to direct the fluid stream 21 at an upward angle or any other angle having a horizontal component. As the droplets pass between the deflector plates 629, they are sorted into multiple droplet streams 123,125 (e.g., two) having different arched trajectories. As shown in FIGS. 84 and 85, the trajectory of each droplet stream leads to one of two droplet intercepting devices 2203. If the droplets are being sorted into more than two droplets streams, a separate intercepting device would need to be provided for each additional droplet stream. Thus, the number of intercepting devices in a collection system of the present invention will depend on the number of streams into which the droplets are being sorted.

Each intercepting device 2203 in the exemplary collection system has an impact surface 2205 positioned to span the trajectory of one of the droplet streams to divert droplets moving along that trajectory to a collection vessel 2207 positioned beneath each intercepting device. The impact surfaces are preferably made of a pliable material. Without being bound by a particular theory, it is believed that pliable materials cushion the impact of droplets striking the surface of the intercepting device, thereby reducing damage to the particles (e.g., sperm cells) in the droplets. For example, the intercepting devices may be constructed of polypropylene, polyethylene, or other similar polymers. Referring to FIGS. 86 and 87, the intercepting devices 2203 have been constructed by cutting a droplet entryway 2211 (e.g., rectangular window) in one side of the bulb 2213 of a pipette 2215. Thus, a portion of the inside wall 2217 of the bulb opposite the droplet entryway forms a curved impact surface 2205 which spans the trajectory of the respective droplet stream. Conveniently, the tube of the pipette serves as a guide 2225 for directing fluid from the impact surface to the collection vessel.

Referring to FIG. 84, the intercepting devices are fastened to a collection system frame 2227, which holds them in place. In order to account for variability in the trajectories of the droplet streams, it is desirable to allow adjustment of the positions of the intercepting devices. For example, the vertical height of each intercepting device may be adjusted by sliding the guide tube up and down in a circular bore through a holder 2229. When the intercepting device is at the desired height, a set screw 2231 may be tightened to hold it at that height. The holder may be attached to a mounting plate 2233 which is attached to the collection system frame, for example by set screws 2235 (e.g., two set screws). The set screws 2235 pass through a horizontal slot 2241 in the mounting plate to allow lateral adjustment of the intercepting device. After adjustment, the set screws may be tightened to hold the circular holder in the desired location. Those skilled in the art will recognize that a variety of other fastening devices could be used to adjust the position of the intercepting device without departing from the scope of the present invention. The collection vessels 2207 are held beneath the intercepting devices in slots 2241 in a tray 2243 for holding the collection vessels. Thus, each collection vessel may be moved within a respective slot as necessary for it to remain in position under the respective intercepting device. Also, a water bath (not shown) may be provided around the collection vessel if desired to control the temperature of the contents of the collection vessel.

Referring to FIG. 85, in one embodiment of the present invention an exit window 2245 (e.g., a rectangular window) has been cut in the back of one of the intercepting devices 2247 to allow one or more droplet streams to pass through the intercepting device. A second intercepting device 2249 is positioned behind the exit window to intercept the droplets that pass through this window. An exemplary entry window for the second intercepting device may be approximately the same size as the exemplary exit window for the first intercepting device. For reasons that will be apparent, it is desirable for the exit window to be significantly smaller than the entry window for the first intercepting device. For instance, an exemplary entry window for the first intercepting device is about ⅝ of an inch high and about ⅜ of an inch wide. In contrast, an exemplary exit window may be ⅛ of an inch high and 5/16 of an inch wide.

During operation of the cytometer, the collection system operates to intercept the droplets in the sorted streams. The intercepted droplets then drain down through the guide tubes 2225 of the intercepting devices 2203 and into the collection vessels 2207. In a case in which a cytometer has an upward pointing cytometer nozzle that directs droplet streams along arched trajectories, for example, the intercepting devices allow the droplets to be intercepted at a point on their trajectory that is significantly closer to the nozzle in comparison to the point at which the droplets would be collected by a conventional collection system (i.e., a collection system without intercepting devices).

Intercepting the droplet streams relatively early along their arched trajectories (e.g., while they are still moving upward) reduces the amount of variation in the location of the droplets at the time the droplets first encounter the collection system. Accordingly, the collection system can tolerate more variation in the trajectories of the droplet streams than a convention collection system could tolerate. Similarly, the droplets are less likely to be buffeted by air currents because of their shorter paths to the collection system.

A balance must be struck between moving the intercepting devices 2203 closer to the nozzle 101 to increase tolerance for trajectory variations and moving the intercepting devices farther away from the nozzle orifice to reduce or minimize the force of impact when droplets impact the intercepting devices, as by positioning the intercepting devices so they intercept the droplet streams substantially at the apex of their trajectories. Accordingly, the best location for the intercepting devices will depend on the durability of the particles (e.g. sperm cells) being sorted, the droplet velocities, and the expected magnitude of variation in the droplet stream trajectories. In the case of droplets containing bovine sperm cells having a velocity at the nozzle orifice of about 16 to 20 m/s, for example, the intercepting devices may be positioned in the range of 4-6 inches from the nozzle orifice. In the embodiment in which a first intercepting device has a exit window and a second intercepting device is positioned behind the first intercepting device, for example, the first intercepting device may be in the range of about 4 and 5 inches from the nozzle. More desirably, the first intercepting device is about 4.5 inches from the nozzle. The second intercepting device may be in the range of about 5 to 6 inches from the nozzle. More desirably, the second intercepting device is about 5.5 inches from the nozzle.

The configuration in which one intercepting device 2203 is positioned to intercept the droplets that pass through an exit window of another intercepting device is particularly advantageous when one is not concerned about the purity of one of the sorted populations (e.g., Y chromosome-bearing sperm in the case of sperm sorted for use in breeding dairy cattle). Those skilled in the art will know that a number of stray droplets 2265 (e.g., a mist of stray droplets) having unknown contents may be produced by the cytometer in addition to the droplets in the sorted streams as shown in FIG. 85. The first intercepting device should be positioned so that the stream of droplets that are being sorted into the population for which there is the greatest tolerance for impurities hit the impact surface 2205 of the first intercepting device and the stream for which purity is most critical passes through the exit window 2245 to hit the impact surface of the second intercepting device. This way the majority of the stray droplets are collected into the collection vessel 2207 containing the population for which there is less concern about purity, as shown in FIG. 85, and will not contaminate the population for which purity is critical. Also by intercepting and collecting the stray droplets, one avoids the need to clean as often as if the stray droplets escape the collection system. In contrast to the first intercepting device, the second intercepting device only diverts droplets that pass through the smaller exit window. This facilitates maintenance of the purity of the population collected by the second intercepting device.

Those skilled in the art will recognize that the exemplary collection system could readily be modified in a number of ways without departing from the scope of the present invention. For example, it would be possible to construct a droplet intercepting device having an integrally formed (or otherwise attached) collection vessel beneath it, without departing from the scope of this invention. Similarly, although the intercepting devices in the embodiment shown in FIGS. 83-87 are modified pipettes, it is understood that the intercepting devices 2203 can be any of a variety of shapes without departing from the scope of this invention. For example, each intercepting device may comprise a flat or curved sheet, a spoon, a bowl, or other similar shape. The only requirement is that the intercepting device is operable to intercept droplets moving along a respective trajectory of a droplet stream and to divert the intercepted droplets into a collection vessel. However, one advantage to constructing the intercepting devices out of a readily available and relatively inexpensive product, such as a pipette, is that it may be more economical to replace and dispose of the used intercepting devices after each sample run rather than clean the intercepting devices between sample runs. This could help reduce costs of operating the collection system.

Collection Fluid

The sorted sperm are collected in a vessel that contains a collection fluid 2301 (FIGS. 56 and 57). Generally, the purpose of the collection fluid includes cushioning the impact of the sperm cells with the collection vessel or providing a fluid support for the cells. Consistent with these considerations, the collection fluid may comprise a buffer or buffered solution and a protein source.

If included, examples of buffers or buffered solutions that may be used in the collection fluid are disclosed above with respect to sample collection and dilution. Typically, these buffers or buffer solutions will be in a concentration of about 0.001 M to about 1.0M and have a pH of about 4.5 to about 8.5, preferably of about 7.0. In one embodiment, the collection fluid contains buffer comprising 0.96% Dulbecco's PBS (w/v) at a pH of about 7.0 In another embodiment, the collection fluid contains a metabolic inhibitor comprising 0.204 g $NaHCO_3$, 0.433 g $KHCO_3$, and 0.473 g $C_6H_8O_7.H_2O$ per 25 mL of purified water (0.097 moles/L of $NaHCO_3$, 0.173 moles/L of $KHCO_3$, 0.090 moles/L $C_6H_8O_7.H_2O$ in water).

If included, the protein source may be any protein source that does not interfere with the viability of the sperm cells and is compatible with the particular buffer or buffered solution being used. Examples of common protein sources include milk (including heat homogenized and skim), milk extract, egg yolk, egg yolk extract, soy protein and soy protein extract. Such proteins may be used in a concentration from about 1% (v/v) to about 30% (v/v), preferably from about 10% (v/v) to about 20% (v/v), and more preferably about 10% (v/v). While milk may be used in combination with a buffer or buffered solution, generally milk is used in the absence of the same, as milk is a solution itself that may serve the same purpose of a buffer or buffered solution. In such instances, the collection fluid may contain about 80% (v/v) to about 90% (v/v) milk.

In addition to or in lieu of the protein source, the collection fluid may also comprise seminal plasma. Seminal plasma serves the dual benefits of improving sperm viability and motility and of stabilizing the sperm membrane (thereby preventing capacitation during the collection and storage of the sperm). Maxwell et al., *Reprod. Fert. Dev.* (1998) 10: 433-440. The seminal plasma may be from the same mammal from which the semen sample was obtained, from a different mammal of the same species, or from a mammal of a different species. If included in the collection fluid, typically the percentage of seminal plasma will be in the range of about 0.5% (v/v) to about 10% (v/v). If used in combination with a protein source, such as for example egg yolk or milk, the total percentage of seminal plasma and protein source will range from about 1% (v/v) to about 30% (v/v). In such instances, the percentage of seminal plasma will be inversely proportional to the percentage of the protein source. Accordingly, in one embodiment, the collection fluid comprises seminal plasma. In another embodiment, the collection fluid contains seminal plasma in an amount of about 0.5% (v/v) to about 10% (v/v), preferably in an amount of about 4% (v/v) to about 6% (v/v), and more preferably in an amount of about 5% (v/v). In another embodiment, the collection fluid contains a protein source and seminal plasma. In yet another embodiment, the collection fluid comprises seminal plasma and egg yolk, the percentage of both totaling between about 1% (v/v) and about 30% (v/v).

Optionally, the collection fluid may also contain a range of additives that are beneficial to sperm viability or motility. Examples of such additives include an energy source, an antibiotic, and a composition which regulates oxidation/reduction reactions intracellularly and/or extracellularly, each of which is discussed above with respect to sample collection and dilution. Such additives may be added to the collection fluid in accordance therewith.

Accordingly, in a certain embodiment, the collection fluid comprises 0.96% Dulbecco's PBS (w/v), 1% (w/v) fructose, 10% (v/v) egg yolk in water, at a pH of about 7.0. In yet another embodiment, the collection fluid further comprises 10 mM pyruvate, 100 µM vitamin K, or 1 mM of lipoic acid.

Alternatively, and in lieu of the use of a collection fluid, the sorted cells may be collected into a vessel containing or coated with a cryoextender used in the subsequent cryopreservation steps and further described below. Accordingly, in one particular embodiment, the sorted cells are collected into a cryoextender. In another embodiment, the collected cells are sorted into a cryoextender comprising water, Triladyl® (Minitube, Verona, Wis., comprising glycerol, tris, citric acid, fructose, 5 mg/100 ml tylosin, 25 mg/100 ml gentamycin, 30 mg/100 ml Spectinomycin, and 15 mg/100 ml Lincomycin), egg yolk, and pyruvic acid. In yet another embodiment, the collection fluid is the cryoextender comprising 25 g Triladyl®, 25 g egg yolk, and 10 mM pyruvic acid in 75 mL of water.

It is to be understood that the percent concentrations of protein in the collection fluid disclosed herein are those prior to the addition of the flow sorted cells. The addition of the flow sorted cells will dilute the final concentration of the collection fluid to about ½₀ that of what it was prior to the addition of the flow sorted cells. Therefore, for example, the collection fluid may initially contain about 10% (v/v) egg yolk. After the flow sorted cells are collected in the collection vessel containing the collection fluid, the final concentration of egg yolk will be reduced to about 0.5% (v/v).

Pre-Treatment of Intercepting Devices and/or Collection Vessels

In order to minimize possible damage to particles (e.g., sperm cells) that may be sorted according to the present invention, the intercepting devices 2203 and/or collection vessels 2207 (FIGS. 56-60) may be treated prior to use. Such pre-treatment may comprise, for example, contacting or soaking the intercepting devices and collection vessels in a bath containing a composition that will serve to minimize the impact between the particle and the intercepting device. Upon removal of the intercepting devices and collection vessels from the bath, a certain amount of the composition will remain on the intercepting devices and collection vessels and serve as a cushioning agent for the particles in the droplets. The composition, therefore, should have characteristics suitable for providing the desired cushioning effect. In addition, the composition should also be compatible with the particle or cell being sorted, the sheath fluid, and the collection fluid. Consistent with these considerations, the composition used to treat the intercepting devices and collection vessels may comprise a buffer or buffered solution, a sheath fluid, a collection fluid, a cryoextender, any components contained in the buffered solution, sheath fluid, collection fluid, or cryoextender, or any combination thereof. Buffers, buffered solutions, sheath fluids, and collection fluids used for the staining and separation of sperm cells according to the methods of the present invention are described above. Accordingly, in one embodiment, the intercepting devices and collection vessels are contacted with (e.g., soaked in or brushed with) sheath fluid. In another embodiment, the intercepting devices and collection vessels are contacted with collection fluid. In yet another embodiment, the intercepting devices and collection vessels are contacted with a cryoextender described below.

The contacting or soaking of the intercepting devices and collection vessels with the composition preferably occurs for a period of time sufficient to allow the composition to adhere to the surfaces of the intercepting devices and collection vessels. Such a period of time is generally less than about 90 minutes, preferably less than about 60 minutes, more preferably about 30 to about 60 minutes, and most preferably about 60 minutes. In still another embodiment, the intercepting devices and collection vessels are merely contacted with the composition prior to use.

In lieu of or in combination with the contacting of the intercepting devices and collection vessels with the above-described composition, the intercepting devices and collection vessels may also be contacted with specific components contained in the sheath fluid, the collection fluid, and/or the cryoextender, such as for example, BSA, SSS, egg yolk, egg yolk extract, milk (including heat homogenized and skim), milk extract, soy protein, and soy protein extract. Accordingly, in one embodiment, the intercepting devices and collection vessels are contacted with sheath fluid and subsequently contacted with 0.1% (v/v) bovine serum albumin. In another embodiment, the intercepting devices and collection vessels are contacted with sheath fluid and subsequently contacted with 10% (v/v) egg yolk. In another embodiment, the intercepting devices and collection vessels are soaked in collection fluid and subsequently contacted with 0.1% (v/v) bovine serum albumin. In another embodiment, the intercepting devices and collection vessels are soaked in collection fluid and subsequently contacted with 10% (v/v) egg yolk.

Although the intercepting devices and collection vessels receive the same pre-treatment in each embodiment described above, it is possible to use different pre-treatment protocols for the intercepting devices and the collection vessels without departing from the scope of this invention. Likewise, some of the intercepting devices or collection vessels could receive one pre-treatment and others of the intercepting devices or collection vessels could receive a different pre-treatment without departing from the scope of this invention. Certain advantages of the pre-treatment can also be obtained by pre-treating only the intercepting devices or only the collection vessels, again without departing from the scope of this invention.

Concentration

As noted above, the sorted sperm collected by the flow cytometer have been diluted by the addition of various buffers and extenders, the staining fluid, the sheath fluid, and the collection fluid. Typically, the concentration of sperm cells after sorting by flow cytometry as described above is in the range of about $0.7\text{-}1.4\times10^6$ sperm cells/ml. Therefore, it is important to concentrate the sorted sperm cells to minimize the dilution shock to the sperm and to attain the proper concentration of sperm for cryopreservation and artificial insemination. Standard practice in the animal breeding industry, for example, is to perform artificial insemination with sperm at a concentration of either about $20\times10^6$ or about $40\times10^6$ sperm cells/ml. One way to concentrate the sperm cells is through centrifugation of the fluid collected by the cytometer. Another way to concentrate the sperm is to pass the fluid collected by the cytometer through a filtration system. These methods are discussed in more detail below.

A. Centrifugation

Any conventional centrifuge can be used to concentrate sperm. However in a commercial operation it is preferable to use a centrifuge having the capacity to centrifuge a large batch of sperm cells at once. During centrifugation a majority of the sperm cells will collect in a pellet at the bottom of the centrifuge tube due to the centrifugal force acting on the sperm cells. The magnitude of the centrifugal force is conventionally stated as the number of times the centrifugal force exceeds the gravitational force. Because the centrifugal force is the critical parameter and because the magnitude of the centrifugal force at any given speed (angular velocity) will vary depending of the length of the radius of curvature, the speed of centrifugation is typically specified by stating the magnitude of the centrifugal force. For example, a 600 g force means the angular velocity of the centrifuge is selected so the resulting centrifugal force will be 600 times the force of gravity. The majority of the fluids and any sperm cells that escape being centrifuged into the pellet will be in the supernatant. Generally, the supernatant is removed and the sperm cells in the pellet are resuspended for further processing as described below. It is important to maximize the percentage of sperm that are concentrated in the pellet, while at the same time minimizing damage to the sperm cells.

According to one method of the present invention, a centrifuge tube containing about $10 \times 10^6$ sorted sperm cells is placed in a centrifuge. To facilitate concentration, centrifuge tubes may be used as the collection vessels in the collection system of the cytometer. This avoids the need to transfer the sorted sperm cells to a centrifuge tube before centrifugation. The tube is centrifuged at a speed and for a duration that is sufficient to cause a pellet of concentrated sperm cells to form in the bottom of the tube. The speed and duration of the centrifugation is desirably selected in consideration of several factors, including: the fact that sperm cells are fragile and can be damaged by centrifugation at an excessive speed; the size of the centrifuge tube will affect the time required for sperm cells to move to the bottom of the tube; and the sperm cells are more likely to be damaged by centrifugation at a given speed the longer the centrifugation continues. Thus, in one embodiment of the present invention the centrifuge tube is centrifuged at 550-800 g for a period of about 6-10 minutes. According to another embodiment of the present invention, the centrifuge tube is centrifuged at 650-750 g for a period of about 6-10 minutes. In still another embodiment, the centrifuge tube is centrifuged at 700 g for a period of about 6-10 minutes. In yet another embodiment, the centrifuge tube is centrifuged at 700 g for a period of about 7 minutes.

As demonstrated in the following experiments, the speed of the centrifuge and the duration of centrifugation may affect the percentage of sperm cells recovered and the motility of the recovered sperm cells. The experiments were conducted without actually sorting the sperm cells. Instead, various fluids including buffers, extenders, sheath fluids and a staining fluid were added to semen samples to simulate the sorting process. The samples were then centrifuged in an attempt to concentrate the sperm cells.

Centrifuge Example I

In centrifuge example I bovine semen was collected and evaluated as described above. The semen sample was diluted with a quantity of Tris-citric acid ("TCA") having a pH of 7.3 to attain a concentration of $150 \times 10^6$ sperm cells/ml. Spermatozoa were stained with Hoechst 33342 (100 μM) at 41° C. for twenty minutes. Two 15 ml tubes were prepared with buffers for the simulation. Tube 1 was partially filled with 750 μl of phosphate buffered saline ("PBS") with 10% egg yolk and 14.25 ml PBS with 0.1% bovine serum albumin ("BSA"). Tube 2 was partially filled with 750 ul TCA with 10% egg yolk and 14.25 ml PBS with 0.1% BSA. Each of the two tubes received 100 ul of the solution containing the stained spermatozoa, which were then incubated at room temperature for 20 minutes. The two tubes were then divided into two aliquots of 7 ml each. One aliquot from each tube was centrifuged at 2250 rpm (about 540 g) for 7 minutes in a fixed bucket centrifuge. The other aliquot from each of the two tubes was centrifuged at 2500 rpm (about 660 g) for 7 minutes. Immediately after centrifugation, 10 ml pipettes were used to remove and save the supernatant from each aliquot. The pellets were resuspended in 200 ul of TCA with 10% egg yolk (pH 7.0). Pre- and post-centrifuge sperm motility was observed under a phase contrast microscope. Fifty ul of a fixative (0.1% glutarldehyde in 3.4% Na citrate) was added to each pellet and supernatant to immobilize the sperm for concentration determination with a hemacytometer. Total numbers of spermatozoa were calculated on the basis of volume used/recovered multiplied by the corresponding sperm concentration as determined by the hemacytometer. The recovery rate was calculated as the total number of sperm in the pellet divided by the sum of the total number of sperm in the pellet and the total number of sperm in the supernatant.

Figure 88:
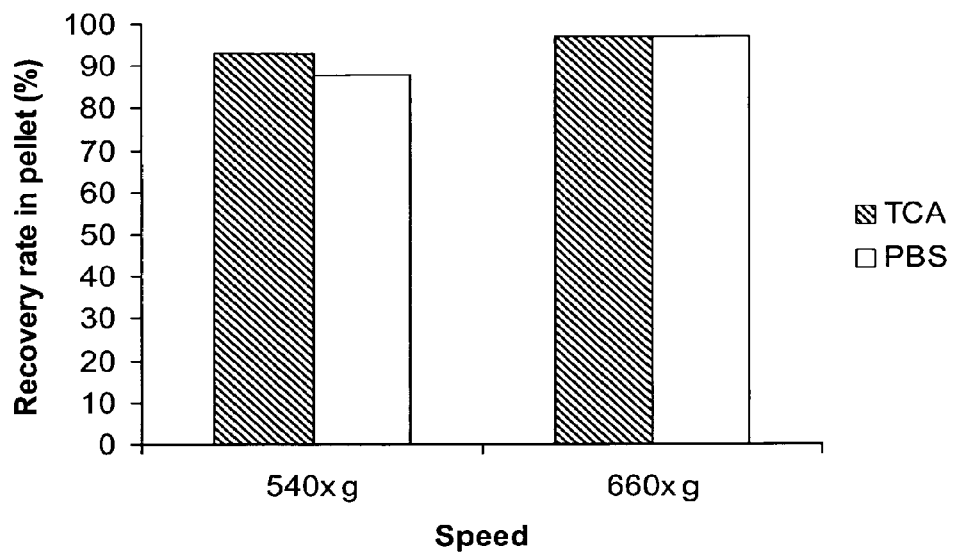
FIGS. 88-95 show graphical results of several sperm centrifugation experiments.
Figure 89:
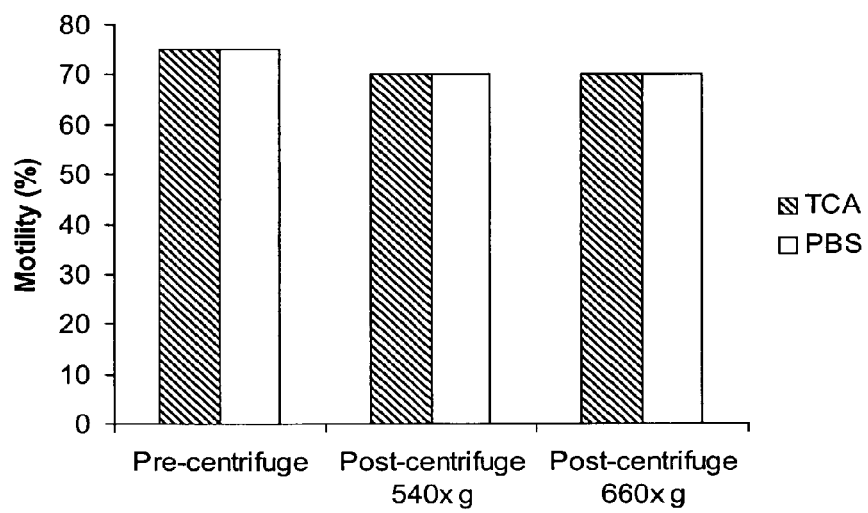

The results, as shown in FIGS. 88 and 89 show there is little difference in sperm cell motility caused by varying the centrifuge speed. The results also show that motility was slightly better using TCA compared to PBS.

Centrifuge Example II

In centrifuge example II semen samples from three bulls were collected and evaluated as described above. One of the samples was disqualified for failure to meet initial quality control standards. The other two semen samples were diluted with a quantity of TCA having a pH of 7.3 in order to obtain a sperm concentration of $150 \times 10^6$ sperm/ml. The spermatozoa were stained with a 10 μM Hoechst 33342 solution at 41° C. for twenty minutes. A simulated buffer containing 1500 μl PBS with 10% egg yolk and 28.3 ml PBS with 0.1% BSA was added to each of two tubes. Two hundred μl of the stained spermatozoa ($30 \times 10^6$ sperm cells) were added to each tube and incubated at room temperature for twenty minutes. Three 9 ml aliquots of semen mixture were taken from each of the two tubes for centrifugation. One aliquot from each of the two samples was centrifuged for seven minutes in a 15 ml centrifuge tube at each of the following speeds: 550 g; 650 g: and 750 g. The temperature during centrifugation was 22° C. Immediately after centrifugation, supernatant was removed with a 10 ml pipette, leaving about 200-300 μl supernatant in the pellet. The pellets were resuspended with 200 μl of TCA having 10% (v/v) egg yolk having a pH of 7.0. Pre- and post-sort sperm motility was observed under a phase contrast microscope. Severe sperm agglutination was noted in the post-centrifuge samples from one of the two bulls. Fifty μl of a fixative (0.1% glutardehyde in 3.4% Na citrate) was added to each supernatant and pellet to immobilize the sperm for concentration determination. Recovery rate was determined according to the formula set forth in centrifuge experiment I.

Figure 90:
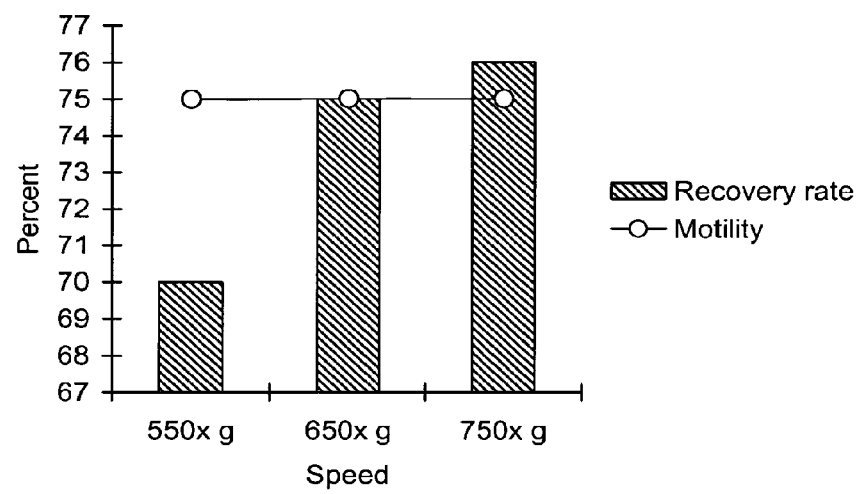

The results are shown in FIG. 90. The results show improved recovery rate of sperm cells at 650 g compared to 550 g. However, there was little difference in recovery rate between 650 g and 750 g. There was no significant difference in sperm cell motility caused by varying the speed of the centrifuge.

Centrifuge Example III

Figure 91:
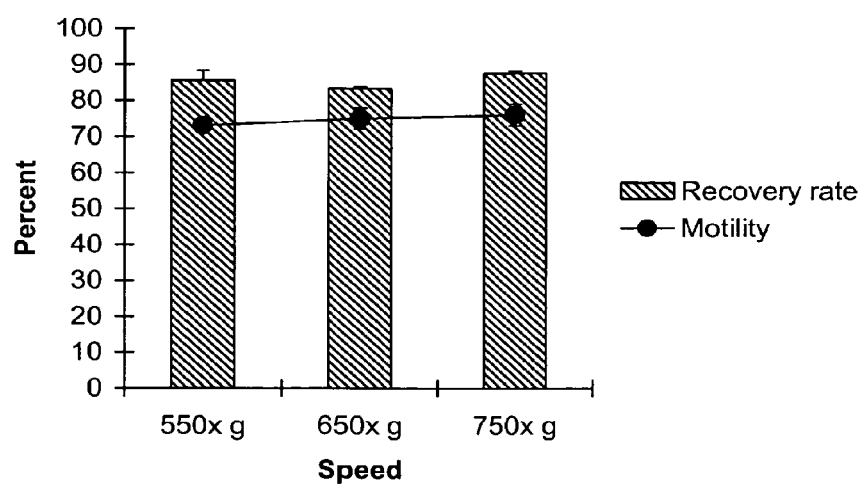

For centrifuge example III, the procedure of centrifuge example II was substantially repeated with the same three bulls on a different day. The results are shown in FIG. 91. The results confirm that there is little difference in the recovery rate at 650 g compared to 750 g.

Centrifuge Example IV

Semen was collected from two different bulls on two different days. Semen was transported and evaluated in the manner described above. Based on sperm concentration of raw semen, spermatozoa were diluted with Tris-citric acid (TCA, pH 7.3) plus 10 mM pyruvate, to a concentration of $150 \times 10^6$ sperm/ml. The spermatozoa were stained with 10 µM Hoechst 33342 at 41° C. for 20 min. After staining, 267 µl of the solution containing the stained spermatozoa were diluted to a concentration of $1\times10^6$ sperm/ml by addition of the following simulated buffers: 2 ml PBS with 10% (v/v) egg yolk; and 37.733 ml PBS with 0.1% (w/v) bovine serum albumin (BSA). The stained spermatozoa and simulated buffers were incubated at room temperature for at least 20 minutes. Four 9 ml aliquots were taken from the stained spermatozoa and simulated buffer mixture obtained from each bull. The four aliquots from the first bull were centrifuged at varying combinations of centrifuge speed and duration in the following sequence:
  (1) 700 g for 7 minutes for the first aliquot;
  (2) 700 g for 10 minutes for the second aliquot;
  (3) 650 g for 10 minutes for the third aliquot; and
  (4) 650 g for 7 minutes for the fourth aliquot.
The four aliquots from the second bull were centrifuged at varying combinations of centrifuge speed and duration in the following sequence:
  (1) 700 g for 10 minutes for the first aliquot;
  (2) 700 g for 7 minutes for the second aliquot;
  (3) 650 g for 10 minutes for the third aliquot; and
  (4) 650 g for 7 minutes for the fourth aliquot.
All centrifugation was performed in 15 ml centrifuge tubes in a swing head centrifuge (Allegra 6R, Beckman Coulter Inc. Fullerton, Calif.) at 22° C. The time interval between semen collection at farm and centrifugation in lab was 4-5 hours. Immediately after centrifugation, supernatant was removed with 10 ml pipettes, leaving ~250 µl supernatant with each pellet. The pellets were resuspended in 250 µA of Delbecco's PBS (pH 7.0). Sperm motility and progressive motility were observed using a Hamilton-Thorn Motility Analyzer (two slides per sample; two chambers per slide) after staining but before centrifugation and again after centrifugation. Sperm concentration was determined by hemacytometer measurement of a 100 µl aliquot of the pre-centrifuge stained spermatozoa and simulated buffer mixture that had been placed in the freezer and a 10 µl aliquot of the resuspended pellet mixed with 90 µl fixative (0.1% glutaraldehyde in 3.4% Na citrate). Recovery rate was determined as in Centrifuge Example I. The results are shown in FIGS. 92 and 93.

Figure 92:
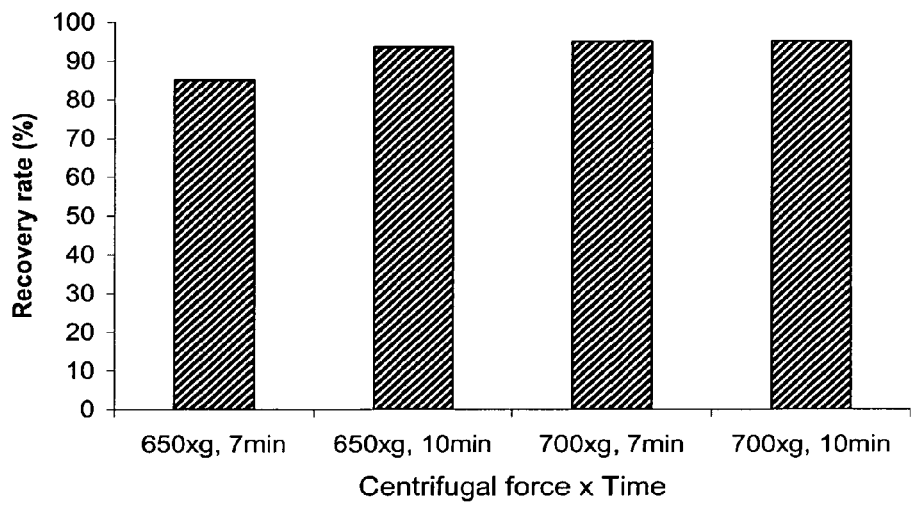
Figure 93:
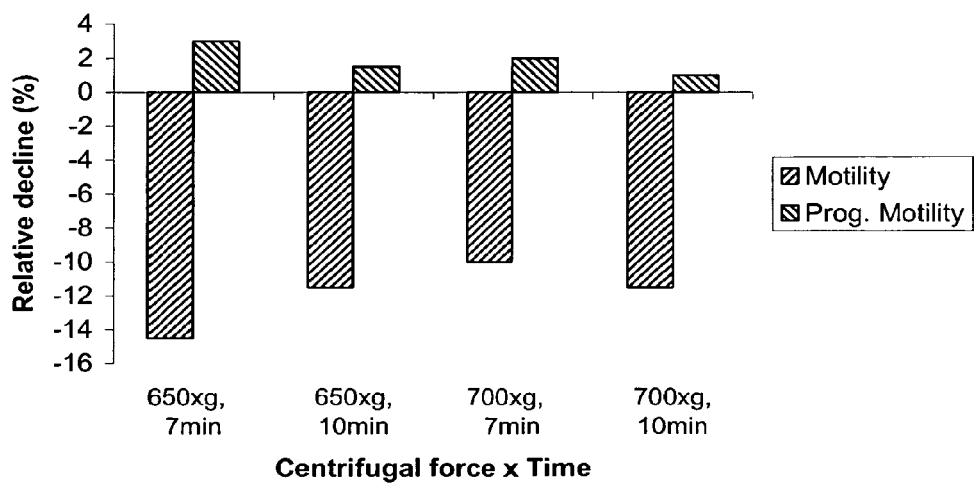

The data indicate that >85% of the spermatozoa can be recovered after centrifugation at 650 g or 700 g, for 7 or 10 minutes (FIG. 92). However, recovery rate was slightly better (95%) at 700 g. The decline in motility after centrifugation (compared to before centrifugation) in all treatments could be due to the presence of dead/abnormal/fragile spermatozoa which could not withstand the stress of centrifugal force. Sperm motility declined by 10-14% (FIG. 93) in all treatments. The higher decline in sperm motility (14%) at 650 g for 7 min might be due to the longer exposure of sperm to simulated buffer as centrifugation at 650 g was conducted after 700 g. Centrifugation did not show any adverse effect on progressive motility of spermatozoa, rather there was improvement by 2-3%.

Centrifuge Example V

Semen was collected from one bull on two different days. Semen was evaluated, diluted and stained with Hoechst 33342, and further diluted in simulated buffers as described in Centrifuge Example IV. Four 9 ml aliquots of the stained spermatozoa and simulated buffer mixture were obtained for each of the two semen samples. The aliquots from the first sample were centrifuged at one of the following combinations of centrifuge speed and duration in the following sequence:
  (1) 750 g for 10 minutes for the first aliquot;
  (2) 750 g for 7 minutes for the second aliquot;
  (3) 700 g for 10 minutes for the third aliquot; and
  (4) 700 g for 7 minutes for the fourth aliquot.
For the aliquots obtained from the second sample, the combinations of centrifuge speed and duration were the same, but the sequence was modified as follows:
  (1) 750 g for 7 minutes for the first aliquot;
  (2) 750 g for 10 minutes for the second aliquot;
  (3) 700 g for 7 minutes for the third aliquot; and
  (4) 700 g for 10 minutes for the fourth aliquot.
Centrifugation was conducted in a 15 ml centrifuge tube in a swing head centrifuge (Allegra 6R, Beckman Coulter Inc. Fullerton, Calif.) at 22° C. The interval between semen collection at farm and centrifugation in laboratory was about 6.5 hours for the first sample, and about 4 hours for the second sample. Post centrifugation processing, i.e. removal of supernatant, resuspension of pellet, determination of sperm concentration, and motility estimation via Hamilton-Thorn Motility Analyzer, were conducted following the same procedure as described in Example IV. The results are shown in FIGS. 94 and 95.

Figure 94:
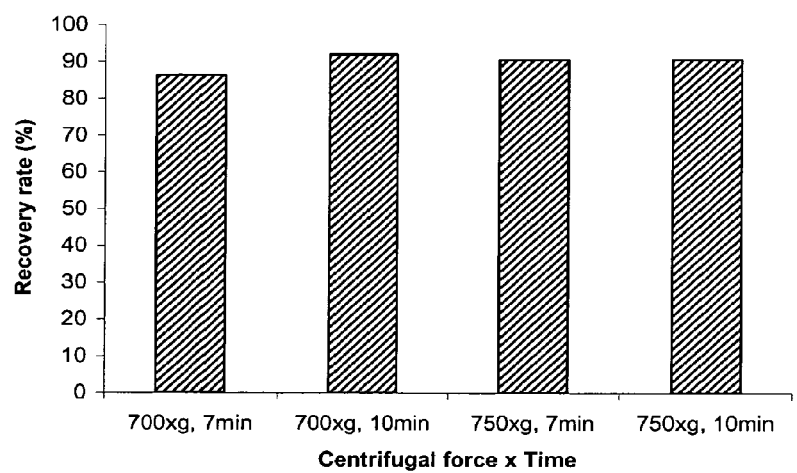
Figure 95:
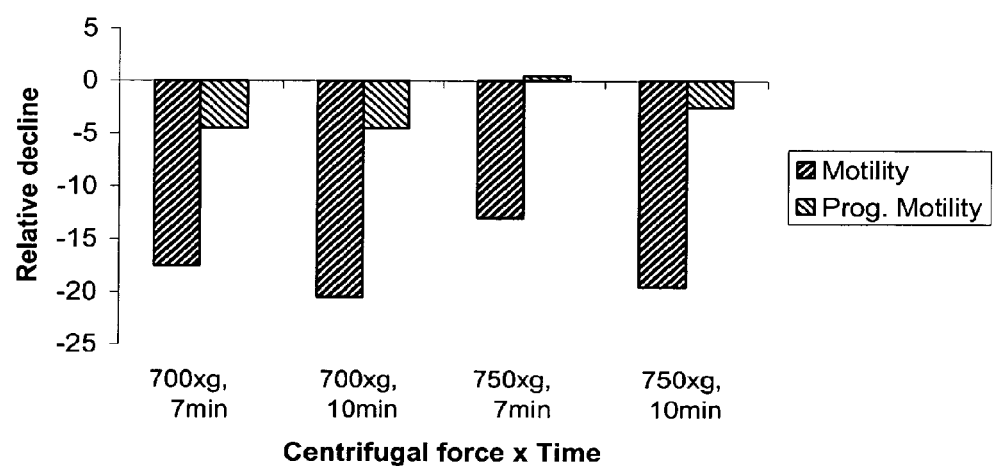

The results show that >85% of the sperm population in highly diluted suspension can be recovered with 700 g or 750 g in 7 minutes or 10 minutes (FIG. 94). An increase in g force to 750 g did not improve the recovery rate significantly. As was the case in Centrifuge Example IV, the decline in motility after centrifugation (as compared to before centrifugation) was observed in all treatments. In the present experiment, sperm motility declined by 13-20% (FIG. 95) which is little higher than in Centrifuge Example IV. The variation could be due to variation in semen sample and longer time interval from semen collection to centrifugation (6 hours) in one replicate. As explained in Example IV, the decline in sperm motility (about 20%) at low speed centrifugation (700×g, for 7 or 10 min) might be due to the longer exposure of sperm to simulated buffer as they were centrifuged after 750 g centrifugation. The decline in progressive motility was negligible (1-5%).

B. Secondary Centrifugation

In order to recover sperm that might otherwise be lost in the supernatant, it is possible to centrifuge the supernatant after it has been separated from the pellet. Without being bound by a particular theory, applicants believe the pellet/supernatant interphase impedes movement of spermatozoa into the pellet. Removal of the interphase by separating the pellet from the supernatant will allow further centrifugation of the supernatant to cause sperm cells that would have remained in the supernatant to form a second pellet. The second pellet can be resuspended and added to resuspended sperm from the first pellet.

C. Filtration

Figure 96:
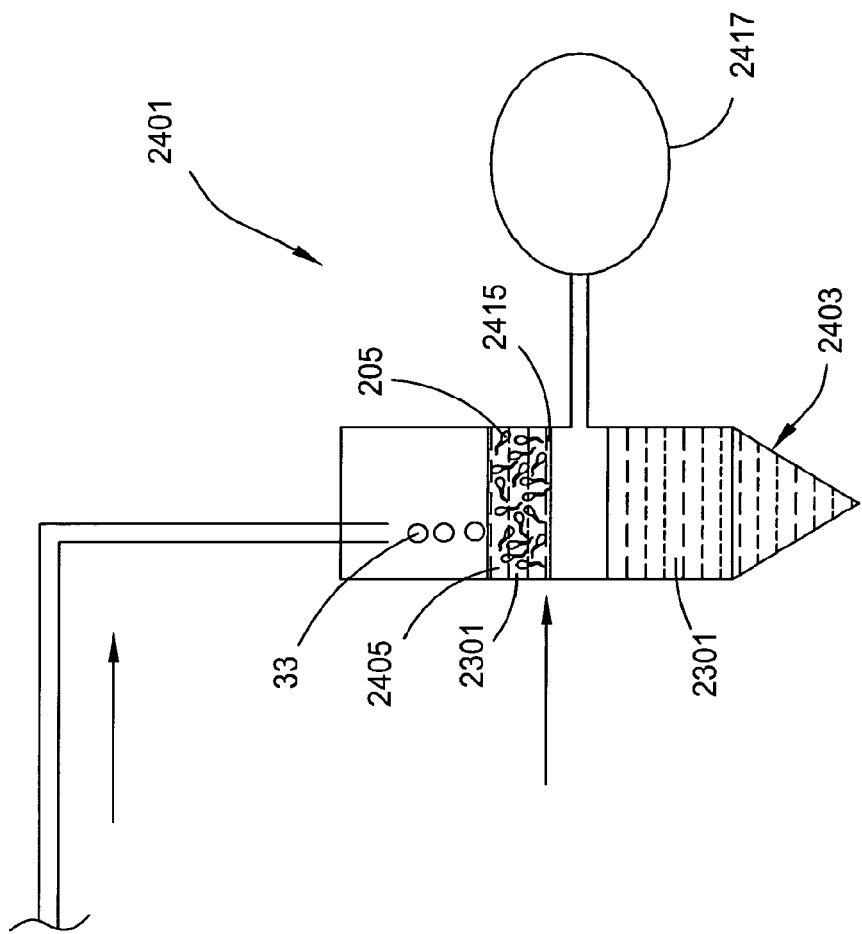

An alternative concentration method that may be used to avoid loss of sperm cells in the supernatant is filtration. As shown in FIG. 96, according to one exemplary embodiment a filter 2415 is incorporated in a collection vessel 2403. The size of the pores in the filter are desirably in the range of about 0.2-1 microns. It is also desirable that the filter is not a depth filter (e.g., a filter having tortuous passages in which sperm tails can be caught). Rather it is desirable that the filter be as thin as possible. For example, it is desirable that the filter thickness be in the range of 50 µm to 500 µm; more desirable that the filter thickness be in the range of 75 µm to 250 µm; and most desirable that the filter thickness be in the range of 100 µm to 150 µm. A low level vacuum 2417 is applied to remove the fluids through the filter as the droplets 33 are collected. It is important to use a low level vacuum (less than 20 inches of mercury, e.g., 15 inches of mercury) to avoid inflicting damage to the sperm cells. In one embodiment the vacuum is low enough that the fluid removal rate is about 1.0 ml/15 seconds. According to another embodiment of the present invention, the vacuum is applied intermittently to allow the sperm cells a chance to recover. In still another embodiment, the filter 2415 is constructed of a material that is compatible with sperm cells, yet has no binding affinity for them. At the completion of the sort, about 80-90% of the fluids will have been removed through the filter. However, enough fluid remains (about 10-20%) that the sperm cells are in a concentrated slurry 2405, thereby preventing the sperm cells from forming a filter cake. The concentrated suspension may be transferred to another container 2419, as shown in FIG. 97 for example. A syringe mechanism 2409 with a cannula-tip filter 2411 can be used to remove some of the remaining liquid from this container 2419. However, enough fluids are left in the container to prevent the sperm cells from caking on the filter 2411. The same considerations apply to the cannula tip filter 2411 as the filter 2415 in the collection vessel. Thus, the cannula filter 2411 pore size is desirably in the range of about 0.2-1.0 microns and the cannula filter is relatively thin to avoid having sperm tails getting caught in tortuous passages in the filter. For example, a DynaGard® hollow polypropylene fiber syringe tip filter, which is commercially available from Spectrum Laboratories, Inc. of Rancho Dominguez, Calif. may be used for the cannula tip filter. As shown in FIG. 98, a resuspension fluid 2413 is flushed through the cannula-tip filter to wash cells that may be sticking to the filter surface back into the slurry. The resuspension fluid may include a quantity of the filtered fluid and/or a suitable extender. After a quantity of resuspension fluid sufficient to remove sperm cells from the filter has been back flushed through the filter, additional resuspension fluid may be added if desired. The total quantity of resuspension fluid is selected to bring the concentration to a desired concentration (e.g., about $20 \times 10^6$ sperm cells/ml). Thus, the filtration process of this embodiment is a three-step process involving the use of a filter in the collection vessel, filtration using a cannula filter, and resuspension to obtain the desired concentration.

In an alternative two-step filtration process, the first and second steps of the three-step process described above are combined so that removal of all fluid is through a cannula filter. In this process the sorted sperm cells are directed to a collection vessel that does not have a filter. The fluids are removed by low vacuum and/or intermittent vacuum as described above that is applied through the cannula-tip filter 2411. When the sperm cells are in a concentrated slurry, a resuspension fluid, such as for example, an extender, is flushed back through the cannula filter to obtain the desired concentration of sperm cells.

Filtration Example I

Figure 99:
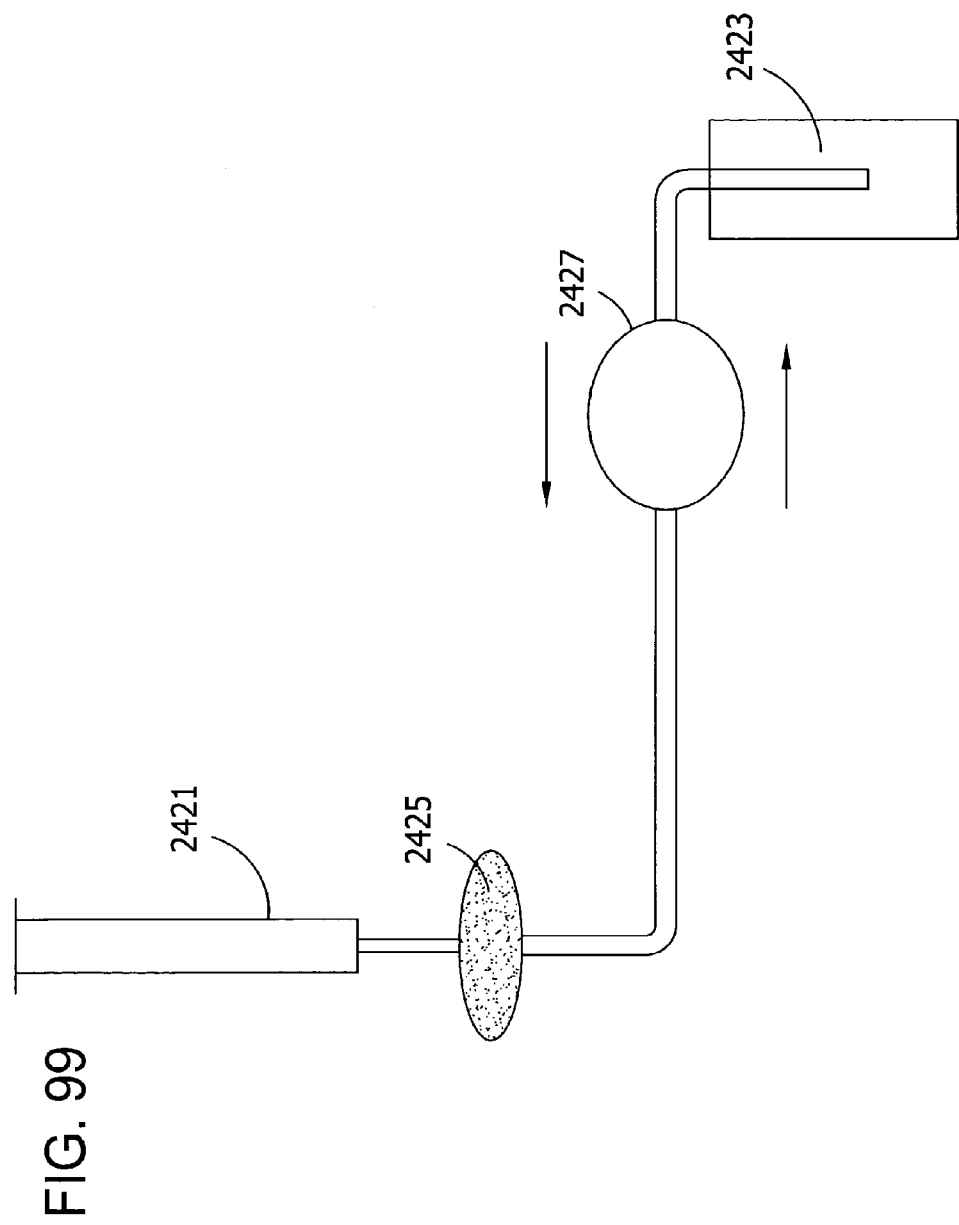
FIG. 99 is a schematic diagram of one embodiment of a filtration system used to filter sperm cells.
Figure 101:
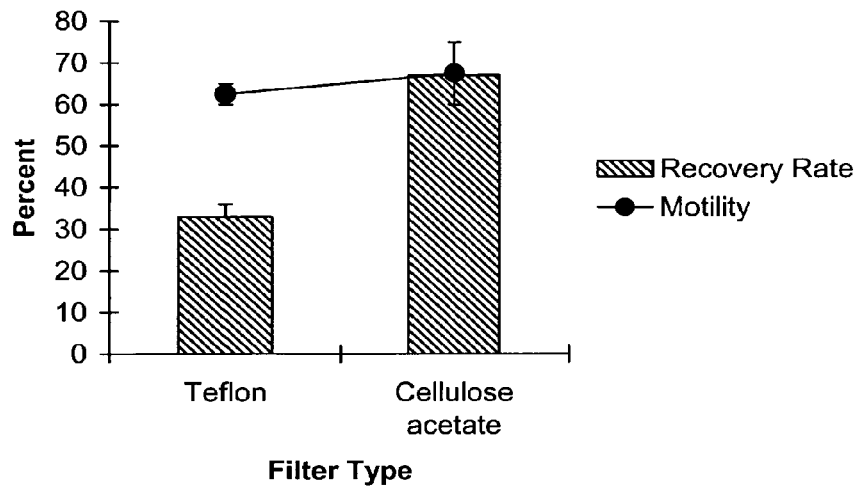
FIGS. 101 and 102 show graphical results of sperm cell filtration experiments.

Filtration example I shows the recovery rate and motility of sperm cells after concentration by a three-step filtration process of the present invention. Semen samples were collected from three bulls and evaluated as provided in the sample preparation section above. One of the three semen samples was disqualified for failing to meet minimum initial quality criteria. Two remaining samples were diluted with a quantity of TCA (pH 7.3) necessary to attain a concentration of $150 \times 10^6$ sperm cells/ml. Five hundred ul PBS with 10% egg yolk and 9.5 ml PBS with 0.1% BSA was added to each of two 15 ml test tubes. Sixty-seven ul of semen sample (about $10 \times 10^6$ sperm cells) was added to each test tube and incubated for twenty minutes at room temperature. Referring to FIG. 99, a vacuum pump 2427 was used to apply negative pressure to draw a four ml aliquot of the diluted semen 2423 through a filter 2425. The filtrate 2429 was collected in a syringe 2421. After filtration sperm cells on the filter were flushed back with 1 ml TCA buffer in a 15 ml tube. Sperm motility was assessed visually. Pre- and post-filtration samples were mixed with a fixative (0.1% glutardehyde in 3.4 Na citrate) to immobilize the sperm cells. Sperm concentration was determined using a hemacytometer. Total number of sperm cells was calculated on the basis of volume multiplied by the concentration of sperm cells. The recovery rate was calculated as the total number of sperm cells in the flushed back portion divided by the total number of sperm cells in the aliquot prior to filtration. The process was repeated with a different filter. The experiment tested both of the following filters: (1) a 1.0 μm PTFE (not FTPE) membrane disc (syringe) filter (which is available from Pall Corporation, Life Science Group, Ann Arbor, Mich., Cat #PN4226T or VWR, Batavia, Ill., Cat. #28143-928); and (2) 0.8 SFCA (surfactant free cellulose acetate) membrane disc (syringe) filter (Corning, Inc., Corning, N.Y., Cat. #431221; VWR Batavia, Ill., Cat. #28200-028). The results are shown in FIG. 101. More spermatozoa were recovered with cellulose acetate filters as compared to PTFE filter, i.e. 67 vs 33% due to low protein binding affinity of cellulose acetate. Visual motility of spermatozoa recovered ranged from 63% (PTFE) to 68% (Cellulose acetate).

Filtration Example II

Figure 100:
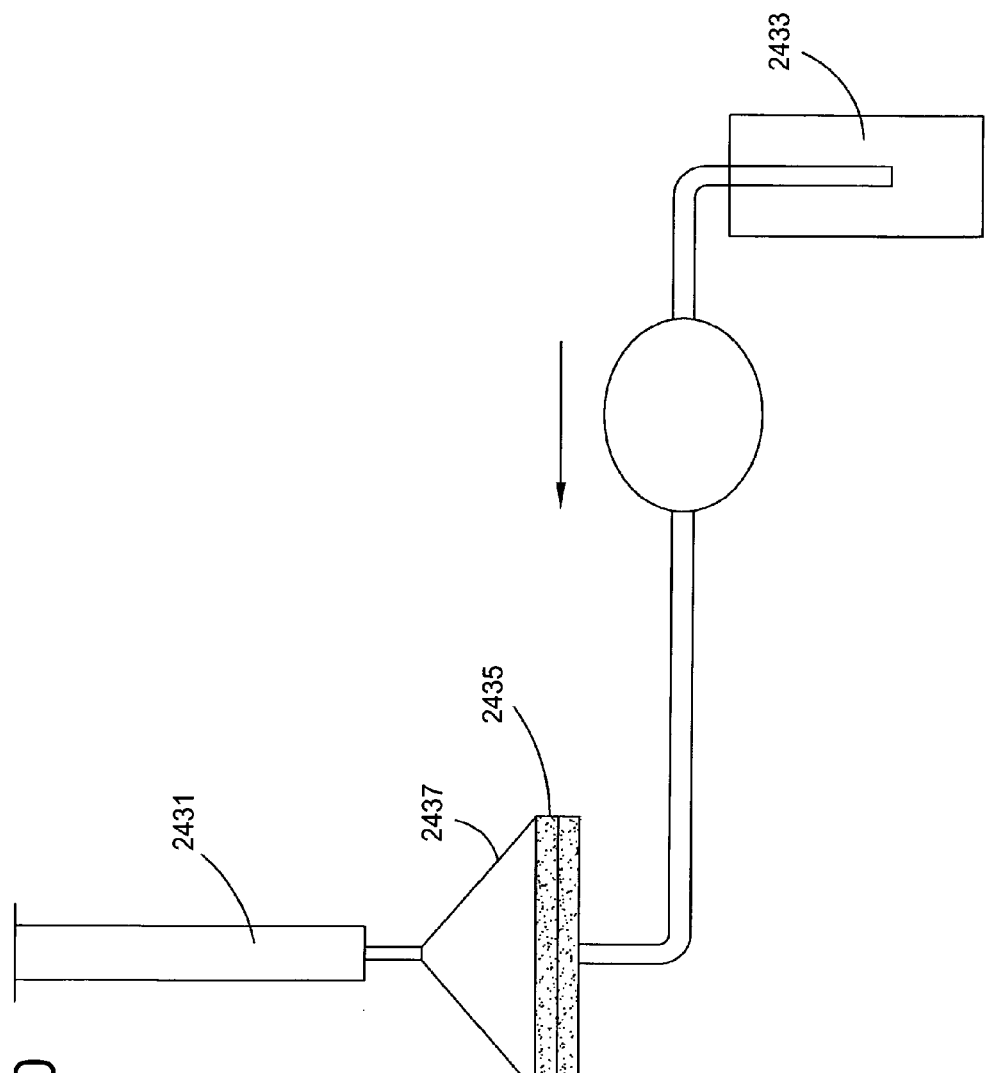
FIG. 100 is a schematic diagram of another filtration system used to filter sperm cells.
Figure 102:
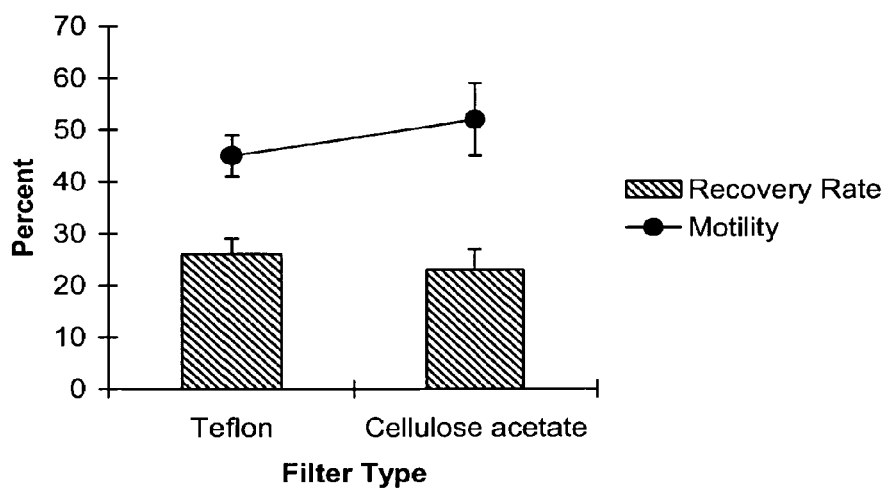

Filtration example II shows the recovery rate and motility of sperm cells after concentration by at two-step filtration process of the present invention. Semen samples were collected from three bulls and evaluated as provided in the sample preparation section above. The three samples were diluted with a quantity of TCA (pH 7.3) necessary to attain a concentration of $150 \times 10^6$ sperm cells/ml. One and one half ml of PBS with 10% egg yolk and 28.3 ml PBS with 0.1% BSA was added to each of 50 test tubes. Two hundred μl of semen sample (about $30 \times 10^6$ sperm cells) was added to each test tube and incubated for twenty minutes at room temperature. Referring to FIG. 100, a syringe 2431 was used to apply negative pressure to draw a 6 ml aliquot of the diluted semen 2433 from each test tube through a filter 2435. The filter was placed in a filter holder 2437 (a Swinnex filter holder from Millipore Corporation, Billerica, Mass. Cat #SX0002500,). After filtration, the filtration holder 2437 was disconnected from the syringe and the tubing, keeping the filter holder intact. Spermatozoa on the filter were collected by turning the filter assembly upside down and back flushing 1 with ml of TCA buffer using a 3 ml syringe having a small piece of tubing at the tip in a 15 ml test tube. Sperm motility was assessed visually. Pre- and post-filtration samples were mixed with a fixative (0.1% glutardehyde in 3.4 Na citrate) to immobilize the sperm cells. Sperm concentration was determined using a hemacytometer. Total number of sperm cells and the recovery rate were calculated as specified in Filtration example 1. The process was repeated twice to test different filters. The experiment tested both of the following filters: (1) a 0.2 μm Teflon membrane filter (which is available from X-Partek, P. J Cobert Associates Inc. St. Louis Cat. #944106; and (2) a 0.8 cellulose acetate membrane filter (Millipore Corporation, Billerica, Mass. Cat. #AAWP 02500). The results are shown in FIG. 102. In both filters, the recovery rate of spermatozoa was low (~25%). It was low in Teflon filter as in example I. However, low recovery rate and visual motility of flushed back spermatozoa in cellulose acetate filter might be due to the material used by different vendor and/or ability of spermatozoa to attach with filter holder/assembly.

D. Dense Medium Concentration

Another alternative method of concentrating the collected sperm relies on flotation of sperm cells in a high-density medium. According to this method, a high-density medium is added to the collected sperm cells to raise the specific gravity of the suspension above about 1.3. For example, a colloidal silica suspension such as is available under the Percoll® and Isolate® tradenames may be used to increase the specific gravity of the suspension. The sperm cells will float to the top of the suspension, where they can be skimmed or otherwise collected, because of the increased specific gravity of the suspension. A resuspension fluid is added to the cells that have been collected from the surface to bring the final concentration to about $20 \times 10^6$ sperm cells/ml. Some of the suspension fluid may be removed by one of the filtration methods described above prior to addition of the high density medium to reduce the quantity of high density medium required to attain the desired specific gravity.

Cryoextension

A. Cryoprotection

Once the sperm have been sorted and collected in the collection vessels, they may be used for inseminating female mammals. This can occur almost immediately, requiring little additional treatment of the sperm. Likewise, the sperm may also be cooled or frozen for use at a later date. In such instances, the sperm may benefit from additional treatment to minimize the impact upon viability or post-thaw motility as a result of cooling and freezing.

Generally, a cryoextender comprises a buffer or buffered solution, a protein source, and a cryoprotectant. Examples of buffers and buffered solutions that may be used in the cryoextender are disclosed above with respect to sample collection and extension. Typically, these buffers will be in a concentration of about 0.001M to about 1.0M and have a pH of about 4.5 to about 8.5, preferably of about 7.0.

If included, a protein source may be added to provide support to the cells and to cushion the contact of the cells with the collection vessel. The protein source may be any protein source that does not interfere with the viability of the sperm cells and is compatible with the particular buffer or buffered solution being used. Examples of common protein sources include milk (including heat homogenized and skim), milk extract, egg yolk, egg yolk extract, soy protein and soy protein extract. Such proteins may be found in a concentration from about 10% (v/v) to about 30% (v/v), preferably from about 10% (v/v) to about 20% (v/v), and more preferably about 20% (v/v). While milk may be used in combination with a buffer or buffered solution, generally milk is used in the absence of the same, as milk is a solution itself that may serve the same purpose of a buffer or buffered solution. In such instances, the cryoextender would contain about 80% (v/v) to about 90% (v/v) milk.

A cryoprotectant is preferably included in the cryoextender to lessen or prevent cold shock or to maintain fertility of the sperm. Numerous cryoprotectants are known in the art. Selection of a cryoprotectant suitable for use with a given extender may vary, and depends upon the species from which the sperm to be frozen were obtained. Examples of suitable cryoprotectants include, for example, glycerol, dimethyl sulfoxide, ethylene glycol, propylene glycol, trehalose, Triladyl® and combinations thereof. If included, generally, these cryoprotectants are present in the cryoextender in an amount of about 1% (v/v) to about 15% (v/v), preferably in an amount of about 5% (v/v) to about 10% (v/v), more preferably in an amount of about 7% (v/v), and most preferably in an amount of about 6% (v/v).

In one particular embodiment, the cryoextender comprises water, Triladyl®, egg yolk, and pyruvic acid. In yet another embodiment, the cryoextender comprises 25 g Triladyl®, 25 g egg yolk, and 10 mM pyruvic acid in 75 mL of water.

Optionally, the cryoextender may also contain a range of additives that are beneficial to sperm viability or motility and that prevent or lessen the detrimental side effects of cryopreservation. Such additives may include, for example, an energy source, an antibiotic, or a composition which regulates oxidation/reduction reactions intracellularly and/or extracellularly, each of which is discussed above with respect to sample collection and dilution. Such additives may be added to the cryoextender in accordance therewith.

B. Cryopreservation of Sorted Sperm Cells

In most cases, it will not be possible to use the sperm cells that have been sorted as described above for immediate artificial insemination. Particularly in the case of a commercial sperm sorting operation, the sorted sperm cells must be stored and/or transported before they can be used for artificial insemination. This will usually require cryopreservation of the sperm cells. The sorted sperm may be loaded into elongate cylinders (known as "straws" in the breeding industry) and cryopreserved to preserve the sperm during transportation and storage. Cryopreserved sperm cells can be stored for long periods of time in liquid nitrogen. To use the cryopreserved sperm, the straw may be immersed in a heated water bath to thaw the sperm. Then the straw is loaded into an artificial insemination gun which is used to inseminate a female animal. Several precautions must be taken to protect the sperm cells during cryopreservation. Otherwise the sperm cells will be so damaged (as indicated by a low post-thaw motility rate of 5-10%) that they are not suitable for use in artificial insemination.

Conventional cryopreservation methods involve sequentially adding a protein source (e.g., egg yolk), cooling the sperm to a temperature of about 4-5° C., adding a cryoprotectant (e.g., glycerol), maintaining the sperm and cryoprotectant at a steady temperature in the range of about 4-5° C. for a period of time sufficient to allow the sperm cells to equilibrate with the cryoprotectant, and then supercooling the sperm, as by immersing the sperm cells in liquid nitrogen at −196° C. for storage. Those skilled in the art will recognize that the purpose of the protein source is to protect sperm from damage as they cool from about 14° C. to about 8° C., which is the temperature at which sperm cells are most susceptible to cold shock. In contrast, the cryoprotectant protects the sperm cells from damage at temperatures below 0° C. Even though the temperatures involved in cryopreservation are well below freezing and the term "freezing" is sometimes used to describe cryopreservation, those skilled in the art will also know that cryopreserved sperm are not actually frozen. To be precise, the cryopreserved sperm are in a supercooled state. The conventional period during which sperm cells and cryoprotectant are maintained at a steady temperature can last anywhere from 60 minutes to many hours. The overall time to complete cryopreservation using conventional methods generally exceeds four hours. Furthermore, it is believed that up to 50% of the sperm cells are killed in conventional cryopreservation processes. Though sperm are cryopreserved using conventional methods according to some embodiments of the present invention, other embodiments of the present invention employ improved cryopreservation methods to reduce the time required for cryopreservation and/or to improve the health of the cryopreserved sperm.

Figure 103:
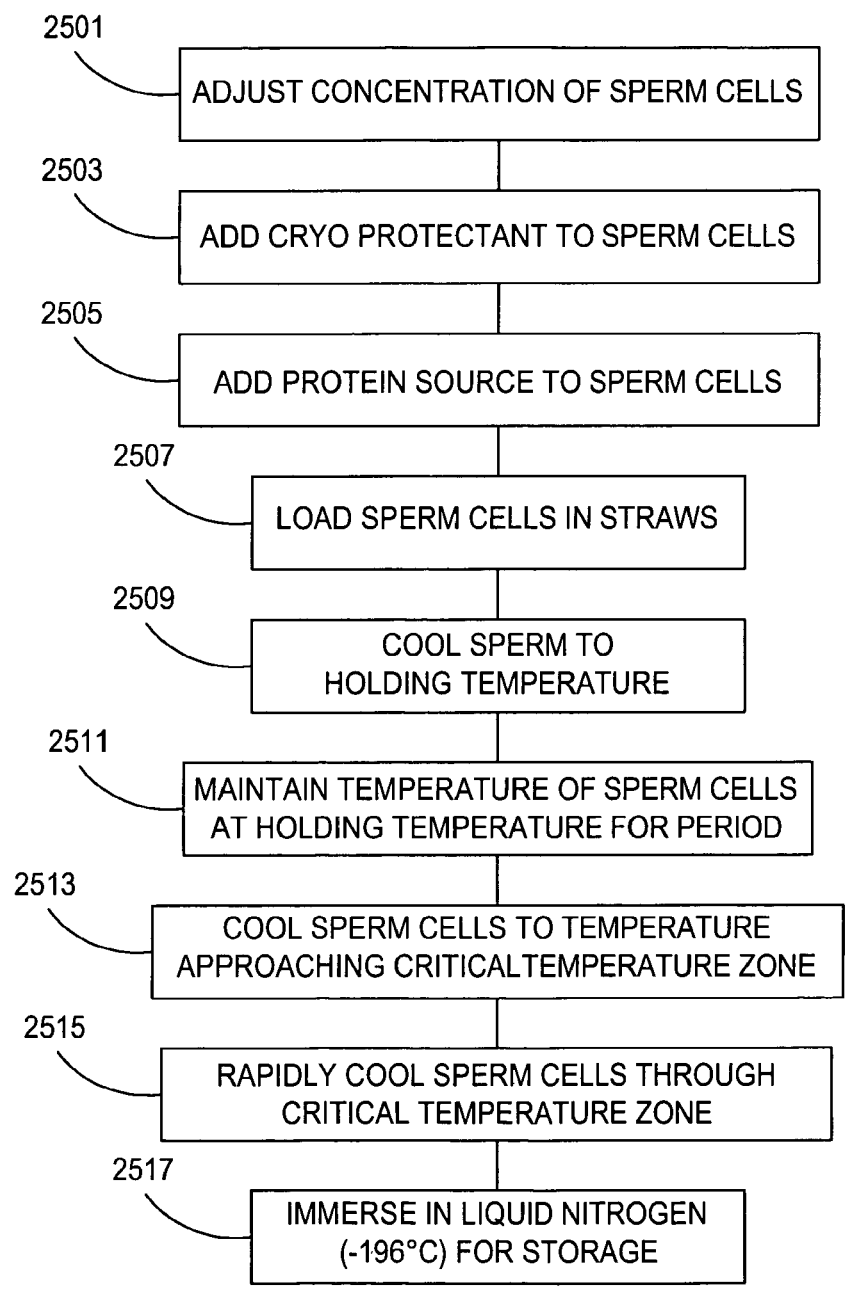
FIG. 103 is a work flow diagram for one embodiment of a cryopreservation method of the present invention.

FIG. 103 shows a work flow diagram outlining the steps of one exemplary embodiment of an improved method of cryopreserving sperm according to the present invention. At step 2501, the concentration of a solution containing sorted sperm cells is adjusted to be in the range of about 1 million-40 million sperm/ml, depending on the standard used by the targeted consumer (e.g., breeding association). For example, the sperm concentration may be adjusted to be in the range of about 20 million to 24 million sperm/ml. Adjustment of the sperm concentration may include addition of resuspension fluid, buffers and/or extenders to concentrated sperm as described above. At step 2503, a cryoprotectant (e.g., glycerol) is added before the sperm are cooled. The sperm cells begin equilibrating with the cryoprotectant as soon as they come into contact with the cryoprotectant. At step 2505, a protein source (e.g., egg yolk) is also added to the solution containing the sperm cells as described above.

The sperm cell solution, protein source, and cryoprotectant are loaded into conventional 0.5 or 0.25 ml artificial insemination straws using a conventional loading machine at step 2507. Those skilled in the art will be familiar with a number of conventional apparatus and techniques that may be used to load semen into straws. For example, U.S. Pat. No. 5,249,610, issued Oct. 5, 1993 to Cassou, et al. and incorporated herein by reference, provides instruction about the filling of straws with bovine semen using a disposable injector nozzle. Moreover, equipment for filling straws is commercially available from Minitube of America, located in Verona Wis. Any of these or similar conventional loading methods and apparatus can be used to load the sorted sperm cells into straws.

After loading, the sperm cells are cooled to a holding temperature at step 2509. In general, the holding temperature should be selected with the following considerations in mind: holding sperm cells at a temperature that is too high (e.g., 10° C.) may cause unnecessary damage from cold shock; equilibration of sperm cells with a cryoprotectant (e.g., glycerol) is believed to be most active at temperatures in the range of 4-5° C.; and holding sperm cells at temperatures that are too low (e.g., <0°) is believed to be damaging to the sperm cells. Thus, according to one embodiment, the holding temperature is in the range of 0-8° C. More desirably, the holding temperature is in the range of 2-6° C. Even more desirably, the holding temperature is in the range of 4-5° C. In another embodiment, the cooling rate used for this step 2509 is selected to minimize damage to the sperm cells. For example, the cooling rate may be controlled (e.g., substantially constant) to provide homogenous cooling and to prevent the sperm from suffering temperature shock. The cooling rate should also cool the sperm quickly enough to reduce their metabolism before they incur membrane damage, but slowly enough that they do not suffer from temperature shock. One can control the cooling rate by placing the straws containing the sperm cells in a programmable freezer (e.g., an IceCube 1810CD freezer which is available commercially from Minitube of America, located in Verona, Wis.) to cool them. According to one embodiment, the programmable freezer cools the sperm from about room temperature (typically in the range of about 22 and 24° C.) at a constant cooling rate of 0.1 and 0.3° C./minute. More desirably, the cooling rate is in a range of about 0.15 and 0.25° C./min. Even more desirably, the cooling rate is about 0.2° C./min. In another embodiment, the cooling rate is selected so the sperm are cooled from their initial temperature to the holding temperature in about 90 minutes. In still another embodiment, the cooling rate is selected to cool the sperm from their initial temperature to the holding temperature at a constant cooling rate in about 90 minutes. The cooling rates referred to above actually refer to the rate of the cooling of the chamber of the programmable freezer, but because of the thin walls and long, thin shape of the straw (e.g., about 5.25 inches long, less than 3 mm in diameter, and about 0.15 mm in wall thickness) and the conductive properties of the straw, the temperature difference between the sperm cells and the cooling chamber is not significant.

After the sperm cells have been cooled to the holding temperature, at step 2511 they are kept at or near that temperature for a period to allow substantial completion of their equilibration with the cryoprotectant. For example, the programmable freezer described above can be programmed to hold the sperm cells at a steady temperature during the period. According to another embodiment of the present invention, the sperm cells are held at the holding temperature for a period that is shortened compared to conventional methods because the sperm have already been equilibrating with the cryoprotectant during the cooling process. For example, the period may be in the range of about 10 and 60 minutes. More desirably, the period is in the range of about 20 and 40 minutes. Even more desirably, the period is about 30 minutes. In another embodiment the period is less than 60 minutes. In yet another embodiment, the period is less than 40 minutes. The relatively short holding period offers a number of advantages in a commercial sperm sorting process. First, it reduces the time required to process sorted sperm which can translate to cost savings. Also, the sperm cells still perform metabolic processes at temperatures in the range of 0-8° C. so reducing the time for which sperm need to held at this temperature can improve the health of the sperm cells, which will increase the value of the sperm cells to animal breeders who are concerned about artificial insemination success rates.

After the sperm cells have been held at the holding temperature for a period described above, the sperm cells are cooled at step 2513 to a temperature that approaches the critical temperature zone for sperm cryopreservation. Those skilled in the art will know that the critical temperature zone is the zone at which ice crystal formation and changes in osmotic pressure damage the sperm cells. This temperature may vary depending on the solution in which the sperm cells are cryopreserved, but the critical temperature zone is generally in the range of −18 and −35° C. Sometimes this critical temperature zone is reported to be in the range of about −18 and −30° C. Thus, according to yet another embodiment of the present invention, the cooling rate used to cool the sperm cells from the holding temperature to a temperature that approaches −18° C. (e.g., −15° C.) is selected to protect the health of the sperm. Relevant factors to consider include that fact that the sperm cells are still equilibrating with the cryoprotectant during this period, the fact that sperm are still performing some metabolic functions, and the fact that the sperm are still somewhat sensitive to rapid temperature change. Again, it is desirable that the cooling rate be a controlled rate, such as a rate that may be programmed into the programmable freezer described above. More desirably, the cooling rate used to cool the sperm from the holding temperature to a temperature that approaches about −18° C. is a constant cooling rate. Thus, according to another embodiment of the present invention, the sperm cells are cooled from the holding temperature to about −15° C. at a cooling rate in the range of about 1.0-5.0° C./min. More desirably, the cooling rate is in the range of about 2.0-4.0° C./min. Even more desirably, the cooling rate is about 3.0° C./min.

Step 2515 involves rapidly cooling the sperm cells through the critical temperature zone to limit the time sperm cells dwell therein. Thus, according to one embodiment of the present invention, the cooling rate through the critical temperature zone about (e.g., −18° C. to about −30° C.) is selected to be much faster than the cooling rate used to cool sperm cells to the holding temperature and the cooling rate used to cool sperm cells to the temperature approaching the critical temperature zone. Thus, the steeper cooling rate is desirably in the range of from about 8-40° C. per minute. More desirably, the steeper cooling rate is in the range of from about 8-12° C. per minute. Most desirably, the steeper cooling rate is about 10° C. per minute. The temperature range over which the steeper cooling rate is used may extend beyond the critical temperature zone. Thus, in yet another embodiment of the present invention, the sperm cells are cooled at one of the steeper cooling rates described above from about −15° C. to about −40° C. In still another embodiment, the sperm cells are cooled at one of the steeper cooling rates described above from about −15° C. to about −80° C. The step of cooling the sperm through the critical temperature zone at a steeper rate may be accomplished in the programmable freezer described above.

After the sperm cells have been cooled below the critical temperature zone (e.g., to −80° C.), the straws containing the sorted sperm are immersed in liquid nitrogen (−196° C.) at step 2517 to provide maximum useful life of the sorted sperm cells. The use of liquid nitrogen to store cryopreserved sperm is widespread in the animal breeding industry in the context of unsorted sperm. Thus, those skilled in the art will be familiar with technologies involving the transportation and storage of sperm in liquid nitrogen, which need not be discussed in great detail herein. It is sufficient to note that conventional containers are available to provide for long term storage of bulk quantities of artificial insemination straws in liquid nitrogen and that smaller and more portable containers are also available for providing storage of artificial insemination straws in liquid nitrogen for transport to customers and/or for transport to a farm having one or more female animals to be inseminated with cryopreserved sperm.

One advantage of the cryopreservation methods described herein is that the cryopreservation can be completed in less time than is required according to conventional methods. Perhaps relatedly, the decline in motility due to cryopreservation according to the present invention is only about 5-11%, as indicated by the example discussed below. Thus, cryopreservation according to the present invention preserves the health of the sperm cells as indicated by tests showing that sperm cells cryopreserved according to the present invention have greater than 50% (e.g., about 60%) motility after they are thawed in a 37° C. water bath for about 50 seconds. As discussed above, sperm motility may be analyzed by an automatic machine (e.g., the IVOS sperm analyzer from Hamilton Thorn Research) or by visual examination.

It should be noted that the cryopreservation methods described above are contemplated as being used in a commercial scale sperm sorting process. Thus, according to one embodiment of the present invention, the steps of the inventive methods described herein are performed simultaneously on a batch of sorted sperm cells to quickly cryopreserve the entire batch of sperm cells in a manner that preserves their health. For example, by using the multi-channel flow cytometry apparatus described below, it is possible to obtain about $840 \times 10^6$ sorted X chromosome-bearing sperm cells in the collection system of the apparatus in about 20 minutes. This is enough sperm cells to fill several dozen straws. Moreover, a batch can include the combined sperm cells by two or more different sorting cytometers. After being concentrated as described above, the sperm cells can be loaded into any number of straws and cryopreserved as a batch. For example, according to one embodiment of the invention, it takes about 5 minutes to add an extender (including both a protein source and a cryoprotectant) to a batch of sperm cells, and about 15 minutes to load the sperm cells into artificial insemination straws using an automatic loading machine. All the straws in the batch are cooled simultaneously in a programmable freezer. Furthermore, the capacity of some programmable freezers allows simultaneous cryopreservation of thousands of artificial insemination straws. For example, the IceCube 1810CD freezer referred to above has the capacity to cryopreserve simultaneously over 2.500 0.5 ml straws or over 3.800 0.25 ml straws. Thus, one could wait to start the cooling step until multiple batches have been obtained. Alternatively, multiple batches could be obtained substantially at the same time by running multiple multi-channel flow cytometry machines (see below) in parallel and simultaneously cooling multiple batches obtained therefrom together in a programmable freezer. In one embodiment of the present invention, it takes a period of less than 220 minutes to cool the sperm cells from room temperature to a supercooled state and immerse them in liquid nitrogen (−196° C.). In another embodiment, the supercooling period is less than 190 minutes. In still another embodiment, the supercooling period is less than 150 minutes.

Those skilled in the art will recognize that substantial modifications may be made to the foregoing exemplary methods without departing from the scope of the present invention. For example, the sperm cells may be cryopreserved in a container other than an artificial insemination straw. Likewise, the steps in the method that involve changing or maintaining temperature may be performed by any suitable means, including water baths, liquid nitrogen vapors, and conventional programmable or non-programmable freezers, for example. Furthermore, a wide variety of substances or combinations of substances could be used as the protein source and/or the cryoprotectant without departing from the scope of the present invention. These substances include substances and concentrations of substances listed above in connection with the discussions regarding buffers, extenders, cryoprotectants, sheath fluids, and collection fluids. Moreover, the order of some steps in the method may be varied without departing from the scope of this invention. Although FIG. 95 indicates that the cryoprotectant is added after the concentration of the sorted sperm is adjusted, it is also contemplated that a cryoprotectant can be added before the concentration is adjusted without departing from the scope of the present invention. For example, the cryoprotectant may be provided in the collection fluid or in the sheath fluid used in connection with a flow cytometer. Some of the benefits of the present invention may also be obtained by partially cooling the sperm cells and then adding the cryoprotectant. Likewise, the order in which the protein source is added may be varied as long as the protein source is effective to protect the sperm cells from cold shock as they pass through the temperature range of about 14 to 8° C.

Cryopreservation Example I

Figure 104:
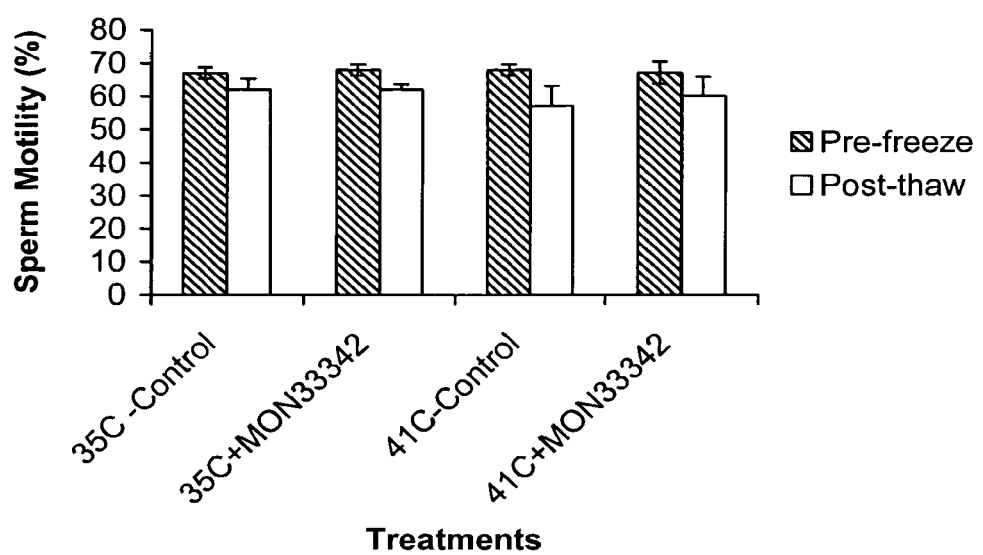
FIG. 104 shows graphical results for a sperm cell cryopreservation experiment.

Bovine semen was collected, transported, and evaluated as described above. Two test tubes containing 5 ml each of TCA buffer (pH 7.3) were placed in one of two water baths for at least five minutes. One water bath was at a temperature of 35° C. and the other water bath was at 41° C. Spermatozoa at 24° C. were added to each tube so that the final concentration in each tube was $150 \times 10^6$ sperm/ml. The two tubes were each divided into two aliquots which were kept in respective water baths. After the sperm had equilibrated with the TCA buffer for five minutes, 80 µM Hoechst 33342 was added to one of 35° C. aliquots and one of the 41° C. aliquots. After addition of the Hoechst 33342, all four aliquots were incubated for 20 minutes in their respective water bath. After incubation, the test tubes were removed from the water baths and left at room temperature (about 25° C.) for five minutes. Then the contents of each test tube were diluted with a TCA extender containing 20% egg yolk and 6% glycerol (v/v) (pH 7.0) to a final concentration of $20 \times 10^6$ sperm/ml. The contents of each test tube were then used to fill a 0.5 ml artificial insemination straw. Each of the four straws was placed in a programmable freezer (an IceCube 1810CD freezer from Minitube of America, Wis.). The following cooling sequence was programmed into the programmable freezer: (1) 22° C. to 4° C. @ −0.2° C./min; (2) hold at 4° C. for 30 min; (3) 4° C. to −15° C. @ −3.0° C./min; and (4) −15° C. to −80° C. @ −10.0° C./min. After reaching −80° C., the straws were immersed in liquid nitrogen (−196° C.) for 45 minutes. Then the straws were immersed in a 37° C. water bath for 50 seconds to thaw. Sperm motility was checked under a phase contrast microscope both before and after cryopreservation. The results are shown in FIG. 104. The post-thaw motility was generally on the order of 60%. This represents a decline in motility of only about 5-11% compared to before cryopreservation. Analysis of variance revealed no significant effect of either Hoechst 33342 or incubation at 41° C. on post-thaw sperm motility.

Operation of the System

Figure 82:
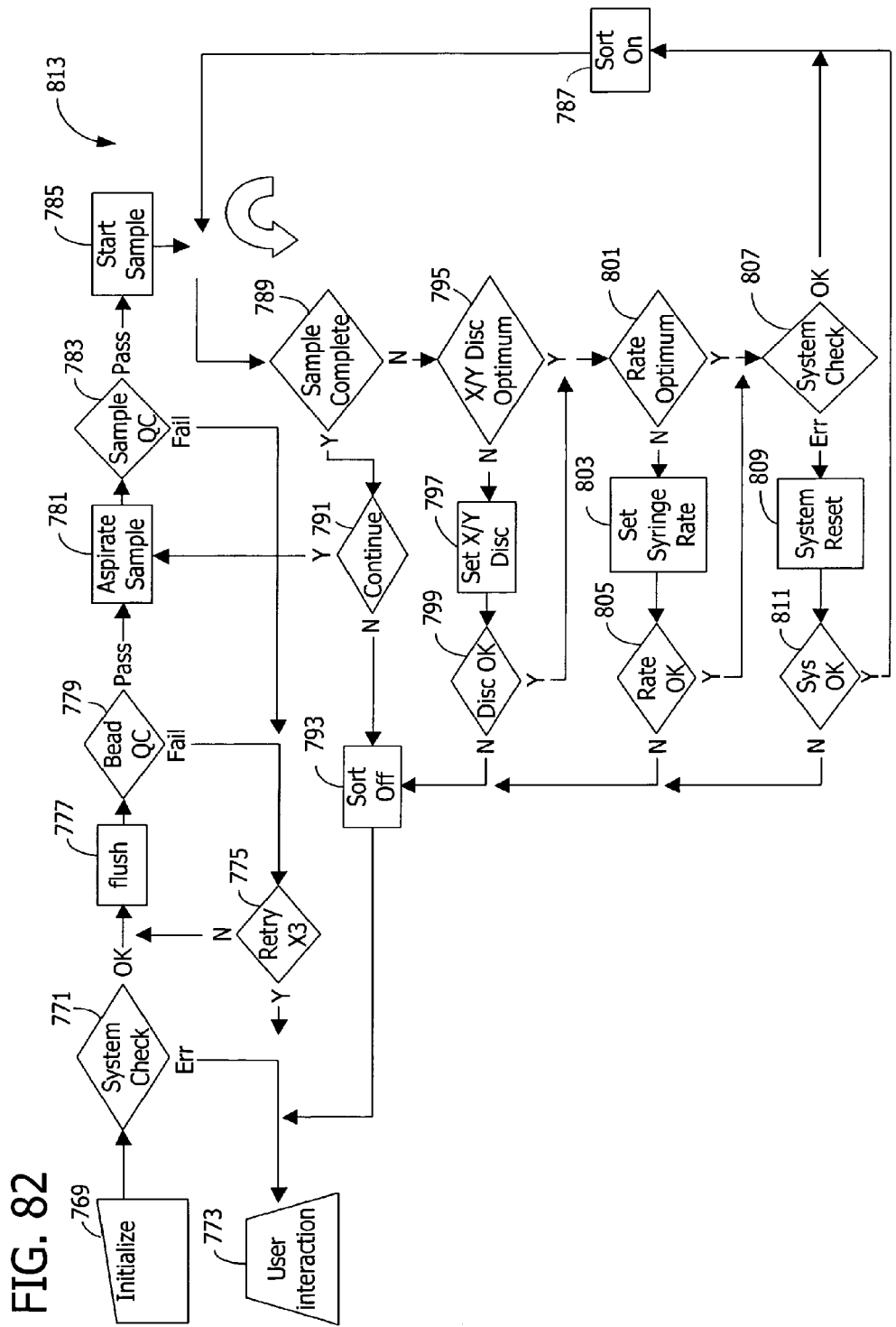
FIG. 82 is a decision flow diagram showing the overall operation of one embodiment of a sorting apparatus of the present invention.

The overall operation 813 of the flow cytometry system 9 will now be described with reference to FIG. 82 and in the specific context of sperm cells (e.g., bovine sperm cells), but it will be understood that the description is exemplary only, and that the system can be used to process other types of particles.

The first series of steps leading up to the six second repeat loop involve calibration of the system. After initializing 769, a system check 771 is performed to confirm, among other things, that the processor 131 or processors are operational. If an error is detected after three failed system checks 775, user interaction 773 is requested. If the system check is positive, the microprocessor directs the system to flush 777 the nozzle system with a suitable fluid, and then a quality control material 779, such as beads or bovine nuclei, are run through the system to initialize the detection parameters (see 739 in FIG. 72) and confirm that the system is operating within an acceptable quality control. This involves an evaluation of the control material to test the sensitivity and precision of the system to confirm that the system can adequately discriminate a sample. If the quality control is not confirmed after three attempts 775, user intervention 773 is requested.

If the quality control material indicates an acceptable level of quality control, a sample 781 is aspirated and a portion or aliquot of the sample to be sorted is checked for quality 783. Sample quality may be determined by a calculation of a quality factor (Q-factor) of the sample. For example, the type of cells may be detected in a first aliquot of the sample. During this detection, the initialized detection parameters (741) are rechecked and the initial discrimination parameters (745) are generated. If the type of cells detected in the aliquot indicates that the sample meets or exceeds a preset standard (e.g., that the sample can be discriminated to yield a certain purity or motility and, in particular, that there are sufficient live X cells available for processing), then the system continues operation. If sample quality fails three times 775, user interaction is requested.

Continued operation involves sorting 785 of the remainder of the sample employing a six second repeated loop. At the beginning of the loop, the microprocessor confirms that sorting of the sample is not complete 789. If the sorting of the sample is complete 789, the microprocessor proceeds to aspirate the next sample 781 if it is available or to turn off the sorting operation 793 if additional sample is not available. If the sample is not complete 789, the microprocessor initially checks the X/Y discrimination 795 of the sample to confirm that it is within an optimum range. In other words, drift analysis as noted above (761 in FIG. 72) is conducted. If any changes should be made, such changes are implemented and the discrimination 795 is again checked. If the discrimination is still unacceptable at this point, the sort is turned off 793 and user interaction is requested.

Otherwise, the system proceeds to determine whether the fluid delivery system is delivering fluid and cells at a rate which is within an optimum range 801. This determination depends on the type of control strategy used. For the high recovery control strategy, the optimum rate would be determined by evaluating purity or looking at x/x+~X of the collected population. If the determined purity is higher than a required purity level, the feed input rate of the cells is increased by increasing a rate control signal provided to the syringe pump 803. This would tend to increase coincident cells and decrease purity because more coincident cells including ~X cells would be collected with the X cells. If the determined purity is lower than the required purity, the feed input rate of the cells is decreased by decreasing a rate control signal provided to the syringe pump to reduce the frequency of coincident cells 803. Thus, the cell input rate is a function of the determined purity of the collected population as compared to a desired purity level, e.g., a function of the identified ~X sperm cells collected.

For the high purity control strategy, the optimum rate would be determined by calculating lost X cells, e.g., discarded X/discarded X+collected X. If the quantity or percentage of lost X cells are less than an acceptable level, the input rate of the cells is increased by increasing a rate control signal provided to the syringe pump 803. This would tend to increase coincident cells and increase the number of discarded X cells because more cells including X cells would be discarded with the Y cells. If the quantity or percentage of lost X cells is higher than the acceptable level, the input rate of the cells is decreased by decreasing a rate control signal provided to the syringe pump 803 to decrease coincident cells. Thus, the cell input rate is a function of the determined lost X cells of the discarded population as compared to number of X cells in the collected population, e.g., a function of the number of X sperm cells not collected.

If this modified rate is acceptable 805, the system proceeds to another system check 807. If the system check is acceptable 807, the sort continues in the six second loop. If not, the system is reset 809. If after reset the system is not acceptable or if the revised feed rate is not acceptable 811, the sort is turned off 793 and user intervention is requested 773.

The sorted droplet streams are collected by the collection system 2201. Droplets that are sorted into the population of X cells pass through the exit window 2245 in the first intercepting device 2247 to be intercepted by the second intercepting device 2249. From there, the droplets containing the X cells flow into a collection vessel 2207. Other droplets are intercepted by the first intercepting device 2247 and directed to the waste trough 2805. Of course droplets intercepted by the first intercepting device could also be saved, as noted above. When a suitable amount of X-bearing sperm cells have been collected in the collection vessel, sorting may be interrupted to allow concentration of sperm cells in the collection vessel 2207. A new collection vessel may be placed under the first intercepting device 2247 or the collected fluid may be poured into a different container and the collection vessel replaced. Then sorting may resume. The sperm cells in the collected fluid are concentrated, loaded in straws, and frozen as described above.

Temperature Control During Operation

Temperature control throughout the process may be used to improve the results of the process. As has already been discussed above, the temperature of the sperm may be controlled during various steps in the process (e.g., staining and cryopreservation). In several embodiments of this invention, the temperatures of the sperm cells throughout the various steps of the method are controlled to achieve improved results.

Figure 105:
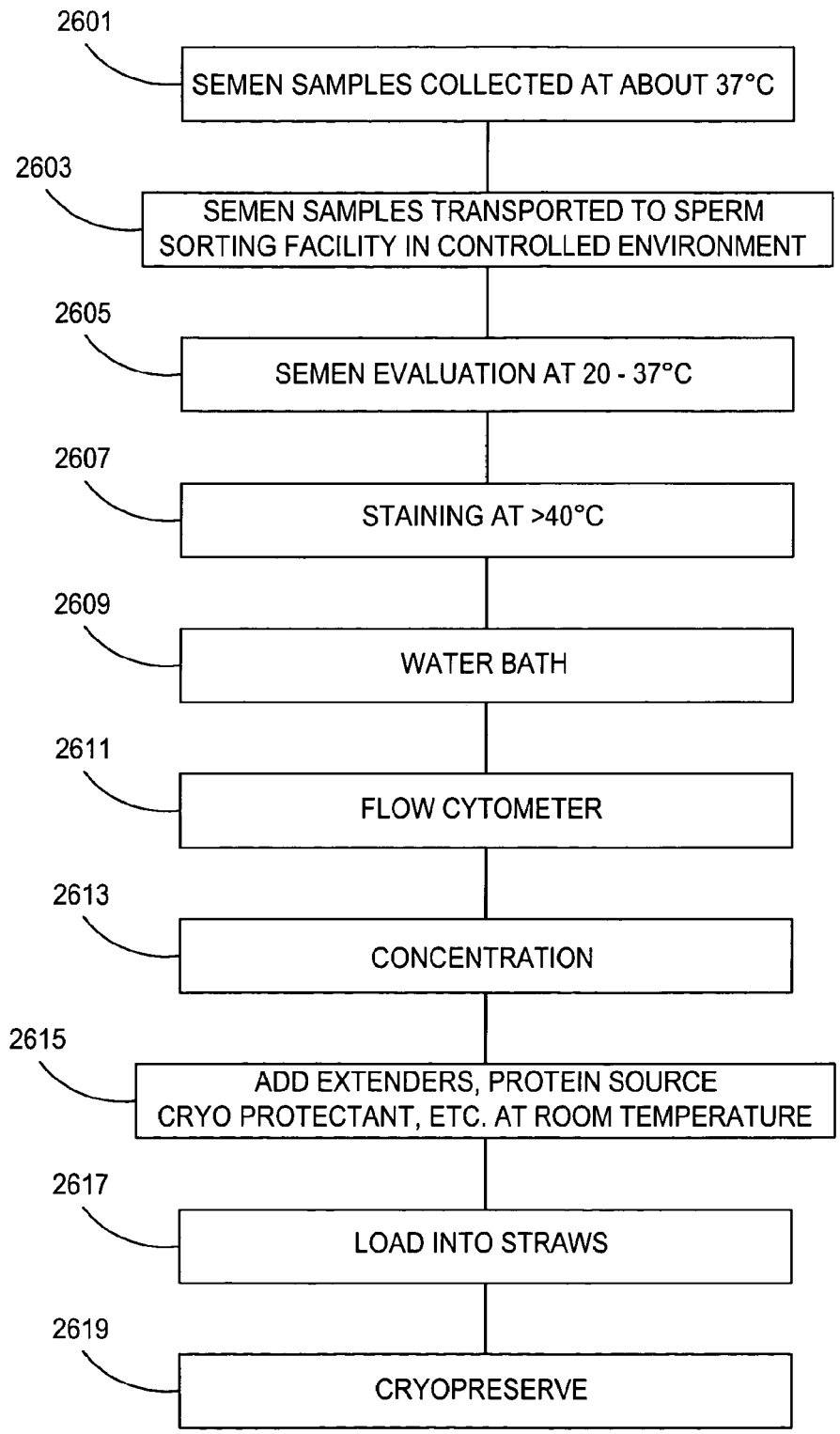
FIG. 105 is a work flow diagram for one embodiment of a method of processing sperm cells according to the present invention.

For example, FIG. 105 is a work flow diagram of one embodiment of a method of temperature control according to the present invention. The temperature of semen samples at the time they are collected will be determined by the body temperature of the animal from which they are collected. For example, at step 2601 bovine semen samples are collected at about 37° C. An insulated container is used for transportation of the semen samples to the lab from the collection site at step 2603. The insulated container retards cooling of the sperm.

During sample evaluation at step 2605, the temperature is maintained below the collection temperature, but in excess of a temperature corresponding to a glass transition temperature below which the sperm cells suffer membrane damage. For example the temperature may be maintained in the range of about 18-37° C. In another embodiment, the temperature may be maintained in the range of about 24-37° C. during sample evaluation. In a particular embodiment, the sperm cells are placed in an environment having a temperature in the range of about 22-25° C. during sample evaluation. Depending on the temperature of the sperm upon arrival at the lab, the effect of placing them in an environment having a temperature in the range of about 22-25° C. may be to continue slow cooling of the sperm, to maintain the temperature of the sperm, or to slightly raise the temperature of the sperm. In one embodiment, the temperature may be elevated (e.g., to 40° C. or higher) for staining at step 2607 as discussed in the staining section. In another embodiment, the temperature of the sperm cells during the staining step may be in the range of about 20-40° C., as is also discussed above.

At step 2609, the stained semen mixture is held in a water bath until such time that the mixture is introduced into a flow cytometer. The temperature of the water bath may be similar to the temperature used for the staining step. In one embodiment the temperature of the water bath is in the range of about 40-47° C. In another embodiment, the temperature of the water bath is in the range of about 20-37° C. In still another embodiment, the temperature of the water bath is in the range of about 20-25° C. After being held in the water bath for any time between one minute and two hours, the stained sperms cells are sorted by flow cytometry as discussed above at step 2611. At step 2613, the collected sperm cells are concentrated. Concentration may be performed in an environment that has a temperature that will not significantly change the temperature of the sperm cells. For example, in one embodiment, concentration may be performed in an environment having a temperature in the range of about 20 and 25° C. An extender, protein source, and cryoprotectant are added to the concentrated sperm at step 2615. Then, at step 2617 the sperm cells are loaded into artificial insemination straws. In one embodiment, the loading step is performed in an environment having a temperature that will not significantly change the temperature of the sperm cells. Finally, at step 2619 the temperature of the sperm is controlled during cryopreservation as discussed above.

In another embodiment, sperm cells may be stained at still lower temperatures without departing from the scope of the present invention. For example, it may be desired to sort the sperm cells in a flow cytometer at a relatively low temperature (e.g., about 0° C. to about 8° C.). This may require modification of the overall temperature control. First, when cooling the sperm cells prior to introduction into a flow cytometer, egg yolk and other common protein sources that protect the sperm cells from cold shock at temperatures below the glass transition temperature generally may not be used as such protein-containing substances tend to foul and/or clog the fluidics of the flow cytometer. Thus, it is desirable to cool the sperm cells before performing the staining step in order to take advantage of natural cold shock protectants found in neat semen, such as for example, the seminal fluid. Any attempt to stain the sperm cells prior to cooling would require addition of buffers to protect the sperm which would dilute the neat semen and reduce the natural protection against cold shock.

Accordingly, one embodiment of the present invention for sorting the sperm cells at a temperature in the range of about 0° C. to about 8° C. includes placing the sperm cells in an environment having a temperature less than about 8° C. to cool the sperm cells to a temperature in the range of about 0° C. to about 8° C. prior to staining. Any method may be used to cool the sperm cells, but it is desirable to use a method that protects against rapid temperature fluctuations of the sperm cells during the cooling process. For example, in one embodiment, a container holding the sperm cells is placed in a room temperature water bath, which in turn is placed in an environment having a temperature less than about 8° C. In another embodiment, the temperature of the sperm cells is monitored and ice is added to the water bath to further cool the sperm cells. The staining step may be performed as described above except that the staining mixture is subjected to a temperature in the range of about 0° C. to about 8° C. Due to the lower temperature, the incubation period required to stain the cells is considerably longer. Once the sperm cells have been cooled to 8° C. or below, it is desirable to avoid warming them. Thus, another embodiment of the present invention is to operate the flow cytometer in an environment having a temperature in the range of about 0° C. to about 8° C. Similarly, another embodiment of the present invention is to collect the sorted sperm cells in a collection vessel that is surrounded by an environment having a temperature in the range of about 0° C. to about 8° C. Still another embodiment of the present invention is to add any extenders, cryoprotectants, buffers, protein sources, antibiotics, antioxidants, or other additives at a temperature in the range of about 0° C. to about 8° C. With respect to addition of the cryoprotectant, it may be desirable to add slightly more of the cryoprotectant than would be added absent sorting the sperm cells at a temperature in the range of about 0° C. to about 8° C. Thus, in one particular embodiment, a cryoprotectant containing 7% glycerol (v/v) is added to sperm cells after the sperm cells have been sorted at a temperature in the range of about 0° C. to about 8° C.

Supercooling of the sperm cells from the temperature in the range of about 0° C. to about 8° C. proceeds generally as described in the cryopreservation section above. However, the sperm cells will need to be held at a temperature in the range of about 0° C. to about 8° C. for a period of time after addition of the cryoprotectant before supercooling to allow time for the sperm cells to equilibrate with the cryoprotectant. Thus, according to one embodiment, the sperm cells are allowed to equilibrate with the cryoprotectant for a period in the range of about 30 minutes to about 3 hours. In another embodiment, the sperm cells are allowed to equilibrate with the cryoprotectant for a period in the range of 1-2 hours. In another particular embodiment, the sperm cells are allowed to equilibrate with the cryoprotectant for a period of about 90 minutes.

Conventional temperature control apparatus and methods (e.g., water baths, incubators, coolers, and freezers) may be used to heat or cool the sample to attain or maintain the specified temperatures in the foregoing embodiments of the invention. It is understood that placing a sample in an environment having a different temperature than the sample, will cause the temperature of the sample to change over time. There may even be temperature variations within the sample. As has been mentioned, it is desirable to change the temperature of the sample gradually to help maintain the health of the sperm. Gradual temperature change also serves to reduce the temperature variation within the sample. As is well known by those skilled in the art, the rate of temperature change of the sample will be influenced by many factors, including the volume of the sample, the size and shape of the sample container, and the magnitude of the temperature difference between the sample and the environment. However, those skilled in the art will readily be able to select an appropriate method and apparatus to achieve the desired temperature control after considering all the relevant factors.

Those skilled in the art will recognize that there is room for substantial variation in the exemplary temperature control without departing from the scope of the invention. In general, once the sperm cells have been chilled, it is desirable to avoid warming them. Furthermore, temperature variations discussed above in connection with sample collection, staining, sorting, droplet collection, concentration, and cryopreservation can be incorporated into the overall temperature control without departing from the scope of the present invention. Moreover, the time at which sperm cells remain at any temperature can also impact the health of the sperm. Thus, processing according to the embodiment in which temperature is controlled throughout the process is desirably completed within a timeline as discussed below.

Timeline for Operation

Generally, it is desirable to complete the sperm sorting process in the least amount of time possible to reduce the damage to the sperm. As discussed above, the present invention may include staining at an elevated temperature to reduce the time needed to stain the sperm cells. For example, certain embodiments of the improved staining method described reduce the time require for staining to about 10 minutes. Likewise, the novel cytometer described above may be used to sort sperm cells in less time than would be required by a conventional cytometer. For example, a flow cytometer using the technology discussed above can collect between 2,000 and 10,000 sperm cells having a desired DNA characteristic per second. Furthermore, the cryopreservation process may be used to reduce the time needed to complete cryopreservation of the processed sperm cells compared to conventional cryopreservation methods. Accordingly, one embodiment of the present invention involves processing sperm pursuant to an overall method to take advantage of one or more of the timesaving innovations to reduce the time required to complete the entire process. For example, according to one embodiment of the present invention, a batch of sperm cells (e.g., an ejaculate) is collected from a male mammal (e.g., bull), evaluated for quality control, stained, sorted according to a specified DNA characteristic, loaded into one or more containers (e.g., straws), and cryopreserved within a period of about 12 hours from the time of collection. In another embodiment, the period is less than about 8 hours. In another embodiment, the period is less than about 6 hours. In still another embodiment, the period is less than about 3 hours. In yet another embodiment, the period of time is less than about 2 hours. In another embodiment, the period of time is less than about 1 hour.

Multi-Channel Sorting Apparatus and Method

In order to sort more sperm in less time, it is possible to use more than one cytometry unit in parallel to sort that same sperm sample. One way to do this is to simply divide the stained sperm cells into multiple aliquots and run each aliquot through a different cytometer. However, as will be discussed below, certain advantages may be obtained by designing an apparatus that comprises multiple cytometry units in a single integrated multi-channel cytometry unit.

Multi-Channel System Sharing Integrated Platform

FIGS. 106-116 show one embodiment of the invention comprising a multi-channel cytometry system, generally designated 1001, where multiple single-channel flow cytometry units, designated 1003, are ganged together as an integrated system to produce sorted product. Four such units are illustrated in this particular embodiment, but this number can vary. The units may be integrated in various ways, as by sharing an integrated platform comprising one or more of the following elements (1) a common supply of particles 1005; (2) a common source of electromagnetic radiation 1007; (3) a common housing 1009; (4) a common input for controlling operation of the units 1011; (5) a common output 1019 allowing evaluation of the operation of one unit relative to another unit; (6) a common fluid delivery system 1021; (7) a common temperature control system 1023; (7) a common power source 1025; (8) a common waste recovery system 1027; (9) a common deflector plate system 1029; and (9) a common cleaning system 1031. In one embodiment, the system includes all of these elements, but it will be understood that a multi-channel system of this invention can include any combination of elements. The use of common elements is beneficial because it allows the system to be run more efficiently and profitably, achieves more consistent results among channels by reducing the number of variables, facilitates any troubleshooting that may be needed, and is economical. The multi-channel approach also makes the sorting system more amenable to scale up or scale-down.

Each of the cytometry units 1003 has components similar to certain components of the flow cytometry apparatus 9 of the previous embodiment and, for convenience, corresponding parts are designated by the same reference numbers with the addition of a prime ('). In general, each unit comprises a nozzle system 101', a mount for mounting the nozzle system 331', a transducer 105', and an epi-illumination optics instrument 417' for focusing a beam of light 25' on the fluid stream 21' exiting the nozzle orifice 103', all as previously described. Each unit further comprises a photodetector 117' operable as in the first embodiment to detect fluorescence emissions 31' from the particles in the stream 21' and to convert the emissions 31' to electrical signals 701' which are processed to classify the particles by a specified DNA characteristic. Each unit 1003 is also equipped for sorting the droplets 33' into different groups or populations 123', 125' according to the classification of particles contained in the droplets 35'. The populations of droplets sorted by the units are collected by the collection system 2201.

A. Common Housing and Modularity

The flow cytometry units are mounted in a modular arrangement in a common housing 1009. In the embodiment shown in FIGS. 106 and 109-113, the housing has a base 1069 and two side walls 1071 extending up from the base. The side walls have a lower pair of shoulders 1073 for supporting a lower cover panel 1075 at the front of the housing 1077, and an upper pair of shoulders 1081. A lower cover panel 1075 at the front of the housing 1077 is mounted between the lower shoulders 1073. The upper shoulders 1081 support an upper cover panel 1083 at the rear of the housing 1085. The front and rear of the housing 1077, 1085 are substantially open to provide access to the equipment inside. It will be understood that the housing 1009 may have other configurations without departing from the scope of the invention. Further, it will be understood that the various units could be installed in separate housings.

The flow cytometry units 1003 are mounted side-by-side as modules on an appropriate framework 1087 in the housing 1009. Specifically, the nozzle mounts 331' for positioning the nozzles 101' are releasably attached to a cross bar 1089 (FIG. 106) affixed to the side walls 1071 of the housing, and the bases 429' of the epi-illumination instruments 417' are releasably fastened to an angled mounting plate 1093 extending between the side walls 1071 of the housing toward the rear of the housing 1085 (FIG. 109), the arrangement being such that a particular unit can be installed or removed as a module. This modularity facilitates installation, removal for maintenance and/or replacement, and enables any number of flow cytometry units 1003 to be readily added as needed or desired to increase the throughput capacity of the system.

B. Common Fluid Supply and Delivery Systems

The fluid delivery system 1021 of this embodiment is equipped to provide appropriate fluids to each of the cytometry units 1003. As illustrated schematically in FIG. 108, the system generally comprises a pump 1105 for conveying carrier fluid IT from a common supply of carrier fluid 1107 under pressure, a gas pressure system 1115 for conveying fluid from a common supply 1117 of sheath fluid 19' under pressure, and a manifold system 1121 for receiving the fluids from respective supplies and delivering the fluids under pressure to the various cytometry units 1003, as needed. In the specific embodiment of FIG. 116, the supply of carrier fluid comprises a vessel 1123 containing a suitable volume of such fluid (e.g., 5 ml.). The vessel is held by a holder 1125, which may be a block 1133 having a cavity 1135 sized to receive the vessel 1123. The block also has a second cavity 1137 for holding a vessel 1139 containing a suitable buffer material for conditioning the system during use, as will be described later.

The pump 1105 for delivering carrier fluid from the vessel is desirably (but not necessarily) a syringe pump 1141 as previously described. The plunger of the pump is movable through an intake stroke to aspirate a selected volume of carrier fluid 17' from the vessel 1139 and through a discharge stroke to dispense carrier fluid through a supply line 1147 to the manifold 1177 and from there to the various nozzles 101' of the system. The syringe pump is also operable to aspirate fluid from the vessel 1139 containing buffer and to pump the buffer through the system in a manner to be described. A three-way valve 1149 controls the flow of carrier and buffer fluids to and from the pump 1141. The pump is driven by a variable speed motor under the control of the processor 131'. By way of example, the pump may be driven by a stepper motor which operates at selectively variable speeds to pump carrier fluid to the manifold system 1121 at rates necessary to obtain the desired throughput from the units 1003. Multiple syringe pumps or other types of fluid delivery devices can be used instead of a single syringe pump.

In one embodiment the supply 1117 of sheath fluid comprises a vessel 1155, e.g., a tank connected to the manifold 1177 by means of a supply line 1157. The gas pressure system 1115 is operable to pressurize the tank and comprises a source of pressurized gas 1161 (e.g., air or nitrogen) communicating with the tank via a gas line 1163 having a regulator 1165 in it for controlling the pressure supplied to the tank, and a two-way valve 1167 which, in a first position, establishes communication between the tank and the gas source, and in a second position, is operable to vent the tank. The gas pressure regulator 1165 is a conventional regulator adjustable to control the pressure supplied from the air source. The gas pressure system 1115 also includes a gas line 1169 for pressurizing a supply 1173 of cleaning solution (e.g., de-ionized water in a tank) which can be used to flush the fluid circuitry in a manner to be described hereinafter. Flow through the gas line is controlled by a two-way valve 1167 operable in the same manner as valve 1167.

Figure 116:
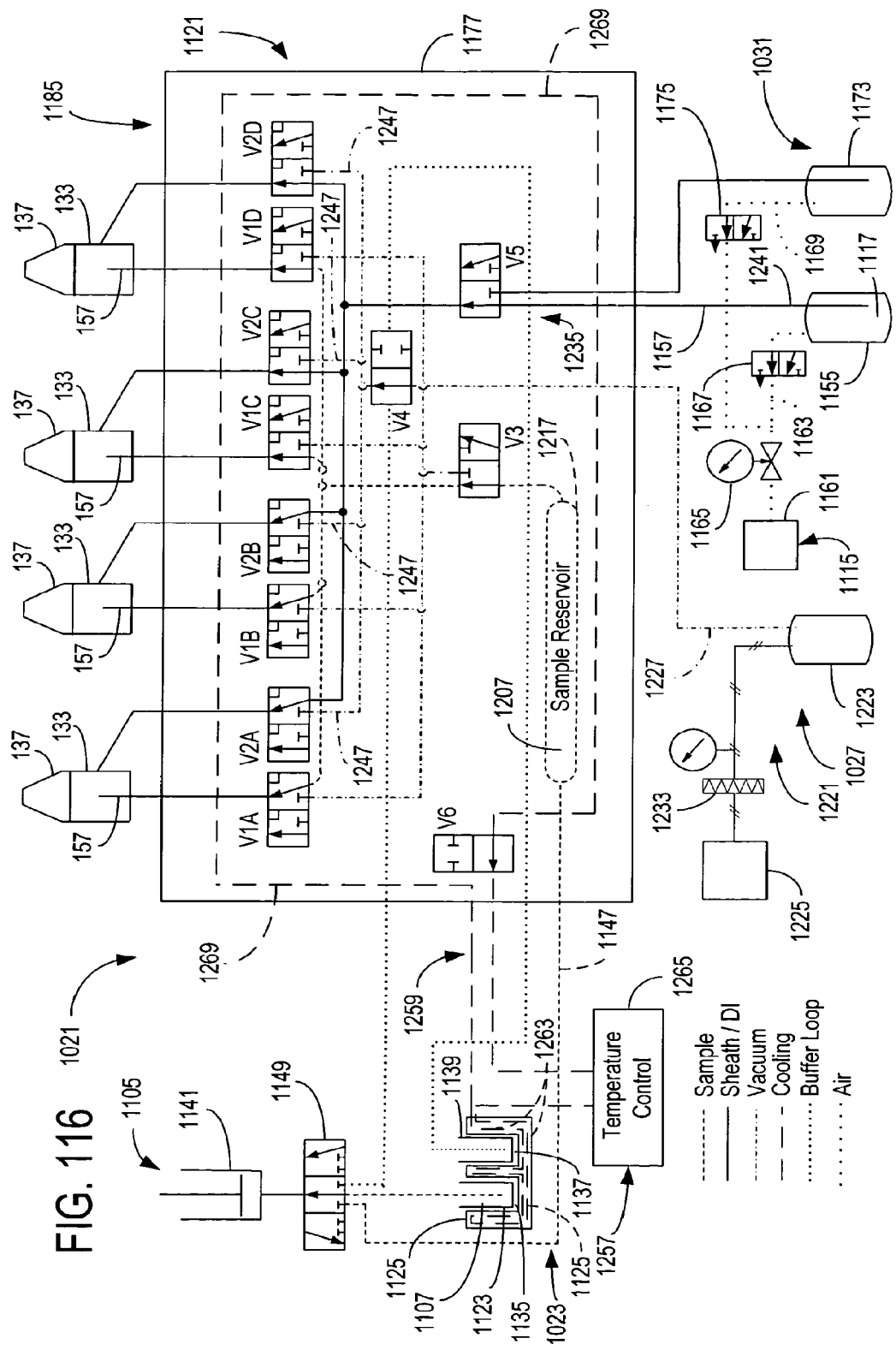
FIG. 116 is a schematic diagram of one embodiment of a fluid delivery system for a multi-channel sorter of the present invention.

In one embodiment, the manifold 1177 comprises a laminated block 1179 (FIG. 112) of material having passages 1181 formed in it to define a fluid flow circuit 1185 such as that shown diagrammatically in FIG. 116. (The passages may be formed by machining grooves in faces of the laminations prior to assembly of the laminations to form the block.) The fluid circuit includes inlets 1189, 1191 connected to the syringe pump 1141 and to the supply 1117 of sheath fluid, and sets of outlets 1193, for providing such fluids to the flow cytometry units 1003, each such set including a carrier fluid outlet and a sheath fluid outlet. Flow through the various flow passages 1181 is controlled by valves V1-V6 which, in one embodiment, are solenoid-operated valves in housings attached to the manifold block 1179. The block is desirably of substantially transparent material (e.g., acrylic plastic) to facilitate monitoring of the system 1121 and trouble-shooting. In the embodiment shown, the manifold 1177 is attached to a frame member 1203 extending between the side walls 1071 of the housing 1009 adjacent the bottom of the housing below the nozzle systems 101'. The inlets and outlets 1193, of the manifold 1177 may comprise fittings 1205 threaded into the block, such as flangeless nut and ferrule fittings available from Upchurch Scientific, a division of Scivex. It will be understood that the design and construction of the fluid circuit 1185 in general and the manifold 1177 in particular may vary without departing from the scope of the present invention.

Referring to FIG. 116, the manifold fluid circuit 1185 for the carrier fluid 17' includes a sample reservoir 1207 for holding a limited supply of carrier fluid (e.g., 1.0 ml). If the carrier fluid contains sperm cells, for example, providing such a reservoir close to the nozzles 101' is beneficial to the viability and motility of the sperm cells, since the storage of such cells, even for short periods of time, in small spaces may be detrimental to motility. Flow of carrier fluid from the sample reservoir 1207 to the nozzles 101' is controlled by a series of two-way valves V1A-V1D, one for each nozzle. Each valve VIA-V1D has a first position establishing fluid communication between the needle 1217 of the sample reservoir and the needle 157' of a respective nozzle for delivery of carrier fluid 17' to the needle under pressure generated by the syringe pump 1141, and a second position establishing fluid communication between the needle 1217 and a waste system, generally designated 1221, which is common to all of the flow cytometry units 1003. In the embodiment shown, the waste system 1221 comprises a waste tank 1223 for holding waste material, a mechanism 1225 such as a vacuum pump for generating a vacuum in the waste tank, and waste lines 1227 connecting the valves VIA-V1D and the waste tank. A valve V3 is provided in the waste line upstream from the waste tank for opening and closing the waste line, as needed. A suitable hydrophobic filter 1233 is provided in the line connecting the waste tank 1223 and the vacuum pump 1225.

The manifold fluid circuit 1185 for the sheath fluid 19' includes a plurality of valves V2A-V2D. Each valve has a first position establishing fluid communication with the supply 1117 of sheath fluid in the tank for delivery of sheath fluid 19' to a respective flow body 133' via a sheath supply line 1241, and a second position establishing fluid communication between the flow body and the waste tank via a waste line 1247. The pressure at which the sheath fluid is delivered to the flow bodies 133' will depend on the sheath tank pressure (as controlled by the regulator 1165) which may range from 1 to 100 psi, more desirably from 10 to 50 psi, even more desirably 15 to 40 psi, and even more desirably from about 20 to 30 psi.

While the use of a common supply for all of the units has various advantages, it is contemplated that at least some of the flow cytometry units could be supplied with sample material from separate sources.

C. Common Power Supply and Input and Output Controls

The flow cytometry units 1003 also share a common power supply 1025, common power delivery systems, a common input (GUI) 715' for controlling operation of the channels by the microprocessor 131', and a common output provided to the microprocessor allowing evaluation of the operation of one channel relative to another channel. For example, the common output includes providing the digitized signals from each epi-illumination system to the microprocessor for an indication of the fluorescence intensity measured by each channel, for an indication of the rate at which each channel is separating particles, for an indication of the staining variations (which may be indicated by the intensity difference of fluorescence pulses from X and Y cells) and for an indication of the decision boundaries 763 used by each channel for discriminating between particles. As another example, the common output includes providing the output signals from the break-off sensors 389' to the microprocessor for an indication of the droplet break-off location 107' of each channel.

D. Common Temperature Control

Optionally, a temperature control system, generally designated 1257, is provided to regulate the temperature of the contents of the vessels 1123 in the holding block 1133 and the temperature of the manifold 1177. Such temperature control reduces the variability of the system, thus providing more consistent measurements between channels and, for certain types of cells (e.g., sperm cells), helping to maintain the viability of the cells.

In one embodiment, the temperature control system 1257 comprises a fluid flow circuit 1259 comprising fluid passages 1263 in the holding block 1133 and fluid passages 1269 in the manifold block 1179, and a control unit 1265 for circulating a thermal fluid (e.g., water) through the circuit at a selected temperature. The temperature is desirably such as to maintain the fluid, especially the carrier fluid, at an optimal temperature to maximize cell viability and, if sperm cells are involved, sperm motility. A valve shut-off V6 is positioned in the circuit for controlling flow through the circuit. The temperature control unit may be used to maintain the sperm cells at the desired temperature prior to sorting as discussed above.

All of the valves in the fluid delivery system 1021 are operated by conventional means, such as solenoids, under control of an operator or suitable programming. The various fluid flow lines connecting the components of the system outside the manifold block 1179 are desirably of substantially transparent plastic tubing for observing any blockages. For example, the tubing may be 0.0625 in. OD tubing of FEP polymer. The flow lines of the temperature control system 1257 are desirably somewhat larger (e.g., 0.125 in. OD) to provide greater flow capacity.

E. Common Light Beam and Beam Splitting System

As previously noted, the multi-channel system shares a common source of electromagnetic radiation or beam light 1007. By way of example (and not limitation), the source may be a laser beam from a UV multiline laser primarily having wavelengths of 351.1 nm and 363.8 nm. Alternatively, it may be desirable to use a pulsed laser (e.g., a mode-locked laser), particularly to synchronize digital sampling with a pulsed laser (as discussed in the pulsed laser section) in order to increase the effective power delivered to each cytometry unit, thereby increasing the number of cytometry units that can be operated with a single laser.

The power required to generate the laser beam will vary depending on the requirements of each flow cytometry unit and the number of units. For example, if there are N units and each unit requires a light beam having an effective power of W watts, then it will be necessary to generate a laser beam having a power of (W×N)+L, where L equals the system power loss among the optical elements of the system. Using a single laser to supply all of the flow cytometry units is economical compared to a system using multiple lasers. It is also efficient and provides for more consistent measurements from one channel to the next, because there is no variability on account of different beam characteristics (e.g., beam intensity, light polarity, beam divergence) or electrical noise resulting from the use of multiple lasers.

Figure 117:
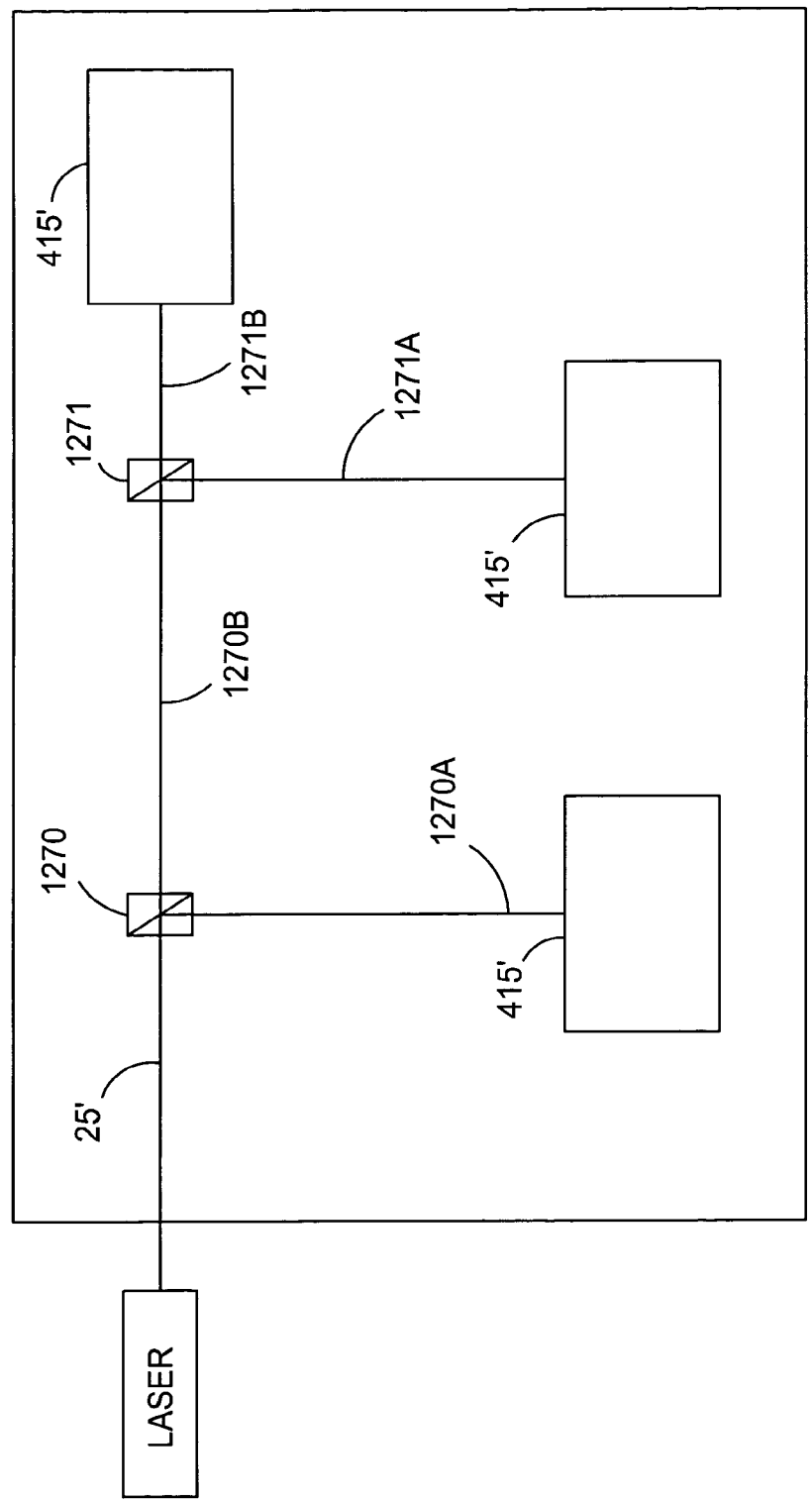
FIGS. 117 and 118 are schematic diagrams of two different laser beamsplitting systems.
Figure 118:
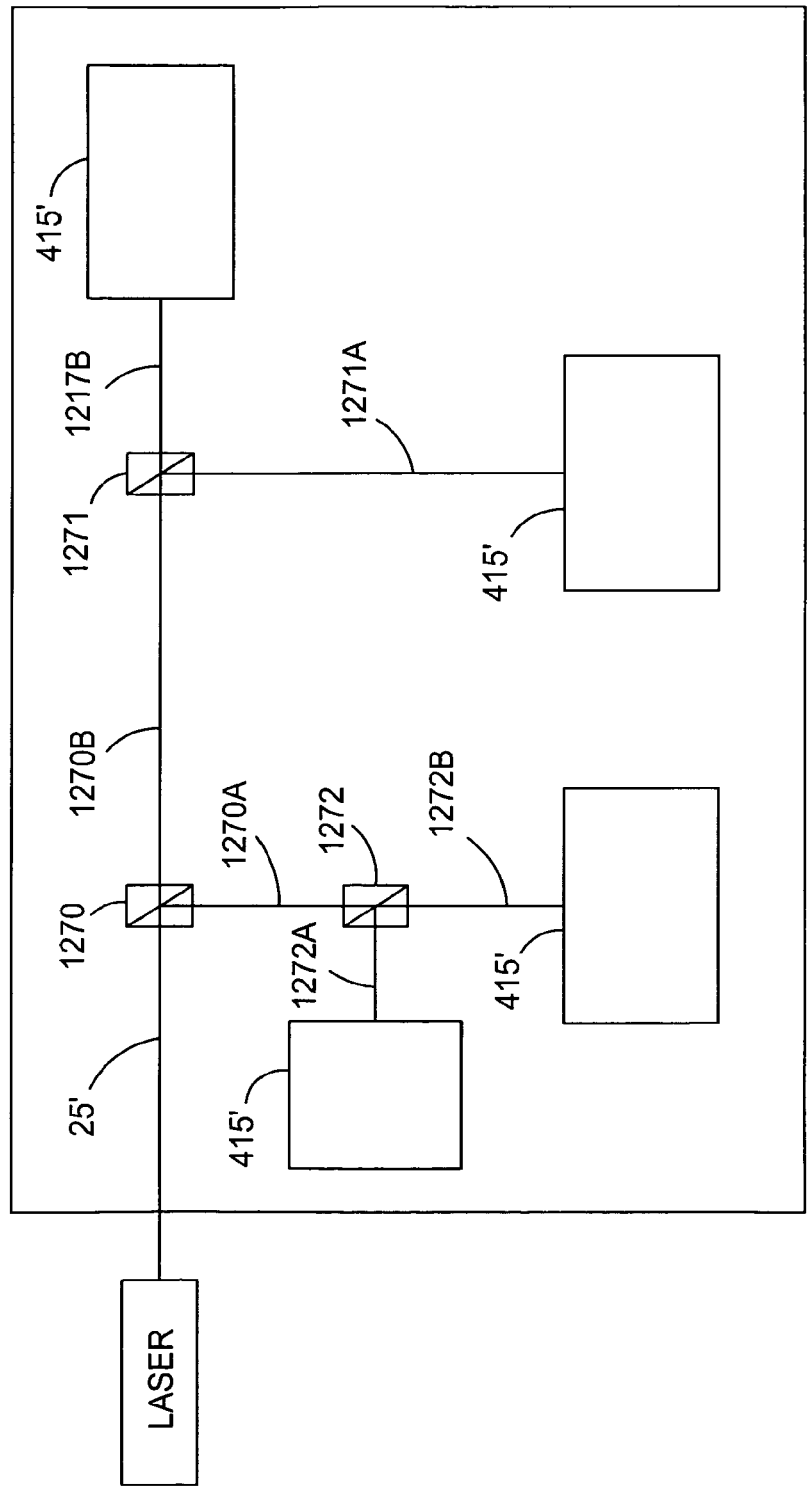

According to one embodiment of the present invention, a beam splitting and guidance system is used to split a single laser beam into three or more separate beams. As shown in FIG. 117, for example, a 50/50 beamsplitter 1270 (i.e., a beamsplitter that is operable to divide a single beam into two separate beams having approximately equal intensity) can be used to split a single beam 25' into two beams 1270A, 1270B. By using a second 50/50 beamsplitter 1271 to split one of the two beams 1270B into two additional beams 1271A, 1271B, one can generate a total of three beams 1270A, 1271A, 1271B from a single beam 25'. Each beam can be directed into the optics system of a flow cytometer, for example an epi-illumination optics system 415' as shown in FIG. 117. One could also use additional 50/50 beamsplitters to split the single laser beam into any number of additional separate beams. As shown schematically in FIG. 118, for example, a third beamsplitter 1272 can be added to the 3-way beamsplitting system (FIG. 117) so that the three 50/50 beamsplitters 1270, 1271, 1272 can be used to split a single 25' beam into four separate beams 1271A, 1271B, 1272A, 1272B. From this one can readily appreciate that the single beam can be split into any number of separate beams. Other beam splitting arrangements may be used to split the incoming source beam into multiple light beams for the various units.

Figure 106:
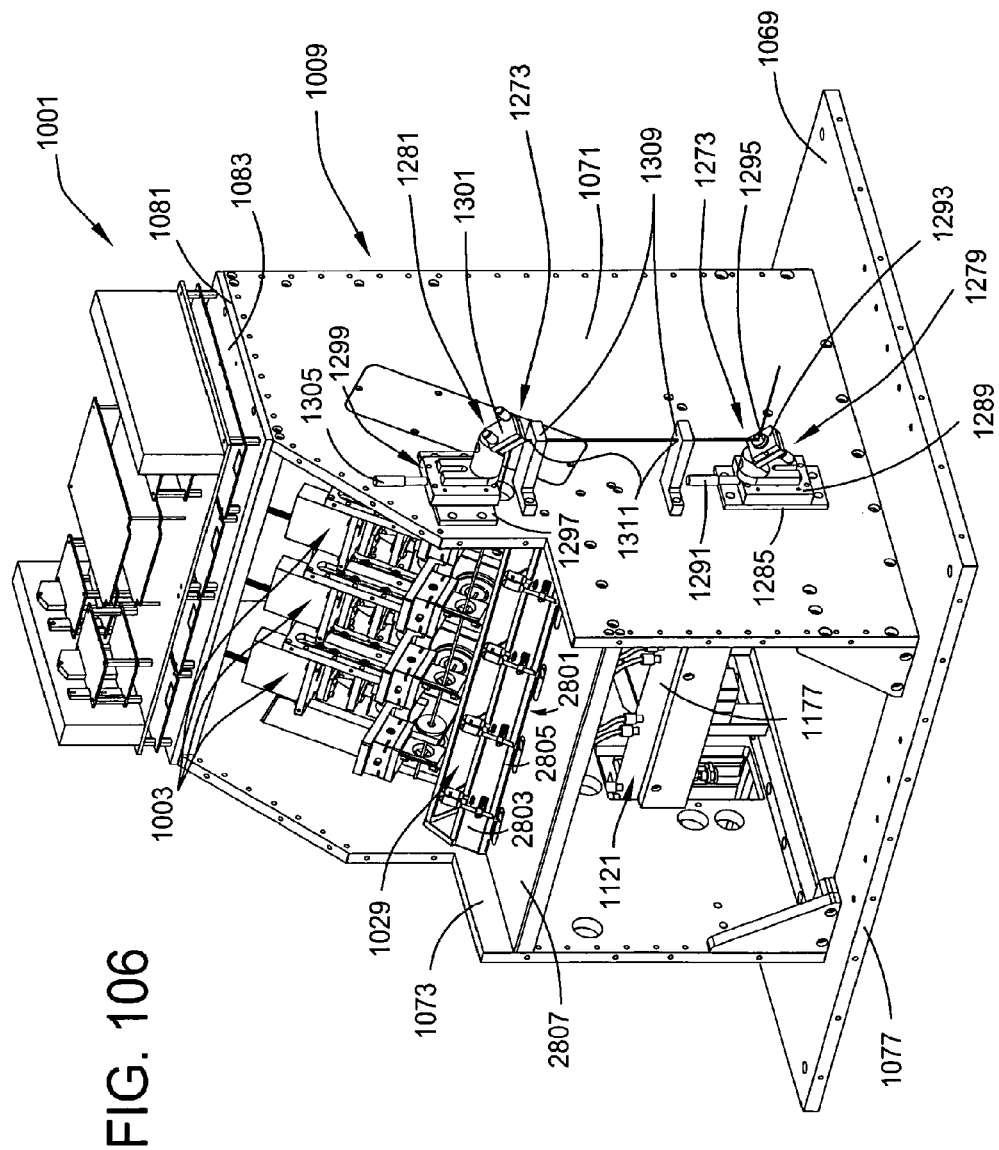
FIG. 106 is a perspective view of one embodiment of a multi-channel particle sorter of the present invention with parts broken away to show internal features of the sorter.
Figure 109:
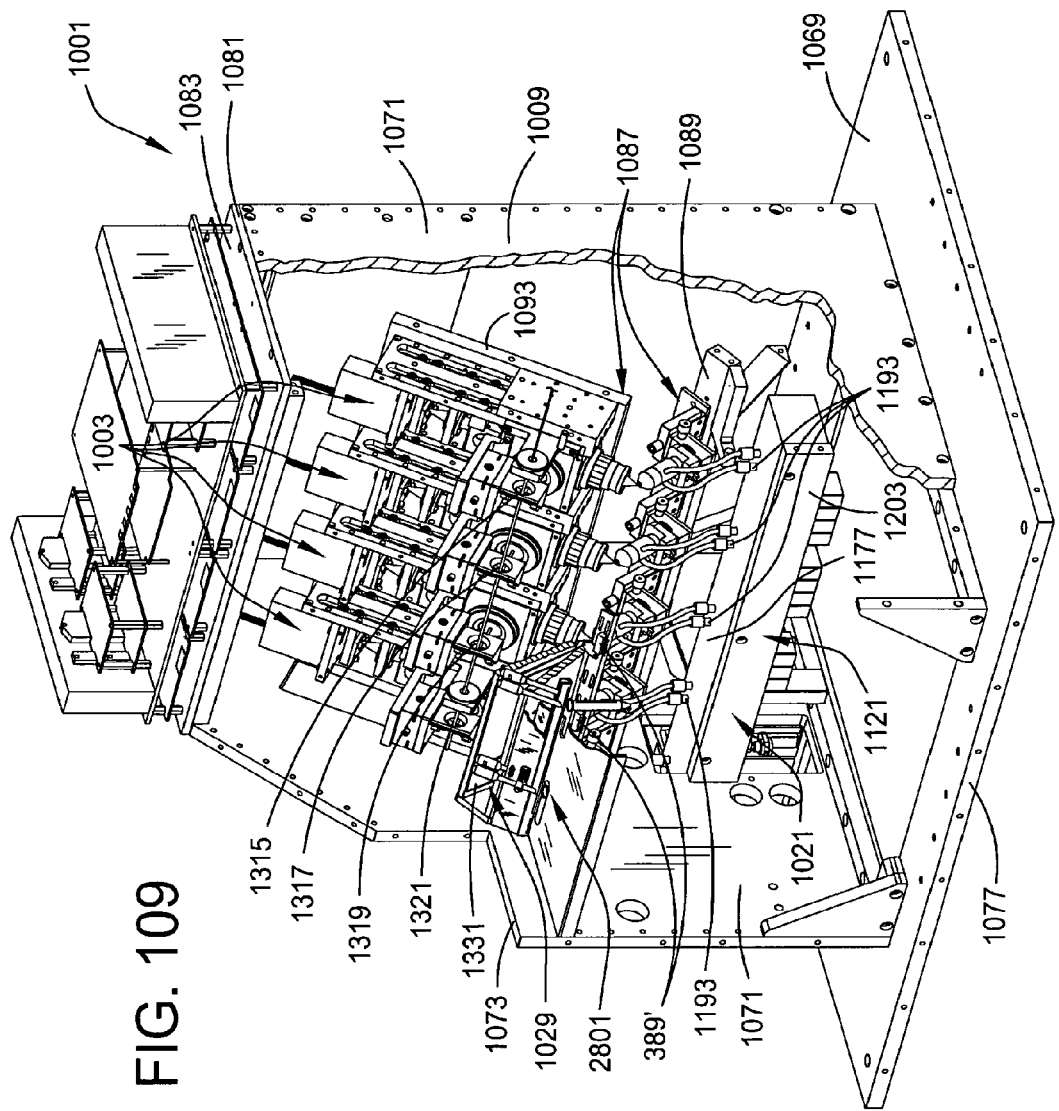
FIG. 109 is a perspective view of the particle sorter shown in FIG. 106 with additional elements removed or partially removed to better show internal features of the sorter.
Figure 110:
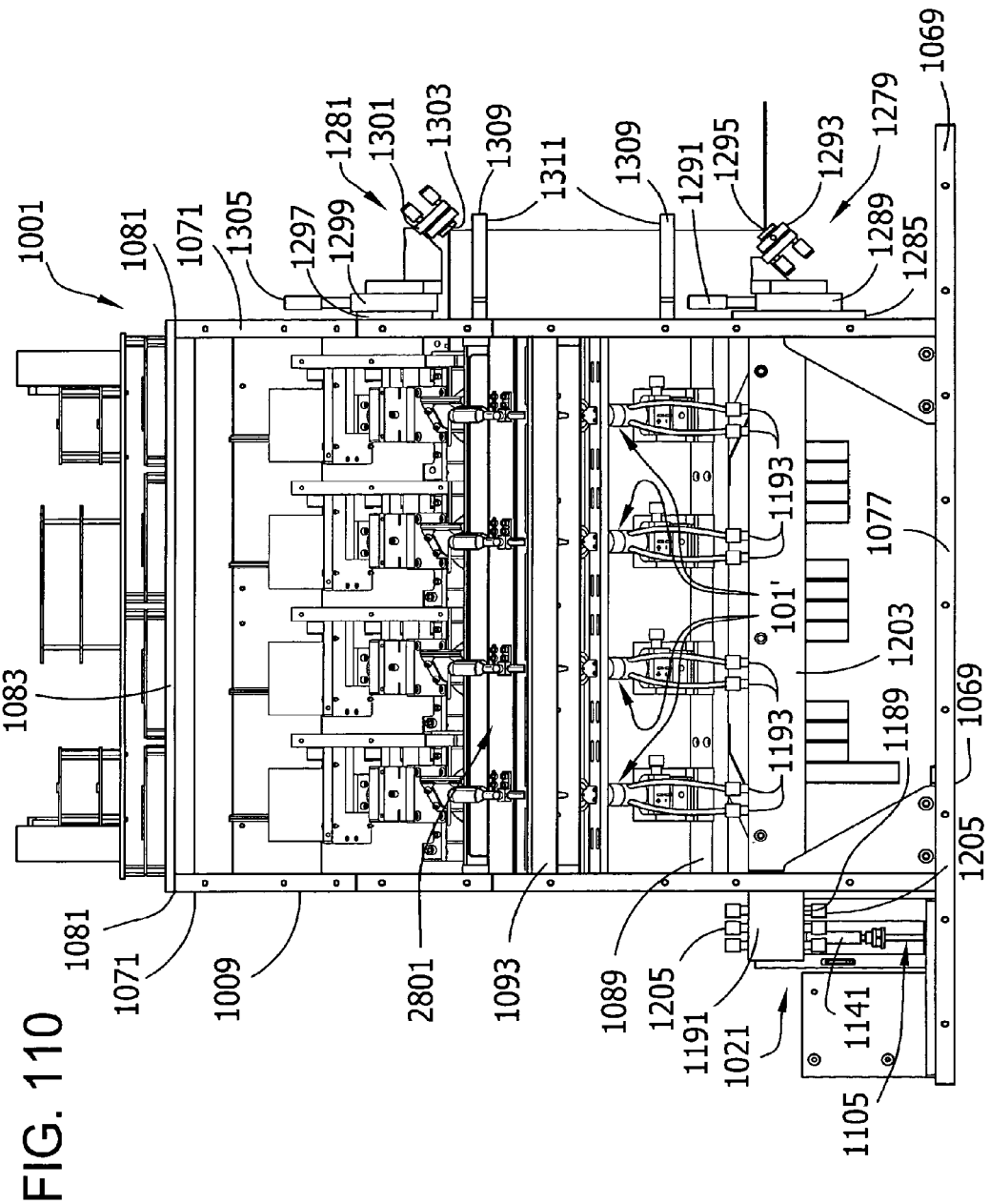
FIG. 110 is a front elevation of the particle sorter shown in FIG. 106.
Figure 111:
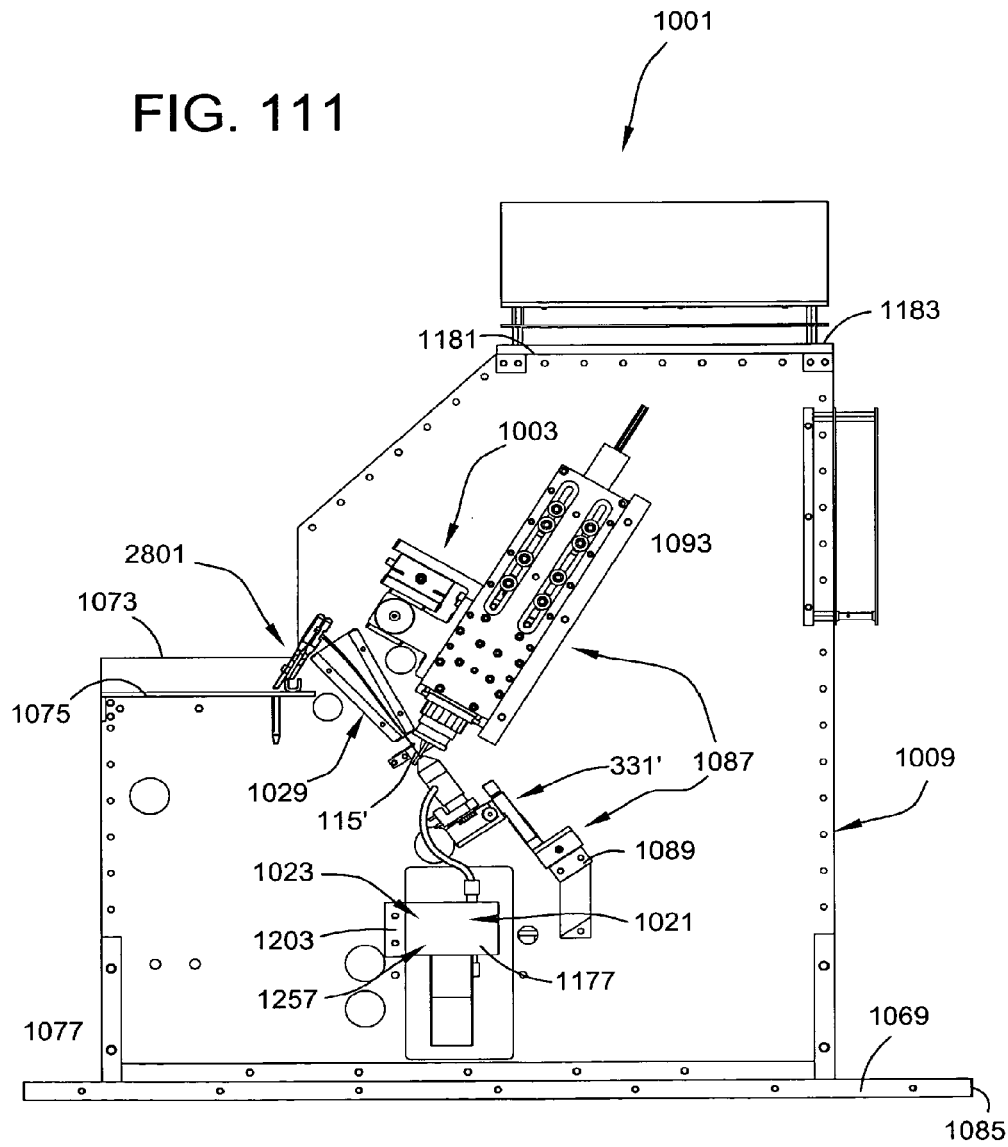
FIG. 111 is a side elevation of the particle sorter shown in FIG. 106 with the side wall of the housing removed to show internal features of the sorter.
Figure 112:
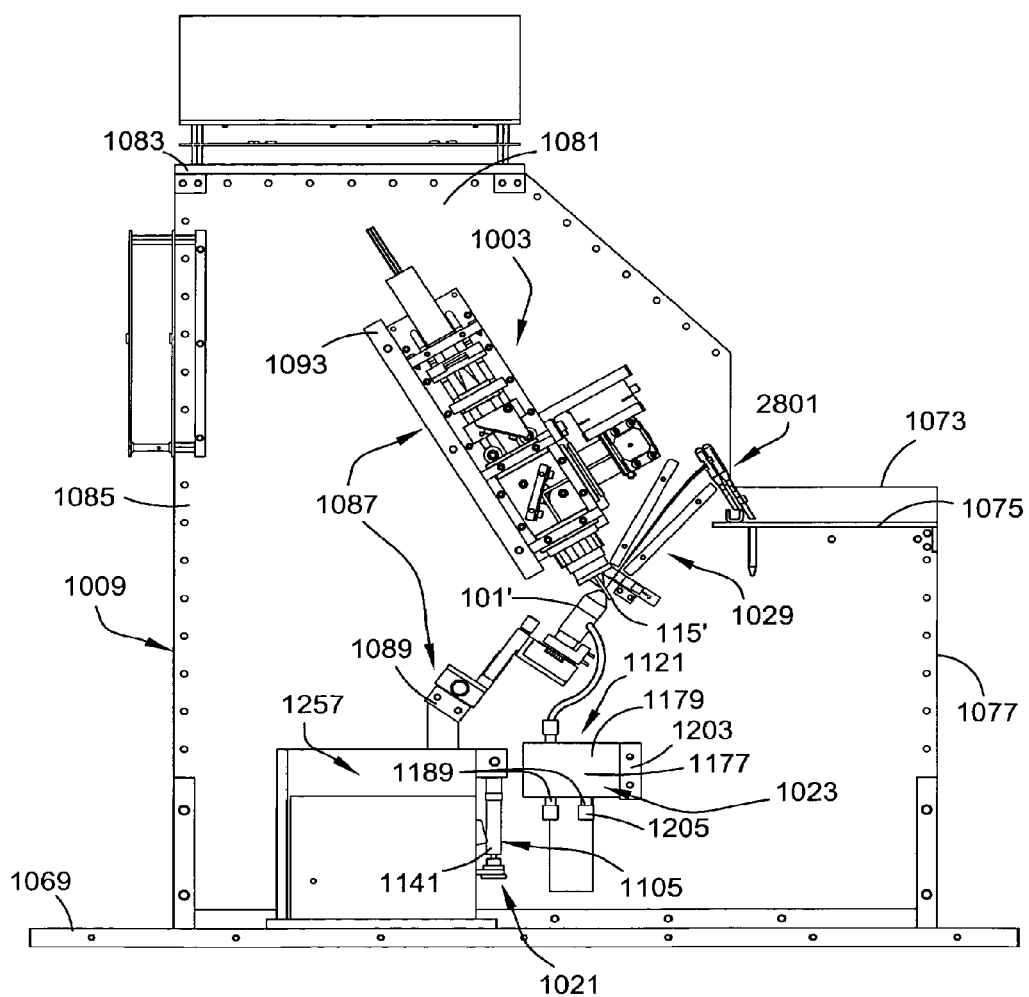
FIG. 112 is a side elevation of the particle sorter shown in FIG. 106 (taken from the side opposite the side from which FIG. 107 was taken) with the side wall removed to show internal features of the sorter.
Figure 113:
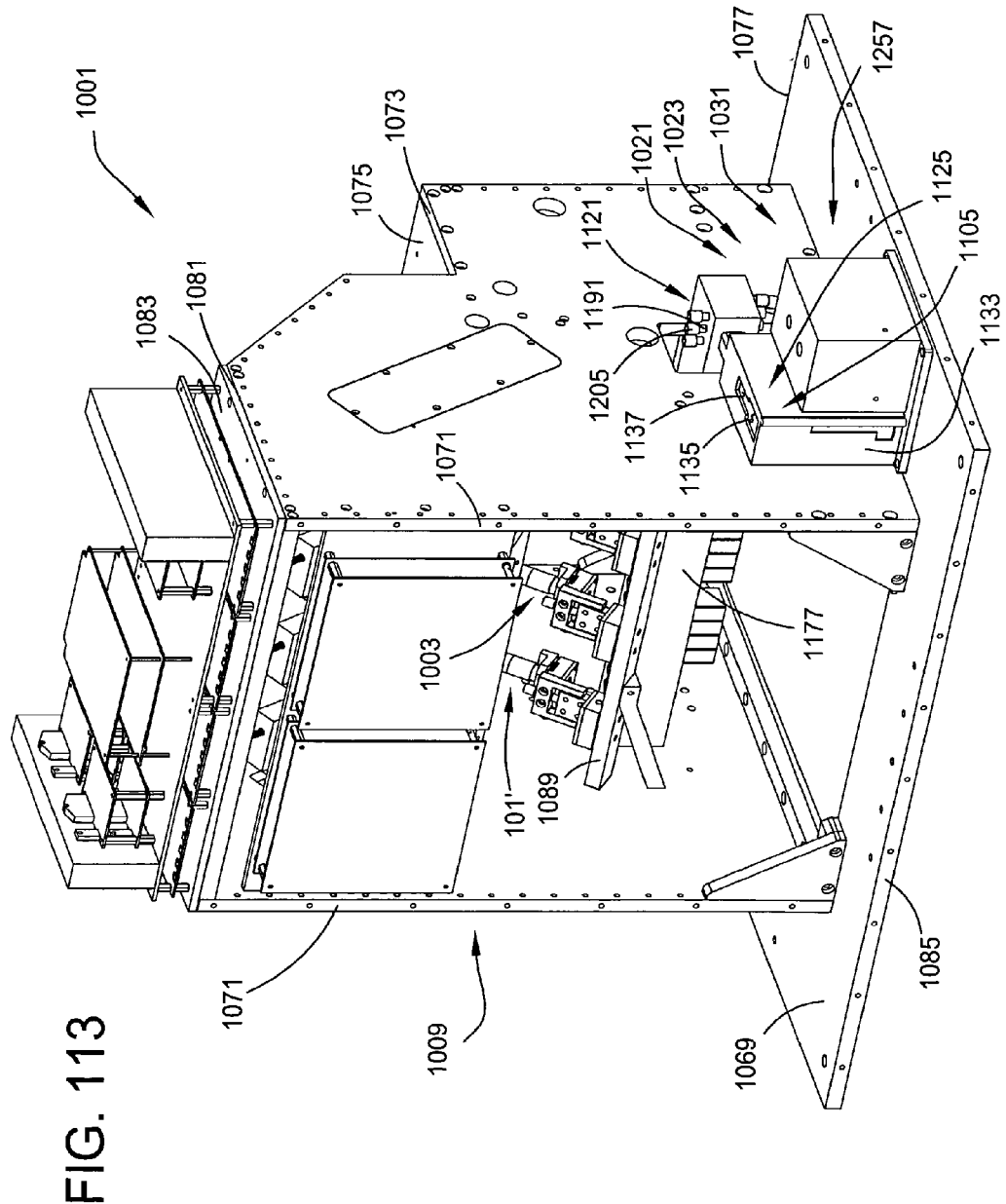
FIG. 113 is a perspective view of the particle sorter shown in FIG. 106 taken from an angle behind the sorter and with the back cover removed to show internal features of the sorter.
Figure 114:
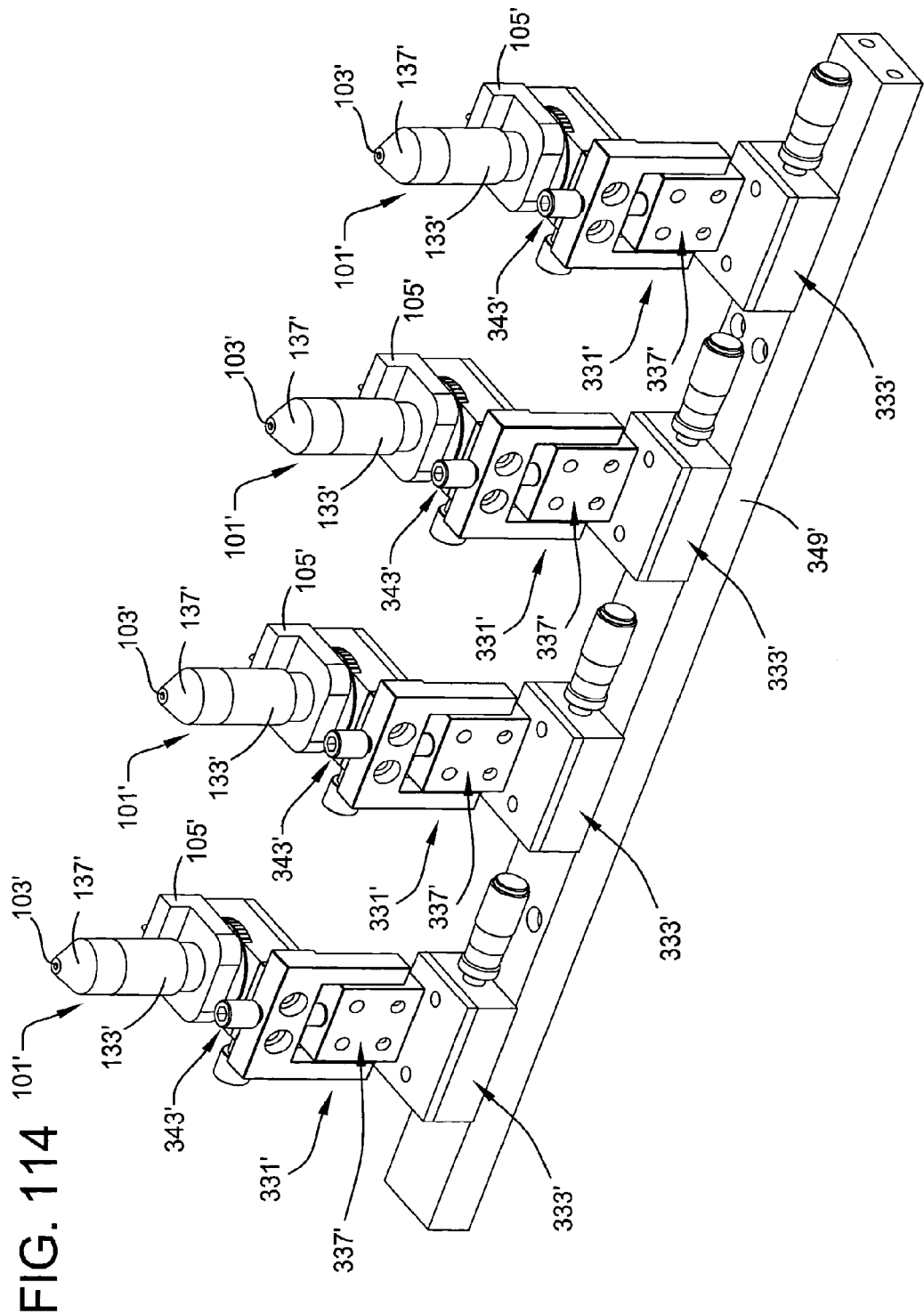
FIG. 114 is a perspective view of a portion of the particle sorter shown in FIG. 106 showing the mounting of multiple nozzle systems to a cross bar.
Figure 115:
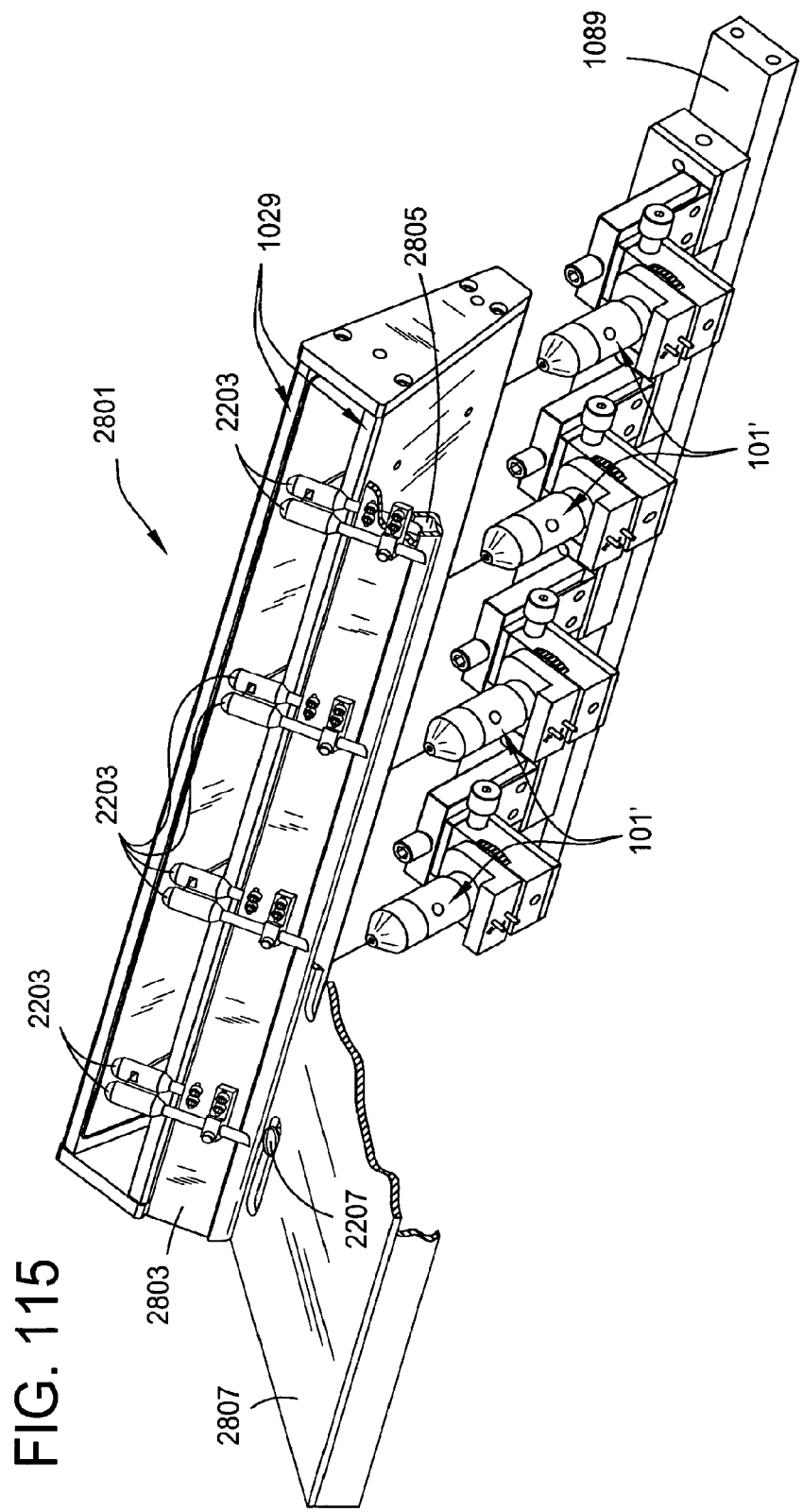
FIG. 115 is a perspective view of a portion of the particle sorter shown in FIG. 106 showing the relative positions of the collection system and other parts of the particle sorter.

One desirable embodiment of a beamsplitting system is shown in FIGS. 106 and 109. A beam guidance system 1273 is provided for guiding the common beam 1007 to the optics instruments 417' of the various flow cytometry units 1003. In the embodiment illustrated in FIGS. 106 and 111, the guidance system 1273 includes a lower mirror assembly 1279 mounted on one side wall 1071 of the housing 1009, an upper mirror assembly 1281 mounted on the side wall 1071 above the lower mirror assembly, and a series of reflecting filters 1283, one associated with each optics instrument 417'. The lower mirror assembly is operable to reflect a beam 1007 from a suitable source upwardly to the upper mirror assembly, and the upper mirror assembly is operable to reflect the beam through an opening in the side wall 1071 to the reflecting filters 431' of the various instruments 417'.

In one embodiment, the lower mirror assembly includes a base 1285 fastened to the side wall 1071 of the housing 1009, a stage 1289 movable vertically on the base by a suitable mechanism 1291, such as a micrometer, a bitable platform 1293 on the stage (e.g., a kinematic optical mount Model P100-P available from Newport), and a mirror 1295 on the platform, the position of the mirror being adjustable by moving the stage and the mirror platform to the appropriate locations. The upper mirror assembly is similar to the lower assembly, comprising a base 1297, a vertically movable stage 1299, a tiltable platform on the stage 1301, and a mirror 1303 on the platform. A pair of target plates 1309 are affixed to the side wall of the housing 1009 between the upper and lower mirror assemblies. The target plates 1309 have vertically aligned holes 1311 therein to facilitate adjustment of the upper and lower mirrors so that an incoming beam 1007 is precisely reflected toward the reflecting filters 431' of the instruments 417', all of which filters are aligned with the incoming beam.

Each of the first three reflecting filters 1315, 1317, 1319 functions as a beam splitter, i.e., it functions to reflect a specified percentage of the beam and to pass the remaining percentage of the beam. For example, in the case of four epi-illumination instruments, the reflecting filters 431' of the first three instruments each reflect a percentage of the laser light 1007, so that each of the first three units of the series receives 25% of the electromagnetic radiation of the original beam 1007. For example, the reflecting filters of the first, second and third units may reflect 25%, 33% and 50% of the incident light, respectively. The last reflecting filter 1321 of the series desirably reflects all of the remaining light (about 25% of the original beam) to the last instrument of the series. As a result, each of the four instruments should receive the same intensity of radiation (light) to interrogate the cells in respective streams.

Depending on the beam splitting devices used in the above system 1273, it may be desirable that the laser beam have a particular polarization. The transmittence-to-reflectance ratio of dielectric filters can vary depending on the polarization of the light. Further, when dealing with linearly polarized light, dielectric filters (which are manufactured for use at a specified angle of incidence) can be too sensitive to variations in the angle of incidence. Circularly or elliptically polarized light alleviates this problem to some extent because the polarization vector of the light is in a variety of different orientations with respect to the optical axis of a dielectric filter as the light interacts with the filter. Thus, elliptically or circularly polarized light simulates randomly polarized light, which provides more tolerance for variations in the angle of incidence on a dielectric filter. Accordingly, if the laser described above generates a beam of light having a vertical polarization, for example, it may be advantageous to convert the light to circularly polarized light before it is split. As will be understood by those skilled in the art, this can be accomplished by passing the beam through a ¼-wave retardation plate (filter) of polarizing material having its optical axis rotated 45 degrees relative to the plane of the laser polarization. The beam thus transmitted by the waveplate will have approximately circular polarization, and it can be more easily split to provide multiple beams to the optics systems of respective flow cytometer units.

Moreover, by rotating the wave retardation plate to alter the angle between the laser polarization and the optical axis of the material used to make the waveplate, eccentricity can be introduced into the approximately circular polarization of the beam (i.e., the polarization can be made more elliptical). Changing the eccentricity of the elliptical polarization of the beam can change the transmittance-to-reflectance ratio of the dielectric filters by causing the polarization vector for a greater percentage of the light to have a particular angle with respect to the optical axis of the dielectric filter. Accordingly, if the balance of light among the multiple cytometry units is outside the desired range, one can rotate the waveplate to increase or decrease the eccentricity of the elliptically polarized light, thereby altering the reflectance-to-reflectance ratios of the various filters until a better balance is achieved. Similarly, if the waveplate is transmitting elliptically polarized light, one can influence the reflectance-to-reflectance ratio of one of the filters by rotating that filter.

Regardless of the method used to split the single beam into multiple separate beams. Balance of the power delivered to each cytometry unit can be achieved by selectively blocking a percentage of the light to bring all the cytometry units down to the same level of power. For example, the neutral density filter 447' of each epi-illumination system 415' can be selected to block more or less of the light to balance the illuminating power delivered by the beam splitting and guidance system to each individual cytometry unit. If one channel of a multi-channel unit receives significantly more illumination from the beam splitting and guidance system, a neutral density filter 467' that transmits less light can be used in the epi-illumination system 415' of that channel to bring the illumination power for that channel more in line with the other channels. It is desirable, though not essential, that channel-to-channel variations in the illuminating power be less than about 10%. It is even more desirable that the channel-to-channel variations be less than about 5%.

It will also be appreciated that pulsed laser scanning, as described above, may be desirable for multi-channel flow cytometry. For example, the UV multiline laser can be replaced with a mode-locked pulsed laser operating at about 85 MHz to allow more flow cytometry channels to be powered by a single laser. For example, the peak power provided in each pulse of a mode-locked laser emitting pulses having a width (duration) of about 12 picoseconds at a frequency of about 85 MHz is approximately 800 times the average power output of the laser. Thus, a mode-locked laser (e.g., a Vanguard 350 from Spectra-Physics) can provide enough illumination energy to operate a few dozen cytometry units (e.g., 32 cytometry units) while operating at only about 350 milliwatts.

The use of fiber optics for supplying light to the units is also contemplated. In this embodiment, fibers are used to direct light from the laser to respective units, thus eliminating the need for the guidance system described above.

F. Common Deflector Plates

In the embodiment shown in FIGS. 106 and 108-116, the sorting system 119' of each flow cytometry unit 1003 is substantially identical to the sorting system 119 described in the first embodiment, except that the units desirably share two common deflector plates 1331 extending across the width of the housing 1009 at the front of the housing. There are advantages to using a common set of deflector plates, including a consistent charge from one channel to the next, the use of a common power supply, a larger plate area providing a more stable electric field and more uniform droplet deflection, and a consistent angle of deflection for collection of sorted samples. The deflector plates 1331 are mounted on a frame 1333 fastened to the housing 1009. Alternatively, separate plates could be provided for each unit.

G. Common Collection System

Figure 107:
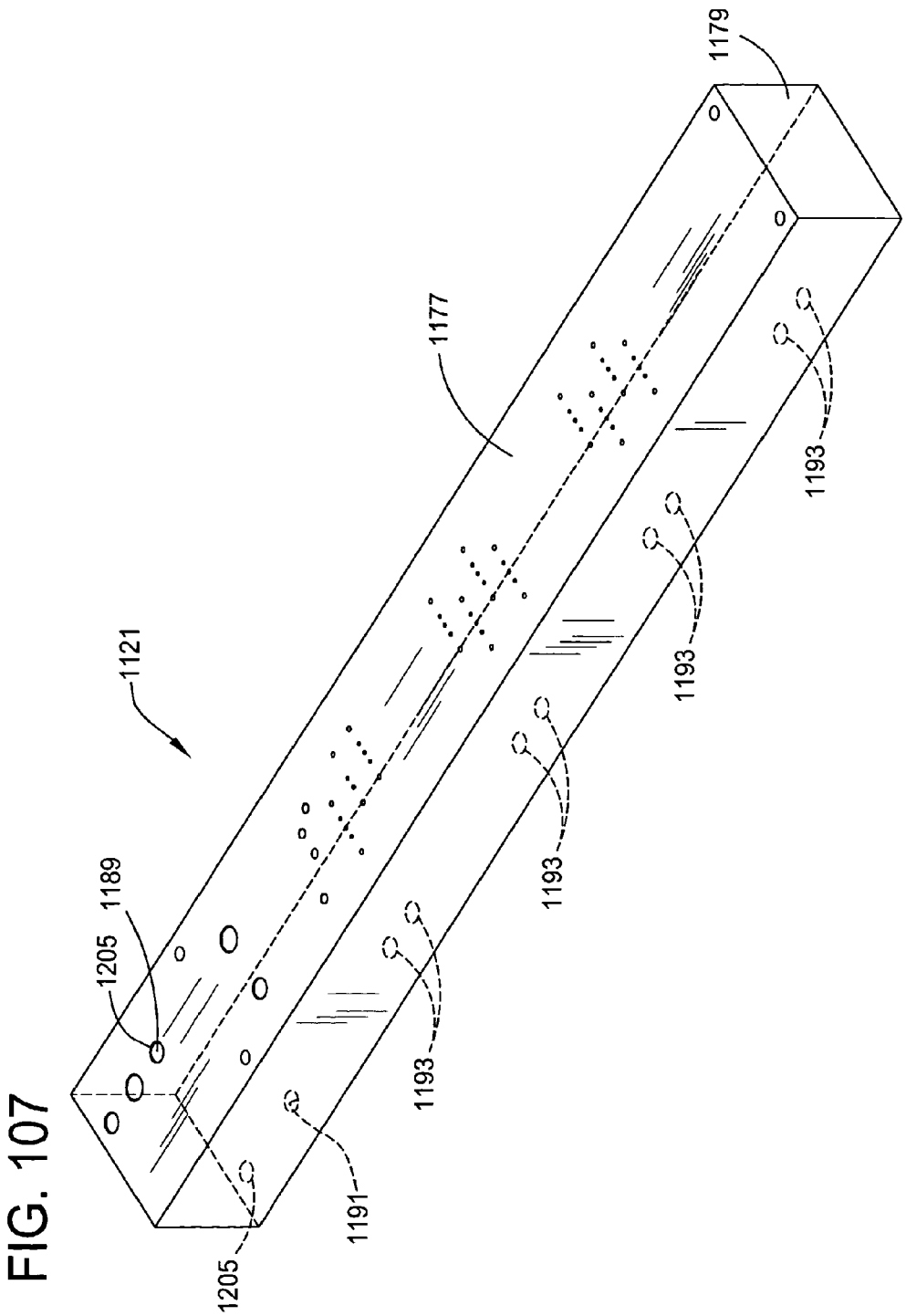
FIG. 107 is a perspective view of a manifold system that may be used for fluid delivery in the multi-channel particle sorter of FIG. 106.
Figure 108:
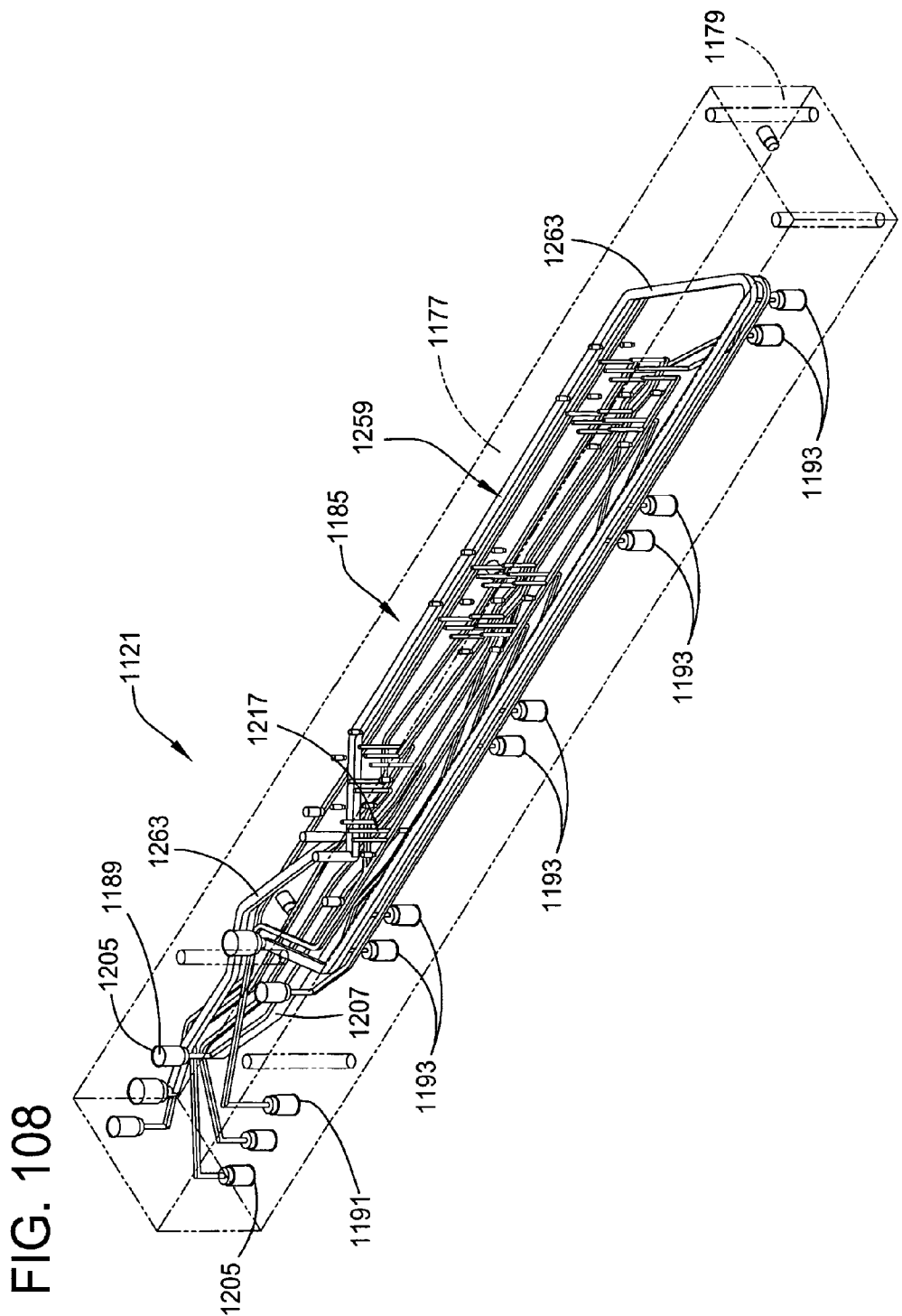
FIG. 108 is a perspective view of the manifold system of FIG. 107 showing internal fluid connections of the manifold system.

In the embodiment shown in FIGS. 107 and 116, a common collection system 2801 includes two intercepting devices for each cytometry unit as described above in connection with the collection system 2201 for the single unit. However, a common frame 2803 is provided to hold all eight of the intercepting devices. Also, one of the two intercepting devices for each cytometry unit directs fluid into a common waste trough 2805 rather than a collection vessel. The waste trough makes it easier to discard sorted droplets that contain particles of little value (e.g., Y-chromosome bearing sperm cells for breeding dairy cows). If it is desirable to retain all the sorted droplets, the waste trough can be removed and collection vessels can be placed under each intercepting device. The four collection vessels in the embodiment shown in FIGS. 107 and 116 rest in openings in the surface of a collection tray 2807. A common water bath (not shown) may be provided under the surface of the collection tray to control the temperature of the contents of the collection vessels.

H. Multi-Channel Control

The various flow cytometry units are controlled by the microprocessor 131', (or other suitable processing system) which desirably has a common input and a common output as discussed above.

Desirably, the operational parameters of each flow cytometry unit 1003 can be set independently of the other units so that such parameters can be varied as between units. These parameters may include, for example, the frequency of droplet formation, the control and sorting strategies utilized by a particular unit, the criteria used by each unit to classify and sort particles in the fluid supplied to the unit, and other parameters. For example, in certain situations it may be desirable to supply one or more units with carrier fluid 17' at a first flow rate and other units a second (different) flow rate. Similarly, it may be desirable to use one control sorting strategy (e.g., a "high efficiency" strategy) for one or more units while using a different strategy (e.g., a "low loss" strategy) for other units. By controlled variation of these parameters among the units, based on historical data and data collected on a real-time basis, the throughput of the units can be managed and the results of the system optimized. The capability of independent operation also allows selected units to be operated in the event fewer than all of the units are needed or available.

I. Operation of Multi-Channel System

The operation of the multi-channel system of this embodiment is similar to that described previously, except that the multiple flow cytometry units are adapted to conduct flow cytometry operations in parallel (i.e., during the same time period or overlapping time periods) for higher throughput.

Prior to the start of a run, the fluid delivery system 1021 is flushed, if necessary, with cleaning solution from the tank 1173 by moving the valve V5 to its cleaning position. The system is then conditioned by with buffer fluid using the syringe pump 1141. During this procedure, the valves V1A-V1D and V2A-V2D are moved to establish communication with the waste receptacle 1223 which is under vacuum. As a result, the cleaning solution and/or buffer fluid flows through the system to waste. This process cleans the system 1021, primes the syringe pump 1141 and removes air bubbles from the system.

With the three-way valve 1149 suitably positioned, the syringe pump 1141 is operated through an intake stroke to aspirate a quantity of carrier fluid 17' containing particles, e.g., sperm cells, following which the valve 1149 is moved to establish communication with the manifold 1177 and the syringe pump moves through a discharge stroke to pump a volume of carrier fluid into the sample reservoir 1207 to fill it. The temperature of the carrier fluid 17' is controlled by the temperature control system 1257 to maintain the cells in the carrier fluid at the desired temperature. With the valves V1A-V1D positioned to establish communication with the sample reservoir 1207, further operation of the syringe pump 1141 forces carrier fluid through the lines to the needles of respective nozzle assemblies for flow through the nozzles 101', as previously described. At the same time, and with the valves V2A-V2D positioned to establish communication with the sheath fluid tank 1155, sheath fluid 19' is forced through the supply lines to respective flow bodies and through the nozzles, also as previously described. This process continues for an appropriate length of time sufficient to pump a suitable volume of fluid through the system 1001. The duration of a particular run will vary depending on the quantity of carrier fluid in the supply vessel, the rate at which the carrier fluid is pumped through the system, and the number of channels in the system. For example, a run may continue for only a limited period of time (e.g., 15 minutes during which about one ml. of carrier fluid is delivered to each nozzle) or it may continue indefinitely, with the supply of fluid being replenished as needed.

In the event a needle 157' becomes clogged, the appropriate valve V1 is moved to establish communication with the waste receptacle 1223. Sheath fluid 19' entering the flow body 133' will then flow under the force of the vacuum 1225 back through the needle 157' to waste, thus flushing and clearing the needle. If there is a need to shut off the flow to a particular nozzle, the valves V1 and V2 are simply switched to their waste positions.

Although the system described herein with respect to both the single channel and multi-channel configurations has been described with regard to particle separation, such as the separation of X and Y cells, it is contemplated that such particles include any particles having different characteristics which may be arbitrarily noted as characteristic A and characteristic B. Further, it will be understood that in some embodiments, the sorting function can be eliminated entirely, so that the flow cytometry apparatus (single-channel or multi-channel) operates only to classify the particles and not to sort them.

While the multi-channel system is described above in the context of operating the flow cytometry units in parallel, it will be understood that the units could also be operated in series. For example, it is contemplated that particles in one stream could be sorted by one unit into multiple populations, and that one or more of such sorted populations could then be passed through one or more other units in series to perform additional sorting operations to sort different particles using the same or different sorting strategies.

J. Upright Multi-Channel Embodiment

Figure 120:
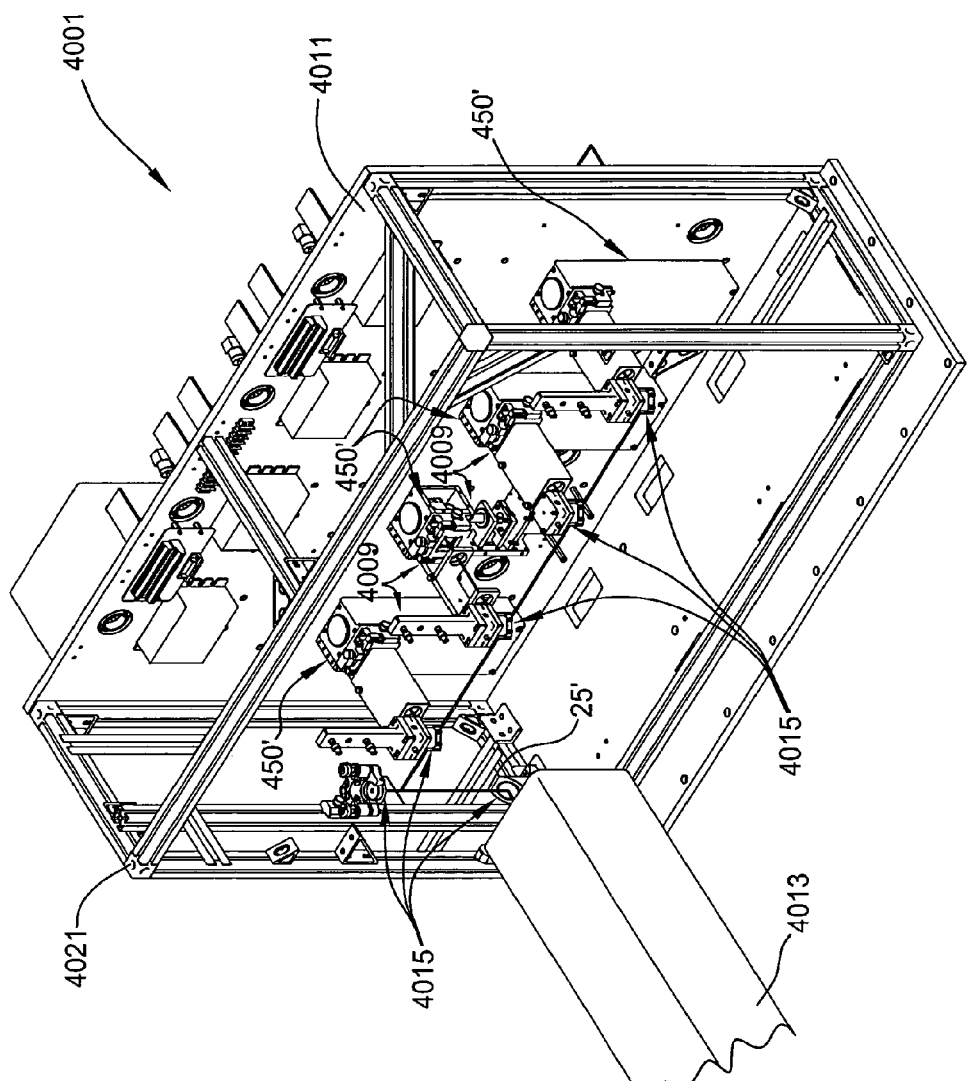

FIGS. 119 and 120 show another exemplary multi-channel flow cytometry system. This system, generally designated 4001 comprises four cytometry units 4009 ganged together. The nozzle system 101', epi-illumination optics system 450', deflector plates 629', sample station 4051, contamination prevention mechanism 4031 and other components of each unit 4009 are mounted on a shared vertical mounting board 4011. Referring to FIG. 120, a single laser 4013 and a beam splitting and guidance system 4015, which is substantially similar to the beam splitting and guidance system 1273 described above, provide illumination for each epi-illumination system 450'. The laser 4013 passes through a hole 4019 (FIG. 119) in a common housing 4021 containing the beam splitting and guidance system 4115. The beam splitting and guidance system 4115 and epi-illumination systems 450' are on one side of the board 4011. The focusing lens assembly 491' of each epi-illumination system 450' extends through the board 4011 to the other side (similarly to the configuration show in the single channel system shown FIGS. 26 & 27), on which the remainder of the components for the units 4009 are mounted.

The units 4009 are all oriented so that their nozzle systems 101' direct the fluid streams 21' downward. Each unit 4009 also has a collection system 4031, which includes a collection vessel 4033 for collecting droplets 33 containing a desired population of particles and a waste container 4035 for collecting other droplets 33. A water bath (not shown) or other temperature control may be used to control the temperature of the collection vessel 4033.

The multiple flow cytometry units 4009 can also share a common power supply (not shown), a common input for controlling operation of the units (not shown), and a common output (not shown) allowing comparative evaluation of the operation of the units 4009 relative to one another. As demonstrated by comparison of the two exemplary multi-channel embodiments 1001, 4001, the nature of the integrated platform and the sharing of features between or among multiple flow cytometry units in a multi-channel system can be varied extensively without departing from the scope of the present invention.

Impact of Multi-Channel Processing on Overall Process

The overall process described above can be performed with multi-channel sperm sorting to decrease the time required to sort the sperm cells. With few exceptions, the method does not change. One minor change is that sorted sperm cells will be collected in multiple collection vessels. The contents of the multiple collection vessels can be combined for concentration if desired. Alternatively, the contents of each collection vessel can be concentrated separately. It will be appreciated that the time required to sort a batch of sperm cells (e.g., an ejaculate) from collection to completion of the cryopreservation step can be significantly reduced by using multiple cytometry units to process the batch. For example, if four cytometry units operate in parallel to process the batch of sperm cells, the time required to complete sorting is reduced to approximately one quarter of the time required to sort the batch using a single cytometry unit. Thus, by substituting the step of sorting sperm with four cytometry units operating in parallel with the step of sorting sperm with a single cytometry unit, the exemplary timeline for completion of the method from collection to completion of the freezing step can be reduced. The time can be reduced even further by increasing the number of cytometers operating in parallel to sort the sperm cells in the sample, subject to the practical limitations involved in operating a parallel system having more than four such units. Thus, according to one embodiment of the present invention, the sorting step in the overall process described above is performed by sorting the sperm cells according to a specified DNA characteristic in a multi-channel flow cytometry apparatus. In yet another embodiment, a sperm processing method comprises the step of sorting sperm cells according to a specified DNA characteristic in a multi-channel flow cytometry apparatus in which each channel collects in the range of about 2,000-10,000 sperm cells having a desired DNA characteristic per second.

Multi-Channel Sorting Example I

Bull semen was collected from a sexually mature bull using an artificial vagina and the sample transported to a nearby staining facility in a temperature-controlled container at 37° C. Upon receipt, the semen was analyzed for concentration, visual motility, motility and progressive motility by the Hamilton-Thorn Motility Analyzer (IVOS), according to standard and well known procedures (Farrell et al. *Theriogenology*, 49(4): 871-9 (March 1998)).

Six tubes of 1 mL of $150 \times 10^6$ sperm/mL sperm suspension were prepared by suspending an aliquot of semen in 41° C. TCA #2 buffer containing 10 mM pyruvate bringing the overall pH to 7.35. Then varying amounts of 10 mM Hoechst 33342 solution in water were added to the sperm samples to yield final dye concentrations of 200, 300, 400, 500, 600, & 700 µM Hoechst 33342. Each of the six samples was incubated at 41° C. for approximately 30 minutes. The samples were analyzed by flow cytometry and the % CV of the X cell population was estimated by iterative computer algorithm for the 200, 300, and 400 µM Hoechst 33342 samples. The % CV for the 300 and 200 µM Hoechst 33342 were both ascertained to be within the acceptable range near 1.3% CV. Accordingly, it was determined that a concentration of 250 µM Hoechst 33342 would be used to stain a batch of sperm cells for further processing.

Two tubes containing 2 mL each of $150 \times 10^6$ sperm/mL sperm suspension were prepared by suspending an aliquot of semen in 41° C. TCA #2 buffer containing 10 mM pyruvate (again bringing the overall pH to 7.35). Then 10 mM Hoechst 33342 solution in water was added to each of the two sperm suspensions to yield a final dye concentration of 250 µM Hoechst 33342. The sperm suspensions were maintained in a 41° C. water bath for 30 min. After 30 minutes, the sperm suspensions were removed from the 41° C. water bath and 4 µL of 25 mg/mL FD&C #40 was added to one of the suspensions. The other was stored at ambient temperature to provide comparison samples for the assessment assays.

The stained and quenched sperm suspension was loaded onto the sample port of one channel of a four channel droplet sorting flow cytometer. Delbecco's PBS was used as the sheath fluid. The cytometer was equipped with a orienting nozzle as described above and having a 60 micron orifice. An semicircular baffle plate was installed perpendicular to the longitudinal axis of the nozzle as described above. The transducer was operated at 54 KHz and the droplet break-off location was controlled manually. An epi-illumination optics system as described above was used to direct approximately 25% of the beam of a continuous, wave laser to intersect the fluid stream at a perpendicular angle. The focusing and collection lens had a 0.65 numerical aperture. The beam was focused to a spot having a width less than 3 µm for slit scanning the sperm cells. Digital signal processing was used to extract the critical slope difference and pulse area for each detected pulse waveform. Classification parameters for classification of X cells, Y cells, and undetermined cells in the two-dimensional CSD and pulse area feature space were manually entered into the processing system for classifying sperm cells according to chromosome content.

Sperm were sorting according to X and Y chromosome content using a coincidence accept sort strategy for collection of X cells, assigning a 50/50 probability that each unclassified sperm was an X cell or Y cell. The sample fluid rate was manually adjusted to maintain purity of collected X cell population (as indicated by the GUI) at 85% or better and to maintain the rate of X cell collection above a minimum rate. After approximately fifteen million X sperm had been collected in a tube that had been soaked in sheath fluid for at least one hour and then coated with 0.5 mL of 10% egg yolk in TCA #2 buffer at pH 7.0, the tube was removed and replaced with an additional tube that has been similarly prepared.

Figure 121:
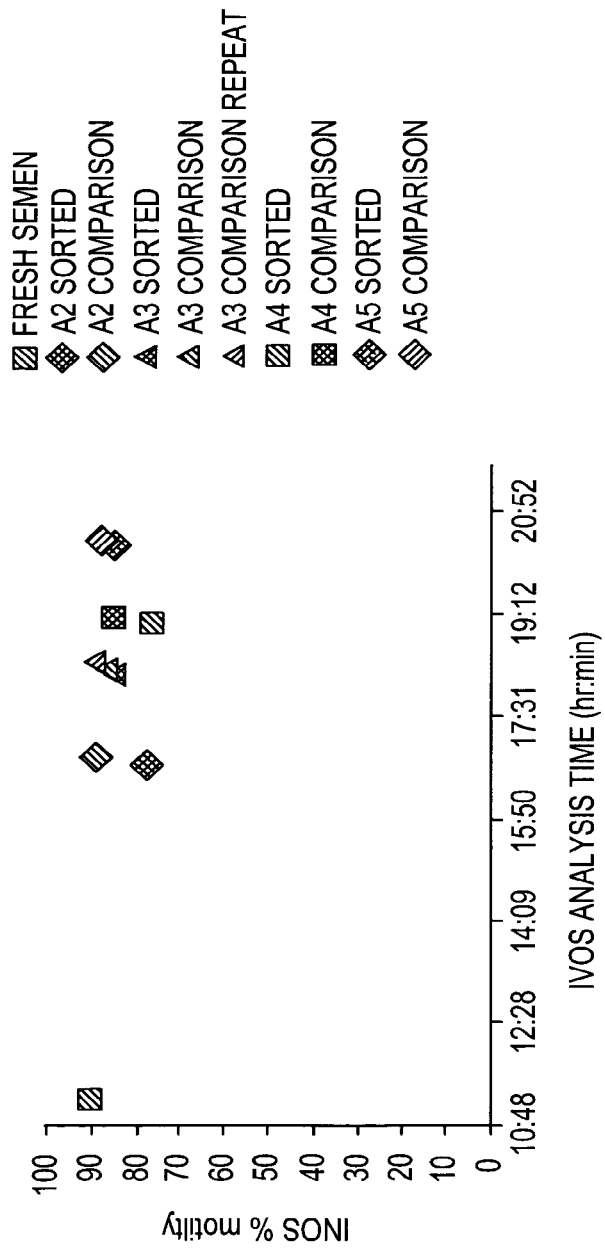
FIGS. 121-134 show graphical results of various experiments.
Figure 122:
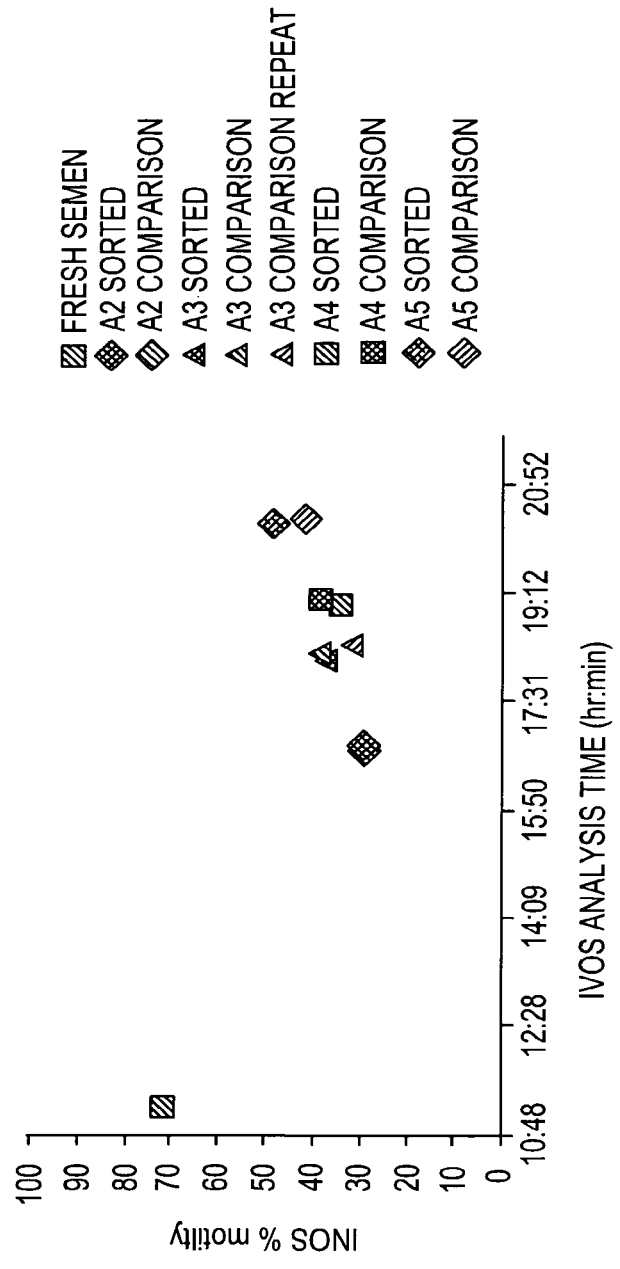
Figure 123:
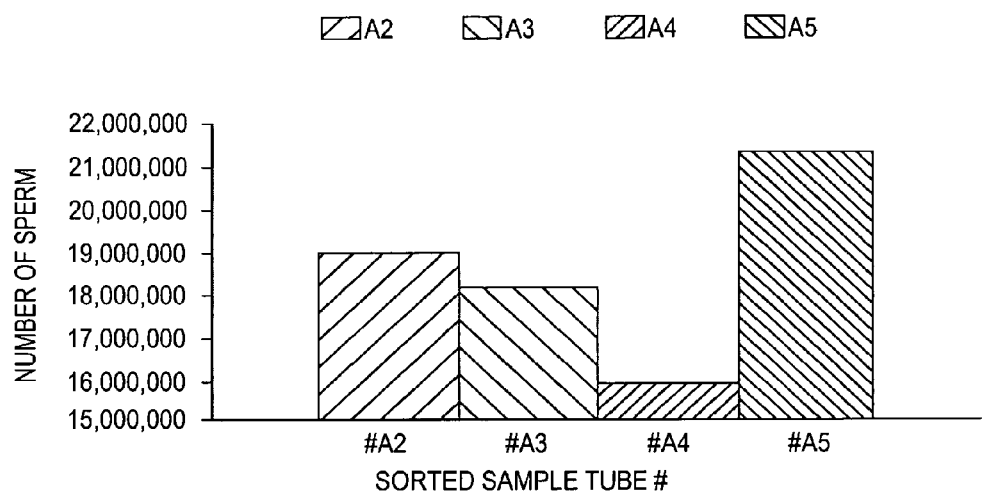
Figure 124:
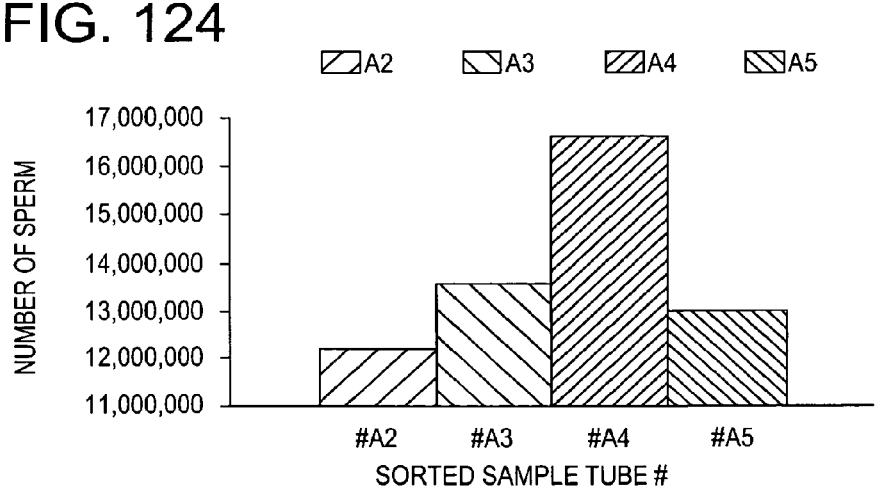
Figure 125:
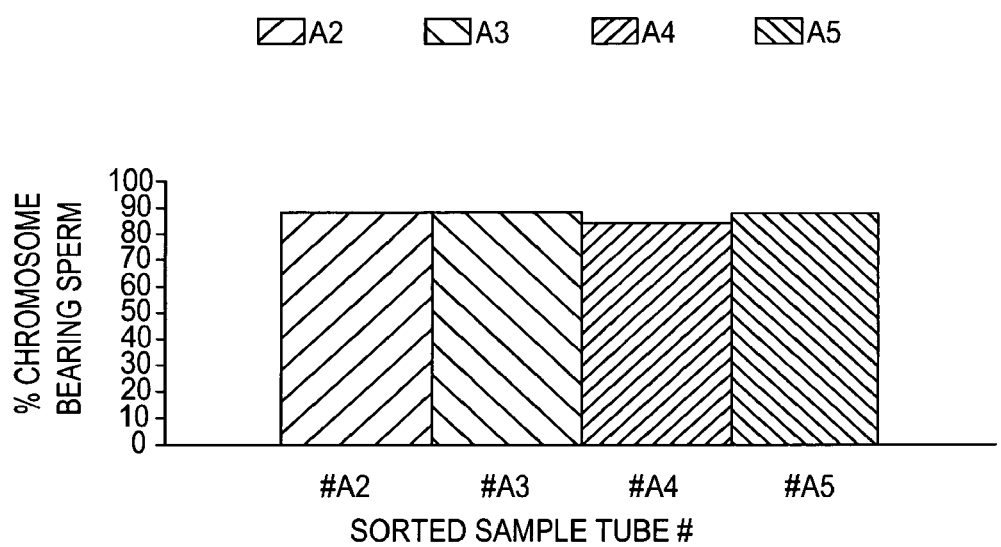

Immediately after removing a collection tube from the flow cytometer, a comparison sample from the stained, but not sorted, sperm suspension was prepared. The sorted and comparison samples were centrifuged for 7 min @ 750 g in a 15 mL tube. The supernatants were removed using a transfer pipette to yield a concentration of approximately 40 million sperm/mL. TCA #2 buffer pH 7.0 was added to the sperm suspensions to yield a final concentration of approximately 20 million sperm/mL. This process continued until the flow cytometer had produced four collection tubes (A2-A5). The sorted samples and 'non-sorted' comparison samples were assessed by IVOS. Sorted sample A3 and its non-sorted comparison sample were tested for % intact acrosomes by differential interference contrast microscopy. All the sorted samples were counted by hemacytometer to determine the output rate of sorted sperm per hour. The % X chromosome bearing sperm was confirmed by flow cytometer reanalysis. Results of the IVOS assessment for the sorted and 'non-sorted' comparison samples are provided in FIGS. 121 (motility) and 122 (progressive motility). The total number of sperm sorted into each collection tube is shown in FIG. 123. The rate of sperm sorted per hour for each collection period is shown in FIG. 124. Percentage of X chromosome bearing sperm for each sorted sample is listed in FIG. 125. Results of the assessment of the acrosome integrity were 72% intact acrosomes for the sorted sample and 78% for the non-sorted comparison sample.

The results demonstrate the technical ability to yield more than 5,000 sorted X cells per second at greater than 85% purity per channel of multi-channel flow cytometry system for sustained periods. The results also show the technical ability to yield more than 7,000 X cells per second at greater than 85% purity for sustained periods under ideal conditions. Further, the results indicate that samples of sorted sperm cells obtained by such high-speed flow cytometric sorting will suffer only slight declines in motility, indicating that the sorted sperm will have good fertility.

Multi-channel Sorting Example II

Bull semen was collected from a sexually mature bull using an artificial vagina. The ejaculate was split into two aliquots. The first aliquot of 250 µL of semen was suspended in 5 mL of 37° C. Triladyl®. The second aliquot, which comprised the remained of the ejaculate, was suspended in two parts 37° C. carbonate buffer (pH 6.1-6.2). Both aliquots were transported at 37° C. in a temperature-controlled container to a processing facility. At the processing facility, the first aliquot was floated in ~120 mL of 37° C. water in a 200 mL beaker and placed in a cold room to slowly cool to 5° C. The second aliquot was analyzed for concentration, motility and progressive motility by the Hamilton-Thorn Motility Analyzer (IVOS), according to standard and well known procedures (Farrell et al. *Theriogenology*, 49(4): 871-9 (March 1998)).

Three 1 mL tubes of $150 \times 10^6$ sperm/mL sperm suspension were prepared by transferring sub-aliquots containing 150 million sperm from the second aliquot to empty tubes, centrifuging at 500 g for 5 min, removing the supernatants, and re-suspending the sperm pellets in 1 mL of 28° C. TCA #2 buffer containing 10 mM pyruvate pH 7.35. Ten mM Hoechst 33342 solution in water was added to each of the three tubes in various amounts to yield final dye concentrations of 100, 150, & 200 µM Hoechst 33342. Each of the three tubes was held at 28° C. for approximately 60 minutes. Sperm from each of the three tubes was analyzed by flow cytometry and the CV of total fluorescence intensity of the X population was determined for the 100, 150, and 200 µM Hoechst 33342 staining conditions using an interactive computer algorithm. The CVs for the 150 and 200 µM Hoechst 33342 were both within the acceptable range near 1.3%. Thus, it was determined to use staining conditions including 150 µM Hoechst 33342 concentration for sorting.

One tube containing 5 mL of $150 \times 10^6$ sperm/mL sperm suspension was prepared by transferring a sub-aliquot containing 750 million sperm from the second aliquot, centrifuging at 500 g for 5 min, removing the supernatant, and re-suspending the sperm pellet in 28° C. TCA #2 buffer containing 10 mM pyruvate (pH 7.35). Ten mM Hoechst 33342 solution in water was added to the tube in an amount yielding a final dye concentration of 150 µM Hoechst 33342. The tube was maintained in a 28° C. water bath for 60 min. After 60 minutes, the tube was removed from the 28° C. water bath and 10 µL of 25 mg/mL FD&C #40 was added.

The now stained and quenched sperm suspension was loaded onto the sample port of one channel of a multi-channel droplet sorting flow cytometer system. The sperm suspension was maintained at 28° C. Using substantially the same instrument settings as set forth in Multi-channel Example I, X & Y chromosome bearing sperm were separated by the flow cytometry system using a coincidence abort sort strategy for a period necessary to place an enriched X cell population of approximately eighteen million sperm into a collection tube that had been prepared by soaking with sheath buffer for at least one hour and then adding 0.5 mL of Triladyl® cryo-preservation media containing 10 mM pyruvate pH 6.6. The sperm cells were introduced into the flow cytometry system at a rate of between about 25,000 and 30,000 cells/second. An enriched population of X cells was collected at a rate varying from 4,500 per second to 6,000 per second. When approximately eighteen million sperm had been sorted into a collection tube, the tube was removed and replaced with another tube that had been similarly prepared. Immediately after removal of a collection tube from the flow cytometer, the sorted sperm suspension was centrifuged for 7 min @ 700 g. The supernatant was removed using a transfer pipette to yield a concentration of approximately 100 million sperm/mL. Triladyl® cryo-preservation media containing 10 mM pyruvate (pH 6.6) was added to the sperm suspensions to yield a final concentration of approximately 50 million sperm/mL. This process continued until the flow cytometer had produced three collection tubes (D1-D3). Approximately 52 million sperm were sorted in 259 min yielding an overall collection rate of about 12 million enriched X sperm per hour of sorting. The re-suspended sorted sample tubes were floated in -120 mL of 28° C. water in a 200 mL beaker and placed in a 5° C. Cold room to slowly cool.

Figure 126:
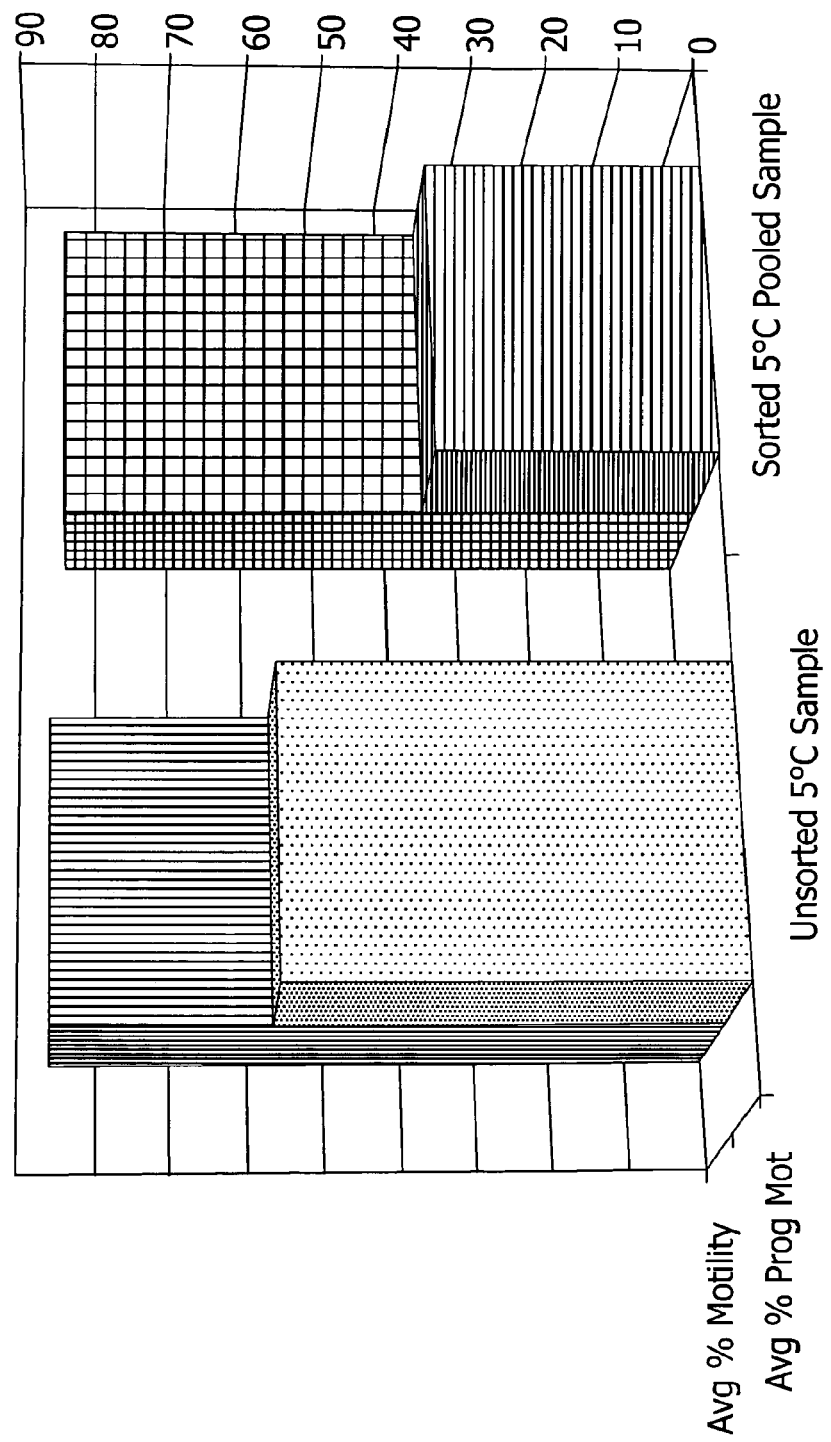

After the sorted samples reached 5° C., the three tubes of sorted sperm were combined into one tube. The pooled sample was analyzed by IVOS to determine the % motility, % progressive motility, and concentration. Additional Triladyl® cryo-preservation media containing 10 mM pyruvate pH 6.6 was added to the sample to yield a final concentration of approximately 50 million sperm per mL. The % X-chromosome bearing sperm in the sorted pooled sample was 87% as determined by flow cytometer re-analysis. A summary of the IVOS assessment compared to the non-sorted sample of the same ejaculate is illustrated in FIG. 126.

The pooled sorted sample and the first aliquot were loaded into standard 0.25 cc straws in a 5° C. cold room. The loaded straws were transferred to a programmable freezer and frozen by the following program: 5 min @ 5° C., cool from 5° C. to -12° C. @ 4° C./min, cool from -12° C. to -100° C. @ 40° C./min, cool from -100° C. to -140° C. a 20° C./min, hold at -140° C. After the straws had reached -140° C., they were quickly removed from the freezer and plunged into liquid nitrogen.

Figure 127:
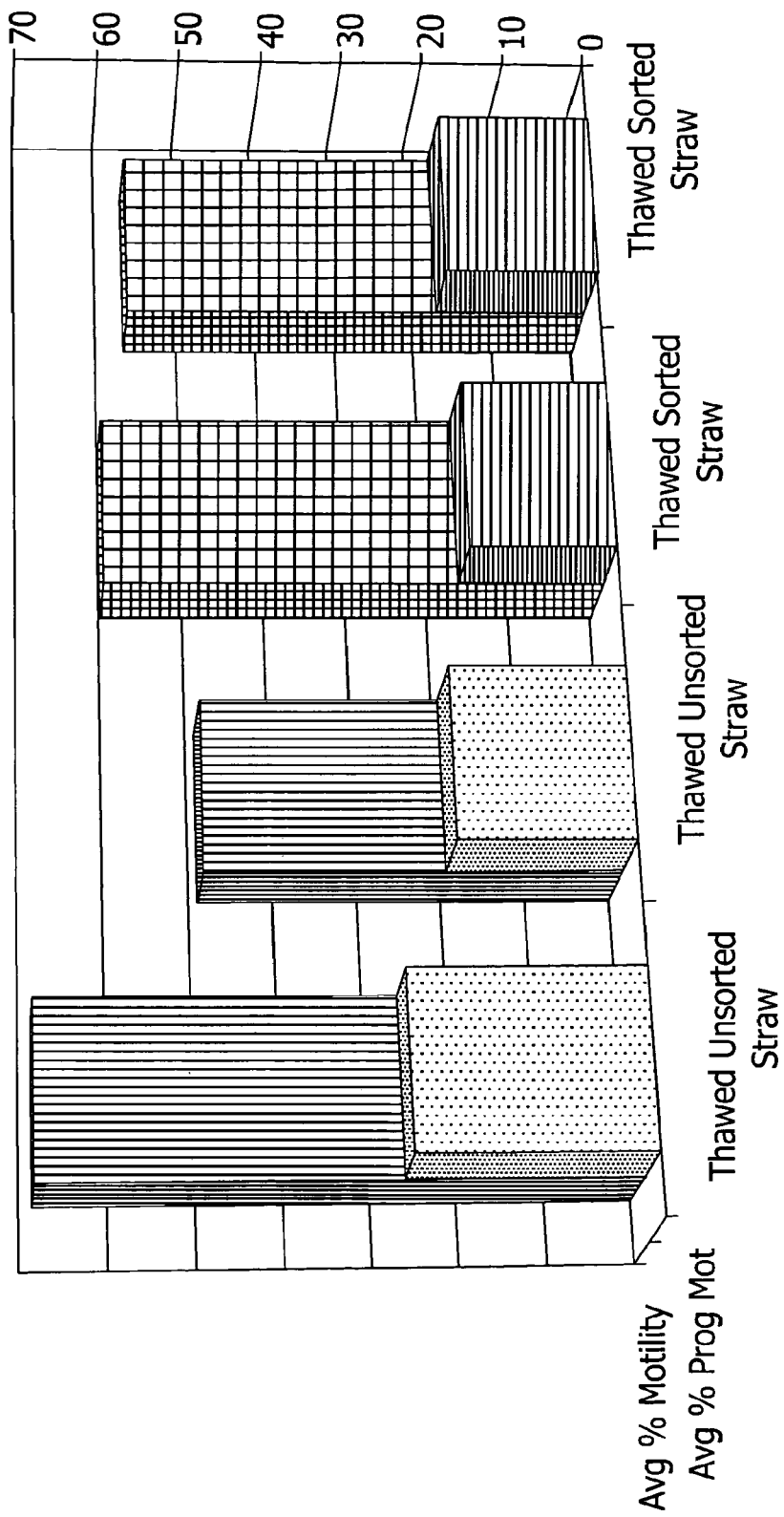
Figure 128:
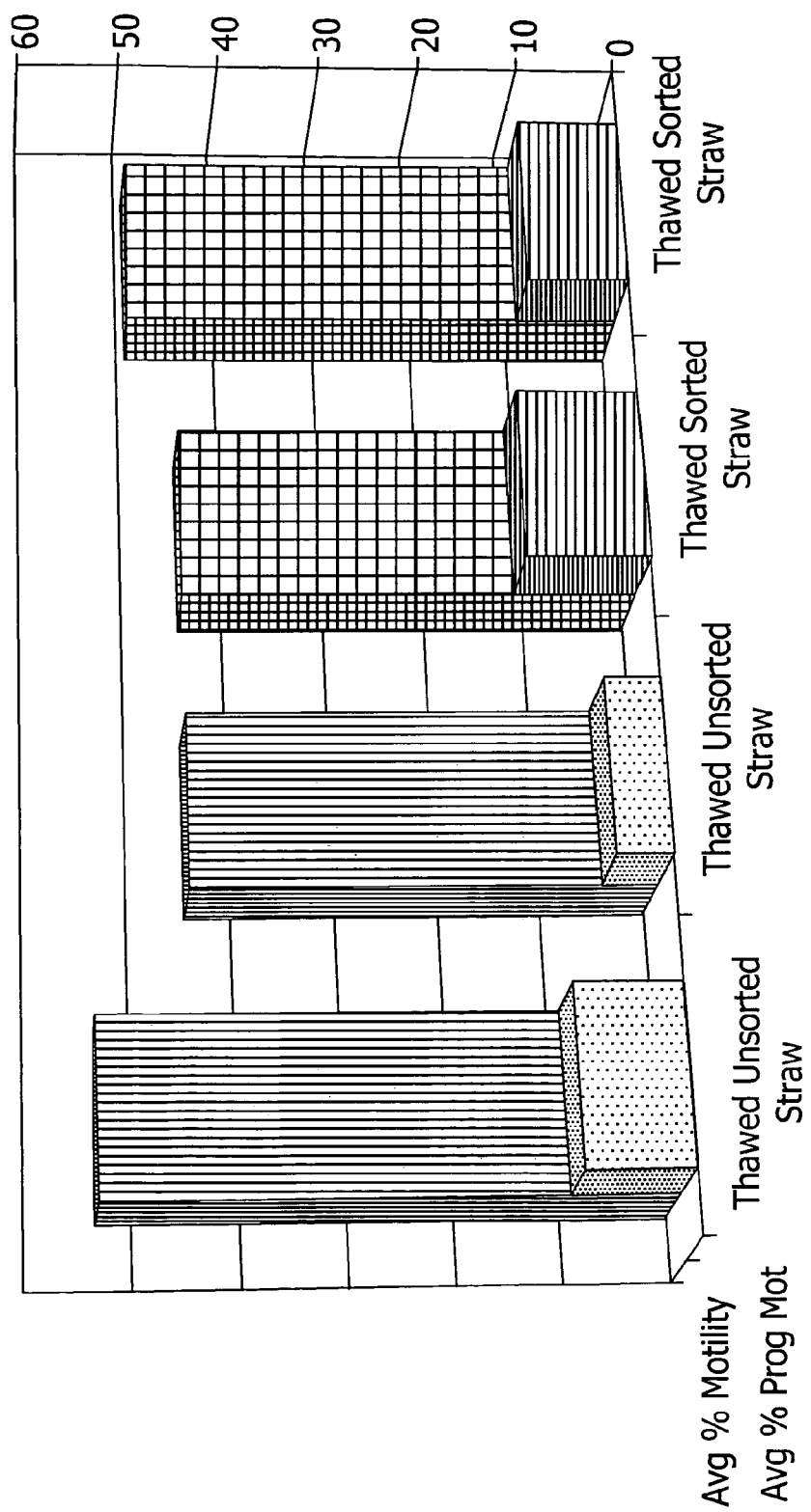

Thawed straws were analyzed by IVOS for % motility and % progressive motility after incubation at 37° C. for 30 and 120 minutes. Results from a set of two sorted and unsorted straws are summarized in FIG. 127 and FIG. 128.

Multi-Channel Sorting Example III

Bull semen was collected from a sexually mature bull using an artificial vagina and the ejaculate split into two aliquots. A first aliquot of 250 µL of semen was suspended in 5 mL of 37° C. Triladyl®. A second aliquot, which comprised the remainder of the ejaculate, was suspended in two parts 37° C. carbonate buffer (two parts 0.097 moles/L of $NaHCO_3$, 0.173 moles/L of $KHCO_3$, 0.090 moles/L $C_6H_3O_7 \cdot H_2O$ in water) (pH 6.1-6.2). Both aliquots were transported at 37° C. in a temperature-controlled container to the processing facility. At the processing facility, the first aliquot was floated in -120 mL of 37° C. water in a 200 mL beaker and placed in a cold room to slowly cool to 5° C. The second aliquot was analyzed for concentration, motility and progressive motility by the Hamilton-Thorn Motility Analyzer (IVOS), according to standard and well known procedures (Farrell et al. *Theriogenology*, 49(4): 871-9 (March 1998)).

Two tubes of $150 \times 10^6$ sperm/mL sperm suspension were prepared by transferring into each of two empty tubes a fraction containing 900 million sperm from the second aliquot, centrifuging each tube at 500×g for 5 minutes, removing the supernatant from each tube, and re-suspending each sperm pellet in 6 mL of 28° C. TCA #2 buffer containing 10 mM pyruvate (pH 7.35). 10 mM Hoechst 33342 solution in water was added to each of the two tubes to yield final dye concentrations of 200 µM Hoechst 33342 in one tube and 400 µM Hoechst 33342 in the other tube. Each of the two tubes was held at 28° C. for approximately 120 minutes. Sperm from each of the tubes was analyzed by flow cytometry and the CV of total fluorescence intensity of the X population was determined for the 200 µM and 400 µM Hoechst 33342 staining conditions using an interactive computer algorithm. The CVs for the 200 µM and 400 µM Hoechst 33342 were both within the acceptable range of about 1.3%. The sperm suspension stained with a concentration of 200 µM Hoechst 33342 was chosen for sorting. 104 of 25 mg/mL FD&C #40 was added to this tube of stained sperm suspension just prior to sorting.

The stained sperm suspension was loaded onto the sample port of one channel of a multi-channel droplet sorting flow cytometer system. The sperm suspension was maintained at 28° C. Using substantially the same instrument settings as set forth in Multi-channel Example I, X & Y chromosome bearing sperm were separated by the flow cytometry system using a coincidence abort sort strategy for a period of time necessary to place an enriched X chromosome bearing cell population of approximately eighteen million sperm into a collection tube that had been prepared by soaking with sheath buffer for at least one hour and then adding 0.5 mL of Triladyl® cryo-preservation media (pH 6.6). The sperm cells were introduced into the flow cytometry system at a rate of between about 25,000 and 30,000 cells/second. An enriched population of X chromosome bearing cells was collected at a rate varying from 4,500 per second to 6,000 per second. When approximately eighteen million sperm had been sorted into a collection tube, the tube was removed and replaced with another tube that had been similarly prepared. Immediately after removal of a collection tube from the flow cytometer, the sorted sperm suspension was centrifuged for 7 min @ 700×g. The supernatant was removed using a transfer pipette to yield a concentration of approximately 100 million sperm/mL. Triladyl® cryo-preservation media (pH 6.6) was added to the sperm suspensions to yield a final concentration of approximately 50 million sperm/mL. This process continued until the flow cytometer had produced two collection tubes (C1-C3). Approximately 35 million sperm were sorted in 193 minutes yielding an overall collection rate of 11 million enriched X chromosome bearing cells per hour of sorting. The re-suspended sorted sample tubes were floated in ~120 mL of 28° C. water in a 200 mL beaker and placed in a 5° C. cold room to slowly cool.

Figure 129:
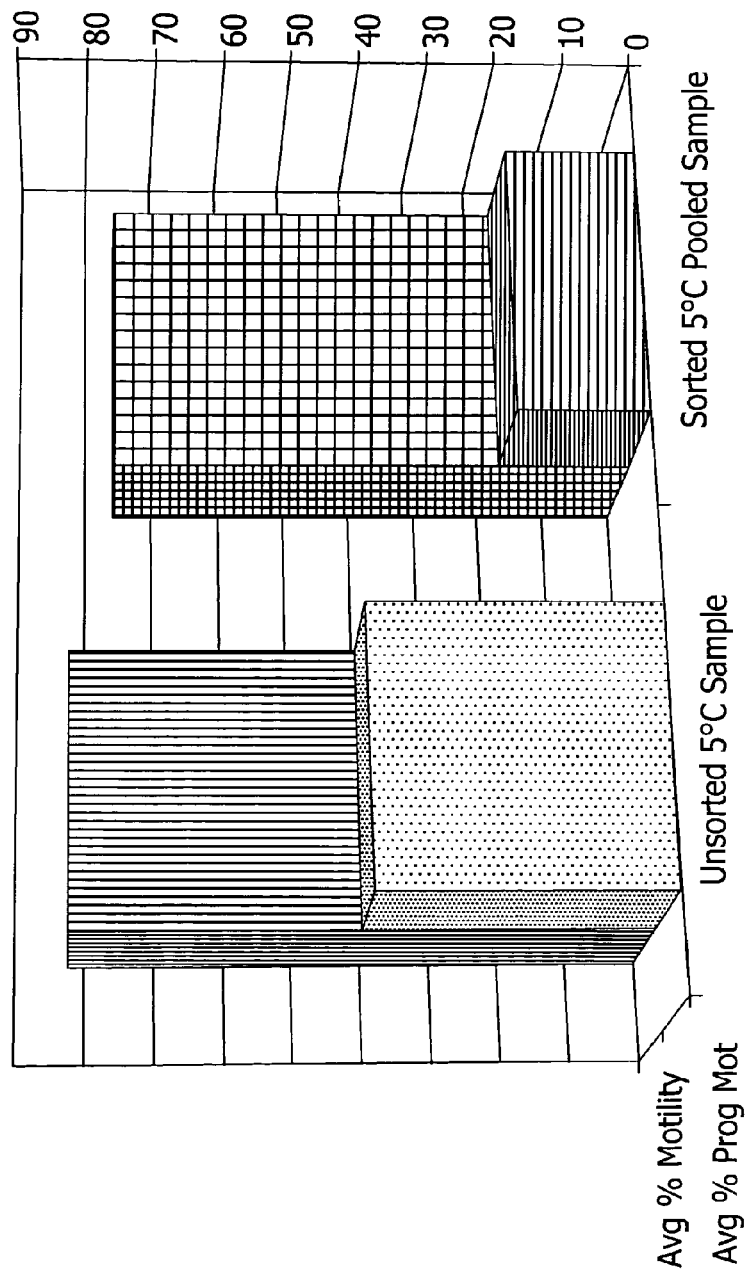

After the sorted samples reached 5° C., the three tubes of sorted sperm were combined into one tube. The pooled sample was analyzed by IVOS to determine the % motility, % progressive motility and concentration. Additional Triladyl® cryo-preservation media (pH 6.6) was added to the sample to yield a final concentration of approximately 50 million sperm per mL. The % X-chromosome bearing sperm in the sorted pooled sample was 88% as determined by flow cytometer re-analysis. A summary of the IVOS assessment compared to the non-sorted sample of the same ejaculate is illustrated in FIG. 129.

The pooled sorted sample and unsorted sample (i.e., the first aliquot from above) were loaded into standard 0.25 cc straws in the 5° C. cold room. The loaded straws were transferred to a programmable freezer and frozen by the following program: 5 min @ 5° C., cool from 5° C. to −12° C. @ 4° C./min, cool from −12° to −100° C. @ 40° C./min, coot from −100° C. to −140° C. @ 20° C./min, hold at −140° C. After the straws had reached −140° C., they were quickly removed from the freezer and plunged into liquid nitrogen.

Figure 130:
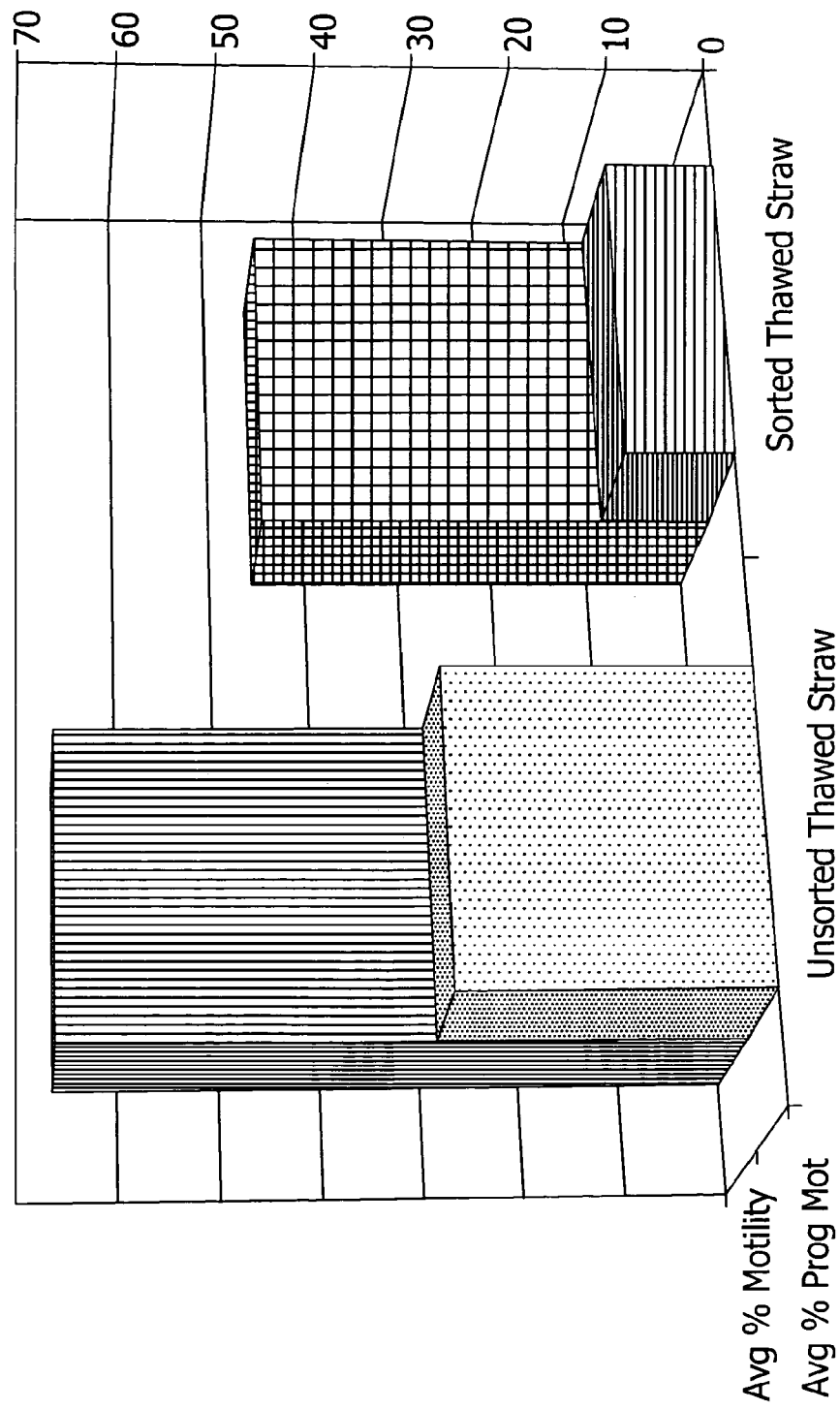
Figure 131:
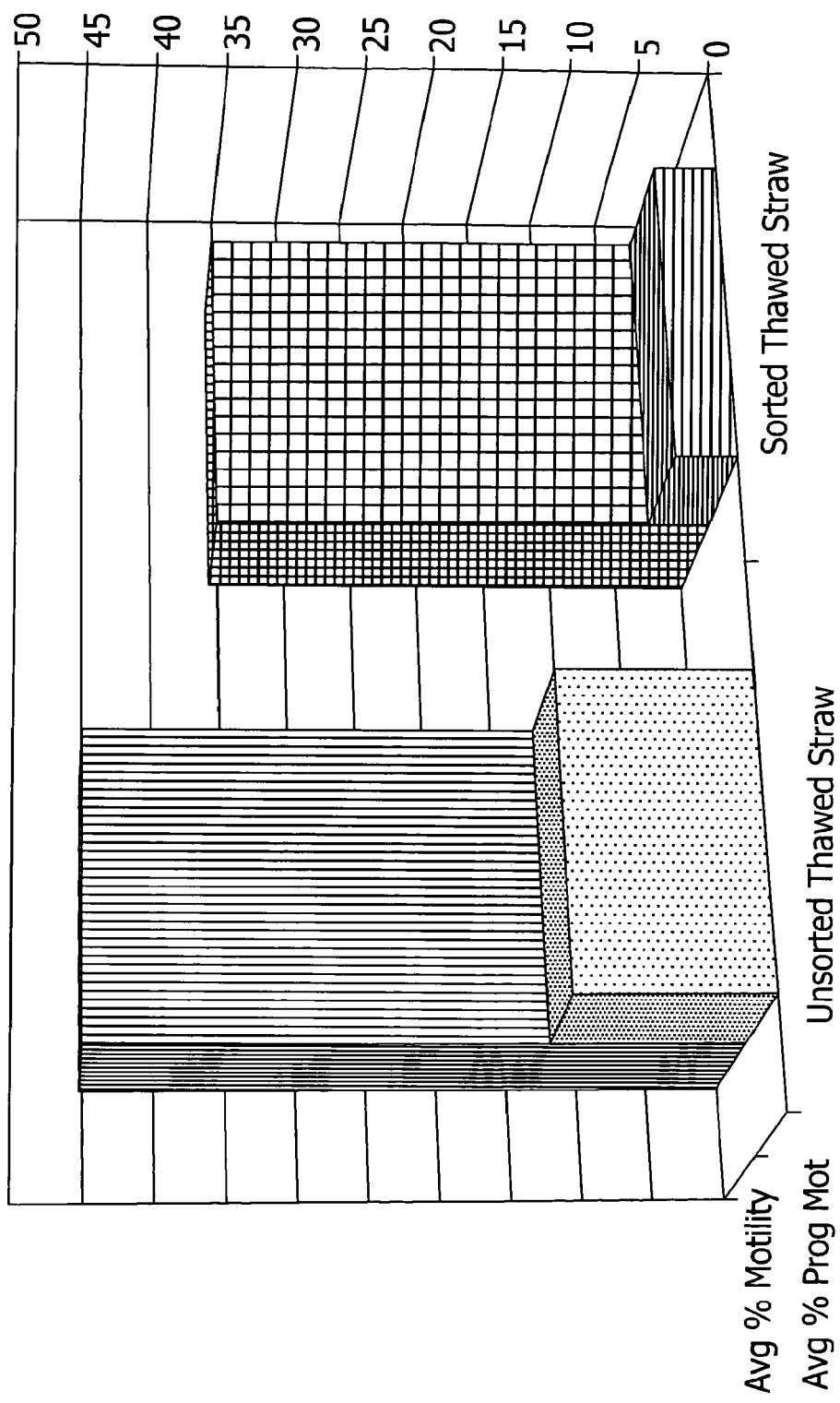

Thawed straws were analyzed by IVOS for % motility and % progressive motility after incubation at 37° C. for 30 and 120 minutes. Results from a set of sorted and unsorted straws are summarized in FIG. 130 and FIG. 131.

Multi-Channel Sorting Example IV

Bull semen was collected from a sexually mature bull using an artificial vagina and the ejaculate split into two aliquots. The first aliquot of 250 µL of semen was suspended in 5 mL of 37° C. Triladyl®. The second aliquot, which comprised the remained of the ejaculate, was suspended in two parts 37° C. carbonate buffer (two parts 0.097 moles/L of $NaHCO_3$. 0.173 moles/L of $KHCO_3$, 0.090 moles/L $C_6H_8O_7.H_2O$ in water) (pH 6.1-6.2) and held under $CO_2$. Both aliquots were transported at 37° C. in a temperature-controlled container to the processing facility. At the processing facility, the first aliquot was floated in ~120 mL of 37° C. water in a 200 mL beaker and placed in the cold room to slowly cool to 5° C. The second aliquot was analyzed for concentration, motility and progressive motility by the Hamilton-Thorn Motility Analyzer (IVOS), according to standard and well known procedures (Farrell et al. *Theriogenology*, 49(4): 871-9 (March 1998)).

A 5 mL tube of $150 \times 10^6$ sperm/mL sperm suspension was prepared by transferring a fraction containing 750 million sperm from the second aliquot (pH 6.1-6.2) to an empty tube and adding 28° C. carbonate buffer (pH 7.35) to a final volume of 5 ml. To this sperm suspension, 10 mM Hoechst 33342 solution in water was added to yield a final dye concentration 150 µM Hoechst 33342. The suspension was held at 41° C. under $CO_2$ for approximately 40 minutes and then placed at 28° C. for sorting. Ten µL of 25 mg/mL FD&C #40 was added to the tube of stained sperm suspension just prior to sorting.

The stained sperm suspension was loaded onto the sample port of one channel of a multi-channel droplet sorting flow cytometer system. The sperm suspension was maintained at 28° C. X & Y chromosome bearing sperm were separated by the flow cytometry using a coincidence abort sort strategy for a time period necessary to place an enriched X chromosome bearing cell population of approximately eighteen million sperm into a collection tube that had been prepared by soaking with sheath buffer for at least one hour and then adding 0.5 mL of Triladyl® cryo-preservation media (pH 6.6). The sperm cells were introduced into the flow cytometry system at a rate of between about 25,000 and 30,000 cells/second. An enriched population of X chromosome bearing cells was collected at a rate varying from 4,500 per second to 6,000 per second. When approximately eighteen million sperm had been sorted into a collection tube, the tube was removed and replaced with another tube that has been similarly prepared. Immediately after removal of a collection tube from the flow cytometer, the sorted sperm suspension was centrifuged for 7 min a 700×g. The supernatant was removed using a transfer pipette to yield a concentration of approximately 100 million sperm/mL. Triladyl® cryo-preservation media and pyruvate (pH 6.6) was added to the sperm suspensions to yield a final concentration of approximately 50 million sperm/mL. This process continued until the flow cytometer had produced two collection tubes (C2-C3). The re-suspended sorted sample tubes were floated in ~120 mL of 28° C. water in a 200 mL beaker and placed in a 5° C. cold room to slowly cool.

Figure 132:
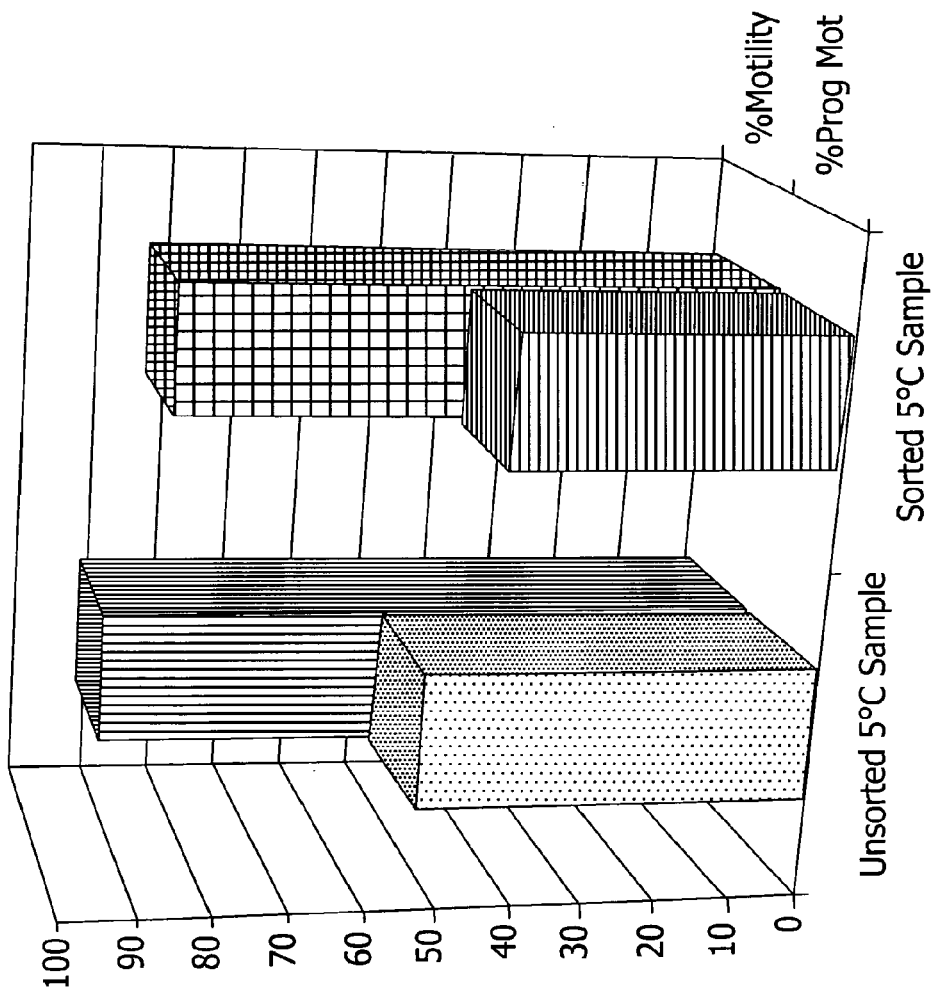

After the sorted samples reached 5° C., the two tubes of sorted sperm were combined into one tube. The pooled sample was analyzed by IVOS to determine the % motility, % progressive motility and concentration. Additional Triladyl® cryo-preservation media and pyruvate (pH 6.6) was added to the sample to yield a final concentration of approximately 50 million sperm per mL. A summary of the IVOS assessment compared to the non-sorted sample of the same ejaculate is illustrated in FIG. 132.

The pooled sorted sample and unsorted sample (i.e., the first aliquot from above) were loaded into standard 0.25 cc straws in the 5° C. cold room. The loaded straws were transferred to a programmable freezer and frozen by the following program: 5 min @ 5° C., cool from 5° C. to −12° C. @ 4° C./min, cool from −12° C. to −100° C. @ 40° C./min, cool from −100° C. to −140° C. @ 20° C./min, hold at −140° C. After the straws had reached −140° C., they were quickly removed from the freezer and plunged into liquid nitrogen.

Figure 133:
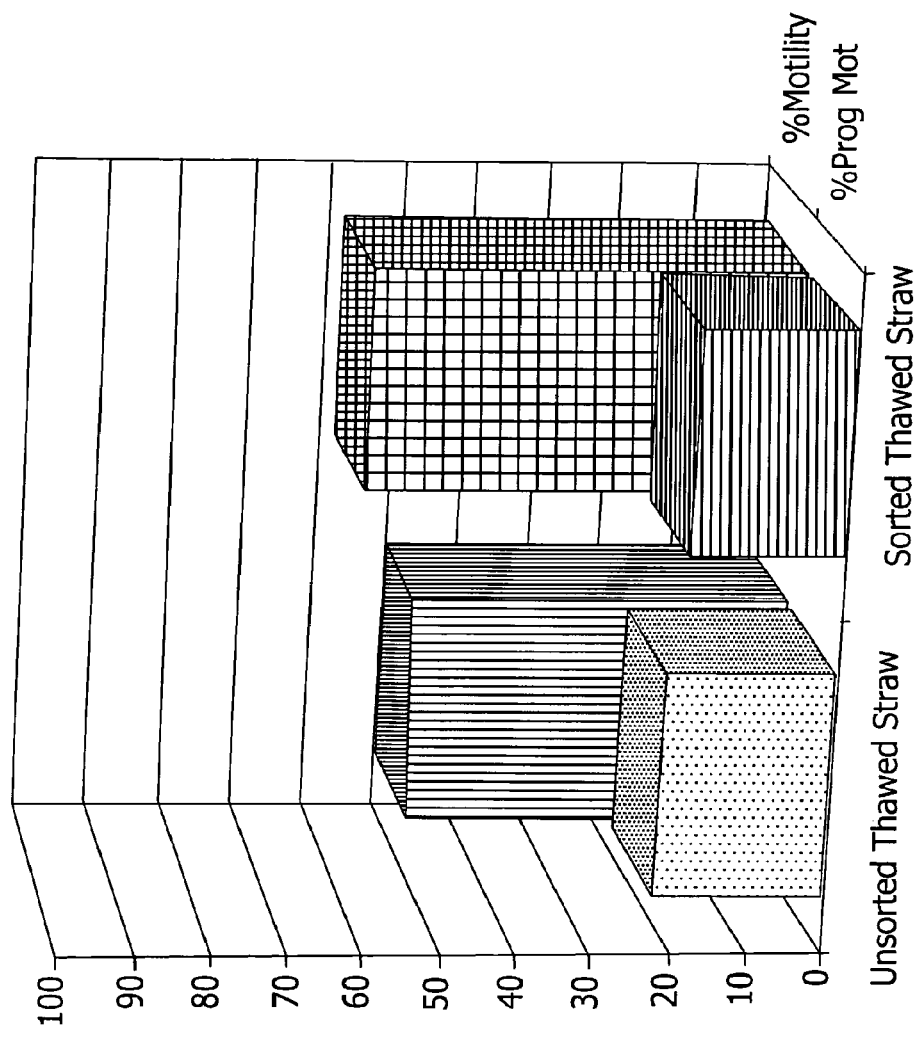
Figure 134:
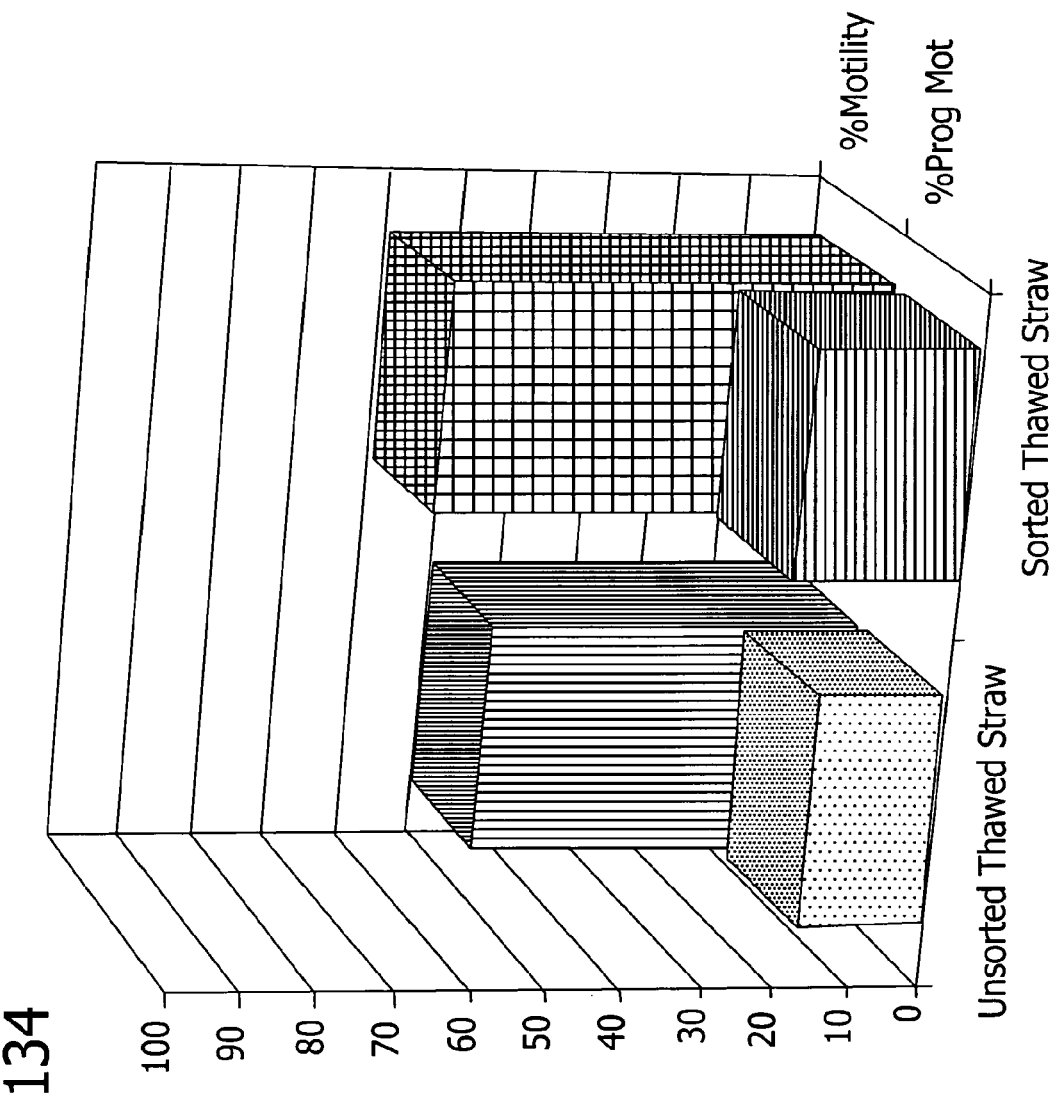

Thawed straws were analyzed by IVOS for % motility and % progressive motility immediately after thawing and after incubation at 37° C. for 30 minutes. Results from a set of sorted and unsorted straws are summarized in FIG. 133 and FIG. 134.

Capillary Tube Nozzle System

Figure 135:
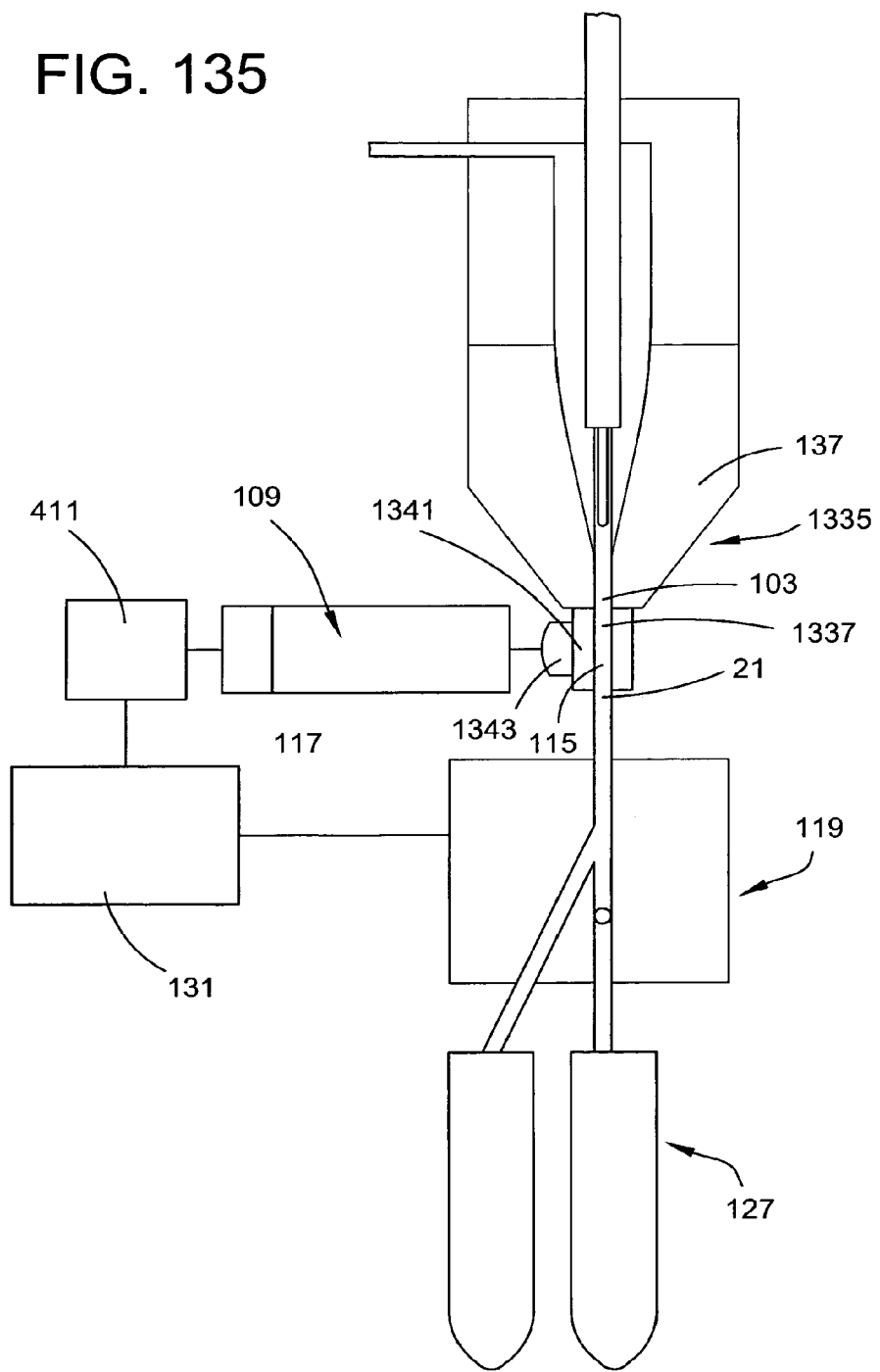
FIG. 135 is a schematic diagram of one alternative embodiment for a nozzle system of the present invention wherein the nozzle directs the fluid stream through a capillary tube.

FIG. 135 illustrates an alternative nozzle system, generally designated 1335, similar to that described above except that a capillary tube 1337 (of quartz or fused silica, for example) is connected to the nozzle 137 so that fluid exiting the nozzle orifice 103 is directed into and through the tube. The optics system 109 of the flow cytometer is optically coupled to the side of the tube in a suitable manner, as by a chamber 1341 filled with a light-transmitting medium such as oil or gel having a known index of refraction. The use of a capillary tube, compared to the jetting of the fluid stream through open space, has the benefit of reducing the lensing of the stream 21 due to the acoustical energy supplied by the transducer 105, and enabling the focusing lens 1343 to be positioned immediately adjacent the fluid stream for increasing resolution of the emission signals.

Figure 137:
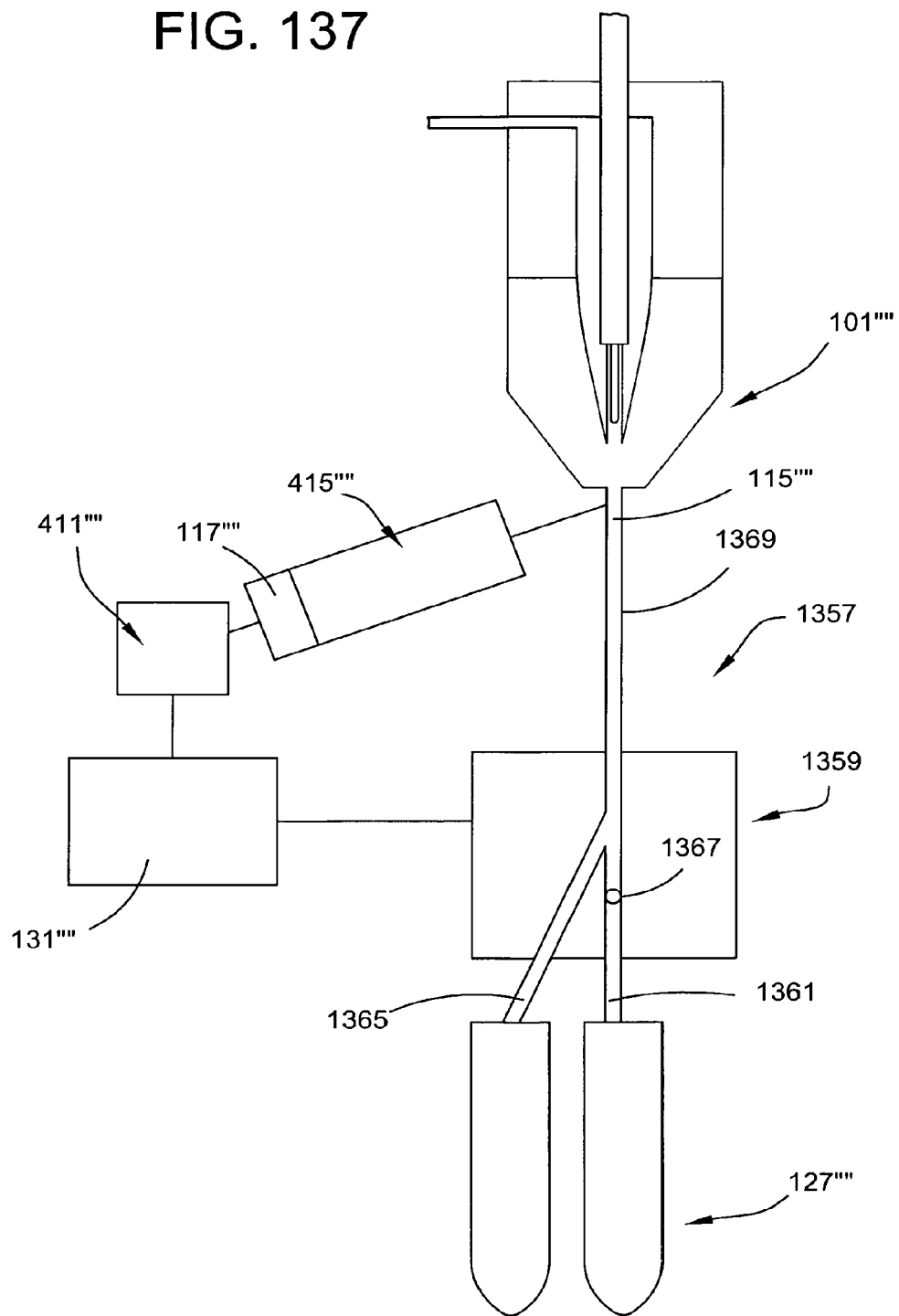
FIG. 137 is a schematic diagram of an alternative sorting system based on fluidic switching that may be used in an apparatus employing the technology of the present invention.

After the particles have been interrogated and classified, they may be sorted using any conventional techniques known to those skilled in the art, as by use of a fluid switching device shown in FIG. 137 or other suitable devices such as photo-damage systems or droplet sorting systems.

Sorting Techniques Other Than Droplet Sorting
Photo-Damage Sorting

Figure 136:
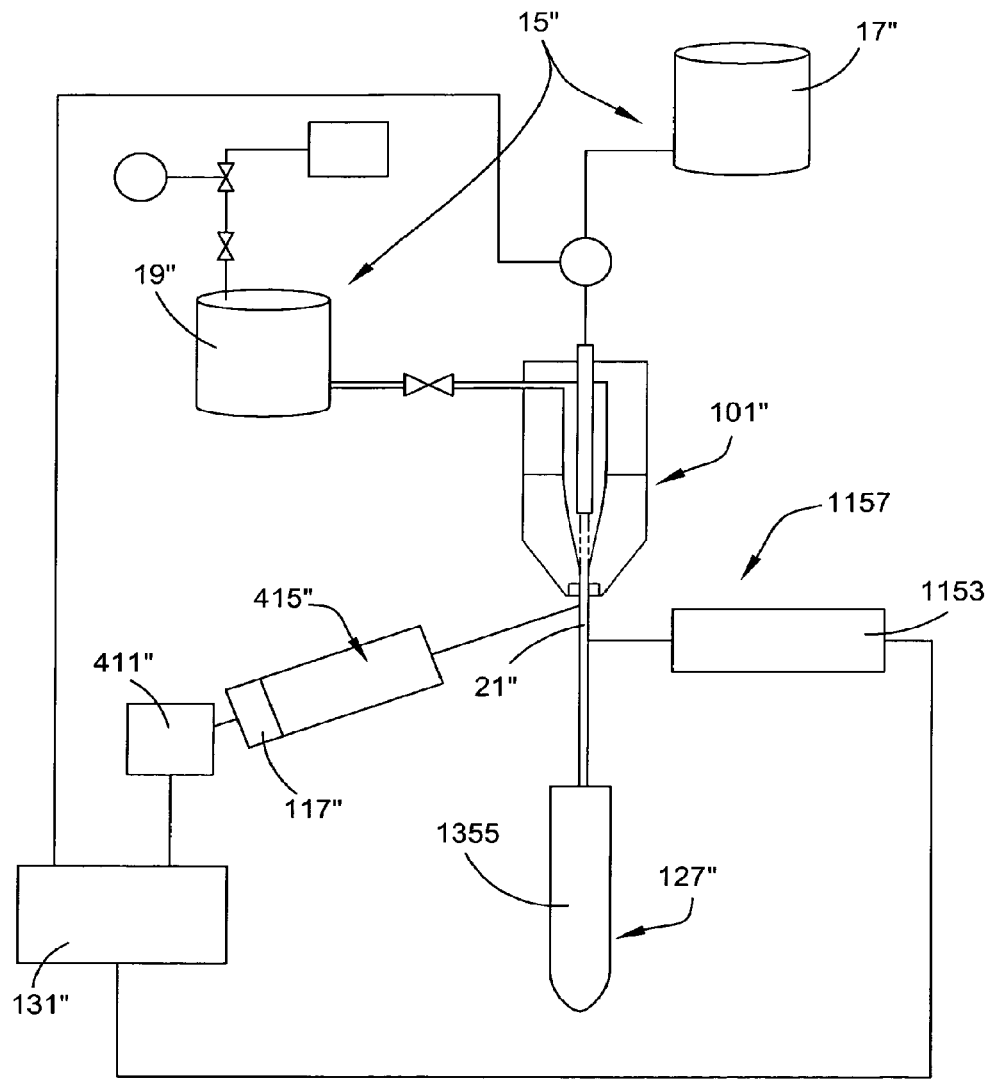
FIG. 136 is a schematic diagram of one embodiment of a photo damage sorting system of the present invention.

The flow cytometry improvements of this invention are applicable not only to droplet cell sorting as described above, but also to other sorting techniques, such as sorting by photo-damage (laser ablation). Photodamage sorting is discussed in U.S. Pat. No. 4,395,397, which is incorporated herein by reference in its entirety. FIG. 136 schematically illustrates one embodiment of a single-channel flow cytometry photo-damage system, generally designated by the reference number As shown in FIG. 136, the photo-damage sorting system 1351 is similar to the droplet sorting system of FIG. 2, and corresponding parts are designated by corresponding reference numbers with the addition of a double prime ("). In general, the system comprises the same components as the system of FIG. 2, except that the droplet sorting components are eliminated (e.g., the transducer 105, the charging device 627, the deflector plates 629, and associated power sources 635). Instead these components are replaced by a laser 1353 or similar device which is responsive to instructions received from the microprocessor 131" to ablate undesired particles in the fluid stream 21". As a result, the stream collected in a collection receptacle 1355 contains a desired population of particles. For example, if the particles being analyzed are sperm cells and the intended result is to collect sperm cells having a characteristic A (e.g., a desired chromosome content), then the microprocessor receives signals from the epi-illumination system 415" which identifies cells not having characteristic A and selectively activates the laser to ablate such cells or otherwise render them ineffective.

Different control sorting strategies can be employed in a photo-damage system, including the "high recovery" and "high purity" sorting strategies discussed above in the context of a droplet sorter. In a photo-damage system, particles contained in the fluid stream are spaced at various intervals along the stream and generally follow one after another in single file. The particles have different characteristics, some having a characteristic A, for example, and others having a characteristic B. The sequence of particles is random, so viewed as a continuous procession, the particles can be divided into different particle series, one following another, including a first particle series consisting only of one or more particles having characteristic A, a second particle series consisting only of one or more particles having characteristic B and a third particle series consisting of two or more closely spaced particles at least one of which has characteristic A and at least one of which has characteristic B. The latter (third) group generally corresponds to the closely spaced particles in a "coincident" droplet discussed previously, at least for sorting strategy purposes. Thus, the two or more particles in the third group may be closely spaced in the sense that the spatial separation between the particles is insufficient to allow accurate discrimination/classification of the particles, or because such separation is insufficient to permit one particle in the series to be ablated by the laser without damaging the other particle(s) in the same series. In any event, the closely spaced particles in each (or at least some) of the third series of particles can be ablated or not ablated, depending on the sorting strategy employed. It should be noted that multiple particles in a first series or multiple particles in a second series could be "closely spaced", but since the particles in any such series have the same characteristic (A or B), they are treated as a single-particle series, at least for sorting strategy purposes.

The photo-damage system can be a single-channel system or a multi-channel system, as described above.

Fluid Switching Sorting

It is contemplated that the principles of this invention can also be applied to flow cytometry systems using fluid switching techniques, as disclosed, for example, in U.S. Pat. Nos. 6,432,246 (Adair), 4,756,427 (Goöhde, et al.), and 3,791,517 (Friedman), which are incorporated herein by reference in their entireties. FIG. 137 is a partial view showing such a system, generally designated 1357. It is substantially identical to the system shown in FIG. 2 except that the nozzle system 101" includes a capillary tube 1369 (e.g., see FIG. 135), and the sorting system comprises a fluid-switching device 1359 coupled to the capillary tube 1369 downstream from the interrogation location 115'. The construction and operation of the fluid-switching device can incorporate any conventional fluid switching technology such as disclosed in the above-referenced patents. In general, the device functions to sort desired particles from undesired particles in response to instructions received from the processor by intermittently diverting portions of the fluid stream containing the desired/undesired particles along separate flow paths 1361, 1365 for collection in vessels or the like. The switching is commonly achieved by selectively actuating a transducer 1367 in one of the flow paths.

The various sorting strategies described above in regard to droplet sorting and photo-damage sorting can also be employed in a fluid-switching system. In the fluid-switching system, particles contained in the fluid stream are also spaced at various intervals along the stream and generally follow one after another in single file. The particles have different characteristics, some having a characteristic A, for example, and others having a characteristic B, and the sequence of particles is random. Therefore, as discussed above in regard to the photo-damage system, the procession of particles can be divided into different particle series, one following another, including a first particle series comprising one or more particles having characteristic A, a second particle series comprising one or more particles having characteristic B and a third particle series comprising two or more closely spaced particles at least one of which has characteristic A and at least one of which has characteristic B. The latter (third) group generally corresponds to the closely spaced particles in a "coincident" droplet discussed previously, at least for sorting strategy purposes. Thus, the two or more particles in the third group may be closely spaced in the sense that the spatial separation between the particles is insufficient to allow accurate discrimination/classification of the particles, or because such separation is insufficient to permit one particle in the series to be diverted by the fluid-switching device separate from the another particle in the same series. In any event, the closely spaced particles in each (or at least some) of the third series of particles can be diverted to one collection location or another, depending on the sorting strategy employed. As explained above in connection with photo-damage sorting, multiple particles in a first series or multiple particles in a second series could be "closely spaced", but since the particles in any such series have the same characteristic (A or B), they are treated as a single-particle series for the purpose of sorting strategy.

The fluid switching system can be a single-channel system or a multi-channel system, as described above.

Droplet Interference Sorting

Figure 138:
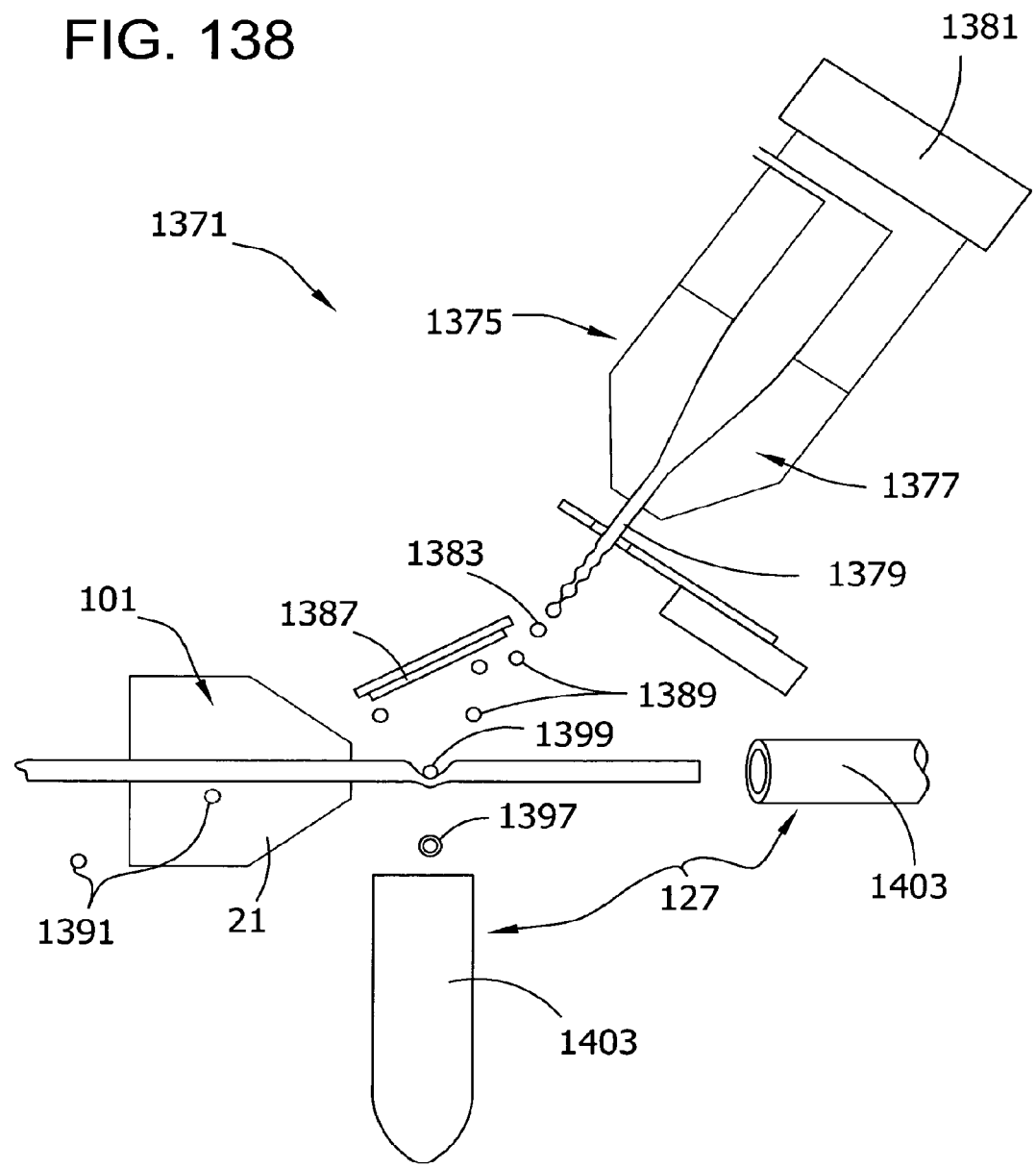
FIG. 138 is a schematic diagram of an alternative sorting system based on a high-speed droplet interference stream that diverts selected discrete segments of the fluid stream carrying the analyzed particles.
Figure 72:
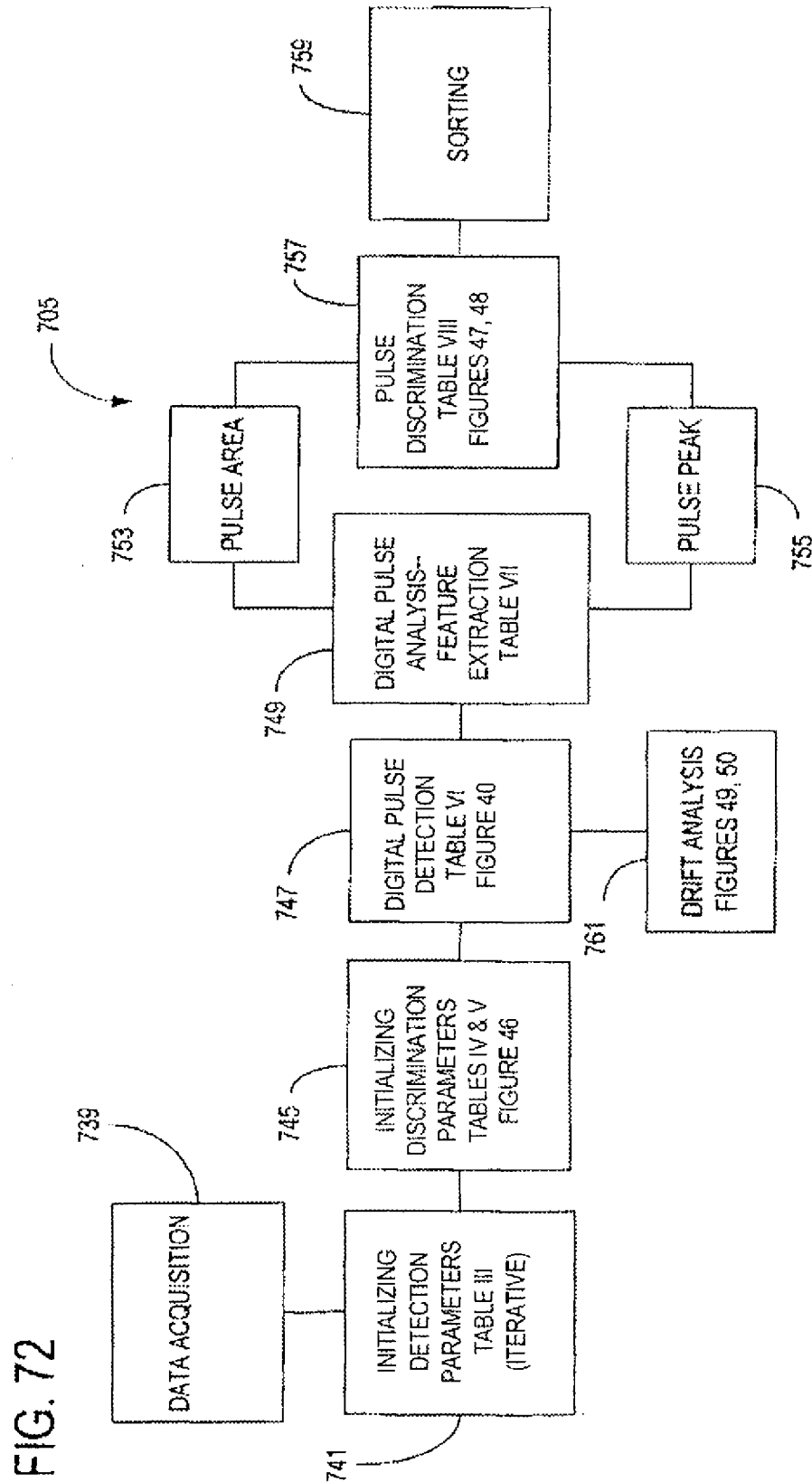

It is also contemplated that the technology of this invention can be used in conjunction with a droplet interference fluidic switching technique. For example, a high-speed droplet interference sorting system 1371, shown schematically in FIG. 138, may be used to sort particles by diverting selected segments of the coaxial carrier and sheath fluid stream.

In contrast to some other sorting techniques, the droplet interference sorting technique does not require the coaxial carrier and sheath stream to be formed into droplets. Thus, there is no need to couple the nozzle system 101''' used for delivery of the carrier and sheath fluids with a droplet generation system. By way of example only, passing the carrier and sheath fluids through a nozzle system at 60 psi to create a 50 micron diameter stream is one suitable arrangement for formation of a laminar coaxial fluid stream for delivery of particles to the droplet interference sorting system. Particles in the coaxial fluid stream are analyzed and classified by the optics system 109 and processor 131 as they move through the interrogation location 115''', as has been described above for the other sorting systems. Sorting occurs downstream from the interrogation location, at a location where the coaxial fluid stream intersects a high-speed droplet interference stream 1373.

The droplet interference stream 1373 is generated by a droplet generation system 1375 similar to the droplet generation system used for droplet sorting. A high-speed fluid stream 1379 passes through a high-speed nozzle system 1377 that is coupled to a piezoelectric transducer 1381 or other source of acoustical energy for causing the high-speed fluid stream to break into droplets 1383 downstream from the high-speed nozzle. For example, a particle-free fluid at 1500 psi may be passed through the high-speed nozzle to form a 70 micron diameter high-speed fluid jet. The high-speed nozzle may be oscillated at 400 KHz to form high-speed droplets. The high-speed droplets 1383 pass through an electric field generated by one or more electric deflection plates 1387 so that the path of the high-speed droplets may be controlled by selectively applying an electric charge to the droplets, as was done to control the path of droplets in the droplet sorting system. The high-speed droplet interference stream is directed so some high-speed droplets intersect the coaxial fluid stream at a point 1399 downstream from the interrogation location. For example, uncharged droplets 1389 may be directed to collide with the fluid stream while charged droplets 1391 are deflected away from the coaxial fluid stream. When a high-speed droplet collides with the coaxial fluid stream, a segment 1397 of the fluid stream and any particles contained therein are diverted from the path they would have otherwise taken. The application of a charge or no charge to a high-speed droplet may be timed so the arrival of that droplet at the intersection 1399 with the coaxial fluid stream coincides with the arrival of a particular segment of the coaxial fluid stream. Thus, by selectively charging high-speed droplets depending on the classification of particles contained within the coaxial stream segments, one can sort particles by diverting all coaxial fluid stream segments that contain one or more selected particles and not diverting other coaxial stream segments or vice-versa. Collection capillaries 1403 having a slight vacuum may be used to collect both the diverted 1397 and undiverted coaxial stream segments. The droplet interference sorting system may be set up so the high-speed droplets merge with diverted coaxial stream segments or so the high-speed droplets remain separate from the diverted stream segments after collision with the coaxial stream segments.

Because there are no particles or cells in the high-speed droplet interference stream 1373, it is possible to use very high pressures and very high droplet frequencies without damaging the particles or cells to be sorted. This allows sorting of stream segments each having less volume (e.g., four times less volume) than the volume of a droplet in the droplet sorting system. This greatly increases the maximum throughput of the system while also reducing the dilution factor of the sorted particles. Moreover, because finely filtered liquid with no cells or particles is used to form the droplet interference stream, more consistent droplet formation is possible because the droplet formation nozzle is less likely to become clogged or suffer from protein buildup than the nozzle system used in the droplet sorting system. Another advantage is that the distance between particle analysis at the interrogation location and the sorting point 1399 can be reduced (e.g., by a factor of four), allowing more accurate prediction of the time of arrival of a particular particle at the sorting point. Furthermore, the droplet interference system allows more flexibility in adjustment of nozzle size or pressure for the coaxial fluid stream. If desired, the droplet interference sorting system can be combined with the capillary tube nozzle system. A multi-channel droplet interference sorting system may use a high-pressure fluidic pump to supply multiple droplet interference stream generating nozzles with fluid from a common fluid supply.

When introducing elements of the present invention or the embodiment(s) thereof, the articles "a," "an," "the," and "said" are intended to mean that there are one or more of the elements. The terms "comprising," "including," and "having" are intended to be inclusive and mean that there may be additional elements other than the listed elements. The term "or" is intended to include "and/or" and is intended to mean "one or another or both." Thus, an indication of "ABC or DEF" means (1) ABC, or (2) DEF, or (3) both ABC and DEF. The term "and/or" is intended to have the same meaning as "or" as defined above. Thus, the term "and/or" is intended to include "or" and is intended to mean "one or another or both." For example, an indication of "ABC and/or DEF" means (1) ABC, or (2) DEF, or (3) both ABC and DEF.

In view of the above, it will be seen that the several objects of the invention are achieved and other advantageous results attained.

As various changes could be made in the above constructions, products, and methods without departing from the scope of the invention, it is intended that all matter contained in the above description and shown in the accompanying drawings shall be interpreted as illustrative and not in a limiting sense.

Comments on Inventive Features

Those skilled in the art will recognize that the invention described above includes many inventive aspects, including at least the following:

A. Multi-Channel Sorting Apparatus

A1. A multi-channel system for sorting particles according to one or more characteristics of the particles, said system comprising:

multiple flow cytometry units each of which is operable to sort a desired population of particles in a mixture of particles by interrogating a stream of fluid containing said particles using a beam of electromagnetic radiation, said units sharing an integrated platform comprising at least one of the following elements: (1) a common supply of particles; (2) a common source of electromagnetic radiation; (3) a common housing; (4) a common input for controlling operation of the units; (5) a common processor for receiving and processing information from the units; and (6) a common fluid delivery system for delivering fluid containing said particles to said flow cytometry units.

A2. The system of A1 wherein said particles are cells.

A3. The system of A1 wherein said particles are sperm cells.

A4. The system of A1 wherein said system comprises at least element (2), and wherein one or more of said multiple flow cytometry units comprises a jet-in-air droplet sorting flow cytometry unit.

A5. The system of A1 wherein said integrated platform comprises at least elements (2) and (3).

A6. The system of A1 wherein said integrated platform comprises at least elements (4) and (5).

A7. The system of A1 wherein said integrated platform comprises at least element (2), said common source comprising a single laser beam.

A8. The system of A7 further comprising a beam splitting system for splitting the single laser beam into multiple beams and directing the multiple beams into optics systems of respective flow cytometry units.

A9. The system of A8 wherein said single laser beam comprises a plurality of pulses, each pulse having a peak power that is greater than the average power output of the laser.

A10. The system of A1 wherein said integrated platform comprises at least element (3), said flow cytometry units comprising interchangeable modules removably mounted in the housing.

A11. The system of A1 wherein each flow cytometry unit comprises an epi-illumination optics system for interrogating a respective fluid stream.

A12. The system of A1 further comprising a collection system for collecting said desired population of particles from each unit.

A13. The system of A1 wherein said integrated platform comprises at least element (5), and wherein said common output comprises an indication of the fluorescence intensity measured by each unit.

A14. The system of A1 wherein said integrated platform comprises at least element (5), and wherein said common output comprises an indication of the rate at which each unit is separating particles.

A15. The system of A1 wherein said integrated platform comprises at least element (5), and wherein said common output comprises an indication of particle staining variations.

A16. The system of A1 wherein said integrated platform comprises at least element (5), and wherein said common output comprises an indication of a decision boundary used by each unit for discriminating between particles.

A17. The system of A1 wherein each of said flow cytometry units comprises a droplet sorting system.

A18. The system of A1 wherein said integrated platform comprises at least element (5), and wherein said common output comprises an indication of a droplet break-off location of each unit.

A19. The system of A1 wherein at least one of said flow cytometry units comprises a photo-damage system.

A20. The system of A1 wherein at least one of said flow cytometry units comprises a fluid-switching sorting system.

A21. The system of A1 wherein said flow cytometry units are adapted to operate in parallel.

A22. The system of A1 wherein the integrated platform comprises at least a shared laser operable to emit a plurality of electromagnetic radiation pulses, wherein each pulse has a peak power exceeding the average power of the laser, and wherein one or more of said flow cytometry units comprises:

a flow channel for directing a fluid stream containing sample particles through a particle interrogation location;

a beam guidance system operable to direct a portion of the electromagnetic radiation in a pulse to the interrogation location;

a timing circuit operable to produce a timing signal indicative of the arrival of electromagnetic radiation at the interrogation location;

a detector adapted to detect electromagnetic radiation from the interrogation location and operable to output a time-varying analog signal indicative of the intensity of the detected electromagnetic radiation;

an analog to digital converter adapted to receive the time-varying analog signal as input and to sample the analog signal to produce a digitized output; and an electronic processor operable to analyze the digitized output from the analog to digital converter as a function of the timing signal.

A23. The system of A1 wherein the multiple flow cytometry units comprise three or more flow cytometry units.

A24. The system of A1 wherein the multiple flow cytometry units comprise at least twelve flow cytometry units.

A25. The system of claim A1, wherein the integrated platform comprises at least element (5), and wherein the common processor performs at least one of: (1) receiving and processing said information in real time; and (2) receiving and processing said information to permit evaluation of the operation of one unit relative to another unit.

A26. The system of A1 wherein each flow cytometry unit comprises a sensor operable to generate a time-varying output signal indicative of at least one characteristic of the particles, wherein said integrated platform comprises at least element (5) and said information received by the common processor comprises the output signals from the respective sensors, and wherein the processor is operable to receive the output signals as a substantially continuous stream and to substantially continuously process the output signals in real time.

A27. The system of A1 wherein said integrated platform comprises a common processor operable to send control signals to the flow cytometry units in real time during a sorting process to adjust their operation as a function of said information received by the common processor, and wherein the flow cytometry units are responsive to the control signals.

B. Multi-Channel Sorting Method

B1. A multi-channel method of sorting particles according to one or more characteristics of the particles, said method comprising:

providing a plurality of flow cytometry units;

operating said flow cytometry units to conduct a plurality of flow cytometry operations, said operations comprising forming separate fluid streams each containing a mixture of particles, and sorting desired populations of particles in said mixtures of particles by interrogating the streams using beams of electromagnetic radiation; and sharing at least one of the following elements while conducting said operations: (1) a common supply of particles for said streams; (2) a common source of electromagnetic radiation for said beams; (3) a common operations control input; (4) a common processor for receiving and processing information from the units; (5) a common system for delivering fluid to said streams; and (6) a common housing for said flow cytometry units.

B2. The method of B1 wherein said particles are cells.

B3. The method of B1 wherein said particles are sperm cells.

B4. The method of B1 wherein at least one of said multiple flow cytometry units comprises a jet-in-air droplet sorting flow cytometry unit.

B5. The method of B1 further comprising at least sharing said common source of electromagnetic radiation in the form of a single laser beam, said method further comprising splitting the single laser beam into multiple beams and directing the multiple beams into optics systems of respective flow cytometry units.

B6. The method of B5 further comprising reflecting a percentage of beam light of the single beam toward the optics system of one of said flow cytometry units, and passing a percentage of beam light of the single beam for transmission to the optics system of another of said flow cytometry units.

B7. The method of B6 further comprising using a solid state laser to form said single laser beam.

B8. The method of B7 further comprising mode-locking the solid state laser so that the single laser beam comprises a plurality of pulses, wherein each pulse has a peak power that is greater than the average power output of the laser.

B9. The method of B1 further comprising sharing at least element (6), and wherein said method further comprises removably mounting said flow cytometry units in the common housing.

B10. The method of B1 further comprising at least sharing said common source of electromagnetic radiation in the form of a shared laser; the method further comprising the steps of:

emitting a plurality of electromagnetic radiation (EMR) pulses from a laser, wherein the peak power of each pulse exceeds the average power of the laser;

directing each pulse into a beam splitting and guidance system to intermittently illuminate each fluid stream and the particles contained therein by directing a portion of the energy in the pulses along a beam path from the laser to each interrogation location;

detecting EMR from at least one interrogation location;

generating a time-varying analog signal indicative of the intensity of the detected EMR from said interrogation location;

generating a timing signal indicative of the arrival of a pulse at said interrogation location;

converting the time-varying analog signal into a digital signal; and analyzing the digital signal to determine characteristics of the particles in the fluid stream flowing through the respective interrogation location.

B11. The method of B1 further comprising using a first sorting strategy in a first operation of said operations and a second sorting strategy different from the first sorting strategy in a second operation of said operations.

B12. The method of B1 further comprising collecting a population of desired particles sorted by each flow cytometry unit, and combining the population collected from one unit with a population collected from a different unit to produce a blended population of desired particles.

B13. The method of B1 further comprising varying the rate at which fluid is delivered to one or more of the flow cytometry units as a function of at least one of the following: (1) the purity of a first sorted population; and (2) the quantity of desired particles in a second population.

B14. The method of B1 further comprising conducting said flow cytometry operations in parallel.

B15. The method of B1 wherein the sharing step comprises sharing at least element (4), the method further comprising using the common processor to do at least one of the following: (1) receive and process said information in real time; and (2) receive and process said information to permit evaluation of the operation of one unit relative to another unit.

B16. The method of B1 wherein the sharing step comprises sharing at least element (4), the method further comprising using a sensor for each respective cytometry unit to generate a time-varying output signal indicative of at least one characteristic of the particles and using the common processor to receive the respective output signals as a substantially continuous stream and to process the output signals in real time.

B17. The method of B1 wherein the sharing step comprises sharing at least element (4), the method further comprising sending a control signal to one or more of the flow cytometry units in real time during a sorting process to adjust the unit's operation as a function of the information received by the common processor.

C. [Reserved]

D. Multi-Channel Analyzer

D1. A multi-channel system for classifying particles according to one or more characteristics of the particles, said system comprising:

a plurality of flow cytometry units each of which is operable to classify particles in a mixture of particles by interrogating a stream of fluid containing said particles using a beam of electromagnetic radiation, said units sharing an integrated platform comprising at least one of the following elements: (1) a common supply of particles; (2) a common housing; (3) a common input for controlling operation of the units; (4) a common processor for receiving and processing information from the units; and (5) a common fluid delivery system for delivering fluid containing said particles to said flow cytometry units.

D2. The system of D1 wherein said integrated platform further comprises a common source of electromagnetic radiation.

D3. The system of D1 wherein said particles are cells.

D4. The system of D1 wherein said particles are sperm cells.

D5. The system of D1 wherein said integrated platform comprises at least elements (3) and (4).

D6. The system of D5 wherein said integrated platform further comprises a common source of electromagnetic radiation.

D7. The system of D1 wherein said integrated platform further comprises a common source of electromagnetic radiation, said common source comprising a single laser beam.

D8. The system of D7 further comprising a beam splitting system for splitting the single laser beam into multiple beams and directing the multiple beams into optics systems of respective flow cytometry units.

D9. The system of D1 wherein said integrated platform comprises at least element (2), said flow cytometry units comprising interchangeable modules removably mounted in the housing.

D10. The system of D1 wherein each flow cytometry unit comprises an epi-illumination optics system for interrogating a respective fluid stream.

D11. The system of D1 wherein said integrated platform comprises at least element (4), and wherein said processor is operable to output an indication of the fluorescence intensity measured by each unit.

D12. The system of D1 wherein said integrated platform comprises at least element (4), and wherein said processor is operable to output an indication of the rate at which each unit is separating particles.

D13. The system of D1 wherein said integrated platform comprises at least element (4), and wherein said processor is operable to output an indication of particle staining variations.

D14. The system of D1 wherein said integrated platform comprises at least element (4), and wherein said processor is operable to output an indication of a decision boundary used by each unit for discriminating between particles.

D15. The system of D1 wherein said flow cytometry units are adapted to operate in parallel.

D16. The system of D1 wherein said plurality of flow cytometry units are operable to sort the particles.

D17. The system of D16 wherein the integrated platform further comprises a common source of electromagnetic radiation, and wherein said plurality of flow cytometry units comprises a jet-in-air droplet sorting flow cytometry unit.

D18. The system of D1 wherein said integrated platform comprises at least element (4), and wherein the common processor is operable to perform at least one of the following: (1) receive and process said information in real time; and (2) receive and process said information to permit evaluation of the operation of one unit relative to another unit.

D19. The system of claim D1 wherein each flow cytometry unit comprises a sensor operable to generate a time-varying output signal indicative of at least one characteristic of the particles, wherein said integrated platform comprises at least element (4) and said information received by the common processor comprises output the signals from the respective sensors, and wherein the processor is operable to receive the output signals as a substantially continuous stream and to process the output signals in real time.

D20. The system of D1 wherein said integrated platform comprises a common processor operable to send control signals to the flow cytometry units in real time during a sorting process to adjust their operation as a function of said information received by the common processor, and wherein the flow cytometry units are responsive to the control signals.

E. Multi-Channel Analyzing Method

E1. A multi-channel method of classifying particles according to one or more characteristics of the particles, said method comprising:

providing a plurality of flow cytometry units;

operating said flow cytometry units to conduct a plurality of flow cytometry operations, said operations comprising forming separate fluid streams each containing a mixture of particles, and classifying particles in said mixtures of particles by interrogating the streams using beams of electromagnetic radiation; and sharing at least one of the following elements to conduct said operations: (1) a common supply of particles for said streams; (2) a common operations control input; (3) a common processor for receiving and processing information from the units; (4) a common system for delivering fluid to said streams; and (5) a common housing for said flow cytometry units.

E2. The method of E1 further comprising sharing a common source of electromagnetic radiation for said beams.

E3. The method of E2 wherein said plurality of flow cytometry units comprises a jet-in-air droplet sorting flow cytometry unit.

E4. The method of E1 further comprising operating said plurality of flow cytometers to sort said mixture of particles based on their classification.

E5. The method of E1 wherein said particles are cells.

E6. The method of E1 wherein said particles are sperm cells.

E7. The method of E1 further comprising sharing a common source of electromagnetic radiation for said beams in the form of a single laser beam, splitting the single laser beam into multiple beams, and directing the multiple beams into optics systems of respective flow cytometry units.

E8. The method of E7 wherein the sharing step comprises at least element (5), the method further comprising guiding said single laser beam into said common housing prior to splitting the beam.

E9. The method of E7 further comprising reflecting a percentage of beam light of the single beam toward the optics system of one of said flow cytometry units, and passing a percentage of beam light of the single beam for transmission to the optics system of another of said flow cytometry units.

E10. The method of E1 wherein the sharing step comprises at least element (5), the method further comprising removably mounting said flow cytometry units in the common housing.

E11. The method of E1 comprising operating each flow cytometry unit to interrogate a respective fluid stream using an epi-illumination optics system.

E12. The method of E1 further comprising operating said flow cytometry units in parallel.

E13. The method of E1 wherein said plurality of flow cytometry units comprise twelve or more flow cytometry units.

E14. The method of E1 wherein the sharing step comprises sharing at least element (4), the method further comprising using the common processor to perform at least one of the following: (1) receive and process said information in real time; and (2) receive and process said information to permit evaluation of the operation of one unit relative to another unit.

E15. The method of E1 wherein the sharing step comprises sharing at least element (4), the method further comprising using a sensor for each respective cytometry unit to generate a time-varying output signal indicative of at least one characteristic of the particles and using the common processor to receive the respective output signals as a substantially continuous stream and to process the output signals in real time.

E16. The method of E1 wherein the sharing step comprises sharing at least element (4), the method further comprising sending a control signal to one or more of the flow cytometry units in real time during a sorting process to adjust the unit's operation as a function of the information received by the common processor.

F. [Reserved]

G. Method of Splitting Single Laser for Multi-Channel Cytometry

G1. A method of sorting particles using a system comprising a three or more flow cytometry units each of which is operable to sort a desired population of particles from a mixture of particles by interrogating a stream of fluid containing said particles using a beam of light, said method comprising:
generating a single laser beam;
splitting the single beam into three or more light beams and directing the light beams into optics systems of the flow cytometry units; and
operating the flow cytometry units to sort particles.

G2. The method of G1 wherein each cytometry unit interrogates the fluid stream with a light beam of about the same intensity.

G3. The method of G1 wherein each unit requires a light beam having a power of W watts, and wherein said method further comprises generating said single laser beam having a power of $(W \times N)+L$, where N equals the number of flow cytometry units and L equals power loss in the system.

G4. The method of G1 further comprising balancing the amount of beam light used by the cytometry units to interrogate respective fluid streams by using one or more filters to attenuate the intensity of at least one of said three or more light beams.

G5. The method of G4 further comprising adjusting the intensity of beam light entering respective units so that each unit receives the same amount of beam light within a tolerance of 10%.

G6. The method of G1 wherein at least one of said flow cytometry units uses a droplet sorting process to sort said particles.

G7. The method of G1 wherein at least one of said flow cytometry units uses a photo-damage process to sort said particles.

G8. The method of G1 wherein at least one of said flow cytometry units uses a fluid-switching sorting process to sort said particles.

G9. The method of G1 wherein said flow cytometry units are mounted in a common housing, the method further comprising guiding said single laser beam into said common housing prior to splitting the beam.

G10. The method of G9 further comprising reflecting a percentage of beam light of the single laser beam toward the optics system of one of said flow cytometry units and passing a percentage of beam light of the single laser beam for transmission to the optics system of another of said flow cytometry units.

G11. The method of G1 wherein the step of splitting a single beam comprises splitting a single beam into four separate beams.

G12. The method of G11 wherein the splitting step comprises using a 50/50 beamsplitter to split the single beam into two beams, using a second 50/50 beamsplitter to split one of the two beams into two additional beams, and using a third 50/50 beamsplitter to split the other of the two beams into two more additional beams.

H. Apparatus for Sorting Using Sort Strategy

H1. In a flow cytometry system for sorting a mixture of particles including particles having a characteristic A and particles having a characteristic B, said system comprising a fluid delivery system for delivering a fluid containing said particles, a flow cytometry apparatus for receiving said fluid, forming it into a stream and using flow cytometry to classify the particles according to said characteristics, and a sorting system for sorting the particles according to said classification and according to a sorting strategy to provide at least one population containing desired particles, the improvement comprising:
a control responsive to information received from the flow cytometry apparatus for controlling the sorting system to vary its sorting strategy or for controlling the fluid delivery system to vary the rate at which fluid is delivered as a function of at least one of the following: (1) the purity of said at least one population with respect to either characteristic A particles or characteristic B particles; and (2) the quantity of characteristic A particles or characteristic B particles in said at least one population relative to the total quantity of characteristic A particles or characteristic B particles in said stream.

H2. The system of H1 wherein the particles are cells and characteristics A and B relate to physical characteristics of the cells.

H3. The system of H1 wherein the particles are sperm cells, and wherein characteristic A is indicative of a live X sperm cell.

H4. The system of H3 wherein characteristic B is indicative of other than a live X cell (~X).

H5. The system of H4 further comprising maintaining the purity of said at least one population at more than 85% but less than 95%.

H6. The system of H1 wherein the control increases the rate of fluid delivery when said purity is greater than a desired purity and decreases the rate of fluid delivery when said purity is less than said desired purity.

H7. The system of H1 wherein the control determines the purity of said at least one population based on output signals from the flow cytometry apparatus, said system further comprising an operator input to the control for indicating a desired purity, and wherein the control varies the rate of fluid delivery so that the purity corresponds to the desired purity.

H8. The system of H7 wherein the control increases the rate of fluid delivery when the quantity of characteristic A particles in said at least one population is greater than an acceptable quantity of characteristic A particles in the at least one population, and wherein the control decreases the rate of fluid delivery when the quantity of characteristic A particles in said at least one population is less than said acceptable quantity.

H9. The system of H8 wherein the control determines the quantity of characteristic A particles in said at least one population based on output signals from the flow cytometry apparatus, said system further comprising an operator input to the control for indicating an acceptable quantity of characteristic A particles in said at least one population, and wherein the control varies the fluid delivery rate to obtain said acceptable quantity in said at least one population.

H10. The system of H1 wherein said stream is formed to contain particles following generally one after another in a series which comprises sequential sets of particles, including first particle sets each comprising one or more particles having characteristic A, second particle sets each comprising one or more particles having characteristic B, and third particle sets each comprising two or more closely spaced particles at least one of which has characteristic A and at least one of which has characteristic B.

H11. The system of H10 wherein said sorting system is operable to use a sorting strategy in which said first particle sets are selected for collection in said at least one population and said second and third particle sets are not selected for collection in said at least one population.

H12. The system of H10 wherein said sorting system is operable to use a sorting strategy in which said first and third particle sets are selected for collection in said at least one population and said second particle set is not selected for collection in said at least one population.

H13. The system of H1 wherein said sorting system comprises a droplet sorting system.

H14. The system of H1 wherein said sorting system comprises a photo-damage sorting system.

H15. The system of H1 wherein said sorting system comprises a fluid-switching sorting system.

I. Method for Sorting Particles Using Sorting Strategy

I1. A method of using a flow cytometry system to sort a mixture of particles including particles having a characteristic A and particles having a characteristic B, said method comprising:
delivering a fluid containing said particles;
forming the fluid into a stream and using flow cytometry to classify the particles in the stream according to said characteristics;
sorting the particles in the stream according to said classification and according to a sorting strategy thereby to provide at least one population containing desired particles; and
varying the sorting strategy or varying the rate at which fluid is delivered as a function of at least one of the following: (1) the purity of said at least one population with respect to either characteristic A particles or characteristic B particles; and (2) the quantity of characteristic A particles or characteristic B particles in said at least one population relative to the total quantity of characteristic A particles or characteristic B particles in said stream.

I2. The method of I1 wherein the particles are cells and characteristics A and B relate to physical characteristics of the cells.

I3. The method of I1 wherein said particles are sperm cells, and wherein characteristic A is indicative of a live X sperm cell.

I4. The method of I3 wherein characteristic B is indicative of other than a live X cell (~X).

I5. The method of I3 further comprising maintaining said purity at more than 85% but less than 95%.

I6. The method of I1 further comprising increasing the rate of fluid delivery when said purity is greater than a desired purity and decreasing the rate of fluid delivery when said purity is less than the desired purity.

I7. The method of I1 further comprising increasing the rate of fluid delivery when the quantity of characteristic A particles in said at least one population is greater than an acceptable quantity of characteristic A particles in the at least one population, and decreasing the rate of fluid delivery when the quantity of characteristic A particles in said at least one population is less than said acceptable quantity.

I8. The method of I1 further comprising forming the stream to contain particles following generally one after another in a series which comprises sequential sets of particles, including first particle sets each comprising one or more particles having characteristic A, second particle sets each comprising one or more particles having characteristic B, and third particle sets each comprising two or more closely spaced particles at least one of which has characteristic A and at least one of which has characteristic B.

I9. The method of I8 further comprising sorting said particles according to a sorting strategy in which only first particles sets are selected for collection in said at least one population.

I10. The method of I8 further comprising sorting said particles according to a sorting strategy in which first and third particle sets are selected for collection in said at least one population.

I11. The method of I1 wherein said sorting comprises using a droplet sorting process.

I12. The method of I1 wherein said sorting comprises using a photo-damage sorting process.

I13. The method of I1 wherein said sorting comprises using a fluid-switching sorting process.

J. Droplet Sorter Including Sort Strategy

J1. A system for sorting a mixture of particles including particles having a characteristic A and particles having a characteristic B, said system comprising:
a fluid delivery system for delivering a fluid stream containing said particles;
a flow cytometry apparatus for receiving said stream, forming droplets containing said particles, and sorting said droplets into different populations according to a sorting strategy, said droplets including first droplets each containing one or more particles having characteristic A, second droplets each containing one or more particles having characteristic B and third droplets each containing one or more particles having characteristic A and one or more particles having characteristic B; and
a control responsive to information received from the flow cytometry apparatus for controlling the flow cytometry apparatus to vary the sorting strategy or for controlling the fluid delivery system to vary the rate at which fluid is delivered as a function of at least one of the following: (1) the purity of at least one droplet population with respect to either characteristic A particles or characteristic B particles; and (2) the quantity of characteristic A particles or characteristic B particles in at least one droplet population relative to the total quantity of characteristic A particles or characteristic B particles in said stream.

J2. The system of J1 wherein the control controls the fluid delivery system to maintain the rate at which fluid is delivered as substantially constant, and wherein the control varies the sort strategy.

J3. The system of J2 wherein the control varies the sort strategy in order to vary the percentage of third droplets in one of the droplet populations.

J4. The system of The system of J1 wherein the control controls the fluid delivery system to vary the rate at which fluid is delivered as a function of the purity of said at least one droplet population.

J5. The system of J4 wherein said purity is at least 85% and not more than 95%.

J6. The system of J1 wherein the control controls the fluid delivery system to vary the rate at which fluid is delivered as a function of the quantity of characteristic A particles in said at least one droplet population relative to the total quantity of characteristic A particles in said stream.

J7. The system of J6 wherein the rate at which the fluid is delivered is varied so that the quantity of characteristic A particles in said at least one droplet population represents at least about 60% of the total quantity of characteristic A particles in said stream.

J8. The system of J1 wherein said particles are sperm cells, and wherein characteristic A is indicative of a live X sperm cell.

J9. The system of J1 wherein the ratio of characteristic A particles to characteristic B particles in said mixture is a known ratio, and wherein said control is operable classify some of the particles as having characteristic A or characteristic B and to vary the fluid delivery rate as a function of the ratio of classified particles to the known ratio.

J10. The system of J1 wherein the control determines a purity of the sorted particles based on output signals from the flow cytometry apparatus, said system further comprising an operator input to the control for indicating a desired purity, and wherein the control varies the rate so that the purity of said at least one droplet population generally corresponds to the desired purity.

K. Droplet Sorting Method Including Sort Strategy

K1. A method of sorting a mixture of particles including particles having a characteristic A and particles having a characteristic B, said system comprising:

delivering a fluid stream containing said particles;

forming droplets containing said particles;

sorting said droplets into different populations according to a sorting strategy, said droplets including first droplets each containing one or more particles having characteristic A, second droplets each containing one or more particles having characteristic B and third droplets each containing one or more particles having characteristic A and one or more particles having characteristic B; and varying the sorting strategy or varying the rate at which fluid is delivered as a function of at least one of the following: (1) the purity of at least one droplet population with respect to either characteristic A particles or characteristic B particles; and (2) the quantity of characteristic A particles or characteristic B particles in at least one droplet population relative to the total quantity of characteristic A particles or characteristic B particles in said stream.

K2. The method of K1 further comprising maintaining the rate at which fluid is delivered as substantially constant, and varying the sorting strategy.

K3. The method of K2 further comprising varying the sorting strategy in order to vary the percentage of third droplets in one of the droplet populations.

K4. The method of K1 further comprising varying the rate at which fluid is delivered as a function of the purity of at least one of the droplet populations.

K5. The method of K4 further comprising maintaining said purity in the range of 85% to 95%.

K6. The method of K1 further comprising varying the rate at which fluid is delivered as a function of the quantity of characteristic A particles in said at least one droplet population relative to the total quantity of characteristic A particles in said stream.

K7. The method of K6 wherein the rate at which the fluid is delivered is varied so that the quantity of characteristic A particles in said at least one of the droplet populations represents at least about 60% of the total quantity of characteristic A particles in said stream.

K8. The method of K1 wherein said particles are sperm cells, and wherein characteristic A is indicative of a live X sperm cell.

K9. The method of K1 further comprising increasing the rate when the purity of said at least one droplet population is greater than the desired purity and decreasing the rate when the purity of said at least one droplet population is less than the desired purity.

L. Variable Flow Rate Droplet Sorter Having Feedback Loop

L1. A system for sorting a mixture of particles including particles having a characteristic A and particles having a characteristic B, said system comprising:

a variable rate fluid delivery system for delivering a fluid stream containing said particles;

a flow cytometry apparatus for receiving said stream, forming droplets containing said particles, and sorting said droplets into different populations according to a sorting strategy, said droplets including first droplets each containing one or more particles having characteristic A, second droplets each containing one or more particles having characteristic B and third droplets each containing one or more particles having characteristic A and one or more particles having characteristic B; and a control responsive to information received from the flow cytometry apparatus for controlling the fluid delivery system to vary the rate at which fluid is delivered from the fluid delivery system as a function of at least one of the following: (1) the purity of at least one of the droplet populations with respect to either characteristic A particles or characteristic B particles; and (2) the quantity of characteristic A particles or characteristic B particles in at least one droplet population relative to the total quantity of characteristic A particles or characteristic B particles in said stream.

L2. The system of L1 wherein the control controls the fluid delivery system to vary the rate at which fluid is delivered as a function of the purity of at least one of the droplet populations.

L3. The system of L2 wherein the purity is at least 85% and not more than 95%.

L4. The system of L1 wherein the control controls the fluid delivery system to vary the rate at which fluid is delivered as a function of the quantity or percentage of characteristic A particles in at least one droplet population relative to the total quantity of characteristic A particles in said stream.

L5. The system of L4 wherein the rate at which the fluid is delivered is varied so that the quantity of characteristic A particles in said at least one of the droplet populations represents at least about 60% of the total quantity of characteristic A particles in said stream.

L6. The system of L1 wherein the particles are cells, and wherein characteristics A and B relate to physical characteristics of the cells.

L7. The system of L1 wherein said cells are sperm cells, and wherein characteristic A is indicative of a live X sperm cell.

L8. The system of L7 wherein at least some of the droplets in said at least one droplet population contain at least one live X cell and at least one Y cell in the same droplet, and wherein said purity of said at least one droplet population is measured by $X/(X+Y)$.

L9. The system of L8 wherein said control is operable to vary the rate of fluid delivery to maintain said purity at more than 85% but less than 95%.

L10. The system of L7 wherein characteristic B is indicative of cells which are not live X cells.

L11. The system of L7 wherein said control is operable to vary the rate of fluid delivery so that percentage of live X cells in said at least one droplet population is at least 60% of the total number of live X cells in said first, second and third pluralities of droplets.

L12. The system of L11 wherein the purity of said at least one droplet population is maintained at less than 95%.

L13. The system of L1 wherein the ratio of characteristic A particles to characteristic B particles in said mixture is a known ratio, and wherein said control is operable to classify some of the particles has having characteristic A or characteristic B and vary the fluid delivery rate as a function of the ratio of the classified particles to the known ratio.

L14. The system of L1 wherein the particles having characteristic A are live X sperm cells and the particles having characteristic B are sperm cells which are not live X sperm cells, and wherein said control is operable to vary the fluid delivery rate as a function of the ratio of classified sperm cells to 50%.

L15. The system of L1 wherein the control increases the rate when the purity of said at least one droplet population is greater than a desired purity and decreases the rate when the purity of said at least one droplet population is less than the desired purity.

L16. The system of L1 wherein the control determines a purity of the sorted particles based on output signals from the flow cytometry apparatus, said system further comprising an operator input to the control for indicating a desired purity, and wherein the control varies the rate so that the purity of said at least one droplet population generally corresponds to the desired purity.

M. Droplet Sorting Method Using Variable Flow Rate and Feedback

M1. A method of sorting a mixture of particles including particles having a characteristic A and particles having a characteristic B, said system comprising:
 delivering a fluid stream containing said particles;
 forming droplets containing said particles;
 sorting said droplets into different populations according to a sorting strategy, said droplets including first droplets each containing one or more particles having characteristic A, second droplets each containing one or more particles having characteristic B and third droplets each containing one or more particles having characteristic A and particles having characteristic B; and
 varying the rate at which fluid is delivered as a function of at least one of the following: (1) the purity of at least one of the droplet populations with respect to either characteristic A particles or characteristic B particles; and (2) the quantity of characteristic A particles or characteristic B particles in at least one droplet population relative to the total quantity of characteristic A particles or characteristic B particles in said stream.

M2. The method of M1 further comprising varying the rate at which fluid is delivered as a function of the purity of at least one of the droplet populations.

M3. The method of M2 wherein said purity is at least 85% and not more than 95%.

M4. The method of M1 further comprising varying the rate at which fluid is delivered as a function of the quantity of characteristic A particles in at least one droplet population relative to the total quantity of characteristic A particles in said stream.

M5. The method of M4 further comprising varying the fluid delivery rate so that the quantity of characteristic A particles in said at least one of the droplet populations represents at least about 60% of the total quantity of characteristic A particles in said stream.

M6. The method of M1 wherein the particles are cells, and wherein characteristics A and B relate to physical characteristics of the cells.

M7. The method of M1 wherein said cells are sperm cells, and wherein characteristic A is indicative of a live X sperm cell.

M8. The method of M7 wherein at least some of said droplets in said at least one of the droplet populations contain at least one live X cell and at least one Y cell in the same droplet, and wherein said purity of said at least one droplet population is measured by X/(X+Y).

M9. The method of M8 further comprising varying the rate of fluid delivery to maintain said purity at more than 85% but less than 95%.

M10. The method of M7 wherein characteristic B is indicative of cells which are not live X cells.

M11. The method of M7 further comprising varying the rate of fluid delivery so that percentage of live X cells in said at least one droplet population is at least 60% of the total number of live X cells in said first, second and third pluralities of droplets.

M12. The method of M11 further comprising maintaining the purity of said at least one droplet population at less than 95%.

M13. The method of M1 wherein the ratio of characteristic A particles to characteristic B particles in said mixture is a known ratio, and said method further comprises varying the fluid delivery rate as a function of the ratio of classified particles to the known ratio.

M14. The method of M1 wherein the particles having characteristic A are live X sperm cells and particles having characteristic B are not live X sperm cells, said method further comprising varying the fluid delivery rate as a function of the ratio of classified sperm cells to 50%.

M15. The method of M1 further comprising increasing the rate when the purity of said at least one droplet population is greater than the desired purity and decreasing the rate when the purity of said at least one droplet population is less than the desired purity.

N. Sperm Sorting System for High Purity Sort Strategy

N1. A system for sorting X and Y sperm cells, said system comprising:
 a variable rate fluid delivery system for delivering a fluid stream containing X and Y sperm cells;
 a flow cytometry apparatus for (1) receiving said stream and forming droplets containing said particles, said droplets comprising first droplets each containing one or more X sperm cells, second droplets each containing one or more Y sperm cells, and third plurality of droplets each containing one or more X sperms cells and one or more Y sperm cells, (2) sorting said first droplets from said second and third droplets, (3) collecting said first droplets to provide at least one population of X sperm cells, and (4) identifying a quantity of X sperm cells in the at least one population; and
 a control responsive to instructions received from the flow cytometer apparatus for varying the rate at which the fluid is delivered to the flow cytometer apparatus as a function of the quantity of identified X sperm cells in said at least one population relative to the total number of X cells in said first, second and third droplets.

N2. The system of N1 wherein said flow cytometry apparatus is operable to identify the number of X cells collected in said at least one population, and wherein the control varies the rate at which fluid is delivered to the flow cytometer apparatus to maintain the quantity of X cells collected in said at least one population at or above an acceptable quantity relative to the total number of X cells in said first, second and third droplets.

N3. The system of N2 wherein said acceptable quantity is at least 60% of said total number of X cells.

N4. The system of N3 wherein said X cells are live X cells.

N5. The system of N2 wherein the control is operable to increase the rate of fluid delivery when the quantity of X cells in said at least one population is above said acceptable quantity and to decrease the rate of fluid delivery when the quantity of X cells in said at least one population is below said acceptable quantity.

O. Sperm Sorting Method Including High-Purity Sort Strategy

O1. A method of sorting X and Y sperm cells, said method comprising:

delivering a fluid stream containing X and Y sperm cells to a first location and causing said stream to break into droplets at a second location, said droplets comprising first droplets each containing one or more X sperm cells, second droplets each containing one or more Y sperm cells, and third plurality of droplets each containing one or more X sperms cells and one or more Y sperm cells;

sorting said first droplets from said second and third droplets;

collecting said first droplets to provide at least one population of X sperm cells;

identifying a quantity of X sperm cells collected in said at least one population; and varying the rate at which fluid is delivered to said first location as a function of the quantity of identified X sperm cells collected in said at least one population relative to the total number of X cells in said first, second and third droplets.

O2. The method of O1 further comprising varying the rate at which fluid is delivered to said first location to maintain the quantity of X cells collected in said at least one population at or above an acceptable quantity relative to the total number of X cells in said first, second and third droplets.

O3. The method of O2 wherein said acceptable quantity is at least 60% of said total number of X cells.

O4. The method of O3 wherein said X cells are live X cells.

O5. The method of O1 further comprising increasing the rate of fluid delivery when the quantity or percentage of X cells collected in said at least one population is above said acceptable quantity and decreasing the rate of fluid delivery when the quantity or percentage of X cells collected in said at least one population is below said acceptable quantity.

P. Sperm Sorter for High-Recovery Sort Strategy

P1. System for sorting X and Y sperm cells, said system comprising:

a variable rate fluid delivery system for delivering a fluid stream containing X and Y sperm cells;

a flow cytometer apparatus for (1) receiving said stream and forming droplets containing said particles, said droplets comprising first droplets each containing one or more X sperm cells, second droplets each containing one or more Y sperm cells, and third plurality of droplets each containing one or more X sperms cells and one or more Y sperm cells, (2) sorting said first and third droplets from said second droplets, (3) collecting said first and third droplets to provide at least one population of X sperm cells, and (4) identifying a quantity of Y sperm cells in the at least one population; and a control responsive to instructions received from the flow cytometer apparatus for varying the rate at which the fluid is delivered to the flow cytometer apparatus as a function of the quantity of identified Y sperm cells in said at least one population.

P2. The system of P1 wherein said control varies the rate at which fluid is delivered to the flow cytometer system to maintain the purity of said at least one population at or above a desired purity.

P3. The system of P2 wherein said control is operable to increase the fluid delivery rate when the purity of said at least one population is greater than said desired purity and to decrease the fluid delivery rate when the purity is less than said desired purity.

P4. The system of P2 wherein said desired purity is no greater than 95%.

P5. The system of P2 wherein said X sperm cells are live cells.

Q. Sperm Sorting Method Including High-Recovery Sort Strategy

Q1. A method of sorting X and Y sperm cells, said method comprising:

delivering a fluid stream containing X and Y sperm cells to a first location and causing said stream to break into droplets at a second location, said droplets comprising first droplets each containing one or more X sperm cells, second droplets each containing one or more Y sperm cells, and third plurality of droplets each containing one or more X sperms cells and one or more Y sperm cells;

sorting said first and third droplets from said second droplets;

collecting said first and third droplets to provide at least one population of X sperm cells;

identifying a quantity of Y sperm cells collected in said at least one population; and varying the rate at which fluid is delivered to said first location as a function of the quantity of identified Y sperm cells collected in said at least one population.

Q2. The method of Q1 further comprising varying the rate at which fluid is delivered to maintain the purity of said at least one population with respect to X cells at or above a desired purity.

Q3. The method of Q2 further comprising increasing the fluid delivery rate when the purity of said at least one population is greater than said desired purity and decreasing the fluid delivery rate when the purity is less than said desired purity.

Q4. The method of Q2 wherein said desired purity is no greater than 95%.

Q5. The method of Q2 wherein said X sperm cells are live cells.

Q6. A method of sorting X and Y sperm cells using flow cytometry, said method comprising:

delivering a fluid stream containing X and Y sperm cells to a first location and causing said stream to break into droplets at a second location, said droplets comprising first droplets each containing one or more X sperm cells, second droplets each containing one or more Y sperm cells, and third plurality of droplets each containing one or more X sperms cells and one or more Y sperm cells;

sorting said first and third droplets from said second droplets; and collecting said first and third droplets to provide at least one population of X sperm cells.

Q7. The method of Q6 wherein said X sperm cells are live cells and not dead X cells.

Q8. A method of sorting X and Y sperm cells using flow cytometry, said method comprising:

delivering a fluid stream containing X and Y sperm cells and causing said stream to break into droplets;

interrogating the fluid stream before it breaks into droplets to identify which sperm cells will reside in which droplets;

sorting droplets containing X sperm cells from droplets not containing X sperm cells; and collecting said droplets containing X sperm cells, including droplets containing at least one X sperm cell and at least one Y sperm cell.

Q9. The method of Q8 wherein said X sperm cells are live X cells and not dead X cells.

R. Photodamage Sorting Having Sort Strategy

R1. In a flow cytometry system for sorting a mixture of particles including particles having a characteristic A and particles having a characteristic B, said system comprising a fluid delivery system for delivering a fluid containing said particles, a flow cytometry apparatus for receiving said fluid, forming it into a stream and using flow cytometry to classify the particles according to said characteristics, and a sorting system comprising a laser for ablating selected particles in the stream according to said classification and according to a sorting strategy to provide at least one population containing desired particles, the improvement comprising:

a control responsive to information received from the flow cytometry apparatus for controlling the laser to vary its sorting strategy or for controlling the fluid delivery to vary the rate at which fluid is delivered as a function of at least one of the following: (1) the purity of said at least one population with respect to either characteristic A particles or characteristic B particles; and (2) the quantity of unablated characteristic A particles or unablated characteristic B particles in said at least one population relative to the total quantity of characteristic A particles or characteristic B particles in said stream.

R2. The system of R1 wherein the particles are cells, and wherein characteristics A and B relate to physical characteristics of the cells.

R3. The system of R1 wherein said cells are sperm cells, and wherein characteristic A is indicative of a live X sperm cell.

R4. The system of R3 wherein characteristic B is indicative of other than a live X cell (~X).

R5. The system of R1 wherein the control increases the rate of fluid delivery when the purity of said at least one population is greater than a desired purity and decreases the rate of fluid delivery when the purity is less than the desired purity.

R6. The system of R1 wherein the control determines said purity based on output signals from the flow cytometry apparatus, said system further comprising an operator input to the control for indicating a desired purity, and wherein the control varies the rate of fluid delivery to obtain the desired purity.

R7. The system of R1 wherein said stream is formed into a stream containing particles following generally one after another in a series which comprises sequential sets of particles, including first particle sets each comprising one or more particles having characteristic A, second particle sets each comprising one or more particles having characteristic B, and third particle sets each comprising two or more closely spaced particles at least one of which has characteristic A and at least one of which has characteristic B.

R8. The system of R7 wherein said laser ablates only the second particle sets.

R9. The system of R8 wherein said control maintains the purity of said at least one population at more than 85% but less than 95%.

R10. The system of R7 wherein characteristic B is indicative of other than a live X cell (~X) and said laser is operable to ablate the second particle sets and the third particle sets in the stream.

R11. The system of R10 wherein the control increases the rate of fluid delivery when the quantity of unablated characteristic A particles in said at least one population is greater than an acceptable quantity of unablated characteristic A particles in the at least one population, and wherein the control decreases the rate of fluid delivery when the quantity of unablated characteristic A particles in said at least one population is less than said acceptable quantity.

R12. The system of R10 wherein the control determines the quantity of unablated characteristic A particles in said at least one population based on output signals from the flow cytometry apparatus, said system further comprising an operator input to the control for indicating an acceptable quantity of unablated characteristic A particles in said at least one population, and wherein the control varies the fluid delivery rate to obtain the acceptable quantity of unablated characteristic A particles in said at least one population.

S. Photodamage Sorting Method Including Sort Strategy

S1. A method of using a flow cytometry system to sort a mixture of particles including particles having a characteristic A and particles having a characteristic B, said method comprising:

delivering a fluid containing said particles;

forming the fluid into a stream and using flow cytometry to classify the particles in the stream according to said characteristics;

sorting the particles in the stream by ablating selected particles according to said classification and according to a sorting strategy thereby to provide at least one population containing desired particles; and varying the sorting strategy or varying the rate at which fluid is delivered as a function of at least one of the following: (1) the purity of said at least one population with respect to either characteristic A particles or characteristic B particles; and (2) the quantity of unablated characteristic A particles or unablated characteristic B particles in said at least one population relative to the total quantity of characteristic A particles or characteristic B particles in said stream.

S2. The method of S1 wherein the particles are cells, and wherein characteristics A and B relate to physical characteristics of the cells.

S3. The method of S1 wherein said cells are sperm cells, and wherein characteristic A is indicative of a live X sperm cell.

S4. The method of S1 further comprising increasing the rate of fluid delivery when the purity of said at least one population is greater than a desired purity and decreasing the rate of fluid delivery when the purity is less than the desired purity.

S5. The method of S1 further comprising forming said fluid into a stream containing particles following generally one after another in a series which comprises sequential sets of particles, including first particle sets each comprising one or more particles having characteristic A, second particle sets each comprising one or more particles having characteristic B, and third particle sets each comprising two or more closely spaced particles at least one of which has characteristic A and at least one of which has characteristic B.

S6. The method of S5 further comprising ablating the second particles sets and not the first and third particle sets.

S7. The method of S6 further comprising maintaining the purity of said at least one population at more than 85% but less than 95%.

S8. The method of S5 further comprising ablating the second and third particle sets and not the first particle sets.

S9. The method of S8 further comprising increasing the rate of fluid delivery when the quantity of unablated characteristic A particles in said at least one population is greater than an acceptable quantity of unablated characteristic A particles in the at least one population, and decreasing the rate of fluid delivery when the quantity of unablated characteristic A particles in said at least one population is less than said acceptable quantity.

T. Photodamage Sorter Having Variable Flow Rate and Feedback

T1. In a flow cytometry system for sorting a mixture of particles including particles having a characteristic A and particles having a characteristic B, said system comprising a variable rate fluid delivery system for delivering a fluid containing said particles, a flow cytometry apparatus for receiving said fluid, forming it into a stream and using flow cytometry to classify the particles according to said characteristics, and a sorting system comprising a laser for ablating selected particles in the stream according to said classification and according to a sorting strategy to provide at least one population containing desired particles, the improvement comprising:

a control responsive to information received from the flow cytometry apparatus for controlling the laser to vary the rate at which fluid is delivered as a function of at least one of the following: (1) the purity of said at least one population with respect to either characteristic A particles or characteristic B particles; and (2) the quantity of unablated characteristic A particles or unablated characteristic B particles in said at least one population relative to the total quantity of characteristic A particles or characteristic B particles in said stream.

T2. The system of T1 wherein the particles are cells and characteristics A and B relate to physical characteristics of the cells.

T3. The system of T2 wherein said cells are sperm cells and characteristic A is indicative of a live X sperm cell.

T4. The system of T3 wherein characteristic B is indicative of other than a live X cell (~X) and said laser ablates only the second particle sets.

T5. The system of T4 further comprising maintaining the purity of said at least one population at more than 85% but less than 95%.

T6. The system of T2 wherein characteristic B is indicative of other than a live X cell (~X), and wherein said laser ablates the second and third particles sets.

T7. The system of T1 wherein the control increases the rate of fluid delivery when the purity of the at least one population is greater than the desired purity and decreases the rate of fluid delivery when the purity is less than the desired purity.

T8. The system of T1 wherein the control determines a purity of the at least one population based on output signals from the flow cytometry apparatus, said system further comprising an operator input to the control for indicating a desired purity, and wherein the control varies the rate of fluid delivery to obtain the desired purity.

T9. The system of T8 wherein the control increases the rate of fluid delivery when the quantity of characteristic A particles in said at least one population is greater than an acceptable quantity of characteristic A particles in said at least one population, and wherein the control decreases the rate of fluid delivery when the quantity of characteristic A particles in the at least one population is less than an acceptable quantity of characteristic A particles in the at least one population.

T10. The system of T8 wherein the control determines the total number of characteristic A particles in said at least one population based on output signals from the flow cytometry apparatus, said system further comprising an operator input to the control for indicating an acceptable quantity of characteristic A particles in the at least one population, and wherein the control varies the rate so that the quantity of characteristic A particles in the at least one population to obtain said acceptable quantity or percentage.

T11. The system of T1 wherein said stream is formed into a stream containing particles following generally one after another in a series which comprises sequential sets of particles, including first particle sets each comprising one or more particles having characteristic A, second particle sets each comprising one or more particles having characteristic B, and third particle sets each comprising two or more closely spaced particles at least one of which has characteristic A and at least one of which has characteristic B.

T12. The system of T11 wherein characteristic A is indicative of a live X sperm cell (X), wherein characteristic B is indicative of other than a live X cell (~X), wherein the laser ablates the second particles sets and third particle sets and not the first particle set, and wherein the control varies the rate at which the fluid is delivered to the flow cytometer apparatus as a function of the number of live X sperm cells in the at least one population.

T13. The system of T11 wherein characteristic A is indicative of a live X sperm cell (X), wherein characteristic B is indicative of other than a live X cell (~X), wherein the laser ablates the second particle sets and not the first and third particle sets, and wherein the control varies the rate at which the fluid is delivered to the flow cytometer system as a function of the number of ~X sperm cells in said at least one population.

U. Photodamage Sorting Method Including Variable Flow Rate Sort Strategy

U1. A method of using a flow cytometry system to sort a mixture of particles including particles having a characteristic A and particles having a characteristic B, said method comprising:

delivering a fluid containing said particles;

forming the fluid into a stream and using flow cytometry to classify the particles in the stream according to said characteristics;

sorting the particles in the stream by ablating selected particles according to said classification and according to a sorting strategy thereby to provide at least one population containing desired particles; and varying the rate at which fluid is delivered as a function of at least one of the following: (1) the purity of said at least one population with respect to either characteristic A particles or characteristic B particles; and (2) the quantity of unablated characteristic A particles or unablated characteristic B particles in said at least one population relative to the total quantity of characteristic A particles or characteristic B particles in said stream.

U2. The method of U1 wherein the particles are cells and characteristics A and B relate to physical characteristics of the cells.

U3. The method of U2 wherein said cells are sperm cells and characteristic A is indicative of a live X sperm cell.

U4. The method of U3 wherein characteristic B is indicative of other than a live X cell (~X) and said laser ablates only the second particle sets.

U5. The method of U4 further comprising maintaining the purity of said at least one population at more than 85% but less than 95%.

U6. The method of U2 wherein characteristic B is indicative of other than a live X cell (~X), and wherein said laser ablates the second and third particles sets.

U7. The method of U1 wherein the control increases the rate of fluid delivery when the purity of the at least one population is greater than the desired purity and decreases the rate of fluid delivery when the purity is less than the desired purity.

U8. The system of U1 wherein the control determines a purity of the at least one population based on output signals from the flow cytometry apparatus, said system further comprising an operator input to the control for indicating a desired purity, and wherein the control varies the rate of fluid delivery to obtain the desired purity.

U9. The system of U8 wherein the control increases the rate of fluid delivery when the quantity of characteristic A particles in said at least one population is greater than an acceptable quantity of characteristic A particles in said at least one population, and wherein the control decreases the rate of fluid delivery when the quantity of characteristic A particles in the at least one population is less than an acceptable quantity of characteristic A particles in the at least one population.

U10. The system of U8 wherein the control determines the total number of characteristic A particles in said at least one population based on output signals from the flow cytometry apparatus, said system further comprising an operator input to the control for indicating an acceptable quantity of characteristic A particles in the at least one population, and wherein the control varies the rate so that the quantity of characteristic A particles in the at least one population to obtain said acceptable quantity or percentage.

U11. The system of U1 wherein said stream is formed into a stream containing particles following generally one after another in a series which comprises sequential sets of particles, including first particle sets each comprising one or more particles having characteristic A, second particle sets each comprising one or more particles having characteristic B, and third particle sets each comprising two or more closely spaced particles at least one of which has characteristic A and at least one of which has characteristic B.

U12. The system of U11 wherein characteristic A is indicative of a live X sperm cell (X), wherein characteristic B is indicative of other than a live X cell (~X), wherein the laser ablates the second particles sets and third particle sets and not the first particle set, and wherein the control varies the rate at which the fluid is delivered to the flow cytometer apparatus as a function of the number of live X sperm cells in the at least one population.

U13. The system of U11 wherein characteristic A is indicative of a live X sperm cell (X), wherein characteristic B is indicative of other than a live X cell (~X), wherein the laser ablates the second particle sets and not the first and third particle sets, and wherein the control varies the rate at which the fluid is delivered to the flow cytometer system as a function of the number of ~X sperm cells in said at least one population.

V. Fluid Switching Particle Sorter Including Sort Strategy

V1. In a flow cytometry system for sorting a mixture of particles including particles having a characteristic A and particles having a characteristic B, said system comprising a fluid delivery system for delivering a fluid containing said particles, a flow cytometry apparatus for receiving said fluid, forming it into a stream and using flow cytometry to classify the particles according to said characteristics, and a fluid switching sorting system for sorting selected particles in the stream according to said classification and according to a sorting strategy to provide at least one population containing desired particles, the improvement comprising:

a control responsive to information received from the flow cytometry apparatus for controlling the fluid switching sorting system to vary its sorting strategy or for controlling the fluid delivery system to vary the rate at which fluid is delivered as a function of at least one of the following: (1) the purity of said at least one population with respect to either characteristic A particles or characteristic B particles; and (2) the quantity of characteristic A particles or characteristic B particles in said at least one population relative to the total quantity of characteristic A particles or characteristic B particles in said stream.

V2. The system of V1 wherein the particles are cells, and wherein characteristics A and B relate to physical characteristics of the cells.

V3. The system of V1 wherein said cells are sperm cells, and wherein characteristic A is indicative of a live X sperm cell.

V4. The system of V3 wherein characteristic B is indicative of other than a live X cell (~X).

V5. The system of V1 wherein the control increases the rate of fluid delivery when the purity of said at least one population is greater than a desired purity and decreases the rate of fluid delivery when the purity is less than the desired purity.

V6. The system of V1 wherein the control determines said purity based on output signals from the flow cytometry apparatus, said system further comprising an operator input to the control for indicating a desired purity, and wherein the control varies the rate of fluid delivery to obtain the desired purity.

V7. The system of V1 wherein said stream is formed into a stream containing particles following generally one after another in a series which comprises sequential sets of particles, including first particle sets each comprising one or more particles having characteristic A, second particle sets each comprising one or more particles having characteristic B, and third particle sets each comprising two or more closely spaced particles at least one of which has characteristic A and at least one of which has characteristic B.

V8. The system of V7 wherein said laser ablates only the second particle sets.

V9. The system of V8 wherein said control maintains the purity of said at least one population at more than 85% but less than 95%.

V10. The system of V7 wherein characteristic B is indicative of other than a live X cell (~X) and said laser is operable to ablate the second particle sets and the third particle sets in the stream.

V11. The system of V10 wherein the control increases the rate of fluid delivery when the quantity of unablated characteristic A particles in said at least one population is greater than an acceptable quantity of unablated characteristic A particles in the at least one population, and wherein the control decreases the rate of fluid delivery when the quantity of unablated characteristic A particles in said at least one population is less than said acceptable quantity.

V12. The system of V10 wherein the control determines the quantity of unablated characteristic A particles in said at least one population based on output signals from the flow cytometry apparatus, said system further comprising an operator input to the control for indicating an acceptable quantity of unablated characteristic A particles in said at least one population, and wherein the control varies the fluid delivery rate to obtain the acceptable quantity of unablated characteristic A particles in said at least one population.

W. Method of Fluid Switching Sorting Including Sort Strategy

W1. A method of using a flow cytometry system to sort a mixture of particles including particles having a characteristic A and particles having a characteristic B, said method comprising:

delivering a fluid containing said particles;

forming the fluid into a stream and using flow cytometry to classify the particles in the stream according to said characteristics;

sorting the particles in the stream by diverting selected particles in the stream according to said classification and according to a sorting strategy thereby to provide at least one population containing desired particles; and varying the sorting strategy or varying the rate at which fluid is delivered as a function of at least one of the following: (1) the purity of said at least one population with respect to either characteristic A particles or characteristic B particles; and (2) the quantity of characteristic A particles or characteristic B particles in said at least one population relative to the total quantity of characteristic A particles or characteristic B particles in said stream.

W2. The method of W1 wherein the particles are cells, and wherein characteristics A and B relate to physical characteristics of the cells.

W3. The method of W1 wherein said cells are sperm cells, and wherein characteristic A is indicative of a live X sperm cell.

W4. The method of W1 further comprising increasing the rate of fluid delivery when the purity of said at least one population is greater than a desired purity and decreasing the rate of fluid delivery when the purity is less than the desired purity.

W5. The method of W1 further comprising forming said fluid into a stream containing particles following generally one after another in a series which comprises sequential sets of particles, including first particle sets each comprising one or more particles having characteristic A, second particle sets each comprising one or more particles having characteristic B, and third particle sets each comprising two or more closely spaced particles at least one of which has characteristic A and at least one of which has characteristic B.

W6. The method of W5 further comprising ablating the second particles sets and not the first and third particle sets.

W7. The method of W6 further comprising maintaining the purity of said at least one population at more than 85% but less than 95%.

W8. The method of W5 further comprising ablating the second and third particle sets and not the first particle sets.

W9. The method of W8 further comprising increasing the rate of fluid delivery when the quantity of unablated characteristic A particles in said at least one population is greater than an acceptable quantity of unablated characteristic A particles in the at least one population, and decreasing the rate of fluid delivery when the quantity of unablated characteristic A particles in said at least one population is less than said acceptable quantity.

X. Fluid Switching Sorter Including Variable Flow Rate Sort Strategy

X1. In a flow cytometry system for sorting a mixture of particles including particles having a characteristic A and particles having a characteristic B, said system comprising a fluid delivery system for delivering a fluid containing said particles, a flow cytometry apparatus for receiving said fluid, forming it into a stream and using flow cytometry to classify the particles according to said characteristics, and a fluid switching sorting system for sorting selected particles in the stream according to said classification to provide at least one population containing desired particles, the improvement comprising:
a control responsive to information received from the flow cytometry apparatus for controlling the fluid delivery system to vary the rate at which fluid is delivered as a function of at least one of the following: (1) the purity of said at least one population with respect to either characteristic A particles or characteristic B particles; and (2) the quantity of characteristic A particles or characteristic B particles in said at least one population relative to the total quantity of characteristic A particles or characteristic B particles in said stream.

X2. The system of X1 wherein the particles are cells, and wherein characteristics A and B relate to physical characteristics of the cells.

X3. The system of X1 wherein said cells are sperm cells, and wherein characteristic A is indicative of a live X sperm cell.

X4. The system of X3 wherein characteristic B is indicative of other than a live X cell (~X).

X5. The system of X1 wherein the control increases the rate of fluid delivery when the purity of said at least one population is greater than a desired purity and decreases the rate of fluid delivery when the purity is less than the desired purity.

X6. The system of X1 wherein the control determines said purity based on output signals from the flow cytometry apparatus, said system further comprising an operator input to the control for indicating a desired purity, and wherein the control varies the rate of fluid delivery to obtain the desired purity.

X7. The system of X1 wherein said stream is formed into a stream containing particles following generally one after another in a series which comprises sequential sets of particles, including first particle sets each comprising one or more particles having characteristic A, second particle sets each comprising one or more particles having characteristic B, and third particle sets each comprising two or more closely spaced particles at least one of which has characteristic A and at least one of which has characteristic B.

X8. The system of X7 wherein said laser ablates only the second particle sets.

X9. The system of X8 wherein said control maintains the purity of said at least one population at more than 85% but less than 95%.

X10. The system of X7 wherein characteristic B is indicative of other than a live X cell (~X) and said laser is operable to ablate the second particle set and the third particle sets in the stream.

X11. The system of X10 wherein the control increases the rate of fluid delivery when the quantity of unablated characteristic A particles in said at least one population is greater than an acceptable quantity of unablated characteristic A particles in the at least one population, and wherein the control decreases the rate of fluid delivery when the quantity of unablated characteristic A particles in said at least one population is less than said acceptable quantity.

X12. The system of X10 wherein the control determines the quantity of unablated characteristic A particles in said at least one population based on output signals from the flow cytometry apparatus, said system further comprising an operator input to the control for indicating an acceptable quantity of unablated characteristic A particles in said at least one population, and wherein the control varies the fluid delivery rate to obtain the acceptable quantity of unablated characteristic A particles in said at least one population.

Y. Fluid Switching Sorting Method Including Variable Flow Rate and Feedback

Y1. A method of using a flow cytometry system to sort a mixture of particles including particles having a characteristic A and particles having a characteristic B, said method comprising:
delivering a fluid containing said particles;
forming the fluid into a stream and using flow cytometry to classify the particles in the stream according to said characteristics;
sorting the particles in the stream by diverting selected particles in the stream according to said classification thereby to provide at least one population containing desired particles; and
varying the rate at which fluid is delivered as a function of at least one of the following: (1) the purity of said at least one population with respect to either characteristic A particles or characteristic B particles; and (2) the quantity of characteristic A particles or characteristic B particles in said at least one population relative to the total quantity of characteristic A particles or characteristic B particles in said stream.

Y2. The method of Y1 wherein the particles are cells, and wherein characteristics A and B relate to physical characteristics of the cells.

Y3. The method of Y1 wherein said cells are sperm cells, and wherein characteristic A is indicative of a live X sperm cell.

Y4. The method of Y1 further comprising increasing the rate of fluid delivery when the purity of said at least one population is greater than a desired purity and decreasing the rate of fluid delivery when the purity is less than the desired purity.

Y5. The method of Y1 further comprising forming said fluid into a stream containing particles following generally one after another in a series which comprises sequential sets of particles, including first particle sets each comprising one or more particles having characteristic A, second particle sets each comprising one or more particles having characteristic B, and third particle sets each comprising two or more closely spaced particles at least one of which has characteristic A and at least one of which has characteristic B.

Y6. The method of Y5 further comprising ablating the second particles sets and not the first and third particle sets.

Y7. The method of Y6 further comprising maintaining the purity of said at least one population at more than 85% but less than 95%.

Y8. The method of Y5 further comprising ablating the second and third particle sets and not the first particle sets.

Y9. The method of Y8 further comprising increasing the rate of fluid delivery when the quantity of unablated characteristic A particles in said at least one population is greater than an acceptable quantity of unablated characteristic A particles in the at least one population, and decreasing the rate of fluid delivery when the quantity of unablated characteristic A particles in said at least one population is less than said acceptable quantity.

Z. [Reserved]

AA. A/D Converter for PMT Output Signals and DSP Analyzing and Classifying

AA1. In a flow cytometry system for sorting a mixture of particles including particles having a characteristic A and particles having a characteristic B, said system comprising a fluid delivery system for delivering a fluid containing said particles, a flow cytometry apparatus for receiving said fluid, forming it into a stream and using flow cytometry to classify the particles according to said characteristics, and a sorting system for sorting the particles according to said classification and according to a sorting strategy to provide at least one population containing desired particles, the improvement comprising:

an analog to digital converter synchronously sampling a time-varying analog output from said flow cytometry apparatus and providing an output including digital information corresponding to said time-varying analog output wherein said time-varying analog output and the corresponding digital information are indicative of characteristic A or characteristic B;

a digital signal processor analyzing and classifying the digital information and providing a sorting signal to said sorting system as a function of the analyzed and classified digital information.

AA1A. The system of AA1 wherein the time-varying analog output comprises a series of waveform pulses, each of which is representative of characteristic of a particle, wherein the digital signal processor detects portions of the digital information corresponding to the waveform pulses and classifies said detected portions, and wherein the digital signal processor provides said sorting signal as a function of said detected and classified portions.

AA1B. The system of AA1 further comprising a control responsive to information received from the flow cytometry apparatus for controlling the sorting system to vary its sorting strategy or for controlling the fluid delivery system to vary the rate at which fluid is delivered as a function of at least one of the following: (1) the purity of said at least one population with respect to either characteristic A particles or characteristic B particles; and (2) the quantity of characteristic A particles or characteristic B particles in said at least one population relative to the total quantity of characteristic A particles or characteristic B particles in said stream.

AA2. The system of AA1B wherein the particles are cells and characteristics A and B relate to physical characteristics of the cells.

AA3. The system of AA1B wherein the particles are sperm cells, and wherein characteristic A is indicative of a live X sperm cell.

AA4. The system of AA3 wherein characteristic B is indicative of other than a live X cell (~X).

AA5. The system of AA4 further comprising maintaining the purity of said at least one population at more than 85% but less than 95%.

AA6. The system of AA1 wherein the control increases the rate of fluid delivery when said purity is greater than a desired purity and decreases the rate of fluid delivery when said purity is less than said desired purity.

AA7. The system of AA1 wherein the control determines the purity of said at least one population based on output signals from the flow cytometry apparatus, said system further comprising an operator input to the control for indicating a desired purity, and wherein the control varies the rate of fluid delivery so that the purity corresponds to the desired purity.

AA8. The system of AA7 wherein the control increases the rate of fluid delivery when the quantity of characteristic A particles in said at least one population is greater than an acceptable quantity of characteristic A particles in the at least one population, and wherein the control decreases the rate of fluid delivery when the quantity of characteristic A particles in said at least one population is less than said acceptable quantity.

AA9. The system of AA8 wherein the control determines the quantity of characteristic A particles in said at least one population based on output signals from the flow cytometry apparatus, said system further comprising an operator input to the control for indicating an acceptable quantity of characteristic A particles in said at least one population, and wherein the control varies the fluid delivery rate to obtain said acceptable quantity in said at least one population.

AA10. The system of AA1 wherein said stream is formed to contain particles following generally one after another in a series which comprises sequential sets of particles, including first particle sets each comprising one or more particles having characteristic A, second particle sets each comprising one or more particles having characteristic B, and third particle sets each comprising two or more closely spaced particles at least one of which has characteristic A and at least one of which has characteristic B.

AA11. The system of AA10 wherein said sorting system is operable to use a sorting strategy in which said first particle sets are selected for collection in said at least one population and said second and third particle sets are not selected for collection in said at least one population.

AA12. The system of AA10 wherein said sorting system is operable to use a sorting strategy in which said first and third particle sets are selected for collection in said at least one population and said second particle set is not selected for collection in said at least one population.

AA13. The system of AA1 wherein said sorting system comprises a droplet sorting system.

AA14. The system of AA1 wherein said sorting system comprises a photo-damage sorting system.

AA15. The system of AA1 wherein said sorting system comprises a fluid-switching sorting system.

AA16. The system of AA1 wherein said digital signal processor includes instructions for detecting pulses corresponding to the digital information, instructions for extracting features in the detected pulses, and instructions for discriminating the detected pulses as a function of their extracted features.

AA17. The system of AA16 wherein said digital signal processor includes instructions for defining a decision boundary discriminating between the extracted features representing characteristics A and the extracted features representing characteristic B.

AA18. The system of AA17 wherein said digital signal processor adjusts the relative location of the decision boundary with respect to the extracted features representing characteristic A and with respect to the extracted features representing characteristic B as a function of at least one of the following: (1) the purity of said at least one population with respect to either characteristic A particles or characteristic B particles; and (2) the quantity of characteristic A particles or characteristic B particles in said at least one population relative to the total quantity of characteristic A particles or characteristic B particles in said stream.

AA19. The system of AA1 wherein said digital signal processor comprises a data management processor for assembling the digital information into a continuous stream.

AA20. The system of AA1 wherein said digital signal processor comprises a pulse detection processor for detecting waveform pulses represented by the digital information, and wherein said digital signal processor classifies the digital information as a function of the detected waveform pulses.

AA21. The system of AA20 further comprising a filter for filtering the analog output at a frequency equal to or less than one half the continuous sampling rate of the converter, wherein the converter converts the filtered analog output into corresponding digital information, and wherein said digital signal processor classifies the digital information as a function of a discrimination boundary.

AA22. The system of AA21 wherein the continuous sampling rate is about 105 MHz or higher.

AA23. The system of AA1 wherein said digital signal processor comprises a feature extraction and discrimination processor for defining a decision boundary discriminating between extracted features representing characteristics A and extracted features representing characteristic B, and wherein the feature extraction and discrimination processor extracts features represented by said digital information and classifies the features as a function of the decision boundary.

AA24. The system of AA1 wherein said digital signal processor comprises a sort processor responsive to the classifying for providing the sort signals to said sorting system.

AA25. The system of AA1 wherein the processor innumerates the number of classified particles having characteristic A or having characteristic B.

AA26. The system of AA1 wherein said digital signal processor classifies the digital information as a function of reducing a coefficient of variation of a population of the particles having characteristic A to be substantially equal to or less than a preset amount or as a function of minimizing a coefficient of variation of a population of the particles having characteristic B to be substantially equal to or less than a preset amount.

AA27. The system of AA26 wherein the preset amount is about 1.5% or less.

AA27a. The system of AA26 wherein the preset amount is about 1.3% or less.

AA28. The system of AA1 wherein said digital signal processor classifies the digital information such that a population of the particles having characteristic A and a population of the particles having characteristic B correspond to a computer model of three populations including a first model population of particles having characteristic A, a second model population of particles having characteristic B and a third model population of unaligned particles, said model estimating population statistics for each of the first, second and third model populations.

AA29. The system of AA28 wherein the third model population comprises two populations of unaligned particles, and wherein the model estimates the population statistics for the two populations.

AA30. The system of AA1 wherein said digital signal processor comprises a pulse detection processor for detecting waveform pulses represented by the digital information, and wherein said digital signal processor classifies the digital information as a function of a coefficient of variation of a population of the particles having characteristic A or as a function of a coefficient of variation of a population of the particles having characteristic B.

AA30a. The system of AA30 further comprising a filter for filtering the analog output at a frequency equal to or less than one half the continuous sampling rate of the converter, wherein the converter converts the filtered analog output into corresponding digital information, and wherein said digital signal processor classifies the digital information as a function of a coefficient of variation of a population of the particles having characteristic A or as a function of a coefficient of variation of a population of the particles having characteristic B.

AA30b. The system of AA1 wherein said digital signal processor comprises a feature extraction and discrimination processor for defining a decision boundary discriminating between extracted features representing characteristics A and extracted features representing characteristic B, and wherein the feature extraction and discrimination processor extracts features represented by said digital information and classifies the features as a function of a coefficient of variation of a population of the particles having characteristic A or as a function of a coefficient of variation of a population of the particles having characteristic B.

AA31. A method of using a flow cytometry system to sort a mixture of particles including particles having a characteristic A and particles having a characteristic B, said method comprising:

delivering a fluid containing said particles;

forming the fluid into a stream and using flow cytometry to detect the particles in the stream according to said characteristics;

sorting the particles in the stream and according to a sorting strategy thereby to provide at least one population containing desired particles;

converting an analog output from said flow cytometry into corresponding digital information wherein the analog output is indicative of characteristic A or characteristic B; and analyzing and classifying the digital information and sorting the particles as a function of the analyzed and classified digital information.

AA31A. The method of AA31 further comprising varying the sorting strategy or varying the rate at which fluid is delivered as a function of at least one of the following: (1) the purity of said at least one population with respect to either characteristic A particles or characteristic B particles; and (2) the quantity of characteristic A particles or characteristic B particles in said at least one population relative to the total quantity of characteristic A particles or characteristic B particles in said stream.

AA32. The method of AA31 wherein the particles are cells and characteristics A and B relate to physical characteristics of the cells.

AA33. The method of AA31 wherein the particles are sperm cells, and wherein characteristic A is indicative of a live X sperm cell.

AA34. The method of AA33 wherein characteristic B is indicative of other than a live X cell (~X).

AA35. The method of AA33 further comprising maintaining said purity at more than 85% but less than 95%.

AA36. The method of AA31 further comprising increasing the rate of fluid delivery when said purity is greater than a desired purity and decreasing the rate of fluid delivery when said purity is less than the desired purity.

AA37. The method of AA31 further comprising increasing the rate of fluid delivery when the quantity of characteristic A particles in said at least one population is greater than an acceptable quantity of characteristic A particles in the at least one population, and decreasing the rate of fluid delivery when the quantity of characteristic A particles in said at least one population is less than said acceptable quantity.

AA38. The method of AA31 further comprising forming the stream to contain particles following generally one after another in a series which comprises sequential sets of particles, including first particle sets each comprising one or more particles having characteristic A, second particle sets each comprising one or more particles having characteristic B, and third particle sets each comprising two or more closely spaced particles at least one of which has characteristic A and at least one of which has characteristic B.

AA39. The method of AA38 further comprising sorting said particles according to a sorting strategy in which only first particles sets are selected for collection in said at least one population.

AA40. The method of AA38 further comprising sorting said particles according to a sorting strategy in which first and third particle sets are selected for collection in said at least one population.

AA41. The method of AA31 wherein said sorting comprises using a droplet sorting process.

AA42. The method of AA31 wherein said sorting comprises using a photo-damage sorting process.

AA43. The method of AA31 wherein said sorting comprises using a fluid-switching sorting process.

AA44. The method of AA31 further comprising detecting waveform pulses represented by the digital information, extracting features of the waveform pulses from the digital information, and discriminating the detected waveform pulses as a function of their extracted features.

AA45. The method of AA44 further comprising defining a decision boundary discriminating between the extracted features representing characteristics A and the extracted features representing characteristic B.

AA46. The method of AA45 further comprising adjusting the relative location of the decision boundary with respect to the extracted features representing characteristic A and with respect to the extracted features representing characteristic B as a function of at least one of the following: (1) the purity of said at least one population with respect to either characteristic A particles or characteristic B particles; and (2) the quantity of characteristic A particles or characteristic B particles in said at least one population relative to the total quantity of characteristic A particles or characteristic B particles in said stream.

AA47. The method of AA31 wherein said converting comprises synchronously sampling the analog output.

AA48. The method of AA31 wherein classifying the digital information comprises classifying the digital information as a function of minimizing a coefficient of variation of a population of the particles having characteristic A to be substantially equal to or less than a preset amount or as a function of minimizing a coefficient of variation of a population of the particles having characteristic B to be substantially equal to or less than a preset amount.

AA49. The method of AA48 wherein the preset amount is about 1.5% or less.

AA50. The method of AA31 wherein classifying the digital information comprises classifying the digital information such that a population of the particles having characteristic A and a population of the particles having characteristic B correspond to a computer model of three populations including a first model population of particles having characteristic A, a second model population of particles having characteristic B and a third model population of unaligned particles, said model estimating population statistics for each of the first, second and third model populations.

AA51. The method of AA31 wherein classifying the digital information comprises classifying the digital information as a function of a coefficient of variation of a population of the particles having characteristic A or as a function of a coefficient of variation of a population of the particles having characteristic B.

BB. Determining Initial Detection Parameters

BB1. In a flow cytometry system for sorting a mixture of particles including particles having a characteristic A and particles having a characteristic B, said system comprising a fluid delivery system for delivering a fluid containing said particles, a flow cytometry apparatus for receiving said fluid, forming it into a stream and using flow cytometry to classify the particles according to said characteristics, and a sorting system for sorting the particles according to said classification and according to a sorting strategy to provide at least one population containing desired particles, the improvement comprising:

an analog to digital converter synchronously sampling a time-varying analog output from said flow cytometry apparatus and providing an output including digital information corresponding to said time-varying analog output wherein said time-varying analog output and the corresponding digital information are indicative of characteristic A or characteristic B;

a digital signal processor determining background characteristics of said time-varying analog output from said digital information;

detecting waveform pulses represented by said digital information as a function of said determined background characteristics; and providing a sorting signal to said sorting system as a function of the detected waveform pulses.

BB2. The system of claim BB1 wherein said digital signal processor employs an iterative procedure for determining a pulse detection threshold for defining the background characteristics, said iterative procedure including:

computing background statistic estimates from the digital information;

using the computed estimates to apply a pulse detection logic to said digital information in order to identify pulses indicative of characteristic A or characteristic B;

recomputing the estimates without using the digital information corresponding to the identified pulses; and repeating the above procedure until the background statistic estimates converge or a fixed maximum number of iterations occurs.

BB3. The system of BB1 wherein said digital signal processor includes instructions for detecting waveform pulses represented by the digital information, instructions for extracting features in the detected pulses and instructions for discriminating the detected pulses as a function of their extracted features.

BB4. The system of BB3 wherein said digital signal processor includes instructions for defining a decision boundary discriminating between the extracted features representing characteristics A and the extracted features representing characteristic B.

BB5. The system of BB4 wherein said digital signal processor adjusts the relative location of the decision boundary with respect to the extracted features representing characteristic A and with respect to the extracted features representing characteristic B as a function of at least one of the following: (1) the purity of said at least one population with respect to either characteristic A particles or characteristic B particles; and (2) the quantity of characteristic A particles or characteristic B particles in said at least one population relative to the total quantity of characteristic A particles or characteristic B particles in said stream.

BB6. The system of BB1 further comprising a control responsive to information received from the flow cytometry apparatus for controlling the sorting system to vary its sorting strategy or for controlling the fluid delivery system to vary the rate at which fluid is delivered as a function of at least one of the following: (1) the purity of said at least one population with respect to either characteristic A particles or characteristic B particles; and (2) the quantity of characteristic A particles or characteristic B particles in said at least one population relative to the total quantity of characteristic A particles or characteristic B particles in said stream.

BB7. The system of B1 wherein said digital signal processor comprises a pulse detection processor for detecting waveform pulses represented by the digital information, and wherein said digital signal processor classifies the digital information as a function of the detected waveform pulses.

BB8. The system of BB7 further comprising a filter for filtering the analog output at a frequency equal to or less than one half a sampling rate of the converter, and wherein the converter converts the filtered analog output into corresponding digital information.

CC. Generating Initial Discrimination Parameters

CC1. In a flow cytometry system for sorting a mixture of particles including particles having a characteristic A and particles having a characteristic B, said system comprising a fluid delivery system for delivering a fluid containing said particles, a flow cytometry apparatus for receiving said fluid, forming it into a stream and using flow cytometry to classify the particles according to said characteristics, and a sorting system for sorting the particles according to said classification and according to a sorting strategy to provide at least one population containing desired particles, the improvement comprising:

an analog to digital converter synchronously sampling a time-varying analog output from said flow cytometry apparatus and providing an output including digital information corresponding to said time-varying analog output wherein said time-varying analog output and the corresponding digital information are indicative of characteristic A or characteristic B; and a digital signal processor generating initial discrimination parameters from the digital information, discriminating the digital information as a function of the initial discrimination parameters, and providing a sorting signal to said sorting system as a function of the discriminated digital information.

CC2. The system of claim CC1 wherein the digital signal processor employs at least one of the following algorithms to generate the initial discrimination parameters: k-Means, Fuzzy k-Means and Agglomerative Hierarchical.

CC3. The system of CC1 wherein said digital signal processor includes instructions for detecting waveform pulses represented by the digital information, instructions for extracting features in the detected waveform pulses and instructions for discriminating the detected waveform pulses as a function of their extracted features.

CC4. The system of CC3 wherein said digital signal processor includes instructions for defining a decision boundary discriminating between the extracted features representing characteristics A and the extracted features representing characteristic B.

CC5. The system of CC4 wherein said digital signal processor adjusts the relative location of the decision boundary with respect to the extracted features representing characteristic A and with respect to the extracted features representing characteristic B as a function of at least one of the following: (1) the purity of said at least one population with respect to either characteristic A particles or characteristic B particles; and (2) the quantity of characteristic A particles or characteristic B particles in said at least one population relative to the total quantity of characteristic A particles or characteristic B particles in said stream.

CC6. The system of CC1 further comprising a control responsive to information received from the flow cytometry apparatus for controlling the sorting system to vary its sorting strategy or for controlling the fluid delivery system to vary the rate at which fluid is delivered as a function of at least one of the following: (1) the purity of said at least one population with respect to either characteristic A particles or characteristic B particles, and (2) the quantity of characteristic A particles or characteristic B particles in said at least one population relative to the total quantity of characteristic A particles or characteristic B particles in said stream.

DD. Synchronously Sampling Waveform Pulses to Classify

DD1. In a flow cytometry system for sorting a mixture of particles including particles having a characteristic A and particles having a characteristic B, said system comprising:

a fluid delivery system for delivering a fluid containing said particles, and a flow cytometry apparatus for receiving said fluid, forming it into a stream and using flow cytometry to classify the particles according to said characteristics;

an analog to digital converter synchronously sampling a time-varying analog output comprising a series of waveform pulses from said flow cytometry apparatus and providing an output including digital information corresponding to said waveform pulses wherein said waveform pulses and the corresponding digital information are indicative of characteristic A or characteristic B; and a digital signal processor analyzing the digital information and classifying the particle as a function of the analyzed digital information corresponding thereto.

DD2. The system of claim DD1 wherein said digital processor employs a detection threshold for defining the waveform the pulses, and wherein said detection threshold is a function of a background mean estimate and a standard deviation of the digital information computed within a moving window of samples ending with the current sample.

DD3. The system of claim DD1 wherein the digital control employs a statistical anomaly detection analysis, and wherein the digital information statistically anomalous from background characteristics of the digital information is considered part of a digital pulse.

DD4. The system of DD1 wherein said digital signal processor includes instructions for detecting pulses corresponding to the digital information, instructions for extracting features in the detected pulses and instructions for discriminating the detected pulses as a function of their extracted features.

DD5. The system of DD4 wherein said digital signal processor includes instructions for defining a decision boundary discriminating between the extracted features representing characteristics A and the extracted features representing characteristic B.

DD6. The system of DD5 wherein said digital signal processor adjusts the relative location of the decision boundary with respect to the extracted features representing characteristic A and with respect to the extracted features representing characteristic B as a function of at least one of the following: (1) the purity of at least one population with respect to either characteristic A particles or characteristic B particles; and (2) the quantity of characteristic A particles or characteristic B particles in at least one population relative to the total quantity of characteristic A particles or characteristic B particles in said stream.

DD7. The system of DD1 further comprising a filter for filtering the analog output at a frequency equal to or less than one half a sampling rate of the converter, and wherein the converter converts the filtered analog output into corresponding digital information.

DD8. The system of DD1 further comprising a control responsive to information received from the flow cytometry apparatus for controlling the sorting system to vary its sorting strategy or for controlling the fluid delivery system to vary the rate at which fluid is delivered as a function of at least one of the following: (1) the purity of at least one population with respect to either characteristic A particles or characteristic B particles; and (2) the quantity of characteristic A particles or characteristic B particles in at least one population relative to the total quantity of characteristic A particles or characteristic B particles in said stream.

DD9. The system of DD1 wherein the processor innumerates the number of classified particles having characteristic A or having characteristic B.

DD10. The system of DD1 further comprising a pulsed illumination device in synchronization with synchronous sampling for illuminating the particles to produce the corresponding waveform pulses.

DD11. The system of DD10 wherein said digital signal processor comprises a pulse detection processor for detecting waveform pulses represented by the digital information, and wherein said digital signal processor classifies the digital information as a function of a coefficient of variation of a population of the particles having characteristic A or as a function of a coefficient of variation of a population of the particles having characteristic B.

EE. Feature Extraction

EE1. In a flow cytometry system for sorting a mixture of particles including particles having a characteristic A and particles having a characteristic B, said system comprising a fluid delivery system for delivering a fluid containing said particles, a flow cytometry apparatus for receiving said fluid, forming it into a stream and using flow cytometry to classify the particles according to said characteristics, and a sorting system for sorting the particles according to said classification and according to a sorting strategy to provide at least one population containing desired particles, the improvement comprising:

an analog to digital converter synchronously sampling a time-varying analog output from said flow cytometry apparatus and providing an output including digital information corresponding to said time-varying analog output wherein said time-varying analog output and the corresponding digital information are indicative of characteristic A or characteristic B;

a digital signal processor extracting features from the digital information and providing a sorting signal to said sorting system as a function of the extracted features.

EE2. The apparatus of claim EE1 wherein the extracted feature corresponds to one or more of the following features: pulse area, pulse peak, pulse inner area, pulse width, pulse gaussianity, pulse lagging peak or pulse slope.

EE3. The apparatus of claim EE2 wherein the extracted feature comprises an approximation of a derivative of the pulse or slope of the pulse at a point of the pulse relative to an average peak height of the pulse.

EE4. The apparatus of claim EE3 wherein said point along the pulse corresponds to a point at which there is a difference between a first derivative of a pulse produced by particles having characteristic A and a first derivative of a pulse produced by particles having characteristic B.

EE5. The apparatus of claim EE3 wherein the time-varying analog output corresponds to a fluorescence emission pulse from the particles, and wherein said point along the pulse corresponds to a point at which a difference between a first derivative of a pulse produced by particles having characteristic A and a first derivative of a pulse produced by particles having characteristic B is at or near a maximum.

EE6. The apparatus of claim EE3 wherein the time-varying analog output corresponds to a fluorescence emission pulse from the particles, and wherein said point along the pulse is a function of a peak height of the fluorescence emission pulses.

EE7. The apparatus of EE1 wherein said digital signal processor includes instructions for detecting waveform pulses represented by the digital information, instructions for extracting features in the detected waveform pulses and instructions for discriminating the detected waveform pulses as a function of their extracted features.

EE8. The apparatus of EE7 wherein said digital signal processor includes instructions for defining a decision boundary discriminating between the extracted features representing characteristics A and the extracted features representing characteristic B.

EE9. The apparatus of EE8 wherein said digital signal processor adjusts the relative location of the decision boundary with respect to the extracted features representing characteristic A and with respect to the extracted features representing characteristic B as a function of at least one of the following: (1) the purity of said at least one population with respect to either characteristic A particles or characteristic B particles; and (2) the quantity of characteristic A particles or characteristic B particles in said at least one population relative to the total quantity of characteristic A particles or characteristic B particles in said stream.

EE10. The apparatus of EE1 further comprising a control responsive to information received from the flow cytometry apparatus for controlling the sorting system to vary its sorting strategy or for controlling the fluid delivery system to vary the rate at which fluid is delivered as a function of at least one of the following: (1) the purity of said at least one population with respect to either characteristic A particles or characteristic B particles; and (2) the quantity of characteristic A particles or characteristic B particles in said at least one population relative to the total quantity of characteristic A particles or characteristic B particles in said stream.

EE11. The apparatus of EE1 wherein said digital signal processor comprises a pulse detection processor for detecting waveform pulses represented by the digital information and for classifying the detected waveform pulses.

EE12. The apparatus of EE11 further comprising a filter for filtering the analog output at a frequency equal to or less than one half a sampling rate of the converter, and wherein the converter converts the filtered analog output into corresponding digital information.

FF. Discriminating Waveform Pulses

FF1. In a flow cytometry system for sorting a mixture of particles including particles having a characteristic A and particles having a characteristic B, said system comprising a fluid delivery system for delivering a fluid containing said particles, a flow cytometry apparatus for receiving said fluid, forming it into a stream and using flow cytometry to classify the particles according to said characteristics, and a sorting system for sorting the particles according to said classification and according to a sorting strategy to provide at least one population containing desired particles, the improvement comprising:

an analog to digital converter synchronously sampling a time-varying analog output comprising waveform pulses from said flow cytometry apparatus and providing an output including digital information corresponding to said waveform pulses wherein said waveform pulses and the corresponding digital information are indicative of characteristic A or characteristic B;

a digital signal processor discriminating the digital information as indicative of characteristic A or as indicative of characteristic B and providing a sorting signal to said sorting system as a function of the discriminated digital information.

FF2. The apparatus of FF1 wherein said digital signal processor includes instructions for detecting waveform pulses represented by the digital information, instructions for extracting features in the detected waveform pulses, and instructions for discriminating the detected waveform pulses as a function of their extracted features.

FF3. The apparatus of FF2 wherein said digital signal processor includes instructions for defining a decision boundary discriminating between the extracted features representing characteristics A and the extracted features representing characteristic B.

FF4. The apparatus of FF3 wherein said digital signal processor adjusts the relative location of the decision boundary with respect to the extracted features representing characteristic A and with respect to the extracted features representing characteristic B as a function of at least one of the following: (1) the purity of said at least one population with respect to either characteristic A particles or characteristic B particles; and (2) the quantity of characteristic A particles or characteristic B particles in said at least one population relative to the total quantity of characteristic A particles or characteristic B particles in said stream.

FF5. The apparatus of FF1 wherein said digital signal processor comprises a pulse detection processor for detecting waveform pulses corresponding to the digital information, and wherein said digital signal processor classifies the digital information as a function of the detected waveform pulses.

FF6. The apparatus of FF5 further comprising a filter for filtering the analog output at a frequency equal to or less than one half a sampling rate of the converter, and wherein the converter converts the filtered analog output into corresponding digital information.

FF7. The apparatus of FF1 further comprising a control responsive to information received from the flow cytometry apparatus for controlling the sorting system to vary its sorting strategy or for controlling the fluid delivery system to vary the rate at which fluid is delivered as a function of at least one of the following: (1) the purity of said at least one population with respect to either characteristic A particles or characteristic B particles; and (2) the quantity of characteristic A particles or characteristic B particles in said at least one population relative to the total quantity of characteristic A particles or characteristic B particles in said stream.

FF8. The apparatus of FF1 further comprising a pulsed illumination device in synchronization with synchronous sampling for illuminating the particles to produce the corresponding waveform pulses.

FF9. The apparatus of FF8 wherein said digital signal processor comprises a pulse detection processor for detecting waveform pulses represented by the digital information, and wherein said digital signal processor classifies the digital information as a function of a coefficient of variation of a population of the particles having characteristic A or as a function of a coefficient of variation of a population of the particles having characteristic B.

GG. LED Array Break-Off Sensor

GG1. An apparatus for use with a continuous stream of fluid which is breaking into droplets at a break-off location, comprising:

a light source positioned on one side of the stream to illuminate the stream;

a linear photoarray positioned on the other side of the stream adapted to be oriented along an axis substantially parallel to the stream, said photoarray adapted to detect light from the light source which passes through the stream and said photoarray adapted to provide an output signal corresponding to the detected light;

a control for receiving the output signal and providing a location signal corresponding to a location of the break-off point.

GG2. The apparatus of GG1 further comprising a display for providing a display indicating the location of the break-off location.

GG3. The apparatus of GG1 further comprising a transducer applying a force to stream for varying the location of the break-off location, said transducer varying an amplitude of the force as a function of an input signal, and wherein the location signal from the detector is provided to the transducer as the input signal.

GG4. The apparatus of GG3 further comprising a look up table for specifying variations of the amplitude of the force applied to the stream as a function of the location of the break-off location.

HH. Flow Cytometry Break-Off Sensor

HH1. In a flow cytometry system for sorting a mixture of particles including particles having a characteristic A and particles having a characteristic B, said system comprising a fluid delivery system for delivering a fluid containing said particles, a flow cytometry apparatus for receiving said fluid, forming it into a stream and using flow cytometry to classify the particles according to said characteristics, and a sorting system for sorting the particles according to said classification and according to a sorting strategy to provide at least one population containing desired particles, the improvement comprising:

a light source positioned at the second location on one side of the stream to illuminate the stream;

a linear photoarray positioned at the second location on the other side of the stream adapted to be oriented along an axis substantially parallel to the stream, said photoarray adapted to detect light from the light source which passes through the stream and said photoarray adapted to provide an output signal corresponding to the detected light;

a control for receiving the output signal indicative of a position of the second location, said control varying operation of said transducer as a function of the output signal.

HH2. The apparatus of HH1 further comprising a control responsive to information received from the flow cytometry apparatus for controlling the sorting system to vary its sorting strategy or for controlling the fluid delivery system to vary the rate at which fluid is delivered as a function of at least one of the following: (1) the purity of said at least one population with respect to either characteristic A particles or characteristic B particles; and (2) the quantity of characteristic A particles or characteristic B particles in said at least one population relative to the total quantity of characteristic A particles or characteristic B particles in said stream.

HH3. The apparatus of HH1 further comprising a display for providing a display indicating the location of the break-off location.

HH4. The apparatus of HH1 further comprising a transducer applying a force to stream for varying the location of the break-off location, said transducer varying an amplitude of the force as a function of an input signal, and wherein the location signal from the detector is provided to the transducer as the input signal.

HH5. The apparatus of HH4 further comprising a look up table for specifying variations of the amplitude of the force applied to the stream as a function of the location of the break-off location.

II. Droplet Sorter Having Epi-Illumination Optics

II1. Apparatus for sorting particles contained in a fluid stream according to one more characteristics of the particles, said system comprising:

flow cytometry apparatus for delivering a fluid stream containing said particles to a first location and for causing the stream to break into droplets at a second location, said flow cytometry apparatus being operable using flow cytometry to classify the particles according to said characteristics and to sort said droplets according to the classification of particles contained in the droplets;

said flow cytometry apparatus comprising an epi-illumination optics system including a focusing lens, said optics system being operable to direct a laser beam through said focusing lens in a forward direction along a beam axis intersecting the fluid stream at said first location so that said cells pass through the beam, resulting in emissions of electromagnetic radiation from the cells directed along said beam axis in a rearward direction.

II2. The apparatus of II1 wherein said particles are cells.

II3. The apparatus of II1 wherein said particles are sperm cells.

II4. The system of II3 wherein said beam is focused by said optics system as a spot on the fluid stream at said first location, said spot having a generally elliptical shape with a length along a major axis extending generally at right angles to the direction of fluid stream flow and a width along a minor axis extending generally parallel to the direction of fluid stream flow, said width being less than the length of the head of a sperm cell passing through the spot.

II5. The apparatus of II3 wherein said optics system includes a single photodetector to the rear of said focusing lens for detecting said emissions.

II6. The apparatus of II1 wherein said flow cytometry apparatus further comprises a nozzle having an interior surface configured to exert a force on the particles tending to bring them into a desired orientation prior to passing through said beam.

II7. The apparatus of II4 wherein said nozzle is rotatable about a longitudinal axis of the nozzle to adjust said desired particle orientation relative to the beam axis.

II8. The apparatus of II1 wherein said flow cytometry apparatus comprises a nozzle oriented to direct the fluid stream in an upward, non-vertical direction.

II9. The apparatus of II1 wherein said nozzle has an exterior surface coated with a non-reflective, non-emissive coating.

II10. The apparatus of II1 wherein said optics system includes a single photodetector to the rear of said focusing lens for detecting said emissions.

II11. The apparatus of II1 wherein said flow cytometry apparatus comprises a nozzle having a nozzle orifice, and a capillary tube extending from the orifice through which said fluid stream is delivered to said first location.

II12. The apparatus of II9 wherein said first location is inside said capillary tube.

II13. The system of II1 wherein said flow cytometry apparatus comprises a plurality of flow cytometry units operable to analyze multiple fluid streams simultaneously, each flow cytometry unit comprising said epi-illumination optics system.

JJ. Method of Sorting Particles Using Epi-Illumination Optics

JJ1. A method of sorting particles contained in a fluid stream according to one more characteristics of the particles, said method comprising:

delivering a fluid stream containing said particles to a first location and causing the stream to break into droplets at a second location; and using a flow cytometry process to classify the particles according to said characteristics and to sort said droplets according to the classification of particles contained in the droplets, said flow cytometry process comprising directing a laser beam through a focusing lens in a forward direction along a beam axis intersecting the fluid stream at said first location so that said cells pass through the beam, resulting in emissions of electromagnetic radiation from the cells directed along said beam axis in a rearward direction.

JJ2. The method of JJ1 wherein said particles are cells.

JJ3. The method of JJ1 wherein said particles are sperm cells.

JJ4. The method of JJ3 wherein the step of delivering a fluid stream comprises directing said stream through a nozzle orifice having a diameter of 50 to 70 microns at a pressure of 20-40 psi and at a rate of 30,000 to 50,000 sperm cells per second.

JJ5. The method of JJ3 further comprising focusing said beam on said fluid stream as a spot of generally elliptical shape having a length along a major axis extending generally at right angles to the direction of fluid stream flow and a width along a minor axis extending generally parallel to the direction of fluid stream flow, said width being less than the length of the head of a sperm cell passing through the beam spot.

JJ6. The method of JJ5 wherein the head of said sperm cell includes a DNA region having a length in the direction of stream flow, and wherein said beam spot width is less than the length of said DNA region.

JJ7. The method of JJ3 further comprising generating a plurality of separate fluid streams each containing sperm cells and, for each such stream, carrying out steps (a) (b).

JJ8. The method of JJ7 further comprising using a common laser beam to illuminate said fluid streams.

JJ9. The method of JJ1 further comprising exerting a force on the particles tending to bring them into a desired orientation prior to passing through said beam.

JJ10. The method of JJ4 further comprising flowing the fluid stream through a nozzle configured for exerting said force, and rotating the nozzle about a longitudinal axis of the nozzle to adjust said desired particle orientation relative to the beam axis.

JJ11. The method of JJ1 wherein said flow cytometry process further comprises using only one photodetector to detect the emission of electromagnetic radiation.

KK. Photodamage Sorter Having Epi-Illumination Optics

KK1. Apparatus for sorting particles contained in a fluid stream according to one more characteristics of the particles, said system comprising:
a flow cytometry apparatus for delivering a fluid stream containing said particles to a first location, classifying the particles according to said characteristics, and sorting said particles according to said classification into at least one population containing desired particles; and
a laser for ablating particles in said stream,
said flow cytometry apparatus comprising an epi-illumination optics system including a focusing lens, said optics system being operable to direct a laser beam through said focusing lens in a forward direction along a beam axis intersecting the fluid stream at said first location so that said cells pass through the beam, resulting in emissions of electromagnetic radiation from the cells directed along said beam axis in a rearward direction.

KK2. The apparatus of KK1 wherein said particles are cells.

KK3. The apparatus of KK2 wherein said cells are sperm cells.

KK4. The apparatus of KK1 wherein said flow cytometry apparatus further comprises a nozzle having an interior surface configured to exert a force on the particles tending to bring them into a desired orientation prior to passing through said beam.

KK5. The apparatus of KK4 wherein said nozzle is rotatable about a longitudinal axis of the nozzle to adjust said desired particle orientation relative to the beam axis.

KK6. KK1 (copy claims AA2 etc.)

LL. Method of Sorting Particles Using Epi-Illumination Optics and Photodamage

LL1. A method of sorting particles contained in a fluid stream according to one more characteristics of the particles, said method comprising:
using a flow cytometry process to classify particles in a fluid stream according to said characteristics and to sort said particles according to said classification of particles; and
ablating particles in said fluid stream,
said flow cytometry process comprising directing a laser beam through a focusing lens in a forward direction along a beam axis intersecting the fluid stream so that said cells pass through the beam, resulting in emissions of electromagnetic radiation from the cells directed along said beam axis in a rearward direction.

MM. Sperm Sorter Having Epi-Illumination Optics

MM1. A system for sorting sperm cells according to chromosomal DNA characteristics, comprising:
flow cytometry apparatus for delivering a fluid stream containing said cells to a first location and for causing the stream to break into droplets at a second location, said flow cytometry apparatus being operable to classify the cells according to said DNA characteristics and to sort said droplets according to the classification of cells contained in the droplets,
said flow cytometry apparatus comprising an epi-illumination optics system including a focusing lens, said optics system being operable to direct a laser beam through said focusing lens in a forward direction along a beam axis intersecting the fluid stream at said first location so that said cells pass through the beam, resulting in emissions of electromagnetic radiation from the cells directed along said beam axis in a rearward direction.

MM2. The system of MM1 wherein said optics system further comprises a photodetector on said beam axis to the rear of said focusing lens operable to detect and convert at least some of said emissions into electrical signals indicative of said DNA characteristics.

MM3. The system of MM1 wherein said droplets are sorted into first droplets each of which contains at least one live X sperm cell and second droplets each of which contains at least one Y cell.

MM4. The system of MM3 wherein at least some of the first droplets contain a live X cell and a live Y cell.

MM5. The system of MM1 wherein said flow cytometry apparatus comprises a nozzle having an interior surface configured to exert a force on the cells tending to bring them into a desired orientation prior to passing through said beam.

MM6. The system of MM5 wherein said nozzle is rotatable about a longitudinal axis of the nozzle to adjust said desired cell orientation relative to the beam axis.

MM7. The system of MM1 wherein said beam axis intersects the fluid stream at an angle of incidence which is skewed relative to a longitudinal axis of the stream at said first location.

MM8. The system of MM1 wherein said beam is focused by said optics system as a spot on the fluid stream at said first location, said spot having a generally elliptical shape with a length along a major axis extending generally at right angles to the direction of fluid stream flow and a width along a minor axis extending generally parallel to the direction of fluid stream flow, said width being less than the length of the head of a sperm cell passing through the beam spot.

MM9. The system of MM8 wherein the head of said sperm cell includes a DNA region having a length in the direction of stream flow, and wherein said beam spot width is less than the length of said DNA region.

MM10. The system of MM1 wherein said flow cytometry apparatus comprises a plurality of flow cytometry units operable to analyze multiple fluid streams simultaneously, each flow cytometry unit comprising said epi-illumination optics system.

MM11. The system of MM1 wherein said flow cytometry apparatus comprises a nozzle oriented to direct the fluid stream in an upward, non-vertical direction.

MM12. The system of MM1 wherein said optics system includes only one photodetector for detecting said emissions.

MM13. The system of MM1 further comprising a collector for collecting at least said first droplets.

MM14. The system of MM1 wherein said flow cytometry apparatus comprises a nozzle having a nozzle orifice, and a capillary tube extending from the orifice through which said fluid stream is delivered to said first location.

MM15. The system of MM14 wherein said first location is inside said capillary tube.

MM16. The system of MM15 wherein said optics system is optically coupled to said capillary tube for transmission of the beam into the stream flowing through the tube.

NN. Method of Sorting Sperm Using Epi-Illumination Optics

NN1. A method of sorting animal sperm cells according to their chromosomal DNA characteristics, comprising the steps of:
- (a) delivering a fluid stream containing said cells to a first location and causing the stream to break into droplets at a second location;
- (b) directing a laser beam through a focusing lens in a forward direction along a beam axis intersecting the fluid stream at said first location so that said cells pass through the beam, resulting in emissions of electromagnetic radiation from the cells directed along said beam axis in a rearward direction;
- (c) detecting and converting at least some of said emissions into electrical signals indicative of said DNA characteristics;
- (d) processing said electrical signals and classifying the cells according to said DNA characteristics; and
- (e) sorting said droplets according to the classification of cells contained in the droplets.

NN2. The method of NN1 wherein said droplets are sorted into first droplets each of which contains at least one live X sperm cell and second droplets each of which contains at least one Y cell.

NN3. The method of NN2 wherein at least some of said first droplets contain a live X cell and a live Y cell.

NN4. The method of NN1 wherein step (a) comprises directing said stream through a nozzle orifice having a diameter of 50 to 70 microns at a pressure of 20-40 psi and at a rate of 30,000 to 50,000 sperm cells per second.

NN5. The method of NN1 further comprising exerting a force on the cells tending to bring them into a desired orientation prior to passing through said beam.

NN6. The method of NN5 wherein said sperm cells have heads with wide faces and narrow edges, and wherein said desired orientation is one where the beam strikes said wide faces.

NN7. The method of NN6 wherein said fluid delivery step comprises directing said stream through a nozzle, and wherein said method further comprises rotating the nozzle about a longitudinal axis of the nozzle to adjust said desired cell orientation relative to the beam axis.

NN8. The method of NN1 further comprising focusing said beam on said fluid stream as a spot of generally elliptical shape having a length along a major axis extending generally at right angles to the direction of fluid stream flow and a width along a minor axis extending generally parallel to the direction of fluid stream flow, said width being less than the length of the head of a sperm cell passing through the beam spot.

NN9. The method of NN8 wherein the head of said sperm cell includes a DNA region having a length in the direction of stream flow, and wherein said beam spot width is less than the length of said DNA region.

NN10. The method of The method of NN5 wherein step (d) comprises deflecting at least said first droplets.

NN11. The method of NN1 further comprising directing at least some of said emissions through a filtering system including a spatial filter having an aperture with length and width dimensions, at least one of said dimensions being adjustable to vary the size of the aperture.

NN12. The method of NN1 further comprising directing said fluid stream along an upward, non-vertical trajectory.

NN13. The method of NN1 further comprising generating a plurality of separate fluid streams each containing sperm cells and, for each such stream, carrying out steps (a), (b), (c) and (d).

NN13A. The method of NN13 further comprising using a common laser beam to illuminate said fluid streams.

NN14. The method of NN13 wherein said fluid streams contain fluid from a common supply of fluid.

NN15. The method of NN1 wherein said fluid stream is delivered to said first location through a capillary tube.

OO. Sperm Analyzer Having Epi-illumination Optics

OO1. Apparatus for classifying animal sperm cells by chromosomal DNA characteristics, comprising:
- a nozzle system for delivering a fluid stream containing sperm cells to a first location and for exerting a force on the sperm cells tending to bring them into a desired orientation before the stream reaches said first location;
- an epi-illumination optics system for directing a beam of electromagnetic radiation in a forward direction along a beam axis which intersects said fluid stream at said first location at an angle of incidence other than 0 degrees stream so that said cells pass through the beam, resulting in emissions of electromagnetic radiation from the cells directed along said beam axis in a rearward direction;
- a photodetector operable to detect and convert at least some of said emissions into electrical signals indicative of said DNA characteristics; and
- a processor for processing said electrical signals and classifying the cells according to said DNA characteristics.

OO2. The apparatus of OO1 wherein said nozzle system is part of a droplet cell sorting system.

OO3. The apparatus of OO1 wherein said nozzle system is part of a photo-damage cell sorting system.

OO4. The apparatus of OO1 wherein said nozzle system is part of a fluid-switching cell sorting system.

OO5. The apparatus of OO1 wherein said optics system further comprises a photodetector on said beam axis to the rear of said focusing lens operable to detect and convert at least some of said emissions into electrical signals indicative of said DNA characteristics OO6. The apparatus of OO1 wherein said flow cytometry apparatus comprises a nozzle having an interior surface configured to exert a force on the cells tending to bring them into a desired orientation prior to passing through said beam.

OO7. The apparatus of OO6 wherein said nozzle is rotatable about a longitudinal axis of the nozzle to adjust said desired cell orientation relative to the beam axis.

OO8. The apparatus of OO1 wherein said beam axis intersects the fluid stream at an angle of incidence which is skewed relative to a longitudinal axis of the stream at said first location.

OO9. The apparatus of OO1 wherein said beam is focused by said optics system as a spot on the fluid stream at said first location, said spot having a generally elliptical shape with a length along a major axis extending generally at right angles to the direction of fluid stream flow and a width along a minor axis extending generally parallel to the direction of fluid stream flow, said width being less than the length of the head of a sperm cell passing through the beam spot.

OO10. The apparatus of OO9 wherein the head of said sperm cell includes a DNA region having a length in the direction of stream flow, and wherein said beam spot width is less than the length of said DNA region.

OO11. The apparatus of OO1 wherein said flow cytometry apparatus comprises a plurality of flow cytometry units operable in parallel to analyze multiple fluid streams simultaneously, each flow cytometry unit comprising said epi-illumination optics system.

OO12. The apparatus of OO1 wherein said nozzle system comprises a nozzle oriented to direct the fluid stream in an upward, non-vertical direction.

OO13. The apparatus of OO1 wherein said optics system includes only one photodetector for detecting said emissions.

OO14. The apparatus of OO1 wherein said flow cytometry apparatus comprises a nozzle having a nozzle orifice, and a capillary tube extending from the orifice through which said fluid stream is delivered to said first location.

OO15. The apparatus of OO14 wherein said first location is inside said capillary tube.

OO16. The apparatus of OO15 wherein said optics system is optically coupled to said capillary tube for transmission of the beam into the stream flowing through the tube.

PP. Method of Analyzing Sperm Using Epi-Illumination Optics

PP1. A method of classifying animal sperm cells by chromosomal DNA characteristics, comprising the steps of:

(a) delivering a fluid stream containing sperm cells to a first location and exerting a force on the sperm cells tending to bring them into a desired orientation before the stream reaches said first location;

(b) directing a beam of electromagnetic radiation in a forward direction along a beam axis which intersects said fluid stream at said first location at an angle of incidence other than 0 degrees stream so that said cells pass through the beam, resulting in emissions of electromagnetic radiation from the cells directed along said beam axis in a rearward direction;

(c) detecting and converting at least some of said emissions into electrical signals indicative of said DNA characteristics; and (d) processing said electrical signals and classifying the cells according to said DNA characteristics.

PP2. The method of PP1 further comprising sorting said cells according to said DNA characteristics.

PP3. The method of PP1 further comprising using a photodamage sorting process to sort said cells.

PP4. The method of PP1 further comprising using a fluid-switching sorting process to sort said cells.

PP5. The method of PP1 further comprising using a droplet sorting process to sort said cells.

PP6. The method of PP1 wherein step (a) comprises directing said stream through a nozzle orifice having a diameter of 50 to 70 microns at a pressure of 20-40 psi and at a rate of 30,000 to 50,000 sperm cells per second.

PP7. The method of PP1 further comprising exerting a force on the sperm cells tending to bring them into a desired orientation prior to passing through said beam.

PP8. The method of PP7 wherein said sperm cells have heads with wide faces and narrow edges, and wherein said desired orientation is one where the beam strikes said wide faces.

PP9. The method of PP8 wherein said fluid delivery step comprises directing said stream through a nozzle, and wherein said method further comprises rotating the nozzle about a longitudinal axis of the nozzle to adjust said desired cell orientation relative to the beam axis.

PP10. The method of PP1 further comprising focusing said beam on said fluid stream as a spot of generally elliptical shape having a length along a major axis extending generally at right angles to the direction of fluid stream flow and a width along a minor axis extending generally parallel to the direction of fluid stream flow, said width being less than the length of the head of a sperm cell passing through the beam spot.

PP11. The method of PP10 wherein the head of said sperm cell includes a DNA region having a length in the direction of stream flow, and wherein said beam spot width is less than the length of said DNA region.

PP12. The method of PP1 further comprising directing at least some of said emissions through a filtering system including a spatial filter having an aperture with length and width dimensions, at least one of said dimensions being adjustable to vary the size of the aperture.

PP13. The method of PP1 further comprising directing said fluid stream along an upward, non-vertical trajectory.

PP14. The method of PP1 further comprising generating a plurality of separate fluid streams each containing sperm cells and, for each such stream, carrying out steps (a), (b), (c) and (d).

PP15. The method of PP14 further comprising using a common laser beam to illuminate said fluid streams.

PP16. The method of PP14 wherein said fluid streams contain fluid from a common supply of fluid.

PP17. The method of PP1 wherein said fluid stream is delivered to said first location through a capillary tube.

QQ. Particle Analyzer Having Skewed Angle of Incidence Epi-Illumination Optics QQ1. Apparatus for analyzing particles contained in a fluid stream, comprising:

an epi-illumination optics system for directing a beam of electromagnetic radiation in a forward direction along a beam axis which intersects said fluid stream at an angle of incidence which is skewed relative to a longitudinal axis of the fluid stream;

said epi-illumination system including a focusing lens on said beam axis path for focusing said beam of electromagnetic radiation on the fluid stream as a spot, said particles being adapted to pass through said spot resulting in emissions of electromagnetic radiation from the particles directed along said beam axis in a rearward direction; and a photodetector to the rear of the focusing lens for detecting and converting at least some of said emissions into electrical signals to be processed to obtain information regarding said particles.

QQ2. The apparatus of QQ1 wherein said angle of incidence is in the range of 5 to 45 degrees.

QQ3. The apparatus of QQ1 wherein said angle of incidence is in the range of 15 to 30 degrees.

QQ4. The apparatus of QQ1 wherein said particles are cells, and wherein said information relates to DNA characteristics of the cells.

QQ5. The apparatus of QQ1 wherein said particles are sperm cells, and wherein said information relates to the X/Y chromosomal DNA characteristics of the cells.

QQ6. The apparatus of QQ5 further comprising a nozzle system for directing said fluid stream and for exerting a force on the sperm cells tending to bring them into a desired orientation before the stream passes through said beam.

QQ7. The apparatus of QQ1 wherein said nozzle system comprises a nozzle, and wherein said beam strikes said fluid stream at a location less than 1.0 mm from the nozzle.

QQ8. The apparatus of QQ1 further comprising a droplet cell sorting system for sorting said particles according to said information.

QQ9. The apparatus of QQ1 further comprising a photodamage cell sorting system for sorting said particles according to said information.

QQ10. The apparatus of QQ1 further comprising a fluid-switching cell sorting system for sorting said particles according to said information.

RR. Method of Analyzing Particles Using Skewed Epi-Illumination Optics

RR1. A method of analyzing particles contained in a fluid stream, comprising:

directing a beam of electromagnetic radiation in a forward direction along a beam axis which intersects said fluid stream at an angle of incidence which is skewed relative to a longitudinal axis of the fluid stream;

focusing said beam of electromagnetic radiation on the fluid stream as a spot, said particles being adapted to pass through said spot resulting in emissions of electromagnetic radiation from the particles directed along said beam axis in a rearward direction;

detecting and converting at least some of said emissions into electrical signals indicative of characteristics of the particles; and processing said electrical signals to obtain information regarding said characteristics.

RR2. RR1 (add claims similar to QQ2-etc.)

SS. Cell Analyzer Having Epi-Illumination Optics and Elliptical Spot Focus

SS1. Apparatus for analyzing DNA characteristics of cells in a fluid stream, each cell comprising a DNA region having a length in the direction of stream flow, said apparatus comprising:

an epi-illumination optics system for directing a beam of electromagnetic radiation in a forward direction along a beam axis so that the beam intersects said fluid stream;

said optics system including a focusing lens on said beam axis for focusing the beam on the fluid stream as a generally elliptical spot having a length along a major axis extending generally at right angles to the direction of fluid stream flow and a width along a minor axis extending generally parallel to the direction of fluid stream flow, the width of the beam spot being less than the length of said DNA region, said cells being adapted to pass through said spot resulting in an emissions of electromagnetic radiation from the cells directed along said beam axis in a rearward direction, including emissions from said DNA regions indicative of said DNA characteristics;

a photodetector to the rear of the focusing lens for detecting and converting at least some of said emissions from said DNA regions into electrical signals indicative of said DNA characteristics; and a system for processing said electrical signals, identifying said DNA characteristics, and classifying the cells according to said DNA characteristics.

SS2. The apparatus of SS1 wherein said spot width is less than about 3.0 µm.

SS3. The apparatus of SS2 wherein said spot length is greater than about 80 µm.

SS4. The apparatus of SS1 wherein said cells are sperm cells and said DNA characteristics are indicative of the sex of the sperm cells.

SS5. The apparatus of SS1 further comprising a nozzle system for exerting a force on the cells in the stream tending to bring them into a desired orientation before the stream passes through said beam.

SS6. The apparatus of SS1 further comprising a droplet cell sorting system for sorting said particles according to said DNA characteristics.

SS7. The apparatus of SS1 further comprising a photo-damage cell sorting system for sorting said particles according to said DNA characteristics.

SS8. The apparatus of SS1 further comprising a fluid-switching cell sorting system for sorting said particles according to said DNA characteristics.

SS9. Apparatus for analyzing chromosomal DNA characteristics of animal sperm cells in a fluid stream having a direction of flow, each sperm cell having a head with a nucleus comprising a localized chromosome region containing at least one chromosome, said nucleus having a length in the direction of stream flow, said apparatus comprising:

an optics system for focusing a beam of electromagnetic radiation on the fluid stream as a generally elliptical spot having a length along a major axis extending generally at right angles to the direction of stream flow and a width along a minor axis extending generally parallel to the direction of stream flow, the width of the beam spot being less than the length of said nucleus, said sperm cells being adapted to pass through said spot resulting in a emissions of electromagnetic radiation from the sperm cells, including emissions from said chromosome regions indicative of chromosomal characteristics of the regions;

a photodetector for detecting and converting at least some of said emissions from the chromosome regions into electrical signals indicative of said chromosomal characteristics; and a processor for processing said electrical signals, identifying said chromosomal characteristics, and classifying the sperm cells according to said chromosomal characteristics.

SS10. The apparatus of claim SS9 wherein said chromosomal characteristics are indicative of the sex of the sperm cells.

SS11. The apparatus of claim SS10 wherein said sperm cells are bovine sperm cells.

SS12. The apparatus of claim SS10 wherein said chromosome region is localized within an area of the nucleus extending no more than about 20% of the nucleus length on either side of a longitudinal center of the nucleus.

SS13. The apparatus of claim SS10 wherein said chromosome region is localized within an area of the nucleus extending no more than about 10%-15% of the nucleus length on either side of a longitudinal center of the nucleus.

SS14. The apparatus of claim SS9 further comprising an analog to digital converter synchronously sampling a time-varying analog output from said photodetector and providing an output including digital information corresponding to said time-varying analog output wherein said time-varying analog output and the corresponding digital information are indicative of said chromosomal characteristics; and wherein said processor comprises a digital signal processor analyzing and classifying the digital information.

SS15. The apparatus of claim SS9 wherein said spot width is less than about 3.0 µm.

SS16. The apparatus of claim SS15 wherein said spot length is about 80 µm.

SS17. The apparatus of claim SS9 further comprising a nozzle system for exerting a force on the sperm cells in the stream tending to bring them into a desired orientation before the stream passes through said beam.

SS18. The apparatus of claim SS9 further comprising a droplet cell sorting system for sorting said sperm cells according to said chromosomal DNA characteristics.

SS19. The apparatus of claim SS9 further comprising a photo-damage sperm cell sorting system for sorting said sperm cells according to said chromosomal DNA characteristics.

SS20. The apparatus of claim SS9 further comprising a fluid-switching sperm cell sorting system for sorting said sperm cells according to said chromosomal DNA characteristics.

TT. Method of Analyzing Cells Using Epi-Illumination Optics and Elliptical Spot Focus TT1. A method of analyzing DNA characteristics of cells in a fluid stream, each cell comprising a DNA region having a length in the direction of stream flow, said method comprising:

directing a beam of electromagnetic radiation in a forward direction along a beam axis so that the beam intersects said fluid stream;

focusing said beam of electromagnetic radiation on the fluid stream as a generally elliptical spot having a length along a major axis extending generally at right angles to the direction of fluid stream flow and a width along a minor axis extending generally parallel to the direction of fluid stream flow, the width of the beam spot being less than the length of said DNA region, said cells being adapted to pass through said spot resulting in an emissions of electromagnetic radiation from the cells directed along said beam axis in a rearward direction;

detecting and converting said emissions into electrical signals indicative of said DNA characteristics; and processing said electrical signals, including differentiating between electrical signals from emissions from the DNA region of a sperm head and electrical signals from emissions from other regions of the sperm cell; and classifying the cells according to said DNA characteristics.

TT2. The method of TT1 wherein said cells are sperm cells.

TT3. The method of TT1 further comprising exerting a force on the cells in the stream tending to bring them into a desired orientation before the stream passes through said beam.

TT4. The method of TT1 further comprising droplet sorting said cells according to said DNA characteristics.

TT5. The method of TT1 further comprising photo-damage sorting said particles according to said DNA characteristics.

TT6. The method of TT1 further comprising fluid-switching sorting said particles according to said DNA characteristics.

TT7. A method of analyzing chromosomal DNA characteristics of animal sperm cells in a fluid stream having a direction of flow, each sperm cell having a head with a nucleus comprising a localized chromosome region containing at least one chromosome, said nucleus having a length in the direction of stream flow, said method comprising:

focusing a beam of electromagnetic radiation on the fluid stream as a generally elliptical spot having a length along a major axis extending generally at right angles to the direction of stream flow and a width along a minor axis extending generally parallel to the direction of stream flow, the width of the beam spot being less than the length of said nucleus, said sperm cells being adapted to pass through said spot resulting in a emissions of electromagnetic radiation from the sperm cells, including emissions from said chromosome regions indicative of chromosomal characteristics of the regions;

detecting and converting at least some of said emissions from the chromosome regions into electrical signals indicative of said chromosomal characteristics;

processing said electrical signals, including identifying said chromosomal characteristics; and classifying the sperm cells according to said chromosomal characteristics.

TT8. The method of claim TT7 wherein said chromosomal characteristics are indicative of the sex of the sperm cells.

TT9. The method of claim TT8 wherein said sperm cells are bovine sperm cells.

TT10. The method of claim TT8 wherein said chromosome region is localized within an area of the nucleus extending no more than about 20% of the nucleus length on either side of a longitudinal center of the nucleus.

TT11. The method of claim TT10 wherein said chromosome region is localized within an area of the nucleus extending no more than about 10%-15% of the nucleus length on either side of a longitudinal center of the nucleus.

TT12. The method of claim TT7 wherein said electrical signals comprise a time-varying analog output, and further comprising synchronously sampling the time-varying analog output and providing an output including digital information corresponding to said time-varying analog output wherein said time-varying analog output and the corresponding digital information are indicative of said chromosomal characteristics; wherein said processing comprises analyzing the digital information; and wherein said classifying comprises classifying analyzed digital information.

TT13. The method of claim TT7 wherein said spot width is less than about 3.0 μm.

TT14. The method of claim TT13 wherein said spot length is greater than about 180 μm.

TT15. The method of claim TT7 further comprising exerting a force on the sperm cells in the stream tending to bring them into a desired orientation before the stream passes through said beam.

TT16. The method of claim TT7 further comprising droplet sorting droplet said sperm cells according to said chromosomal DNA characteristics.

TT17. The method of claim TT7 further comprising a photo-damage sorting said sperm cells according to said chromosomal DNA characteristics.

TT18. The method of claim TT7 further comprising fluid-switching sorting sperm cells according to said chromosomal DNA characteristics.

UU. Sperm Sorter Having Only One Photodetector

UU1. Apparatus for classifying and sorting sperm cells according to chromosomal DNA characteristics of the cells, said apparatus comprising:

a nozzle system for delivering a fluid stream containing said cells to a first location and for causing the stream to break into droplets at a second location, said nozzle system comprising a nozzle having an interior surface configured to exert a force on the cells tending to bring them into a desired orientation before reaching said first location;

an optics system for directing a beam of electromagnetic radiation to intersect the fluid stream at said first location so that cells in the stream pass through said beam resulting in emissions of electromagnetic radiation from the cells;

only one photodetector for detecting and converting at least some of said emissions into electrical signals; and a system for classifying the cells according to said DNA characteristics and for sorting said droplets according to the classification of cells contained in the droplets.

UU2. The apparatus of UU1 wherein said optics system is an epi-illumination system.

VV. Orienting Nozzle

VV1. A nozzle for use in flow cytometry apparatus for sorting animal sperm cells in a fluid stream by chromosome content, said nozzle comprising:

a nozzle body having an interior surface and an orifice through which said fluid stream is adapted to flow;

said interior surface of the nozzle comprising first, second and third axially tapered regions for progressively accelerating the speed of said fluid stream in a downstream direction toward said nozzle orifice, at least two of said regions having generally elliptical cross sectional shapes oriented in different directions for applying torsional forces to said fluid stream tending to bring the sperm cells into a desired orientation.

VV2. The nozzle of VV1 wherein said generally elliptical cross sectional shape of one of said at least two regions is oriented at about 90 degrees relative to the generally elliptical cross sectional shape of the other of said at least two regions.

VV3. The nozzle of VV2 wherein said generally elliptical cross sectional shapes of the first and second regions are oriented in substantially the same direction to define a first torsional zone, and wherein the generally elliptical cross sectional shape of the third region, constituting a second torsional zone, is oriented at about 90 degrees relative to the generally elliptical cross sectional shapes of the first and second regions.

VV4. The nozzle of VV3 wherein the first torsional zone has an axial length of 3.0-4.5 mm and the second torsional zone has an axial length of 3.5-5.0 mm.

VV5. The nozzle of VV1 wherein the third region tapers at an angle of 42-48 degrees.

VV6. The nozzle of VV1 wherein all of said regions have generally elliptical cross sectional shapes.

VV7. The nozzle of VV1 wherein said nozzle body has an exterior surface with a non-reflective coating thereon.

VV8. The nozzle of VV1 further comprising a mount for mounting said nozzle in a position pointing upward to direct said fluid stream along an upward trajectory.

VV9. The nozzle of VV8 wherein said nozzle body is rotatable on said mount on a longitudinal axis of the body.

WW. Method of Orienting Sperm Cells

WW1. A method of orienting animal sperm cells in flow cytometry apparatus, said method comprising:

introducing a fluid containing sperm cells into a fluid stream;

directing the fluid stream containing said sperm cells under a pressure in the range of 20 to 40 psi through a nozzle having one or more tapered regions for accelerating the speed of said fluid stream in a downstream direction toward a nozzle orifice having a diameter in the range of 50-70 microns, one or more of said tapered regions having a generally elliptical cross sectional shape for applying a torsional force to said fluid stream tending to bring the cells into a desired orientation as they pass through said orifice at a rate in the range of 30,000 to 50,000 sperm cells per second.

WW2. The method of WW1 wherein said nozzle has three or more tapered regions for progressively accelerating the fluid stream toward the nozzle orifice.

WW3. The method of WW2 wherein said nozzle has two torsional zones defined by interior surfaces of the nozzle in said three or more tapered regions.

WW4. The method of WW3 wherein said nozzle has a flow axis through said orifice, and wherein at least some of said interior nozzle surfaces have generally elliptical shapes which are rotated relative to one another about said axis.

WW5. The method of WW1 further comprising directing said stream along an upward non-vertical trajectory.

WW6. The method of WW1 further comprising rotating the nozzle body on a central longitudinal axis of the body while directing said stream.

XX. Particle Sorter Having Upward Pointing Nozzle

XX1. Apparatus for sorting particles using flow cytometry, comprising:

a nozzle system for delivering a fluid stream containing said particles through a nozzle orifice along an upward, non-vertical trajectory;

an optics system for directing a beam of electromagnetic radiation to intersect said fluid stream at said first location resulting in emissions of electromagnetic radiation from the particles;

a photodetector operable to detect and convert at least some of said emissions into electrical signals indicative of said particle characteristics;

a processor for processing said electrical signals and classifying the particles according to said characteristics; and a sorting system for sorting said particles according to the classification of the particles.

XX2. The apparatus of XX1 wherein said sorting system comprises a droplet sorting system.

XX3. The apparatus of XX1 wherein said sorting system comprises a photo-damage sorting system.

XX4. The apparatus of XX1 wherein said sorting system comprises a fluid-switching sorting system.

XX5. The apparatus of XX1 wherein said nozzle system comprises a nozzle having a non-reflective coating thereon.

XX6. The apparatus of XX1 wherein said upward trajectory at the nozzle orifice is at an angle in the range of 5-85 degrees off horizontal.

XX7. The apparatus of XX1 wherein said upward trajectory at the nozzle orifice is at an angle in the range of 15-75 degrees off horizontal.

XX8. The apparatus of XX1 wherein said upward trajectory at the nozzle orifice is at an angle in the range of 30-65 degrees off horizontal.

XX9. The apparatus of XX1 wherein said upward trajectory at the nozzle orifice is at an angle in the range of 45-60 degrees off horizontal.

YY. Method of Sorting Particles Using Upward Pointing Nozzle

YY1. Method of sorting particles using flow cytometry, comprising:

delivering a fluid stream containing said particles through a nozzle orifice along an upward, non-vertical trajectory to a first location;

directing a beam of electromagnetic radiation to intersect said fluid stream at said first location resulting in emissions of electromagnetic radiation from the particles;

detecting and converting at least some of said emissions into electrical signals indicative of said particle characteristics;

processing said electrical signals and classifying the particles according to said characteristics; and sorting said particles according to the classification of the particles.

YY2. The method of YY1 wherein said sorting step comprises sorting by using a droplet sorting process.

YY3. The method of YY1 wherein said sorting step comprises sorting by using a photo-damage sorting process.

YY4. The method of YY1 wherein said sorting step comprises sorting by using a fluid-switching sorting process.

ZZ. Process Parameters

ZZ1. A method of separating a desired cell population from a mixture of cells using flow cytometry, said population having a light detectable characteristic, said method comprising:

directing a stream of fluid containing said cells through a nozzle orifice having a diameter of from about 50 to 70 μm at a pressure in the range of about 20 to 40 psi and at a cell rate of about 30,000 to 50,000 cells per second;

causing the fluid stream to break into droplets at a frequency of about 20 to 100 KHz, and sorting the droplets using flow cytometry to separate said desired cell population from said mixture of cells.

ZZ2. The method of ZZ1 wherein said cells are sperm cells.

ZZ3. The method of ZZ2 wherein said desired cell population contains live X cells.

AAA. Business Method

AAA1. A method of doing business including the handling of semen having cells therein, said method comprising:
  obtaining a supply the semen;
  using a programmable machine to conduct a plurality of integrated flow cytometry operations, said operations comprising: (a) receiving said supply of semen; (b) forming multiple streams containing said cells; and (c) sorting said cells into a first population of cells having characteristic A and a second population of cells having characteristic B; and
  distributing the first or the second population for commercial use.

AAA2. The method of AAA1 wherein said cells are sperm cells, and wherein characteristic A is indicative of a live X sperm cell.

AAA3. The method of AAA2 wherein the semen is bovine semen, and wherein the first population is sold for use in artificially inseminating cows.

AAA4. The method of AAA3 wherein said programmable machine is operable to conduct said operations in parallel.

BBB. Business Method

BBB1. A method of doing business including the handling of a sample of semen having cells therein, said method comprising:
  obtaining a supply of semen;
  using a programmable machine to conduct a plurality of integrated flow cytometry operations, said operations comprising: (a) receiving said supply of semen; and (b) sorting said cells from an initial portion of said supply into different populations, including a first population containing cells having characteristic A and a second population containing cells having characteristic B; and
  sorting said cells from the remaining portion of said supply into different groups, including a first group containing cells having characteristic A and a second group containing cells having characteristic B, only if the cells initially sorted from the initial portion meet or exceed a preset standard.

BBB2. The method of BBB1 further comprising distributing the first or the second population for commercial use.

BBB3. The method of BBB1 wherein the preset standard is a minimum recovery rate of cells having characteristic A or characteristic B or a minimum purity for at least one of the populations.

BBB4. The method of BBB1 further comprising conducting said plurality of integrated flow cytometry operations in parallel.

CCC. Business Method

CCC1. A method of doing business including the handling of a sample of semen having cells therein, said method comprising:
  obtaining a supply of semen;
  using a machine to conduct a plurality of integrated flow cytometry operations, said operations comprising: (a) receiving said supply of semen; and (b) sorting said cells from a first portion of said supply into different populations, including a first population containing cells having characteristic A and a second population containing cells having characteristic B, and sorting said cells from a second portion of said supply into different populations, including a first population containing cells having characteristic A and a second population containing cells having characteristic B; and
  blending one of the populations of the first portion with one of the populations of the second portion to obtain a blended population.

CCC2. The method of CCC1 wherein the first population of the first portion has an unacceptable purity, wherein the first population of the second portion has an acceptable purity, and wherein the blended Population has an Acceptable Purity.

DDD. Droplet Interference Sorting w/ Epi-Illumination

DDD1. A droplet interference system for sorting sperm cells according to chromosomal DNA characteristics, comprising:
  flow cytometry apparatus for delivering a fluid stream containing said cells to a first location and for causing selected stream segments of the fluid stream to be hit by a droplet from a droplet interference fluid stream at a second location, thereby separating the selected segments and cells contained therein from the fluid stream, said flow cytometry apparatus being operable to classify the cells according to said DNA characteristics and to sort the stream segments according to the classification of cells contained in the stream segments,
  said flow cytometry apparatus comprising an epi-illumination optics system including a focusing lens, said optics system being operable to direct a laser beam through said focusing lens in a forward direction along a beam axis intersecting the fluid stream at said first location so that said cells pass through the beam, resulting in emissions of electromagnetic radiation from the cells directed along said beam axis in a rearward direction.

DDD2. The system of DDD1 wherein said optics system further comprises a photodetector on said beam axis to the rear of said focusing lens operable to detect and convert at least some of said emissions into electrical signals indicative of said DNA characteristics.

DDD3. The system of DDD1 wherein the cells are sperm cells and the DNA characteristics comprises sex chromosome content of the sperm cells.

DDD4. The system of DDD3 wherein said beam is focused by said optics system as a spot on the fluid stream at said first location, said spot having a generally elliptical shape with a length along a major axis extending generally at right angles to the direction of fluid stream flow and a width along a minor axis extending generally parallel to the direction of fluid stream flow, said width being less than the length of the head of a sperm cell passing through the beam spot.

DDD5. The system of DDD4 wherein the head of said sperm cell includes a DNA region having a length in the direction of stream flow, and wherein said beam spot width is less than the length of said DNA region.

DDD6. The system of DDD1 wherein said flow cytometry apparatus comprises a nozzle having an interior surface configured to exert a force on the cells tending to bring them into a desired orientation prior to passing through said beam.

DDD7. The system of DDD6 wherein said nozzle is rotatable about a longitudinal axis of the nozzle to adjust said desired cell orientation relative to the beam axis.

DDD8. The system of DDD1 wherein said flow cytometry apparatus comprises a plurality of flow cytometry units operable to analyze multiple fluid streams simultaneously, each flow cytometry unit comprising said epi-illumination optics system.

DDD9. The system of DDD1 wherein said optics system includes only one photodetector for detecting said emissions.

DDD10. The system of DDD1 wherein said flow cytometry apparatus comprises a nozzle having a nozzle orifice, and a capillary tube extending from the orifice through which said fluid stream is delivered to said first location.

DDD11. The system of DDD10 wherein said first location is inside said capillary tube.

DDD12. The system of DDD11 wherein said optics system is optically coupled to said capillary tube for transmission of the beam into the stream flowing through the tube.

A'. Cryopreservation a. (Add Cryoprotectant then Cool)

A1'. A method of cryopreserving sperm cells comprising the steps of:
adding a cryoprotectant to a quantity of sperm cells;
cooling said quantity of sperm cells and said cryoprotectant to a holding temperature in a range of about 0-8° C.;
maintaining said sperm cells and said cryoprotectant substantially at said holding temperature for a period of less than 60 minutes; and
supercooling said quantity of sperm cells to a temperature of −40° C.

A2'. The method of claim A1' wherein said holding temperature is in a range of about 2-6° C.

A3'. The method of claim A1' wherein said holding temperature is in a range of about 4-5° C.

A4'. The method of claim A1' wherein the step of adding a cryoprotectant comprises adding glycerol.

A5'. The method of claim A1' wherein the step of adding a cryoprotectant comprises adding about 6% glycerol (v/v).

A6'. The method of claim A1' wherein said holding period is less than about 40 minutes.

A7'. The method of claim A1' wherein said holding period is about 30 minutes.

A8'. The method of claim A1' wherein the cooling step comprises cooling said quantity of sperm at a substantially constant cooling rate.

A9'. The method of claim A8' wherein the cooling rate is selected so that said quantity of sperm cells is cooled from a temperature above a glass transition temperature below which sperm cells are subject damage from cold shock to the holding temperature in about 90 minutes.

A10'. The method of claim A8' wherein the substantially constant cooling rate is in the range of about 0.1-0.3° C. per minute.

A11'. The method of claim A8' wherein the substantially constant cooling rate is in the range of about 0.15-0.25° C. per minute.

A12'. The method of claim A11' wherein said holding period is less than about 40 minutes in length.

A13'. The method of claim A1' wherein the cooling step is performed by using a programmable freezer to cool the sperm cells at a programmed rate.

A14'. The method of claim A13' wherein said holding period is less than 40 minutes in length.

A15'. The method of claim A14' wherein the programmed cooling rate comprises a constant cooling rate of about 0.2° C. per minute.

A16'. The method of claim A1' wherein the step of supercooling said quantity of sperm comprises cooling the sperm cells at a first cooling rate to a temperature that approaches a critical temperature zone at which ice crystal formation and changes in osmotic pressure damage sperm cells and cooling the sperm at a second cooling rate faster than said first cooling rate to a temperature that is less than about −30° C.

A17'. The method of claim A16' wherein said first cooling rate is in the range of about 1-5° C. per minute.

A18'. The method of claim A16' wherein said first cooling rate is in the range of about 2-4° C. per minute.

A19'. The method of claim A16' wherein said first cooling rate is about 3° C. per minute.

A20'. The method of claim A16' wherein said second cooling rate is in the range of about 8-12° C. per minute.

A21'. The method of claim A16' wherein said second cooling rate is about 10° C. per minute.

A22'. The method of claim A16' wherein the sperm cells are cooled to a temperature of about −15° C. at said first cooling rate.

A23'. The method of claim A22' wherein the sperm cells are cooled from about −15° C. to a temperature of about −80° C. at said second cooling rate.

A24'. The method of claim A16' wherein the sperm cells are cooled to a temperature of about −18° C. at said first cooling rate.

A25'. The method of claim A24' wherein the sperm cells are cooled from about −18° C. to a temperature of about −80° C. at said second cooling rate.

A26'. The method of claim A16' wherein the sperm cells are cooled at said first rate and said second rate in a programmable freezer.

A27'. The method of claim A1' wherein the step of adding a cryoprotectant to a quantity of sperm cells comprises adding a cryoprotectant to a sheath fluid and using said sheath fluid in a flow cytometer that analyzes sperm cells.

A28'. The method of claim A27' further comprising the step of using said flow cytometer to sort said sperm cells into a population of sperm cells having a desired characteristic to obtain said quantity of sperm cells.

A29'. The method of claim A1' wherein the steps of cooling said quantity of sperm, maintaining said sperm cells at the holding temperature, and supercooling said quantity of sperm cells are all completed in less than 220 minutes.

A30'. The method of claim A1' wherein the steps of cooling said quantity of sperm, maintaining said sperm cells at the holding temperature, and supercooling said quantity of sperm cells are all completed in less than about 190 minutes.

A31'. The method of claim A1' wherein the steps of cooling said quantity of sperm, maintaining said sperm cells at the holding temperature, and supercooling said quantity of sperm cells are all completed in less than about 150 minutes.

A32'. The method of claim A1' further comprising the step of loading said quantity of sperm cells into an artificial insemination straw after the cryoprotectant has been added to said quantity of sperm cells.

A33'. The method of claim A1' wherein said quantity of sperm cells constitutes a first quantity of sperm cells, the method further comprising the steps of obtaining a sorted population of sperm cells comprising more than $500 \times 10^6$ sperm cells from a flow cytometer to thereby obtain a plurality of quantities of sperm cells including said first quantity of sperm cells, loading each of said plurality of quantities of sperm cells into an artificial insemination straw, and performing the steps of cooling, maintaining, and supercooling on each of said plurality of quantities of sperm cells in a batch process to obtain a batch of artificial insemination straws containing cryopreserved sperm cells.

A34'. The method of claim A33' wherein said sorted population of sperm cells comprises more than $800 \times 10^6$ sperm cells.

A35'. The method of claim A33' wherein the steps of the method are completed in less than about 240 minutes.

A36'. The method of claim A33' wherein the steps of the method are completed in less than about 210 minutes.

A37'. The method of claim A33' wherein the steps of the method are completed in less than about 170 minutes.

A38'. The method of claim A1' further comprising the step of staining said quantity of sperm cells with a DNA selective fluorescent dye before the cooling step.

A39'. The method of claim A38' wherein said DNA selective dye comprises Hoechst 33342.

A40'. The method of claim A39' wherein said step of staining said quantity of sperm comprises the step of incubating said quantity of sperm cells for a period of time in a solution comprising Hoechst 33342 at a temperature that exceeds 40° C.

b. Cold Temperature Sorting

A41'. A method of cryopreserving sperm cell comprising the steps of:

cooling a quantity of sperm cells to a holding temperature in the range of about 0-8° C.; adding a cryoprotectant to said quantity of sperm cells; and maintaining said sperm cells and said cryoprotectant substantially at said holding temperature for a period of less than 60 minutes.

A42'. The method of claim A41' wherein said period is in the range of about 30 minutes to less than 60 minutes.

A43'. The method of claim A41' wherein the step of adding a cryoprotectant comprises adding glycerol.

A44'. The method of claim A41' wherein the step of adding a cryoprotectant comprises adding about 7% glycerol (v/v/).

B'. Nozzle with Baffle

B1'. A nozzle for use in flow cytometry apparatus for analyzing particles in a fluid stream, said fluid stream comprising a sheath stream surrounding a core stream containing said particles, said nozzle comprising:

a nozzle having an interior surface defining a flow path for said fluid stream, and an orifice for exit of the fluid stream from the nozzle; and a baffle in the nozzle positioned in said flow path upstream from said orifice for deflecting the fluid stream as it moves along said flow path, the baffle and interior surface of the nozzle being configured to orient the particles in a desired orientation as they exit the orifice.

B2'. The nozzle of claim B1' wherein said baffle is configured for deflecting said core stream away from a central longitudinal axis of the nozzle and toward said interior surface of the nozzle.

B3'. The nozzle of claim B1' wherein said nozzle has a first cross sectional flow area upstream of said baffle and a second cross sectional flow area different from said first cross sectional flow area at the baffle.

B4'. The nozzle of claim B3' wherein said second cross sectional flow area is smaller than said first cross sectional flow area.

B5'. The nozzle of claim B3' wherein said first and second cross sectional flow areas have different shapes.

B6'. The nozzle of claim B5' wherein said second cross sectional flow area is generally semi-cylindrical.

B7'. The nozzle of claim B1' wherein said interior surface of the nozzle is shaped to define at least two axially tapered regions downstream from said baffle for progressively accelerating the speed of the fluid stream in a downstream direction toward the nozzle orifice.

B8'. The nozzle of claim B7' wherein said baffle is configured for deflecting said core stream toward a portion of said interior surface of the nozzle defining at least one of said at least two axially tapered regions.

B9'. The nozzle of claim B8' wherein said at least two axially tapered regions have generally elliptical cross sectional shapes oriented in different directions for applying torsional forces to said fluid stream that tend to bring the particles into said desired orientation.

B10'. The nozzle of claim B9' wherein said generally elliptical cross sectional shape of one of said at least two regions is oriented at about 90 degrees relative to the generally elliptical cross sectional shape of the other of said at least two regions.

B11'. The nozzle of claim B1' wherein the nozzle has an exterior surface with a non-reflective coating thereon.

B12'. The nozzle of claim B1' further comprising a mount for mounting said nozzle in a position pointing upward to direct said fluid stream along an upward trajectory.

B13'. The nozzle of claim B13' wherein the nozzle is rotatable on said mount about a longitudinal axis of the nozzle.

B14'. The nozzle of claim B1' wherein said baffle comprises a baffle member for deflecting said fluid stream and a holder for holding said baffle member in fixed position in said nozzle.

B15'. The nozzle of claim B14' wherein said baffle member comprises a baffle plate.

B16'. The nozzle of claim B15' wherein said baffle plate has a first leg extending generally transversely relative to said fluid stream and a second leg extending generally in the direction of said fluid stream.

B17'. The nozzle of claim B15' wherein said holder comprises a generally cylindrical shell holding said baffle plate and positioned in said nozzle.

B18'. The nozzle of claim B16' wherein said interior surface of the nozzle has a region of generally elliptical cross section downstream from said baffle, and wherein said first and second legs of the baffle member intersect along a line which is substantially parallel with a major axis of said generally elliptical cross section.

B19'. The nozzle of claim B16' wherein said interior surface of the nozzle has a region of generally elliptical cross section downstream from said baffle, and wherein said first and second legs of the baffle member intersect along a line which is substantially perpendicular to a major axis of said generally elliptical cross section.

B20'. The nozzle of claim B15' wherein the baffle plate is generally perpendicular to a longitudinal axis of the nozzle.

B21'. The nozzle of claim B20' wherein the baffle plate has a semi-circular shape.

B22'. The nozzle of claim B20' wherein the baffle plate has a semi-elliptical shape.

B23'. The nozzle of claim B20' wherein the interior surface of the nozzle is shaped to define a shoulder and the holder comprises an o-ring seal capable of pressing the baffle plate against the shoulder to hold the baffle plate in a desired position.

B24'. The method of claim B20' wherein the baffle holder holds the baffle plate in a position in which the baffle plate intersects the longitudinal axis of the nozzle.

B25'. The nozzle of claim B1' wherein said particles comprise sperm cells.

C'. Nozzle with Baffle (Method)

C1'. A method of orienting particles in a flow cytometry apparatus, said method comprising:

causing a fluid stream having a core stream of sample fluid containing said particles and a sheath stream of sheath fluid surrounding the core stream to flow through a nozzle having an interior surface that generally tapers from an upstream portion of the nozzle to an orifice at the downstream end of the nozzle; and deflecting the core stream as it flows through the nozzle to subject the particles in the core stream to hydrodynamic forces that tend to cause the particles to assume a desired orientation.

C2'. The method of claim C1' wherein the nozzle has a longitudinal axis and the step of deflecting the core stream comprises deflecting the core stream away from the longitudinal axis toward said interior surface.

C3'. The method of claim C1' wherein the nozzle has a longitudinal axis and the step of deflecting the path of the core stream comprises deflecting the core stream from a path that generally coincides with the longitudinal axis to a deflected path, at least a portion of the deflected path being offset from the longitudinal axis of the nozzle.

C4'. The method of claim C1' wherein the nozzle has a longitudinal axis, the method further comprising introducing the core stream into the sheath stream at a location that is offset from the longitudinal axis.

C5'. The method of claim C1' wherein the deflecting step comprises using a baffle to deflect the core stream.

C6'. The method of claim C1' wherein the deflecting step comprises using a baffle plate to deflect the core stream and using a baffle holder to hold the baffle plate in position in the nozzle.

C7'. The method of claim C6' wherein the baffle plate intersects the longitudinal axis of the nozzle.

C8'. The method of claim C1' wherein the nozzle has an interior surface that is shaped to define at least one torsional zone for subjecting the particles to hydrodynamic orienting forces.

C9'. The method of claim C8' wherein that at least one torsional zone comprises a tapered region of the nozzle having a generally elliptical cross section.

C10'. The method of claim C8' wherein said interior surface is shaped to define multiple torsional zones.

C11'. The method of claim C10' wherein each of said multiple torsional zones comprises a tapered region of the nozzle having a generally elliptical cross section.

C12'. The method of claim C11' wherein the generally elliptical cross section for a first of the multiple torsional zones is oriented in a different direction that the generally elliptical cross section for a second of the multiple torsional zones.

C13'. The method of claim C1' wherein the step of deflecting the core stream comprises using a baffle to deflect the core stream, the method further comprising the step of causing the fluid stream to flow through a first cross sectional flow area and then a second cross sectional flow area downstream from the first cross sectional flow area, wherein the first and second cross sectional flow areas have different shapes.

C14'. The method of claim C15' wherein the second cross sectional flow area is smaller than the first cross sectional flow area.

D'. Nozzle with Asymmetric Injection Needle (Apparatus)

D1'. A nozzle system for use in a flow cytometer for analyzing particles in a fluid stream, said fluid stream comprising a sheath stream surrounding a core stream containing said particles, said nozzle system comprising:
a nozzle having a longitudinal axis, an interior surface defining a flow path for said fluid stream, and an orifice at the downstream end of the nozzle for exit of the fluid stream from the nozzle, said interior surface being shaped to define at least one torsional zone comprising an axially tapered region having a generally elliptical cross section for orienting said particles in a desired orientation as the fluid stream flows through the torsional zone toward the orifice; and
a conduit from a particle source to the nozzle, said conduit being positioned to introduce said core stream into the nozzle at a location that is offset with respect to the longitudinal axis of the nozzle.

D2'. The nozzle system of claim D1' wherein said location is upstream from said at least one torsional zone.

D3'. The nozzle system of claim D1' wherein said at least one torsional zone constitutes a first torsional, said nozzle further comprising a second torsional zone.

D4'. The nozzle system of claim D3' wherein said location is upstream from the first torsional zone and at least a portion of the second torsional zone.

D5'. The nozzle system of claim D3' wherein the second torsional zone comprises an axially tapered region of the nozzle having a generally elliptical cross section.

D6'. The nozzle system of claim D5' wherein the major axis of the generally elliptical cross section of the first torsional zone is oriented in a different direction than the major axis of the generally elliptical cross section of the second torsional zone.

D7'. The nozzle system of claim D6' wherein the generally elliptical cross section of the first torsional zone is oriented at an angle of about 90 degrees with respect to the generally elliptical cross section of the second torsional zone.

D8'. The nozzle system of claim D7' wherein said location is upstream from the first torsional zone and at least a portion of the second torsional zone.

E'. Asymmetric Sample Introduction (Method)

E1'. A method of orienting particles in a flow cytometer comprising:
causing a sheath fluid to flow through a nozzle having a longitudinal axis and at least one torsional zone comprising an axially tapered region of the nozzle having a generally elliptical cross section; and
introducing a core fluid stream containing particles into the sheath fluid stream at a location that is offset from said longitudinal axis for flow of the sheath fluid stream and core fluid stream through the at least one torsional zone.

E2'. The method of claim E1 wherein the step of causing the fluid stream through at least one torsional zone comprises causing the core stream to flow along a flow path, a portion of said flow path being offset from the longitudinal axis of the nozzle, and subjecting said particles to hydrodynamic orientation forces generated by said torsional zone while said particles are moving along said offset portion of the flow path.

E3'. The method of claim E1 wherein said at least one torsional zone constitutes a first torsional zone, the method further comprising the step of causing the sheath fluid stream and core fluid stream to flow through a second torsional zone for orienting the particles in a desired orientation.

E4'. The method of claim E3 wherein said second torsional zones comprises a tapered region in the nozzle having generally elliptical cross sectional area.

E5'. The method of claim E4 wherein the major axis of the generally elliptical cross sectional area of the first torsional zone is oriented in a different direction than the major axis of the generally elliptical cross sectional area of the second torsional zone.

E6'. The method of claim E4 wherein the major axis of the generally elliptical cross sectional area of the first torsional zone is perpendicular to the major axis of the generally elliptical cross sectional area of the second torsional zone.

F'. Concentration of Sorted Sperm by Secondary Centrifugation

F1'. A method of processing animal sperm cells comprising the steps of:
collecting sperm cells from a male animal;
sorting the sperm cells into one of multiple populations of sperm cells on the basis of one or more specified DNA characteristics;

obtaining a quantity of sperm cells having a desired DNA characteristic from one of said multiple populations of sperm cells, said quantity of sperm cells being contained in a volume of collection fluid;

subjecting said volume of collection fluid to a first centrifugation process to form a first pellet of sperm cells and a supernatant overlying the first pellet;

separating the first pellet from the supernatant;

subjecting the supernatant to additional centrifugation to form a second pellet of sperm cells that remained in the supernatant after the first centrifugation; and adding a volume of resuspension fluid to the first and second pellets to obtain a suspension of sperm cells having the desired DNA characteristic, the amount of said volume of resuspension fluid being selected to result in a desired concentration of sperm cells in the suspension.

F2'. The method of claim F1' wherein the first centrifugation process comprises centrifuging at a speed sufficient to generate a g-force in the range of 550-800 g.

F3'. The method of claim F2' wherein the first centrifugation process comprises centrifuging said volume of collection fluid at said speed for a period in the range of 7-10 minutes.

F4'. The method of claim F1' wherein said one or more specified DNA characteristics comprises whether the sperm cell contains an X or a Y sex chromosome.

F5'. The method of claim F1' further comprising obtaining a plurality of quantities of sperm cells having a desired DNA characteristic and distributing said plurality of quantities of sperm cells to animal breeders through a commercial distribution system.

G'. Filtration with Low Pressure

G1'. A method of processing animal sperm cells comprising the steps of:

collecting sperm cells from a male animal;

sorting the sperm cells to obtain a quantity of sperm cells having a desired characteristic, said quantity of sorted sperm cells being contained in a first volume of fluid having a first concentration of sperm cells therein; and subjecting the sperm cells to a concentration step in which the concentration of said sperm cells is increased to a second concentration greater than said first concentration, wherein said concentration step comprises flowing at least a portion of the first volume of fluid through a first filter at a pressure differential across the first filter of less than about 20 in. mercury, said filter having filter pores sufficiently small to inhibit passage of said sperm cells therethrough, and retaining a second volume of unfiltered fluid containing said sperm cells.

G2'. The method of claim G1' wherein the pressure differential across the filter during said flowing is substantially constant.

G3'. The method of claim G1' further comprising the step of intermittently reducing the pressure differential across the filter for a period and then substantially restoring the pressure differential.

G4'. The method of claim G3' wherein the step of reducing the pressure differential comprises the step of reducing the pressure differential to about zero.

G5'. The method of claim G1' wherein the filter pores have a size of in the range of about 0.2-1.0 microns.

G6'. The method of claim G1' wherein about 80%-90% of said first volume of fluid flows through said first filter.

G7'. The method of claim G1' wherein said second volume of unfiltered fluid is sufficient to prevent caking of the sperm cells on said first filter.

G8'. The method of claim G1' further comprising flowing at least a portion of said second volume of unfiltered fluid through a second filter having filter pores sufficiently small to inhibit passage of said sperm cells therethrough, retaining a third volume of unfiltered fluid containing said sperm cells, and flushing said second filter with a resuspension fluid to remove sperm cells from the second filter for addition to said third volume to arrive at said second concentration.

G9'. The method of claim G8' wherein about 80% of the second volume of unfiltered fluid flows through said second filter.

G10'. The method of claim G8' wherein said third volume of unfiltered fluid is sufficient to prevent caking of the sperm cells on said second filter.

G11'. The method of claim G8' wherein said second filter is a thin filter having a thickness in the range of about 50-500 microns.

G12'. The method of claim G8' wherein said second filter is a thin filter having a thickness in the range of about 75-250 microns.

G13'. The method of claim G8' wherein said second filter is a thin filter having a thickness in the range of about 100-150 microns.

G14'. The method of claim G1' wherein said first filter is a thin filter having a thickness in the range of about 50-500 microns.

G15'. The method of claim G1' wherein said first filter is a thin filter having a thickness in the range of about 75-250 microns.

G16'. The method of claim G1' wherein said first filter is a thin filter having a thickness in the range of about 100-150 microns.

H'. Overall Temperature Control (High Temperature Staining)

H1'. A method of processing sperm cells comprising the steps of:

collecting a semen sample containing sperm cells from a male animal;

transporting the semen sample to a sperm processing facility;

conducting an initial quality control check on the semen;

staining the sperm cells in said semen sample with a DNA selective fluorescent dye that selectively binds to DNA in the sperm cells by exposing said sperm cells to a DNA selective fluorescent dye to form a staining mixture, and subjecting the staining mixture to a temperature of at least about 40° C.;

using a flow cytometer to sort the sperm cells on the basis of a specified DNA characteristic;

obtaining a quantity of sperm cells having a desired DNA characteristic suspended in a volume of fluid;

adjusting the concentration of sperm cells in said suspension by performing a concentration process to achieve a desired concentration; and supercooling said quantity of sperm cells.

H2'. The method of claim H1' further comprising maintaining the temperature of the sperm cells from the time they are collected until the beginning of the staining step at temperatures in the range of about 20-37° C. and insulating the sperm cells from temperature fluctuations during that time.

H3'. The method of claim H2' wherein the step of insulating the sperm cells comprises keeping the semen sample in an insulated container during transportation to the processing facility.

H4'. The method of claim H1' further comprising the step of placing the stained sperm cells in an environment having a temperature in the range of about 18-25° C. before they are introduced into said flow cytometer to cool the sperm cells from the temperature they attained during the staining step before beginning the sorting step.

H5'. The method of claim H1' wherein the supercooling step comprises cooling the sperm cells from a temperature that exceeds 20° C. to a temperature in the range of about 0-8° C., and adding a protein source and cryoprotectant to said sperm cells before the temperature of the sperm cells has been cooled below 20° C.

H6'. The method of claim H5' further comprising using a programmable freezer to: (a) cool the sperm cells to a holding temperature in the range of about 0-8° C.; (b) maintain the sperm at said holding temperature for a period of less than about 60 minutes to allow the sperm cells to substantially equilibrate with the cryoprotectant; (c) cool the sperm at a first cooling rate to a temperature that approaches a critical temperature zone in which ice crystal formation and changes in osmotic pressure damage sperm cells; and (d) cool the sperm cells through said critical temperature zone at a second cooling rate faster than said first cooling rate.

H7'. The method of claim H6' further comprising cooling the sperm cells from said holding temperature to about −15° C. at said first cooling rate.

H8'. The method of claim H7' further comprising cooling the sperm cells from about −18° C. to at least about −30° C. at said second cooling rate.

H9'. The method of claim H6' further comprising cooling the sperm cells from said holding temperature to about −18° C. at said first cooling rate.

H10'. The method of claim H6' further comprising using the programmable freezer to cool the sperm cells to said holding temperature at a cooling rate in the range of about 0.1-0.3° C. per minute.

H11'. The method of claim H10' further comprising using the programmable freezer to cool the sperm cells from said holding temperature to a temperature of about −15° C. at said first rate of about 1-5° C. per minute.

H12'. The method of claim H6' further comprising using the programmable freezer to cool the sperm cells from a temperature of about −18° C. to at least about −30° C. at said second cooling rate of about 8-12° C. per minute.

H13'. The method of claim H12' further comprising using the programmable freezer to cool the sperm cells from said holding temperature to a temperature of at least about −15° C. at said first cooling rate of about 1-5° C. per minute.

H14'. The method of claim H6' wherein the sperm cells are maintained at said holding temperature for a period of about 30 minutes.

H15'. The method of any one of claims H1'-H14' wherein the staining mixture further comprises an antioxidant.

H16'. The method of claim H15' wherein the antioxidant is selected from the group consisting of pyruvate, vitamin K, lipoic acid, and a combination thereof.

H17'. The method of any one of claims H1' or H5'-H16' further comprising placing the stained sperm cells in an environment having a temperature of at least about 37° C. until they are introduced into a flow cytometer.

H18'. The method of any one of claims H1' or H5'-H16' further comprising placing the stained sperm cells in an environment having a temperature of at least about 40° C. until they are introduced into a flow cytometer.

H19'. The method of claim H1' wherein the step of obtaining a quantity of sperm cells comprises obtaining a population of live sperm cells having said desired DNA characteristic at a rate of at least 5,000 sperm cells per second.

H20'. The method of claim H19' wherein the purity of said population is at least 85%.

J'. Overall Temperature Control (without High-Temp Staining)

J1'. A method of processing sperm cells comprising the steps of:
collecting a semen sample containing sperm cells from a male animal;
transporting the semen sample to a sperm processing facility;
performing an initial quality control check on the semen sample;
staining sperm cells in said semen sample with DNA selective fluorescent dye;
sorting the sperm cells with a flow cytometer to obtain one or more populations of sperm cells having a desired DNA characteristic;
obtaining a quantity of sperm cells having the desired DNA characteristic suspended in a fluid;
adjusting the concentration of said quantity of sperm cells to attain a desired concentration of sperm cells having the desired DNA characteristic in a fluid suspension;
adding a cryoprotectant to a quantity of sperm cells having said desired characteristic while said quantity of sperm cells has a temperature in excess of a glass transition temperature below which sperm cells are subject to damage from cold shock;
cooling said quantity of sperm cells and cryoprotectant said from said glass transition temperature to a holding temperature in the range of about 0-8° C.;
maintaining said quantity of sperm cells and cryoprotectant in a temperature range of about 0-8° C. for period of less than 60 minutes; and
supercooling said quantity of sperm to a temperature below −40° C.

J2'. The method of claim J1' wherein said cryoprotectant is added while said quantity of sperm cells has a temperature in excess of about 20° C.

J3'. The method of claim J1' wherein the stained sperm cells are placed in an environment having a temperature in the range of about 20-25° C. until they are sorted in a flow cytometer.

J4'. The method of claim J1' further comprising using a programmable freezer to cool said quantity of sperm at a first cooling rate from said holding temperature to a temperature that approaches a critical temperature zone in which ice crystal formation and changes in osmotic pressure damage sperm cells, and then to cool said quantity of sperm cells through said critical temperature zone at a second cooling rate that is faster than said first cooling rate.

J5'. The method of claim J1' wherein the step of maintaining said quantity of sperm cells comprises holding said quantity of sperm cells at said holding temperature for a period of less than about 40 minutes.

J6'. The method of claim J1' wherein the step of maintaining said quantity of sperm cells comprises holding said quantity of sperm cells at said holding temperature for a period of about 30 minutes.

J7'. The method of any one of claims J1'-J6' wherein the staining step further comprises adding an antioxidant to the sperm cells.

J8'. The method of claim J7' wherein the antioxidant is selected from the group consisting of pyruvate, vitamin K, lipoic acid, and a combination thereof.

J9'. The method of claim J1' wherein the step of obtaining a quantity of sperm cells having a desired DNA characteristic comprises obtaining a population of live sperm cells having said desired DNA characteristic at a rate of at least 5,000 sperm cells per second.

J10'. The method of claim J9' wherein the purity of said population of sperm cells is at least 85%.

K'. Overall Temperature Control (Cold Staining)

K1'. A method of processing sperm cells comprising the steps of:
collecting a semen sample containing sperm cells from a male animal;
transporting the semen sample to a sperm processing facility;
performing an initial quality control check on the semen sample;
cooling the sperm cells to a temperature in the range of about 0-8° C. before any substantial dilution of the sperm cells is performed;
forming a mixture comprising a solution containing the sperm cells and a DNA selective dye and subjecting the mixture to a temperature in the range of 0-8° C. to stain the sperm cells;
sorting the sperm cells with a flow cytometer to obtain one or more populations of sperm cells having a desired DNA characteristic;
obtaining a quantity of sperm cells having the desired DNA characteristic suspended in a fluid;
adjusting the concentration of said quantity of sperm cells to attain a desired concentration of sperm cells having the desired DNA characteristic in a fluid suspension;
adding a cryoprotectant to said quantity of sperm cells;
holding said quantity of sperm cells and said cryoprotectant at a holding temperature in the range of about 0-8° C. for a period in the range of about 30 minutes to 3 hours; and
supercooling said quantity of sperm cells to a temperature below 40°.

K2'. The method of claim K1' further comprising the step of substantially avoiding warming the cells at any time during the process.

K3'. The method of claim K1' wherein the step of cooling the sperm cells to a temperature in the range of 0-8° comprises placing a container holding the sperm cells into a water bath that is substantially the same temperature as the pre-cooled sperm cells and placing the water bath in an environment having a temperature less than about 8° C.

K4'. The method of claim K3' wherein the cooling step further comprises monitoring the temperature of the sperm cells as they cool and adding ice to the water bath after the sperm cells have cooled to a temperature less than about 10° C.

K5'. The method of claim K1' wherein said holding period is in the range of about 1-2 hours.

K6'. The method of claim K1' wherein said holding period is in the range of about 90 minutes.

K7'. The method of claim K1' wherein said holding period is in the range of about 30 minutes to less than 60 minutes.

K8'. The method of claim K1' wherein the step of supercooling said quantity of sperm cells comprises using a programmable freezer to cool said quantity of sperm at a first cooling rate from said holding temperature to a temperature that approaches a critical temperature zone in which ice crystal formation and changes in osmotic pressure damage sperm cells, and then to cool said quantity of sperm cells through said critical temperature zone at a second cooling rate that is faster than said first cooling rate.

K9'. The method of claim K1' wherein the step of adding a cryoprotectant comprises adding glycerol.

K10'. The method of claim K1' wherein the step of adding a cryoprotectant comprises adding 7% glycerol (v/v).

K11'. The method of claim K1' where in the step of obtaining a quantity of sperm cells having a desired DNA characteristic comprises obtaining a population of live sperm cells having said desired DNA characteristic at a rate of at least 5,000 sperm cells per second.

K12'. The method of claim K11' wherein the purity of said population of sperm cells is at least 85%.

L'. Collection System (Apparatus)

L1'. A collection system for collecting a stream of droplets sorted by a droplet sorting flow cytometer that produces a stream of droplets moving along a trajectory that includes a horizontal component, the system comprising an intercepting device for intercepting droplets in said stream as they move along said trajectory, and a collection vessel disposed to collect said intercepted droplets.

L2'. The collection system of claim L1' wherein the intercepting device comprises an impact surface disposed across said trajectory against which said droplets are adapted to impact.

L3'. The collection system of claim L2' wherein the impact surface is disposed across said trajectory at a location at which said droplets have an upward velocity component.

L4'. The collection system of claim L2' wherein at least some of the droplets contain particles and the impact surface is coated with a substance that reduces damage to said particles upon impact with the impact surface.

L5'. The collection system of claim L4' wherein said substance comprises one or more substances selected from the group consisting of egg yolk, bovine serum albumin, and phosphate buffered saline.

L6'. The collection system of claim L4' wherein said particles are sperm cells.

L7'. The collection system of claim L2' wherein said intercepting device is configured for guiding said intercepted droplets to the collection vessel.

L8'. The collection system of claim L7' wherein the intercepting device comprises a guide below said impact surface for guiding said droplets down to said collection vessel.

L9'. The collection system of claim L7' wherein the intercepting device comprises a hollow enclosure defining said impact surface and having an entry window for entry of droplets moving along said trajectory into said enclosure for impact against said impact surface.

L10'. The collection system of claim L1' wherein said stream of droplets constitutes a first stream of droplets, said intercepting device constitutes a first intercepting device, said collection vessel constitutes a first collection vessel, and said cytometer also produces a second stream of droplets moving along a second trajectory that is different from said first trajectory, said collection system further comprising a second intercepting device for intercepting droplets moving along said second trajectory and a second collection vessel for collecting droplets intercepted by the second intercepting device.

L11'. The collection system of claim L10' wherein said first intercepting device has a window therein through which said second stream is adapted to pass, and wherein said second intercepting device is positioned behind said first intercepting device for intercepting droplets in the second stream passing through said window.

L12'. The collection system of claim L10' wherein said second intercepting device is configured for guiding said intercepted droplets in the second stream to the second collection vessel.

L13'. The collection system of claim L1' wherein said droplets contain particles, the collection system further comprising a substance coating the impact surfaces of the intercepting devices for reducing damage to said particles upon impact.

L14'. The collection system of claim L13' wherein said particles comprise live sperm cells.

L15'. The collection system of claim L13' wherein said substance comprises a substance selected from the group consisting of: egg yolk, bovine serum albumin, and phosphate buffered saline.

L16'. The collection system of claim L1' in combination with a flow cytometer positioned to direct a droplet stream into the intercepting device.

M'. Collection System (Method)

M1'. A method of collecting droplets sorted by a droplet sorting flow cytometer that produces a stream of droplets moving along a trajectory that includes a horizontal component, said method comprising the steps of:

intercepting said droplets as they move along said trajectory; and collecting said intercepted droplets in a first collection vessel.

M2'. The method of claim M1' wherein said collecting step comprises guiding said intercepted droplets into said first collection vessel.

M3'. The method of claim M2' wherein said intercepting step comprises positioning an impact surface across said trajectory at a location at which said droplets have an upward velocity component.

M4'. The method of claim M3' further comprising adjusting the position of said impact surface to accommodate different droplet trajectories.

M5'. The method of claim M1' wherein said flow cytometer produces first and second streams of droplets moving along respective first and second trajectories, each trajectory having a horizontal component, said method further comprising intercepting said droplets in said second stream as they move along said second trajectory, and collecting said intercepted droplets of the second stream in a second collection vessel.

M6'. The method of claim M5' wherein said first and second trajectories lie substantially in one plane.

M7'. The method of claim M5' wherein droplets in said first stream are intercepted by positioning a first impact surface across said first trajectory at a location at which said droplets have an upward velocity component, and wherein droplets in said second stream are intercepted by positioning a second impact surface across said second trajectory at a location at which said droplets have an upward velocity component.

M8'. The method of claim M7' wherein said second impact surface is positioned at a different elevation than said first impact surface.

M9'. The method of claim M1' wherein said droplets contain particles and the step of intercepting the said droplets comprises using an intercepting device to intercept said droplets, the method further comprising contacting said intercepting device with a composition to reduce damage to said particles.

M10'. The method of claim M9' wherein said particles comprise live sperm cells.

M11'. The method of claim M10' wherein said composition comprises a substance selected from the group consisting of: egg yolk, bovine serum albumin, and phosphate buffered saline.

M12'. The method of claim M10' wherein the step of contacting said intercepting device with a composition comprises soaking said intercepting device in said composition for a period that is sufficient for the composition be absorbed by and/or adhere to the intercepting device.

M13'. The method of claim M12' wherein said period is in the range of about 30-90 minutes.

M14'. The method of claim M13' wherein said period is in the range of about 30-60 minutes.

M15'. The method of claim M14' wherein said period is about 60 minutes.

M16'. The method of any of claims M10'-M15' wherein the step of collecting said droplets comprises collecting said droplets in a collection vessel, the method further comprising the step of contacting the collection vessel with a composition to reduce damage to said particles.

M17'. The method of claim M16' further wherein the step of contacting the collection vessel with a composition to reduce damage to the particles comprises contacting the collection vessel with the same composition used to contact the intercepting device.

M18'. The method of claim M16' wherein the step of contacting the collection vessel with a composition to reduce damage to said particles comprises soaking the collection vessel in said composition for a period that is sufficient for the composition to be absorbed by and/or adhere to the collection vessel.

M19'. The method of claim M18' wherein said period is in the range of about 30-90 minutes.

M20'. The method of claim M18' wherein said period is about 60 minutes.

N'. Synergistic Combinations a. Multi-Channel FCM (with Sort Strategy)

Na1'. A method of processing animal sperm cells comprising the steps of:

sorting the sperm cells into different populations of sperm cells on the basis of one or more specified DNA characteristics using a flow cytometry process comprising delivering a sample fluid containing the sperm cells to a plurality of flow cytometry units each of which is operable to sort the sperm cells on the basis of said one or more DNA characteristics, and operating said units while sharing an integrated platform comprising at least one of the following elements: (1) a common supply of sperm cells; (2) a common source of electromagnetic radiation; (3) a common housing; (4) a common input for controlling operation of the units; (5) a common processor for receiving and processing information from the units to permit evaluation of the operation of one unit relative to another unit; and (6) a common fluid delivery system for delivering fluid containing said sperm cells to said flow cytometry units; and varying the rate at which sample fluid is delivered to one or more of the flow cytometry units as a function of at least one of the following: (1) the purity of a first sorted population of sperm cells having a desired DNA characteristic; and (2) the quantity of sperm cells having said desired DNA characteristic in a second sorted population.

Na2'. The method of claim Na1' further comprising operating said flow cytometry units in parallel.

Na3'. The method of claim Na1' wherein said one or more specified DNA characteristics comprises whether a sperm cell contains an X or a Y sex chromosome.

b. Multi-Channel FCM with Digital Processing

Nb1'. A method of processing animal sperm cells comprising the steps of:

sorting the sperm cells into different populations of sperm cells on the basis of one or more specified DNA characteristics using a flow cytometry process comprising delivering a sample fluid containing the sperm cells to a plurality of flow cytometry units each of which is operable to sort the sperm cells on the basis of said one or more DNA characteristics, and operating said units while sharing an integrated platform comprising at least one of the following elements: (1) a common supply of sperm cells; (2) a common source of electromagnetic radiation; (3) a common housing; (4) a common input for controlling operation of the units; (5) a common processor for receiving and processing information from the units to permit evaluation of the operation of one unit relative to another unit; and (6) a common fluid delivery system for delivering fluid containing said sperm cells to said flow cytometry units; and using one or more analog to digital converters to synchronously sample a time-varying output from each flow cytometry unit and provide an output including digital information corresponding to said time-varying analog output wherein said time-varying analog output and the corresponding digital information are indicative of said specified DNA characteristic.

Nb2'. The method of claim Nb1' wherein said one or more specified DNA characteristics comprises whether a sperm cell has an X or a Y sex chromosome.

c. Multi-Channel FCM (w/ High-Temperature Staining)

Nc1'. A method of processing animal sperm cells comprising the steps of:

forming a staining mixture containing the sperm cells and a DNA selective fluorescent dye, and subjecting the staining mixture to a temperature of at least about 40° C.; and sorting the sperm cells into different populations of sperm cells on the basis of one or more specified DNA characteristics using a flow cytometry process comprising delivering a sample fluid containing the sperm cells to a plurality of flow cytometry units each of which is operable to sort the sperm cells on the basis of said one or more DNA characteristics, and operating said units while sharing an integrated platform comprising at least one of the following elements: (1) a common supply of sperm cells; (2) a common source of electromagnetic radiation; (3) a common housing; (4) a common input for controlling operation of the units; (5) a common processor for receiving and processing information from the units to permit evaluation of the operation of one unit relative to another unit; and (6) a common fluid delivery system for delivering fluid containing said sperm cells to said flow cytometry units.

Nc2'. The method of claim Nc1' wherein the dye is a UV excitable or a visible light excitable dye.

Nc3'. The method of claim Nc2' wherein the dye is selected from the group consisting of a bisbenzimide, SYBR-14, and a conjugate, an analog, or a derivative thereof.

Nc4'. The method of any one of claims Nc1'-Nc3' wherein the staining mixture is subjected to the temperature for a period of time sufficient to allow the dye to bind the DNA such that X and Y bearing sperm cells can be differentially sorted based upon fluorescence.

Nc5'. The method of claim Nc4' wherein the period of time is in the range of about 1-160 minutes.

Nc6'. The method of any one of claims Nc1'-Nc5' wherein the staining mixture further comprises an antioxidant.

Nc7'. The method of claim Nc1' wherein said one or more characteristics comprises whether a sperm cell contains an X or a Y sex chromosome.

d. Multi-Channel (with Rapid Cryopreservation)

Nd1'. A method of processing animal sperm cells comprising the steps of:

sorting the sperm cells into different populations of sperm cells on the basis of one or more specified DNA characteristics using a flow cytometry process comprising delivering a sample fluid containing the sperm cells to a plurality of flow cytometry units each of which is operable to sort the sperm cells on the basis of said one or more DNA characteristics, and operating said units while sharing an integrated platform comprising at least one of the following elements: (1) a common supply of sperm cells; (2) a common source of electromagnetic radiation; (3) a common housing; (4) a common input for controlling operation of the units; (5) a common processor for receiving and processing information from the units to permit evaluation of the operation of one unit relative to another unit; and (6) a common fluid delivery system for delivering fluid containing said sperm cells to said flow cytometry units;

obtaining a quantity of sperm cells having a desired DNA characteristic from one or more of the sorted populations of sperm cells;

adding a cryoprotectant to said quantity of sperm cells;

cooling said quantity of sperm cells and the cryoprotectant to a holding temperature of about 0-8° C.;

maintaining said sperm cells and said cryoprotectant substantially at said holding temperature for a period of less than 60 minutes; and supercooling said quantity of sperm cells to a temperature of −40° C.

Nd2'. The method of claim Nd1' wherein the step of adding a cryoprotectant comprises adding glycerol.

Nd3'. The method of claim Nd1' wherein said one or more specified DNA characteristics comprises whether a sperm cell has an X or a Y sex chromosome.

Nd4'. The method of claim Nd1' wherein the step of cooling said quantity of sperm cells to said holding temperature comprises using a cooling rate that is selected so that said quantity of sperm cells is cooled from a temperature above a glass transition temperature below which sperm cells are subject to damage from cold shock to said holding temperature in about 90 minutes.

Nd5'. The method of claim Nd4' wherein the cooling rate is a substantially constant cooling rate in the range of about 0.1-0.3° C. per minute.

Nd6'. The method of claim Nd1' wherein the step of supercooling said quantity of sperm comprises cooling the sperm cells at a first cooling rate to a temperature that approaches a critical temperature zone at which ice crystal formation and changes in osmotic pressure damage sperm cells and cooling the sperm at a second cooling rate faster than said first cooling rate to a temperature that is less than about −30° C.

Nd7'. The method of Nd1' further comprising:

forming a staining mixture containing the sperm cells and a DNA selective fluorescent dye, and subjecting the staining mixture to a temperature of at least about 40° C.

e. Sort Strategy (with High-Temperature Staining)

Ne1'. A method of processing animal sperm cells comprising the steps of:

forming a staining mixture containing the sperm cells and a DNA selective fluorescent dye, and subjecting the staining mixture to a temperature of at least about 40° C.;

delivering a fluid stream of said staining mixture containing the sperm cells to a first location and causing said stream to break into droplets at a second location, said droplets comprising first droplets each containing one or more sperm cells having a desired sex chromosome, second droplets each containing one or more sperm cells having an undesired sex chromosome, and third droplets each containing one or more sperm cells having the desired sex chromosome and one more sperm cells having the undesired sex chromosome;

sorting said first droplets from said second and third droplets;

collecting said first droplets to provide at least one population of sperm cells having a desired sex chromosome;

identifying a quantity of sperm cells having the desired sex chromosome in said at least one population; and varying the rate at which fluid is delivered to said first location as a function of the quantity of sperm cells identified as having the desired sex chromosome in said at least one population relative to the total number of sperm cells having the desired sex chromosome in said first, second, and third droplets.

Ne2'. A method of processing animal sperm cells comprising the steps of:

forming a staining mixture containing the sperm cells and a DNA selective fluorescent dye, and subjecting the staining mixture to a temperature of at least about 40° C.;

delivering a fluid stream of said staining mixture containing the sperm cells to a first location and causing said stream to break into droplets at a second location, said droplets comprising first droplets each containing one or more sperm cells having a desired sex chromosome, second droplets each containing one or more sperm cells having an undesired sex chromosome, and third droplets each containing one or more sperm cells having the desired sex chromosome and one more sperm cells having the undesired sex chromosome;

sorting said first droplets and third droplets from said second droplets;

collecting said first and third droplets to provide at least one population of sperm cells having a desired sex chromosome;

identifying a quantity of sperm cells having the undesired sex chromosome in said at least one population; and varying the rate at which fluid is delivered to said first location as a function of the quantity of sperm cells identified as having the undesired sex chromosome in said at least one population.

f. High-Temp Staining (w/ Rapid Cryopreservation)

Nf1'. A method of processing animal sperm cells comprising the steps of:

forming a staining mixture containing the sperm cells and a DNA selective fluorescent dye, and subjecting the staining mixture to a temperature of at least about 40° C.;

sorting said sperm cells in said staining mixture on the basis of a specified DNA characteristic;

obtaining a quantity of sperm cells having a desired DNA characteristic;

adding a cryoprotectant to said quantity of sperm cells;

cooling said quantity of sperm cells and the cryoprotectant to a holding temperature of about 0-8° C.;

maintaining said sperm cells and said cryoprotectant substantially at the holding temperature for a period of less than 60 minutes; and supercooling said quantity of sperm cells to a temperature of −40° C.

Nf2'. The method of claim Nf1 wherein the step of adding a cryoprotectant comprises adding glycerol.

Nf3'. The method of claim Nf1 wherein said specified DNA characteristic is whether a sperm cell contains an X or a Y sex chromosome.

Nf4'. The method of claim Nf1 wherein the step of cooling said quantity of sperm cell comprises using a cooling rate that is selected so that said quantity of sperm cells is cooled to about 0-8° C. in about 90 minutes.

Nf5'. The method of claim Nd4 wherein the cooling rate is a substantially constant cooling rate in the range of about 0.1-0.3° C. per minute.

Nf6'. The method of claim Nf1 wherein the step of supercooling said quantity of sperm comprises cooling the sperm cells at a first cooling rate to a temperature that approaches a critical temperature zone at which ice crystal formation and changes in osmotic pressure damage sperm cells and cooling the sperm at a second cooling rate faster than said first cooling rate to a temperature that is less than about −30° C.

g. Multiple Combinations

Ng1'. (high-temperature staining/Multi-channel sorting/rapid cryopreservation)

A method of processing animal sperm cells comprising the steps of:

forming a staining mixture containing the sperm cells and a DNA selective fluorescent dye, and subjecting the staining mixture to a temperature of at least about 40° C.;

sorting the sperm cells in said staining mixture into different populations of sperm cells on the basis of one or more specified DNA characteristics using a flow cytometry process comprising delivering a sample fluid to a plurality of flow cytometry units each of which is operable to sort the sperm cells on the basis of said one or more DNA characteristics, and operating said units while sharing an integrated platform comprising at least one of the following elements: (1) a common supply of sperm cells; (2) a common source of electromagnetic radiation; (3) a common housing; (4) a common input for controlling operation of the units; (5) a common processor for receiving and processing information from the units to permit evaluation of the operation of one unit relative to another unit; and (6) a common fluid delivery system for delivering fluid containing said sperm cells to said flow cytometry units;

obtaining a quantity of sperm cells having a desired DNA characteristic;

adding a cryoprotectant to said quantity of sperm cells;

cooling said quantity of sperm cells and the cryoprotectant to a holding temperature of about 0-8° C.;

maintaining said sperm cells and said cryoprotectant substantially at the holding temperature for a period of less than 60 minutes; and supercooling said quantity of sperm cells to a temperature of −40° C.

Ng2'. (High temperature staining/multi-channel sorting/high purity sort strategy)

A method of processing animal sperm cells comprising the steps of:

forming a staining mixture containing the sperm cells and a DNA selective fluorescent dye, and subjecting the staining mixture to a temperature of at least about 40° C.;

delivering a fluid stream of said staining mixture containing the sperm cells to each of a plurality of flow cytometry units and using the flow cytometry units to break each fluid stream into droplets, said droplets comprising first droplets each containing one or more sperm cells having a desired sex chromosome, second droplets each containing one or more sperm cells having an undesired sex chromosome, and third droplets each containing one or more sperm cells having the desired sex chromosome and one more sperm cells having the undesired sex chromosome;

sorting said first droplets from said second and third droplets using a droplet sorting flow cytometry process comprising operating said plurality of flow cytometry units while sharing an integrated platform comprising at least one of the following elements: (1) a common supply of sperm cells; (2) a common source of electromagnetic radiation; (3) a common housing; (4) a common input for controlling operation of the units; (5) a common processor for receiving and processing information from the units to permit evaluation of the operation of one unit relative to another unit; and (6) a common fluid delivery system for delivering fluid containing said sperm cells to said flow cytometry units;

collecting said first droplets to provide at least one population of sperm cells having a desired sex chromosome;

identifying a quantity of sperm cells having the desired sex chromosome in said at least one population; and varying the rate at which fluid is delivered to one or more of the flow cytometry units as a function of the quantity of sperm cells identified as having the desired sex chromosome in said at least one population relative to the total number of sperm cells having the desired sex chromosome in said first, second, and third and third droplets.

Ng3'. (High temperature staining/multi-channel sorting/high recovery sort strategy)

A method of processing animal sperm cells comprising the steps of:

forming a staining mixture containing the sperm cells and a DNA selective fluorescent dye, and subjecting the staining mixture to a temperature of at least about 40° C.;

delivering a fluid stream of said staining mixture containing sperm cells to each of a plurality of flow cytometry units and using the flow cytometry units to break each fluid stream into droplets, said droplets comprising first droplets each containing one or more sperm cells having a desired sex chromosome, second droplets each containing one or more sperm cells having an undesired sex chromosome, and third droplets each containing one or more sperm cells having a desired sex chromosome and one more sperm cells having an undesired sex chromosome;

sorting said first droplets and third droplets from said second droplets using a droplet sorting flow cytometry process comprising operating said plurality of flow cytometry units while sharing an integrated platform comprising at least one of the following elements: (1) a common supply of sperm cells; (2) a common source of electromagnetic radiation; (3) a common housing; (4) a common input for controlling operation of the units; (5) a common processor for receiving and processing information from the units to permit evaluation of the operation of one unit relative to another unit; and (6) a common fluid delivery system for delivering fluid containing said sperm cells to said flow cytometry units;

collecting said first and third droplets to provide at least one population of sperm cells having a desired sex chromosome;

identifying a quantity of sperm cells having the undesired sex chromosome in said at least one population; and varying the rate at which fluid is delivered to one or more of the flow cytometry units as a function of the quantity of sperm cells identified as having the undesired sex chromosome in said at least one population.

Ng4'. (High temperature staining/multi-channel sorting/sort strategy/rapid cryopreservation)

A method of processing animal sperm cells comprising the steps of:

forming a staining mixture containing the sperm cells and a DNA selective fluorescent dye, and subjecting the staining mixture to a temperature of at least about 40° C.;

delivering a fluid stream of said staining mixture containing sperm cells to each of a plurality of flow cytometry units, using the flow cytometry units to break each fluid stream into droplets, and sorting said droplets according to one or more specified DNA characteristics of the sperm cells contained in the droplets to obtain one or more populations of sperm cells having a desired DNA characteristic by using a droplet sorting flow cytometry process comprising operating said plurality of flow cytometry units while sharing an integrated platform comprising at least one of the following elements: (1) a common supply of sperm cells; (2) a common source of electromagnetic radiation; (3) a common housing; (4) a common input for controlling operation of the units; (5) a common processor for receiving and processing information from the units to permit evaluation of the operation of one unit relative to another unit; and (6) a common fluid delivery system for delivering fluid containing said sperm cells to said flow cytometry units;

varying the rate at which fluid is delivered to one or more of the flow cytometry units as a function of at least one of the following: (1) the purity of said one or more populations of sperm cells having a desired DNA characteristic; and (2) the quantity of sperm cells having the desired DNA characteristic in said one or more populations of sperm cells relative to the total number of sperm cells having the desired DNA characteristic in said droplets;

adding a cryoprotectant to protect a quantity of sperm cells obtained from said one or more populations of sperm cells;

cooling said quantity of sperm cells and said cryoprotectant to a holding temperature of about 0-8° C.;

maintaining said sperm cells and said cryoprotectant substantially at said holding temperature for a period of less than 60 minutes; and supercooling said quantity of sperm cells to a temperature of −40° C.

O'. Overall Time Line

O1'. A method of processing animal sperm cells comprising the steps of:

collecting sperm cells from a male animal;

staining the sperm cells with a DNA selective fluorescent dye;

illuminating the sperm cells with electromagnetic radiation to cause the DNA selective fluorescent dye to emit fluorescent light;

detecting the fluorescent light emitted by the sperm cells;

analyzing the fluorescent light emitted by the sperm cells to determine one or more specified DNA characteristics of the sperm cell;

sorting the sperm cells into multiple populations of sperm cells on the basis of said one or more specified DNA characteristics;

obtaining a quantity of sperm cells having a desired DNA characteristic from one of said multiple populations of sperm cells; and supercooling said quantity of sperm cells;

wherein the step of supercooling is completed less than about 12 hours after the sperm cells are collected.

O2'. The method of claim O1' wherein the step of supercooling said quantity of sperm cells is completed less than about 8 hours after the sperm cells are collected.

O3'. The method of claim O1' wherein the step of supercooling said sperm cells is completed less than about 6 hours after the sperm cells are collected.

O4'. The method of claim O1' wherein the step of supercooling said quantity of sperm cells is completed less than about 3 hours after the sperm cells are collected.

O5'. The method of claim O1' wherein the step of supercooling said quantity of sperm cells is completed less than about 2 hours after the sperm cells are collected.

O6'. The method of claim O1' wherein the step of supercooling said quantity of sperm cells is completed less than about 1 hour after the sperm cells are collected.

O7'. The method of claim O1' wherein the sperm cells comprise live sperm cells.

O8'. The method of claim O7' wherein said one or more DNA characteristics comprises whether the sperm cell contains an X or a Y sex chromosome.

O9'. The method of claim O1' further comprising the steps of thawing said quantity of sperm cells after the supercooling step and then fertilizing an egg cell with a sperm cell from said quantity of sperm cells by artificial insemination.

O10'. The method of claim O1' further comprising producing a plurality of quantities of sperm cells having a desired characteristic and distributing said plurality of quantities of sperm cells to animal breeders through a commercial distribution system.

P'. Sort Speeds

P1'. A method of sorting live sperm cells according to chromosome content comprising:

(a) adding a DNA selective fluorescent dye to a supply of live sperm cells;

(b) causing a sample fluid containing said sperm cells and a sheath fluid to flow through an orienting nozzle that tends to rotate the sperm cells into a desired orientation, said sample fluid and sheath fluid exiting the nozzle as a fluid stream comprising a core stream formed by the sample fluid and sperm cells and a sheath fluid stream surrounding the core stream;

(c) applying acoustical energy to the nozzle to cause the fluid stream to break into a stream of droplets at a droplet break-off location downstream from the nozzle;

(d) directing a beam of electromagnetic radiation to intersect the fluid stream at an interrogation location upstream from the droplet break-off location to excite the fluorescent dye in the sperm cells, thereby causing fluorescent emissions from the sperm cells;

(e) detecting the fluorescent emissions with a photodetector that outputs a time-varying analog signal indicative of the intensity of the detected fluorescent emissions;

(f) electronically processing said time-varying analog signal to determine the chromosomal content of a plurality of the sperm cells;

(g) selectively applying an electrostatic charge to the fluid stream to selectively apply or not apply an electrical charge to the droplets according to the chromosomal content of sperm cells contained in the droplets;

(h) using an electric field to deflect the droplets according to their charge, thereby separating sperm cells contained in droplets having the same charge from sperm cells contained in droplets having a different charge; and (i) collecting at least one population of live sperm cells at a rate of at least 5,000 sperm cells per second.

P2'. P1' wherein the at least one population collected in the collecting step has a purity of at least 85%.

P3'. P1' wherein said collecting step comprises collecting the at least one population of live sperm cells at a rate of at least 6,000 sperm cells per second.

P4'. P1' wherein said collecting step comprises collecting the at least one population of live sperm cells at a rate of at least 7,000 sperm cells per second.

P5'. P1' further comprising operating two or more cytometry units in parallel so that each performs steps (b) through (i) while they share an integrated platform, said integrated platform comprising one or more of the following: (1) a common supply of particles; (2) a common source of electromagnetic radiation; (3) a common housing; (4) a common input for controlling operation of the units; (5) a common processor for receiving and processing information from the units to permit evaluation of the operation of one unit relative to another unit; and (6) a common fluid delivery system for delivering fluid containing said particles to said flow cytometry units.

P6'. P5' wherein the step of operating said two or more flow cytometry units while they share an integrated platform comprises operating a mode-locked solid state laser to produce a single beam comprising a plurality of electromagnetic pulses, the peak power of each pulse being greater than the average power output of the laser, splitting the single beam into two or more beams, and directing each of said two or more beams to one of the flow cytometry units.

R'. CSD & Slit Scanning a. Sperm Cells

R1'. A method of analyzing chromosomal DNA characteristics of animal sperm cells in a fluid stream having a direction of flow, each sperm cell having a head with a nucleus comprising a localized chromosome region containing at least one chromosome, said nucleus having a length in the direction of stream flow, said method comprising:

focusing a beam of electromagnetic radiation on the fluid stream as a generally elliptical spot having a length along a major axis extending generally at right angles to the direction of stream flow and a width along a minor axis extending generally parallel to the direction of stream flow, the width of the beam spot being less than the length of said nucleus, said sperm cells being adapted to pass through said spot resulting in emissions of electromagnetic radiation from the sperm cells, including emissions from said chromosome regions indicative of chromosomal. DNA characteristics of the regions;

detecting and converting at least some of said emissions from the chromosome regions into time-varying analog electrical signals indicative of said chromosomal DNA characteristics;

digitally sampling the time-varying analog signal and providing an output including digital information corresponding to said time-varying analog signal;

analyzing the digital information to extract information indicative of a derivative characteristic of the time-varying analog signals; and classifying at least some of the sperm cells as having a particular chromosomal DNA characteristic based at least in part on said extracted information.

R2'. The method of claim R1' wherein said chromosomal DNA characteristics are indicative of the sex of the sperm cells.

R3'. The method of claim R2' wherein said sperm cells are bovine sperm cells.

R4'. The method of claim R3' wherein said chromosome region is localized within an area of the nucleus extending no more than about 20% of the nucleus length on either side of a longitudinal center of the nucleus.

R5'. The apparatus of claim R3' wherein said chromosome region is localized within an area of the nucleus extending no more than about 10%-15% of the nucleus length on either side of a longitudinal center of the nucleus.

R6'. The method of claim R1' wherein the digitally sampling step comprises synchronously sampling the time-varying analog output.

R7'. The method of claim R1' wherein said spot width is less than about 3.0 μm.

R8'. The method of claim R7' wherein said spot length is greater than about 100 μm.

R9'. The method of claim R1' further comprising exerting a force on the sperm cells in the stream tending to bring them into a desired orientation before the stream passes through said beam.

R10'. The method of claim R1' further comprising droplet sorting droplet said sperm cells according to said chromosomal DNA characteristics.

R11'. The method of claim R1' further comprising a photo-damage sorting said sperm cells according to said chromosomal DNA characteristics.

R12'. The method of claim R1' further comprising fluid-switching sorting sperm cells according to said chromosomal DNA characteristics.

R13'. The method of claim R1' wherein said derivative characteristic comprises the slope of the time-varying analog signal at a point of the signal relative to a threshold value.

b. Generic Particles

R14'. A method of analyzing particles in a fluid stream having a direction of flow, said method comprising:

focusing a beam of electromagnetic radiation on the fluid stream as a generally elliptical spot having a length along a major axis extending generally at right angles to the direction of stream flow and a width along a minor axis extending generally parallel to the direction of stream flow, the width of the beam spot being less than the size of said particles, said particles being adapted to pass through said spot resulting in emissions of electromagnetic radiation from the particles;

detecting and converting at least some of said emissions into time-varying analog electrical signals indicative of characteristics of the particles;

digitally sampling the time-varying analog signal and providing an output including digital information corresponding to said time-varying analog signal;

analyzing the digital information to extract information indicative of a derivative characteristic of the time-varying analog signals; and classifying at least some of the particles as having a particular characteristic based at least in part on said extracted information.

R15'. The method of claim R14' wherein the digitally sampling step comprises synchronously sampling the time-varying analog output.

R16'. The method of claim R14' further comprising droplet sorting droplet said particles according to said classification.

R17'. The method of claim R14' further comprising a photo-damage sorting said sperm cells according to said chromosomal DNA characteristics.

R18'. The method of claim R14' further comprising fluid-switching sorting sperm cells according to said chromosomal DNA characteristics.

R19'. The method of claim R14' wherein derivative characteristic comprises the slope of the time-varying analog signal at a point of the signal relative to a threshold value.

S'. Pulsed Laser FCM Apparatus

S1'. A flow cytometry apparatus comprising:

a flow channel for directing a fluid stream containing sample particles through a particle interrogation location;

a laser operable to emit a plurality of electromagnetic radiation (EMR) pulses, each pulse having a peak power that exceeds the average power of the laser, said pulses being directed along a beam path from the laser to the particle interrogation location;

a timing circuit operable to produce a timing signal indicative of the of arrival of pulses at the interrogation location;

a detector adapted to detect EMR from the interrogation location and operable to output a time-varying analog signal indicative the intensity of the detected EMR;

an analog to digital converter adapted to receive the time-varying analog signal as input and to sample the analog signal to produce a digitized output; and an electronic processor operable to analyze the digitized output from the analog to digital converter as a function of the timing signal.

S2'. The apparatus of S1' wherein the laser is operable to emit EMR pulses having a width of about 1-100 picoseconds at a pulse frequency of about 50-150 MHz at a power of about 100-500 milliwatts.

S3'. The apparatus of S2' wherein the laser is operable to emit EMR pulses having a width of about 5-20 picoseconds at a frequency of about 70-100 MHz.

S4'. The apparatus of S1' wherein the timing circuit comprises a sensor adapted to sense light corresponding to the EMR pulses including scattered light generated by interaction of each pulse with the fluid stream or including light of the EMR pulse.

S5'. The apparatus of S1' wherein the timing circuit comprises a clock that is operable to trigger the laser to emit a pulse.

S6'. The apparatus of S1' wherein the detector is adapted to detect fluorescent emissions stimulated by the excitation energy of the pulses.

S7'. The apparatus of S1' wherein the laser comprises a mode-locked solid state laser.

S8'. The apparatus of S1' wherein the laser comprises a Q-switched laser.

S9'. The apparatus of S1' wherein the laser comprises a cavity dumping laser.

S10'. The apparatus of S1' wherein the detector is a photomultiplier tube.

S11'. The apparatus of S9' wherein the photomultiplier tube has a response time of less than about 2 nanoseconds.

S12'. The apparatus of S1' wherein the electronic processor is operable to process the digitized output as a pulse waveform.

S13'. The apparatus of S12' wherein the electronic processor is operable to extract at least one of the following features from the digitized output: critical slope difference; pulse rise time; pulse peak; and pulse area.

T'. Pulsed Laser Method

T1'. A method of analyzing particles contained in a fluid stream as they flow through an interrogation location, said method comprising the steps of:

emitting a plurality of electromagnetic radiation (EMR) pulses from a laser, wherein the peak power of each pulse exceeds the average power of the laser;

intermittently illuminating the fluid stream and the particles contained therein by directing said pulses along a beam path from the laser to the interrogation location;

detecting EMR from the interrogation location;

generating a time-varying analog signal indicative of the intensity of the detected EMR;

generating a timing signal indicative of the arrival of a pulse at the interrogation location;

converting the time-varying analog signal into a digital signal; and analyzing the digital signal to determine characteristics of the particles in the fluid stream.

T2'. The method of T1' wherein the step of converting the time-varying analog signal to a digital signal comprises sampling the analog signal at a time that is synchronized to coincide with the illumination of the fluid stream by a pulse.

T3'. The method of T1' wherein the step of illuminating the fluid stream results in excitation of a fluorophore associated with said particles and the step of converting the time-varying analog signal to a digital signal comprises sampling the analog signal at a predetermined time after illumination of the interrogation and within the fluorescent lifetime decay of said fluorophore.

T4'. The method of T1' wherein each pulse contains sufficient power to saturate said fluorophore.

T5'. The method of T1' wherein the step of detecting light from the interrogation location comprises using a photomultiplier tube to detect fluorescent emissions from a fluorophore associated with said particles.

T6'. The method of T1' wherein the step of emitting pulses of electromagnetic radiation comprises the step of emitting between about 50-150 million pulses per second, wherein each pulse has a width between about 1-100 picoseconds.

T7'. The method of T1' wherein the step of generating a timing signal comprises sensing scattered light resulting from interaction of a pulse with the fluid stream.

T8'. The method of T1' wherein the step of generating a timing signal comprises generating a clock signal and the step of emitting a plurality of EMR pulses from a laser comprises using the clock signal to trigger the laser to emit a pulse.

T9'. The method of T1' wherein the step of analyzing the digital signal comprises analyzing the digital signal as a pulse waveform.

T10'. The method of T9' wherein the step of analyzing the digital signal further comprises extracting at least one of the following features from the signal: critical slope difference; pulse rise time; pulse peak; and pulse area.

T11'. The method of T1' wherein said particles comprise sperm cells.

U' [Reserved]

V'. CV Optimization

V1'. A process for evaluating a set of conditions for staining a population of cells for sorting, the population comprising a first type and a second type of cell, the process comprising:
  (a) staining a fraction of the population of cells with a fluorescent dye under a set of staining conditions;
  (b) exposing the stained cells to electromagnetic radiation as the stained cells are passed through an interrogation location of a flow cytometer at a rate, R;
  (c) determining a fluorescence emission characteristic of the exposed cells;
  (d) using the determined fluorescence characteristic to classify the exposed cells into two or more sub-populations of cells, one of the sub-populations being an enriched sub-population of the first cell type;
  (e) determining a coefficient of variation for the fluorescence emission characteristic of the cells of the enriched sub-population to provide an indication of sorting efficiency for the staining conditions; and
  (f) determining whether to modify any staining condition under which cells are to be stained or the rate, R, at which the stained cells are to be passed through the interrogation location of the flow cytometer in order to improve sorting efficiency.

V2'. The process of claim V1', wherein said fraction comprises a first fraction and said set of staining conditions comprises a first set of staining conditions, the process further comprising staining a second fraction of said population of cells under a second set of staining conditions different from the first set and performing steps (b) through (e) with said second fraction of the population of cells.

V3'. The process of claim V2' wherein the second fraction is stained after the coefficient of variation has been determined for the first fraction.

V4'. The process of claim V2' wherein the second set of staining conditions differs from the first set of staining conditions by at least one of the following: (1) concentration of the fluorescent dye; (2) the length of a staining period used to stain the cells; and (3) a temperature of the cells during a staining period used to stain the cells.

V5'. The process of claim V2', further comprising staining a third fraction of said population of cells under a third set of staining conditions different from the first and second sets and performing steps (b) through (e) with the third fraction of the population of cells.

V6'. The process of claim V5', further comprising staining a fourth fraction of said population of cells under a fourth set of staining conditions different from the first, second, and third sets and performing steps (b) through (e) with the fourth fraction of the population of cells.

V7'. The process of claim V6', further comprising staining a fifth fraction of said population of cells under a fifth set of staining conditions different from the first, second, third and fourth sets and performing steps (b) through (e) with the fifth fraction of the population of cells.

V8'. The process of claim V2', further comprising selectively varying conditions in the first set of staining conditions based upon said determination in order to obtain the second set of staining conditions.

V9.' The process of claim V2', wherein a modified staining condition as determined by performing step (f) on the second fraction is applied to the staining of the remainder of the population of cells.

V10'. The process of claim V1', wherein multiple fractions of cells are stained in step (a), each fraction being stained under a unique set of staining conditions, wherein steps (b) through (e) are performed for each fraction, and wherein step (f) comprises using the respective coefficients of variation to determine the set of staining conditions to be used to stain additional cells in said population.

V11'. The process of claim V1', wherein the cells are sperm cells.

V12'. The process of claim V11', wherein the first cell type comprises X chromosome bearing sperm cells.

V13'. The process of claim V1' wherein step (a) comprises staining the cells with Hoechst 33342.

V14'. The process of claim V1' wherein said fluorescence emission characteristic comprises a feature of a fluorescence pulse waveform corresponding to movement of a cell through the interrogation location, and wherein said feature is indicative of at least one of the following: (1) total fluorescence intensity; and (2) peak fluorescence intensity.

V15'. The process of claim V1' further comprising determining before step (f) whether the coefficient of variation from step (e) is equal to or less than a predetermined coefficient of variation and repeating steps (a) through (e) using a different set of staining conditions to stain a different fraction of the cells each time until the coefficient of variation determined in step (e) is equal to or less than the predetermined coefficient of variation, and wherein step (f) comprises determining to use the staining conditions to stain additional cells if the coefficient of variation from step (e) for the respective staining conditions is equal to or less than the predetermined coefficient of variation.

V16' A process for evaluating a set of conditions for staining a population of cells for sorting, the population comprising a first type and a second type of cell, the process comprising:
  (a) staining a fraction of the population of cells with a fluorescent dye under a set of staining conditions;
  (b) exposing the stained cells to electromagnetic radiation as the stained cells are passed through an interrogation location of a flow cytometer at a rate, R;
  (c) determining a fluorescence emission characteristic of the exposed cells;
  (d) using the determined fluorescence emission characteristic to classify the exposed cells into two or more sub-populations of cells, one of the sub-populations being an enriched sub-population of the first cell type;
  (e) determining a coefficient of variation for the fluorescence emission characteristic of the cells of the enriched sub-population to provide an indication of sorting efficiency for the staining conditions;
  (f) determining whether to modify any staining condition under which the fraction of cells are to be stained or the rate, R, at which the stained cells are passed through the interrogation location of the flow cytometer in order to improve sorting efficiency; and (g) applying the modified staining condition to the remainder of the population of cells.

V17'. The process of claim V16' further comprising sorting the remainder of the population of cells in a flow cytometer to obtain an enriched sample population of the first cell type.

V18'. The process of claim V16', wherein said fraction comprises a first fraction and said set of staining conditions comprises a first set of staining conditions, the process further comprising staining a second fraction of said population of cells under a second set of staining conditions different from the first set and performing steps (b) through (e) with said second fraction of the population of cells.

V19'. The process of claim V18' wherein the second fraction is stained after the coefficient of variation has been determined for the first fraction.

V20'. The process of claim V18', wherein the second set of staining conditions differs from the first set by at least one of the following: (1) concentration of the fluorescent dye; (2) the length of a staining period used to stain the cells; and (3) the temperature of the cells during a staining period used to stain the cells.

V21'. The process of claim V18', further comprising staining a third fraction of said population of cells under a third set of staining conditions different from the first and second sets and performing steps (b) through (f) with the third fraction of the population of cells.

V22'. The process of claim V21', further comprising staining a fourth fraction of said population of cells under a fourth set of staining conditions different from the first, second, and third sets and performing steps (b) through (f) with the fourth fraction of the population of cells.

V23'. The process of claim V22', further comprising staining a fifth fraction of said population of cells under a fifth set of staining conditions different from the first, second, third and fourth sets and performing steps (b) through (f) with the fifth fraction of the population of cells.

V24'. The process of claim V18', further comprising prior to step (g), selecting a set of staining conditions for use in step (g) that results in a coefficient of variation level for the fluorescence emission characteristic that is equal to or less than a predetermined coefficient of variation.

V25'. The process of claim V24', wherein the predetermined coefficient of variation is about 1.3% or less.

V26'. The process of claim V16', further comprising determining before step (f) whether the coefficient of variation from step (e) is equal to or less than a predetermined coefficient of variation and repeating steps (a) through (e) using a different set of staining conditions to stain a different fraction of the cells each time until the coefficient of variation determined in step (e) is equal to or less than the predetermined coefficient of variation, and wherein step (f) comprises determining to use the staining conditions to stain additional cells if the coefficient of variation from step (e) for the respective staining conditions is equal to or less than the predetermined coefficient of variation.

V27'. The process of claim V16', wherein the cells are sperm cells.

V28'. The process of claim V27', wherein the first cell type comprises X chromosome bearing sperm cells.

V29'. The process of claim V16', wherein step (a) comprises staining the cells with Hoechst 33342.

V30'. The process of claim V16'; wherein said fluorescence emission characteristic comprises a feature of a fluorescence pulse waveform corresponding to movement of a cell through the interrogation location, and wherein said feature is indicative of at least one of the following: (1) total fluorescence intensity; and (2) peak fluorescence intensity.

W'. Automated Calibration Using Epi-Illumination Sensors

W1'. An apparatus for automatically calibrating a droplet sorting flow cytometer that selectively applies or does not apply one of a set of one or more electrical charges to a plurality of droplets as they break off of a continuous fluid stream at a droplet break-off location and electrostatically sorts the droplets into two or more separate droplet streams, the selection of the electrical charge for each droplet being dependent on the expected contents of the droplet based on a drop delay setting representing an estimate of the time elapsing between the moment a particle contained in the continuous fluid stream is detected at an interrogation location of the flow cytometer and the arrival of that particle at the droplet break-off location, the apparatus comprising:

(a) an epi-illumination sensor downstream of the interrogation location for illuminating droplets in one of said separate droplet streams, detecting any fluorescence emissions emitted by particles contained in the droplets, and generating an output signal representative of the detected fluorescence emissions; and (b) a control operable to analyze the output signal and to automatically adjust at least one of: (1) the drop delay setting; and (2) the amplitude of a charge in said set of charges.

W2'. The apparatus of W1' wherein the control adjusts the drop delay setting as a function of the difference between the detected fluorescence emissions and the fluorescence emissions that would have been produced by droplets having the expected contents.

W3'. The apparatus of W1' wherein the control adjusts the amplitude of a charge in said set of charges as a function of variation in an average peak intensity of fluorescence emissions detected for droplets containing fluorescent particles.

W4'. The apparatus of W1' wherein said epi-illumination sensor comprises a light source, a dichroic filter, a lens system, and a photodetector.

W5'. The apparatus of W4' wherein the epi-illumination sensor further comprises a fiber optic cable operable to conduct light from the light source to the location at which the sensor illuminates the droplets.

W6'. The apparatus of W5' wherein the electrical field is generated by a pair of electrically charged deflector plates, and wherein the epi-illumination sensor is positioned to illuminate said droplets as they pass between said deflector plates.

W7'. The apparatus of W6' wherein the epi-illumination sensor is positioned to illuminate said droplets through a hole in an electrically insulated support holding at least one of the deflector plates as the droplets move through an electric field generated by one or more of the deflector plates.

W8'. The apparatus of W4' wherein the light source is operable to illuminate particles at the interrogation location.

W9'. The apparatus of W1' further comprising an epi-illumination sensor as set forth in paragraph (a) of claim W1' for each of the remainder of said two or more separate droplet streams, said control being operable to analyze the output signals from the epi-illumination sensor for each droplet stream and to automatically adjust at least one of: (1) the drop delay setting as a function of the difference between the detected fluorescence emissions for one or more of the streams and the fluorescence emissions that would have been produced by droplets having the expected contents in the respective droplet stream; and (2) the amplitude of a charge in said set of charges as a function of variation in an average peak intensity of fluorescence emissions detected for droplets containing fluorescent particles at least one of said one or more droplet streams.

W10'. The apparatus of W9' wherein the electrical field is generated by a pair of electrically charged deflector plates, and wherein the epi-illumination sensor is positioned to illuminate said droplets as they pass between said deflector plates.

W11'. The apparatus of W10' wherein the epi-illumination sensor is positioned to illuminate said droplets through a hole in an electrically insulated support holding at least one of the deflector plates as the droplets move through an electric field generated by one or more of the deflector plates.

W12'. The apparatus of W1' wherein the control is operable to automatically maintain the phase of droplet charging within about 36 degrees above or below an optimal phase with respect to droplet formation.

W13'. The apparatus of W12' wherein the control is operable to automatically maintain the phase of droplet charging within about 10.8 degrees above or below an optimal phase with respect to droplet formation.

X'. Automated Calibration Method

X1'. A method of continuously verifying proper sort calibration in a droplet sorting flow cytometer that selectively applies or does not apply one of a set of one or more electrical charges to a plurality of droplets as they form from a continuous fluid stream at a droplet break-off location and electrostatically sorts the droplets into two or more separate droplet streams, the selection of the electrical charge for each droplet being dependent on the expected contents of the droplet based on a drop delay setting representing an estimate of the time elapsing between the moment a particle contained in the continuous fluid stream is detected at an interrogation location of the flow cytometer and the arrival of that particle at the droplet break-off location, the method comprising:

(a) illuminating droplets in one of said separate droplet streams by directing an illumination beam along a beam axis in a forward direction through a lens system to cause emission of fluorescent light by any particles contained in the droplets;

(b) using said lens system to collect some of said fluorescent light and direct it in a rearward direction along the beam axis;

(c) detecting at least some of the collected fluorescent light and generating an output signal representative of the detected light; and (d) analyzing the output signal and, based on the analysis, automatically adjusting at least one of: (1) the drop delay setting; and (2) the amplitude of a charge in said set of charges.

X2'. The method of X1' wherein the adjusting step comprises adjusting the drop delay setting as a function of the difference between the detected fluorescence emissions and the fluorescence emissions that would have been produced by droplets having the expected contents.

X3'. The method of X1' wherein the adjusting step comprises adjusting the amplitude of a charge in said set of charges as a function of variation in an average peak intensity of fluorescence emissions detected for droplets containing fluorescent particles.

X4'. The method of X1' wherein the illuminating step comprises using a fiber optic cable to guide light from the light source to a position adjacent said sorted droplet streams.

X5'. The method of X1' wherein the electrical field is generated by a pair of electrically charged deflector plates, and wherein the illuminating step comprises illuminating the droplets as they move between the deflector plates.

X8'. The method of X5' wherein at least one of the deflector plates is held by an electrically insulated support, and wherein the illuminating step comprises illuminating the droplets through a hole in the support as the droplets move through the electric field.

X7'. The method of X1' further comprising using the light source to illuminate the particles at the interrogation location.

X8'. The method of X1' further comprising performing steps (a)-(c) for each of the remainder of said two or more droplet streams, and wherein step (d) further comprises analyzing each of the respective output signals and adjusting at least one of: (1) the drop delay setting as a function of the difference between the detected fluorescence emissions and the fluorescence emissions that would have been produced by droplets having the expected contents; and (2) the amplitude of a charge in said set of charges as a function of variations in the average peak intensity of fluorescence emissions detected for droplets containing fluorescent particles at least one of said droplet streams.

X9'. The method of X8' wherein the electrical field is generated by a pair of electrically charged deflector plates, and wherein the illuminating step comprises illuminating the droplets as they move between the deflector plates.

X10'. The method of X9' wherein at least one of the deflector plates is held by an electrically insulated support, and wherein the illuminating step comprises illuminating the droplets through holes in the support as the droplets move through the electric field.

Y'. Test Stream Calibration Method

Y1'. A method of continuously verifying proper sort calibration in a droplet sorting flow cytometer that selectively applies or does not apply one of a set of one or more electrical charges to a plurality of droplets as they form from a continuous fluid stream at a droplet break-off location and electrostatically sorts the droplets into two or more separate droplet streams, the selection of the electrical charge for each droplet being dependent on the expected contents of the droplet based on a drop delay setting representing an estimate of the time elapsing between the moment a particle contained in the continuous fluid stream is detected at an interrogation location of the flow cytometer and the arrival of that particle at the droplet break-off location, the method comprising:

selecting droplets estimated to have substantially zero probability of containing a particle;

applying one charge of said set of charges to the selected droplets in order to form a test stream out of the selected droplets;

illuminating the droplets in the test stream; and detecting any light emitted or scattered by any particles in the selected droplets.

Y2'. The method of Y1' further comprising adjusting the drop delay setting if light detecting in the detecting step exceeds a threshold level.

Y3'. The method of Y2' wherein the adjusting step is performed automatically.

Y4'. The method of Y1' wherein the charge applied in the charging step is a neutral charge.

Y5'. The method of Y1' wherein the illuminating and detecting steps are performed using an epi-illumination sensor.

Z'. Sort Correction System

Z1'. A sort system correction system for a droplet sorting flow cytometer comprising:

a charging element for selectively applying one electrical charge from a set of electrical charges to each droplet in a stream of droplets as the droplets form from a continuous fluid stream at a droplet break-off location;

a pair of electrically charged deflector plates downstream from the charging element positioned so the droplets pass between the deflector plates to sort the droplets according to their charge;

and a debris removal system comprising at least one of the following elements: (1) a selectively activatable air system for removing debris from the charging element; and (2) a selectively activatable air system for removing debris from the deflector plates.

Z2'. The system of Z1' wherein said debris removal system comprises element (1) and element (2).

Z3'. The system of Z1' wherein the debris removal system is adapted to be automatically activated by a processor upon determination by the processor that debris from stray droplets is interfering with droplet sorting.

Z4'. The system of Z1' wherein the debris removal system comprises element (1), and wherein said selectively activatable air system of element (1) comprises a vacuum passage having an opening adjacent said charging element for vacuuming debris off the charging element.

Z5'. The system of Z1' wherein the debris removal system comprises element (2), and wherein sa Z6.' A method of operating a droplet sorting flow cytometer system, the method comprising:

using a charging element to selectively apply one electrical charge from a set of electrical charges to each droplet in a stream of droplets as the droplets form from a continuous fluid stream at a droplet break-off location;

passing the droplets between a pair of electrically charged deflector plates downstream from the charging element to sort the droplets according to their charge;

using a processor to determine whether debris is interfering with droplet sorting; and removing said debris using a debris removal system under the control of the processor if the processor determines that debris is interfering with droplet sorting, said debris removal system comprising at least one of the following elements: (1) a selectively activatable air system for removing debris from the charging element; and (2) a selectively activatable air system for removing debris from the deflector plates.

Reservation of Rights

Applicants expressly reserve all rights with respect to filing amended claims and continuation and/or divisional applications to prosecute claims directed to any inventive aspect identified above and any other subject matter described in the specification or shown in the drawings.

What is claimed is:

1. A nozzle for use in flow cytometry apparatus for analyzing particles in a fluid stream, said fluid stream comprising a sheath stream surrounding a core stream containing said particles, said nozzle comprising:
   a nozzle having an interior surface defining a flow path for said fluid stream, and an orifice for exit of the fluid stream from the nozzle;
   a sample injection needle disposed within the nozzle; and
   a baffle plate located downstream of the sample injection needle in the nozzle positioned in said flow path upstream from said orifice for deflecting the fluid stream as it moves along said flow path, the baffle plate and interior surface of the nozzle being configured to orient the particles in a desired orientation as they exit the orifice.

2. The nozzle of claim 1, wherein said nozzle has a first cross sectional flow area upstream of said baffle plate and a second cross sectional flow area different from said first cross sectional flow area at the baffle plate.

3. The nozzle of claim 2, wherein said second cross sectional flow area is smaller than said first cross sectional flow area.

4. The nozzle of claim 2, wherein said first and second cross sectional flow areas have different shapes.

5. The nozzle of claim 4, wherein said second cross sectional flow area is generally semi-cylindrical.

6. The nozzle of claim 1, wherein said interior surface of the nozzle is shaped to define at least two axially tapered regions downstream from said baffle plate for progressively accelerating the speed of the fluid stream in a downstream direction toward the nozzle orifice.

7. The nozzle of claim 6, wherein said baffle plate is configured for deflecting said core stream toward a portion of said interior surface of the nozzle defining at least one of said at least two axially tapered regions.

8. The nozzle of claim 7, wherein said at least two axially tapered regions have generally elliptical cross sectional shapes oriented in different directions for applying torsional forces to said fluid stream that tend to bring the particles into said desired orientation.

9. The nozzle of claim 8, wherein said generally elliptical cross sectional shape of one of said at least two regions is oriented at about 90 degrees relative to the generally elliptical cross sectional shape of the other of said at least two regions.

10. The nozzle of claim 1, wherein the nozzle has an exterior surface with a non-reflective coating thereon.

11. The nozzle of claim 1, further comprising a holder for holding said baffle plate in fixed position in said nozzle.

12. The nozzle of claim 11, wherein said baffle plate has a first leg extending generally transversely relative to said fluid stream and a second leg extending generally in the direction of said fluid stream.

13. The nozzle of claim 12, wherein said interior surface of the nozzle has a region of generally elliptical cross section downstream from said baffle plate, and wherein said first and second legs of the baffle plate intersect along a line which is substantially parallel with a major axis of said generally elliptical cross section.

14. The nozzle of claim 12, wherein said interior surface of the nozzle has a region of generally elliptical cross section downstream from said baffle plate, and wherein said first and second legs of the baffle plate intersect along a line which is substantially perpendicular to a major axis of said generally elliptical cross section.

15. The nozzle of claim 11, wherein said holder comprises a generally cylindrical shell holding said baffle plate and positioned in said nozzle.

16. The nozzle of claim 11, wherein the baffle plate has a semi-circular shape or has semi-elliptical shape.

17. The nozzle of claim 11, wherein the interior surface of the nozzle is shaped to define a shoulder and the holder comprises an o-ring seal capable of pressing the baffle plate against the shoulder to hold the baffle plate in a desired position.

18. The method of claim 11, wherein the baffle holder holds the baffle plate in a position in which the baffle plate intersects a longitudinal axis of the nozzle.

19. A method of orienting particles in a flow cytometry apparatus, said method comprising:
   forming a fluid stream by introducing a core stream of sample fluid containing particles into a sheath fluid so that the sheath fluid surrounds the core stream;
   flowing the fluid stream having a core stream and sheath fluid through a nozzle having an interior surface defining a flow path that generally tapers from an upstream portion of the nozzle to an orifice at the downstream end of the nozzle; and deflecting the core stream with a baffle plate as it flows through the nozzle to subject the particles in the core stream to hydrodynamic forces that tend to cause the particles to assume a desired orientation.

20. The method of claim 19, wherein the nozzle has a longitudinal axis and the step of deflecting the core stream comprises deflecting the core stream away from the longitudinal axis toward said interior surface with said baffle plate in the nozzle positioned in said flow path.

21. The method of claim 19, wherein the nozzle has a longitudinal axis and the step of deflecting the path of the core stream comprises deflecting the core stream from a path that generally coincides with the longitudinal axis to a deflected path, at least a portion of the deflected path being offset from the longitudinal axis of the nozzle.

22. The method of claim 19, wherein the nozzle has a longitudinal axis, the method further comprising introducing the core stream into the sheath fluid at a location that is offset from the longitudinal axis.

23. The method of claim 19, wherein the nozzle has an interior surface that is shaped to define at least one torsional zone comprising a tapered region having a generally elliptical cross section for subjecting the particles to hydrodynamic orienting forces.

24. The method of claim 23, wherein said interior surface is shaped to define multiple torsional zones.

25. The method of claim 24, wherein each of said multiple torsional zones comprises a tapered region of the nozzle having a generally elliptical cross section, wherein the generally elliptical cross section for a first of the multiple torsional zones is oriented in a different direction than the generally elliptical cross section for a second of the multiple torsional zones.

* * * * *

UNITED STATES PATENT AND TRADEMARK OFFICE
CERTIFICATE OF CORRECTION

PATENT NO. : 8,709,825 B2
APPLICATION NO. : 13/782459
DATED : April 29, 2014
INVENTOR(S) : Gary Durack et al.

It is certified that error appears in the above-identified patent and that said Letters Patent is hereby corrected as shown below:

On the Title page of the patent,

Item (60), Related U.S. Application Data, lines 4-5, "and a division of application No. 12/794,921," should be replaced with -- and a continuation of application No. 12/794,921, --

In the Drawings,

Please replace Fig. 72 with attached Replacement Sheet 76

In the Specification,

Column 22, line 58, "50□g to about 800□g per ml of" should be replaced with -- 50μg to about 800μg per ml of --

Column 23, line 9, "about 10□M to" should be replaced with -- about 10μM to --
Column 23, lines 20 through 21, "from about 1□M to about 100□M, preferably from about 10□M to about 100□M, and more preferably about 100□M." should be replaced with -- from about 1μM to about 100μM, preferably from about 10μM to about 100μM, and more preferably about 100μM. --

Column 31, line 34, "Table 1 below." should be replaced with -- Table II below. --
Column 31, line 36, "TABLE 1" should be replaced with -- TABLE II --

Column 56, line 48, "Table II" should be replaced with -- Table III --
Column 56, line 52, "TABLE II" should be replaced with -- TABLE III --

Column 57, line 1, "Table II -continued" should be replaced with -- Table III -continued --
Column 57, line 39, "Table II" should be replaced with -- Table III --
Column 57, line 47, "Table II" should be replaced with -- Table IV --

Signed and Sealed this
Twenty-fourth Day of February, 2015

Michelle K. Lee
*Deputy Director of the United States Patent and Trademark Office*

CERTIFICATE OF CORRECTION (continued)
U.S. Pat. No. 8,709,825 B2

Column 58, line 25, "TABLE 2" should be replaced with -- TABLE IV --
Column 58, line 47, Table IV" should be replaced with -- Table V --
Column 58, line 50, "TABLE IV" should be replaced with -- TABLE V --

Column 59, line 1, "TABLE IV -continued" should be replaced with -- TABLE V -continued --

Column 60, line 48, "Table V" should be replaced with -- Table VI --
Column 60, line 52, "TABLE V" should be replaced with -- TABLE VI --

Column 61, line 1, "TABLE V -continued" should be replaced with -- TABLE VI -continued --
Column 61, line 58, "Table VI lists the" should be replaced with -- Table VII lists the --

Column 62, line 15, "TABLE VI" should be replaced with -- TABLE VII --

Column 76, lines 54-55, "Table 6 summarizes" should be replaced with -- Table VIII summarizes --
Column 76, lines 58-59, "Table VII," should be replaced with -- Table VIII, --
Column 76, line 61, "Table 3." should be replaced with -- Table V. --

Column 77, line 1, "TABLE VII" should be replaced with -- TABLE VIII --